US009803250B2

(12) United States Patent
Fredricks et al.

(10) Patent No.: US 9,803,250 B2
(45) Date of Patent: Oct. 31, 2017

(54) BROAD RANGE PCR-BASED COMPOSITIONS AND METHODS FOR THE DETECTION AND IDENTIFICATION OF FUNGAL PATHOGENS

(75) Inventors: David N. Fredricks, Seattle, WA (US); Prasanna D. Khot, Mountlake Terrace, WA (US); Daisy L. Ko, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 167 days.

(21) Appl. No.: 12/625,361

(22) Filed: Nov. 24, 2009

(65) Prior Publication Data

US 2010/0129821 A1 May 27, 2010

Related U.S. Application Data

(60) Provisional application No. 61/118,230, filed on Nov. 26, 2008.

(51) Int. Cl.
 *C12Q 1/68* (2006.01)
 *C12P 19/34* (2006.01)
(52) U.S. Cl.
 CPC ........... *C12Q 1/6895* (2013.01); *C12Q 1/686* (2013.01); *C12Q 2600/156* (2013.01)
(58) Field of Classification Search
 CPC .. C12C 1/686; C12C 1/6895; C12C 2600/156
 See application file for complete search history.

(56) References Cited

U.S. PATENT DOCUMENTS

| | | | | |
|---|---|---|---|---|
| 6,150,517 A | * | 11/2000 | Hogan et al. | ................. 536/25.3 |
| 6,387,652 B1 | | 5/2002 | Haugland et al. | |
| 7,427,472 B2 | | 9/2008 | Lindsey et al. | |
| 2007/0042354 A1 | | 2/2007 | Engelhard et al. | |
| 2011/0189676 A1 | * | 8/2011 | Hall et al. | .................... 435/6.11 |

FOREIGN PATENT DOCUMENTS

JP 2008054563 A 3/2008

OTHER PUBLICATIONS

Vollmer, T. et al., J. Clin. Microbiol., vol. 46, pp. 1919-1926 (Apr. 2008).*
Maaroufi, Y. et al. (J. Clin. Microbiol., vol. 41, pp. 3293-3298 (2003).*
QIAamp DNA Mini and Blood Mini Handbook, pp. 1-72 (2010).*
Nagao, K. et al., J. Dermatol. Sci., vol. 39, pp. 23-31 (2005).*
Skladny, H. et al., J. Clin. Microbiol., vol. 37, pp. 3865-3871 (1999).*
Loeffler, J. et al., J. Infect. Dis., vol. 185, pp. 1203-1206 (2002).*
Kurtzman, C.P. et al., J. Clin. Microbiol., vol. 35, pp. 1216-1223 (1997).*
Van der Auwera, G. et al., Mol. Biol. Evol., vol. 12, pp. 671-678 (1995).*
Van der Auwera, G. et al., FEBS Letters, vol. 338, pp. 133-136 (1994).*
Ribes, J.A. et al., Clin. Microbiol. Rev., vol. 13, pp. 236-301 (2000).*
Kappe, R. et al., J. Med. Microbiol., vol. 47, pp. 811-820 (1998).*
Kasai, M. et al., J. Clin. Microbiol., vol. 46, pp. 3690-3702 (Sep. 2008).*
GenBank Accession No. AF113481 (Dec. 1999).*
GenBank Accession No. U13369 (Oct. 1994).*
Abd-Elsalam, K.A., Afr. J. Biotechn., vol. 2, pp. 91-95 (2003).*
Hendolin, P.H. et al., J. Clin. Microbiol., vol. 38, pp. 4186-4192 (2000).*
Tarai, B. et al., Indian J. Med. Res., vol. 123, pp. 671-678 (2006).*
Leaw, S.N. et al., J. Clin. Microbiol., vol. 44, pp. 693-699 (2006).*
Wu, Z. et al., J. Environ. Monit., vol. 4, pp. 377-382 (2002).*
Baskova, L. et al., J. Med. Microbiol., vol. 56, pp. 1167-1173 (2007).*
International Search Report for Application PCT/US09/65770, mailed on Apr. 29, 2010.
Khot et al., "Development and optimization of quantitative PCR for the diagnosis of invasive aspergillosis with bronchoalveolar lavage fluid". BMC Infectious Diseases, May 29, 2008 (May 29, 2008), vol. 8, No. 73, pp. 1-13; abstract, p. 3-4, fig 1, DNA extraction from BAL fractions,; p. 5, (iii) Aspergillus targeted 18S qPCR; p. 6, right col, para 1.
Henry et al., "Identification of *Aspergillus* Species Using Internal Transcribed Spacer Regions 1 and 2". Journal of Clinical Microbiology, Apr. 2000, vol. 38, No. 4, pp. 1510? 1515; abstract; p. 1511, Primers.; p. 1512, fig 1, Table 1.
Hinrikson et al., Assessment of Ribosomal Large-Subunit D1-D2, Internal Transcribed Spacer 1, and Internal Transcribed Spacer 2 Regions as Targets for Molecular Identification of Medically Important *Aspergillus* Species. Journal of Clinical Microbiology, May 2005, vol. 43, No. 5, pp. 2092?2103; abstract, p. 2093, PCR amplification of the D1-D2 region of the large subunit (28S) rRNA gene.
Written Opinion of the International Searching Authority for Application PCT/US09/65770, mailed on Apr. 29, 2010.
Iwen, Med. Mycol. 40(1):87-109 (2002).
Khot, Appl. Environ. Microbiol. 76(6):1559-65 (2009).
Kurtzman, J. Clin. Microbiol. 35(5):1216-1223 (1997).
Rakeman, J. Clin. Microbiol. 43(7):3324-3333 (2005).
Ellepola and Morrison, Microbiology 43(S):65-84 (2005).
European Search Report dated Jan. 16, 2014, Application No. 09 829 763.3.

* cited by examiner

*Primary Examiner* — Teresa Strzelecka
(74) *Attorney, Agent, or Firm* — Hahn Loeser & Parks, LLP—San Diego

(57) ABSTRACT

Disclosed herein are methods for detecting a fungal pathogen in a patient sample, involving isolating the sample, carrying out a PCR reaction on the sample to generate an amplicon that includes a region of the fungal 28S ribosomal RNA gene, and detecting the PCR amplicon. Also disclosed are sequences of primers for specifically detecting a broad range of fungal pathogens in the presence of human ribosomal DNA. In certain embodiments, the amplicon is detected by sequencing or by two-dimensional melt-curve analysis. In yet other embodiments, more than one fungal pathogen is detected in a sample using the methods disclosed herein.

22 Claims, 73 Drawing Sheets

| Species | ITS1 (18SF-5.8SR) | ITS2 (5.8SF-1R) | ITS2 (5.8SF-2R) | ITS2 (5.8SF-3R) | 28S (9F-12R) | 28S (10F-12R) | 28S (12F-13R) | 28S (15F-22R) | 28S (18F-22R) | 28S (18F-23R) | 28S (23F-25R) |
|---|---|---|---|---|---|---|---|---|---|---|---|
| Absidia corymbifera | − | + | − | − | +++ | +++ | +++ | − | ++ | +++ | + |
| Aspergillus candidus | +++ | +++ | − | + | +++ | +++ | +++ | +++ | +++ | +++ | + |
| Aspergillus flavus | +++ | +++ | +++ | +++ | +++ | +++ | ++ | +++ | +++ | +++ | ++ |
| Aspergillus fumigatus | +++ | +++ | +++ | +++ | +++ | +++ | +++ | +++ | +++ | +++ | +++ |
| Aspergillus oryzae | +++ | +++ | +++ | +++ | +++ | +++ | ++ | +++ | +++ | +++ | +++ |
| Aspergillus terreus | +++ | +++ | +++ | +++ | +++ | +++ | +++ | +++ | +++ | +++ | +++ |
| Aspergillus ustus | +++ | +++ | +++ | +++ | +++ | +++ | +++ | +++ | +++ | +++ | +++ |
| Candida albicans | +++ | +++ | +++ | +++ | +++ | +++ | +++ | +++ | +++ | +++ | +++ |
| Candida dubliensis | +++ | +++ | +++ | +++ | +++ | +++ | +++ | +++ | +++ | +++ | +++ |
| Candida glabrata | +++ | +++ | +++ | +++ | +++ | +++ | +++ | +++ | +++ | +++ | +++ |
| Candida guilliermondii | +++ | +++ | +++ | +++ | +++ | +++ | +++ | +++ | +++ | +++ | +++ |
| Candida kefyr | +++ | +++ | +++ | +++ | +++ | +++ | ++ | +++ | +++ | +++ | +++ |
| Candida krusei | − | ++ | ++ | + | +++ | +++ | + | − | +++ | +++ | − |
| Candida lusitaniae | +++ | +++ | +++ | +++ | +++ | +++ | +++ | +++ | +++ | ++ | − |
| Candida tropicalis | +++ | +++ | +++ | +++ | + | − | +++ | − | − | +++ | ++ |
| Cryptococcus neoformans | − | ++ | + | − | +++ | +++ | +++ | +++ | ++ | +++ | ++ |
| Cunninghamella bertholletiae | +++ | ++ | ++ | ++ | +++ | +++ | +++ | +++ | +++ | ++ | ++ |
| Fusarium solani | +++ | +++ | +++ | +++ | +++ | +++ | +++ | +++ | +++ | +++ | +++ |
| Mucor racemosus | − | ++ | ++ | − | + | +++ | ++ | − | − | +++ | − |
| Paecilomyces variotii | +++ | +++ | +++ | +++ | +++ | +++ | +++ | +++ | +++ | +++ | ++ |
| Penicillium notatum | − | ++ | +++ | +++ | +++ | +++ | +++ | − | − | − | − |
| Rhizomucor miehei | +++ | +++ | +++ | +++ | +++ | +++ | +++ | ++ | +++ | +++ | +++ |
| Rhizopus oryzae | +++ | +++ | +++ | +++ | +++ | − | +++ | +++ | +++ | +++ | +++ |
| Rhodotorula glutinis | +++ | +++ | +++ | +++ | +++ | +++ | +++ | +++ | +++ | +++ | +++ |
| Saccharomyces cerevisiae | +++ | +++ | +++ | +++ | +++ | +++ | +++ | +++ | +++ | +++ | +++ |
| Scedosporium apiospermum | ++ | +++ | +++ | +++ | +++ | +++ | +++ | +++ | +++ | +++ | + |
| Sum of +++ [a] | 21 | 22 | 20 | 21 | 24 | 25 | 16 | 21 | 22 | 23 | 10 |
| Sum of ++ | 1 | 3 | 2 | 1 | 0 | 0 | 8 | 0 | 3 | 2 | 6 |
| Sum of + | 0 | 1 | 3 | 2 | 1 | 0 | 2 | 0 | 0 | 0 | 7 |
| Sum of − | 4 | 0 | 1 | 2 | 1 | 1 | 0 | 5 | 1 | 1 | 3 |
| Effect of 1 μg human DNA [b] | none | none | none | none | none | none | none | none | none | none | none |
| Sum of distance matrix [d] | 642.5 | 1055.8 | ND | ND | ND | 310.8 | 470.6 | 67.5 | 74.5 | 117.3 | 358.3 |
| Sum of distance matrix [e] | 97914 | 113386 | ND | ND | ND | 82452 | 61321 | 17522 | 9629 | 28716 | 66445 |
| Amplicon length [f] | 295 ±70 | 254 ±43 | ND | ND | ND | 339 ±7 | 198 ±25 | 299 ±1 | 147 ±1 | 308 ±46 | 263 ±10 | a- PCR yield reflected by intensity level of product bands on a 1.5% agarose gel. '+++', '++', '+' indicate decreasing intensity levels and '−' represents no amplification.

b- Cross-reactivity evaluated based on the ability to amplify 10 fg of A. fumigatus DNA in the presence of 1 μg of human genomic DNA.

c- The sum of distance matrix was estimated from amplicons of 50 fungal species representing 30 genera. A higher value indicates greater sequence diversity among fungi for the selected amplicon.

d- Distances based on Tajima-Nei algorithm and Neighbor Joining tree building method.

e- Distances based on absolute nucleotide differences and Neighbor Joining tree building method.

f- Mean amplicon lengths ± standard deviation of 50 fungal species representing 30 genera.

g- Distances and amplicon length estimated for 46 sequences due to unavailability of sequence data for some.

ND- Distances not estimated because the amplicon overlaps significantly with another in the Table which has a greater breadth of fungi detected.

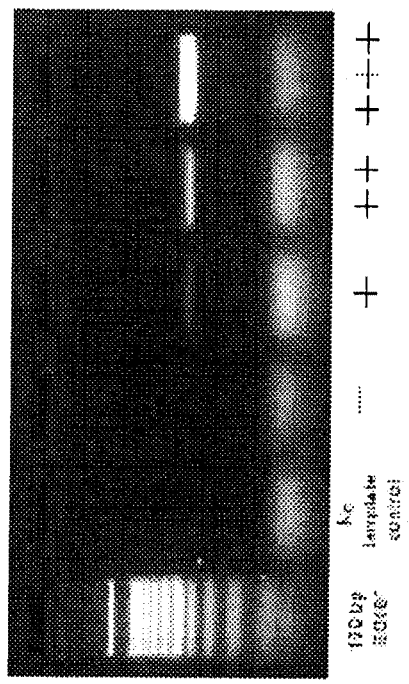

| 28S(10F-12R) | A. fumigatus | A. niger | A. oryzae | A. terreus | C. albicans | C. dubliniensis | C. glabrata | C. guilliermondii | C. kefyr | C. krusei | C. lusitaniae | C. parapsilosis | C. tropicalis | C. immitis | C. posadasi | C. neoformans | C. bertholletiae | F. oxysporum | F. solani | H. capsulatum | M. racemosus | P. varioti | P. brasiliensis | P. chrysogenum | P. carinii | R. miehei | R. oryzae | R. glutinis | S. cerevisiae |
|---|---|---|---|---|---|---|---|---|---|---|---|---|---|---|---|---|---|---|---|---|---|---|---|---|---|---|---|---|---|
| Aspergillus fumigatus | 94 | | | | | | | | | | | | | | | | | | | | | | | | | | | | |
| Aspergillus niger | 92 | 9 | | | | | | | | | | | | | | | | | | | | | | | | | | | |
| Aspergillus oryzae | 92 | 2 | 4 | | | | | | | | | | | | | | | | | | | | | | | | | | |
| Aspergillus terreus | 94 | 4 | | | | | | | | | | | | | | | | | | | | | | | | | | | |
| Candida albicans | 93 | 64 | 63 | 60 | | | | | | | | | | | | | | | | | | | | | | | | | |
| Candida dubliniensis | 94 | 64 | 65 | 60 | 1 | | | | | | | | | | | | | | | | | | | | | | | | |
| Candida glabrata | 102 | 59 | 62 | 58 | 55 | 26 | | | | | | | | | | | | | | | | | | | | | | | |
| Candida guilliermondii | 89 | 65 | 66 | 64 | 61 | 26 | 29 | | | | | | | | | | | | | | | | | | | | | | |
| Candida kefyr | 97 | 57 | 60 | 56 | 12 | 13 | 19 | 27 | | | | | | | | | | | | | | | | | | | | | |
| Candida krusei | 99 | 56 | 59 | 55 | 27 | 27 | 41 | 36 | 41 | | | | | | | | | | | | | | | | | | | | |
| Candida lusitaniae | 103 | 60 | 62 | 53 | 33 | 33 | 59 | 55 | 60 | 42 | | | | | | | | | | | | | | | | | | | |
| Candida parapsilosis | 94 | 64 | 65 | 61 | 48 | 48 | 41 | 86 | 27 | 36 | 51 | | | | | | | | | | | | | | | | | | |
| Candida tropicalis | 93 | 68 | 67 | 60 | 4 | 3 | 28 | 13 | 31 | 42 | 56 | 8 | | | | | | | | | | | | | | | | | |
| Coccidioides immitis | 93 | 16 | 17 | 64 | 11 | 10 | 34 | 16 | 57 | 57 | 64 | 63 | 63 | | | | | | | | | | | | | | | | |
| Coccidioides posadasi | 93 | 16 | 16 | 12 | 64 | 63 | 56 | 64 | 57 | 57 | 64 | 63 | 63 | 0 | | | | | | | | | | | | | | | |
| Cryptococcus neoformans | 89 | 71 | 72 | 70 | 73 | 63 | 69 | 66 | 67 | 78 | 86 | 73 | 72 | 71 | 71 | | | | | | | | | | | | | | |
| Cunninghamella bertholletiae | 114 | 110 | 110 | 108 | 111 | 110 | 117 | 108 | 117 | 116 | 117 | 108 | 105 | 107 | 107 | 107 | | | | | | | | | | | | | |
| Fusarium oxysporum | 88 | 40 | 44 | 39 | 70 | 70 | 62 | 66 | 60 | 64 | 74 | 68 | 72 | 43 | 43 | 75 | 111 | | | | | | | | | | | | |
| Fusarium solani | 88 | 38 | 41 | 37 | 48 | 73 | 65 | 69 | 27 | 31 | 73 | 72 | 76 | 40 | 40 | 71 | 112 | 8 | | | | | | | | | | | |
| Histoplasma capsulatum | 94 | 12 | 14 | 11 | 13 | 65 | 60 | 67 | 58 | 42 | 63 | 65 | 69 | 14 | 14 | 71 | 114 | 41 | 41 | | | | | | | | | | |
| Mucor racemosus | 78 | 89 | 88 | 89 | 66 | 88 | 67 | 84 | 63 | 57 | 64 | 87 | 68 | 90 | 90 | 84 | 86 | 81 | 83 | 86 | | | | | | | | | |
| Paecilomyces varioti | 95 | 15 | 16 | 15 | 89 | 93 | 59 | 31 | 91 | 57 | 86 | 64 | 86 | 11 | 11 | 73 | 113 | 45 | 43 | 9 | 86 | | | | | | | | |
| Paracoccidioides brasiliensis | 91 | 14 | 13 | 12 | 65 | 65 | 56 | 65 | 58 | 59 | 64 | 61 | 69 | 13 | 13 | 72 | 109 | 41 | 38 | 7 | 83 | 10 | | | | | | | |
| Penicillium chrysogenum | 95 | 8 | 13 | 14 | 62 | 64 | 56 | 64 | 53 | 56 | 66 | 60 | 65 | 20 | 20 | 73 | 111 | 44 | 42 | 16 | 90 | 19 | 17 | | | | | | |
| Pneumocystis carinii | 90 | 58 | 61 | 8 | 60 | 61 | 60 | 61 | 57 | 53 | 64 | 54 | 64 | 61 | 61 | 73 | 111 | 65 | 63 | 58 | 85 | 59 | 56 | 57 | | | | | |
| Rhizomucor miehei | 84 | 86 | 86 | 56 | 52 | 65 | 59 | 47 | 52 | 59 | 59 | 58 | 58 | 81 | 81 | 98 | 114 | 88 | 94 | 87 | 94 | 88 | 84 | 80 | 86 | | | | |
| Rhizopus oryzae | 63 | 77 | 75 | 86 | 97 | 88 | 56 | 33 | 100 | 95 | 75 | 95 | 86 | 72 | 72 | 76 | 109 | 71 | 73 | 77 | 33 | 75 | 70 | 77 | 74 | 78 | | | |
| Rhodotorula glutinis | 100 | 81 | 86 | 81 | 77 | 78 | 82 | 75 | 80 | 101 | 111 | 80 | 85 | 85 | 85 | 90 | 124 | 87 | 90 | 81 | 101 | 84 | 80 | 78 | 65 | 101 | 92 | | |
| Saccharomyces cerevisiae | 100 | 60 | 63 | 56 | 24 | 24 | 11 | 25 | 15 | 47 | 60 | 26 | 28 | 57 | 57 | 65 | 120 | 64 | 67 | 61 | 95 | 60 | 57 | 62 | 49 | 99 | 82 | 80 | |
| Scedosporium apiospermum | 98 | 48 | 45 | 46 | 78 | 78 | 72 | 76 | 68 | 68 | 79 | 77 | 81 | 47 | 47 | 82 | 121 | 30 | 30 | 46 | 95 | 48 | 43 | 49 | 67 | 101 | 86 | 94 | 75 |

| 28S(15F-22R) | A. corymbifera | A. fumigatus | A. niger | A. oryzae | A. terreus | C. albicans | C. dubliniensis | C. glabrata | C. guilliermondii | C. kefyr | C. krusei | C. lusitaniae | C. parapsilosis | C. tropicalis | C. immitis | C. posadasi | C. neoformans | C. bertholletiae | F. oxysporum | F. solani | H. capsulatum | M. racemosus | P. variotii | P. brasiliensis | P. chrysogenum | P. carinii | R. miehei | R. oryzae | R. glutinis | S. cerevisiae |
|---|---|---|---|---|---|---|---|---|---|---|---|---|---|---|---|---|---|---|---|---|---|---|---|---|---|---|---|---|---|---|
| Aspergillus fumigatus | 18 | 0 | | | | | | | | | | | | | | | | | | | | | | | | | | | | |
| Aspergillus niger | 18 | 0 | 0 | | | | | | | | | | | | | | | | | | | | | | | | | | | |
| Aspergillus oryzae | 18 | 0 | 0 | 0 | | | | | | | | | | | | | | | | | | | | | | | | | | |
| Aspergillus terreus | 18 | 6 | 6 | 6 | 6 | | | | | | | | | | | | | | | | | | | | | | | | | |
| Candida albicans | 17 | 6 | 6 | 6 | 7 | 0 | | | | | | | | | | | | | | | | | | | | | | | | |
| Candida dubliniensis | 17 | 6 | 6 | 6 | 7 | 1 | 0 | | | | | | | | | | | | | | | | | | | | | | | |
| Candida glabrata | 18 | 7 | 7 | 7 | 8 | 3 | 3 | 0 | | | | | | | | | | | | | | | | | | | | | | |
| Candida guilliermondii | 17 | 6 | 6 | 6 | 9 | 2 | 2 | 1 | 0 | | | | | | | | | | | | | | | | | | | | | |
| Candida kefyr | 18 | 9 | 9 | 9 | 9 | 3 | 3 | 2 | 3 | 0 | | | | | | | | | | | | | | | | | | | | |
| Candida krusei | 19 | 8 | 8 | 8 | 9 | 2 | 2 | 1 | 2 | 3 | 0 | | | | | | | | | | | | | | | | | | | |
| Candida lusitaniae | 20 | 6 | 6 | 6 | 6 | 3 | 3 | 4 | 3 | 4 | 3 | 0 | | | | | | | | | | | | | | | | | | |
| Candida parapsilosis | 17 | 6 | 6 | 6 | 9 | 2 | 3 | 6 | 4 | 6 | 5 | 6 | 0 | | | | | | | | | | | | | | | | | |
| Candida tropicalis | 20 | 9 | 9 | 9 | 9 | 4 | 5 | 6 | 5 | 8 | 8 | 6 | 5 | 0 | | | | | | | | | | | | | | | | |
| Coccidioides immitis | 17 | 1 | 1 | 1 | 1 | 5 | 5 | 6 | 5 | 6 | 7 | 8 | 5 | 8 | 0 | | | | | | | | | | | | | | | |
| Coccidioides posadasi | 17 | 1 | 1 | 1 | 1 | 5 | 5 | 6 | 5 | 6 | 7 | 8 | 5 | 8 | 0 | 0 | | | | | | | | | | | | | | |
| Cryptococcus neoformans | 18 | 6 | 6 | 6 | 6 | 7 | 7 | 8 | 7 | 10 | 9 | 10 | 7 | 10 | 5 | 5 | 0 | | | | | | | | | | | | | |
| Cunninghamella bertholletiae | 10 | 22 | 22 | 22 | 22 | 23 | 23 | 24 | 23 | 24 | 25 | 24 | 23 | 26 | 21 | 21 | 22 | | | | | | | | | | | | | |
| Fusarium oxysporum | 20 | 5 | 5 | 5 | 5 | 9 | 9 | 10 | 9 | 12 | 11 | 10 | 9 | 12 | 4 | 4 | 9 | 10 | 0 | | | | | | | | | | | |
| Fusarium solani | 11 | 3 | 3 | 3 | 3 | 7 | 7 | 9 | 7 | 9 | 7 | 7 | 7 | 7 | 3 | 3 | 5 | 21 | 4 | 3 | | | | | | | | | | |
| Histoplasma capsulatum | 17 | 1 | 1 | 1 | 1 | 5 | 5 | 6 | 5 | 8 | 8 | 8 | 5 | 8 | 0 | 0 | 5 | 16 | 4 | 8 | | | | | | | | | | |
| Mucor racemosus | 16 | 15 | 15 | 15 | 15 | 15 | 15 | 16 | 15 | 16 | 17 | 18 | 15 | 18 | 14 | 14 | 16 | 24 | 17 | 4 | 14 | | | | | | | | | |
| Paecilomyces variotii | 20 | 5 | 5 | 5 | 5 | 6 | 6 | 6 | 6 | 8 | 7 | 8 | 6 | 8 | 4 | 4 | 6 | 21 | 8 | 4 | 0 | 18 | | | | | | | | |
| Paracoccidioides brasiliensis | 17 | 1 | 1 | 1 | 1 | 5 | 5 | 6 | 5 | 8 | 7 | 8 | 5 | 9 | 0 | 0 | 5 | 21 | 4 | 3 | 0 | 15 | 4 | | | | | | | |
| Penicillium chrysogenum | 17 | 1 | 1 | 1 | 1 | 6 | 6 | 7 | 6 | 9 | 8 | 9 | 6 | 9 | 2 | 2 | 6 | 21 | 4 | 3 | 2 | 15 | 6 | 2 | | | | | | |
| Pneumocystis carinii | 27 | 18 | 18 | 18 | 18 | 20 | 20 | 21 | 20 | 20 | 22 | 21 | 20 | 23 | 17 | 17 | 19 | 29 | 19 | 8 | 17 | 20 | 21 | 17 | 18 | | | | | |
| Rhizomucor miehei | 24 | 32 | 32 | 32 | 32 | 31 | 31 | 32 | 31 | 31 | 33 | 30 | 31 | 34 | 31 | 31 | 33 | 25 | 32 | 19 | 31 | 26 | 32 | 31 | 32 | 34 | | | | |
| Rhizopus oryzae | 16 | 13 | 13 | 13 | 13 | 13 | 13 | 14 | 13 | 14 | 15 | 16 | 13 | 16 | 12 | 12 | 14 | 18 | 15 | 8 | 12 | 2 | 16 | 12 | 13 | 20 | 28 | | | |
| Rhodotorula glutinis | 13 | 7 | 7 | 7 | 7 | 8 | 8 | 8 | 8 | 8 | 11 | 11 | 8 | 11 | 4 | 4 | 6 | 21 | 10 | 4 | 6 | 13 | 10 | 6 | 6 | 18 | 29 | 13 | | |
| Saccharomyces cerevisiae | 20 | 9 | 9 | 9 | 9 | 3 | 3 | 2 | 3 | 4 | 3 | 6 | 6 | 9 | 8 | 8 | 8 | 24 | 10 | 7 | 8 | 18 | 12 | 8 | 9 | 21 | 30 | 16 | 11 | |
| Scedosporium apiospermum | 56 | 45 | 44 | 44 | 44 | 46 | 46 | 45 | 46 | 47 | 45 | 45 | 46 | 49 | 43 | 43 | 44 | 60 | 43 | 41 | 43 | 55 | 47 | 43 | 45 | 58 | 69 | 53 | 47 | 45 |

| 28S(23F-25R) | A. fumigatus | A. niger | A. oryzae | A. terreus | C. albicans | C. dubliniensis | C. glabrata | C. guilliermondii | C. kefyr | C. krusei | C. lusitaniae | C. parapsilosis | C. tropicalis | C. immitis | C. posadasi | C. neoformans | F. oxysporum | F. solani | H. capsulatum | M. racemosus | P. variotti | P. brasiliensis | P. chrysogenum | P. carinii | R. oryzae | S. cerevisiae |
|---|---|---|---|---|---|---|---|---|---|---|---|---|---|---|---|---|---|---|---|---|---|---|---|---|---|---|
| Aspergillus niger | 11 | | | | | | | | | | | | | | | | | | | | | | | | | |
| Aspergillus oryzae | 10 | 8 | | | | | | | | | | | | | | | | | | | | | | | | |
| Aspergillus terreus | 8 | 12 | 10 | | | | | | | | | | | | | | | | | | | | | | | |
| Candida albicans | 65 | 64 | 64 | 61 | | | | | | | | | | | | | | | | | | | | | | |
| Candida dubliniensis | 65 | 64 | 64 | 60 | 1 | | | | | | | | | | | | | | | | | | | | | |
| Candida glabrata | 62 | 61 | 60 | 58 | 21 | 19 | | | | | | | | | | | | | | | | | | | | |
| Candida guilliermondii | 73 | 72 | 71 | 68 | 21 | 19 | 31 | | | | | | | | | | | | | | | | | | | |
| Candida kefyr | 70 | 67 | 68 | 64 | 27 | 24 | 20 | 32 | | | | | | | | | | | | | | | | | | |
| Candida krusei | 66 | 68 | 63 | 64 | 35 | 33 | 39 | 38 | 40 | | | | | | | | | | | | | | | | | |
| Candida lusitaniae | 65 | 69 | 67 | 66 | 37 | 38 | 48 | 45 | 56 | 49 | | | | | | | | | | | | | | | | |
| Candida parapsilosis | 71 | 68 | 70 | 66 | 7 | 6 | 24 | 22 | 28 | 40 | 42 | | | | | | | | | | | | | | | |
| Candida tropicalis | 66 | 65 | 65 | 62 | 7 | 6 | 25 | 22 | 30 | 38 | 40 | 12 | | | | | | | | | | | | | | |
| Coccidioides immitis | 24 | 27 | 25 | 21 | 61 | 52 | 64 | 67 | 68 | 68 | 63 | 68 | 63 | | | | | | | | | | | | | |
| Coccidioides posadasi | 25 | 28 | 26 | 22 | 60 | 61 | 63 | 66 | 67 | 67 | 62 | 67 | 62 | 1 | | | | | | | | | | | | |
| Cryptococcus neoformans | 88 | 88 | 89 | 84 | 71 | 71 | 72 | 68 | 74 | 73 | 79 | 73 | 70 | 80 | 79 | | | | | | | | | | | |
| Fusarium oxysporum | 70 | 73 | 73 | 71 | 69 | 68 | 73 | 73 | 76 | 77 | 77 | 71 | 71 | 76 | 75 | 91 | | | | | | | | | | |
| Fusarium solani | 69 | 72 | 72 | 70 | 68 | 67 | 72 | 74 | 76 | 72 | 74 | 70 | 70 | 75 | 74 | 91 | 4 | | | | | | | | | |
| Histoplasma capsulatum | 21 | 27 | 24 | 21 | 66 | 66 | 64 | 72 | 71 | 64 | 68 | 72 | 68 | 20 | 21 | 96 | 104 | 102 | | | | | | | | |
| Mucor racemosus | 108 | 109 | 108 | 108 | 94 | 94 | 100 | 94 | 95 | 92 | 94 | 93 | 94 | 106 | 105 | 84 | 68 | 67 | 106 | | | | | | | |
| Paecilomyces variotti | 8 | 14 | 14 | 11 | 61 | 61 | 58 | 69 | 66 | 66 | 62 | 67 | 62 | 21 | 22 | 82 | 70 | 69 | 18 | 109 | | | | | | |
| Paracoccidioides brasiliensis | 18 | 22 | 19 | 17 | 59 | 60 | 60 | 66 | 66 | 59 | 63 | 68 | 62 | 11 | 12 | 82 | 69 | 68 | 9 | 106 | 16 | | | | | |
| Penicillium chrysogenum | 13 | 15 | 15 | 12 | 62 | 62 | 61 | 70 | 67 | 69 | 65 | 68 | 63 | 21 | 22 | 82 | 69 | 69 | 22 | 108 | 5 | 19 | | | | |
| Pneumocystis carinii | 90 | 88 | 90 | 86 | 63 | 62 | 70 | 68 | 69 | 68 | 74 | 61 | 62 | 83 | 82 | 76 | 73 | 75 | 88 | 91 | 90 | 86 | 88 | | | |
| Rhizopus oryzae | 101 | 103 | 99 | 99 | 87 | 86 | 91 | 89 | 91 | 87 | 85 | 88 | 86 | 98 | 97 | 85 | 99 | 99 | 95 | 30 | 101 | 98 | 100 | 83 | | |
| Saccharomyces cerevisiae | 67 | 64 | 65 | 63 | 30 | 27 | 15 | 34 | 19 | 43 | 54 | 31 | 28 | 67 | 66 | 75 | 72 | 73 | 71 | 101 | 63 | 63 | 66 | 68 | 96 | |
| Scedosporium apiospermum | 57 | 60 | 61 | 61 | 68 | 69 | 67 | 75 | 73 | 67 | 73 | 67 | 71 | 69 | 68 | 89 | 33 | 35 | 66 | 99 | 61 | 62 | 62 | 70 | 95 | 70 |

Figure 8
*Absidia corymbifera* rRNA gene (SEQ ID NO: 55)

```
ATTAACTATCCCCAAAGGTGTTTATTCTTCTCGTGCTAAACCATGATGTACGAAAAAGTTAGTTGTTAACTTAAAAACA
ACTCTTGGCAATGGATCTCTTGGTTCTCGCATCGATGAAGAGCGTAGCAAAGTGCGATAATTATTGCGACTTGCATTCA
TAGCGAATCATCGAGTTCTCGAACGCATCTTGCGCCTAGTAGTCAATCTACTAGGCACAGTTGTTTCAGTATCTGCAAC
TACCAATCAGTTCAACTTGGTTCTTTGAACCTAAGCGAGCTGGAAATGGGCTTGTGTTGATGGCATTCAGTTGCTGTCA
TGGCCTTAAATACATTTAGTCCTAGGCAATTGGCTTTAGTCATTTGCCGGATGTAGACTCTAGAGTGCCTGAAGAGCA
ACGACTTGGTTAGTGAGTTCATAATTCCAAGTCAATCAGTCTCTTCTTGAACTAGGTCTTAATCTTTACGGACTAGTGA
GAGGATCTAACTTGGGTCTTCTCTCTTGAACAAACTCACATCTAGATCTGAAATCAACTGAGATCACCCGCTGAACTTAA
GCATATCAATAAGCGGAGGAAAAGAAAATAACCATGGATTCCCCTAGTAACGGCGAGTGAAGAGGGAAAAGCTCAAA
GTTGGAACCTGGCTGCCCTAGGCAGTCCGGATTGTAAACTAAAGAGCGTGATTCCAGGCAAGCCGGTTGACCAAGTCC
TTTGGAATGAGGCGCCACTGAGGGTGAGAGCCCCGTAAGTCGACTGAGCATTTGTCTTTTGTGTTTCGCGTTCAAAGA
GTCAGGTTGTTTGGGAATGCAGCCTAAAGCTGGTGGTAAATCCCACCTAAAGCTAAATACAGGCGAGAGACCGATAG
CGAACAAGTACCGTGAGGGAAAGATGAAAAGAACTTTGAAAAGAGAGTTAAACAGTATGTGAAATTGCCAAGAGGGA
AGCATTTGGAGTTAGATTGACTAGGAGTTAATCAGCTTGGTCTTTGGACTGGGTGTACTTGACTTCTTACAGTCTGCCA
ATAGCAGTTAGTCCTAGTGGAAAAAACCAGAGGGAAAGGTAGTCCTTCGGGATGTTTATAGACCTTTGGAAAATACACT
GGGATTGACTGAGGAATGCAGTAGATGCCACTAAGGCTTCGTCTAGTGGGTGCTAGGCAAAGGTACTTGGTATTTTCA
GCTTGCTGATGTGCTAGGTTACTCGAGTCTAGTCGCCTACTAGAACTGTAATCTACTTTGGTTATTGGCTTAATGACTC
TAAATGGCCCGTCTTGAAACACGGACCAAGGAGTCCACCACAGGTGCGAGTATTAGGGTGGCAAACCCATAATGCGC
AATGAAAGTGACACTTTAAGCTACCAAGGTTCCTTCGGGGGCCTGCAGTAGCCTCAGGCATGGACGTTTTATACTGAA
ATGACCTAGAGAAAGCACTTGTGATGGGACCCGAAAGATGGTGAACTATGCTTGAGTAGGATGAAGCCAGAGGAAAC
TCTGGTGGAGGTCCGAAGCGGTTCTGACGTGCAAATCGATCGTCAAACTTGAGCATAGGGGCGAAAGACTAATCGAA
CCATCTAGTAGCTGGTTCCTGCCGAAGTTTCCCTCAGGATAGCAGAAACTCAAAGGCAGTTTTACGTGGTAAAGCGAA
TGATTAGAGGCCTTGGGGACGAAATGTCCTTAACCTATTCTCAAACTTTAAATATGTAAGATGTCCTTCTTTCTTAGTT
GAAGTTGGACCATCGAATGTCGAGTTTCTAGTGGGCCATTTTTGGTAAGCAGAACTGGCGATGCGGGATGAACCGAAC
GCAAAGTTAAAGCGCCGGAATACTCGCTCATCAGACACCCACAAAGGTGTTAGTTCATCTAGACAGCAGGACGGTGG
CCATGGAAGTCGGAATCCGCTAAGGAGTGTGTAACAACTCACCTGCCGAATGAACTAGCCCTGAAAATGGATGGCGCT
TAAGCGAGTTGCTTATACTTTGCCCATAGGGTAAAAGCGATGCTCTATGGAGTAGGCAGGCGTGGAGGTCTAGTTGCG
AAGCTCTGACCGTAAGGTTGAGTGGAACGGCCTCTAGTGCAGATCTTGGTGGTAGTAGCAAATATTCAAGTGAGAACC
TTGAAGACTGAAGTGGAGAAGGGTTCCTCGAGAACATTAGTTGGTCGAGGGTTAGTCGATCCTAAGAGATAGGGAAGT
TCCGTTTTATCAAAGTGCTCAATTTACTTGGGCCGCGCTATCGACATCCAAAGGGAAACTGGTTAAAATTCCAGTACTGGGACAC
AGGTCTTTTGCGGCAACGCAAATGAACTTGGCGACGCTGGCATGGATCCCGAGAAGAGTTCTCTTTTCTTTTTAACAGT
TTATCTTTGACCATGAAATCAGTTTATCTGGAGAAATGGTTAAAGTGCTGGAAGAGTCCTACACTTTTAGTAGGATTCG
GTGCATCCATTACAGTCCTTGAAAAGCCAGGGGAAACTTATAGACTTTGTGCCTAGTCGTACCCATAACCGCAGCAGG
TCTCCTAGGTGTTAAGCCTCTAGTTGATGGAACAATGTAGATAAGGGAAGTCGGCAAAATAGATCCGTAACTTCGGGA
TAAGGATTGGCTCTAAGGGCTGGGTAGATTTGAGCCTAGGTCTTCGGTGAGTTGGGACTTGGTGCTGGGGCTTTCGGG
CTCTGGTGCTAGGATCTAGCTTGCCACTTGGCCTAGGAAGTTCGGTCTACAATTAACAGCCAACTTAGAACTGGTACG
GACAAGGGGAATCTGACTGTCTAATTAAAACATAGCATTGCGATGGTCAGAAAGTGATTTTGACGCAATGTGATTTCT
GCCCAGTGCTCTGAATGTCAAAGTGAAGAAATTCAACCAAGCGCGGGTAAACGGCGGGAGTAACTATGACTCTCTTAA
GGTAGCCAAATGCCTCGTCATCTAATTAGTGACGCGCATGAATGGATTAACGAGATTCCCACTGTCCCTATCTACTATC
TAGCGAAACCACAGCCAAGGGAACGGGCTTGGCAGAATCAGCGGGGAAAGAAGACCCTGTTGAGCTTGACTCTAGTT
TGCATTGTGAAAAGACATAGAGGGTGTAGCATATGAGGGAGACTTCGGTCGCCAGTGAAATACCTCAACCTCTATTGT
TTTTTTACTTAAATATTCAAGTGGGACTGGGTAGCAATACCTATGTTCTAGTATTAAGCCTACATTGTTAGGTGACCCA
CGATATTGACATTGTCAAGTGGGGAGTTTGGCTGGGGCGGCACATCTGTTAAACAATAACGCAGGTGTCCTAAGGGGG
ACTCAGTGAGAACAGAAATCTCACGTAGAGCAAAAGGGCAAAAGTCCCCTTGATTTTGATTTTCAGTGTGAATACAAA
CCATGAAAGTGTGGCCTATCGATCCTTTAGTTSCTYRGRATTTRAGSCTAGAGGTGCCAGAAAAGTTACCACAGGGATA
ACTGGCTTGTGGCAGCCAAGCGTTCATAGCGACGTTGCTTTTTGATTCTTCGATGTCGGCTCTTCCTATCATACTGAAG
CAGAATTCAGTAAGCGTTGGATTGTTCACCCACTAATAGGGAACGTGAGCTGGGTTTAGACCGTCGTGAGACAGGTTA
GTTTTACCCTACTGATGGAATTGGTGTCTCAACAGTAATTGAAGTTAGTACGAGAGGAACCCTTCATTCAGATAATTG
GTATTTGCGCCTGGTTGAAAGGCCAATGGCGCGAAGCTACCATCTGCTGGATAATGGCTGA
```

Figure 9
*Cunninghamella bertholletiae* rRNA gene (SEQ ID NO: 56)

```
CGATTGAATGGTCATAGTGAGCATGTGGGATCTTTGAAGGCTGGTTGGCAACAACCGGCTTTTGAGGAGAACTATGGC
AAACTAGATTATTTAGAGGAAGTAAAAGTCGTAACAAGGTTTCCGTAGGTGAACCTGCGGAAGGATCATTACATATTG
GGTCAAAAGAATAGTTTGAAAAAGGCTATTTTTTTTTGACTTAAAAAACTTATCCACAGTGTGGGAAATGTCTTCTAAC
GCTTGTGCCTGGTTCAGTCTAGTGCTGCCACTTGAGTTTATCCTTAGATCAAGGGATCTTTGGGTAGTTGTTCATTATTT
TCTCTCTCTTTTTAGGGGGGGGAGATTAATGATGGGCACCTCTTGTAAAGGGGATAAGATTACTTTTATTATACTAAA
TTTTACTGAACTGATAGACCATAAATCTATGGTTGTTTTTTATTATAATTAAAAAAAAAAAACAACTTTCAGCAATGGA
TCTCTCGGCTTTCGTATCGATGAAGAACGCAGCAAATCGCGATATGTAATGTGATCTGCCTATAGTGAATCATCAAAT
CTTTGAACGCATCTTGCACCTTATGGTATTCCATAAGGTACGTCTGTTTCAGTACCACTAATAAATCTCTCTCTATCCTT
GATGATAGAAAAAAAGAGATAAATTATTACTGGTCCTGGTGATTCTTTTTTTTTTTTATTAAAAAGAACCACTCTCG
GCCTAAATATAAGGCTCGACTTTTTTTTACCAGATCTTGCATCTAGTAAAAACCTAGTCGGCTTTAATAGATTTTTATT
TTCTATTAAGTTTATAGCCATTCTTATATTTTTTAAAATCTTGGCCTGAAATCAGATGGGACTACCCGCTGAACTTAAG
CATATCAATAAGCGGAGGAAAAGAAAATAACAATGATTCCCCTAGTARCGGCGAGTGAAGAGGGAAAAGCTCAAAGT
TGGAACCTGGTAGGCATAGCTTACCCGGATTGTAAACTAAAGTTTTCGAGTCGTTTAGTCAGCCAGGTAAATAAGTCC
TCTGGAAAGGGGCGACATAGAGGGTGAAATCCCCGTCTTTGGCCTGAGTTTTGATTAGGCGTTTGGCTTGGAAACGAA
GAGTCAGGTTGTTTGGGAATGCAGCCTAAAATGGGAGGTAAATCTCTCCTAAAGCTAAATATTGACGAAAGACCGATA
GCGAACAAGTACCGTGAGGGAAAGATGAAAAGCACTTTGAAAAGAGGGTCAAAAAGTACGTGAAATTGCTGAAAGGG
AACCGTATGAAATCAGATCTACTGGTAGGTAATCAATCTTTCCTTTGGGAAGGATGCACTTGCCTACTATGTATGCCAG
CGACATTTTGGTTGGGAGGAAAAAAATAAAGGAAATGTAGCTTAGGTTTCGGCTTAGGTGTTATAGTCCTTTATAAAA
TACTCTCGGCTGGAATGAGGAACGCAGCAAACCGTAAGGCGAAGATTTCAGGCGCTTAGAGGGAATAATTAGAGAAT
TTCTGCTTCGGGTGGTGCTTTGATTATTACCTTTAACACGCTTGGAGTTCTTTTAATTTGCTTAGGTTGTTGGCTTAATG
ATTTTATATGACCCGTCTTGAAACACGGACCAAGGAGTCCACCATAGGCGCGAGTCTTTGGGTGTAAAAACCCATGGG
CGGAAGGAAATTGACTAAGATACCAAGGCGCAAGCTGGCAGTATCCCCCGGCGTAGACGTTTTTATACTGAAATGACT
GAGGGCAAGCGCTTATGATGGGACCCGAAAGATGGTGAACTATACTTGAATAGGGTAAAGCCAGAGGAAACTCTGGT
GGAAGCTCGCAGCGATTCTGACGTGCAAATCGATCGTCAAATTTGAGTATAGGGGCGAAAGACTAATCGAACCATCTA
GTAGCTGGTTCCTGCCGAAGTTTCCCTCAGGATAGCAGAAGCTCGTAGGCAGTTTTATGAGGTAAAGCGAATGATTAG
AGGCCTAGGGGGCTTATTGCCCTTTACCTATTCTCAAACTTTAAATATGTAAGACGTTTGGCTTGCTTAATTGAAGTCA
AACATATGAATGCAGAGCTTTTAGTGGGCCATTTTTGGTAAGCAGAACTGGCGATGCGGGATGAACCGAACGTAAAGT
TAAGGTGCCCAAATTCACGCTCATCAGACACCAGAAAAGGTGTTAGTTCATCTAGACAGCAGGACGGTGGCCATGGA
AGTCGGAATCCGCTAAGGAGTGTGTAACAACTCACCTGCCGAATGAACTAGCCCTGAAAATGGATGGCGCTTAAGCGT
GATACCTATACTTTACCGTCAAAGTAAAAGCGAAGCTTTGACGAGTAGGCAGGCGTGGAGGTTTTGTATAGAAGCCTT
GGGCGTGAGCTCGGGTGAAACGGCCTCTAGTGCAGATCTTGGTGGTAGTAGCAAATATTCTAATGAGAATTTTGAAGA
CTGAAGTGGAGAAAGGTTCCTAGAGAACAGTAGTTGGTCTAGGGTTAGTCGCTCCTAAGGCACAGGGAAGTTCTGTCA
AATGCAGATCCATTTTATGGGTCCAGGTGCCGAAAGGGAAACTGGTTAATATTCCAGTACTAGGATAGGGGGTTCTAA
TATGGTAACATAACGGATCTTGGGGACATTGGTATGAAGCCCAGAAAGAGTTAACTTTTCTTTCTTACGGTCTCTTAAG
TTGATATTCCTTGGAAACGGTTTAGCCGGAGCAAAGGTGTATCGGCCGGTAAAGCATGATTTTTTATGATCATGTCTGG
AGCCTTCATAACGATCCTTGAAAACCCAAGGGACATATATGGCCTTCCTACCTAGGCGTACTCATAACCGCAGCAGGT
CTCCAAGGTTAACAGCCTCTAGTTGATAGAATAATGTAGGTAAGGGAAGTCGGCAAATTAGATCCGTAACTTCGGGAT
AAGGATTGGCTCTAAGGGTTAGGTAGGAAACGTATTAGATGGATGAAGAGGTGAGTCTGGAGAAGGCTGGTTGGGGC
AACCTGACTGGCTTTTTTTGGGCAATCCTCTTGTACCGTCTAATGGCGGCCTACAATAATAACCACTTAGAACTGGTAC
GGACAAAGGGAATCTGACTGTCTAATTAAAACATAGCATTGTGATAGTCAGAAAGTGATTTTGACACAATGTGATTTC
TGCCCAGTGCTCTGAATGTCAAAGTGAAGAAATTCAACCAAGCGCGGGTAAACGGCGGGAGTAACTATGACTCTCTTA
AGGTAGCCAAATGCCTCGTCATCTAATTAGTGACGCGCATGAATGGATTAACGAGATTCCCACTGTCCCTATCTACTA
TCTAGCGAAACCACAGCCAAGGGAACGGGCTTGGCAGAATCAGCGGGGAAAGAAGACCCTGTTGAGCTTGACTCTAG
TTTGACATTGTGAAAAGACATAGAGGGTGTAGAATAAGTGGGAGCTCCGGCGCCAGTGAAATACCACTACCTCTATTG
TTTTTTTACTTAGATAATTATAAGGGATTAGGTGGCAACACCTACTTTCTAGACAGAATCCACTTCGTGTGGAGACCCT
CGTTATTGACATTGTCAAGTGGGGAGTTTGGCTGGGGCGGCACATCTGTTAAACAATAACGCAGGTGTCCTAAGGGGG
GCTCAGCGAGACGAGAAATTTCGCGTAGAGTAAAAGGGCAAAAGTCCCCTTGATTTTGATTTTCAGTGTGAATACAAA
CCATGAAAGTGTGGCCTATCGATCCTTTAGTTGCTAAAGATTTTAGCCTAGAGGTGCCAGAAAAGTTACCACAGGGAT
AACTGGCTTGTGGCAGCCAAGCGTTCATAGCGACGTTGCTTTTTGATTCTTCGATGTCGGCTCTTCCTATCATACTGAA
GCAGAATTCAGTAAGCGTTGGATTGTTCACCCACTAATAGGGAACGTGAGCTGGGTTTAGACCGTCGTGAGACAGGTT
AGTTTTACCCTACTGATGTTAATGGGTATCGTAACAGTAATTGAAGTTAGTACGAGAGGAACCCTTCATTCAGATAATT
GGTATTTGCGGCTGGTTGTCCAGCCAATGCCGCGAAGCTACCGT
```

Figure 10
*Fusarium solani* rRNA gene (SEQ ID NO: 57)

TAAGAGGAAGTAAAAGTCGTAACAAGGTTTCGTTGGTGAACCAGCGGAGGGATCATTACCGAGTTATACAACTCATCA
ACCCTGTGAACATACCTATAACGTTGCCTCGGCGGGAACAGACGGCCCCGTAACACGGGCCGCCCCCGCCAGAGGACC
CCCTAACTCTGTTTCTATAATGTTTCTTCTGAGTAAACAAGCAAATAAATTAAAACTTTCAACAACGGATCTCTTGGCTC
TGGCATCGATGAAGAACGCAGCGAAATGCGATAAGTAATGTGAATTGCAGAATTCAGTGAATCATCGAATCTTTGAAC
GCACATTGCGCCCGCCAGTATTCTGGCGGGCATGCCTGTTCGAGCGTCATTACAACCCTCAGGCCCCGGGCCTGGCGT
TGGGGATCGGCGGAAGCCCCCTGCGGGCACAACGCCGTCCCCCAAATACAGTGGCGGTCCCGCCGCAGCTTCCATTGC
GTAGTAGCTAACACCTCGCAACTGGAGAGCGGCGCGGCCACGCCGTAAAACACCCAACTTCTGAATGTTGACCTCGAA
TCAGGTAGGAATACCCGCTGAACTTAAGCATATCAATAAGCGGAGGAAAAGAAACCAACAGGGATTGCCCCAGTAAC
GGCGAGTGAAGCGGCAACAGCTCAAATTTGAAATCTGGCTCTCGGGCCCGAGTTGTAATTTGTAGAGGATGCTTTTGGT
GAGGTGCCTTCCGAGTTCCCTGGAACGGGACGCCATAGAGGGTGAGAGCCCCGTCTGGTTGGACACCGATCCTCTGTA
AAGCTTCTTCGACGAGTCGAGTAGTTTGGGAATGCTGCTCTAAATGGGAGGTATATGTCTTCTAAAGCTAAATACCGGC
CAGAGACCGATAGCGCACAAGTAGAGTGATCGAAAGATGAAAAGAACTTTGAAAAGAGAGTTAAAAAGTACGTGAAA
TTGTTGAAAGGGAAGCGCTTGTGACCAGACTTGGGCTTGGTTGATCATCCGGGGTTCTCCCCGGTGCACTCTTCCGGCT
CAGGCCAGCATCAGTTCGCCCTGGGGGATAAAGGCTTCGGGAATGTGGCTCTCTCCGGGGAGTGTTATAGCCCGCTGCG
TAATACCCTGTGGCGGACTGAGGTTCGCGCATTCGCAAGGATGCTGGCGTAATGGTCATCAGTGACCCGTCTTGAAACA
CGGACCAAGGAGTCGTCTTCGTATGCGAGTGTTCGGGTGTCAAACCCCTACGCGAAATGAAAGTGAACGCAGGTGAGA
GCTTCGGCGCATCATCGACCGATCCTGATGTTATCGGATGGATTTGAGTAAGAGCATACGGGGCCGGACCCGAAAGAA
GGTGAACTATGCCTGTGTAGGGTGAAGCCAGAGGAAACTCTGGTGGAGGCTCGCAGCGGTTCTGACGTGCAAATCGAT
CGTCAAACATGGGCATGGGGGCGAAAGACTAATCGAACCTTCTAGTAGCTGGTTTCCGCCGAAGTTTCCCTCAGGATAG
CAGTGTTGAACTCAGTTTTATGAGGTAAAGCGAATGATTAGGGACTCGGGGGCGCTATTTAGCCTTCATCCATTCTCAA
ACTTTAAATATGTAAGAAGCCCTTGTTGCTTAATTGAACGTGGGCATTCGAATGAATCAACACTAGTGGGCCATTTTTG
GTAAGCAGAACTGGCGATGCGGGATGAACCGAACGCGAGGTTAAGGTGCCAGAGTAGACGCTCATCAGACACCACAA
AAGGTGTTAGTACATCTTGACAGCAGGACGGTGGCCATGGAAGTCGGAATCCGCTAAGGACTGTGTAACAACTCACCT
GCCGAATGTACTAGCCCTGAAAATGGATGGCGCTCAAGCGTCCACCCATACCTCGCCCTCAGGGTAGAAACGATGCC
CTGAGGAGTAGGCGGACGTGGAGGTCAGTGACGAAGCCTAGGGCGTGAGCCCGGGTTGAACGGCCTCTAGTGCAGATC
TTGGTGGTAGTAGCAAATACTTCAATGAGAACTTGAAGGACCGAAGTGGGGAAAGGTTCCATGTGAACAGCGGTTGGA
CATGGGTTAGTCGATCCTAAGCCATAGGGAAGTTCCGTTTCAAAGGCGCACTATGCGCCGTCNTGGCGAAAGGGGAGC
CGGTCAATATTCCGGCACCTGGATGTGGGTTTTGCGCGGCAACGCAACGTGAACGCCGGAGACGCGCGGGGGCCCGG
GCAGAGTTCTCTTTTCTTCTTAACAGTCTCTCACCCTGAAATCGGTTTGTCCGGAGCTAGGGTTTAATGGCTGGAAGAGC
CCAGCACCTCTGCTGGGTCCGGTGCGCTCTCGACGTCCCTTGAAAATCCGCGGGAAGAAATAATTCTCACGCCAGGTCG
TACTCATAACCGCAGCAGGTCTCCAAGGTGAACAGCCTCTGGTTGATAGAACAATGTAGATAAGGGAAGTCGGCAAAA
TAGATCCGTAACTTCGGGGATAAGGATTGGCTCTAAGGGTTGGGCACGCAGGGGCCTTGGGCGGCAGCCATGGGGGCAGG
CTGCTTCTAGCCGGGCAACCGGCCGGCGGCGGCCAGCACCCGTGCGCTGATGCCCTTGGCAGGCTTCGGCCGTCCGGC
GTGCGGTTAACAACCAACTTAGAACTGGTACGGACAAGGGGAATCTGACTGTCTAATTAAAACATAGCATTGCGATGG
CCAGAAAGTGGTGTTGACGCAATGTGATTTCTGCCCAGTGCTCTGAATGTCAAAGTGAAGTAATTCAACCAAGCGCGG
GTAAACGGCGGGAGTAACTATGACTCTCTTAAGGTAGCCAAATGCCTCGTCATCTAATTAGTGACGCGCATGAATGGAT
TAACGAGATTCCCACTGTCCCTATCTACTATCTAGCGAAACCACAGCCAAGGGAACGGGCTTGGCAGAATCAGCGGGG
AAAGAAGACCCTGTTGAGCTTGACTCTAGTTTGACATTGTGAAAAGACATAGGAGGTGTAGAATAGGTGGGAGCTTCG
GCGCGGTGAAATACCACTACTCCTATTGTTTTTTTACTTATTCAATGAAGCGGGGCTGGATTTTCGTCCAACTTCTGGTT
TTAAGGTCCTTCGCGGGCCGACCCGGGTTGAAGACATTGTCAGGTGGGGAGTTTGGCTGGGGCGGCACATCTGTTAAAC
CATAACGCAGGTGTCCTAAGGGGGTCTCATGGAGAACAGAAATCTCCAGTAGAGCAAAAGGGCAAAAGTCCCCTTGAT
TTTGATTTTCAGTGTGAATACAAACCATGAAAGTGTGGCCTATCGATCCTTTAGTCCCTCGACATTTGAGGCTAGAGGT
GCCAGAAAGTTACCACAGGGATAACTGGCTTGTGGCGGCCAAGCGTTCATAGCGACGTCGCTTTTTGATCCTTCGATG
TCGGCTCTTCCTATCATACCGAAGCAGAATTCGGTAAGCGTTGGATTGTTCACCCACTAATAGGGAACGTGAGCTGGGT
TTAGACCGTCGTGAGACAGGTTAGTTTTACCCTACTGATGACCTCGCCGCAATGGTAATTCAGCTTAGTACGAGAGGAA
CCGCTGATTCAGATAATTGGTTTTTGCGGCTGTCCGACCGGGCAGTGCCGCGAAGCTACCATCTGCTGGATAATGGCTG
AACGCCTCTAAGTCAGAATCCATGCCAGAACGCGGTGATACCGCCCGCACGTACAGATGGACAAGAATAGGCTTCGGC
TTAGCGTCTTAGCAGGCGATTCTTCCGCGGCGCACGAAGCGCGTCGTGGTATTTCGCGTATTGTAATTTCAACACGAGC
GGGGTCAAATCCTTTGCAGACGACTTAGCTGTGCGAAACGGTCCTGTAAGCAGTAGAGTAGCCTG

Figure 11
*Mucor racemosus* rRNA gene (SEQ ID NO: 58)

TAGGTGAACCTGCGGAAGGATCATTAAATAATCAATAATCTTGGCTTGTCCATTATTATCTATTTACTGTGAACTGTATT
ATTATTTGACATTTGAGGGATGTTCCAATGTTATAAGGATAGACATTGGAAATGTTAACCGAGTCATAATCAGGTTTAG
GCCTGGTATCCTATTATTATTTACCAAATGAATTCAGAATTAATATTGTAACATAGACCTAAAAAATCTATAAAACAAC
TTTTAACAACGGATCTCTTGGTTCTCGCATCGATGAAGAACGTAGCAAAGTGCGATAACTAGTGTGAATTGCATATTCA
GTGAATCATCGAGTCTTTGAACGCAACTTGCGCTCATTGGTATTCCAATGAGCACGCCTGTTTCAGTATCAAAACAAAC
CCTCTATCCAACTTTTGTTGTATAGGATTATTGGGGGCCTCTCGATCTGTATAGATCTTGAAATCCCTGAAATTTACTAA
GGCCTGAACTTGTTTAAATGCCTGAACTTTTTTTTAATATAAAGGAAAGCTCTTGTAATTGACTTTGATGGGGCCTCCCA
AATAAATCTTTTTTAAATTTGATCTGAAATCAGGCGGGATTACCCGCTGAACTTAAGCATATCAATAAGCGGAGGAAAA
GAAAATAACAATGATTTCCCTAGTAACGGCGAGTGAAGAGGAAAGAGCTCAAAGTTGGAACCTGTTTGGCTTAGCTAA
ACCGGATTGTAAACTGTAGAAACATTTTCCAGATACACTAGACAAAAAAGTCCTTTGGAACAGGGCATCATAGAGGGT
GAGAATCCCGTCTTTGGTCTAAGTAGTTGTCTATTGTGATATGTTTTCAAAGAGTCAGGTTGTTTGGGAATGCAGCCTAA
ATTGGGTGGTAAATCTCACCTAAAGCTAAATATTTGCGAGAGACCGATAGCGAACAAGTACCGTGAGGGAAAGATGAA
AAGAACTTTGAAAAGAGAGTTAAACAGTATGTGAAATTGTTAAAAGGGAACCGTTTGGAGCCAGATTGGCTTGATTGT
AATCAACCTAGAATTCGTTTTGGGTGCACTTGCAGTCTATGCCTGCCAACGACAGTTTGATTTGGAGGAAAAAATTAAT
AGGAATGTGGCCTTTCGAGGTGTTATAGCCTATTATCATACTCTGGATTGGACTGAGGAACGCAGCGAATGCCTTTAGG
CAAGATTGCTGGGCGCTTTCCCTAATAAATGTTAGAATTTCTGCTTCGGGTGGTGCTAATGTTTAAAGGAGGAACCCGC
TTAGTATATTTTTTATTCGCTTAGGTTTGTTGGCTTAATGACTCTAAATGACCCGTCTTGAAACACGGACCAAGGAGTCC
ACCATAAGTGCAAGTATTTGGGTGCCAAACCCATATGCGTAAGGAAACTGATTGATACGAAATCGCGAGATGGCAGTA
TCACCCGGCGCTGACGTTTTATACTGAATTGACCGAGGTAAAGCACTTATGATGGGACCCGAAAGATGGTGAACTATGC
CTGAATAGGGTGAAGCCAGAGGAAACTCTGGTGGAGGCTCGTAGCGATTCTGACGTGCAAATCGATCGTCAAATTTGG
GTATAGGGGCGAAAGACTAATCGAACCATCTAGTAGCTGGTTCCTGCCGAAGTTTCCCTCAGGATAGCAAAAACTTAA
AAGCAGTTTTATGAGGTAAAGCGAATGATTAGAGGCCTTGGGGACGAAATGTCCTTAACCTATTCTCAACTTTAAATAT
GTAAGACGACCTGTTTGCTTAATTGAAGCAGGTCATTGAATGTGAGTTTTTAGTGGGCCATTTTTGGTAAGCAGAACTG
GCGATGCGGGATGAACCGAACGGAAAGTTAAGGTGCCGGAATACACGCTCATCAGACACCACAAAAGGTGTTAGTTCA
TCTAGACAGCAGGACGGTGGCCATGGAAGTCGGAATCCGCTAAGGAGTGTGTAACAACTCACCTGCCGAATGAACTAG
CCCTGAAAATGGATGGCGCTTAAGCGTGTTACCCATACTTTCCCGTTATTGTAAAAGCGAAGCAATAACGAGTAGGCAG
GCGTGGAGGTTTTTATAAACTGTTAAGAAGCTCTTGGTGTGAACCGGAGTGAAACAGCCTCTAGTGCAGATCTTGGTGG
TAGTAGCCAAATATTCAAATGAGAACTTTGAAGACTGAAGTGGAGAAGGTTCCTGGAGAACATTATTTGGTCCCGGGG
TAGTCGATCCTAGAGGTAGGGAAGTTCCGTTATTTCAAAGTGATCAATTTTGATCCGCCTATCGAAAGGGAAACAGTTT
AATATTACTGTACTAGGACGAGGATTTTCTGCGGCAACGCAAATGAACTTGGAGACATCAGTGTGGGTCCCGGGAAGA
GTTATCTTTTCTTTTTAACAACTTTGTTGTAGACCTTGAAATCTGTTTAGCAGGAGAAAAGGTTTACCGGTTGGTAGAGC
ATAGTACTTTTTGCTATGTCCGGTGCATTCACAACGATCCTTGAAAATCCAAGGGAAAGAATAATTTTCTCGCCTAGTC
GTACTCATAACCGCAGCAGGTCTCCAAGGTGAAAAGCCTCTAGTTGATAGAACAATGTAGATAAGGGAAGTCGGCAAA
ATAGATCCGTAACTTCGGGATAAGGATTGGCTCTAAGGGTTGGGTAGATATGGACTTTTGGTATGGTTGATTTCTAGGC
GATTTCAAATGATTTCGGTTGTTTGATTTTGCTCGGAGATCTTCGTTAACCAAGAGAGCCCAGTTTACGTTTAACAACCA
ACTTAGAACTGGTACGGACAAGGGGAATCTGACTGTCTAATTAAAACATAGCATTGCGATGGCCAGAAAGTGGTGTTG
ACGCAATGTGATTTCTGCCCAGTGCTCTGAATGTCAAAGTGAAGAAATTCAACCAAGCGCGGGTAAACGGCGGGAGTA
ACTATGACTCTCTTAAGGTAGCCAAATGCCTCGTCATCTAATTAGTGACGACGCATGAATGGATTAACGAGATTCCCACT
GTCCCTATCTACTATCTAGCGAAACCACAGCCAAGGGAACGGGCTTGGCAGAATCAGCGGGGAAAGAAGACCCTGTTG
AGCTTGACTCTAGTTTGACATTGTGAAAAGACATAGAGGGTGTAGCATAAGTGGGAGCTTCGGCGCCAGTGAAATACC
ACTACCTTTATCGTTTTTTACTTAAATAATTAAGTGGGATTGAGTCGCAAGACTCACCTTCTAGTATTAAGCATCTTCG
GATGTGACCCACGTTATTGACATTGTCAAGTGGGGAGTTTGGCTGGGCGGCACATCTGTTAAAAGATAACGCAGGTGT
CCTAAGGGGGACTCAACGAGAACAGAAATCTCGTGTAGAATAAAAGGGTAAAAGTCCCCTTGATTTTGATTTTCAGTGT
GAATACAAACCATGAAAGTGTGGCCTATCGATCCTTTAGAATCTCAAGATTTGAGGCTAGAGGTGCCAGAAAAGTTAC
CACAGGGATAACTGGCTTGTGGCAGCCAAGCGTTCATAGCGACGTTGCTTTTTGATTCTTCGATGTCGGCTCTTCCTATC
ATACTGAAGCAGAATTCAGTAAGCGTTGGATTGTTCACCCACTAATAGGGAACGTGAGCTGGGTTTAGACCGTCGTGA
GACAGGTTAGTTTTACCCTACTGATGGTATTGGTATCGTAACAGTAATTGAAGTTAGTACGAGAGGAACCCTTCATTCA
GATAATTGGTATTTGCGGCTGGTTGAAAGGCCAATGCCGCGAAGCTACCATCTGCTGGATAATGGCTGAACGCCTCTAA
GTCAGAATCCATGCTGAAAACGATACTACTGTGTTTTGATTGTACCAGATGAGTACTAATAAAGCTTCGGCTTGAAAAC
CTTTACTTGTGAGCTAGGCTTGGTAACGGAAATGTTGCTAGGTCTACTTGCTAATGATAATGCTAATACATCAAAATGA
TAAATCGCATGCAGACGACATGAAATGGACGGGGTATTGTAAGTACTAGAGTAGCCTG

Figure 12
Paecilomyces variotii rRNA gene (SEQ ID NO: 59)

```
CGATTGAATGGCTCAGTGAGGCCTTCGGACTGGCTCAGGGGGGTTGGCAACGACCGCCCAGAGCCGGAAAGTTGGTCA
AACTTGGTCATTTAGAGGAAGTAAAAGTCGTAACAAGGTTTCCGTAGGTGAACCTGCGGAAGGATCATTACCGAGTGA
GGGTCCCTCGGGGCCCAACCTCCCATCCGTGTTGTCCTGACACCTGTTGCTTCGGCGGGCCCGCCGTGGTTCACGCCCC
GGCCGCCGGGGGGTTCACGCCCCCGGGCCCGCGCCCGCCGAAGACCCCTGGAACGCTGCCTGGAAGGTTGCCGTCTGA
GTATACAATCAATCAATTAAAACTTTCAACAACGGATCTCTTGGTTCCGGCATCGATGAAGAACGCAGCGAAATGCGAT
AAGTAATGTGAATTGCAGAATTCCGTGAATCATCGAATCTTTGAACGCACATTGCGCCCCTGGCATTCCGGGGGGCAT
GCCTGTCCGAGCGTCATTGCTAACCCTCCAGCCCGGCTGGTGTGTTGGGCCGCCGTCCCCCCTCCCCGGGGACGGGCC
CGAAAGGCAGCGGCGGCGTCGCGTCCGGTCCTCGAGCGTATGGGGCTCTGTCACACGCTTCAGTAGAACCGGCCGGCT
TGCTGGCCATCACCTATATTTTTCTCTTAGGTTGACCTCGGATCAGGTAGGGATACCCGCTGAACTTAAGCATATCAATA
AGCGGAGGAAAAGAAACCAACAGGGATTGCCCCAGTAACGGCGAGTGAAGCGGCAAGACTCAAATTTGAAATCTGG
CCCCTCCGGGGTCCGAGTTGTAATTTGCAGAGGATGCTTCGGGCGCGGTCCCCGTCTAAGTACCCTGGAACGGGTCGTC
ATAGAGGGTGAGAATCCCGTCTGGGACGGGTGGCCGTGTCCGTGTGAAGCTCCTTCGACGAGTCGAGTTGTTTGGGAAT
GCAGCTCTAAATGGGTGGTAAATTTCATCTAAAGCTAAATATTGGCCGGAGACCGATAGCGCACAAGTAGAGTGATCG
AAAGATGAAAAGCACTTTGAAAAGAGAGTTAAACAGCACGTGAAATTGTTGAAAGGGAAGCGCTTGCGACCAGACTC
GCCCGCGGGGGTTCAGCCGGTACTCGTACCGGTGTACTCCCCCGGGGGCGGGCCAGCGTCGGTTTGGGCGGTCGGTCA
AAGGCCTCCGGAATGTGTCGCCCCCCGGGGCGTCTTATAGCCGGAGGTGCAATGCGGCCAGCCTGGACCGAGGAACGC
GCTTCGGCTCGGACGCTGGCGTAATGGTCGTAAGCGGCCCGTCTTGAAACACGGACCAAGGAGTCTAACATCTACGCG
AGTGTTCGGGTGTCAAACCCGTCCGCGCAGTGAAAGCGAACGGAGGTGGGAACCCCCCCGGGGTGCACCATCGACCG
ATCCTGATGTCTTCGGATGGATTTGAGTAAGAGCGTAGCTGTTGGGACCCGAAAAGATGGTGAACTATGCCTGAATAGG
GCGAAGCCAGAGGAAACTCTGGTGGAGGCTCGCAGCGGTTCTGACGTGCAAATCGATCGTCGAATTTGGGTATAGGGG
CGAAAGACTAATCGAACCATCTGGTAGCTGGTTCCTGCCGAAGTTTCCCTCAGGATAGCAGTAACGTTTTCAGTTTTAT
GAGGTAAAGCGAATGATTAGAGGCCTTGGGGTTGAAACAACCTTAACCTATTCTCAAACTTTAAATATGTAAGAAGCC
CTTGTTGCTTAGTTGAACGTGGGCATTTGAATGTATCGTTACTAGTGGGCCATTTTTGGTAAGCAGAACTGGCGATGCG
GGATGAACCGAACGCGAGGTTAAGGTGCCGGAATGCACGCTCATCAGACACCACAAAAGGTGTTAGTTCATCTAGACA
GCCCGACGGTGGCCATGGAAGTCGGAATCCGCTAAGGAGTGTGTAACAACTCACGGGCCGAATGAACTAGCCCTGAAA
ATGGATGGCGCTCAAGCGTGCTACCCATACCTCGCCGTCGGGGTAGAAACGATGCCCCGACGAGTAGGCAGGCGTGGA
GGTCCGTGACGAAGCCTTGGGAGTGATCCCGGGTCGAACGGCCTCTAGTGCAGATCTTGGTGGTAGTAGCAAATACTC
AAATGAGAACTTTGAGGACTGAAGTGGGGAAAGGTTCCATGTGAACAGCAGTTGGACATGGGTTAGTCGATCCTAAGA
CATAGGGAAATTCCGTTTGAAAGCGCGCCCTCGTGCGCCGTTCGTCGAAAGGGAAGCCGGTTAATATTCCGGCACCTGG
ATGTGGATTCTCCACGGCAACGTAACTGAACGCGGAGACGTCGGCGGGGGTCCTGGGAAGAGTTCTCTTTTCTTCTTGA
CGGCCTATCACCCTGAAATCGGTTTGTCCGGAGCTAGGGTTCCATGGCCGGCAGAGCCCCGCACCTTTGCGGGGTCCGG
TGCACTCCCGACGACCCTTGAAAATCCGCGGGAAGGAATAGTTTTCACGCCAGGTCGTACTCATAACCGCAGCAGGTCT
CCAAGGTGAAAAGCCTCTAGTTGATAGAACAATGTAGATAAGGGAAGTCGGCAAAATAGATCCGTAACTTCGGGATAA
GGATTGGCTCTAAGGATCGGGTACGTTGGGCCTTGGGGGGAAGCCCCCGGAGCAGGAGGGCACTAGCCGGGCAACCG
GCCGGCGCCCTCCAGCATCGGCGGTGGACGCCCTTGGCAGGCCTCGGCCGTCCGGCGTACGCTTAACGATCAACTTA
GAACTGGTACGGACAAGGGGAATCTGACTGTCTAATTAAAACATAGCATTGCGATGGCCAGAAAGTGGTGTTGACGCA
ATGTGATTTCTGCCCAGTGCTCTGAATGTCAAAGTGAAGAAATTCAACCAAGCGCGGGTAAACGCGGGAGTAACTAT
GACTCTCTTAAGGTAGCCAAATGCCTCGTCATCTAATTAGTGACGCGCATGAATGGATTAACGAGATTCCCACTGTCCC
TATCTACTATCTAGCGAAACCACAGCCAAGGGAACGGGCTTGGCAGAATCAGCGGGGAAAGAAGACCCTGTTGAGCTT
GACTCTAGTTTGACATTGTGAAAAGACATATGGGGTGTAGAATAGGTGGGAGCTCCGGCGCCAGTGAAATACCACTAC
CTTTATCGTTTTTTTACTTATTCAATGAAGCGGAACTGGGCTTCACCGCCCAACTTCTGGCGTTAAGGTCCTTCGCGGGC
CGATCCGGGTTGAAGACATTGTCAGGTGGGGAGTTTGGCTGGGCGGCACATCTGTTAAACCATAACGCAGGTGTCCT
AAGGGGGACTCATGGAGAACAGAAATCTCCAGTAGAACAAAAGGGTAAAAGTCCCCTTGATTTTGATTTTCAGTGTGA
ATACAAACCATGAAAGTGTGGCCTATCGATCCTTTAGTCCCTCGAAATTTGAGGCTAGAGGTGCCAGAAAAGTTACCAC
AGGGATAACTGGCTTGTGGCAGCCAAGCGTTCATAGCGACGTTGCTTTTTGATCCTTCGATGTCGGCTCTTCCTATCATA
CCGAAGCAGAATTCGGTAAGCGTTGGATTGTTCACCCACTAATAGGGAACGTGAGCTGGGTTTAGACCGTCGTGAGAC
AGGTTAGTTTTACCCTACTGATGAAGGTCGCCGCAACGGTAATTCAATTTAGTACGAGAGGAACCGTTGATTCAGATAA
TTGGTTTTTGCGGCTGTCTGACCAGGCAGTGCCGCGACGCTACCATCTGCCGGATTATGGCTGAACGCCTCTAAGTCAG
AATCCGTGCCGGAACGCGGCGATTTCGCCCCGCACGTCGTAGTTGGATACGAATAGGCCTTCGGGCCATGCACCTCAGC
AGGCTGGCGACGGCCCCCGGGGAGAAACCCCCGGGGGCTGGCTGGCGGATTGCAATGTCACCTCGCGCGGGGATAGAT
CCTCTGCAGACGACTGAAGTGACCAAGCGGGTCGTGTAAGCGGTCAAGTACT
```

Figure 13

*Penicillium chrysogenum* rRNA gene (SEQ ID NO: 60)

```
GACCCCCCAGAGCCGARAACTTGGTCAAACTCGGTCATTTAGAGGAAGTAAAAGTCGTAACAAGGTTTCCGTAGGTGA
ACCTGCGGAAGGATCATTACCGAGTGAGGGCCCTCTGGGTCCAACCTCCCACCCGTGTTTATTTTACCTTGTTGCTTCGG
CGGGCCCGCCTTAACTGGCCGCCGGGGGGCTTACGCCCCCGGGCCCGCGCCCGCCGAAGACACCCTCGAACTCTGTCT
GAAGATTGTAGTCTGAGTGAAAATATAAATTATTTAAAACTTTCAACAACGGATCTCTTGGTTCCGGCATCGATGAAGA
ACGCAGCGAAATGCGATACGTAATGTGAATTGCAAATTCAGTGAATCATCGAGTCTTTGAACGCACATTGCGCCCCTG
GTATTCCGGGGGGCATGCCTGTCCGAGCGTCATTGCTGCCCTCAAGCACGGCTTGTGTGTTGGGCCCCGTCCTCCGATC
AATACGACTTGGGTTTGCTTGAAAGACGGTAGTGGTAAGGCGGGATCGCTTTGACAATGGCTTAGGTCTAACCAAAAA
CATTGCTTGCGGCGGTAACGTCCACCACGTATATCTTCAAACTTTGACCTCAAATCAGGTAGGACTACCCGCTGAACTT
AAGCATATCAATAAGCGGAGGAAAAGAAACCAACAGGGATTGCCTCAGTAGCGGCGAGTGAAGCGGCAAAAGCTCAA
ATTTGAAATCTGGCGTCTTTGGCGTCCGAGTTGTAATTTGAAGAAGGTATCTTTGGGCCCGGCTCTTGTCTATGTTCCCT
GGAACGGGACGTCATAGAGGGTGAGAATCCCGTATGGGATGGGGTGTCCGCGCCCGTGTGAAGCTCCTTCGACGAGTC
GAGTTGTTTGGGAATGCAGCTCTAAATGGGTGGTAAATTTCATCTAAAGCTAAATATTGGCCGGAGACCGATAGCGCAC
AAGTAGAGTGATCGAAAGATGAAAAGCACTTTGAAAAGAGAGTTAAAAAGCACGTGAAATTGTTGAAAGGGAAGCGC
TTGCGACCAGACTCGCTCGCGGGGTTCAGCCGGCATTCGTGCCGGTGTACTTCCCCGCGGGCGGGCCAGCGTCGGTTTG
GGCGGTCGGTCAAAGGCCCTCGGAAGGTAACGCCCCTAGGGGCGTCTTATAGCCGAGGGTGCAATGCGACCTGCCTAG
ACCGAGGAACGCGCTTCGGCTCGGACGCTGGCATAATGGTCGTAAACGACCCGTCTTGAAACACGGACCAAGGAGTCT
AACATCTACGCGAGTGTTCGGGTGTCAACCCGTGCGCGAAGTGAAAGCGAACGGAGGTGGGAACCCTCACGGGTGCAC
CATCGACCGATCCTGAAGTCTTCGGATGGATTTGAGTAAGAGCGTAGCTGTTGGGACCCGAAAGATGGTGAACTATGC
CTGAATAGGGCGAAGCCAGAGGAAACTCTGGTGGAGGCTCGTAGCGGTTCTGACGTGCAAATCGATCGTCGAATTTGG
GTATAGGGGCGAAAGACTAATCGAACCATCTGGTAGCTGGTTCCTGCCGAAGTTTCCCTCAGGATAGCAGTAACGCGA
ATTCAGTTTTATGAGGTAAAGCGAATGATTAGAGGCCTTGGGGTTGAAACAACCTTAACCTATTCTCAAACTTTAAATA
TGTAAGAAGCCCTTGTTGCTTAATTGAACGTGGGCATTAGAATGATGCGTTACTAGTGGGCCATTTTTGGTAAGCAGAA
CTGGCGATGCGGGATGAACCGAACGCGAGGTTAAGGTGCCGGAATACACGCTCATCAGACACCACAAAAGGTGTTAGT
TCATCTAGACAGCCCGACGGTGGCCATGGAAGTCGGAATCCGCTAAGGAGTGTGTAACAACTCACGGGCCGAATGAAC
TAGCCCTGAAAATGGATGGCGCTTAAGCGTGTTACCCATACCTCGCCGTCAGGGTAGAAACGATGCCCTGACGAGTAG
GCAGGCGTGGGGGTCCGTGACGAAGCCTTGGGAGTGATCCCGGGTCGAACGGCCCCTAGTGCAGATCTTGGTGGTAGT
AGCAAATACTCAAATGAGAACTTTGAGGACTGAAGTGGGGAAAGGTTCCATGTGAACAGCAGTTGGACATGGGTTAGT
CGATCCTAAGGCATAGGGAAGTTCCGTTTGAAAGGCGCCCTCGTGCGCCGTGTGCCGAAAGGGAAGCCGGTTAACATT
CCGGCACCTAGATGTGGATTCTCCACGGCAACGTAACTGAACGCGGAGACGTCGGCGGGGGTCCTGGGAAGAGTTCTC
TTTTCTTCTTGACAGCCTATCACCCTGAAATCGGTTTGTCCGGAGCTAGGGTTCTATGGCTGGCAGAGCGCCGCACTTTT
GCGGCGTCCGGTGCGCCCCGACGACCCTTGAAAATCCGCGGGAAGGAATAGTTTTCACGCTAGGTCGTACTCATAAC
CGCAGCAGGTCTCCAAGGTGAACAGCCTCTAGTTGATAGAACAATGTAGATAAGGGAGTCGGCAAAATGGATCCGTAA
CTTCGGGATAAGGATTGGCTCTAAGGGTCGGGCTCGCTGGGCCTTGGGGGGAACCTCCTGGAGCAGTAGGGCACTAGC
CGGGCAACCGGCCGGCGCCCCGCAGCACCGGGTTGGGGACGCCCTTGGCAGGCTTCGGCCGTCCGGCGGGCGATTAAC
GACCAACTTAGAACTGGTACGGACAAGGGGAATCTGACTGTCTAATTAAAACATAGCATTGCGATGGCCAGAAAGTGG
TGTTGACGCAATGTGATTTCTGCCCAGTGCTCTGAATGTCAAAGTGAAGAAATTCAACCAAGCGCGGGTAAACGGCGG
GAGTAACTATGACTCTCTTAAGGTAGCCAAATGCCTCGTCATCTAATTAGTGACGCGCATGAATGGATTAACGAGATTC
CCACTGTCCCTATCTACTATCTAGCGAAACCACAGCCAGGGGAACGGGCCTGGCAGAATCAGCGGGGAAAGAAGACCC
TGTTGAGCTTGACTCTAGTTTGACATTGTGAAAAGACATATGGGGTGTAGAATAGGTGGGAGCTCCGGCGCCAGTGAA
ATACCACTACCTTTATCGTTTTTTACTTATTCAATGAAGCGGAACTGGGCTTCACCGCCCATCTTCTAGCGTTAAGGTC
CTTCGCGGGCCGATCCGGGTTGAAGACATTGTCAGGTGGGGAGTTTGGCTGGGGCGGCACATCTGTTAAACAACAACG
CAGGTGTCCTAAGGGGGACTCATGGAGAACAGAAATCTCCAGTAGAACAAAAGGGTAAAAGTCCCCTTGATTTTGATT
TTCAGTGTGAATACAAACCATGAAAGTGTGGCCTATCGATCCTTTAGTCCCTCGAAATTTGAGGCTAGAGGTGCCAGAA
AAGTTACCACAGGGATAACTGGCTTGTGGCAGCCAAGCGTTCATAGCGACGTTGCTTTTTGATTCTTCGATGTCGGCTCT
TCCTATCATACCGAAGCAGAATTCGGTAAGCGTTGGATTGTTCACCCACTAATAGGGAACGTGAGCTGGGTTTAGACCG
TCGTGAGACAGGTTAGTTTTACCCTACTGATGAAGGTTGTCGCAACAGTAATTGAACTTAGTACGAGAGGAACCGTTCA
TTCAGATAATTGGTTTTTGCGGCTGTCTGACCAGGCAGTGCCGCACGCTACCATCTGCCGGATTATGGCTGAACGCCT
CTAAGTCAGAATCCGTGCCGGAACGCGGCGATTTCGCCCCGCACGTCGTAGTTGGATACGAATAGGCCTTCGGGCCAT
GCACCTCAGCAGGCTGGCGACGGCTCCCGGGGAGAAACCCTCGGGAGCTGGCTAGCGGATTGTAATGTCACCTCGCGC
GGGGATAGATCCTCTGCAGACGACTGAAGTGACCAAGCGGGTCGTGTAAGCGGTCAAGTAGCCTTGTTGCTAC
```

Figure 14
*Rhizomucor miehei* rRNA gene (SEQ ID NO: 61)

```
GGTCCGAAGCTTTAGCCGAACTATGGCAAACTTCTCCATTTAGAGGAAGTAAAAGTCGTAACAAGGTTTCCGTAGGTG
AACCTGCGGAAGACATTAAAAAAGTTGATATCATGGTGACCCCTTTACGGGGGTGAGCCATGATTTCTTCTCCCTTTTT
GTGCAATGTTTGAGGGATTGCTCCAGATCTCTCTTTCCTTTTTTTTACGTATTGATTTGACTGAACATTTTTGTTTTAAA
ATGAAAAAAAGTTTTGAAGCCAATCAATTGGTTCAAGACAAATCAAATTTTGAAACAACTTTAAGCAATGGATCACTT
GGTTCTCGCATCGATGAAGAGCGTAGCAAATTGCGAAAAGTAATGCGATCTGCAGCCTTTGCGAATCATCGAATTCTC
GAACGCATCTTGCACCCTTTGGTTCATCCATTGGGTACGTCTAGTTCAGTATCTTTTTGAAACCCTAAAGATTCAATTT
TGTTGTTGAATCTTTGGATTTGCGGTGCTGATGGGGGGGAGGACAAAGCAAATCTTTTGTGTTCCCCCGTTCAAGCTAC
TCGAACAGTTTTTGAGTTTTTGGCCTTTTTAGATTGGTGAACATTCTTGAAGGGCTTACTTTGATATCTAAAATTTTCGA
ATTTTGGGTTATCATTGCTTTGAGAAAACCCCATCTAAAAGCAAAAACTCTATATAAACTTTTTTTTTTTTCATTCATG
GATCTGAACTTAGACGGGACTACCCGCTGAACTTAAGCATATCAATAAGCGGAGGAAAAGAAAATAACAATGATACC
CTTAGTAGCGGCGAGCGAAGTGGGTAAAGCTCAAGTTTAAAACCTGTTTGTCATAGACAAACCGGATTGTAAACTATG
GACATGTTATCCAGGCTCTTTGGACCTTCAAGTCCTTTGGAATAAGGCTTCACAGAGGGTGACAATCCCGTAGAGGGT
CTTGAACAGAGTCTATTGCGATGCATGCTCCAAGAGTCAGGTTGTTTGGGAATGCAGCCTAAAGTGGGAGGTAAATCC
CTCCTAAAGCTAAATATTGGCGAGAAACCGATAGCAAACAAGTACCGTGAGGGAAAGTTGAAAAGGACTTTGAAAAG
AGAGTCAAAAGTACGTGAAATTGCTTAAAGGGAAGCGTTTGGAGCTAGTTTGGCTAGTCTGTTATCAGCCTGAGCTTC
GGCTTTGGTGTACTATCAGGCTATTTTTGCCGGCCAACTCTCAGGATTGAAAGGAAAGCTTGGTGCTTTGGAGTCTAAA
GAGACCCTCGCGGAAGCCTCTGGTGGAGCGTGGTCTGCCCTTGGCCCTTTTGAGCCTATAGTTGGCTTAATGGCTCTAA
ACGGCCCGTCTTGAAACACGGACCAAGGAGTCCACCACTGTTGCGAGTGTTTGGGTGGCAAACCCATACGCGAAATG
AAAGTGAAAGCTATGAAATCCGCAAGGATGGCAATAGCGTCCGGCCTTTAGGACCGAGACAAAGCAATAGTGATGGG
ACCCGAAAGATGGTGAACTATGCTTGAGTAGAGTGAAGCCAGAAGAAATTCTGGTGGAAGCTCGTAACGGTTCTGAC
GTGCAAATCGATCGTCGAACTTGAGCATAGGGGCGAAAGACTAATCGAACCATCTAGTAGCTGGTTCCTGCCGAAGTT
TCCCTCAGGATAGCAGAAGCTTATAGGCAGTTTTATGTGGTAAAGCGAATGATTAGAGGTCTTGGGGACGCAATGTCC
TTAACCTATTCTCAAACTTTAAATATGTAAGACGTTCTTGCTGCTTGAATTATGAGCGTCGAATGCTGAGCT
TCTAGTGGGCCGTTCTTGGTAAGCAGGACTGGCGATGCGGGATGAACCGAACGCAAAGATAAGGCGTCAAAGAACAC
GCTCATCAGACACCACAAAAGGTGTTGGTTCATCTAGACAGCAGGACGGTGGCCATGGAAGTCGGAATCCGCTAAGG
AGTGTGTAACAACTCACCTGCCGAATGAACCAGCCCTGAAAATTAATGACGCTGAAGCGTGTCGCCTATACTTTGCCG
TCAAAGTTTAAGCGAAGCTTTGACGAGTAGGCAGGCGTGGAGGTTATGAGCATCGAAGCCTTTGGCGTGAGCCTAGGT
GGAGCAGCCTCTAGTGCAGATCTTGGTGGTAGTAGCAAATATTCAAATGAGATCTTTGAAGACTGAAGTGGAGAAGGG
TTCCTCGAGAACATTGGTTGGTCGAGGGTTAGTCGATCCTAAGAGATAGGGTAGTTCCGTTTTACCAAATGGTCCTTTG
GACCATCCTATCGAAAGGGAAGCTGGTTAATATTCCAGCACCAAGACATGGATTCTATGCGGCAACGCAGATGAACAT
AGGGACATTGGCATGGATCCTGGGAAGAGTTCTCTTTTCTTTTTGACAGCGTTTTCTTAAGCCATGAAATCGGTCTAAC
CGGTGCAATGTTTGCTTAAGAGCTGTTAGAGTACCGCAATTTTTGTGGTATCCAGAGCATTCATGACGATCCTTGAAAA
CCTATGGGAAAGAATGAATTTCATGCTTGGTCGTACCCATAACCGCATCAGGTCTCCAAGGTGAAAAGCCTCTAGTTG
ATGGAAGAATGTAGATAAGGGAAGTCGGCAAATTGGATCCGTAACTTCGGGAGAAAGGATTGGCTCTAAGGGTTGGGT
GCTTTAAGAACCAGGCCTTAGCGGCCTGAGCAATCGGGCTGCTTCCAGGCTTGGAGCTCTTGGGCACGCTTAACAACC
AGCTTAGAACTGGTACGGACCAAGGGAATCTGACTGTCTAATTAAAACATAGCATTGCGATTGCCATAAAGTGGTATT
GACGCAATGTGATTTCTGCCCAGTGCTCTGAATGTCAAAGTGAAGAAATTCAACCAAGCGCGGGTAAACGGCGGGAG
TAACTATGAGAGCTTTGTGATATAGTCCAGTTTCAGAACTGCTAATTAGTGACGCGCATGAATGGATTAACGAGATTC
CCACTGTCCCTATCTACTATCCAGCGAAACCACAGCCAAGGGAACGGGCTTGGCAAAATCAGCGGGGAAAGAAGACC
CTGTTGAGCTTGACTCTAGTTTGACATTGTGAAAAGACATAGGGGGGTGTAGAAATATGTGGGAGCTTCGGCGCCAGTG
AAATACCACAACCCTTATAGTTTTTTTACTTAAATAATCAAGTGGGAGAAGGCTTCACGGCCTATCTTCTAGCGTTAAG
CAGTCTTCGGGCTGCGACCCATGTTATTGACATTGTCAAGTGGGGAGTTTGGCTGGGGCGGCACATCTGTTAAACGAT
AACGCAGGTGTCCTAAGGGGAGCTCAACGAGAACAGAAATCTCGTGTAGAGCAAAAGGGCAAAAGCTCCCTTGATTT
TGATTTTCAGCGTGAATACGAACCATGAAAGTGTGGCCTATCGATCCTTTATGCCATTTCCTTAGGATTTAAGGCTAGA
GGTGCCGGAAAAGTTACCACAGGGATAACTGGCTTGTGGCAGCCAAGCGTTCATAGCGACGTTGCTTTTTGATTCTTC
GATGTCGGCTCTTCCTATCATACAGAAGCAGAATTCTGTAAGCGTTGGATTGTTCACCCACTAATAGGGAACGTGAGC
TGGGTTTAGACCGTCGTGAGACAGGTTAGTTTTACCCTACTGATGAATCAGTAGGCGTCCCGACAGTAATTGAAGTTA
GTACGAGAGGAACCCTTCATTCAGATAATTGGTTTTTGCGGTTGGTTGAAAGGCCAATGCCGCGAAGCTACCATCTGC
TGGATAATGGCTGAAAGCCTCTAAGTCAGAATCCATGCTGGTTAAGGGACGCTAAAACCAGACCTTTAAAGCGCGAG
AAAGTGCTCAAATAGATCTCTTATGGGATCGAATGCCTAATATGAGGTTATCCTCTTGGGTTGAAAGGCTCAAGTCGG
ATACCTCTCATGATAATGTCTAGCTTAAAGGTTGTAAATCTCGAGCAGACGACTTGAAATCGACGGGCTATTGTAAGC
```

Figure 15

*Rhodotorula glutinis* rRNA gene (SEQ ID NO: 62)

```
CGATTGAATGGCTTAGTGAGGCCTCCGGATTGGCTATTGGGAGCTCGCGAGAGCACCTGACTGCTGAGAAGTTGTACG
AACTTGGTCATTTAGAGGAAGTAAAAGTCGTAACAAGGTTTCCGTAGGTGAACCTGCGGAAGGATCATTAGTGAATCT
AGGGTGTCCAATTTAACTTGGAGCCCGAACTCTCACTTTCTAACCCTGTGCATCTGTTATTGGTTAGTAGCTCTTCGGA
GTGAACTCCATTCACTTACAAACACAAAGTCTATGAATGTATACAAAATTATAACAAAACAAAACTTTCAACAACGGA
TCTCTTGGCTCTCGCATCGATGAAGAACGCAGCGAAATGCGATACGTAATGTGAATTGCAGAATTCAGTGAATCATCG
AATCTTTGAACGCACCTTGCGCTCCTTGGTATTCCGAGGAGCATGCCTGTTTGAGTGTCATGAAATCTTCAACCCACCT
CTTTCTTAGTGAATCTGGTGGTGCTTGGTTTCTGAGCGCTGCTCTGCTTCGGCTTAGCTCGTTCGTAATGCATTAGCATC
CGCAACCGAACTTCGGATTGACTTGGCGTAATAGACTATTCGCTGAGGATTCTAGTCTCGTACTAGAGCCGGGTTGGG
TTAAAGGAAGCTTCTAATCCTAAAGTCTATTTTTTGATTAGATCTCAAATCAGGTAGGACTACCCGCTGAACTTAAGCA
TATCAATAAGCGGAGGAAAAGAAACTAACAAGGATTCCCCTAGTAGCGGCGAGCGAAGCGGGAAGAGCTCAAATTTA
TAATCTGGCACCTTCGGTGTCCGAGTTGTAATCTCTAGAAGTGTTTTCCGCGTTGGACCGCACACAAGTCTGTTGGAAT
ACAGCGGCACAGTGGTGATACCCCCGTACACGGTGCGGACGCCCAGCGCTTTGTGATACACTTTCAATGAGTCGAGTT
GTTTGGGAATGCAGCTCAAATTGGGTGGTAAATTCCATCTAAAGCTAAATATTGGCGAGAGACCGATAGCGAACAAGT
ACCGTGAGGGAAAGATGAAAAGCACTTTGGAAAGAGAGTTAACAGTACGTGAAATTGTTGGAAGGGAAACGCTTGAA
GTCAGACTTGCTTGCCGGAGCTTGCTTCGGTTTGCAGGCCAGCATCAGTTTTCCGGGGTGGATAATGGTGGTTTGAAG
GTAGCAGCCTCGGCTGTGTTATAGCTTTTCCACTGGATACATCCTGGGGGACTGAGGAACGCAGCGTGCTTTTTGCGAA
GGTTTCGACCTTTTCACGCTTAGGATGCTGGTGTAATGACTTTAAACGACCCGTCTTGAAACACGGACCAAGGAGTCT
AACATGCTCGCGAGTATTTGGGTGTCAAACCCGGATGCGCAATGAAAGTGAATGTAGGTGGGAACCGCAAGGTGCAC
CATCGACCGATCTGGATCTTTTGAGATGGATTTGAGTAAGAGCGCGTATGTTGGGACCCGAAAGATGGTGAACTATGC
CTGAATAGGGCGAAGCCAGAGGAAACTCTGGTGGAGGCTCGTAGCGGTTCTGACGTGCAAATCGATCGTCGAATTTGG
GTATAGGGGCGAAAGACTAATCGAACCATCTAGTAGCTGGTTCCTGCCGAAGTTTCCCTCAGGATAGCAGAAACTCAC
ATCAGTTCTATGAGGTAAAGCGAATGATTAGAGGCCTTGGGGTTGAAACAACCTTAACCTATTCTCAAACTTTAAATA
TGTAGGAAGTCCTTGCTACTTAATTGAGCGAGGACATGCGAATGAGAGTTTCTAGTGGGCCATTTTTGGTAAGCAGAA
CTGGCGATGCGGGATGAACCGAACGCGAGGTTAAGGTGCCGGAATACACGCTCATCAGACACCACAAAAGGTGTTAG
TTCATCTAGACAGCCGCACGGTGGCCATGGAAGTCGGAATCCGCTAAGGAGTGTGTAACAACTCAACGGCCGAATGA
ACTAGCCCTGAAAATGGATGGCGCTCAAGCGTGTTACCCATACCTCGCCGTCAGCGCTATTGATACGTTGACGAGTAG
GCAGGCGTGGAGGTCCGTATAGAAGCTTTCGGAGTGATCCGGAGTAGAACGGCCTCTAGTGCAGATCTTGGTGGTAGT
AGCAAATATTCAAGTGAGAACCTTGAAGACTGAAGTGGGGAAGGGTTCCATGGTAACAGCAGTTGGACATGGGTGAG
TCGGTCCTAAGAGATAGGGAAACTCCGTTTTAAAGTGTGCGCTTGTTCGCACGGCCTATCGAAAGGGAATACGGTTAA
AATTCCGTAACCGCGATGCAGATTCTGAACGGCAACGTAAATGAACTTGGAGACGTCGGTGAAGGCCCTGGGAAGAG
TTATCTTTTCTCCTTTACAGCTTATAACCCTGGAATCGGATTATCCGGAGATAGGGTCTAATGGCTGGTAGAGCAGCGC
TATTTTGTGCTGTCCGGTGCGTCTTCAACGGCCCGTGAAAATCCGAGGGAATGAAAAAGTCTTGCACGCGATCGTACC
CATATCCGCATCAGGTCCCCAAGGTGATCAGCCTCTAGTCCATAGAATAATGTAGATAAGGGAAGTCGGCAAAATAGA
TCCGTAACTTCGGGAAAAGGATTGGCTCATAGGGTAGGGTACGTCGGGGCCTTGGGCAAAGACAAGGGACCGCGGTG
GGACTACTGCGGCGCAAGCTGCGGCGGACCTGCTGTGGACCCGAGTCGGCGCCCCTGGCCAGTCTTCGGACGTCTGGC
GTACGATTAACTACCAACTATGAACTGGTACGGACAAGGGGAATCTGACTGTCTAATTAAAACATAGCATTGCGATGG
CCAGAAAGTGGTGTTGACGCAATGTGATTTCTGCCCAGTGCTCTGAATGTCAAAGTGAAGAAATTCAACCAAGCGCGG
GTAAACGGCGGGAGTAACTATGACTCTCTTAAGGTAGCCAAATGCCTCGTCATCTAATTAGTGACGCGCATGAATGGA
TTAACGAGATTCCCACTGTCCCTATCTACTATCTAGCGAAACCACAGCCAAGGGAACGGGCTTGGCAAAATAAGCGGG
GAAAGAAGACCCTGTTGAGCTTGACTCTAGTTTGACATTGTGAAGAGACATAGAGGGTGTAGAATAAGTGGGAGCTTC
GGCGCCGGTGAAATACCACTACCTTTATCGTTTCTTTACTTATTCAATGAAGCGGAGCTGGGATTAACGTCCCACGTTT
TGGCATTAAGGTCCTTCGCGGGCTGATCCGGGTTGAAGACATTGTCAGGTGGGAGTTTGCTGGGGCGGCACATCTG
TTAAACAATAACGCAGGTGTCCTAAGGGGGACTCAATGAGAACAGAAATCTCATGTAGAACAAAAGGGTAAAAGTCC
CCTTGATTTTGATTTTCAGTGTGAATACAAACCATGAAAGTGTGGCCTATCGATCCTTTAGTCCCTCGGAATTTGAGGC
TAGAGGTGCCAGAAAAGTTACCACAGGGATAACTGGCTTGTGGCAGCCAAGCGTTCATAGCGACGTTGCTTTTTGATC
CTTCGATGTCGGCTCTTCCTATCATACCGAAGCAGAATTCGGTAAGCGTTGGATTGTTCACCCACTAATAGGGAACGT
GAGCTGGGTTTAGACCGTCGTGAGACAGGTTAGTTTTACCCTACTTTTGAAGGGTTATCGTAATAGTAATTCAACTTAG
TACGAGAGGAACCGTTGATTCGCGTAATTGGTATTTGCGGCTGTCCGATCGGGCAATGCCGCGAAGCTACCACGCGTT
GGATTATGGCTGAACGCCTCTAAGCCAGAATCCGTGCTAGAAACGATGATGTTAGTCCCGCAAATCTTAGTCGAGTAA
AGATAGAGCTTCGGCTCGTAAACCATAGTTGGCTGGTCATGTTCAGTAGGGCGGAAAGGCCTTGCTGTTCTACCGGCG
AATAGCATTCGAAATATTTGCGGGGGTAAATCCTTGCAGACGACTTGAATAGAACGGAGTGCTGTACGCC
```

Figure 16A
*Scedosporium apiospermum* rRNA gene (SEQ ID NO: 63)

```
CTACTACCCGATTGAATGGCTTAGTGAGACCCTCGGATTGGCGTTAAGAAGCCGGCAACGGCATCTTTTGGCCGAGAA
GTTGGTCAAACTTGGTCATTTAGAGGAAGTAAAAGTCGTAACAAGGTTTCCGTAGGTGAACCTGCGGAAGGATCATTA
GTGAATTGCTCTTTGAGCGTTAAACTATATCCATCTACACCTGTGAACTGTTGATTGACTTCGGTCAATTACTTTTACA
AACATTGTGTAATGAACGTCATGTTATTATAACAAAAATAACTTTCAACAACGGATCTCTTGGCTCTCGCATCGATGA
AGAACGCAGCGAAATGCGATAAGTAATGTGAATTGCAGAATTCAGTGAATCATCGAATCTTTGAACGCACATTGCGCC
CGGCAGTAATCTGCCGGGCATGCCTGTCCGAGCGTCATTTCAACCCTCGAACCTCTGTTTCCCAGCGAAGCTCAGGGT
CGGCGTTGGGGCGCTACGGCGAGTCTTCGCGACCCCGTAGGCCCTGAAATACAGTGGCGGTCCCGCCGCGGTTGCCTT
CTGCGTAGTAAAAGTCTTCTTTTGCAAGCTTCGCATTGGGTCCCGGCGGAGGCCTGCCGTCAAACCACATTATAACTTA
AGATGGTTTGACCTCGGATCAGGTAGGGTTACCCGCTGAACTTAAGCATATCAATAAGCGGAGGAAAAGAAACCAAC
AGGGATTGCCTCAGTAACGGCGAGTGAAGCGGCAACAGCTCAAATTTGAAATCTGGCAGCCTCCGGGCGGTCCGAGTT
GTAATTTGAAGAGGATGCTTTTGGCGAGGCGCCTTCCGAGTGCCCTGGAACGGGACGCCACAGAGGGTGAGAGCCCC
GTATGGTTGGACGCCGAGCCTCTGTAAAGCTCCTTCGACGAGTCGAGTAGTTTGGGAATGCTGCTCAAAATGGGAGGT
AAACCCCTTCTAAAGCTAAATACTGGCCAGAGACCGATAGCGCACAAGTAGAGTGATCGAAAGATGAAAAGCACTTT
GAAAAGAGAGTTAAATAGCACGTGAAATTGTTGAAAGGGAAGCGCTTGCGACCAGACTTGTGCCCGTCGAATCAGCC
GCCGCTCGTCGGCGGCGCACTTCGGCGGGCTCAGGCCAGCATCAGTTCGCTGCAGGGGGAGAAAGGCGGTGGGAATG
TGGCTCTTCGGAGTGTTATAGCCCGCCGCGCAATACCCCTCGGCGGACTGAGGACCGCGCATCTGCAAGGATGCTGGC
GTAATGGTCGTCAGCGACCCGTCTTGAAACACGGACCAAGGAGTCGTCCTAATATGCGAGTGTTCGGGTGTAAAACCC
CTGCGCGTAATGAAAGTGAACGGAGGTGAGAGCTTCGGCGCATCATCGACCGATCCTGATGTTCTCGGATGGATTTGA
GTAAGAGCATATTGGGCGGACCCGAAAGAAGGTGAACTATGCCTGTATAGGGTAAAGCCAGAGGAAACTCTGGTGG
AGGCTCGCAGCGGTTCTGACGTGCAAATCGATCGTCAAATATGGGCATGGGGGCGAAAGACTAATCGAACCTTCTAGT
AGCTGGTTTCCGCCGAAGTTTCCCTCAGGATAGCAGTGTTGAATTTCTCAGTTTTATGAGGTAAAGCGAATGATTAGG
GACTCGGGGGCGCTATTAAGCCTTCATCCATTCTCAAACTTTAAATATGTAAGAAGCCCTTGTTACTTAACTGAACGTG
GGCATTCGAATGTATCAACACTAGTGGGCCATTTTTGGTAAGCAGAACTGGCGATGCGGGATGAACCGATCGCGGGGA
TAAGGTGCCGGAGTGGACGCTCATCAGACACCACAAAAGGTGTTATCACATCTTGACAGCAGGACGGTGGCATGA
AGTCGGAATCCGCTAAGGACTGTGTAACAACTCACCTGCCGAATGTGATAGCCCTGAAAATGGATGGCGCTCAAGCGT
CCCACCCATACCCCGCCCTCAGGGTAGACACTATGCCCTGAGGAGTAGGCGGACGTGGAGGTCAGTGACGAAGCCTA
GGGCGTGAGCCCGGGTCGAACGGCCTCTAGTGCAGATCTTGGTGGTAGTAGCAAATACTTCAATGAGATCTTGAAGGA
CCGAAGTGGGGAAAGGTTCCATATGAACAGCGGTTGGATATGGGTAAGCCGATCCTAAGCCATAGGGAAGTTCCGTTT
CAAAGGGGCACTAATCGCCCGTATGGCGAAAGGGAAGCCGGTCAATATTCCGGCGCCTGGATGTGGGTTTTACGCGG
CAACGCAAACGAAAGCGGAGACGAGGGCGGGGGCCCTGGGTAGAGTTCTCTTTTCTTCTTAACGGCCTAGTGACCCTG
GAATCGGTTTGTCCGGAGATAGGGTTCAACGGCCGGAAGAGCCCAGCACTTCTGCTGGGTCCGGTGCGCTCCCGACCT
CCCTTGAAAATCCGCTGGAGGGAATAATTCTCACGCCAGTTCGTACTCATAACCGCAGCAGGTCTCCAAGGTGAACAG
CCTCTGGTTGATAGAACAACGTAGATAAGGGAAGTCGGCAAAATAGATCCGTAACTTCGGGAAAAGGATTGGCTCTA
AGGGTTGGGCACGTTGGGCTTCTGGCGGACGCCCCGGGAGCAGACGGCCACTAGCCGGGCAACCGGCCGGGGCTGT
CAGCATCTGGGCGCGCGGAAGCCTTTAGCAGGCCTTCGGGCCGTCCGGCGTGCAGTTAACAACCAACTTAGAACTGGTGC
GGACAGGGGGAATCTGACTGTCTAATTAAAACATAGCATTGCGATGGCCAGAAAGTGGTGTTGACGCAATGTGATTTC
TGCCCAGTGCTCTGAATGTCAAAGTGAAGAAATTCAACCAAGCGCGGGTAAACGGCGGGAGTAACTATGACTCAACG
TGCAGCTCCGGAACGGAAACGCACAGCGTTGCCTGTAGTGGAAGAAACAACAGCAACTTAAGAGGGTCAAGCAGCGT
AAAAGGCGACTGCTAGTGGACCCGGGCCTGCTGGGAGGCCCGCGGATTCCGCGACACTGTCAAATTGCGGGGAGTT
CCTAAAGCCTCTTGCTACCGCGGCCCGCCGCCGAAAGGTAGGGTGCAGCACCAGGGTAATGACCTCGGGGATGGTAAAAA
CGCAGAGGATGCTAACAATGGATGATCCGCAGCCAAGTCCTACGTCCCAGGGGGCCCCGACACTTCGTTTTGCTCGG
AGGGGGCCAGGCACCGGGATAGGGATGCAGTTCAACGACTAGACGGCAGTGGGTCCGAGGGGGGCGAGCAAGCGTCC
CACCCGTGCTGGGTGGGAGCCCCCCGCTGAACGGGCTTAAGGTATAGTCTGCTGGTCTCCCGAAAGGGATGCACCCAC
TGAAGAAATGCTCTTAAGGTAGCCAAATGCCTCGTCATCTAATTAGTGACGCGCATGAATGGATCAACGAGATTCCCA
CTGTCCCTATCTACCATCTAGCGAAACCACAGCCAAGGGAACGGGCTTGGCAGAATCAGCGGGGAAAGAAGACCCTG
TTGAGCTTGACTCTAGTTTGACATTGTGAAAAGACATAGGAGGTGTAGAATAGGTGGGAGCTTCGCGCCGGTGAAAT
ACCACTACTCCTATTGTTTTTTACTTATTCAGTGAAGCGGGGCTGGACTTACGTCCAACTTCTGGTGTTAAGGTCCTT
CGCGGGCCGACCCGGGTTGAAGACATTGTCAGGTGGGGAGTTTGGCTGGGGCGGCACATCTGCTAAACCATAACGCA
GATGTCCTAAGGGGGGCTCATGGAGAACAGAAATCTCCAGTAGAACAAAAGGGTAAAAGTCCCCTTGATTTTGATTTT
CAGTGTGAATACAAACCATGAAAGTGTGGCCTATCGATCCTTTAGTCCCTCGGGGTTTGAGGCTAGAGGTGCCAGAAA
AGTTACCACAGGGATTAACGAAAAAAACGTTACGGCTATCGTAATGAAAATAGTCCCAGGCGGCGCCATGACAAGCG
CCGCCTAGTCCGGCAGGCCCCGTACAGCGCTGGGGCCTGCGACTGTTCTGTAACTCAGTCGGCTTCGGGGGAGGTTCA
GGCCTCCCCCGCGGCTTGGGCAAAACACCTGGATGCGGGAAGTCTCGTTAGGTCAGCGGTAGCAAGCCCGTGGTGGT
AACGCCCCGGGTTAAGCCAGTGTCAAGGCGGCTAATAACCCACTGAATAGAGATAATCCGCAGCTCGACCCGGCCA
CACTCACCGGCAAACGGTGCAAGGGCTGGGCAGTTCAACGCTCGCTAAGGTGTTGGTGAGAGGGTCCCAGTGGACCT
```

Figure 16B

```
CTTGCTTAAGGTACGGGCTACTCCCACCCGAGAGGGTGTCGTGTCTACCGGCTGCGCACGCCGAGAAGCACGAAGCAG
GGCGGTAAAACGAAGCCCTGTGGGTAGAAAGGAACTGGCTTGTGGCGGCCAAGCGTTCATAGCGACGTCGCTTTTTGA
TCCTTCGATGTCGGCTCTTCCTATCATACCGAAGCAGAATTCGGTAAGCGTTGGATTGTTCACCCACTAATAGGGAAC
GTGAGCTGGGTTTAGACCGTCGTGAGACAGGTTAGTTTTACCCTACTGATGAACTCGCCGCAATGGTAATTCAGCTCA
GTACGAGAGGAACCGCTGATTCAGATAATTGGTTTTTGCGGCTGTCCGACCGGGCAGTGCCGCGACGCTACCATCTGC
TGGATAATGGCTGAACGCCTCTAAGTCAGAATCCATGCCAGAAAGCGGCGATATACCCGCACGTCTAGACGGACAAG
AATAGGCTCCGGCTTAGTGTCTTAGCGGGCGGATGGTCCGCCAGGCTCGAAGTGCCTGGCGGTGATTCGCGAATTGTA
ATTTCGATGCGCGCGGGGATGAATCCTTGCAGACGACTTAGTTGTGCGAAAGGGTCCTGTAAGCAGTAGAGTAGCCTG
TTTGGTTACG
```

Figure 17
*Antrodia vaillantii* rRNA gene (SEQ ID NO: 64)

```
CTTGGTCATTTAGAGGAAGTAAAAGTCGTAACATCCGTAGGTGAACCTGCGGAAGGATCATTAATGAATTTCAATGGA
GTTGTAGCTGGCTCTAACAAGGGCATGTGCACACTCTATTCGTTATATTATACACCTGTGCACCTTTTGTAGTTCGGTTG
TTACGGGGAGAGTCGAAAGGCTTTCTCAGACCCCCGTTCTATGTTTTTATTATAAACCTTTGAATGTCTTTGAATGTCTG
CATTAATAATGCATTTTATACAACTTTCAGCAACGGATCTCTTGGCTCTCGCATCGATGAAGAACGCAGCGAAATGCGA
TAAGTAATGTGAATTGCAGAATTCAGTGAATCATCGAATCTTTGAACGCACCTTGCGCTCCTTGGTATTCCGAGGAGCA
TGCCTGTTTGAGTGTCATGGAATTATCAAACCTTTCTTTAAATTTATTTTAAAGGTTGGCTTGGACTTGGAGGTTGCTGG
CCGCGCCATTTTGTAGTCAGTCAGCTCCTCTTGAATGCATTAGCTTGAGTCTTTAATGAGTCGGCTTATCGGTGTGATAA
ACTTATGCCGTTAGTCAACTTGTAAACAAATCGAGCTTCTAATCGTCTTTGGACAAACATTATAATATGACCTCTGACTT
CAAATCAGGTAGGATTACCCGCTGAACTTAAGCATATCAATAAGCGGAGGAAAAGAAACTAACAAGGATTCCCCTAGT
AACTGCGAGTGAAGCGGGAAAAGCTCAAATTTAAAATCTGGCAGTTTAATAGCTGTCCGAGTTGTAGTCTGGAGAAGT
GCTTTCCGTGCTAGACCGTGTACAAGTCCCTTGGAACAGGGCGTCATAGAGGGTGAGAATCCCGTCTTTGACACGGACT
ACTAGTGCTTTGTGATGCGCTCTCAAAGAGTCGAGTTGTTTGGGAATGCAGCTCAAAATGGGTGGTAAATTCCATCTAA
AGCTAAATACAGGCGAGAGACCGATAGCGAACAAGTACCGTGAGGGAAAGATGAAAAGCACTTTGGAAAGAGAGTTA
AACAGTACGTGAAATTGCTGAAAGGGAAACGCTTGAAGTCAGTCGCGTTGTCCGGAAATCAGCCTTGCATTTATTTGCT
TGGTGTATTTTCTGGTTGACGGGCCAGCATCGATTTTAATCGTTGGATAAAGGCGAGGGAAATGTGGCACCTTCGGGTG
TGTTATAGTCCCTTGTCACATACAACGGTCGGGATCGAGGAACTCAGCACGCCTTTATTGGTCGGGGTTCGCCCACGTT
TCGTGCTTAGGATGTTGGCATAATGGCTTTAAACGACCCGTCTTGAAACACGGACCAAGGAGTCTAACATACCTGCGAG
TGTTTGGGTGGTAAACCCGAGCGCGTAATTAAAGTAATAGTTGAGATCCCCGTTACAAGGGAGCATCGACGCCCGGAC
TTGACCTTCTGTGATAGCTCTGCGGTAGAGCATGTATGTTGGGACCCGAAAGATGGTGAACTATGCCTGAATAGGGTGA
AGCCAGAGGAAACTCTGGTGGAGGCTCGTAGCGATTCTGACGTGCAAATCGATCGTCAAATTTGGGTATAGGGGCGAA
AGACTAATCGAACCATCTAGTAGCTGGTTCCTGCCGAAGTTTCCCTCAGGATAGCAGAAACTCGTATCAGATTTATGTG
GTAAAGCGAATGATTAGAGGCCTTGGGGTTGAAACAACCTTAACCTATTCTCAAACTTTAAATATGTAAGAACGAGCC
GTCACTTAATTGGACCGCTCGGCGATTGAGGTTTCTAGTGGGCCATTTTTGGTAAGCAGAACTGGCGATGCGGGATGAA
CCGAACGTGAGGTTAAGGTGCCGGAATACACGCTCATCAGACACCACAAAAGGTGTTAGTTCATCTAGCAGAGGAC
GGTGGCCATGGAAGTCGGAATCCGCTAAGGAGTGTGTAACAACTCACCTGCCGAATGAACTAGCCCTGAAAATGGATG
GCGCTCAAGCGTGTTACCCATACCTCACCGTCAGTGTTTAAGTGAAACATTGACGAGTAGGCAGGCGTGGAGGTCAGT
GAAGAAGCCTAGGCAGTAATGCTGGGTGAAACGGCCTCTAGTGCAGATCTTGGTGGTAGTAGCAAATATTCAAGTGAG
AACCTTGAAGACTGAAGTGGAGAAAGGTTCCATGGTAACAGCAGTTGGACATGGGTTAGTCGATCCTAAGAGATAGGG
AAGCTCCGTTTCAAAGTGTACGATTTTTCGTACCGCCTATCGAAAGGGAATCCGGTTAAGATTCCGGAACCAGGATGTG
GATTTTTAACGGCAACGTAAATGAACTTGGAGACGCTGGCGAGGGCCCGGGAAGAGTTATCTTTTCTCCTTAACAGTC
TAACACCCTGAAATCGGTTTGTCCGGAGCTAGGGTTTAATGACTGGTAGAGCTCGACACTTCTGTCGGGTCCGGTGCGT
TCTTGACAGCCCTTGAAAATCCAAGGGAATGAATAATTTTCACACCTGGTCGTACTCATAACCGCAGCAGGTCTCCTAG
GTGAACAGCCTCTAGTTGATAGAACAATGTAGATAAGGGAAGTCGGCAAAATAGATCCGTAACTTCGGGAAAAGGATT
GGCTCTAAGGGTTGGGTACATCGGGCCTTAGTTGGAAGCTACGGGACCAGGCTAGGACTGTTTCGGGGCAACCTGGGA
CGGACTTGGCCAGGGACCTGTCAGTGGATGGCTTTGGCTGCTCTCGGGCGTCCGGTGTACGCTTAACAACCAACTTAGA
ACTGGTACGGACAAGGGGAATCTGACTGTCTAATTAAAACATAGCATTGCGATGGCCAGAAAGTGGTGTTGACGCAAT
GTGATTTCTGCCCAGTGCTCTGAATGTCAAAGTGAAGAAATTCAACCAAGCGCGGGTAAACGGCGGGAGTAACTATGA
CTCTCTTAAGGTAGCCAAATGCCTCGTCATCTAATTAGTGACGCGCATGAATGGATTAACGAGATTCCCACTGTCCCTA
TCTACTATCTAGCGAAACCACAGCCAAGGGAACGGGCTTGGCAGAATCAGCGGGGAAAGAAGACCCTGTTGAGCTTGA
CTCTAGTTTGACATTGTGAAAAGACATAGAGGGTGTAGAATAAGTGGGAGCTTCGGCGCCGGTGAAATACCACTACCT
TTATCGTCTTTTTACTTATTCAATGAGGCGGAGCTGGGATTAACAGTCCCACCTTTTGGCTTCAAGGTCCTTTAAGGGCT
GATCCGGGTTGAAGACATTGTCAGGTGGGGAGTTTGGCTGGGGCGGCACATCTGTTAAAAGATAACGCAGGTGTCCTA
AGGGGGACTCATCGAGAACAGAAATCTCGAGTAGAACAAAAGGGTAAAAGTCCCCTTGATTTTGATTTTCAGTGTGAA
TACAAACCATGAAAGTGTGGCCTATCGATCCTTTAGTCCCTCGGAATTTGAGGCTAGAGGTGCCAGAAAAGTTACCACA
GGGATAACTGGCTTGTGGCAGCCAAGCGTTCATAGCGACGTTGCTTTTTGATCCTTCGATGTCGGCTCTTCCTATCATAC
CGAAGCAGAATTCGGTAAGCGTTGGATTGTTCACCCACTAATAGGGAACGTGAGCTGGGTTTAGACCGTCGTGAGACA
GGTTAGTTTTACCCTACTGATGGAGTGTTATCGTAATAGTAATTGAACTTAGTACGAGAGGAACCGTTCATTCAGATAT
TTGGTATTTGCGCCTGTCCGATCGGGCAATGGCGCGAAGCTATCATCTGCTGGATTATGGCTGAACGCCTCTAAGCCAG
AATCCGTGCTAGAAACGATGATGTTGGTCCCGCACATATAAGTTGCGTTGAAATAGAGCTTTGCTCGTGAACCAAATCA
GGTGGGCTGGGTCGTTCAAGCGGAAATGCTTGTTCGATTTGTCTACGAATTGTAATCATCATATGCGCGGGGTGAATC
CTTTGCAGACGACTTGAATGGGAACGGGGTACTGTAAGCAGTAGAGTAGCCTTGTTGCTACGATCTGCTGAGGTTAAGC
CCTTGTTCTATAGATTTGTT
```

Figure 18

*Aspergillus fumigatus* rRNA gene (SEQ ID NO: 65)

```
GGTCATTTAGAGGAAGTAAAAGTCGTAACAAGGTTTCCGTAGGTGAACCTGCGGAAGGATCATTACCGAGTGAGGGCC
CTCTGGGTCCAACCTCCCACCCGTGTCTATCGTACCTTGTTGCTTCGGCGGGCCCGCCGTTTCGACGGCCGCCGGGGAG
GCCTTGCGCCCCCGGGCCCGCGCCCGCCGAAGACCCCAACATGAACGCTGTTCTGAAAGTATGCAGTCTGAGTTGATTA
TCGTAATCAGTTAAAACTTTCAACAACGGATCTCTTGGTTCCGGCATCGATGAAGAACGCAGCGAAATGCGATAAGTA
ATGTGAATTGCAGAATTCAGTGAATCATCGAGTCTTTGAACGCACATTGCGCCCCCTGGTATTCCGGGGGGCATGCCTG
TCCGAGCGTCATTGCTGCCCTCAAGCACGGCTTGTGTGTTGGGCCCCGTCCCCCTCTCCGGGGGACGGGCCCGAAAG
GCAGCGGCGGCACCGCGTCCGGTCCTCGAGCGTATGGGGCTTTGTCACCTGCTCTGTANGCCCGGCCGGCGCCAGCCG
ACACCCAACTTTATTTTTCTAANGTTGACCTCGGATCANGTAGGGATACCCGCTGAACTTAAGCATATCAATAAGCGGA
GGAAAAGAAACCAACAGGGATTGCCTCAGTAACGGCGAGTGAAGCGGCAAGAGCTCAAATTTGAAAGCTGGCCCCTTC
GGGGTCCGCGTTGTAATTTGCAGAGGATGCTTCGGGTGCAGCCCCCGTCTAAGTGCCCTGGAACGGGCCGTCATANAG
GGTGAGAATCCCGTCTGGGACGGGGTGTCTGCGTCCGTGTGAAGCTCCTTCGACGAGTCGAGTTGTTTGGGAATGCAGC
TCTAAATGGGTGGTAAATTTCATCTAAAGCTAAATACTGGCCGGAGACCGATAGCGCACAAGTAGAGTGATCGAAAGA
TGAAAAGCACTTTGAAAAGAGAGTTAAACAGCACGTGAAATTGTTGAAAGGGAAGCGTTTGCGACCAGACTCGCCCGC
GGGGTTCAGCCGGCATTCGTGCCGGTGTACTTCCCCGTGGGCGGGCCAGCGTCGGTTTGGGCGGCCGGTCAAAGGCCCT
CGGAATGTATCACCTCTCGGGGTGTCTTATAGCCGAGGGTGCAATGCGGCCTGCCTGGACCGAGGAACGCGCTTCGGCT
CGGACGCTGGCGTAATGGTCGTAAATGACCCGTCTTGAAACACGGACCAAGGAGTCTAACATCTACGCGAGTGTTCGG
GTGTCAAACCCGTACGCGCAGTGAAAGCGAACGGAGGTGGGAGCCCCCTCGCGGGGCGCACCATCGACCGATCNTGAT
GTCTTCGGATGGATTTGAGTACGAGCGTAGCTGTGGGGACCCGAAAGATGGTGAACTATGCCTGAATAGGGCGAAGCC
AGAGGAAACTCTGGTGGAGGCTCGCAGCGGTTCTGACGTGCAAATCGATCGTCAAATTTGGGTATAGGGGCGAAAGAC
TAATCGAACCATCTAGTAGCTGGTTCCTGCCGAAGTTTCCCTCAGGATAGCAGTAACGCGGATCAGTTTTATGAGGTAA
AGCGAATGATTAGAGGCCTTGGGGTTGAAACAACCTTAACCTATTCTCAAACTTTAAATATGTAAGAAGCGCTTGTTGC
TTAGTTGAACGTGCGCATTAGAATGAAGCGTTACTAGTGGGCCATTTTTGGTAAGCAGAACTGGCGATGCGGGATGAA
CCGAACGCGAGGTTAAGGTGCCGGAATGCACGCTCATCAGACACCACAAAAGGTGTTAGTTCATCTAGACAGCCCGAC
GGTGGCCATGGAAGTCGGAATCCGCTAAGGAGTGTGTAACAACTCACGGGCCGAATGAACTAGCCCTGAAAATGGATG
GCGCTCAAGCGTGCTACCCATACCTCGCCGTCGGGGTAGAAACGACGCCCCGACGAGTAGGCAGGCGTGGGGGTCCGT
GACGAAGCCTTGGGAGTGATCCCGGGTCGAACGGCCCCTAGTGCAGATCTTGGTGGTAGTAGCAAATACTCAAATGAG
AACTTTGAGGACTGAAGTGGGGAAAGGTTCCATGTGAACAGCAGTTGGACATGGGTTAGTCGATCCTAAGGCATAGGG
AAGTTCCGTTTGAAAGGCGCCCTCGTGCGCCGTGTGCCGAAAGGGAAGCCGGTTAACATTCCGGCACCTGGATGTGGA
TTCTCCACGGCAACGTAACTGAACGCGGAGACGTCGGCGGGGGTCCTGGGAAGAGTTCTCTTTTCTTCTTGACAGCCTT
CCACCCTGAAATCGGTTTGTCCGGAGCTAGGGTTCCATGGCTGGCAGAGCCCCGCACCTTTGCGGGGTCCGGTGCGCCC
CCGACGACCCTTGAAAATCCGCGGGAAGGAATAGTTTTCACGCCAGGTCGTACTCATAACCGCAGCAGGTCTCCAAGG
TGAACAGCCTCTAGTTGATAGAACAATGTAGATAAGGGAAGTCGGCAAAATGGATCCGTAACTTCGGGATAAGGATTG
GCTCTAAGGGTCGGGCCCGCTGGGCCTTGGGGGAAACCCCTCGGAGCAGGGGGGCACTAGCCGGGCAACCGGCCGGC
GCCCCCCAGCACTGGGGCGGGGACGCCCTTGGCAGGCTTCGGCCGTCCGGCGGGCGCTTAACGACCAACTTAGAACTG
GTACGGACAAGGGGAATCTGACTGTCTAATTAAAACATAGCATTGCGATGGCCAGAAAGTGGTGTTGACGCAATGTGA
TTTCTGCCCAGTGCTCTGAATGTCAAAGTGAAGAAATTCAACCAAGCGCGGGTAAACGGCGGGAGTAACTATGACTCT
CTTAAGGTAGCCAAATGCCTCGTCATCTAATTAGTGACGCGCATGAATGGATTAACGAGATTCCCACTGTCCCTATCTA
CTATCTAGCGAAACCACAGCCAAGGGAACGGGCTTGGCAGAATCAGCGGGGAAAGAAGACCCTGTTGAGCTTGACTCT
AGTTTGACATTGTGAAAAGACATATGGGGTGTAGAATAGGTGGGAGCTTCGGCGCCAGTGAAATACCACTACCTTTATC
GTTTTTTTACTTATTCAATGAAGCGGAACTGGGCTTCACCGCCCATCTTCTGGCGTTAAGGTCCTTCGCGGGCCGATCCG
GGTTGAAGACATTGTCAGGTGGGGAGTTTGGCTGGGGCGGCACATCTGTTAAACCACAACGCAGGTGTCCTAAGGGGG
ACTCATGGAGAACAGAAATCTCCAGTAGAACAAAAGGGTAAAAGTCCCCTTGATTTTGATTTTCAGTGTGAATACAAA
CCATGAAAGTGTGGCCTATCGATCCTTTAGTCCCTCGAAATTTGAGGCTAGAGGTGCCAGAAAAGTTACCACAGGGATA
ACTGGCTTGTGGCAGCCAAGCGTTCATAGCGACGTTGCTTTTTGATCCTTCGATGTCGGCTCTTCCTATCATACCGAAGC
AGAATTCGGTAAGCGTTGGATTGTTCACCCACTAATANGGAACGTGAGCTGGGTTTAGACCGTCGTGAGACAGGTTAGT
TTTACCCTACTGATGAAGGTCGCCGCAACGGTAATTCAATTTAGTACNAGAGGAACCGTTGATTCAGATAATTGGTTTT
TGCGGCTGTCTGACCAGGCAGTGCCGCGACGCTACCATCTGCCGGATAATGGCTGAACGCCTCTAAGTCAGAATCCGTG
CCGGAACGCGGCGATGTAGCCCCGCACGTCGTAGTTGGATACGAATAGGCCTCCGGGCCATGTACCTCAGCAGGCTGG
CGACGGCCCCGGGGAGAAACCCCCGAGGGCTGGCTGGCGGATTGCAATGTCACCTCGCGCGGGGATGAATCCTCTGC
AGACGACTGAAGTGACCAAGCGGGTCGTGTAAGCGGTCAAGTAGCCTTGTTGCTACGAGTCGCTGAGCGTCAGCCCGA
TCCTTGGCTAGATTTGTTGGCAAACACCTCCCATCAACGGGCCCGGCAGC
```

Figure 19
*Aspergillus niger* rRNA gene (SEQ ID NO: 66)

```
GGTCATTTAGAGGAAGTAAAAGTCGTAACAAGGTTTCCGTAGGTGAACCTGCGGAAGGATCATTACCGAGTGCGGGTC
CTTTGGGCCCAACCTCCCATCCGTGTCTATTGTACCCTGTTGCTTCGGCGGGCCCGCCGCTTGTCGGCCGCCGGGGGG
CGCCTCTGCCCCCCGGGCCCGTGCCCGCCGGAGACCCCAACACGAACACTGTCTGAAAGCGTGCAGTCTGAGTTGATTG
AATGCAATCAGTTAAAACTTTCAACAATGGATCTCTTGGTTCCGGCATCGATGAAGAACGCAGCGAAATGCGATAACT
AATGTGAATTGCAGAATTCAGTGAATCATCGAGTCTTTGAACGCACATTGCGCCCCTGGTATTCCGGGGGGCATGCCT
GTCCGAGCGTCATTGCTGCCCTCAAGCCCGGCTTGTGTGTTGGGTCGCCGTCCCCCTCTCCGGGGGGACGGGCCCGAAA
GGCAGCGGCGGCACCGCGTCCGATCCTCGAGCGTATGGGGCTTTGTCACATGCTCTGTAGGATTGGCCGGCGCCTGCCG
ACGTTTTCCAACCATTCTTTCCAGGTTGACCTCGGATCAGGTAGGGATACCCGCTGAACTTAAGCATATCAATAAGCGG
AGGAAAAGAAACCAACCGGGATTGCCTCAGTAACGGCGAGTGAAGCGGCAAGAGCTCAAATTTGAAAGCTGGCTCCTT
CGGAGTCCGCATTGTAATTTGCAGAGGATGCTTTGGGTGCGGCCCCCGTCTAAGTGCCCTGGAACGGGCCGTCAGAGA
GGGTGAGAATCCCGTCTTGGGCGGGGTGTCCGTGCCCGTGTAAAGCTCCTTCGACGAGTCGAGTTGTTTGGGAATGCAG
CTCTAAATGGGTGGTAAATTTCATCTAAAGCTAAATACTGGCCGGAGACCGATAGCGCACAAGTAGAGTGATCGAAAG
ATGAAAAGCACTTTGAAAAGAGAGTTAAACAGCACGTGAAATTGTTGAAAGGGAAGCGCTTGCGACCAGACTCGCCCG
CGGGGTTCAGCCGGCATTCGTGCCGGTGTACTTCCCCGTGGGCGGGCCAGCGTCGGTTTGGGCGGCCGGTCAAAGGCC
CCTGGAATGTAGTGCCCTCCGGGGCACCTTATAGCCAGGGGTGCAATGCGGCCAGCCTGGACCGAGGAACGCGCTTCG
GCACGGACGCTGGCATAATGGTCGTAAACGACCCGTCTTGAAACACGGACCAAGGAGTCTAACATCTACGCGAGTGTT
CGGGTGTCAAACCCGTGCGCGCAGTGAAAGCGAACGGAGGTGGGAGCCCCCTTGCGGGGCGCACCATCGACCGATCCT
GATGTCTTCGGATGGATTTGAGTAAGAGCGTAGCTGTGGGGACCCGAAAGATGGTGAACTATGCCTGAATAGGGCGAA
GCCAGAGGAAACTCTGGTGGAGGCTCGCAGCGGTTCTGACGTGCAAATCGATCGTCAAATTTGGGTATAGGGGCGAAA
GACTAATCGAACCATCTAGTAGCTGGTTCCTGCCGAAGTTTCCCTCAGGATAGCAGTAACGCAAAATCAGTTTTATGAG
GTAAAGCGAATGATTAGAGGCATTGGGGTTGAAACAACCTTAACCTATTCTCAAACTTTAAATATGTAAGAAGCCCTTG
TTGCTTAGTTGAACGTGGGCATTAGAATGGAGCGTTACTAGTGGGCCATTTTTGGTAAGCAGAACTGGCGATGCGGGAT
GAACCGAACGCGAGGTTAAGGTGCCGGAATGCACGCTCATCAGACACCACAAAAGGTGTTAGTTCATCTAGACAGCCC
GACGGTGGCCATGGAAGTCGGAATCCGCTAAGGAGTGTGTAACAACTCACGGGCCGAATGAACTAGCCCTGAAAATGG
ATGGCGCTCAAGCGTGCTACCCATACCTCGCCGTCGGGGTAGAAACGATGCCCCGACGAGTAGGCAGGCGTGGGGGTC
CGTGACGAAGCCTTGGGAGTGATCCCGGGTCGAACGGCCCCTAGTGCAGATCTTGGTGGTAGTAGCAAATACTCAAAT
GAGAACTTTGAGGACTGAAGTGGGGAAAGGTTCCATGTGAACAGCAGTTGGACATGGGTTAGTCGATCCTAAGGCATA
GGGAAGTTCCGTTTGAAAGGCGCCCTCGTGCGCCGTGTGCCGAAAGGGAAGCCGGTTAACATTCCGGCACCTGGATGT
GGATTCTCCACGGCAACGTAACTGAACGCGGAGACATCGGCGGGGGTCCTGGGAAGAGTTCTCTTTTCTTCTTGACGGC
CTATCACCCTGAAATCGGTTTGTCCGGAGCTAGGGTTCCACGGCCGGCAGAGCCCTGCACCTTTGCAGGGTCCGGTGCG
CCCCCGACGATCCTTGAAAATCCGCGGGAAGGAATAGTTTTCACGCCAGGTCGTACTCATAACCGCAGCAGGTCTCCA
AGGTGAACAGCCTCTAGTTGATAGAACAATGTAGATAAGGGAAGTCGGCAAAATGGATCCGTAACTTCGGGATAAGGA
TTGGCTCTAAGGGTCGGGCTCGCTGGGCCTTGGGGGAAACCCCTCGGAGCAGGGGGGCACTAGCCGGGCAACCGGCCG
GCGCCCCCCAGCACCGGGTGGGGGACGCCCTTGGCAGGCTTCGGCCGTCCGGCGGGCGCTTAACGACCAACTTAGAAC
TGGTACGGACAAGGGGAATCTGACTGTCTAATTAAAACATAGCATTGCGATGGCCAGAAAGTGGTGTTGACGCAATGT
GATTTCTGCCCAGTGCTCTGAATGTCAAAGTGAAGAAATTCAACCAAGCGCGGGTAAACGGCGGGAGTAACTATGACT
CTCTTAAGGTAGCCAAATGCCTCGTCATCTAATTAGTGACGCGCATGAATGGATTAACGAGATTCCCACTGTCCCTATC
TACTATCTAGCGAAACCACAGCCAAGGGAACGGGCTTGGCAGAATCAGCGGGGAAAGAAGACCCTGTTGAGCTTGACT
CTAGTTTGACATTGTGAAAAGACATATGGGGGTGTAGAATAGGTGGGAGCTTCGGCGCCAGTGAAATACCACTACCTTTA
TCGTTTTTTTACTTATTCAATGAAGCGGAACTGGGCTTCACCGCCCATCTTCTGGCGTTAAGGTCCTTCGCGGGCCGATC
CGGGTTGAAGACATTGTCAGGTGGGGAGTTTGGCTGGGGCGGCACATCTGTTAAACCACAACGCAGGTGTCCTAAGGG
GGACTCATGGAGAACAGAAATCTCCAGTAGAACAAAAGGGTAAAAGTCCCCTTGATTTTGATTTTCAGTGTGAATACA
AACCATGAAAGTGTGGCCTATCGATCCTTTAGTCCCTCGAAATTTGAGGCTAGAGGTGCCAGAAAAGTTACCACAGGG
ATAACTGGCTTGTGGCAGCCAAGCGTTCATAGCGACGTTGCTTTTTGATCCTTCGATGTCGGCTCTTCCTATCATACCGA
AGCAGAATTCGGTAAGCGTTGGATTGTTCACCCACTAATAGGGAACGTGAGCTGGGTTTAGACCGTCGTGAGACAGGT
TAGTTTTACCCTACTGATGAAGGTCGCCGCAACGGTAATTCAATTTAGTACGAGAGGAACCGTTGATTCAGATAATTGG
TTTTTGCGGCTGTCTGACCAGCAGTGCCGCGACGCTACCATCTGCCGGATAATGGCTGAACGCCTCTAAGTCAGAATC
CGTGCCGGAACGCGGCGATGTTGCCCCGCACGTCGTAGTTGGATAGAATAGGCCTCCGGGCCATGCACCTCAGCAGG
CTGGCGACGGCTCCTAGGGAGAAGCCCCTGGGAGCTGGCTGGCGAATTGCAATGTCACCTCGCGCGGGATGAATCCT
CTGCAGACGACTGAAGTGACCAAGCGGGTCGTGTACGCGGTCAAGTAGCCTTGTTGCTACGAGTCGCTGAGCGTCAGC
CCGTCCTTGGCTAGATTTGTGTTATACACCTCCCCCACTGACAGGTCCGGCAGC
```

Figure 20
*Aspergillus oryzae* rRNA gene (SEQ ID NO: 67)

```
GTCAAACCCGGTCATTTAGAGGAAGTAAAAGTCGTAACAAGGTTTCCGTAGGTGAACCTGCGGAAGGATCATTACCGA
GTGTAGGGTTCCTAGCGAGCCCAACCTCCCACCCGTGTTTACTGTACCTTAGTTGCTTCGGCGGGCCCGCCATTCATGGC
CGCCGGGGGCTCTCAGCCCCGGGCCCGCGCCCGCCGGAGACACCACGAACTCTGTCTGATCTAGTGAAGTCTGAGTTG
ATTGTATCGCAATCAGTTAAAACTTTCAACAATGGATCTCTTGGTTCCGGCATCGATGAAGAACGCAGCGAAATGCGAT
AACTAGTGTGAATTGCAGAATTCCGTGAATCATCGAGTCTTTGAACGCACATTGCGCCCCTGGTATTCCGGGGGGCAT
GCCTGTCCGAGCGTCATTGCTGCCCATCAAGCACGGCTTGTGTGTTGGGTCGTCGTCCCCTCTCCGGGGGGGACGGGCC
CCAAAGGCAGCGGCGGCACCGCGTCCGATCCTCGAGCGTATGGGGCTTTGTCACCCGCTCTGTAGGCCCGGCCGGCGC
TTGCCGAACGCAAATCAATCTTTTTCCAGGTTGACCTCGGATCAGGTAGGGATACCCGCTGAACTTAAGCATATCAATA
AGCGGAGGAAAAGAAACCAACCGGGATTGCCTCAGTAACGGCGAGTGAAGCGGCAAGAGCTCAAATTTGAAAGCTGG
CTCCTTCGGGGTCCGCATTGTAATTTGCAGAGGATGCTTCGGGTGCGGCCCCTGTCTAAGTGCCCTGGAACGGGCCGTC
AGAGAGGGTGAGAATCCCGTCTGGGATGGGGTGTCCGCGCCCGTGTGAAGCTCCTTCGACGAGTCGAGTTGTTTGGGA
ATGCAGCTCTAAATGGGTGGTAAATTTCATCTAAAGCTAAATACTGGCCGGAGACCGATAGCGCACAAGTAGAGTGAT
CGAAAGATGAAAAGCACTTTGAAAAGAGAGTTAAAAAGCACGTGAAATTGTTGAAAGGGAAGCGCTTGCGACCAGAC
TCGCCTCCAGGGTTCAGCCGGCATTCGTGCCGGTGTACTTCCCTGGGGGCGGGCCAGCGTCGGTTTGGGCGGCCGGTCA
AAGGCTCCCGGAATGTAGTGCCCTCCGGGGCACCTTATAGCCGGGAGTGCAATGCGGCCAGCCTGGACCGAGGAACGC
GCTTCGGCACGGACGCTGGCATAATGGTCGTAAACGACCCGTCTTGAAACACGGACCAAGGAGTCTAACATCTACGCG
AGTGTTCGGGTGTCAAACCCGTACGCGCAGTGAAAGCGAACGGAGGTGGGAGCCCCCTCGTGGGGCGCACCATCGACC
GATCCTGATGTCTTCGGATGGATTTGAGTAAGAGCGTAAATGTGGGGACCCGAAAGATGGTGAACTATGCCTGAATAG
GGCGAAGCCAGAGGAAACTCTGGTGGAGGCTCGCAGCGGTTCTGACGTGCAAATCGATCGTCAAATTTGGGTATAGGG
GCGAAAGACTAATCGAACCATCTAGTAGCTGGTTCCTGCCGAAGTTTCCCTCAGGATAGCAGTAACGCGAATTCAGTTT
TATGAGGTAAAGCGAATGATTAGAGGCATTGGGGTTGAAACAACCTTAACCTATTCTCAAACTTTAAATATGTAAGAA
GCCCTTGTTGCTTAGTTGAACGTGGGCATTAGAATGGAGCGTTATTAGTGGGCCATTTTTGGTAAGCAGAACTGGCGAT
GCGGGATGAACCGAACGCGAGGTTAAGGTGCCGGAATGCACGCTCATCAGACACCACAAAAGGTGTTAGTTCATCTAG
ACAGCCCGACGGTGGCCATGGAAGTCGGAATCCGCTAAGGAGTGTGTAACAACTCACGGGCCGAATGAACTAGCCCTG
AAAATGGATGGCGCTCAAGCGTGTTACCCATACCTCGCCGCCGGGGTAGAAACGATGCCCCGGCGAGTAGGCAGGCGT
GGAGGTCCGTGACGAAGCCTTGGGAGTGATCCCGGGTCGAACGGCCTCTAGTGCAGATCTTGGTGGTAGTAGCAAATA
CTCAAATGAGAACTTTGAGGACTGAAGTGGGGAAAGGTTCCATGTGAACAGCAGTTGGACATGGGTTAGTCGATCCTA
AGGCATAGGGAAGTTCCGTTTGAAAGGCGCCCTCGTGCGCCGTGTGCCGAAAGGGAAGCCGGTTAACATTCCGGCACC
TGGATGTGGATTCTCCACGGCAACGTAACTGAACGCGGAGACGTCGGCGGGGGTCCTGGGAAGAGTTCTCTTTTCTTCT
TGACAGCCTACCACCCTGAAATCGGTTTGTCCGGAGCTAGGGTTCAATGGCTGGCAGAGCCCCGCACCTTTGCGGGGTC
CGGTGCGCCCCCGACGACCCTTGAAAATCCGCGGGAAGGAATAGTTTTCACGCCAGGTCGTACTCATAACCGCAGCAG
GTCTCCAACGGTGAACAGCCTCTAGTTGATAGAACAATGTAGATAAGGGAAGTCGGCAAAATGGATCCGTAACTTCGGG
ATAAGGATTGGCTCTAAGGGTCGGGCTCGCTGGGCCTTGGGGGGAACCCCTCGGAGCAGGGGGGCACTAGCCGGGCAA
CCGGCCGGCGCCCCCAGCACCGGGTGGGGACGCCCTTGGCAGGCTTCGGCCGTCCGGCGGGCGCTTAACGACCAAC
TTAGAACTGGTACGGACAAGGGGAATCTGACTGTCTAATTAAAACATAGCATTGCGATGGCCAGAAAGTGGTGTTGAC
GCAATGTGATTTCTGCCCAGTGCTCTGAATGTCAAAGTGAAGAAATTCAACCAAGCGCGGGTAAACGGCGGGAGTAAC
TATGACTCTCTTAAGGTAGCCAAATGCCTCGTCATCTAATTAGTGACGCGCATGAATGGATTAACGAGATTCCCACTGT
CCCTATCTACTATCTAGCGAAACCACAGCCAAGGGAACGGGCTTGGCAGAATCAGCGGGGAAAGAAGACCCTGTTGAG
CTTGACTCTAGTTTGACATTGTGAAAAGACATATGGGGTGTAGAATAGGTGGGAGCTCCGGCGCCAGTGAAATACCAC
TACCTTTATCGTTTTTTTACTTATTCAATGAAGCGGAACTGGGCTTCACCGCCCATCTTCTGGCGTTAAGGTCCTTCGCG
GGCCGATCCGGGTTGAAGACATTGTCAGGTGGGGAGTTTGGCTGGGGCGGCACATCTGTTAAACCACAACGCAGGTGT
CCTAAGGGGGACTCATGGAGAACAGAAATCTCCAGTAGAACAAAAGGGTAAAAGTCCCCTTGATTTTGATTTTCAGTG
TGAATACAAACCATGAAAGTGTGGCCTATCGATCCTTTAGTCCCTCGAAATTTGAGGCTAGAGGTGCCAGAAAAGTTAC
CACAGGGATAACTGGCTTGTGGCAGCCAAGCGTTCATAGCGACGTTGCTTTTTGATCCTTCGATGTCGGCTCTTCCTATC
ATACCGAAGCAGAATTCGGTAAGCGTTGGATTGTTCACCCACTAATAGGGAACGTGAGCTGGGTTTAGACCGTCGTGA
GACAGGTTAGTTTTACCCTACTGATGAAGGTCGCCGCAACGGTAATTCAATTTAGTACGAGAGGAACCGTTGATTCAGA
TAATTGGTTTTTGCGGCTGTCTGACCAGGCAGTGCCGCGACGCTACCATCTGCCGGATAATGGCTGAACGCCTCTAAGT
CAGAATCCGTGCCGGAACGCGGCGATGTTGCCCCGCACGTCGTAGTTGGATACGAATAGGCCTCCGGGCCACGAACCT
CAGCAGGCTGGCGACGGCTCCCCGGGAGAAGCCCCGGGGAGCTGGCTGGCGGATTGCAATGTCACCTCGCGCGGGGAT
GAATCCTCTGCATACGACTGAAGTGACCAAGCGGGTCGTGTAAGCGGTCAAGTAGCCTTGTTGCTACGAGTCGCTGAGC
GTCAGCCCGACCTTGGCTAGATTTGTGTACCA
```

Figure 21
*Aspergillus terreus* rRNA gene (SEQ ID NO: 68)

```
CGGAAAGTTGGTCAAACCCGGTCATTTAGAGGAAGTAAAAGTCGTAACAAGGTTTCCGTAGGTGAACCTGCGGAAGGA
TCATTACCGAGTGCGGGTCTTTATGGCCCAACCTCCCACCCGTGACTATTGTACCTTGTTGCTTCGGCGGGCCCGCCAGC
GTTGCTGGCCGCCGGGGGGCGACTCGCCCCCGGGCCCGTGCCCGCCGGAGACCCCAACATGAACCCTGTTCTGAAAGC
TTGCAGTCTGAGTGTGATTCTTTGCAATCAGTTAAAACTTTCAACAATGGATCTCTTGGTTCCGGCATCGATGAAGAAC
GCAGCGAAATGCGATAACTAATGTGAATTGCAGAATTCAGTGAATCATCGAGTCTTTGAACGCACATTGCGCCCCTGG
TATTCCGGGGGGCATGCCTGTCCGAGCGTCATTGCTGCCCTCAAGCCCGGCTTGTGTGTTGGGCCCTCGTCCCCCGGCTC
CCGGGGGACGGGCCCGAAAGGCAGCGGCGGGCACCGCGTCCGGTCCTCGAGCGTATGGGGCTTCGTCTTCCGCTCCGT
AGGCCCGGCCGGCGCCCGCCGACGCATTTATTTGCAACTTGTTTTTTTCCAGGTTGACCTCGGATCAGGTAGGGATACC
CGCTGAACTTAAGCATATCAATAAGCGGAGGAAAAGAAACCAACCGGGATTGCCTCAGTAACGGCGAGTGAAGCGGC
AAGAGCTCAAATTTGAAAGCTGGCTCCTTCGGGGTCCGCATTGTAATTTGCAGAGGATGCTTCGGGTGCAGCCCCCGTC
TAAGTGCCCTGGAACGGGCCGTCATAGAGGGTGAGAATCCCGTATGGGGCGGGGTGTCTGCGTCCGTGTGAAGCTCCT
TCGACGAGTCGAGTTGTTTGGGAATGCAGCTCTAAATGGGTGGTAAATTTCATCTAAAGCTAAATACTGGCCGGAGACC
GATAGCGCACAAGTAGAGTGATCGAAAGATGAAAAGCACTTTGAAAAGAGAGTTAAACAGCACGTGAAATTGTTGAA
AGGGAAGCGCTTGCAACCAGACTCGCTCGCGGGGTTCAGCCGGGCTTCGGCCCGGTGTACTTCCCCGCGGGCGGGCCA
GCGTCGGTTTGGGCGGCCGGTCAAAGGCCTCCGGAATGTAGCGCCCTTCGGGGCGCCTTATAGCCGGGGGTGCAATGC
GGCCAGCCTGGACCGAGGAACGCGCTTCGGCACGGACGCTGGCATAATGGTTGTAAACGACCCGTCTTGAAACACGGA
CCAAGGAGTCTAACATCTACGCGAGTGTTCGGGTGTCAAACCCGTACGCGCAGTGAAAGCGAACGGAGGTGGGAGCCC
CCTCGCGGGGCGCACCATCGACCGATCCTGATGTCTTCGGATGGATTTGAGTACGAGCGTAGCTGTGGGGACCCGAAA
GATGGTGAACTATGCCTGAATAGGGCGAAGCCAGAGGAAACTCTGGTGGAGGCTCGCAGCGGTTCTGACGTGCAAATC
GATCGTCAAATTTGGGTATAGGGGCGAAAGACTAATCGAACCATCTGGTAGCTGGTTCCTGCCGAAGTTTCCCTCAGGA
TAGCAGTAACGCGGATCAGTTTTATGAGGTAAAGCGAATGATTAGAGGCATTGGGGTTGAAACAACCTTAACCTATTCT
CAAACTTTAAATATGTAAGAAGCGCTTGTTGCTTAGTTGAACGTGCGCATTAGAATGGAGCGTTACTAGTGGGCCATTT
TTGGTAAGCAGAACTGGCGATGCGGGATGAACCGAACGCGAGGTTAAGGTGCCGGAATGCACGCTCATCAGACACCAC
AAAAGGTGTTAGTTCATCTAGACAGCCCGACGGTGGCCATGGAAGTCGGAATCCGCTAAGGAGTGTGTAACAACTCAC
GGGCCGAATGAACTAGCCCTGAAAATGGATGGCGCTCAAGCGTGCTACCCATACCTCGCCGTCGGGGTAGAAACGATG
CCCCGACGAGTAGGCAGGCGTGGAGGTCCGTGACGAAGCCTTGGGCGTGAGCCCGGGTCGAACGGCCTCTAGTGCAGA
TCTTGGTGGTAGTAGCAAATACTCAAATGAGAACTTTGAGGACTGAAGTGGGGAAAGGTTCCATGTGAACAGCAGTTG
GACATGGGTTAGTCGATCCTAAGGCATAGGGAAGTTCCGTTTGAAAGGCGCCCTCGTGCGCCGTGTGCCGAAAGGGAA
GCCGGTTAACATTCCGGCACCTGGATGTGGATTCTCCACGGCAACGTAACTGAACGCGGAGACGTCGGCGGGAGTCCT
GGGAAGAGTTCTCTTTTCTTCTTGACAGCCTATCACCCTGAAATCGGTTTGTCCGGAGCTAGGGTTCCATGGCTGGCAG
AGCCCCGCACCTTTGCGGGGTCCGGTGCGCTCCCGACGACCCTTGAAAATCCGCGGGAAGGAATAGTTTTCACGCCAG
GTCGTACTCATAACCGCAGCAGGTCTCCAAGGTGAACAGCCTCTAGTTGATAGAACAATGTAGATAAGGGAAGTCGGC
AAAATGGATCCGTAACTTCGGGATAAGGATTGGCTCTAAGGGTCGGGCTCGCTGGGCCTTGGGGGGAACCCCCCGGAG
CAGGGAGGCACTAGCCGGGCAACCGGCCGGCGCTTCCCAGCACCGGGGCGGGACGCCCTTGGCAGGCTTCGGCCGTC
CGGCGGGCGCTTAACGACCAACTTAGAACTGGTACGGACAAGGGGAATCTGACTGTCTAATTAAAACATAGCATTGCG
ATGGCCAGAAAGTGGTGTTGACGCAATGTGATTTCTGCCCAGTGCTCTGAATGTCAAAGTGAAGAAATTCAACCAAGC
GCGGGTAAACGGCGGGAGTAACTATGACTCTCTTAAGGTAGCCAAATGCCTCGTCATCTAATTAGTGACGCGCATGAAT
GGATTAACGAGATTCCCACTGTCCCTATCTACTATCTAGCGAAACCACAGCCAAGGGAACGGGCTTGGCAGAATCAGC
GGGGAAAGAAGACCCTGTTGAGCTTGACTCTAGTTTGACATTGTGAAAAGACATATGGGGTGTAGAATAGGTGGGAGC
TCCGGCGCCAGTGAAATACCACTACCTTTATCGTTTTTTTACTTATTCAATGAAGCGGAACTGGGCTTCACCGCCCATCT
TCTGGCGTTAAGGTCCTTCGCGGGCCGATCCGGGTTGAAGACATTGTCAGGTGGGGAGTTTGGCTGGGGCGGCACATCT
GTTAAACCACAACGCAGGTGTCCTAAGGGGGACTCATGGAGAACAGAAATCTCCAGTAGAACAAAAGGGTAAAAGTC
CCCTTGATTTTGATTTTCAGTGTGAATACAAACCATGAAAGTGTGGCCTATCGATCCTTTAGTCCCTCGAAATTTGAGGC
TAGAGGTGCCAGAAAAGTTACCACAGGGATAACTGGCTTGTGGCAGCCAAGCGTTCATAGCGACGTTGCTTTTTGATCC
TTCGATGTCGGCTCTTCCTATCATACCGAAGCAGAATTCGGTAAGCGTTGGATTGTTCACCCACTAATAGGGAACGTGA
GCTGGGTTTAGACCGTCGTGAGACAGGTTAGTTTTACCCTACTGATGAAGGTCGCCGCAACGGTAATTCAATTTAGTAC
GAGAGGAACCGTTGATTCAGATAATTGGTTTTTGCGGCTGTCTGACCAGGCAGTGCCGCGACGCTACCATCTGCCGGAT
AATGGCTGAACGCCTCTAAGTCAGAATCCGTGCCGGAACGCGGCGATGTAGCCCCGCACGTCGTAGTTGGATACGAAT
AGGCCTTCGGGCCCTGAACCTCAGCAGGCTGGCGACGGCGCCCGGGGAGAAGCCCTCGGGTGCTGCTGGCGGATTGC
AATGTCACCTCGCGCGGGGATGAATCCTCTGCAGACGACTGAAGTGACCAAGCGGGTCGTGTAAGCGGTCAAGTAGCC
TTGTTGCTACGAGTCGCTGAGCGTCAGCCCGCCCTTGGCTAGATTTGTGTTTACACCCTCC
```

Figure 22

_Batrachochytrium dendrobatidis_ rRNA gene (SEQ ID NO: 69)

TTTAAAAGAAGCTGGTCAAACTTGGTCATTTAGAGGAAGTAAAAGTCGTACCAAGGTAACCGTAGGTGACCCTGCGGT
TGGATCATTAATATTTGTTTGGGGGGGGGGTTGTTTTATTGATGTGTAAATGTTGATGGAATGACCCATTGTTTTTTCAA
AAAACACCCTTGATATAATACAGTGTGCCATATGTCACGAGTCGAACAAAATTTATTTATTTTTTCGACAAATTAATTG
GAAATTGAATAATTTAATTGAAAAAAATTGAAAATAAATATTAAAAACAACTTTTGACAACGGATCTCTTGGCTCTCGC
AACGATGAAGAACGCAGCGAAATGCGATACGTAATGTGAATTGCAAACCTTTGTGAATCATTAAATCTTTGAACGCAC
ATTGCACTCGTAAAAGAGTATACATGTTTGAGAATTATAAAAATACATTGTCCGAATTGACTGGACAGATATGAACCAT
GTCAAAAATATTTGACAGGTTTTAAAAGTAGTAGTAAAAAAGAGTGATACAAAAAGTAGTAATACAACGTCACACCAA
CAAAAATATAATCTCAAATCATGCAAGATTACCCGCTGAACTTAAGCATATCAATAAGCGGTGGAAAAGAAACTAACA
AGGATTCCCCTAGTAACGGCGAGTGAAGCGGGAATAGCTCAAATTTGAAATCTCACAATAGTGCGAATTGTAGTTTAG
AGAAACCCCATTTTTTTACTAGACAATCAAAAAGTTTTTTGGAATAAAACATCATAGAGGGTGACAATCCCGTTTTTGA
TTGCCAAGTAATAATGTATTGGGATATCCAAGAGTCGGTTTGTTTGGGAATGCAGACCAAAATGGGTGGTAAATACCAT
CTAAAGCTAAATATTGGCGAGAGACCGATAGCGAACAAGTACCGTGAGGGAAAGATGAAAAGAACTTTGAAAAGAGA
GTTAAACAGTACGTGAAATTGTCAAAAGGGAAACGCTTGAAACCAGTATTTAAACATGAATTTCAATTCACCATGTGGT
GAGTCTATATTTGATGATTAGAGTCAACAAGGGTTTGACAAGTGATAAAAACGGCTAGAGTAGACCTATTAGGACAAA
GTCTAGTCAAATGTCACGGGTTGGACTTTTTTTAGTGTAATGTATAACATGTCTTGTTTTGACTGTGGTGGTGTTGAAAT
GCATGCAGATCAATGACACTCCAACAAATCAATTCATACTTACCCACCACAAAAACGTTGAGGAAATGGTTTTAAACG
ACCCGTCTTGAAACACGGACCAAGGAGTCCAACATATATGCAAGTATTTGAGTGAATAAACCCAAATGCAAAATAAAA
GTGAAAAGGTGGGAATATATAGCACCATTGGCCAATTAATAATAATTGAGCAAGAGCATACATGTTGGGACCCGAAAG
ATGGTGAACTATGCCTGAATAGGGTGAAGCCAGAGGAAACTCTGGTGGAGGCTCGTAGCGGTTCTGACGTGCAAATCG
ATCGTCGAATTTGGGTATAGGGGCGAAAGACTAATCGAACCATCTAGTAGCTGGTTCCCTCCGAAGTTTCCCTCAGGAT
AGCAGAAGCTCAGTATCAGTTTTATGAGGTAAAGCGAATGATTAGAGGCCTCGGGGAAGTAAATTCCTTGACCTATTCT
CAAACTTTAAATATGTAAGACGTTGTGGTTACTTGAATGAACCGCGACAGCGAATGAGAGTTTCTAGTGGGCCATTTTT
GGTAAGCAGAACTGGCGATGCGGGATGAACCGAACGTCGAGTTAAGGTGCCAGAATGCACGCTCATTTAGACACCACA
AAAGGTGTTGGTTCATCTAGACAGCAGGACGGTGGCCATGGAAGTTGGAACCCGCCAAGGAGTGTGTAACAACTCACC
TGCCGAATGAACTAGCCCTGAAAATGGATGGCGCTCAAGCGTGCTACCCATACTCGACCGTCGGACCAAATACAATGG
TTTGACGAGTAGGAGGGCGTGGAGGTTTGTGTGGAAGCTTTGGATGTGAATCCGAGTGAAACGGCCTCTAGTGCAGAT
CTTGGTGGTAGTAGCAAATATTCAAAAGAGAACTTTGAAGACTGAAGTGGAGAAAGGTTCCGTGTGAACAGCAGTTGG
ACACGGGTCAGTCGATCCTAAAGAGTAAGGGAAACCTGGTAATGCACAGTGTGCGGACTCTGAAAGGGCATCCGGTTA
ATATTCCGGAACTGGGAGGTGGAATAAGCGGCAACGCAAGACAACTTGGTGACGTTGGTAGGAACCCTAGAAAGAGA
TGTCTTTTCTTTTTAACCAAACAACAACCTTGGAAACGGATGAACCGGAGAAGAGGTTTGGGATGGGCAAAGCACTGCT
TCAGCAGTGTCTGGAGCGTTTCTAACGACCCGTGAAAAACCAAGGGACTAATTTTCACACCTAGTCGTACTCATAACCG
CAGCAGGTCTCCAAGGTGAACAGCCTCTAGTTGATAGAACAATGTAGATAAGGGAAGTCGGCAAAATAGATCCGTAAC
TTTGGGAAAAGGATTGGCTCCAGGGGTTGCGATGTAATCGATATCAACTAATCTGGAACTGGTACGGACATGGGGAAT
CTGACTGTCTAATTAAAACATAGCATTGCGATGGCCAGAAAGTGGTGTTGACGCAATGTGATTTCTGCCCAGTGCTCTG
AATGTCAAAGTGAAGAAATTCAACCAAGCGCGGGTAAACGGCGGGAGTAACTATGACTCTCTTAAGGTAGCCAAATGC
CTCGTCATCTAATTAGTGACGCGCATGAATGGATTAACGAGATTCCCACTGTCCCTATCTACTATCTAGCGAAACCACA
GCCAAGGGAACGGGCTTGGCAGAATCAGCGGGGAAAGAAGACCCTGTTGAGCTTGACTCTAGTTTGACATTGTGAAAA
AACATGGGGGGCGTAGAATAAGTGGGAGCTTTGGCACCGGTGAAATACCACTACCCCCAATGTTTTTTTACTTATTCAA
TGAAGCAGGATTGGCCGTCATGGCCATATTGTAGTGTTTGAACCTGGGTTGAAGACATTGTCAGGTGGGGAGTTTGGCT
GGGGCGGCACATCTGTTAAAAGATAACGCAGGTGTCCCAAGGGAAACTCATCGAGAACAGAAATCTCGAGTAGAACA
AAAGGGTAAACGTTTCCTTGATTTTGATTTTCAGTGTGAATACAAACCATGAAAGTGTGGCCTATCGATCCTTTAAATTC
TGGGTATTTCAGGTTAGAGGTGTCAGAAAAGTTACCACAGGGATAACTGGCTTGTGGCAGCCAAGCGTTCATAGCGAC
GTTGCTTTTTGATCCTTCGATGTCGGCTCTTCCTATCATTGAGAAGCAAAATTCTCAAAGCGTCGGATTGTTCACCCGCC
AACAGGGAACGTGAGCTGGGTTTAGACCGTCGTGAGACAGGTTAGTTTTACCCTACTGATGGAGGGTTGTCACAATAGT
AATTCAACGTAGTACGAGAGGAACTGTTGATTCACATAATTGGTTTTTGCGGTTAGCTGATCAGCTAGTGCCGCGACGC
TACCATGTGTAGGATTACGGCTGAACGCCTCTAAGTCGGAATCCATGCTAAAAGTGATGATGTGTCTCTGGATTGTTGA
TGAAAATAGATGCAAATCGTGTATTGTTTTGGTGTTGAGATGAAAGGGATGAAATCCGTTTTATTTGCGCCTAATAACA
AGTTTGGAATTCAGAGTGGAAATAAAGAGAAGACGACTTTTAATCACCCGGGTATTGTAAGCAGTAGAGTAGCCTTGT
TGTTACGATCTGGTGAGATTAAGCCTTGGGTTTTTTGATTTTTTTTTGGGGTGGAGTTACCTGAGGGTGTTGTATT

Figure 23
*Botrytis cinerea* rRNA gene (SEQ ID NO: 70)

```
CTTGGTCATTTAGAGGAAGTAAAAGTCGTAACAAGGTTTCCGTAGGTGAACCTGCGGAAGGATCATTACAGAGTTCAT
GCCCGAAAGGGTAGACCTCCCACCCTTGTGTATTATTACTTTGTTGCTTTGGCGAGCTGCCTTCGGGCCTTGTATGCTCG
CCAGAGAATACCAAAACTCTTTTTATTAATGTCGTCTGAGTACTATATAATAGTTAAAACTTTCAACAACGGATCTCTTG
GTTCTGGCATCGATGAAGAACGCAGCGAAATGCGATAAGTAATGTGAATTGCAGAATTCAGTGAATCATCGAATCTTT
GAACGCACATTGCGCCCCTTGGTATTCCGGGGGGCATGCCTGTTCGAGCGTCATTTCAACCCTCAAGCTTAGCTTGGTA
TTGAGTCTATGTCAGTAATGGCAGGCTCTAAAATCAGTGGCGGCGCCGCTGGGTCCTGAACGTAGTAATATCTCTCGTT
ACAGGTTCTCGGTGTGCTTCTGCCAAAACCCAAATTTTTCTATGGTTGACCTCGGATCAGGTAGGGATACCCGCTGAAC
TTAAGCATATCAATAAGCGGAGGAAAAGAAACCAACAGGGATTACCTCAGTAACGGCGAGTGAAGCGGTAAAAGCTC
AAATTTGAAATCTGGCTCTTTTAGAGTCCGAATTGTAATTTGTAGAAGATGCTTCGGGTGTGGTTCCGGTCTAAGTTCCT
TGGAACAGGACGTCATAGAGGGTGAGAATCCCGTATGTGACTGGATACCTATGCTCATGTGAAGCTCTTTCGACGAGTC
GAGTTGTTTGGGAATGCAGCTCAAAATGGGAGGTATATTTCTTCTAAAGCTAAATATTGGCCAGAGACCGATAGCGCAC
AAGTAGAGTGATCGAAAGATGAAAAGCACTTTGGAAAGAGAGTTAAACAGTACGTGAAATTGTTGAAAGGGAAGCGC
TTGCAATCAGACTTGCACTTGGTGTTCATCAGGGTCTCGTACCCTGTGTACTTCATCAAGTTCAGGCAGCATCAGTTTG
AGTGGTTAGATAAAGGCTTAGAGAATGTGGCCCTCTTCGGGGGGTGTTATAGCTCTAGGTGCAATGTAGCCTACTTGGA
CTGAGGACCGCGCTTCGGCTAGGATGCTGGCGTAATGGTTGTAAGCGACCCGTCTTGAAACACGGACCAAGGAGTGTA
CCTAATATGCGAGTGTTTGGGTGTTAAACCCATACGCGTAATGAAAGTGAACGCTGGTGAGAACCCTTAAGGGTGCATC
ATCGACCGATCTTGATGTCTTCGGATGGATTTGAGTAAGAGCATATTGGGTGCGACCCGAAAGATGGTGATCTATACGT
GAATAGGGTGAAGCCAGAGGAAACTCTGGTGGAGGCTCGCAGCGGTTCTGACGTGCAAATCGATCGTCAAATTTGCGT
ATAGGGGCGAAAGACTAATCGAACCATCTAGTAGCTGGTTCCTGCCGAAGTTTCCCTCAGGATAGCAGTGTTGTTTTCA
GTTTTATGAGGTAAAGCGAATGATTAGAGGCCTTGGGGTTGAAACAACCTTAACCTATTCTCAAACTTTAAATATGTAA
GAAGTCCTTGTTACTTAATTGAACGTGGACATTCGAATGTACCAACACTAGTGGGCCATTTTTGGTAAGCAGAACTGGC
GATGCGGGATGAACCGAACGCGAGGTTAAGGTGCCGGAATATACGCTCATCAGACACCACAAAAGGTGTTAGTTCATC
TAGACAGCAGGACGGTGGCCATGGAAGTCGGAATCCGCTAAGGAATGTGTAACAACTCACCTGCCGAATGAACTAGCC
CTGAAAATGGATGGCGCTTAAGCGTATTACCCATACCTCGCCGCCAGGGTAGAAACTATGCCCTGGCGAGTAGGCAGG
CGTGGAGGTTGTGACGAAGCCTTGGGAGTGATCCCGGGTAGAACAGCCTCTAGTGCAGATCTTGGTGGTAGTAGCAAA
TACTCAAATGAGAACTTTGAGGACTGAAGTGGGGAAAGGTTCCATGTGAACAGCAGTTGGACATGGGTTAGTCGATCC
TAAGAGATAGGGAAACTCCGTTTTAAAGTGCGCACTTGTGCGCCGTCCCTCGAAAGGGAAACCGGTTAATATTCCGGTA
CCTGGATTTGGATTCTCCACGGCAACGTAACTGAACGCGGAGACGACGGCGGGGGCCCCGGGAAGAGTTCTCTTTTCTT
CTTAACAGCCTATCACCCTGAAATCGGTTTGTCCGGAGCTAGGGTTTAACGGTTGGTAGAGCTCGACACCTCTGTCGGG
TCCGGTGCGCTCTCGACGTCCCTTGAAAATCCGGGAAGGAATAGCTTTCAAGCCAGGTCGTACTCATAACCGCAGCA
GGTCTCCAAGGTGAACAGCCTCTAGTTGATAGAACAATGTAGATAAGGGAAGTCGGCAAAATAGATCCGTAACTTCGG
GAAAAGGATTGGCTCTAAGGGTTGGGTACGTTGGGCCATTAGGGGATGCTCTTGGAGCAGAGGAGCACTAGCCTCACG
GCCGGCGCACCTCAGCATCGAGGGTTTGACGCTTTTGGCAGACTTCGGTCGTCCGGCGTACAATTAACAACCAACTTAG
AACTGGTACGGACAAGGGGAATCTGACTGTCTAATTAAAACATAGCATTGCGATGGCCAGAAAGTGGTGTTGACGCAA
TGTGATTTCTGCCCAGTGCTCTGAATGTCAAAGTGAAGTAATTCAACCAAGCGCGGGTAAACGGCGGGAGTAACTATG
ACTCTCTTAAGGTAGCCAAATGCCTCGTCATCTAATTAGTGACGCGCATGAATGGATTAACGAGATTCCCACTGTCCCT
ATCTACTATCTAGCGAAACCACAGCCAAGGGAACGGGCTTGGCAGAATCAGCGGGGAAAGAAGACCCTGTTGAGCTTG
ACTCTAGTTTGACATTGTGAAAAGACATAGGGGGTGTAGAATAGGTGGGAGCGCAAGCGCCGGTGAAATACCACTACC
CTTATCGTTTTTTTACTTATTCAATAAAGCGGAACTGGGTGTCAAAGCCCAACTTCTAGCATTAAGGTCCTTCGCGGGCT
GATCCGGGTTGAAGACATTGTCAGGTGGGGAGTTTGGCTGGGCGGCACATCTGTTAAACCATAACGCAGGTGTCCTA
AGGGGGACTCATGGAGAACAGAAATCTCCAGTAGAACAAAAGGGTAAAAGTCCCCTTGATTTTGATTTTCAGTGTGAA
TACAAACCATGAAAGTGTGGCCTATCGATCCTTTAGTCCCTCGAAATTTGAGGCTAGAGGTGCCAGAAAAGTTACCACA
GGGATAACTGGCTTGTGGCAGCCAAGCGTTCATAGCGACGTTGCTTTTTGATCCTTCGATGTCGGCTCTTCCTATCATAC
CGAAGCAGAATTCGGTAAGCGTTGGATTGTTCACCCACTAATAGGGAACGTGAGCTGGGTTTAGACCGTCGTGAGACA
GGTTAGTTTTACCCTACTGATGACCGTCGCCGCAATGGTAATTCAGCTTAGTACGAGAGGAACCGCTGATTCAGATAAT
TGGTTTTTGCGGCTGTCTGACAAGGCAGTGCCGCGAAGCTACCATCTGCTGGATAATGGCTGAACGCCTCTAAGTCAGA
ATCCATGCCAGAAAGCGGTGATTTATACCCACACATCGTAGTCGGATACGAATAGGCCTTTGGCCCTGAATCTTAGCTG
GCTGGTAACGGTCCTATTGAAGAAACTCTTTAGGACTAACTGGCGTCTTGCAATTTTACAATGCGTGGGGTTGAATCCT
TTGCATACGACTTAATTGTGCTATACGGTCCTGTAAGTAGTAGAGTAGCCTTGTTGTTACGATCTACTGAGGGTAAGCC
GTCCATAGCCTAGATTTGATTTATAATCTCCCATTTTTAGCTTGTC
```

Figure 24
*Candida albicans* rRNA gene (SEQ ID NO: 71)

TTGGTCATTTAGAGGAAGTAAAAGTCGTAACAAGGTTTCCGTAGGTGAACCTGCGGAAGGATCATTACTGATTTGCTTA
ATTGCACCACATGTGTTTTTCTTTGAAACAAACTTGCTTTGGCGGTGGGCCCAGCCTGCCGCCAGAGGTCTAAACTTAC
AACCAATTTTTTATCAACTTGTCACACCAGATTATTACTAATAGTCAAAACTTTCAACAACGGATCTCTTGGTTCTCGCA
TCGATGAAGAACGCAGCGAAATGCGATACGTAATATGAATTGCAGATATTCGTGAATCATCGAATCTTTGAACGCACA
TTGCGCCCTCTGGTATTCCGGAGGGCATGCCTGTTTGAGCGTCGTTTCTCCCTCAAACCGCTGGGTTTGGTGTTGAGCAA
TACGACTTGGGTTTGCTTGAAAGACGGTAGTGGTAAGGCGGGATCGCTTTGACAATGGCTTAGGTCTAACCAAAAACAT
TGCTTGCGGCGGTAACGTCCACCACGTATATCTTCAAACTTTGACCTCAAATCAGGTAGGACTACCCGCTGAACTTAAG
CATATCAATAAGCGGAGGAAAAGAAACCAACAGGGATTGCCTCAGTAGCGGCGAGTGAAGCGGCAAAAGCTCAAATT
TGAAATCTGGCGTCTTTGGCGTCCGAGTTGTAATTTGAAGAAGGTATCTTTGGGCCCGGCTCTTGTCTATGTTCCTTGGA
ACAGGACGTCACAGAGGGTGAGAATCCCGTGCGATGAGATGACCCGGGTCTGTGTAAAGTTCCTTCGACGAGTCGAGT
TGTTTGGGAATGCAGCTCTAAGTGGGTGGTAAATTCCATCTAAAGCTAAATATTGGCGAGAGACCGATAGCGAACAAG
TACAGTGATGGAAAGATGAAAAGAACTTTGAAAAGAGAGTGAAAAAGTACGTGAAATTGTTGAAAGGGAAGGGCTTG
AGATCAGACTTGGTATTTTGCATGCTGCTCTCTCGGGGGCGGCCGCTGCGGTTTACCGGGCCAGCATCGGTTTGGAGCG
GCAGGATAATGGCGGAGGAATGTGGCACGGCTTCTGCTGTGTGTTATAGCCTCTGACGATACTGCCAGCCTAGACCGA
GGACTGCGGTTTTTACCTAGGATGTTGGCATAATGATCTTAAGTGCCCCGTCTTGAAACACGGACCAAGGAGTCTAACG
TCTATGCGAGTGTTTGGGTGTAAAACCCGTACGCGTAATGAAAGTGAACGAAGGTGGGGGCCCATTAGGGTGCACCAT
CGACCGATCCTGATGTGTTCGGATGGATTTGAGTAAGAGCATAGCTGTTGGGACCCGAAAGATGGTGAACTATGCCTG
AATAGGGTGAAGCCAGAGGAAACTCTGGTGGAGGCTCGTAGCGGTTCTGACGTGCAAATCGATCGTCGAATTTGGGTA
TAGGGGCGAAAGACTAATCGAACCATCTAGTAGCTGGTTCCTGCCGAAGTTTCCCTCAGGATAGCAGAAGCTCGTATCA
GTTTTATGAGGTAAAGCGAATGATTAGAAGTCTTGGGGTTGAAATGACCTTAACTTATTCTCAAACTTTAAATATGTAA
GAAGTCCTTGTTGCTTAATTGAACGTGGACAATTGAATGAAGAGCTTTTAGTGGGCCATTTTTGGTAAGCAGAACTGGC
GATGCGGGATGAACCGAACGTGAAGTTAAAGTGCCGGAATGCACGCTCATCAGACACCACAAAAGGTGTTAGTTCATC
TAGACAGCCGGACGGTGGCCATGGAAGTCGGAATCCGCTAAGGAGTGTGTAACAACTCACCGGCCGAATGAACTAGCC
CTGAAAATGGATGGCGCTCAAGCGTGCTACTTATACTTCACCGTGATTGCTGTTTTGACGCTTTCACGAGTAGGCAGGC
GTGGAGGTCAGTGACGAAGCCTTTGCTGTAAAGCTGGGTCGAACGGCCTCTAGTGCAGATCTTGGTGGTAGTAGCAAA
TATTCAAATGAGAACTTTGAAGACTGAAGTGGGGAAAGGTTCCATGTCAACAGCAGTTGGACATGGGTTAGTCGATCC
TAAGAGATGGGGAAGCTCCGTTTCAACGTGCTTGATTTTTCAGGCCAACCATCGAAAGGGAATCCGGTTAAAATTCCGG
AACTTGGATATGGATTCTTCACGGCAACGTAACTGAATGTGGAGACGTCGGCGTGAGCCCTGGGAGGAGTTATCTTTTC
TTCTTAACAGCTTATCACCCTGGAATTGGTTTATCCGGAGATGGGGTCTTATGGCTGGAAGAGCGCGGTAATTTTGCCG
CGTCCGGTGCGCTTACGACGGTCCTTGAAAATCCACAGGAAGGAATAGTTTTCATGCCAAGTCGTACTCATAACCGCAG
CAGGTCTCCAAGGTTAACAGCCTCTAGTTGATAGAATAATGTAGATAAGGGAAGTCGGCAAAATAGATCCGTAACTTC
GGGATAAGGATTGGCTCTAAGGATCGGGTGTCTTGGGCCTTGTGTAGACGCGGCGGTGACTGTTGGCGGGCTGTTTTAC
GACGGACTGCTGGTGGATGCTGCTGTAGACACGCTTGGTAGGTCTTTATGGCCGTCCGGGGCACGTTTAACGATCAACT
TAGAACTGGTACGGACAAGGGGAATCTGACTGTCTAATTAAAACATAGCATTGTGATGGTCAGAAAGTGATGTTGACA
CAATGTGATTTCTGCCCAGTGCTCTGAATGTCAAAGTGAAGAAATTCAACCAAGCGCGGGTAAACGGCGGGAGTAACT
ATGACTCTCTTAAGGTAGCCAAATGCCTCGTCATCTAATTAGTGACGCGCATGAATGGATTAACGAGATTCCCACTGTC
CCTATCTACTATCTAGCGAAACCACAGCCAAGGGAACGGGCTTGGCAGAATCAGCGGGGAAAGAAGACCCTGTTGAGC
TTGACTCTAGTTTGACATTGTGAAAAGACATGGAGGGTGTAGAATAAGTGGGAGCTTCGGCGCCGGTGAAATACCACT
ACCTCTATAGTTTTTTTACTTATTCAATGAAGCGGAGCTGGAGGTCAAACTCCACGTTCTAGCATTAAGCCCTCTGGGCG
ATCCGGGTTGAAGACATTGTCAGGTGGGGAGTTTGGCTGGGGCGGCACATCTGTTAAACGATAACGCAGGTGTCCTAA
GGGGGACTCATGGAGAACAGAAATCTCCAGTAGAACAAAAGGGTAAAAGTCCCCTTGATTTTGATTTTCAGTGTGAAT
ACAAACCATGAAAGTGTGGCCTATCGATCCTTTAGTCCCTCGGAATTTGAGGCTAGAGGTGCCAGAAAAGTTACCACA
GGGATAACTGGCTTGTGGCAGTCAAGCGTTCATAGCGACATTGCTTTTTGATTCTTCGATGTCGGCTCTTCCTATCATAC
CGAAGCAGAATTCGGTAAGCGTTGGATTGTTCACCCACTAATAGGGAACGTGAGCTGGGTTTAGACCGTCGTGAGACA
GGTTAGTTTTACCCTACTGATGAATGTTATCGCAATAGTAATTGAACTTAGTACGAGAGGAACCGTTCATTCAGATAAT
TGGTTTTTGCGGCTGTCTGATCAGGCAACGCCGCGAAGCTACCATCTGCTGGATTATGGCTGAACGCCTCTAAGTCAGA
ATCCATGCTAGAACGCGATGATTTTTGCCCTGCACATTTTAGATGGATACGAATAAGACTTTTTAGTCGCTGGACCATA
GCAGGCTGGCAACGGTGCGCTTAGCGGAAAGGCTTTGTGCGCTTGCCGGCGGATAGCAATGTCAACATGCGCGGGAT
AAATCCTTTGCATACGACTTAGATGTACAACGGAGTATTGTAAGCAGTAGAGTAGCCTTGTTGTTACGATCTGCTGAGA
TTAAGCTCTTGTTGTCTGATTTGT

Figure 25
*Candida dublineinsis* rRNA gene (SEQ ID NO: 72)

```
CTTGGTCATTTAGAGGAAGTAAAAGTCGTAACAAGGTTTCCGTAGGTGAACCTGCGGAAGGATCATTACTGATTTGCTT
AATTGCACCACATGTGTTTTGTTCTGGACAAACTTGCTTTGGCGGTGGGCCCCTGCCTGCCGCCAGAGGACATAAACTT
ACAACCAAATTTTTTATAAACTTGTCACGAGATTATTTTTAATAGTCAAAACTTTCAACAACGGATCTCTTGGTTCTCGC
ATCGATGAAGAACGCAGCGAAATGCGATACGTAATATGAATTGCAGATATTCGTGAATCATCGAATCTTTGAACGCAC
ATTGCGCCCTCTGGTATTCCGGAGGGCATGCCTGTTTGAGCGTCGTTTCTCCCTCAAACCCCTAGGGTTTGGTGTTGAGC
AATACGACTTGGGTTTGCTTGAAAGATGATAGTGGTATAAGGCGGAGATGCTTGACAATGCTTAGGTGTAACCAAAA
ACATTGCTAAGGCGGTCTCTGGCGTCGCCCATTTTATTCTTCAAACTTTGACCTCAAATCAGGTAGGACTACCCGCTGAA
CTTAAGCATATCAATAAGCGGAGGAAAAGAAACCAACAGGGATTGCCTCAGTAGCGGCGAGTGAAGCGGCAAAAGCT
CAAATTTGAAATCTGGCGTCTTTGGCGTCCGAGTTGTAATTTGAAGAAGGTATCTTTGGGCCCGGCTCTTGTCTATGTTC
CTTGGAACAGGACGTCACAGAGGGTGAGAATCCCGTGCGATGAGATGGCCCGGGTCTATGTAAAGTTCCTTCGACGAG
TCGAGTTGTTTGGGAATGCAGCTCTAAGTGGGTGGTAAATTCCATCTAAAGCTAAATATTGGCGAGAGACCGATAGCG
AACAAGTACAGTGATGGAAAGATGAAAAGAACTTTGAAAAGAGAGTGAAAAAGTACGTGAAATTGTTGAAAGGGAAG
GGCTTGAGATCAGACTTGGTATTTTGCAAGTTACTCTTTCGGGGGTGGCCTCTGCGGTTTACCGGGCCAGCATCGGTTTG
GAGCGGTAGGATAATGGCGGGGGAATGTGGCACGACTTTGGTTGTGTGTTATAGCCTCTGACGATACTGCCAGCCTAG
ACCGAGGACTGCGGTTTTACCTAGGATGTTGGCATAATGATCTTAAGTCGCCCGTCTTGAAACACGGACCAAGGAGTC
TAACGTCTATGCGAGTGTTTGGGTGTAAAACCCGTACGCGTAATGAAAGTGAACGAAGATGGGGGCCTGTATGGGTGC
ACCATCGACCGATCCTGATGTGTTCGGATGGATTTGAGTAAGAGCATAGCTGTTGGGACCCGAAAGATGGTGAACTAT
GCCTGAATAGGGTGAAGCCAGAGGAAACTCTGGTGGAGGCTCGTAGCGGTTCTGACGTGCAAATCGATCGTCGAATTT
GGGTATAGGGGCGAAAGACTAATCGAACCATCTAGTAGCTGGTTCCTGCCGAAGTTTCCCTCAGGATAGCAGAAGCTC
GTATCAGTTTTATGAGGTAAAGCGAATGATTAGAAGTCTTGGGGTTGAAATGACCTTAACTTATTCTCAAACTTTAAAT
ATGTAAGAAGTCCTTGTTGCTTAATTGAACGTGGACAATTGAATGAAGAGCTTTTAGTGGGCCATTTTTGGTAAGCAGA
ACTGGCGATGCGGGATGAACCGAACGTGAAGTTAAAGTGCCGGAATGCACGCTCATCAGACACCACAAAAGGTGTTAG
TTCATCTAGACAGCCGGACGGTGGCCATGGAAGTCGGAATCCGCTAAGGAGTGTGTAACAACTCACCGGCCGAATGAA
CTAGCCCTGAAAATGGATGGCGCTCAAGCGTGCTACTTATACTTCACCGTGATTGCTTTTTTGACGCTTTCACGAGTAGG
CAGGCGTGGAGGTCAGTGACGAAGCCTTTGCTGTAAAGCTGGGTCGAACGGCCTCTAGTGCAGATCTTGGTGGTAGTA
GCAAATATTCAAATGAGAACTTTGAAGACTGAAGTGGGGAAAGGTTCCATGTCAACAGCAGTTGGACATGGGTTAGTC
GATCCTAAGAGATGGGGAAGCTCCGTTCAACGCGCTTGATTTTTCAGGCCAACCATCGAAAGGGAATCCGGTTAAAAT
TCCGGAACTTGGATATGGATTCTTCACGGCAACGTAACTGAATGTGGAGACGTCGGCGTGAGCCCTGGGAGGAGTTAT
CTTTTCTTCTTAACAGCTTATCACCCTGGAATTGGTTTATCCGGAGATGGGGTCTTATGGCTGGAAGAGCGCGGTAATTT
TGCCGCGTCCGGTGCGCTTACGACGGTCCTTGAAAATCCACAGGAAGGAATAGTTTTCATGCCAAGTCGTACTCATAAC
CGCAGCAGGTCTCCAAGGTTAACAGCCTCTAGTTGATAGAATAATGTAGATAAGGGAAGTCGGCAAAATAGATCCGTA
ACTTCGGGATAAGGATTGGCTCTAAGGATCGGGTGTTTTGGGCCTTGTGTAGACGCGGTGGTGACTGGTGGCGGGCTGT
TTCACGACGGACTGCTGTTGGACGCTGCTGTAGACACGCTTGGTAGGCTCTTGTAGCCGTCCGGGGCACGCTTAACGAT
CAACTTAGAACTGGTACGGACAAGGGGAATCTGACTGTCTAATTAAAACATAGCATTGTGATGGTCAGAAAGTGATGT
TGACACAATGTGATTTCTGCCCAGTGCTCTGAATGTCAAAGTGAAGAAATTCAACCAAGCGCGGGTAAACGGCGGGAG
TAACTATGACTCTCAACCTATAAGGGAGGCAAAAGTAGGGACGCTATGGTTTCCAGAAATGGGCCGAGGTGTTTTTGA
CCTGCTAGTCGATCTGGTTAATTAGGTATTTTGTATATTACTTATCAGAGTATTCTCCTGGTATTATACATTTTACTTTAT
GACGACAACTATTACCCGCGGGACAACCATTTCTTGATTTATTTACTGCAAGTGATTCTAGAATATGGTGATTCCAGTTA
TAACACCAACTGTTATGACACAAGTGTGATACAGTCATAAGCTGTGGGTAACCAGCGGCGACATAACCTGGTACGGGG
AAGGCCTCGAAGCAGTATATATTTTGGGATTGAAAATCGGGTTGCAAAACTTTTGTTTTTGGAAACACGGTTGGTGAGG
AAAAAAAAATATTTTTTCCCCGCACTTGAAGAAATATATGTTGTATGGGGTTAATCCCGTGGCGAGCCGTCAGAGCGCG
AGTTCTGGCAGTGGCCGTCGTAGAGCACGGAAAGGTATGGGCTGGCTCTCTGAGTCGGCTTAAGGTACGTGCCGTCCCA
CACGATGAAAAGTGTGCGGTGCAGAATAGTTCCCACAGAACGAAGCTGCGCCGGAGAAAGCGATTTCTTGGAGCAATG
CTTAAGGTAGCCAAATGCCTCGTCATCTAATTAGTGACGCGCATGAATGGATTAACGAGATTCCCACTGTCCCTATCTA
CTATCTAGCGAAACCACAGCCAAGGGAACGGGCTTGGCAGAATCAGCGGGGAAAAGAAGACCCTGTTGAGCTTGACTCT
AGTTTGACATTGTGAAAAGACATGGAGGGTGTAGAATAAGTGGGAGCTTCGGCGCCGGTGAAATACCACTACCTCTAT
AGTTTTTTTACTTATTCAATGAAGCGGAGCTGGAGGTCAAACTCCACGTTCTAGCATTAAGTCCTTTTGGGCGATCCGGG
TTGAAGACATTGTCAGGTGGGGAGTTTGGCTGGGGCGGCACATCTGTTAAACGATAACGCAGGTGTCCTAAGGGGGAC
TCATGGAGAACAGAAATCTCCAGTAGAACAAAAGGGTAAAAGTCCCCTTGATTTTGATTTTCAGTGTGAATACAAACC
ATGAAAGTGTGGCCTATCGATCCTTTAGTCCCTCGGAATTTGAGGCTAGAGGTGCCAGAAAAGTTACCACAGGGATAA
CTGGCTTGTGGCAGTCAAGCGTTCATAGCGACATTGCTTTTTGATTCTTCGATGTCGGCTCTTCCTATCATACCGAAGCA
GAATTCGGTAAGCGTTGGATTGTTCACCCACTAATAGGGAACGTGAGCTGGGTTTAGACCGTCGTGAGACAGGTTAGTT
TTACCCTACTGATGAATGTTATCGCAATAGTAATTGAACTTAGTACGAGAGGAACCGTTCATTCAGATAATTGGTTTTTG
CGGCTGTCTGATCAGGCAACGCCGCGAAGCTACCATCTGCTGGATTATGGCTGAACGCCTCTAAGTCAGAATCCATGCT
AGAACGCGATGATTTTTGCCCTGCACATTTTAGATGGATACGAATAAGACTTTTGTCGCTGGACCATAGCAGGCTGGCA
ACGGTGCGCTTAGCGGAAAGGCTTTGTGTGCTTGCCGGCGGATAGCAATGTCAACATGCGCGGGATAAATCCTTTGCA
TACGACTTAGATGTACAACGGAGTATTGTAAGCAGTAGAGTAGCCTTGTTGTTACGATCTGCTGAGATTAAGCTTTTGT
TGTCTGATTTGTCTAATCCTGGTTGCCC
```

Figure 26
*Candida glabrata* rRNA gene (SEQ ID NO: 73)

```
GGTCATTTAGAGGAACTAAAAGTCGTAACAAGGTTTCCGTAGGTGAACCTGCGGAAGGATCATTAAAGAAATTTAATT
GATTTGTCTGAGCTCGGAGAGAGACATCTCTGGGGAGGACCAGTGTAGACACTCAGGAGGCTCCTAAAATATTTTCTCT
GCTGTGAATGCTATTTCTCCTGCCTGCGCTTAAGTGCGCGGTTGGTGGGTGTTCTGCAGTGGGGGGAGGGAGCCGACAA
AGACCTGGGAGTGTGCGTGGATCTCTCTATTCCAAAGGAGGTGTTTTATCACACGACTCGACACTTTCTAATTACTACA
CACAGTGGAGTTTACTTTACTACTATTCTTTTGTTCGTTGGGGGAACGCTCTCTTTCGGGGGGGAGTTCTCCCAGTGGAT
GCAAACACAAACAAATATTTTTTTAAACTAATTCAGTCAACACAAGATTTCTTTTAGTAGAAAACAACTTCAAAACTTT
CAACAATGGATCTCTTGGTTCTCGCATCGATGAAGAACGCAGCGAAATGCGATACGTAATGTGAATTGCAGAATTCCGT
GAATCATCGAATCTTTGAACGCACATTGCGCCCTCTGGTATTCCGGGGGGCATGCCTGTTTGAGCGTCATTTCCTTCTCA
AACACATTGTGTTTGGTAGTGAGTGATACTCGTTTTTGAGTTAACTTGAAATTGTAGGCCATATCAGTATGTGGGACAC
GAGCGCAAGCTTCTCTATTAATCTGCTGCTCGTTTGCGCGAGCGGCGGGGGTTAATACTGTATTAGGTTTTACCAACTCG
GTGTTGATCTAGGGAGGGATAAGTGAGTGTTTTGTGCGTGCTGGGCAGACAGACGTCTTTAAGTTTGACCTCAAATCAG
GTAGGGTTACCCGCTGAACTTAAGCATATCAATAAGCGGAGGAAAAGAAACCAACTGGGATTGCCTTAGTAACGGCGA
GTGAAGCGGCAAAAGCTCAAATTTGAAATCTGGTACCTTTGGTGCCCGAGTTGTAATTTGGAGAGTACCACTTTGGGAC
TGTACTTTGCCTATGTTCCTTGGAACAGGACGTCATGGAGGGTGAGAATCCCGTGTGGCGAGGGTGTCAGTTCTTTGTA
AAGGGTGCTCGAAGAGTCGAGTTGTTTGGGAATGCAGCTCTAAGTGGGTGGTAAATTCCATCTAAAGCTAAATACAGG
CGAGAGACCGATAGCGAACAAGTACAGTGATGGAAAGATGAAAAGAACTTTGAAAAGAGAGTGAAAAAGTACGTGAA
ATTGTTGAAAGGGAAGGGCATTTGATCAGACATGGTGTTTTGCGCCCCTTGCCTCTCGTGGGCTTGGGACTCTCGCAGC
TCACTGGGCCAGCATCGGTTTTGGCGGCCGGAAAAAACCTAGGGAATGTGGCTCTGCGCCTCGGTGTAGAGTGTTATAG
CCCTGGGGAATACGGCCAGTCGGGACCGAGGGACTGCGATACTTGTTATCTAGGATGCTGGCATAATGGTTATATGCCGC
CCGTCTTGAAACACGGACCAAGGAGTCTAACGTCTATGCGAGTGTTTGGGTGTTAAACCCGTACGCGTAATGAAAGTG
AACGTAGGTTGGGGCCCTCCACCTGGGGGGTGCACAATCGACCGATCCTGATGTCTTCGGATGGATTTGAGTAAGAGC
ATAGCTGTTGGGACCCGAAAGATGGTGAACTATGCCTGAATAGGGTGAAGCCAGAGGAAACTCTGGTGGAGGCTCGTA
GCGGTTCTGACGTGCAAATCGATCGTCGAATTTGGGTATAGGGGCGAAAGACTAATCGAACCATCTAGTAGCTGGTTCC
TGCCGAAGTTTCCCTCAGGATAGCAGAAGCTCGTATCAGTTTTATGAGGTAAAGCGAATGATTAGAGGTACCGGGGTTG
AAATGACCTTGACCTATTCTCAAACTTTAAATATGTAAGAAGTCCTTGTTGCTTAATTGAACGTGGACATTTGAATGAA
GAGCTTTTAGTGGGCCATTTTTGGTAAGCAGAACTGGCGATGCGGGATGAACCGAACGTGGAGTTAAGGTGCCGGAAT
ACACGCTCATCAGACACCACAAAAGGTGTTAGTTCATCTAGACAGCCGGACGGTGGCCATGGAAGTCGGAATCCGCTA
AGGAGTGTGTAACAACTCACCGGCCGAATGAACTAGCCCTGAAAATGGATGGCGCTCAAGCGTGTTACCTATACTCCG
CCGTCAGGGTTGAAATGAGGCCCTGACGAGTAGGCAGGCGTGGGGGTCAGTGACGAAGCCTAGGCCGTAAGGTCGGGT
CGAACGGCCCCTAGTGCAGATCTTGGTGGTAGTAGCAAATATTCAAATGAGAACTTTGAAGACTGAAGTGGGGAAAGG
TTCCACGTCAACAGCAGTTGGACGTGGGTTAGTCGATCCTAAGAGATGGGGAAGCTCCGTTTCAAAGGCCTGATTTATG
CAGGCCACCATCGAAAGGGAATCCGGTTAAGATTCCGGAACCTGGATGTGGATTCTTCACGGCAACGTAACTGAATGT
GGAGACGTCGGCGCGAGCCCTGGGAGGAGTTATCTTTTCTTCTTAACAGCTTATCACCCTGGAATTGGTTTATCCGGAG
ATGGGGTCTTATGGCTGGAAGAGGCGAGCTCATATGCTCGCTCCGGTGCGCTTGCGACGGCCCTTGAAAATCCACAGG
AAGGAATAGTTTTCACGCCAGGTCGTACTGATAACCGCAGCCAGGTCTCCAAGGTGAACAGCCTCTAGTTGATAGAATA
ATGTAGATAAGGGAAGTCGGCAAAATAGATCCGTAACTTCGGGATAAGGATTGGCTCTAAGGGTCGGGTAGTGAGGGC
CTTGGTCAGACGCGGCGGGGCTGCGTGCGGACTGCCTGGTGGGGCTTGCTCTGCCGGGCGGACTGCATGCGGCTCCTGT
CGTAGACGGTCTTGGTAGGTCTCTTGTAGGCCGTCGCTTGCTGCGATTAACGATCAACTTAGAACTGGTACGGACAAGG
GGAATCTGACTGTCTAATTAAAACATAGCATTGCGATGGTCAGAAAGTGATGTTGACGCAATGTGATTTCTGCCCAGTG
CTCTGAATGTCAAAGTGAAGAAATTCAACCAAGCGCGGGTAAACGGCGGGAGTAACTATGACTCTCTTAAGGTAGCCA
AATGCCTCGTCATCTAATTAGTGACGCGCATGAATGGATTAACGAGATTCCCACTGTCCCTATCTACTATCTAGCGAAA
CCACAGCCAAGGGAACGGGCTTGGCAGAATCAGCGGGGAAAGAAGACCCTGTTGAGCTTGACTCTAGTTTGACATTGT
GAAGAGACATAGAGGGTGTAGCATAAGTGGGAGCTCCGGCGCCAGTGAAATACCACTACCTTTATAGTTTCTTTACTTA
TTCAATTAAGCGGAGCTGGAATTCATTTTCCACGTTCTAGCTTTCAAAGTGCCATTCGGTGCTGATCCGGGTTGAAGAC
ATTGTCAGGTGGGGAGTTTGGCTGGGCGGCACATCTGTTAAACGATAACGCAGATGTCCTAAGGGGGACTCATGGAG
AACAGAAATCTCCAGTAGAACAAAAGGGTAAAAGTCCCCTTGATTTTGATTTTCAGTGTGAATACAAACCATGAAAGT
GTGGCCTATCGATCCTTTAGTCCCTCGGAATTTGAGGCTAGAGGTGCCAGAAAAGTTACCACAGGGATAACTGGCTTGT
GGCAGTCAAGCGTTCATAGCGACATTGCTTTTTGATTCTTCGATGTCGGCTCTTCCTATCATACCGAAGCAGAATTCGGT
AAGCGTTGGATTGTTCACCCACTAATAGGGAACGTGAGCTGGGTTTAGACCGTCGTGAGACAGGTTAGTTTTACCCTAC
TGATGAATGTTACCGCAATAGTAATTGAACTTAGTACGAGAGGAACAGTTCATTCGGATAATTGGTTTTTGCGGCTGTC
TGATCAGGCAATGCCGCGAAGCTACCATCCGCTGGATTATGGCTGAACGCCTCTAAGTCAGAATCCATGCTAGAACGC
GGTGATTCTTTGCCCTGCACAACGTAGATGGATACGAATAAGGCGTCCTTTTGGGCGTCGCTGAACCATAGCAGGCTGG
CGACGGTGCGCTTGGCGGAAAGGCCTTGCGTGCTTGCCGGCGGATAGCAATGTCATTTTGCGCGGGGATAAATCATTTG
TATACGACTTAGATGTACAACGGGGTATTGTAAGCAGTAGAGTAGCCTTGTTGTTACGATC
```

Figure 27
*Candida gulliermundei* rRNA gene (SEQ ID NO: 74)

```
TTGGTCATTTAGAGGAAGTAAAAGTCGTAACAAGGTTTCCGTAGGTGAACCTGCGGAAGGATCATTACAGTATTCTTTT
GCCAGCGCTTAACTGCGCGGCGAAAAAACCTTACACACAGTGTCTTTTTGATACAGAACTCTCTGCTTTGGGTTTGGCCT
AGAGATAGGTTGGGCCAGAGGTTTAACATAAACACAATTTAATTATTTTTACAGTTAGTCAAATTTTGAATTAATCTTC
AAAACTTTCAACAACGGATCTCTTGGTTCTCGCATCGATGAAGAACGCAGCGAAATGCGATAAGTAATATGAATTGCA
GATTTTCGTGAATCATCGAATCTTTGAACGCACATTGCGCCCTCTGGGTATTCCAGAGGGCATGCCTGTTTTGAGCGTCA
TTTCTCTCTCAAACCCCCGGGTTTGGTATTGAGTGATACTCTTAGTCGGGACTAGGCGTTTGCTTGAAAAGTAATTGGCA
TGGGTAGTACTGGATAGTGCTGTCGACCTCTCAATGTATTAGGTTTATCCAACTCGTTGAATGGTGTGGCGGGATATTTC
TGGTATTGTTGGCCCGGCCTTACAACAACCAAACAAGCTTGACCTCAAATCAGGTAGGAATACCCGCTGAACTTAAGCA
TATCAATAAGCGGAGGAAAAGAAACCAACAGGGATTGCCTTAGTAGCGGCGAGTGAAGCGGCAAAAGCTCAAATTTG
AAATCTGGCGCCTTCGGTGTCCGAGTTGTAATTTGAAGATTGTAACCTTGGGGGTTGGCTCTTGTCTATGTTTCTTGGAA
CAGGACGTCACAGAGGGTGAAGAATCCCGTGCGATGAGATGCCCAATTCTATGTAACGGTGCTTTCGAAGAGTCGAGTT
GGTTTGGGGAATGCAGCTCCTAAGTGGGTGGTAAATTCCATCTAAAGCTAAATATTGGCGAGAGACCGATAGCGAACA
AGTACAGTGATGGAAAGATGAAAAGAACTTTGAAAAGAGAGTGAAAAAGTACGTGAAATTGTTGAAAGGGAAGGGTT
TGAGATCAGACTCGATATTTTGTGAGCCTTGCCTTCGTGGCGGGGTGACCCGCAGCTTATCGGGCCAGCATCGGTTTGG
GCGGTAGGATAATGGCGTAGGAATGGTGACTTTACTTCGGTGAAGTGTTAATAGCCTGCGTTGATGCTGCCTGCCTAGA
CCGAGGACTGCGATTTTATCAAGGATGCTGGCATAATGATCCCAAACCGCCCGTCTTGAAACACGGACCCAAGGAGTC
TAACGTCTATGCGAGTGTTTGGGTGTTAAACCCGTACGCGTAATGAAAGTGAACGTAGGTGAGGGCTCTTTTGAGTGCA
TCATCGACCGATCCTGATGTCTTCGGATGGATTTGAGTAAGAGCATAGCTGTTGGGACCCGAAAGATGGTGAACTATAC
CTGAATAGGGTGAAGCCAGAGGAAACTCTGGTGGAGGCTCGTAGCGGTTCTGACGTGCAAATCGATCGTCGAATTTGG
GTATAGGGGCGAAAGACTAATCGAACCATCTAGTAGCTGGTTCCTGCCGAAGTTTCCCTCAGGATAGCAGAAGCTCGT
ATCAGTTTTATGAGGTAAAGCGAATGATTAGAGGTATTGGGGTTGAAATGACCTTAACCTATTCTCAAACTTTAAATAT
GTAAGAAGTCCTTGTTGCTTAATTGAAACGTGGACATTTGAATGAAGAGCTTTTAGTGGGCCATTTTTGGTAAGCAGAA
CTGGCGATGCGGGATGAACCGAACGTGAAGTTAAAGTGCCGGAATACACGCTCATCAGACACCACAAAAGGTGTTAGT
TCATCTAGACAGCCGGACGGTGGCCATGGAAGTCGGAATCCGCTAAGGAGTGTGTAACAACTCACCGGCCGAATGAAC
TAGCCCTGAAAAGTGGATGGCGCTCAAGCGTGTTACTTATACTTCGCCGTCGAGGGTTGATATGATGCCCTGACGAGTA
GGCAGGCGTGGAGGTCAGTGACGAAGCCTTTGCTGTAAAGCTGGGTCGAACGGCCTCTAGTGCAGATCTTGGTGGTAG
TAGCAAATATTCAAATGAGACTTTGAAGACTGAAGTGGGGAAAGGTTCCATGTCAACAGCAGTTGGACATGGGTTAG
TCGATCCTAAGAGATGGGGAAGCTCCGTTTCAAAGTGCTTGATTTTTCAAGCCGCCATCGAAAGGGAATCCGGTTAATA
TTCCGGAACTTGGATATGGATTCTTCACGGTAACGTAACTGAATGTGGAGACGTCGGCGTGAGCCCTGGGAGGAGTTCT
CTTTTCTTCTTAACAGCTTATCACCCTGGAATTGGTTTATCCGGAGATAGGGTCTTATGGCTGGAAGAGCGCAATACTTT
TGTTGCGTCCGGTGCGCTTACGACGGTCCTTGAAAATCCACAGGAAGGAATAGTTTTCATGCCAAGTCGTACTCATAAC
ACGCAGCAGGTCTCCAAGGTTAACAGCCTCTAGTTGATAGAATAATGTAGATAAGGGAAGTCGGCAAAATAGATCCGT
AACTTCGGGATAAGGATTGGCTCTAAGGATCGGGTGTCTTGGGCCTTTACCAGACGCAGCGGAACCGGCGGTGGACTG
TCTAGGAGCAATCTTGGACGGACCGCTGTTGGATCTTGTTGTAGACGGTTTTGGTAGGCTTTTAGCCGTCCGGGGCACG
CTTAACGATCAACTTAGCATCGGTACGGACAAAGGGGAATCTGACTGTCTAATTAAAACATAGCATTGCGATGGTCAG
AAAGGTGAATGTTGACGCAATGTGATTTCTGCCCCAGTTGCTCTGAAATGTCAAAGTGGAAGAAATTCAACCAAGCGC
GGGTAAACGGGCGGGAGTAACTATGACTCTCTTAAGGTAGCCAAATGCCTCGTCATCTAATTAGTGACGCGCATGAAT
GGATTAACGAGATTCCCACTGTCCCTATCTACTATCTAGCGAAACCACAGCCAAGGGAACGGGCTTGGCAGAATCAGC
GGGGAAAGAAGACCCTGTTGAGCTTGACTCTAGTTTGACATTGTGAAAAGACATAGAGGGTGTAGAATAAGTGGGAGC
TTTCGGCGCCGGTGAAATACCACTACCTCTATAGTTTTTTTACTTATTCAATTAAGCGGAGCTGGACTTCATCGTCCACG
TTCTAGCATTAAGGTCTCATTAGAGGCTGATCCCGGGTTGAAGACATTGTCAGGTGGGGGAGTTTGGCTGGGGCGGCAC
ATCTGTTAAACGATAACGCAGGTGTCCTAAGGGGGACTCATGGAGAACAGAAATCTCCAGTAGAACAAAAGGGGTAA
AAGTCCCCTTGATTTTGATTTTCAGTGTGAATACAAACCATGAAAGTGTGGCCTATCGGATCCTTTAGTCCCTCGGAATT
TGAGGCTAGAGGTGCCAGGAAAAGTTACCACAGGGATAACTGGCTTGTGGCAGTCAAGCGTTCATAGCGACATTGCTT
TTTGATTCTTCGATGTCGGCTCTTCCTATCATACCGAAGCAGAATTCGGTAAGCGTTGGAATTGTTCACCCCACTAATAG
GGAACGTGAGCTGGGTTTAGACCGTCGTGAGACAGGTTAGTTTTACCCTACTGATGAATGTTATCGCAATAGTAATTGA
ACTTAGTACGAGAGGAACCGTTCATTCGGATAATTGGTTTTTGCGGCTGTCTGATCAGGCAACGCCGCGAAGCTACCAT
CCGCTGGATTATGGCTGAACGCCTCTAAGTCAGAATCCATGCTAGAAAGCGATGATTCTTGCCTCGCACATTTTAGTTG
GATAAGAATAAGGCTCTTTGAGTCGCTGAACCATAGCAGGCCTAGGTAACGGTACACTTAACGGAAAGGTTTTGTGTG
CTTGCCGGCGGATAGCAATGTCATAATGAGCGGGGATAAATCCTTTGCATACGACTTACATGTACAACGGAGTATTGTA
AGCAGTAGAGTAGCCTTGTTGTTACAGATCTGCTGAGATTAAGCTTCAGTTGTCCGATTTGTTTAGTGTCTAC
```

Figure 28
*Candida kefyr* rRNA gene (SEQ ID NO: 75)

```
TCCGTAGGTGAACCTGCGGAAGGATCATTAAAGATTATGAATGAATAGATTACTGGGGGAATCGTCTGAACAAGGCCT
GCGCTTAATTGCGCGGCCAGTTCTTGATTCTCTGCTATCAGTTTTCTATTTCTCATCCTAAACACAATGGAGTTTTTCTC
TATGAACTACTTCCCTGGAGAGCTCGTCTCTCCAGTGGACATAAACACAAACAATATTTTGTATTATGAAAAACTATTA
TACTATAAAATTAATATTCAAAACTTTCAACAACGGATCTCTTGGTTCTCGCATCGATGAAGAACGCAGCGAATTGCGA
TATGTATTGTGAATTGCAGATTTTCGTGAATCATCAAATCTTTGAACGCACATTGCGCCCTCTGGTATTCCAGGGGGCAT
GCCTGTTTGAGCGTCATTTCTCTCTCAAACCTTTGGGTTTGGTAGTGAGTGATACTCGTCTCGGGTTAACTTGAAAGTGG
CTAGCCGTTGCCATCTGCGTGAGCAGGGCTGCGTGTCAAGTCTATGGACTCGACTCTTGCACATCTACGTCTTAGGTTTG
CGCCAATTCGTGGTAAGCTTGGGTCATAGAGACTCATAGGTGTTATAAAGACTCGCTGGTGTTTGTCTCCTTGAGGCAT
ACGGCTTTAACCAAAACTCTCAAAGTTTGACCTCAAATCAGGTAGGAGTACCCGCTGAACTTAAGCATATCAATAAGCG
GAGGAAAAGAAACCAACCGGGATTGCCTTAGTAACGGCGAGTGAAGCGGCAAAAGCTCAAATTTGAAATCTGGCGTCT
TCGACGTCCGAGTTGTAATTTGAAGAAGGCGACTTTGTAGCTGGTCCTTGTCTATGTTCCTTGGAACAGGACGTCATAG
AGGGTGAGAATCCCGTGTGGCGAGGATCCCAGTTATTTGTAAAGTGCTTTCGACGAGTCGAGTTGTTTGGGAATGCAGC
TCTAAGTGGGTGGTAAATTCCATCTAAAGCTAAATATTGGCGAGAGACCGATAGCGAACAAGTACAGTGATGGAAAGA
TGAAAAGAACTTTGAAAAGAGAGTGAAAAAGTACGTGAAATTGTTGAAAGGGAAGGGCATTTGATCAGACATGGCGTT
TGCTTCGGCTTTCGCTGGGCCAGCATCAGTTTTAGCGGTTGGATAAATCCTCGGGAATGTGGCTCTGCTTCGGTAGAGT
GTTATAGCCCGTGGGAATACAGCCAGCTGGGACTGAGGATTGCGACTTTTGTCAAGGATGCTGGCGTAATGGTTAAATG
CCGCCCGTCTTGAAACACGGACCAAGGAGTCTAACGTCTATGCGAGTGTTTGGGTGTAAAACCCGTACGCGTAATGAA
AGTGAACGTAGGTGAGGGCCCGCAAGGGTGCATCATCGACCGATCCTGATGTCTTCGGATGGATTTGAGTAAGAGCAT
AGCTGTTGGGACCCGAAAGATGGTGAACTATGCCTGAATAGGGTGAAGCCAGAGGAAACTCTGGTGGAGGCTCGTAGC
GGTTCTGACGTGCAAATCGATCGTCGAATTTGGGTATAGGGGCGAAAGACTAATCGAACCATCTAGTAGCTGGTTCCTG
CCGAAGTTTCCCTCAGGATAGCAGAAGCTCGTATCAGTTTTATGAGGTAAAGCGAATGATTAGAGGTACCGGGGTTGA
AATGACCTTGACCTATTCTCAAACTTTAAATATGTAAGAAGTCCTTGTTGCTTAATTGAACGTGGACATTTGAATGAAG
AGCTTTTAGTGGGCCATTTTTGGTAAGCAGAACTGGCGATGCGGGATGAACCGAACGTGGAGTTAAGGTGCCGGAATA
CACGCTCATCAGACACCACAAAAGGTGTTAGTTCATCTAGACAGCCGGACGGTGGCCATGGAAGTCGGAATCCGCTAA
GGAGTGTGTAACAACTCACCGGCCGAATGAACTAGCCCTGAAAATGGATGGCGCTCAAGCGTGTTACCTATACTCCAC
CGTCAGGGTTAATATGATGCCCTGACGAGTAGGCAGGCGTGGAGGTCAGTGACGAAGCCTAGGCTGTAAAGCTGGGTA
GAACGGCCTCTAGTGCAGATCTTGGTGGTAGTAGCAAATATTCAAATGAGAACTTTGAAGACTGAAGTGGGGAAAGGT
TCCACGTCAACAGCAGTTGGACGTGGGTTAGTCGATCCTAAGAAATGGGGAAGCTCCGTTTCAAAGGCCTAATTTTCTA
GGCCACCATCGAAAGGGAATCCGGTTAATATTCCGGAACCTGGATATGGATTCTTCACGGTAACGTAACTGAATGTGG
AGACGTCGGCGCGAGCCCTGGGAGGAGTTATCTTTTCTTCTTAACAGCTTATCACCCCGGAATTGGTTTATCCGGAGAG
GGGGTCTTATGCTGGAAGAGCCCAGCCCTTGTGCTGGGTCCGGTGCGCCCGCGACGGCCCTTGAAAATCCACAGGAA
GGAATAGTTTTCATGCCAGGTCGTACTGATAACCGCAGCAGGTCTCCAAGGTGAACAGCCTCTAGTTGATAGAATAATG
TAGATAAGGGAAGTCGGCAAAATAGATCCGTAACTTCGGGATAAGGATTGGCTCTAAGAAGTCGGCAAAATAGATCCG
TAATTTCGGGATAAGGATTGGCTCTAAGGATCGGGTAGTGAGGGCCTTGGTCAGACGCGGCGGGCATGCTTGTGGACT
GTCTTACTGGGCTTGCTCGGTGGGACGGACTGCTTGCGGGCCTTGTCGTAGACGGCCTTGGTAGGTCTCTTGTAGACCG
TCGCTTGCTACAATTAACGATCAACTTAGAACTGGTACGGACAAGGGGAATCTGACTGTCTAATTAAAACATAGCATTG
CGATGGTCAGAAAGTGATGTTGACGCAATGTGATTTCTGCCCAGTGCTCTGAATGTCAAAGTGAAGAAATTCAACCAA
GCGCGGGTAAACGGCGGGAGTAACTATGACTCTCTTAAGGTAGCCAAATGCCTCGTCATCTAATTAGTGACGCGCATG
AACGGATTAACGAGATTCCCACTGTCCCTATCTACTATCTAGCGAAACCACAGCCAAGGGAACGGGCTTGGCAGAATC
AGCGGGGAAAGAAGACCCTGTTGAGCTTGACTCTAGTTTGACATTGTGAAGAGACATAGAGGGTGTAGCATAAGTGGG
AGCTTCGGCGCCAGTGAAATACCACTACCTTTATAGTTTCTTTACTTATTCAATTAAGCGGAGCTGGAATTCATTTTCCA
CGTTCTAGCATTCAAAGTCCTATACGGGCTGATCCCGGGTTGAAGACATTGTCAGGTGGGAGTTTGGCTGGGGCGGCA
CATCTGTTAAACGATAACGCAGATGTCCTAAGGGGGACTCATGGAGAACAGAAATCTCCAGTAGAACAAAAGGGTAAA
AGTCCCCTTGATTTTGATTTTCAGTGTGAATACAAACCATGAAAGTGTGGCCTATCGATCCTTTAGGTCCTCGGAATTTG
AGGCTAGAGGTGCCAGAAAAGTTACCACAGGGATAACTGGCTTGTGGCAGTCAAGCGTTCATAGCGACATTGCTTTTTG
ATTCTTCGATGTCGGCTCTTCCTATCATACCGAAGCAGAATTCGGTAAGCGTTGGATTGTTCACCCACTAATAGGGAAC
GTGAGCTGGGTTTAGACCGTCGTGAGACAGGTTAGTTTTACCCTACTGATGAATGTTATCGCAATAGTAATTGAACCTA
GTACGAGAGGAACAGTTCATTCGGATAATTGGTTTTTGCGGCTGTCTGACCAGGCATTGCCGCGAAGCTACCATCCGCT
GGATTATGCTGAACGCCTCTAAGTCAGAATCCATGCTAGAACGCGATGATTTCTTTGCCTTGCACAATATAGAAGGAT
ACGAATAAGGCGTCTTTATGGCGTCGCTGAACCATAGCAGGCTGGCAACGGTGCTCTTAGCGGAAAGGCTTTGGGTGCT
TGCCGGCGAATTGCAATGTCATTTTGCGCAAGGATAAATCATTTGTATACGACTTAAATGTACAACAGGGTATTGTAAG
CAGTAGAGTAGCCTTGTTGTTACGATCTGCTGAGATTAAGCCTTCGTTGTCTGATTTGT
```

Figure 29

Candida krusei rRNA gene (SEQ ID NO: 76)
(GenBank® Accession # EF550222 + GenBank® Accession # AB369918)

```
GGAAGTAAAAGTCGTAACAAGGTTTCCGTAGGTGAACCTGCGGAAGGATCATTACTGTGATTTAGTACTACACTGCGTG
AGCGGAACGAAAACAACAACACCTAAAATGTGGAATATAGCATATAGTCGACAAGAGAAATCTACGAAAAACAAACA
AAACTTTCAACAACGGATCTCTTGGTTCTCGCATCGATGAAGAGCGCAGCGAAATGCGATACCTAGTGTGAATTGCAGC
CATCGTGAATCATCGAGTTCTTGAACGCACATTGCGCCCCTCGGCATTCCGGGGGGCATGCCTGTTTGAGCGTCGTTTCC
ATCTTGCGCGTGCGCAGAGTTGGGGGAGCGGAGCGGACGACGTGTAAAGAGCGTCGGAGCTGCGACTCGCCTGAAAG
GGAGCGAAGCTGGCCGAGCGAACTAGACTTTTTTTCAGGGACGCTTGGCGGCCGAGAGCGAGTGTTGCGAGACAACAA
AAAGCTCGACCTCAAATCAGGTAGGAATACCCGCTGAACTTAAGCATATCAATAAGCGGAGGAAAAGAAACCAACAG
GGATTGCCTCAGTAGCGGCGAGTGAAGCGGCAAGAGCTCAGATTTGAAATCGTGCTTTGCGGCACGAGTTGTAGATTG
CAGGTTGGAGTCTGTGTGGAAGGCGGTGTCCAAGTCCCTTGGAACAGGGCGCCCAGGAGGGTGAGAGCCCCGTGGGAT
GCCGGCGGAAGCAGTGAGGCCCTTCTGACGAGTCGAGTTGTTTGGGAATGCAGCTCCAAGCGGGTGGTAAATTCCATC
TAAGGCTAAATACTGGCGAGAGACCGATAGCGAACAAGTACTGTGAAGGAAAGATGAAAAGCACTTTGAAAAGAGAG
TGAAACAGCACGTGAAATTGTTGAAAGGGAAGGGTATTGCGCCCGACATGGGGATTGCGCACCGCTGCCTCTCGTGGG
CGGCGCTCTGGGCTTTCCCTGGGCCAGCATCGGTTCTTGCTGCAGGAGAAGGGGTTCTGGAACGTGGCTCTTCGGAGTG
TTATAGCCAGGGCCAGATGCTGCGTGCGGGGACCGAGGACTGCGGCCGTGTAGGTCACGGATGCTGGCAGAACGGCGC
AACACCGCCCGTCTTGAAACATGGACCAAGGAGTCTAACGTCTATGCGAGTGTTTGGGTGTGAAACCCGTACGCGTAAT
GAAAGTGAACGTAGGTCGGACCCCCTGCCCTCGGGGAGGGGAGCACGATCGACCGATCCCGATGTTTATCGGAAGGAT
TTGAGTAGGAGCATAGCTGTTGGGACCCGAAAGATGGTGAACTATGCCTGAATAGGGTGAAGCCAGAGGAAACTCTGG
TGGAGGCTCGTAGCGGTTCTGACGTGCAAATCGATCGTCGAATTTGGGTATAGGGGCGAAAGACTAATCGAACCATCT
AGTAGCTGGTTCCTGCCGAAGTTTCCCTCAGGATAGCAGAAGCTCGTATCAGTTTTATGAGGTAAAGCGAATGATTAGA
CGTCTCGGGGTCGAAATGACCTTAGCGTATTCTCAAACTTTAAATATGTAAGAAGTCCCTGTTGCTTTATTGAACGCGG
ACGTTTGAATGCAGAGCTTTTAGTGGGCCATTTTTGGTAAGCAGAACTGGCGATGCGGGATGAACCGAACGCGAAGTT
AAGGTGCCGGAATGCACGCTCATCAGACACCACAAAAGGTGTTAGTTCATCCAGACAGCCGGACGGTGGCCATGGAAG
TCGGAATCCGCTAAGGAGTGTGTAACAACTCACCGGCCGAATGAACTAGCCCTGAAAATGCATGGCGCTCAAGCGTGT
TACCTATACTTCGCCGCCATGGCGCAAGGCCTTGGCGAGTAGGCAGGCGTGGGGGTTTGTGACGAAGCCTTGGGCGTG
AGCCTGGGTCGAACGGCCCCTAGTGCAGATCTTGGTGGTAGTAGCAAATATTCAAATGGGAACTTTGAAGACTGAAGT
GGGGAAAGGTTCCGCGTCAACAGCAGTTGGACGCGGGTCAGTCGATCCTAAGAGATGGGGAAGCTCCGTTTCAACGAG
CGCAATTCGCTTGCGCCACCATCGAAAGGGAATCCGGTTAAGATTCCGGAACTTGGATGTGGATTCTTCACGGCAACGT
AACAGAATGCGGAGACGCCGGCGGGAGCCCTGGGAGGAGTTTTCTTTTCTTCTTAACAGCCTAACACCCTGGAATTGGT
TTATCCGGAGAGGGGGTCTTATGGCTGGAAGAGCGTCGCCCTTGCTGCGACGTCCGGTGCGCTTGCGACGGTCCTTGAA
AATCCGCAGGAAGGAATAGTTTTCACGCCAAGTCGTACTCATAACCGCAGCAGGTCTCCAAGGTTAACAGCCTCTAGTT
GATAGAATAATGTAGATAAGGGAAGTCGGCAAAATAGATCCGTAACTTCGGGATAAGGATTGGCTCTAAGGGTTGGGC
GGAGTGCTGGGGCTGCCGGCGCGTGCCGGGTGCTGCGGAGACGCATCTGTGTTCTGCGGCTGCCTGGCGGCGGGCTTG
CGGCCTGTTTTTCAGTCCCGCGGTTAACAACCGACTTAGAACTGGTACGGACAAGGGGAATCTGACTGTCTAATTAAAA
CATAGCATTGCGATGGTCAGAAAGTGATGTTGACGCAATGTGATTTCTGCCCAGTGCTCTGAATGTCAAAGTGAAGAAA
TTCAACCAAGCGCGGGTAAACGGCGGNAGTAACTATGACTCTCTTAAGGTAGCCNAATGCCTCGTCATCTAATTAGTGA
CGCGCATGAATGGATTAACGAGATTCCCACTGTCCCTATCTACTATCTAGCGAAACCACAGCCAAGGGAACGGGCTTG
GCAGAATCAGCGGGGAAAGAAGACCCTGTTGAGCTTGACTCTAGTTTGACATTGTGAAAAGACATAGAGGGTGTAGCA
TAAGTGGGAGCTCCGGCGCCAGTGAAATACCACTACCTTTATCGTTTTTTTACTTATTCAATGAAGCGGAGCTGGTCTTG
ACGACCACGTTCTGGAGCGAAGGCGCCTTGTGCGCTGATCCGGGTTGAAGACATTGTCAGGTGGGGAGTTTGGCTGGG
GCGGCACATCTGTTAAACGATAACGCAGATGTCCTAAGGGGGACTCATGGAGAACAGAAATCTCCAGTAGAACAAAAG
GGTAAAAGTCCCCTTGATTTTGATTTTCAGTGTGAATACAAACCATGAAAGTGTGGCCTATCGATCCTTTAGTCCCTCGG
AATTTGAGGCTAGAGGTGCCAGAAAAGTTACCACAGGGATAACTGGCTTGTGGCAGTCAAGCGCTCATAGCGACATTG
CTTTTTGATTCTTCGATGTCGGCTCTTCCTATCATACCGAAGCAGAATTCGGTAAGCGTTGGATTGTTCACCCACTAATA
GGGAACGTGAGCTGGGTTTAGACCGTCGTGAGACAGGTTAGTTTTACCCTACTGATGAATGTTGTCGCAATAGTAATTG
AACTTAGTACGAGAGGAACCGTTCATTCAGATAATTGGTTTTTGCGGCTGTCTGAGCAGACACTGCCGCCGACGCTACCA
TCTGCTGGATAATGGCTGAACGCCTCTAAGTCAGAATCCATGCTAGAACGGCGACGATTACCTGCCCTCGCACATTTGAG
AAGGATACGAATAAGGCCCTGTGGCCGCCAGAACCGTAGCAGGCCGGCAGCGGTGCGCATGGCGGAAAGGCCGTGTGT
GCTTGCCGGCGGATGGCAATGTCAGGATGCGCGAGGATAAATCCTATGCATACGACTTAGATGTACAACGGGGTATTG
NAAG
```

Figure 30
*Candida lipolytica* rRNA gene (SEQ ID NO: 77)
(GenBank® Accession # AJ616903 + GenBank® Accession # DQ680839)

```
ACGAATCTTTGGAAGTAAAAAAGCGTAACAAGGTTTCCGTAGGTGAACCTGCGGAAGGATCATTATTGATTTTATCTAT
TTCTGTGGATTTCTATTCTATTACAGCGTCATTTTATCTCAATTATAACTATCAACAACGGATCTCTTGGCTCTCACATCG
ATGAAGAACGCAGCGAACCGCGATATTTTTTGTGACTTGCAGATGTGAATCATCAATCTTTGAACGCACATTGCGCGGT
ATGGCATTCCGTACCGCACGGATGGAGGAGCGTGTTCCCTCTGGGATCGCATTGCTTTCTTGAAATGGATTTTTTTAAAC
TCTCAATTATTACGTCATTCACCTCCTCATCCGAGATAGCTTAGCCACGGATTTCACCTCCTTCATCCGAGATTACCCGC
TGAACTTAAGCATATCAATAAGCGGAGGAAAAGAAACCAACAGGGATTGCCTCAGTAACGGCGAGTGAAGCGGCAAA
AGCTCAAATTTGAAACCCTCGGGATTGTAATTTGAAGATTTGGCATTGGAGAAAGCTAACCCAAGTTGCTTGGAATAGT
ACGTCATAGAGGGTGACAACCCCGTCTGGCTAACCGTTCTCCATGTATTGCCTTATCAAAGAGTCGAGTTGTTTGGGAA
TGCAGCTCAAAGTGGGTGGTAAACTCCATCTAAAGCTAAATACTGGTGAGAGACCGATAGCGAACAAGTACTGTGAAG
GAAAGGTGAAAAGAACTTTGAAAAGAGAGTGAAATAGTATGTGAAATTGTTGATAGGGAAGGAAATGAGTGGAGAGT
GGCCGAGGTTTCAGCCGCCCTCGTGGGCGGTGTACTGCCGACGCCGAGTCATCGATAGCGAGACGAGGGTTACAAAT
GGGAGCGCCTTTCGGGCGTTCTCCCCTAACCCTCCACACTGCCACCGACGACATAATCCACCCATTTCACCCGTCTTGA
AACACGGACCAAGGAGTCTAATGGATATGTGAGTGTTAGGGTGGCAAACCCCAGCGCGCAATGAAAGTGAATGGATTC
GTTCAGAATCGACCGAACTTGATTATTATGACAGTTTTGAGTAAACACATCCATTGGGACCCGAAAGATGGTGAACTAT
GCCTGGATAGGGTGAAGTCAGAGGAAACTCTGATGGAGGCTCGTAGCGGTTCTGACGTGCAAATCGATCGTAGGATCT
GGGTATAGGGGCGAAAGACTAATCGAACCATCTAGTAGCTGGTTCCTGCCGAAGTTTCCCTCAGGATAGCAGAAGCTC
ATATCAGTTTTATGAGGTAAAGCGAATGATTAGAAGTATTGGGGGCGAAATGCCCTCGGCTTATTCTCAAACTTTAAAT
ATGTAAGAAGCCTTGGTTACTTAATCGAACCGTGGCTACGAATGAAGAGCTTCTAGTGGGCCATTTTTGGTAAGCAGAA
CTGGCGATGCGGGATGAACCGAACGTGGAGTTAAGGTGCCGGAATACACGCTCATCAGACACCACAAAAGGTGTTAGT
TTATCTAGACAGCCGGACGGTGGCCATGGAAGTCGGAATCCGCTAAGGAGTGTGTCACAACTCACCGGCCGAATGAAC
TAGCCCTGAAAATGGATGGCGCTTAAGCGTGTTACCTATACTCTACCGAGAGGAGGTTTCCTCTCGAGTAGGCAGGCGT
GGGGGTTGTTGAGAAGCGTTGGCCGAGAAGCTGCGTCGAACGGCCCCTAGTGCAGATCTTGGTGGTAGTAGCAAATAT
TCAAATGAGAACTTTGAAGACTGAAGTGGGGAAAGGTTCCGTGTGAACAGCAGTTGGACACGGGTAAGTCGATCCTAA
GGGGTGGCATAACTGTCGCGTACGGCCCGATAAGGGCCTTCTCCAAAAGGGAAGCCGGTTGAAATTCCGGCACTTGGA
TGTGGATTCTCCACGGCAACGTAACTGAATGTGGGGACGGTGGCACAAGTCTTGGAAGGAGTTATCTTTTCTTTTTAAC
GGAGTCAACACCCTGGAATTAGTTTTGTCTAGAGATAGGGTCGTTCCGGAAGAGGGGGGCAGCTTTGTCCCCTCCGAT
GCACTTGTGACGCCCCTTGAAAACCCGCAGGAAGGAATAGTTTTCACGCCAAGTCGTACTGATAACCGCAGCAGGTCT
CCAAGGTGAACAGCCTCTAGTTGATAGAATAATGTAGATAAGGGAAGTCGGCAAAATAGATCCGTAACTTCGGGATAA
GGATTGGCTCTGGGGGTTGGTGGATGGAAGCGTGGGAGACCCCAAGGGACTGGCAGCTGGGCAACTGGCAGCCGGAC
CCGCGGCAGACAACTGCGTCGCTCCGTCCACATCATCAACCGCCCCAGAACTGGTACGGACAAGGGGAATCTGACTGTC
TAATTAAAACATAGCTTTGCGATGGTTGTAAAACAATGTTGACGCAAAGTGATTTCTGCCCAGTGCTCTGAATGTCAAA
GTGAAGAAATTCAACCAAGCGCGCGGGTAAACGGCGGGAGTAACTATGCTCTCTTAAGGTAGCCAAATGCCTCGTCAT
CTAATTAGTGACGCGCATGAATGGATTAACGAGATTCCCACTGTCCCTATCTACTATGTAGCGAAACCACAGCCAAGGG
AACGGGCTTGGCAGAATCAGCGGGGAAAGAAGACCCTGTTGAGCTTGACTCTAGTTTGACATTGTGAAGAGACATAGG
GGGTGTAGAATAAGTGGGAGCTTCGGCGCCGGTGAAATACCACTACCCTTATCGTTTCTTTACTTATTTAGTAAGTGGA
AGTGGTTTAACAACCATTTTCTAGCATTCCTTTCCAGGCTGAAGACATTGTCAGGTGGGGAGTTTGGCTGGGGCGGCAC
ATCTGTTAAAAGATAACGCAGATGTCCTAAGGGGGACTCAATGAGAACAGAAATCTCATGTAGAACAAAAGGGTAAA
AGTCCCCTTGATTTTGATTTTCAGTGTGAATACAAACCATGAAAGTGTGGCCTATCGATCCTTTAGTTGTTCGGAGTTTG
AACCTAGAGGTGCCAGAAAAGTTACCACAGGGATAACTGGCTTGTGGCAGTCAAGCGTTCATGCGACATTGCTTTTTG
ATCCTTCGATGTCGGCTCTTCCTATCATACCGAAGCAGAATTCGGTAAGCGTTGGATTGTTCACCCACTAATAGGGAAC
GTGAGCTGGGTTTAGACCGTCGTGAGACAGGTTAGTTTTACCCTACTGATGGACTTGTTGCAATAGTAATTGAACTTAG
TACGAGAGGAACAGTTCATTCGGATAATTGGTGTTTGCTGCTGTCTGACCAGGCAATGCAGCGAAGCACCACCCGCTGG
GTTATGGCCGAACGCCTCCAAGTCAGAACCCATGCCAGAAGGGAAGAATCAGGGGGAAGGAGGGATATGAAGAAGTA
CCGCAGTACCGGAGGGGGAGGGGGGGTGGATAAGGAAACCGCCCGCCCCCCCCGACTGGAAAGACCCACCCTTGTG
AAATCCATTGTAGACGACTTTAGTATGCGACGAGGTATTGTAAGTAGTAGAGTAGCCTTGTTGTTACGATCTATTGAGA
TTAAGCCTTTGTTGTTTAGATTCGA
```

Figure 31
*Candida lusitaniae* rRNA gene (SEQ ID NO: 78)

TTTTGAGGAAGTAAAAGTCGTAACAAGGTTTCCGTAGGTGAACCTGCGGAAGGATCATTAAAAAATACATTACACATT
GTTTTTGCGAACAAAAAAAATAAATTTTTTTATTCGAATTTCTTAATATCAAAACTTTCAACAACGGATCTCTTGGTTCT
CGCATCGATGAAGAACGCAGCGAATTGCGATACGTAGTATGACTTGCAGACGTGAATCATCGAATCTTTGAACGCACA
TTGCGCCTCGAGGCATTCCTCGAGGCATGCCTGTTTGAGCGTCGCATCCCCTCTAACCCCCGGTTAGGCGTTGCTCCGA
AATATCAAGCCGCGCTGTCAAACACGTTTACAGCACGACATTTCGCCCTCAAATCAGGTAGGACTACCCGCTGAGACTT
AAGCATATCAATAAGCGGAGGAAAAGAAACCAACAGGGATTGCCCCAGTAACGGCGAGTGAAGCGGCAAAAGCTCAA
ATTTGAAATCCTGCGGGAATTGTAATTTGAAGGTTTCGTGGTCTGAGTCGGCCGCGCCCAAGTCCATTGGAACATGGCG
CCTGGGAGGGTGAGAGCCCCGTATGGCGCACGCCGACTCTTTGTACACCGCGGCTCCGACGAGTCGAGTTGTTTGGGA
ATGCAGCTCTAAGTGGAGTGGTAAATTCCATCTAAAGCTAAATATTGGCGAGAGACCGATAGCGAACAAGTACAGTGA
TGGAAAGATGAAAAGCACTTTGAAAAGAGAGTGAAACAGCACGTGAAATTGTTGAAAGGGAAGGGCTTGCAAGCAGA
CACGGTTTTACCGGGCCAGCGTCGAAAAGGGGGGAGGAACAAGAACTCGAGAATGTGGCGCGCACCTTCGGGCGCGC
GTGTTATAGCTCGTGTTGACGCCTCCATCCCTTTTCGAGGCCTGCGATTCTAGGACGCTGGCGTTAATGGTTGCAAGCCGC
CCGTCTTGAAACACGGACCAAGGAGTCTAACGTCTATGCGAGTGTTTGGGTGCAAAACCCCAGCGCGGAATGAAAGTA
AGAGGTTGGAGCCGCAAGGCGCACAATCGACCGACCCTGAAGTGCTCGGACGGGTTTGAGTAGGAGCATAGCTGTTGG
GACCCGAAAGATGGTGAACTATGCCTGGATAGGGTGAAGCCAGAGGAAACTCTGGTGGAGGCTCGCAGCGGTTCTGAC
GTGCAAATCGATCGTCGAATCTGGGTATAGGGGCGAAAGACTAATCGAACCATCTAGTAGCTGCTCTTATGCTCTTCCT
GCCGAAGTTCCTGACGCCTCCATCCCTTTTCGAGGCCTGCGATTCTAGGACGCTGGCGTAATGGTTGCAAGCCGCCCGT
CTTGAAACACGGACCAAGGAGTCTAACGTCTATGCGAGTGTTTGGGTGCAAAACCCCAGCGCGGAATGAAAGTAAGAG
GTTGGAGCCGCAAGGCGCACAATCGACCGACCCTGAAGTGCTCGGACGGGTTTGAGTAGGAGCATAGCTGTTGGGACC
CGAAAGATGGTGAACTATGCCTGGATAGGGTGAAGCCAGAGGAAACTCTGGTGGAGGCTCGCAGCGGTTCTGACGTGC
AAATCGATCGTCGAATCTGGGTATAGGGGCGAAAGACTAATCGAACCATCTAGTAGCTGGTTCCTGCCGAAGTTTCCCT
CAGGATAGCAGAAGCTCGTTACAAACAGTTTTATGAGGTAAAGCGAATGATTAGAGGTCTCGGGGCGGAAATAGCCTT
AGCCTATTCTCAAACTTTAAATATGTAAGAAGTCCTTGTTGCTTAATTGAACGTGGACATACGAATGTAGAGCTTTTAGT
GGGCCATTTTTGGTAAGCAGAACTGGCGATGCGGGATGAACCGAACGCGAAGTTAAAGTGCCGGAATGCACGCTCATC
AGACACCACAAAAGGTGTTAGTTCATCTAGACAGCCGGACGGTGGCCATGGAAGTCGGAATTCCGCTAAGGAGTGTGT
AACAACTCACCGGCCGAATGAACTAGCCCTGAAAATGGATGGCGCTCAAGCGTGCTACTTATACTTCGCCGGCATTTTT
TTTGGAAATGCCGAGTAGGCAGGCGTGGAGGTGGTGACGAAGCCTTGGCTGTGAAGCTGGGTCGAACCGCCTCTAGTG
CAGATCTTGGTGGTAGTAGCAAATATTCAAATGGGAACTTTGAAGACTGAAGTGGGGAAAGGTTCCATGTCAACAGCA
GATGGACATGGGTGAGTCGATCCTAAGGAGCTAAGGTAGTTCTGACTGAACAGCTTCTTTGCGAAGTGTGCTCGAAAGG
GAATCCGGTTAAGATTCCGGAACTTGGATGCGGAACTACACGGCAACGTAACTGAATGCGGAGACGCCGGCGTGGGCC
CTGGGAGGAGTTTTCTTTTTCTTCTAACAGCCTGTGACCCTGGAATTGGATTATCCGGAGAGGGGGTTTTGTGGCTGGA
AGAGCGCGGCATCTTCGCCGCGTCCGGTGCGCCTACGACGGTCCTTGAAAATCCGCAGGAAGCAATTGTTTTCGCGCCA
AGTCGTACTGATAACCGCAGCAGGTCTCCAAGGTTAACAGCCTCTAGTTGATAGAACAATGTAGATAAGGGAAGTCGG
CAAAATAGATCCGTAACTTCGGGATAAGGATTGGCTCTAAGGGTTGGGAGTGTAAGGGACGGGGGTGACGTGGATGAG
TGTAGTGTGGACGGTGCTGGCTTCAAGGCCGGCGCTGTCTGCGCCGTGCTTGTCCTCCAACCCCCCGTTCCCCGCTTCAA
TAACAACCAACTTAGAACTGGTACGGACAAGGGGAATCTGACTGTCTAATTAAAACATAGCATTGCGATGGTCAGAAA
GTGATGTTGACGCAATGTGATTTCTGCCCAGTGCTCTGAATGTCAAAGTGAAGAAATTCAACCAAGCGCGGGTAAACG
GCGGGAGTAACTATGACTCTCTTAAGGTAGCCAAATGCCTCGTCATCTAATTAGTGACGCGCATGAATGGATTAACGAG
ATTCCCACTGTCCCTATCTACTATCTAGCGAAACCACAGCCAAGGGAACGGGCTTGGCAGAATCAGCGGGGAAAGAAG
ACCCTGTTGAGCTTGACTCTAGTTTGACATTGTGAAAAGACATGGAGGGTGTAGAATAAGTGGGAGCTTCGGCGCCGA
GTGAAATACCACTACCTCCATCGTTTTTTTACTTACTGAATGAAGGGGAGCTGGTTGTCATGACCACGTTCTGGATTTAA
GCAGCAATGCAATCCCGGTTCAAGACATTGTCAGGTGGGGAGTTTGGCTGGGGCGGCACATCTGTTAAACGATAACGC
AGATGTCCTAAGGGGGGCTCATGGAGAACAGAAATCTCCAGTAGAACAAAAGGGTAAAAGCCCCCTTGATTTTGATTT
TCAGTGTGAATACAAACCATGAAAGTGTGGCCTATCGATCCTTTAGTCCCTCGGAATTTGAGGCTAGAGGTGCCAGAAA
AGTTACCACAGGGATAACTGGCTTGTGGCAGTCAAGCGTTCATAGCGACATTGCTTTTTGATTCTTCGATGTCGGCTCTT
CCTATCATACCGAAGCAGAATTCGGTAAGCGTTGGATTGTTCACCCACTAATAGGGAACGTGAGCTGGGTTTAGACCGT
CGTGAGACAGGTTAGTTTTACCCTACTGATGGACCGTTGTTGCAATAGTAATTGAACTTAGTACGAGAGGAACCGTTCA
TTCAGATAATTGGTATTTGGCCCTGTCTGATCAGGCACCGGGCCGAAGCTACCATCTGCTGGATTATGGCTGAACGCCT
CTAAGTCAGAATCCATGCTAGAAGCGACGACTCTGCCTCGCGCGTTGCAGTTGGATACAAATACGATGTGGACCATAC
AAGGCGGCGTTTGGCGGCCGTGCGGAAAGGCGCTGTCGCTGGCTGCGGATAGCAATGTCTCGATGCGCGGGGATAAAT
CCTTTGCATACGACTTAGATGTACAACGGAGTATTGTAAGCGGTAGAGTAGCCTTGTTGTTACGATCCGCTGAGATTAA
GCTCTTGTTGGCTGGTTTGTCTACCTAGA

Figure 32
*Candida parapsilosis* rRNA gene (SEQ ID NO: 79)

```
TTGGTCATTTAGAGGAAGTAAAAGTCGTAACAAGGTTTCCGTAGGTGAACCTGCGGAAGGATCATTACAGAATGAAAA
GTGCTTAACTGCATTTTTTCTTACACATGTGTTTTTCTTTTTTTGAAAACTTTGCTTTGGTAGGCCTTCTATATGGGGCCT
GCCAGAGATTAAACTCAACCAAATTTTATTTAATGTCAACCGATTATTTAATAGTCAAAACTTTCAACAACGGATCTCTT
GGTTCTCGCATCGATGAAGAACGCAGCGAAATGCGATAAGTAATATGAATTGCAGATATTCGTGAATCATCGAATCTTT
GAACGCACATTGCGCCCTTTGGTATTCCAAAGGGCATGCCTGTTTGAGCGTCATTTCTCCCTCAAACCCTCGGGTTTGGT
GTTGAGCGATACGCTGGGTTTGCTTGAAAGAAAGGCGGAGTATAAACTAATGGATAGGTTTTTTCCACTCATTGGTACA
AACTCCAAAACTTCTTCCAAATTCGACCTCAAATCAGGTAGGACTACCCGCTGAACTTAAGCATATCAATAAGCGGAGG
AAAAGAAACCAACAGGGATTGCCTTAGTAGCGGCGAGTGAAGCGGCAAAAGCTCAAATTTGAAATCTGGCACTTTCAG
TGTCCGAGTTGTAATTTGAAGAAGGTATCTTTGGGTCTGGCTCTTGTCTATGTTTCTTGGAACAGAACGTCACAGAGGGT
GAGAATCCCGTGCGATGAGATGTCCCAGACCTATGTAAAGTTCCTTCGAAGAGTCGAGTTGTTTGGGAATGCAGCTCTA
AGTGGGTGGTAAATTCCATCTAAAGCTAAATATTGGCGAGAGACCGATAGCGAACAAGTACAGTGATGGAAAGATGAA
AAGAACTTTGAAAAGAGAGTGAAAAAGTACGTGAAATTGTTGAAAGGGAAGGGCTTGAGATCAGACTTGGTATTTTGT
ATGTTACTCTCTCGGGGGTGGCCTCTACAGTTTACCGGGCCAGCATCAGTTTGAGCGGTAGGATAAGTGCAAAGAAATG
TGGCACTGCTTCGGTAGTGTGTTATAGTCTTTGTCGATACTGCCAGCTTAGACTGAGGACTGCGGCTTCGGCCTAGGAT
GTTGGCATAATGATCTTAAGTCGCCCGTCTTGAAACACGGACCAAGGAGTCTAACGTCTATGCGAGTGTTTGGGTGTAA
AACCCGTACGCGTAATGAAAGTGAACGTAGGTAGGACCTCCTTTAGGAGTGCACTATCGACCGATCCTGATGTCTTCGG
ATGGATTTGAGTAAGAGCATAGCTGTTGGGACCCGAAAGATGGTGAACTATGCCTGAATAGGGTGAAGCCAGAGGAAA
CTCTGGTGGAGGCTCGTAGCGGTTCTGACGTGCAAATCGATCGTCGAATTTGGGTATAGGGGCGAAAGACTAATCGAA
CCATCTAGTAGCTGGTTCCTGCCGAAGTTTCCCTCAGGATAGCAGAAGCTCGTATCAGTTTTATGAGGTAAAGCGAATG
ATTAGAAGTCTTGGGGTTGAAATGACCTTAACTTATTCTCAAACTTTAAATATGTAAGAAGTCCTTGTTGCTTAATTGAA
CGTGGACATATGAATGAAGAGCTTTTAGTGGGCCATTTTTGGTAAGCAGAACTGGCGATGCGGGATGAACCGAACGTG
AAGTTAAAGTGCCGGAATACACGCTCATCAGACACCACAAAAGGTGTTAGTTCATCTAGACAGCCGGACGGTGGCCAT
GGAAGTCGGAATCCGCTAAGGAGTGTGTAACAACTCACCGGCCGAATGAACTAGCCCTGAAAATGGATGGCGCTCAAG
CGTGTTACTTATACTTCGCCGTGAGAGGTTGATATGATGCCCTCACGAGTAGGCAGGCGTGGAGGTCAGTGAAGAAGC
CTTTGCTGTGAAGCTGGGTCGAACGGCCTCTAGTGCAGATCTTGGTGGTAGTAGCAAATATTCAAATGAGAACTTTGAA
GACTGAAGTGGGGAAAGGTTCCATGTCAACAGCAGTTGGACATGGGTTAGTCGATCCTAAGAGATGGGGAAGCTCCGT
TTCAATGCGCTTGATTTTTCAAGCCAACCATCGAAAGGGAATCCGGTTAAAATTCCGGAACTTGGATATGGATTCTTCA
CGGCAACGTAACTGAATGTGGAGACGTCGGCGTGAGCCCTGGGAGGAGTTATCTTTTCTTCTTAACAGCTTATCACCCT
GGAATTGGTTTATCCGGAGATGGGGTCTTATGGCTGGCAGAGCGCGGTAATTTTGCCGCGTCCGGTGCGCTCACGACGG
TCCTTGAAAATCCACAGGAAGGAATAGTTTTCATGCCAAGTCGTACTCATAACCGCAGCAGGTCTCCAAGGTTAACAGC
CTCTAGTTGATAGAATAATGTAGATAAGGGAAGTCGGCAAAATAGATCCGTAACTTCGGGATAAGGATTGGCTCTAAG
GATCGGGTGGTTTGGGCCTTGCGTAGAAGTGGTGGTGACTGGCGGCGGGCTGCTTCGGGCGGACTGCTGTTGGACGTC
GCTATAGACACACTTGGTAGGCATTTATGTCGTCCGGATCACGCTTAACGATCAACTTAGAACTGGTACGGACAAGGGG
AATCTGACTGTCTAATTAAAACATAGCATTGTGATGGTCAGAAAGTGATGTTGACACAATGTGATTTCTGCCCAGTGCT
CTGAATGTCAAAGTGAAGAAATTCAACCAAGCGCGGGTAAACGGCGGGAGTAACTATGACTCTCTTAAGGTAGCCAAA
TGCCTCGTCATCTAATTAGTGACGCGCATGAATGGATTAACGAGATTCCCACTGTCCCTATCTACTATCTAGCGAAACC
ACAGCCAAGGGAACGGGCTTGGCAGAATCAGCGGGGAAAGAAGACCCTGTTGAGCTTGACTCTAGTTTGACATTGTGA
AAAGACATGGAGGGTGTAGAATAAGTGGGAGCTTCGGCGCCGGTGAAATACCACTACCTCTATAGTTTTTTTACTTATT
CAATGAAGCGGAGCTGGAGGTAAAACTCCACGTTCTAGCATTAAGGCCTTTTGGCTGATCCGGGTTGAAGACATTGTCA
GGTGGGGAGTTTGGCTGGGGCGGCACATCTGTTAAACGATAACGCAGGTGTCCTAAGGGGGACTCATGGAGAACAGAA
ATCTCCAGTAGAACAAAAGGGTAAAAGTCCCCTTGATTTTGATTTTCAGTGTGAATACAAACCATGAAAGTGTGGCCTA
TCGATCCTTTAGTCCCTCGGAATTTGAGGCTAGAGGTGCCAGAAAAGTTACCACAGGGATAACTGGCTTGTGGCAGTCA
AGCGTTCATAGCGACATTGCTTTTTGATTCTTCGATGTCGGCTCTTCCTATCATACCGAAGCAGAATTCGGTAAGCGTTG
GATTGTTCACCCACTAATAGGGAACGTGAGCTGGGTTTAGACCGTCGTGAGACAGGTTAGTTTTACCCTACTGATGAAT
GTTATCGCAATAGTAATTGAACTTAGTACGAGAGGAACCGTTCATTCAGATAATTGGTTTTTGCGGCTGTCTGATCAGG
CAACGCCGCGAAGCTACCATCTGCTGGATTATGGCTGAACGCCTCTAAGTCAGAATCCATCCTAGAAAGCGATGATTTT
TGCCCTGCACATTTTAGATGGATAAGAATAAGACTTTTTAGTCGCTAGACCATAGCAGGCTGGCAACGGTGCGCTTAGC
GGAAAGGCTTTGTGTGCTTGCCGGCGAATAGCAATGTCGACATGCGCGGGGATAAATCCTTTGTATACGACTTAGATGT
ACAACGGAGTATTGTAAGCAGTAGAGTAGCCTTGTTGTTACGATCTGCTGAGATTAAGCTTCAGTTGTCTGATTTGTCTA
CGAGTTTGCGGGCGAGAG
```

Figure 33
*Candida tropicalis* rRNA gene (SEQ ID NO: 80)

```
CTTGGTCATTTAGAGGAAGTAAAAGTCGTAACAAGGTTTCCGTAGGTGAACCTGCGGAAGGATCATTACTGATTTGCTT
AATTGCACCACATGTGTTTTTTATTGAACAAATTTCTTTGGTGGCGGGAGCAATCCTACCGCCAGAGGTTATAACTAAA
CCAAACTTTTTATTTACAGTCAAACTTGATTTATTATTACAATAGTCAAAACTTTCAACAACGGATCTCTTGGTTCTCGC
ATCGATGAAGAACGCAGCGAAATGCGATACGTAATATGAATTGCAGATATTCGTGAATCATCGAATCTTTGAACGCAC
ATTGCGCCCTTTGGTATTCCAAAGGGCATGCCTGTTTGAGCGTCATTTCTCCCTCAAACCCCCGGGTTTGGTGTTGAGCA
ATACGCTAGGTTTGTTTGAAAGAATTTAACGTGGAAACTTATTTTAAGCGACTTAGGTTTATCCAAAACGCTTATTTTGC
TAGTGGCCACCACAATTTATTTCATAACTTTGACCTCAAATCAGGTAGGACTACCCGCTGAACTTAAGCATATCAATAA
GCGGAGGAAAAGAAACCAACAGGGATTGCCTTAGTAGCGGCGAGTGAAGCGGCAAAAGCTCAAATTTGAAATCTGGC
TCTTTCAGAGTCCGAGTTGTAATTTGAAGAAGGTATCTTTGGGTCTGGCTCTTGTCTATGTTTCTTGGAACAGAACGTCA
CAGAGGGTGAGAATCCCGTGCGATGAGATGATCCAGGCCTATGTAAAGTTCCTTCGAAGAGTCGAGTTGTTTGGGAAT
GCAGCTCTAAGTGGGTGGTAAATTCCATCTAAAGCTAAATATTGGCGAGAGACCGATAGCGAACAAGTACAGTGATGG
AAAGATGAAAAGAACTTTGAAAAGAGAGTGAAAAAGTACGTGAAATTGTTGAAAGGGAAGGGCTTGAGATCAGACTT
GGTATTTTGTATGTTACTTCTTCGGGGGTGGCCTCTACAGTTTATCGGGCCAGCATCAGTTTGGGCGGTAGGAGAATTGC
GTTGGAATGTGGCACGGCTTCGGTTGTGTGTTATAGCCTTCGTCGATACTGCCAGCCTAGACTGAGGACTGCGGTTTAT
ACCTAGGATGTTGGCATAATGATCTTAAGTCGCCCGTCTTGAAACACGGACCAAGGAGTCTAACGTCTATGCGAGTGTT
TGGGTGTAAAACCCGTACGCGTAATGAAAGTGAACGTAGGTGGGGGCCCGTATGGGTGCACCATCGACCGATCCTGAT
GTCTTCGGATGGATTTGAGTAAGAGCATAGCTGTTGGGACCCGAAAGATGGTGAACTATGCCTGAATAGGGTGAAGCC
AGAGGAAACTCTGGTGGAGGCTCGTAGCGGTTCTGACGTGCAAATCGATCGTCGAATTTGGGTATAGGGGCGAAAGAC
TAATCGAACCATCTAGTAGCTGGTTCCTGCCGAAGTTTCCCTCAGGATAGCAGAAGCTCGTATCAGTTTTATGAGGTAA
AGCGAATGATTAGAAGTATTGGGGTTGAAATGACCTTAACTTATTCTCAAACTTTAAATATGTAAGAAGTCCTTGTTGC
TTAATTGAACGTGGACAATTGAATGAAGAGCTTTTAGTGGGCCATTTTTGGTAAGCAGAACTGGCGATGCGGGATGAA
CCGAACGTGAAGTTAAAGTGCCGGAATGCACGCTCATCAGACACCACAAAAGGTGTTAGTTCATCTAGACAGCCGGAC
GGTGGCCATGGAAGTCGGAATCCGCTAAGGAGTGTGTAACAACTCACCGGCCGAATGAACTAGCCCTGAAAATGGATG
GCGCTCAAGCGTGCTACTTATACTTCACCGTGATTGCTAATTTATGATGCTTTCACGAGTAGGCAGGCGTGGAGGTCAG
TGAAGAAGCCTTTGCTGTAAAGCTGGGTCGAACGGCCTCTAGTGCAGATCTTGGTGGTAGTAGCAAATATTCAAATGAG
AACTTTGAAGACTGAAGTGGGGAAAAGGTTCCATGTCAACAGCAGTTGGACATGGGTTAGTCGATCCTAAGAGATGGGG
AAGCTCCGTTTCAAAGCGCTTGATTTTTCAAGCCTACCATCGAAAGGGAATCCGGTTAAAATTCCGGAACTTGGATATG
GATTCTTCACGGTAACGTAACTGAATGTGGAGACGTCGGCATGAGCCCTAGGAGGAGTTATCTTTTCTTCTTAACAGCT
TATCACCCTGGAATTGGTTTATCCGGAGATGGGGTCTTATGGCTGGAAGAGCGCGGTAATTTTGCCGCGTCTGGTGCGC
TCATGACGGTCCTTGAAAATCCACAGGAAGGAATAGTTTTCATGCCAAGTCGTACTCATAACCGCAGCAGGTCTCCTAG
GTTAACAGCCTCTAGTTGATAGAATAATGTAGATAAGGGAAGTCGGCAAAATAGATCCGTAACTTTCGGGATAAGGAT
TGGCTCTAAGGATCGGGTGTCTTGGGCCTTGTGTAGACGCGGTGGTGACTGATGGCGGGCTGTCTTCGGACGGACTGCT
GCCGGACGCTGCTGTAGACACGCTTGGTAGGTTCTTGTAACCGTCCGGGGCACGCTTAACGATCAACTTAGAACTGGTA
CGGACAAGGGGAATCTGACTGTCTAATTAAAACATAGCATTGTGATGGTCAGAAAGTGATGTTGACACAATGTGATTTC
TGCCCAGTGCTCTGAATGTCAAAGTGAAGAAATTCAACCAAGCGCGGGTAAACGGCGGGAGTAACTATGACTCTCTTA
AGGTAGCCAAATGCCTCGTCATCTAATTAGTGACGCGCATGAATGGATTAACGAGATTCCCACTGTCCCTATCTACTAT
CTAGCGAAACCACAGCCAAGGGAACGGGCTTGGCAGAATCAGCGGGGAAAGAAGACCCTGTTGAGCTTGACTCTAGTT
TGACATTGTGAAAAGACATGGAGGGTGTAGAATAAGTGGGAGCTTCGGCGCCGGTGAAATACCACTACCTCTATAGTT
TTTTTACTTATTCAATGAAGCGGAGCTGGAGGTCAAACTCCACGTTCTAGCATTAAGCCTTTTTAGGTGATCCGGGTTGA
AGACATTGTCAGGTGGGGAGTTTGGCTGGGGGCGGGCACATATTGTTTAACGATAACGCAGGTGTCCTAAGGGGGACT
CATGGAGAACAGGAAATCTCCCAGTAGAACAAAAAGGGTAAAAGTCCCCTTGATTTTGATTTTCAGTGTGAATACAAA
CCATGAAAGTGTGGCCTATCGATCCTTTAGTCCCTCGGAATTTGAGGCTAGAGGTGCCAGAAAAGTTACCACAGGGATA
ACTGGCTTGTGGCAGTCAAGCGTTCATAGCGACATTGCTTTTTGATTCTTCGATGTCGGCTCTTCCTATCATACCGAAGC
AGAATTCGGTAAGCGTTGGATTGTTCACCCACTAATAGGGAACGTGAGCTGGGTTTAGACCGTCGTGAGACAGGTTAGT
TTTACCCTACTGATGAATGTTGTCGCAATAGTAATTGAACTTAGTACGAGAGGAACCGTTCATTCAGATAATTGGTTTTT
GCGGCTGTCTGATCAGGCAACGCCGCGAAGCTACCATCTGCTGGATTATGGCTGAACGCCTCTAAGTCAGAATCCATGC
TAGAACGCGACGATTTTTGCCCTACACATTTTAGATGGATACGAATAAGACTTTATGTCGCTGGACCATAGCAGGCTGG
CAACGGTACACTTAGCGGAAAGGCTTTGTGTGCTTGCCGGCCGGATAGCAATGTCAACATGCGTGGGGATAAATCCTTTG
CATACGACTTAGATGTACAACGGAGTATTGTAAGCAGTAGAGTAGCCTTGTTGTTACGATCTGCTGAGATTAAGCTCTT
GTTGTCTGATTTGTCTAGGTGTAGTACTGT
```

Figure 34
*Chaetomium globosum* rRNA gene (SEQ ID NO: 81)

```
CCAAACTTCGGTCATTTAGAGGAAAGTAAAAGTCGTAACAAGGTCTCCGTTGGTGAACCAGCGGAGGGATCATTACAG
AGTTGCAAAACTCCCTAAACCATTGTGAACGTTACCTATACCGTTGCTTCGGCGGGCGGCCCCGGGGTTTACCCCCCGG
GCGCCCCTGGGCCCCACCGCGGGCGCCCGCCGGAGGTCACCAAACTCTTGATAATTTATGGCCTCTCTGAGTCTTCTGT
ACTGAATAAGTCAAAACTTTCAACAACGGATCTCTTGGTTCTGGCATCGATGAAGAACGCAGCGAAATGCGATAAGTA
ATGTGAATTGCAGAATTCAGTGAATCATCGAATCTTTGAACGCACATTGCGCCCGCCAGCATTCTGGCGGGCATGCCTG
TTCGAGCGTCATTTCAACCATCAAGCCCCCGGGCTTGTGTTGGGGACCTGCGGCTGCCGCAGGCCCTGAAAAGCAGTGG
CGGGCTCGCTGTCGCACCGAGCGTAGTAGCATACATCTCGCTCTGGTCGCGCCGCGGGTTCCGGCCGTTAAACCACCTT
TTAACCCAAGGTTGACCTCGGATCAGGTAGGAAGACCCGCTGAACTTAAGCATATCAATAAGCGGAGGAAAAGAAACC
AACAGGGATTGCCCTAGTAACGGCGAGTGAAGCGGCAACAGCTCAAATTTGAAATCTGGCTTCGGCCCGAGTTGTAAT
TTGCAGAGGAAGCTTTAGGCGCGGCACCTTCTGAGTCCCCTGGAACGGGGCGCCATAGAGGGTGAGAGCCCCGTATAG
TTGGATGCCTAGCCTGTGTAAAGCTCCTTCGACGAGTCGAGTAGTTTGGGAATGCTGCTCAAAATGGGAGGTAAATTTC
TTCTAAAGCTAAATACCGGCCAGAGACCGATAGCGCACAAGTAGAGTGATCGAAAGATGAAAAGCACTTTGAAAAGA
GGGTTAAATAGCACGTGAAATTGTTGAAAGGGAAGCGCTTGTGACCAGACTTGCGCCGGGCGGATCATCCGGTGTTCT
CACCGGTGCACTCCGCCCGGCTCAGGCCAGCATCGGTTCTCGCGGGGGGATAAAGGTCCTGGGAACGTAGCTCCTCCG
GGAGTGTTATAGCCCGGGGCGTAATGCCCTCGCGGGGACCGAGGTTCGCGCATCTGCAAGGATGCTGGCGTAATGGTC
ATCAGCGACCCGTCTTGAAACACGGACCAAGGAGTCAAGGTTTTGCGCGAGTGTTTGGGTGTAAAACCCGCACGCGTA
ATGAAAGTGAACGTAGGTGAGAGCTTCGGCGCATCATCGACCGATCCTGATGTTTTCGGATGGATTTGAGTAGGAGCGT
TAAGCCTTGGACCCGAAAGATGGTGAACTATGCTTGGATAGGGTGAAGCCAGAGGAAACTCTGGTGGAGGCTCGCAGC
GGTTCTGACGTGCAAATCGATCGTCAAATCTGAGCATGGGGGCGAAAGACTAATCGAACCATCTAGTAGCTGGTTACC
GCCGAAGTTTCCCTCAGGATAGCAGTGTTGTCTTCAGTTTTATGAGGTAAAGCGAATGATTAGGGACTCGGGGGCGCTT
TTTAGCCTTCATCCATTCTCAAACTTTAAATATGTAAGAAGCCCTTGTTACTTAATTGAACGTGGGCATTCGAATGTACC
AACACTAGTGGGCCATTTTTGGTAAGCAGAACTGGCGATGCGGGATGAACCGAACGCGGGGTTAAGGTGCCGGAGTGG
ACGCTCATCAGACACCACAAAAGGCGTTAGTACATCTTGACAGCAGGACGGTGGCCATGGAAGTCGGAATCCGCTAAG
GACTGTGTAACAACTCACCTGCCGAATGTACTAGCCCTGAAAATGGATGGCGCTCAAGCGTCCCACCCATACCCCGCCC
TCAGGGTAGAAACGATGCCCTGAGGAGTAGGCGGCCGTGGAGGTCAGTGACGAAGCCTAGGGCGTGAGCCCGGGTCG
AACGGCCTCTAGTGCAGATCTTGGTGGTAGTAGCAAATACTTCAATGAGAACTTGAAGGACCGAAGTGGGGAAAGGTT
CCATGTGAACAGCGGTTGGACATGGGTTAGTCGATCCTAAGCCATAGGGAAGTTCCGTTTCAAAGGGGCACTCGTGCCC
CGTGTGGCGAAAGGGAAGCCGGTTAACATTCCGGCACCTGGATGTGGGTTTTGCGCGGTAACGCAACTGAACACGGAG
ACGACGGCGGGGCCCCGGGCAGAGTTCTCTTTTCTTCTTAACGGTCCATCACCCTGAAAACAGTTTGTCTGGAGATAG
GGTTTAACGGCCGGAAGAGCCCGACACTTCTGTCGGGTCCGGTGCGCTCTCGACGTCCCTTGAAAATCCGTGGGAGGG
AATAATTCTCACGCCAGGTCGTACTCATAACCGCAGCAGGTCTCCAAGGTGAACAGCCTCTGGTTGATAGAACAATGTA
GATAAGGGAAGTCGGCAAAATAGATCCGTAACTTCGGGAAAAGGATTGGCTCTAAGGGTTGGGCACGTTGGGCTTTGG
GCGGACGCCCTGGGAGCAGGTCGCCTCTAGCCGGGCAACCGGCGGGGGCTTCCAGCATCCGGGTGCAGATGCCCTTA
GCAGGCTTCGGCCGTCCGGCGTGCGGTTAACAACCAACTTAGAACTGGTACGGACAGGGGGAATCTGACTGTCTAATT
AAAACATAGCATTGCGATGGCCAGAAAGTGGTGTTGACGCAATGTGATTTCTGCCCAGTGCTCTGAATGTCAAAGTGA
AGAAATTCAACCAAGCGCGGGTAAACGGGCGGGGAGTAACTATTGACTCTTTCTTAAGGTTAGCCAAATGCCTCGTCAT
TCTAATTAAGTGACGCGCATGAAATGGATTTAACGAGATTCCCAACTGTCCCTTATCTACTATCTAGGCGAAACCACCA
GCCAAGGGAACGGGCTTGGCCAGAATCCAGCGGGGAAAGAAGACCCCTGTTGAGCTTGACTCTAGTTTTGACATTGTG
AAAAGACATAGGGAGGTGTAGAATAGGTGGGGAGCTTCGGCGCCCGGTGAAATACCACTACTCCTATTGTTTTTTTTAC
TTATTCAATGAAGCGGGGCTGGATTTTCGTCCCAACTTCTGGTTTTAAGGTCCTTCGCGGGCCGACCCGGGTTGAAGAC
ATTGTCAGGTGGGGAGTTTGGCTGGGGCGGCACATCTGTTAAACCATAACGCAGGTGTCCTAAGGGGGGCTCATGGAG
AACAGAAATCTCCAGTAGAACAAAAGGGTAAAAGTCCCCTTGATTTTGATTTTCAGTGTGAATACAAACCATGAAAGT
GTGGCCTATCGATCCTTTAGTCCCTCGAAATTTGAGGCTAGAGGTGCCAGAAAAGTTACCACAGGGATAACTGGCTTGT
GGCGGCCAAGCGTTCATAGCGACGTCGCTTTTTGATCCTTCGATGTCGGCTCTTCCTATCATACCGAAGCAGAATTCGGT
AAGCGTTGGATTGTTCACCCACTAATAGGGAACGTGAGCTGGGTTTAGACCGTCGTGAGACAGGTTAGTTTTACCCTAC
TGATGAACTCATCGCAATGGTAATTCAGCTTAGTACGAGAGGAACCGCTGATTCAGATAATTGGTTTTTGCGGTTGTCC
GACCGGGCAGTGCCGACGAAGCTACCATCTGCTGGATAATGGCTGAACGCCTCTAAGTCAGAATCCATGCCAGAACGC
GATGATACTACCCGCACGTTGTAGACGTATAAGAATAGGCTCCGGCCTCGTATCTTAGCAGGCGATTCCTCCGCCGGCC
TCGAAGTGGTCGGCGGTAATTCGCGTATTGTAATTTCGGCACGCGCGGGATCAAATCCTTTGCAGACGACTTAGCTGTG
CGAAAGGGGTCCTGTAAGCAGTAGAGTAGCCTTGTTGTTACGATCTGCTGAGGGTAAGCCCTTCTTCGCCTAGATTTCC
CAGCGAGAGCCCGCCAGCGAA
```

Figure 35
*Coccidioides immitis* rRNA gene (SEQ ID NO: 82)

```
GTCATTTAGAGGAAGTAAAAGTCGTAACAAGGTTTCCGTAGGTGAACCTGCGGAAGGATCATTAAAGTGGCGTCCGGC
TGCGCACCTCCCCCGCGGGGGTCGCGCGGTCCGTACCTCCCACCCGTGTTTACTGAACTATTGTTGCCTTGGCAGGCCT
GCCGGGCCTCTGGCTGCCGGGGATCGCCCGCCTTGCGCGGCGTCCCGGGCGCGCGCCTGCCAGTGGATCAATTGAACTC
TTATGTGAAGATTGTCAGTCTGAGCATCATAGCAAAAAATCAAACAAAACTTTCAACAACGGATCTCTTGGTTCCGGCA
TCGATGAAGAACGCAGCGAAATGCGATAAGTAATGTGAATTGCAGAATTCCGTGAATCATCGAATCTTTGAACGCACA
TTGCGCCCTCTGGTATTCCGGGGGGCATGCCTGTTCGAGCGTCATTGCAAACCCTTCAAGCACGGCTTGTGTGTTGGGC
CAACGTCCCCGCTTGTGTGGACGGGCCTGAAATGCAGTGGCGGCACCGAGTTCCTGGTGTCTGAGTGTATGGGAAATCA
CTTCATCGCTCAAAGACCCGATCGGGGCCGATCTTTTTTTTTTTTAATATCCGGTTTGACCTCGGATCAGGTAGGAGTA
CCCGCTGAACTTAAGCATATCAATAAGCGGAGGAAAAGAAACCAACAGGGATTGCCTCAGTAACGGCGAGTGAAGCG
GCAAAAGCTCAAATTTGAAATCTGGCTCCATGCGGAGCCCGAGTTGTAATTTGGAGAGGACACTTCGGGTGCGGCCAC
GGCATAAGTTCCTTGGAACAGGACGTCATAGAGGGTGAGAATCCCGTCTTTGGCTGCTGGACCGCGCCCATGCGAAGTT
CCTTCGACGAGTCGAGTTGTTTGGGAATGCAGCTCTAAGTGGGTGGTAAATTTCATCTAAAGCTAAATATTGGCCGGAG
ACCGATAGCGCACAAGTAGAGTGATCGAAAGGTTAAAAGCACCTTGAAAAGGGAGTTAAATAGCACGTGAAATTGTTG
AAAGGGAAGCGCTTGCAACCAGACTCGGTCGTGGGGGCTCAGCGGGCATGAGTGCCCGTGTACTCCCCCATGCTCCGG
GCCAGCATCAGTTCTGGCGGTTGGTTAAAGGCCTCTGGAATGTATCGTCCTCCGGGACGTCTTATAGCCAGGGGCGCAA
TGCGGCCAGCCGGGACTGAGGAACGCGCTTCGGCACGGATGCTGGCATAATGGTTGTAAGCGGCCCGTCTTGAAACAC
GGACCAAGGAGTCTAACATCCACGCGAGTGTTCGGGTGTCAAACCCGTGCGCGCAGTGAAAGCGAACGGAGGTGGGA
GCTCCGCAAGGGTGCACCTATCGACCGATCCTGAAGTCTTCGGATGGATTTGAGTAAGAGCGTGGCTGTGTGGGACCCG
AAAGATGGTGAACTATGCCTGAATAGGGTGAAGCCAGAGGAAACTCTGGTGGAGGCTCGCAGCGGTTCTGACGTGCAA
ATCGATCGTCAAATTTGGGTATAGGGGCGAAAGACTAATCGAACCATCTGGTAGCTGGTTCCTGCCGAAGTTTCCCTCA
GGATAGCAGTAACGTTTTCAGTTTTATGAGGTAAAGCGAATGATTAGAGGCCTTGGGGTTGAAACAACCTTAACCTATT
CTCAAACTTTAAATATGTAAGAAGCCCTTGTTACTTAAGTGAATCGTGGGCATTAGAATGGATCGTTACTAGTGGGCCA
TTTTTGGTAAGCAGAACTGGCGATGCGGGATGAACCGAACGCGAGGTTAAGGTGCCGGAATGCACGCTCATCAGACAC
CACAAAAGGTGTTAGTTCATCTAGACAGCCCGACGGTGGCCATGGAAGTCGGAATCCGCTAAGGAGTGTGTAACAACT
CACGGGCCGAATGAACTAGCCCTGAAAATGGATGGCGCTCAAGCGTGCTACCCATACCTCGCCGTCGGGGTAGAAACG
AAGCCCCGACGAGTAGGCAGGCGTGGAGGTTTGTGACGAAGCCTTGGGAGTGATCCCGGGTCGAACAGCCTCTAGTGC
AGATCTTGGTGGTAGTAGCAAATACTCAAATGAGAACTTTGAGGACTGAAGTGGGGAAAGGTTCCATGTGAACAGCAG
TTGGACATGGGTTAGTCGATCCTAAGACATAGGGTAGTTCCGTTTGAAAGCGCGCCCTAGTGCGCCGTTTGTCGAAAGG
GAAGCCGGTTAATATTCCGGCACCTGGATGTGGATTCTCCACGGCAACGTAACTGAACGCGGAGACGTCGGCAGGAGT
CCTGGGAAGAGTTCTCTTTTCTTCTTGACGGCCTATCACCCTGAAATCGGTTTGTCCGGAGCTAGGGTTTCATGGCCGGC
AGAGCCCCGCACCTTTGCGGGGTCCGGTGCGCTCCTGACGACCCTTGAAAATCCGCGGGAAGGAATAGTTTTCACGCC
AGGTCGTACTCATAACCGCAGCAGGTCTCCAAGGTGAAAAGCCTCTAGTTGATAGAACAATGTAGATAAGGGAAGTCG
GCAAAATAGATCCGTAACTTCGGGAAAAGGATTGGCTCTAAGGGTCGGGCGCGTTGGGCCTTGGGGGAAAGCCTCCGG
AGCAGGAGGGCACTAGCCGGGCAACCGGCGGGCGCCTTCCAGCATCGGGGTGCGGACGCCCTTGGCAGGCTTCGGCCG
TCCGGCGCGCGATTAACGACCAACTTAGAACTGGTACGGACAAGGGGAATCTGACTGTCTAATTAAAACATAGCATTG
CGATGGCCAGAAAGTGGTGTTGACGCAATGTGATTTCTGCCCAGTGCTCTGAATGTCAAAGTGAAGAAATTCAACCAA
GCGCGGGTAAACGGCGGGAGTAACTATGACTCTCTTAAGGTAGCCAAATGCCTCGTCATCTAATTAGTGACGCGCATG
AATGGATTAACGAGATTCCCACTGTCCCTATCTACTATCTAGCGAAACCACAGCCAAGGGAACGGGCTTGGCAAAATC
AGCGGGGAAAGAAGACCCTGTTGAGCTTGACTCTAGTTTGACATTGTGAAAAGACATATCGGGTGTAGAATAGGTGGG
AGCTTCGGCGCCGGTGAAATACCACTACCTTTATTGTTTTTTACTTATTCAATGAAGCGGAACTGGGCTTTACCGCCCA
ACTTCTAGCGTTAAGGTCCTTCGCGGGCTGATCCGGGTTGAAGACATTGTCAGGTGGGGAGTTTGGCTGGGGCGGCACA
TCTGTTAAACCATAACGCAGGTGTCCTAAGGGGGACTCATGGAGAACAGAAATCTCCAGTAGAACAAAAGGGTAAAAG
TCCCCTTGATTTTGATTTTCAGTGTGAATACAAACCATGAAAGTGTGGCCTATCGATCCTTTAGTCCCTCGAAATTTGAG
GCTAGAGGTGCCAGAAAAGTTACCACAGGGATAACTGGCTTGTGGCAGCCAAGCGTTCATAGCGACGTTGCTTTTTGAT
CCTTCGATGTCGGCTCTTCCTATCATACCGAAGCAGAATTCGGTAAGCGTTGGATTGTTCACCCACTAATAGGGAACGT
GAGCTGGGTTTAGACCGTCGTGAGACAGGGTTAGTTTTACCCTACTGATGAAGGGTCGCCGCAACGGTAATTCAATTTA
GTACGAGAGGGAACCGTTGATTCAGATAATTGGTTTTTGCGGCTGTCTGACCAGGCAGTGCCGCGAAGCTACCATCTGC
CGGATTATGGCTGAACGCCTCTAAGTCAGAATCCGTACCGGAACGCGGCGATGTTGCCCCGCACGTTGTAGTTGGATAC
GAATAGGCCTACGGGCCCTGAACCTCAGCAGGTCGGCGACGGCTCCCGGGAAGAGACTCTCGGGCGCCAGCTGACGGA
TTGCAATGTCACCACGCGCGGGGATAGATCCTCTGCAGACGACTGAAATGACCAAGCGGGTCGTGTAAGCGGTCAAGT
AGCCTAGTTGTTACGAGTCGCTGAGCGTCAGCCCGATCCTTGGCTCGATTTGTTGTAAACACCCTCCATCAACATGTTTG
TCTTCGGCAACGCCGG
```

Figure 36
*Coccidioides posadasii* rRNA gene (SEQ ID NO: 83)

```
ATTTAGAGGAAGTAAAAGTCGTAACAAGGTTTCCGTAGGTGAACCTGCGGAAGGATCATTAAAGTGGCGTCCGGCTGC
GCACCTCCCCCGCGGGGGTTCGCGCGGTCCGTACCTCCCACCCGTGTTTACTGAACCATTGTTGCCTTGGCAGGCCTGC
CGGGCCTCCGGCTGCCGGGGATCGCCCGTCTTGCGCGGCGTCCCGGGCGCGCGCCTGCCAGCGGATCAATTGAACTCTT
ATGTGAAGATTGTCAGTCTGAGCATCATAGCAAAAATCAAACAAAACTTTCAACAACGGATCTCTTGGTTCCGGCATCG
ATGAAGAACGCAGCGAAATGCGATAAGTAATGTGAATTGCAGAATTCCGTGAATCATCGAATCTTTGAACGCACATTG
CGCCCTCTGGTATTCCGGGGGGCATGCCTGTTCGAGCGTCATTGCAAACCCTTCAAGCACGGCTTGTGTGTTGGGCCAA
CGTCCCCGCTTGTGTGGACGGGCCTGAAATGCAGTGGCGGCACCGAGTTCCTGGTGTCTGAGTGTATGGGAAATCACTT
CATCGCTCAAAGACCCGATCGGGGCCGATCTCTTTTTTTTATTATATCCGGTTTGACCTCGGATCAGGTAGGAGTACCCG
CTGAACTTAAGCATATCAATAAGCGGAGGAAAAGAAACCAACAGGGATTGCCTCAGTAACGGCGAGTGAAGCGGCAA
AAGCTCAAATTTGAAATCTGGCTCCATGCGGAGCCCGAGTTGTAATTTGGAGAGGACACTTCGGGTGCGGCCACGGCA
TAAGTTCCTTGGAACAGGACGTCATAGAGGGTGAGAATCCCGTCTTTGGCTGCTGGACCGCGCCCATGCGAAGTTCCTT
CGACGAGTCGAGTTGTTTGGGAATGCAGCTCTAAGTGGGTGGTAAATTTCATCTAAAGCTAAATATTGGCCGGAGACCG
ATAGCGCACAAGTAGAGTGATCGAAAGGTTAAAAGCACCTTGAAAAGGGAGTTAAATAGCACGTGAAATTGTTGAAA
GGGAAGCGCTTGCAACCAGACTCGGTCGTGGGGGCTCAGCGGGCATGCGTGCCCGTGTACTCCCCCATGCTCCGGGCC
AGCATCAGTTCTGGCGGTTGGTTAAAGGCCTCTGGAATGTATCGTCCTCCGGGACGTCTTATAGCCAGGGGCGCAATGC
GGCCAGCCGGGACTGAGGAACGCGCTTCGGCACGGATGCTGGCATAATGGTTGTAAGCGGCCCGTCTTGAAACACGGA
CCAAGGAGTCTAACATCCACGCGAGTGTTCGGGTGTCAAACCCGTGCGCGCAGTGAAAGCGAACGGAGGTGGGAGCCC
GCAAGGGTGCACCATCGACCGATCCTGAAGTCTTCGGATGGATTTGAGTAAGAGCGTGGCTGTTGGGACCCGAAAGAT
GGTGAACTATGCCTGAATAGGGTGAAGCCAGAGGAAACTCTGGTGGAGGCTCGCAGCGGTTCTGACGTGCAAATCGAT
CGTCAAATTTGGGTATAGGGGCGAAAGACTAATCGAACCATCTGGTAGCTGGTTCCTGCCGAAGTTTCCCTCAGGATAG
CAGTAACGTTTTCAGTTTTATGAGGTAAAGCGAATGATTAGAGGCCTTGGGGTTGAAACAACCTTAACCTATTCTCAAA
CTTTAAATATGTAAGAAGCCCTTGTTACTTAAGTGAACGTGGGCATTAGAATGGATCGTTACTAGTGGGCCATTTTTGG
TAAGCAGAACTGGCGATGCGGGATGAACCGAACGCGAGGTTAAGGTGCCGGAATGCACGCTCATCAGACACCACAAA
AGGTGTTAGTTCATCTAGACAGCCCGACGGTGGCCATGGAAGTCGGAATCCGCTAAGGAGTGTGTAACAACTCACGGG
CCGAATGAACTAGCCCTGAAAATGGATGGCGCTCAAGCGTGCTACCCATACCTCGCCGTCGGGGTAGAAACGAAGCCC
CGACGAGTAGGCAGGCGTGGAGGTTTGTGACGAAGCCTTGGGAGTGATCCCGGGTCGAACAGCCTCTAGTGCAGATCT
TGGTGGTAGTAGCAAATACTCAAATGAGAACTTTGAGGACTGAAGTGGGGAAAGGTTCCATGTGAACAGCAGTTGGAC
ATGGGTTAGTCGATCCTAAGACATAGGGTAGTTCCGTTTGAAAGCGCGCCCTAGTGCGCCGTTTGTCGAAAGGGAAGCC
GGTTAATATTCCGGCACCTGGATGTGGATTCTCCACGGCAACGTAACTGAACGCGGAGACGTCGGCAGGAGTCCTGGG
AAGAGTTCTCTTTTCTTCTTGACGGCCTATCACCCCTGAAATCGGTTTGTCCGGAGCTAGGGTTTCATGGCCGGCAGAGCC
CCGCACCTTTGCGGGGTCCGGTGCGCTCCTGACGACCCTTGAAAATCCGCGGGAAGGAATAGTTTTCACGCCAGGTCGT
ACTCATAACCGCAGCAGGTCTCCAAGGTGAAAAGCCTCTAGTTGATAGAACAATGTAGATAAGGGAAGTCGGCAAAAT
AGATCCGTAACTTCGGGAAAAGGATTGGCTCTAAGGGTCGGGCGCGTTGGGCCTTGGGGGAAAGCCTCCGGAGCAGGA
GGGCACTAGCCGGGCAACCGGCGGGCGCCTTCCAGCATCGGGGTGCGGACGCCCTTGGCAGGCTTCGGCCGTCCGGCG
CGCGATTAACGACCAACTTAGAACTGGTACGGACAAGGGGAATCTGACTGTCTAATTAAAACATAGCATTGCGATGGC
CAGAAAGTGGTGTTGACGCAATGTGATTTCTGCCCAGTGCTCTGAATGTCAAAGTGAAGAAATTCAACCAAGCGCGGG
TAAACGGCGGGAGTAACTATGACTCTCTTAAGGTAGCCAAATGCCTCGTCATCTAATTAGTGACGCGCATGAATGGATT
AACGAGATTCCCACTGTCCCTATCTACTATCTAGCGAAACCACAGCCAAGGGAACGGGCTTGGCAAAATCAGCGGGGA
AAGAAGACCCTGTTGAGCTTGACTCTAGTTTGACATTGTGAAAAGACATATCGGGTGTAGAATAGGTGGGAGCTTCGG
CGCCGGTGAAATACCACTACCTTTATTGTTTTTTACTTATTCAATGAAGCGGAACTGGGCTTTACCGCCCAACTTCTAG
CGTTAAGGTCCTTCGCGGGCTGATCCGGGTTGAAGACATTGTCAGGTGGGGAGTTTGGCTGGGGCGGCACATCTGTTAA
ACCATAACGCAGGTGTCCTAAGGGGGACTCATGGAGAACAGAAATCTCCAGTAGAACAAAAGGGTAAAAGTCCCCTTG
ATTTTGATTTTCAGTGTGAATACAAACCATGAAAGTGTGGCCTATCGATCCTTTAGTCCCTCGAAATTTGAGGCTAGAG
GTGCCAGAAAAGTTACCACAGGGATAACTGGCTTGTGGCAGCCAAGCGTTCATAGCGACGTTGCTTTTTGATCCTTCGA
TGTCGGCTCTTCCTATCATACCGAAGCAGAATTCGGTAAGCGTTGGATTGTTCACCCACTAATAGGGAACGTGAGCTGG
GTTTAGACCGTCGTGAGACAGGTTAGTTTTACCCTACTGATGAAGGTCGCCGCAACGGTAATTCAATTTAGTACGAGAG
GAACCGTTGATTCAGATAATTGGTTTTTGCGGCTGTCTGACCAGGCAGTGCCGCGAAGCTACCATCTGCCGGATTATGG
CTGAACGCCTCTAAGTCAGAATCCGTACCGGAACGCGGCGATGTTGCCCCGCACGTTGTAGTTGGATACGAATAGGCCT
ACGGGCCCTGAACCTCAGCAGGTCGGCGACGGCTCCCGGGAAGAGACTCTCGGGCGCCAGCTGACGGATTGCAATGTC
ACCACGCGCGGGATAGATCCTCTGCAGACGACTGAAATGACCAAGCGGGTCGTGTAAGCGGTCGAGTAGCCTAGTTG
TTACGAGTCGCTGAGCGTCAGCCCGATCCTTGGCTCGATTTGTTGTAAACACCCTCC
```

Figure 37

*Cryptococcus neoformans* rRNA gene (SEQ ID NO: 84)

```
AGAGGAAGTAAAAGTCGTAACAAGGTTTCCGTAGGTGAACCTGCGGAAGGATCAGTAGAGAATATTGGACTTTGGTCC
ATTTATCTACCCATCTACACCTGTGAACTGTTTATGTGCTTCGGCACGTTTTACACAAACTTCTAAATGTAATGAATGTA
ATCATATTATAACAATAATAAAACTTTCAACAACGGATCTCTTGGCTTCCACATCGATGAAGAACGCAGCGAAATGCGA
TAAGTAATGTGAATTGCAGAATTCAGTGAATCATCGAGTCTTTGAACGCAACTTGCGCCCTTTGGTATTCCGAAGGGCA
TGCCTGTTTGAGAGTCATGAAAATCTCAATCCCTCGGGTTTTATTACCTGTTGGACTTGGATTTGGGTGTTTGCCGCGAC
CTGCAAAGGACGTCGGCTCGCCTTAAATGTGTTAGTGGGAAGGTGATTACCTGTCAGCCCGGCGTAATAAGTTTCGCTG
GGCCTATGGGGTAGTCTTCGGCTTGCTGATAACAACCATCTCTTTTTGTTTGACCTCAAATCAGGTAGGGCTACCCGCTG
AACTTAAGCATATCAATAAGCGGAGGAAAAGAAACTAACAAGGATTCCCTTAGTAACGGCGAGTGAACCGGGAAGAG
CTCAAATTTGAAATCTGGCGTCCTCCGGGCGTCCGAGTTGTAATCTACAGAAACGTTTTCCGTGCTGGACCGTGTCTAA
GTCCCTTGGAATAGGGTATCAAAGAGGGTGACAATCCCGTACTTGACACGATCACCAGTGCTCTGTGATACGTTTTCTA
CGAGTCGCGTTACTTGGGAGTGTAGCGCAAAATGGGTGGTAAACTCCATCTAAAGCTAAATATTGGTGGAAGACCGAT
AGCGAACAAGTACCGTGAGGGAAAGATGAAAAGCACTTTGGAAAGAGAGTTAAACAGTACGTGAAATTGTTGAAAGG
GAAACGATTGAAGTCAGTCGTGTCTATTGGGTTCAGCCAGTTCTGCTGGTGTATTCCCTTTAGACGGGTCAACATCAGTT
CTGATCGGTGGATAAGGGCTGGAGGAATGTGGCACTCTTCGGGGTGTGTTATAGCCTCCTGTCGCATACACTGGTTGGG
ACTGAGGAATGCAGCTCGCCTTTATGCCGGGGTTCGCCCACGTTCGAGCTTAGGATGTTGACAAAATGGCTTTAAACG
ACCCGTCTTGAAACACGGACCAAGGAGTCTAACATATCTGCGAGTGTTTGAGTGTCAAACTCGAGCGCGAAATGAAAG
TGAATGTAGGAGGGATCCGCAAGGAGCACCTTCGACCGATCCTTCTGTGATGGATTTGAGTAAGAGCATATAT
GCTGGGACCCGAAAGATGGTGAACTATGCCTGAATAGGGCGAAGCCAGGGGAAACTCTGGTGGAGGCTCGTAGCGATT
CTGACGTGCAAATCGATCGTCGAATTTGGGTATAGGGGCGAAAGACTAATCGAACCATCTAGTAGCTGGTTCCTGCCGA
AGTTTCCCTCAGGATAGCAGAAACTCGCATCAGTTTTATGAGGTAAAGCGAATGATTAGAGGCCTTGGGGACGAAACG
TCCTTAACCTATTCTCAAACTTTAAATGTGTAAGAAGCACTTGTCACTTAATTGGACGAGCGCATGCGAATGAGAGTTT
CTAGTGGGCCATTTTTGGTAAGCAGAACTGGCGATGCGGGATGAACCGATCGTGAGGTTAAGGTGCCGGAATACACGC
TCATCAGACACCACAAAAGGTGTTAGTTCATCTAGACAGCAGGACGGTGGCCATGGAAGTCGGAATCCGCTAAGGAGT
GTGTAACAACTCACCTGCCGAATGAACTAGCCCTGAAAATGGATGGCGCTCAAGCGTGTTACCCATACCTCACCGTCAG
CGTTGTAGTGACGCGCTGACGAGTAGGCAGGCGTGGAGGTCGACCTAGGCAGTGATGTCGGGTGGAACGG
CCTCTAGTGCAGATCTTGGTGGTAGTAGCAAATATTCAAGTGAGAACCTTGAAGACTGAAGTGGAGAAAGGTTCCATG
GTAACAGCAGTTGGACATGGGTCAGTCGATCCTAAGAGATAGGGAAACTCCGTTTTAAAGCGCACGATTTTCCGTGCCG
CCTATCGAAAGGGAATCCGGTTAAGATTCCGGAACCAGGATGTGGATCATTGACGGTAACGTAAATGAAGTTGGAGAC
GTCGGCAAGGGCCCTGGGAAGAGTTCTCTTTTCTCCTTAACCGCCTACGACCTCGAAATCGGATTATCCGGAGCTGAGG
TTATATGGTGGGTAAAGCACAACACCTCTGTTGTGTCCGGTGCGTCCTTGACGATCCTTGAAAATCCGACGGAACGTAT
AAGTCTCACGCCTGGTCGTACTCATAACCGCAGCAGGTCTCCAAGGTGAACAGCCTCTAGTTGATGGAACAATGTAGAT
AAGGGAAGTCGGCAAAATAGATCCGTAACTTCGGGATAAGGATTGGCTCTAAGGGTTGGGTGCGTCGGGCCGTTGACG
GAAGGAAGCTGGACCTGGCGGGACTGCATGGGGCAACCTGTGTGGACCTGCTGGGATCGGCGACTGGAAGTCTTGGC
AGCCCTCGGGCGTCCGGCGTACGCTTAACAACCAACTTAGAACTGGTACGGACAAGGGGAATCTGACTGTCTAATTAA
AACATAGCATTGCGATGGCCAGAAAATGGTGTTGACGCAATGTGATTTCTGCCCAGTGCTCTGAATGTCAAAGTGAAG
AAATTCAACCAAGCGCGGGTAAACGGCGGGAGTAACTATGACTCTCTTAAGGTAGCCAAATGCCTCGTCATCTAATTA
GTGACGCGCATGAATGGATTAACGAGATTCCCACTGTCCCTATCTACTATCTAGCGAAACCACAGCCAAGGGAACGGG
CTTGGCAGAATCAGCGGGGAAAAGAACCCTGTTGAGCTTGACTCTAGTTTGACATTGTGAAAAGACATGGAGGGTGT
AGAATAAGTGGGAGCTTCGGCGCCGGTGAAATACCACTACCTCCATCGTTTTTTTACTTATTCAATGAAGCGGAGCTGG
GATGAAAGTCCCACCTTCTAGCGTTAAGGTCGTTTACCGGCCGATCCGGGTTGAAGACATTGTCAGGTGGGGAGTTTGG
CTGGGGCGGCACATCTGTTAAAAAATAACGCAGGTGTCCTAAGGGGGACTCATGGAGAACAGAAATCTCCAGTGGAAC
AAAAGGGTAAAAGTCCCCTTGATTTTGATTTTCAGTGTGAATACAAACCATGAAAGTGTGGCCTATCGATCCTTTAGTC
CCTCGGAGTTTGAGGCTAGAGGTGCCAGAAAAGTTACCACAGGGATAACTGGCTTGTGGCAGCCAAGCGTTCATAGCG
ACGTTGCTTTTTGATCCTTCGATGTCGGCTCTTCCTATCATACCGAAGCAGAATTCGGTAAGCGTTGGATTGTTCACCCA
CTAATAGGGAACGTGAGCTGGGTTTAGACCGTCGTGAGACAGGTTAGTTTTACCCTACTGATGGAGTGTCGTCGTAATA
GTAATTGAGGGTAGTACGAGAGGAACTGCTCATTCGTATAATTGGTATTTGCGTCTGTCCGATCGGGCAATGACGCGAA
GCTATCATACGCCAGATTATGGCTGAACGCCTCTAAGTCAGAATCTGTACTAGAAACGACGATTTTGGTCCCGCACATG
TTAGTTGTGTTTAAATAGGCTTCGGCTGTGAACCATATCTGAGGGTTGGGCTGCTTAGGCGGAAAGGCTTAGGTAGTCT
CCTTCGTATTGAAATGGAATATGGGCGGGGGTAAATCCTTTGCAGACGACTTGAATGGGAACGGGGTGCTGTAAGTGG
TAGAGTAGCCTTGTTGCTACGATCCACTGAGGCTAAGCCCTTGTTCTATAGATTTGTCTCTAACATGTTGGGTCTC
```

Figure 38

***Fusarium graminearum* rRNA gene (SEQ ID NO: 85)**

CGGAAAGCTCTCCAAACTCGGTCATTTAGAGGAAGTAAAAGTCGTAACAAGGTCTCCGTTGGTGAACCAGCGGAGGGA
TCATTACCGAGTTTACAACTCCCAAACCCCTGTGAACATACCTTATGTTGCCTCGGCGGATCAGCCCGCGCCCCGTAAA
AAGGGACGGCCCGCCGCAGGAACCCTAAACTCTGTTTTTAGTGGAACTTCTGAGTATAAAAAACAAATAAATCAAAAC
TTTCAACAACGGATCTCTTGGTTCTGGCATCGATGAAGAACGCAGCAAAATGCGATAAGTAATGTGAATTGCAGAATTC
AGTGAATCATCGAATCTTTGAACGCACATTGCGCCCGCCAGTATTCTGGCGGGCATGCCTGTTCGAGCGTCATTTCAAC
CCTCAAGCCCAGCTTGGTGTTGGGAGCTGCAGTCCTGCTGCACTCCCCAAATACATTGGCGGTCACGTCGAGCTTCCAT
AGCGTAGTAATTTACACATCGTTACTGGTAATCGTCGCGGCCACGCCGTTAAACCCCAACTTCTGAATGTTGACCTCGG
ATCAGGTAGGAATACCCGCTGAACTTAAGCATATCAATAAGCGGAGGAAAAGAAACCAACAGGGATTGCCCTAGTAAC
GGCGAGTGAAGCGGCAACAGCTCAAATTTGAAATCTGGCTTTCGGGCCCGAGTTGTAATTTGTAGAGGATGATTTTGAT
GCGGTGCCTTCCGAGTTCCCTGGAACGGGACGCCATAGAGGGTGAGAGCCCCGTCTGGTTGGATGCCAAATCTCTGTAA
ATCTCCTTCGACGAGTCGAGTAGTTTGGGAATGCTGCTCTAAATGGGAGGTATATGTCTTCTAAAGCTAAATACCGGCC
AGAGACCGATAGCGCACAAGTAGAGTGATCGAAAGATGAAAAGCACTTTGAAAAGAGAGTTAAAAAGTACGTGAAAT
TGTTGAAAGGGAAGCGTTTATGACCAGACTTGGGCTTGGTTAATCATCTGGGGTTCTCTCCAGTGCACTTTTCCAGTCCA
GGCCAGCATCAGTTTTCGCCGGGGGATAAAGGCTTCGGGAATGTGGCTCCCCTCGGGGAGTGTTATAGCCCGTTGTGTA
ATACCCTGGTGGGGACTGAGGTTCGCGCTTCTGCAAGGATGCTGGCGTAATGGTCATCAACGACCCGTCTTGAAACACG
GACCAAGGAGTCGTCTTCGTATGCGAGTGTTCGGGTGTCAAACCCCTACGCGTAATGAAAGTGAACGCAGGTGAGAGC
TTCGGCGCATCATCGACCGATCCTGATGTTCTCGGATGGATTTGAGTAAGAGCATACGGGGCCGGACCCGAAAGAAGG
TGAACTATGCCTGTGTAGGGTGAAGCCAGAGGAAACTCTGGTGGAGGCTCGCAGCGGTTCTGACGTGCAAATCGATCG
TCAAACATGGGCATGGGGGCGAAAGACTAATCGAACCTTCTAGTAGCTGGTTTCCGCCGAAGTTTCCCTCAGGATAGCA
GTGTTGAACTCAGTTTTATGAGGTAAAGCGAATGATTAGGGACTCGGGGGCGCTATTTAGCCTTCATCCATTCTCAAAC
TTTAAATATGTAAGAAGCTCTTGTTGCTTAATTGAACGTGAGCATTCGAATGTATCAACACTAGTGGGCCATTTTTGGTA
AGCAGAACTGGCGATGCGGGATGAACCGAACGCGAGGTTAAGGTGCCAGAGTAGACGCTCATCAGACACCACAAAAG
GTGTTAGTACATCTTGACAGCAGGACGGTGGCCATGGAAGTCGGAATCCGCTAAGGACTGTGTAACAACTCACCTGCC
GAATGTACTAGCCCTGAAAATGGATGGCGCTCAAGCGTCTCACCCATACCTCGCCCTCAGGGTAGAAACGAAGCCCTG
AGGAGTAGGCGGACGTGGAGGTCAGTGACGAAGCCTAGGGCGTGAGCCCGGGTTGAACGGCCTCTAGTGCAGATCTTG
GTGGTAGTAGCAAATACTTCAATGAGAACTTGAAGGACCGAAGTGGGGAAAGGTTCCATGTGAACAGCGGTTGGACAT
GGGTTAGTCGATCCTAAGCTATAGGGAAGTTCCGTTTCAAAGGCGCACTTTGCGCCGTCTAGCGAAAGGGGAGCCGGT
CAATATTCCGGCACCTGGATGTGGGTTTTGCGCGGCAACGCAACTGAACGTGGAGACGACGGCGGGGGCCCCAAGCAG
AGTTCTCTTTTCTTCTTAACAGTCTCTCACCCTGAAATCGGTTTGTCCGGAGCTAGGGTTTAATGGCTGGAAGAGCCCGG
CACCTCTGCCGGGTTTGGTGCGCTCTCGACGTCCCTTGAAAATCCACGGGAAGAAATAATTCTCACGCCAGGTCGTACT
CATAACCGCAGCAGGTCTCCAAGGTGAACAGCCTCTGGTTGATAGAACAATGTAGATAAGGGAAGTCGGCAAAATAGA
TCCGTAACTTCGGGAAAAGGATTGGCTCTAAGGGTTGGGCACGTTGGGCCTTGGGCGGACGTCCTGGGAGCAGGCAGC
CACTAGTCGGGCAACCGACCGGAGGCGGCCAGCATCCGGGTGCTGATGCCCTTGGCAGGCTTCGGCCGTCCGGCGTGC
GGTTAACAACCAACTTAGAACTGGTACGGACAAGGGGAATCTGACTGTCTAATTAAAACATAGCATTGCGATGGCCAG
AAAGTGGTGTTGACGCAATGTGATTTCTGCCCAGTGCTCTGAATGTCAAAGTGAAGTAATTCAACCAAGCGCGGGTAA
ACGGCGGGAGTAACTATGACTCTCTTAAGGTAGCCAAATGCCTCGTCATCTAATTAGTGACGCGCATGAATGGATTAAC
GAGATTCCCACTGTCCCTATCTACTATCTAGCGAAACCACAGCCAAGGGAACGGGCTTGGCAGAATCAGCGGGGAAAG
AAGACCCTGTTGAGCTTGACTCTAGTTTGACATTGTGAAAAGACATAGGAGGTGTAGAATAGGTGGGAGCTTCGGCGC
CGGTGAAATACCACTACTCCTATTGTTTTTTACTTATTCAATGAAGCGGGGCTGGATTTACGTCCAACTTCTGGTTTTA
AGGTCCTTCGCGGGCCGACCCGGGTTGAAGACATTGTCAGGTGGGGAGTTTGGCTGGGGCGGCACATCTGTTAAACCA
TAACGCAGGTGTCCTAAGGGGGGCTCATGGAGAACAGAAATCTCCAGTAGAACAAAAGGGTAAAAGTCCCCTTGATTT
TGATTTTCAGTGTGAATACAAACCATGAAAGTGTGGCCTATCGATCCTTTAGTCCCTCGACATTTGAGGCTAGAGGTGC
CAGAAAAGTTACCACAGGGATAACTGGCTTGTGGCGGCCAAGCGTTCATAGCGACGTCGCTTTTTGATCCTTCGATGTC
GGCTCTTCCTATCATACCGAAGCAGAATTCGGTAAGCGTTGGATTGTTCACCCACTAATAGGGAACGTGAGCTGGGTTT
AGACCGTCGTGAGACAGGTTAGTTTTACCCTACTGATGACCTCACCGCAATGGTAATTCAGCTTAGTACGAGAGGAACC
GCTGATTCAGATAATTGGTTTTTGCGGCTGTCCGACCGGGCAGTGCCGCGAAGCTACCATCTGCTGGATAATGGCTGAA
CGCCTCTAAGTCAGAATCCATGCCAGAACGCGGTGATACCACCCGCACGTATAGATGGACAAGAATAGGCCTCGGCTT
AGCGTCTTAGCAGGCGATTCCTCCACGGCGCTCGAAGCGCGTCGTGGTATTTCGCGTATTGTAATTTCAACACGAGCGG
GGTCAAATCCTTTGCAGACGACTTAGCTGTGCGAAACGGTCCTGTAAGCAGTAGAGTAGCCTTGTTGTTACGATCTGCT
GAGGGTAAGCCGTCCTTCGCCTCGATTTCCCCAACGATGACTCTCGCAGGGCGAGGGCGTGG

Figure 39
*Fusarium oxysporum* rRNA gene (SEQ ID NO: 86)

```
GCCGGAAAGCTCTCCAAACTCGGTCATTTAGAGGAAGTAAAAGTCGTAACAAGGTCTCCGTTGGTGAACCAGCGGAGG
GATCATTACCGAGTTTACAACTCCCAAACCCCTGTGAACATACCACTTGTTGCCTCGGCGGATCAGCCCGCTCCCGGTA
AAACGGGACGGCCCGCCAGAGGACCCCTAAACTCTGTTTCTATATGTAACTTCTGAGTAAAACCATAAATAAATCAAA
ACTTTCAACAACGGATCTCTTGGTTCTGGCATCGATGAAGAACGCAGCAAAATGCGATAAGTAATGTGAATTGCAGAA
TTCAGTGAATCATCGAATCTTTGAACGCACATTGCGCCTGCCAGTATTCTGGCGGGCATGCCTGTTCGAGCGTCATTTCA
ACCCTCAAGCACAGCTTGGTGTTGGGACTCGCGTTAATTCGCGTTCCCCAAATTGATTGGCGGTCACGTCGAGCTTCCA
TAGCGTAGTAGTAAAACCCTCGTTACTGGTAATCGTCGCGGCCACGCCGTTAAACCCCAACTTCTGAATGTTGACCTCG
GATCAGGTAGGAATACCCGCTGAACTTAAGCATATCAATAAGCGGAGGAAAAGAAACCAACAGGGATTGCCCTAGTA
ACGGCGAGTGAAGCGGCAACAGCTCAAATTTGAAATCTGGCTCTCGGGCCCGAGTTGTAATTTGTAGAGGATACTTTTG
ATGCGGTGCCTTCCGAGTTCCCTGGAACGGGACGCCATAGAGGGTGAGAGCCCCGTCTGGTTGGATGCCAAATCTCTGT
AAAGTTCCTTCAACGAGTCGAGTAGTTTGGGAATGCTGCTCTAAATGGGAGGTATATGTCTTCTAAAGCTAAATACCGG
CCAGAGACCGATAGCGCACAAGTAGAGTGATCGAAAGATGAAAAGCACTTTGAAAAGAGAGTTAAAAAGTACGTGAA
ATTGTTGAAAGGGAAGCGTTTATGACCAGACTTGGGCTTGGTTAATCATCTGGGGTTCTCCCCAGTGCACTTTTCCAGTC
CAGGCCAGCATCAGTTTTCCCCGGGGGATAAAGGCGGCGGGAATGTGGCTCTCTTCGGGGAGTGTTATAGCCCACCGT
GTAATACCCTGGGGGGGACTGAGGTTCGCGCATCTGCAAGGATGCTGGCGTAATGGTCATCAACGACCCGTCTTGAAA
CACGGACCAAGGAGTCGTCTTCGTATGCGAGTGTTCGGGTGTCAAACCCCTACGCGTAATGAAAGTGAACGCAGGTGA
GAGCTTCGGCGCATCATCGACCGATCCTGATGTTCTCGGATGGATTTGAGTAAGAGCATACGGGGCCGGACCCGAAAG
AAGGTGAACTATGCCTGTATAGGGTGAAGCCAGAGGAAACTCTGGTGGAGGCTCGCAGCGGTTCTGACGTGCAAATCG
ATCGTCAAATATGGGCATGGGGGCGAAAGACTAATCGAACCTTCTAGTAGCTGGTTTCCGCCGAAGTTTCCCTCAGGAT
AGCAGTGTTGAACTCAGTTTTATGAGGTAAAGCGAATGATTAGGGACTCGGGGGCGCTATTTAGCCTTCATCCATTCTC
AAACTTTAAATATGTAAGAAGCTCTTGTTGCTTAATTGAACGTGAGCATTCGAATGTATCAACACTAGTGGGCCATTTTT
GGTAAGCAGAACTGGCGATGCGGGATGAACCGAACGCGAGGTTAAGGTGCCAGAGTAGACGCTCATCAGACACCACA
AAAGGTGTTAGTACATCTTGACAGCAGGACGGTGGCCATGGAAGTCGGAATCCGCTAAGGACTGTGTAACAACTCACC
TGCCGAATGTACTAGCCCTGAAAATGGATGGCGCTCAAGCGTCTCACCCATACCTCGCCCTCAGGGTAGAAACGATGC
CCTGAGGAGTAGGCGGACGTGGAGGTCAGTGACGAAGCCTAGGGCGTGAGCCCGGGTTGAACGGCCTCTAGTGCAGAT
CTTGGTGGTAGTAGCAAATACTTCAATGAGAACTTGAAGGACCGAAGTGGGGAAAGGTTCCATGTGAACAGCGGTTGG
ACATGGGTTAGTCGATCCTAAGCCATAGGGAAGTTCCGTTTCAAAGGTGCACTTTGCACCGTCTGGCGAAAGGGAAGC
CGGTCAATATTCCGGCACCTGGATGTGGGTTTTGCGCGGCAACGCAACTGAACGTGGAGACGACGGCGGGGGCCCGG
GCAGAGTTCTCTTTTCTTCTTAACAGTCTCTCACCCTGAAATCGGTTTGTCCGGAGCTAGGGTTTAATGGCTGGAAGAGC
CCAGCACCTCTGCTGGGTCCGGTGCGCTCTCGACGTCCCTTGAAAATCCACGGGAGGAAATAATTCTCACGCCAGGTCG
TACTCATAACCGCAGCAGGTCTCCAAGGTGAACAGCCTCTGGTTGATAGAACAATGTAGATAAGGGAAGTCGGCAAAA
TAGATCCGTAACTTCGGGATAAGGATTGGCTCTAAGGGTTGGGCACGTTGGGCCTTGGGCGGACGCCTTGGGAGCAGG
CTGCCACTAGTCGGGCAACCGACCGGCGGCGGCCAGCATCCGAGTGTTGATGCCCTTGGCAGGCTTCGGCCGTCCGGC
GTGCGGTTAACAACCAACTTAGAACTGGTACGGACAAGGGGAATCTGACTGTCTAATTAAAACATAGCATTGCGATGG
CCAGAAAGTGGTGTTGACGCAATGTGATTTCTGCCCAGTGCTCTGAATGTCAAAGTGAAGTAATTCAACCAAGCGCGG
GTAAACGGCGGGAGTAACTATGACTCTCTTAAGGTAGCCAAATGCCTCGTCATCTAATTAGTGACGCGCATGAATGGAT
TAACGAGATTCCCACTGTCCCTATCTACTATCTAGCGAAACAAAGCCAAGGGAACGGGCTTGGCAGAATCAGCGGGG
AAAGAAGACCCTGTTGAGCTTGACTCTAGTTTGACATTGTGAAAAGACATAGGAGGTGTAGAATAGGTGGGAGCTTCG
GCGCCGGTGAAATACCACTACTCCTATTGTTTTTTTACTTATTCAATGAAGCGGCGCTGGATTTACGTCCAACTTCTGGT
TTTAAGGTCCTTCGCGGGCCGAGCCGGGTTGAAGACATTGTCAGGTGGGGAGTTTGGCTGGGGCGGCACATCTGTTAAA
CCATAACGCAGGTGTCCTAAGGGGGGCTCATGGAGAACAGAAATCTCCAGTAGAACAAAAGGGTAAAAGTCCCCTTGA
TTTTGATTTTCAGTGTGAATACAAACCATGAAAGTGTGGCCTATCGATCCTTTAGTCCCTCGACATTTGAGGCTAGAGGT
GCCAGAAAAGTTACCACAGGGATAACTGGCTTGTGGCGGCCAAGCGTTCATAGCGACGTCGCTTTTTGATCCTTCGATG
TCGGCTCTTCCTATCATACCGAAGCAGAATTCGGTAAGCGTTGGATTGTTCACCCACTAATAGGGAACGTGAGCTGGGT
TTAGACCGTCGTGAGACAGGTTAGTTTTACCCTACTGATGCATCTCACCGCAATGGTAATTGAGCTTAGTACGAGAGGAA
CCGCTCATTCAGATAATTGGTTTTTGCGGCTGTCCGACCGGGCAGTGCCGCGAAGCTACCATCTGCTGGATAATGGCTG
AACGCCTCTAAGTCAGAATCCATGCCAGAACGCGGTGATACCACCCGCACGTATAGATGGACAAGAATAGGCTTCGGC
TTAGCGTCTTAGCAGGCGATTCTTCCACGGCGCTCGAAGCGCGTCGTGGTATTTCGCGTATTGTAATTTCAACACGAGC
GGGGTCAAATCCTTTGCAGACGACTTAGCTGTGCGAAACGGTCCTGTAAGCAGTAGAGTAGCCTTGTTGTTACGATCTG
CTGAGGGTAAGCCGTCCTTCGCCTCGATTTCCCCAATGGGTTCTCCGGATTTCTGGAGACTTG
```

Figure 40
*Histoplasma capsulatum* rRNA gene (SEQ ID NO: 87)

```
GGTCATTTAGAGGAAGTAAAAGTCGTAACAAGGTTTCCGTAGGTGAACCTGCGGAAGGATCATTACCACGCCGTGGGG
GGCTGGGAGCCTCTGACCGGGACCCCTCCGCCCTCCTACCCGGCCACCCTTGTCTACCGGACCTGTTGCCTCGGCGGTC
CTGCAGCGATGCTGCCGGGGGAGCTTCTCCTCCCCGGGCCCGTGTCCGCCGGGGACACCGCAAGAACCGTCGGTGAAT
GATTGGCGTCTGAGCATGAGAGCGATAATAATCCAGTCAAAACTTTCAACAACGGATCTCTTGGTTCCGACATCGATGA
AGAACGCAGCGAAATGCGATAAGTAATGTGAATTGCAGAATTCCGTGAATCATCGAATCTTTGAACGCACATTGCGCC
CCCTGGTATTCCGGGGGGCATGCCTGTCCGAGCGTCATTGCAACCCTCAAGCGCGGCTTGTGTGTTGGGCCATCGTCCC
CCTGACCGGTGGGACGTGCCCGAAATGCAGTGGCGGTGTCGAGTTCCGGTGCCCGAGTGTATGGGGCTTTGCCACCCG
CTCTGGAGGCCCGGCCGGCTCCGGCCCACCATCTCAACCTCCTTTTTCACACCAGGTTGACCTCGGATCAGGTAGGGAT
ACCCGCTGAACTTAAGCATATCAATAAGCGGAGGAAAAGAAACCAACAGGGATTGCCTCAGTAACGGCGAGTGAAGC
GGCAAGAGCTCAAATTTGAAATCCGGCCCCTCTGGGGGCCTGAGTTGTAATTTGCAGAGGATGCTTCGGGCGCGACCG
CGGTCCAAGTCCCCTGGAACGGGGCGTCGTAGAGGGTGAGAATCCCGTCTCCGGCCGGCCGGTCTCGCCCGTGTGAAG
CTCCTTCGACGAGTCGAGTTGTTTGGGAATGCAGCTCTAAATGGGTGGTAAATTTCATCTAAAGCTAAATACTGGTCGG
AGACCGATAGCGCACAAGTAGAGTGATCGAAAGATGAAAAGCACTTTGAAAAGAGAGTTAAACAGCATGTGAAATTG
TTGAAAGGGAAGCGCTTGCGATCAGAGTCGGCCGCGGGGGTTCAGCGGGCATTCGTTGCCCGTGCAATCCCCCGCGGC
CGGGCCAGCGTCGGTTTCGACGGCCGGTCAAAGGCCCCCGGAATGTGTCGCCTCTCGGGGCGTCTTATAGCCGGGGGT
GCAATGCGGCCAGTCGGGACCGAGGAACGCGCTCCGGCACGGACGCTGGCTTAATGGTCGTCAGCGACCCGTCTTGAA
ACACGGACCAAGGAGTCTAACATCCACGCGAGTGTTCGGGTGTCAAACCCGTCCGCGCAGTGAAAGCGAATGGAGGTG
GGAACCCCTGAGGGTGCACCATCGACCGATCCTGAAGTTTTCGGATGGATTTGAGTAGGAGCGTGCTGTTGGGACCC
GAAAGATGGTGAACTATGCCTGAATAGGGTGAAGCCAGAGGAAACTCTGGTGGAGGCTCGCAGCGGTTCTGACGTGCA
AATCGATCGTCAAATTTGGGTATAGGGGCGAAAGACTAATCGAACCATCTGGTAGCTGGTTCCTGCCGAAGTTTCCCTC
AGGATAGCAGTAACGTTTTCAGTTTTATGAGGTAAAGCGAATGATTAGAGGCCTTGGGGTTGAAACAACCTTAACCTAT
TCTCAAACTTTAAATATGTAAGAAGCCCTTGTTACTTCGTTGAACGTGGGCACTGGAATGGATCGTTACTAGTGGGCCA
TTTTTGGTAAGCAGAACTGGCGATGCGGGATGAACCGAACGCGAGGTTAAGGTGCCGGAATGCACGCTCATCAGACAC
CACAAAAGGTGTTAGTTCATCTAGACAGCCCGACGGTGGCCATGGAAGTCGGAATCCGCTAAGGAGTGTGTAACAACT
CACGGGCCGAATGAACTAGCCCTGAAAATGGATGGCGCTCAAGCGTGCTACCCATACCTCGCCGTCGGGGTAGGATCG
ATGCCCCGACGAGTAGGCAGGCGTGGAGGTCCGTGACGAAGCCCGGGGAGTGATCCCGGGTCGAACGGCCTCTAGTGC
AGATCTTGGTGGTAGTAGCAAATACTCAAATGAGAACTTTGAGGACTGAAGTGGGGAAAGGTTCCATGTGAACAGCAG
TTGGACATGGGTTAGTCGATCCTAAGACATAGGGAAATTCCGTTTGAAAGCGCGCCCTCGTGCGCCGTCCGTCGAAAGG
GAAGCCGGTTAACATTCCGGCACCTGGATGTGGATTCTCCACGGCAACGTAACTGAACGCGGAGACGTCGGCGGGGGT
CCTGGGAAGAGTTCTCTTTTCTTCTTGACGGCCTGTCACCCTGAAATCGGTTTGTCCGGAGCTAGGGTTCAATGGCCGGC
AGAGCCCCGCACCTTTGCGGGGTCCGGTGCGCCCCGACGACCCTTGAAAATCCGCGGGAGGGAATAGTTTTCACGCC
AGGTCGTACTCATAACCGCAGCAGGTCTCCAAGGTGAAAAGCCTCTAGTTGATAGAACAATGTAGATAAGGGAAGTCG
GCAAAATAGATCCGTAACTTCGGGAAAAGGATTGGCTCTAAGGCTTGGGCACGTTGGGCCTTGGGCGGAGACCTCTGG
AGCAGGGGGGCACTAGCCGGGCAACCGGTGGGGGCCCTCCAGCATCGGGGCGTGGACGCCCTCGGCAGGCTTCGCC
GTCCGGCGTGCGATTAACAACCGACTTAGAACTGGTACGGACAAGGGGAATCTGACTGTCTAATTAAAACATAGCATT
GCGATGGCCAGAAAGTGGTGTTGACGCAATGTGATTTCTGCCCAGTGCTCTGAATGTCAAAGTGAAGAAATTCAACCA
AGCGCGGGTAAACGGCGGGAGTAACTATGACTCTCTTAAGGTAGCCAAATGCCTCGTCATCTAATTAGTGACGCGCAT
GAATGGATTAACGAGATTCCCACTGTCCCTATCTACTATCTAGCGAAACCACAGCCAAGGGAACGGGCTTGGCGGAAT
CAGCGGGGAAAGAAGACCCTGTTGAGCTTGACTCTAGTTTGACATTGTGAAAAGACATATCGGGTGTAGAATAGGTGG
GAGCTTCGGCGCCGGTGAAATACCACTACCTTTATCGTTTTTTTACTTATTCAATGAAGCGGAACTGGCTTCACCGCCC
AACTTCTGGCGTTAAGGTCCCTCGCGGACCGATCCGGGTTGAAGACATTGTCAGGTGGGGAGTTTGGCTGGGGCGGCA
CATCTGTTAAACCATAACGCAGGTGTCCTAAGGGGGACTCATGGAGAACAGAAATCTCCAGTAGAACAAAAGGGTAAA
AGTCCCCTTGATTTTGATTTTCAGTGTGAATACAAACCATGAAAGTGTGGCCTATCGATCCTTTAGTCCCTCGAAATTTG
AGGCTAGAGGTGCCAGAAAAGTTACCACAGGGATAACTGGCTTGTGGCAGCCAAGCGTTCATAGCGACGTTGCTTTTT
GATCCTTCGATGCGGCTCTTCCTATCATACCGAAGCAGAATTCGGTAAGCGTTGGATTGTTCACCCACTAATAGGGAA
CGTGAGCTGGGTTTAGACCGTCGTGAGACAGGTTAGTTTTACCCTACTGATGAAGGTCGCCGCAACGGTAATTCAATTT
AGTACGAGAGGAACCGTTGATTCAGATAATTGGTTTTGCGGCTGTCTGACCAGGCAGTGCCGCGACGCTACCATCTGC
CGGATTATGGCTGAACGCCTCTAAGTCAGAATCCGTGCCGGAACGCGGCGATGTCGCCCCGCACGTCGTAGTTGGATA
CGAATAGGCCTCCGGGTCCAGAACCTCAGCAGGCCGGCGATGGTGTTCCGGGGAGAGACCCCCGGGGACCCGCCGGCG
GATTGCAATGTCACCACGCGCGGGGATAGATCCTCTGCAGACGACTGAAATGACCAAGCGGGTCGTGTAAGCGGTCAA
GTAGCCTTGTTGCTACGAGTCGCTGAGCGTCAGCCCGATCCTTGGCTCGATTTGTTGTAACAACCCCC
```

Figure 41
*Hypocrea jecorina* rRNA gene (SEQ ID NO: 88)

```
TCGGTCATTTAGAGGAAGTAAAAGTCGTAACAAGGTCTCCGTTGGTGAACCAGCGGAGGGATCATTACCGAGTTTACA
ACTCCCAAACCCCAATGTGAACGTTACCAATCTGTTGCCTCGGCGGGATTCTCTGCCCCGGGCGCGTCGCAGCCCCGGA
TCCCATGGCGCCCGCCGGAGGACCAACTCAAACTCTTTTTTCTCTCCGTCGCGGCTTCCGTCGCGGCTCTGTTTTACCTT
TGCTCTGAGCCTTTCTCGGCGACCCTAGCGGGCGTCTCGAAAATGAATCAAAACTTTCAACAACGGATCTCTTGGTTCT
GGCATCGATGAAGAACGCAGCGAAATGCGATAAGTAATGTGAATTGCAGAATTCAGTGAATCATCGAATCTTTGAACG
CACATTGCGCCCGCCAGTATTCTGGCGGGCATGCCTGTCCGAGCGTCATTTCAACCCTCGAACCCCTCCGGGGGGTCGG
CGTTGGGGATCGGCCCCTCACCGGGCCGCCCCCGAAATACAGTGGCGGTCTCGCCGCAGCCTCTCCTGCGCAGTAGTTT
GCACACTCGCACCGGGAGCGCGGCGCGGCCACAGCCGTAAAACACCCCAAACTCTGAAATGTTGACCTCGGATCAGGT
AGGAATACCCGCTGAACTTAAGCATATCAATAAGCGGAGGAAAAGAAACCAACAGGGATTGCCCCAGTAACGGCGAG
TGAAGCGGCAACAGCTCAAATTTGAAATCTGGCCCTTTCGGGTCCGAGTTGTAATTTGTAGAGGATGCTTTTGGCAAGG
CGCCGCCCGAGTTCCCTGGAACGGGACGCCACAGAGGGTGAGAGCCCCGTCTGGCTGGCCGCCGAGCCTCTGTAAAGC
TCCTTCGACGAGTCGAGTAGTTTGGGAATGCTGCTCAAAATGGGAGGTATATGTCTTCTAAAGCTAAATATTGGCCAGA
GACCGATAGCGCACAAGTAGAGTGATCGAAAGATGAAAAGCACCTTGAAAAGAGGGTTAAATAGTACGTGAAATTGTT
GAAAGGGAAGCGCTTGTGACCAGACTTGGGCGCGGCGGATCATCCGGGGTTCTCCCCGGTGCACTTCGCCGTGTCCAG
GCCAGCATCAGTTCGTCGCGGGGGAAAAAGGCTTCGGGAACGTGGCTCCCCTGGGAGTGTTATAGCCCGTTGCATAAT
ACCCTGCGGTGGACTGAGGACCGCGCATCTGCAAGGATGCTGGCGTAATGGTCACCAGCGACCCGTCTTGAAACACGG
ACCAAGGAGTCGTCTTCGTATGCGAGTGTTCGGGTGTCAAACCCCTACGCGTAATGAAAGTGAACGCAGGTGAGAGCT
TCGGCGCATCATCGACCGATCCTGATGTTCTCGGATGGATTTGAGTAAGAGCATACGGGGCCGGACCCGAAAGAAGGT
GAACTATGCCTGTATAGGGTGAAGCCAGAGGAAACTCTGGTGGAGGCTCGCAGCGGTTCTGACGTGCAAATCGATCGT
CAAATATGGGCATGGGGGCGAAAGACTAATCGAACCTTCTAGTAGCTGGTTTCCGCCGAAGTTTCCCTCAGGATAGCA
GTGTTGAACTCAGTTTTATGAGGTAAAGCGAATGATTAGGGACCCGGGGGCGCTATATTGCCTTCATCCATTCTCAAAC
TTTAAATATGTAAGAAGCCCTTGTTGCTTAATTGAACGTGGGCATTCGAATGTATCAACACTAGTGGGCCATTTTTGGTA
AGCAGAACTGGCGATGCGGGATGAACCGAACGCGAGGTTAAGGTGCCAGAGTAGACGCTCATCAGACACCACAAAAG
GCGTTAGTACATCTTGACAGCAGGACGGTGGCCATGGAAGTCGGAATCCGCTAAGGACTGTGTAACAACTCACCTGCC
GAATGTACTAGCCCTGAAAATGGATGGCGCTCAAGCGTCTCACCCATACCTCGCCCTCGGGGTAGAAACGATGCCCCG
AGGAGTAGGCGGACGTGGAGGTCGTGACGAAGCCTAGGGCGTGAGCCCGGGTCGAACGGCCTCTAGTGCAGATCTTGG
TGGTAGTAGCAAATACTTCAATGAGAACTTGAAGGACCGAAGTGGGGAAAGGTTCCATGTGAACAGCGGTTGGACGTG
GGTTAGTCGATCCTAAGCCATAGGGAAGTTCCGTTTCAAAGGCGCACTTCGCGCCGTTTGGCGAAAGGGGAGCCGGTC
AATATTCCGGCACCTGGATGTGGGTTTTGCGCGGCAACGCAACTGAACGCGGAGACGACGGCGGGGCCCCGGGCAGA
GTTCTCTTTTCTTCTTAACAGTCTATCACCCTGAAATCGGTTTGTCCGGAGCTAGGGTTTAATGGCTGGAAGAGCCCAGC
ACCTCTGCTGGGTCCGGTGCGCCCTCGACGTCCCTTGAAAATCCGCGGGAAGGAATAATTCTCACGCCAGGTCGTACTC
ATAACCGCAGCAGGTCTCCAAGGTGAACAGCCTCTGGTTGATAGAACAATGTAGATAAGGGAAGTCGGCAAAATAGAT
CCGTAACTTCGGGATAAGGATTGGCTCTAAGGGTTGGGCACGTTGGGCTTTGGACGGACGCCTCGGGAGCAGGCGGCC
ACTAGCCGGGCAACCGGCCGGCGGCTGCCAGCATCTGGGTGCTGATGTCCCTTGCAGGCTTCGGCCGTCCGGCGTGCG
GTTAACAACCAACTTAGAACTGGTACGGACAAGGGGAATCTGACTGTCTAATTAAAACATAGCATTGCGATGGCCAGA
AAGTGGTGTTGACGCAATGTGATTTCTGCCCAGTGCTTCGAATGTCAAAGTGAAGTAATTCAACCAAGCGCGGGTAAAC
GGCGGGAGTAACTATGACTCTCTTAAGGTAGCCAAATGCCTCGTCATCTAATTAGTGACGCGCATGAATGGATTAACGA
GATTCCCACTGTCCCTATCTACTATCTAGCGAAACCACAGCCAAGGGAACGGGCTTGGCAGAATCAGCGGGGAAAGAA
GACCCTGTTGAGCTTGACTCTAGTTTGACATTGTGAAAAGACATAGGAGGTGTAGAATAGGTGGGAGCTTCGGCGCCG
GTGAAATACCACTACTCCTATTGTTTTTTTACTTATTCAATGAAGCGGGGCTGGATTTACGTCCAACTTCTGGTATTAAG
GTCCTTCGCGGGCCGACCCGGGTTGAAGACATTGTCAGGTGGGGAGTTTGGCTGGGGCGGCACATCTGTTAAACCATA
ACGCAGGTGTCCTAAGGGGGGCTCATGGAGAACAGAAATCTCCAGTAGAACAAAAGGGTAAAAGTCCCCTTGATTTTG
ATTTTCAGTGTGAATACAAACCATGAAAGTGTGGCCTATCGATCCTTTAGTCCCTCGACATTTGAGGCTAGAGGTGCCA
GAAAAGTTACCACAGGGATAACTGGCTTGTGGCGGCCAAGCGTTCATAGCGACGTCGCTTTTTGATCCTTCGATGTCGG
CTCTTCCTATCATACCGAAGCAGAATTCGGTAAGCGTTGGATTGTTCACCCACTAATAGGGAACGTGAGCTGGGTTTAG
ACCGTCGTGAGACAGGTTAGTTTTACCCTACTGATGACCTCACCGCAATGGTAATTGAGCTTAGTACGAGAGGAACCGC
TCATTCAGATAATTGGTTTTTGCGGCTGTCCGACCGGGCAGTGCCGCGAAGCTACCATCTGCTGGATAATGGCTGAACG
CCTCTAAGTCAGAATCCATGCCAGAACGCGGTGATAGCACCCGCACGTATAGACGGACAAGAATAGGCTTCGGCTTAG
TGTCTCAGCAGGCGATTCCTCCGCGGTCCTCGAAGCGGGCCGCGGTATTTCGCGTATTGTAATTTCAACACGAGCGGGG
TTAAATCCTTTGCAGACGACTTAGCTGTGCGAAACGGTCC
```

Figure 42

*Lodderomyces elongisporus* rRNA gene (SEQ ID NO: 89)

```
TTTAGAGGAAGTAAAAGTCGTAACAAGGTTTCCGTAGGTGAACCTGCGGAAGGATCATTACAGAATTTTGAGAATTGT
GCTTAACTGCACTTTTCTTATCTACACACGTGTTTTTGTTTTATTCTTAAAACTTGCTTTGGCAGTGGCTGCTTAATTGCT
CTGCTGCCAGAGGATAAACTCAACCTAAATTTTTTATTTTAAACTAGTCAACTGATTATATTTATTAATAGTCAAAACTT
TCAACAACGGATCTCTTGGTTCTCGCATCGATGAAGAACGCAGCGAAATGCGATAAGTAATATGAATTGCAGATATTCG
TGAATCATCGAATCTTTGAACGCACATTGCGCCCTCTGGTATTCCGGAGGGCATGCCTGTTTGAGCGTCATTTCTCCCTC
AAACCCCCGGGTTTGGTGATGAGCAATACGCCAGGTTTGCTTGAAAGTTAGGAGGAGTATTTATAACAATGTATTAGGT
CTAACCACTCCATTGTGCTTAATAAAAAGCTCCAATCTATATTTCAAACTTCGACCTCAAATCAGGTAGGATTACCCGCT
GAACTTAAGCATATCAATAAGCGGAGGAAAAGAAACCAACAGGGATTGCCTTAGTAGCGGCGAGTGAAGCGGCAATA
GCTCAAATTTGAAATCTGGCACTTTCAGTGTCCGAGTTGTAATTTGAAGAAGGTATCTTTGGGTCTAGCTCTTGTCTATG
TTTCTTGGAACAGAACGTCACAGAGGGTGAGAATCCCGTGCGATGAGATGTCTAGATCTATGTAAAGTTCCTTCGAAGA
GTCGAGTTGTTTGGGAATGCAGCTCTAAGTGGGTGGTAAATTCCATCTAAAGCTAAATAATGGCGAGAGACCGATAGC
GAACAAGTACAGTGATGGAAAGATGAAAAGAACTTTGAAAAGAGAGTGAAAAAGTACGTGAAATTGTTGAAAGGGAA
GGGCTTGAGATCAGACTTGGTATTTTGTATGTTACTCTCTCGGGGGTGGCCTCTACAGTTTACCGGGCCAGCATCAGTTT
GAGCGGTAGGAGAATTGCGTAGGAATGTGGCTCGGCCTCGGTCGAGTGTTATAGCCTTCGTCGATACTGCCAGCTTAGA
CTGAGGACTGCGGCTTCGGCCTAGGATGTTGGCATAATGATCTTAAGTCGCCCGTCTTGAAACACGGACCAAGGAGTCT
AACGTCTATGCGAGTGTTTGGGTGTAAAACCCGTACGCGTAATGAAAGTGAACGTAGGTAGGACCTTCTTTTGAAGCGC
ACTATCGACCGATCCTGATGTCTTCGGATGGATTTGAGTAAGAGCATAGCTGTTGGGACCCGAAAGATGGTGAACTATG
CCTGAATAGGGTGAAGCCAGAGGAAACTCTGGTGGAGGCTCGTAGCGGTTCTGACGTGCAAATCGATCGTCGAATTTG
GGTATAGGGGCGAAAGACTAATCGAACCATCTAGTAGCTGGTTCCTGCCGAAGTTTCCCTCAGGATAGCAGAAGCTCG
TATCAGTTTTATGAGGTAAAGCGAATGATTAGAAGTCTTGGGGTTGAAATGACCTTAACTTATTCTCAAACTTTAAATA
TGTAAGAAGTCCTTGTTGCTTAATTGAACGTGGACATATGAATGAAGAGCTTTTAGTGGGCCATTTTTGGTAAGCAGAA
CTGGCGATGCGGGATGAACCGAACGCGAAGTTAAAGTGCCGGAATACACGCTCATCAGACACCACAAAAGGTGTTAGT
TCATCTAGACAGCCGGACGGTGGCCATGGAAGTCGGAATCCGCTAAGGAGTGTGTAACAACTCACCGGCCGAATGAAC
TAGCCCTGAAAATGGATGGCGCTCAAGCGTGTTACTTATACTTCGCCGTGAGAGGTTGATATGATGCCCTCACGAGTAG
GCAGGCGTGGAGGTCAGTGAAGAAGCCTTTGCTGTAAAGCTGGGTCGAACGGCCTCTAGTGCAGATCTTGGTGGTAGT
AGCAAATATTCAAATGAGAACTTTGAAGACTGAAGTGGGGAAAGGTTCCATGTCAACAGCAGTTGGACATGGGTTAGT
CGATCCTAAGAGATAGGGAAGCTCCGTTTCAATGCGCCTGATTATTCAGGCCACTATCGAAAGGGAATCCGGTTAAAAT
TCCGGAACTTGGATATGGATTCTTCACGGTAACGTAACTGAAGTCGATGGAGACGTCGGCGTGAGCCCTGGGAGGAGTTATC
TTTTCTTCTTAACAGCTTATCACCCTGGAATTGGTTTATCCGGAGATGGGGTCTTATGGCTGGAAGAGCGTGGTAATTTT
GCCACGTCCGGTGCGCTTACGACGGTCCTTGAAAATCCACAGGAAGGAATAGTTTTCATGCCAAGTCGTACTCATAACC
GCAGCAGGTCTCCAAGGTTAACAGCCTCTAGTTGATAGAATAATGTAGATAAGGGAAGTCGGCAAAATAGATCCGTAA
CTTCGGGATAAGGATTGGCTCTAAGGATCGGGTGTTTGGGCGACTGCAAGGATCGCGCGACTGACGGCGGACTGC
TTTCGGGCGGACTGCTGTTGGATGCTGCCATAGACACGCTTGGTAGGGATTTATCCCGTCCGGAGCACGCTTAACGATC
AACTTAGAACTGGTACGGACAAGGGGAATCTGACTGTCTAATTAAAACATAGCATTGTGATGGTCAGAAAGTGATGTT
GACACAATGTGATTTCTGCCCAGTGCTCTGAATGTCAAAGTGAAGAAATTCAACCAAGCGCGGGTAAACGGCGGGAGT
AACTATGACTCTCTTAAGGTAGCCAAATGCCTCGTCATCTAATTAGTGACGCGCATGGATTGGATTAACGAGATTCCCAC
TGTCCCTATCTACTATCTAGCGAAACCACAGCCAAGGGAACGGGCTTGGCAGAATCAGCGGGGAAAGAAGACCCTGTT
GAGCTTGACTCTAGTTTGACATTGTGAAAAGACATGGAGGGTGTAGAATAAGTGGGAGCTTCGGCGCCGGTGAAATAC
CACTACCTCTATAGTTTTTTTACTTATTCAATGAAGCGGAGCTGGAGGTAAAACTCCACGTTCTAGCATTAAGGCCTTTT
GGCTGATCCGGGTTGAAGACATTGTCAGGTGGGGAGTTTGGCTGGGCGGCACATCTGTTAAACGATAACGCAGGTGT
CCTAAGGGGGGCTCATGGAGAACAGAAATCTCCAGTAGAACAAAAGGGTAAAAGCCCCCTTGATTTTGATTTTCAGTG
TGAATACAAACCATGAAAGTGTGGCCTATCGATCCTTTAGTCCCTCGGAATTTGAGGCTAGAGGTGCCAGAAAAGTTAT
CACAGGGATAACTGGCTTGTGGCAGTCAAGCGTTCATAGCGACATTGCTTTTTGATTCTTCGATGTCGGCTCTTCCTATC
ATACCGAAGCAGAATTCGGTAAGCGTTGGATTGTTCACCCACTAATAGGGAACGTGAGCTGGGTTTAGACCGTCGTGA
GACAGGTTAGTTTTACCCTACTGATGAATGTTATCGCAATAGTAATTGAACTTAGTACGAGAGGAACCGTTCATTCAGA
TAATTGGTTTTTGCGGCTGTCTGATCAGGCAACGCCGCGAAGCTACCATCTGCTGGATTATGGCTGAACGCCTCTAAGT
CAGAATCCATGCTAGAAAGCGATGATTTTTGCCCTGCACATTTTAGATGGATACGAATAAGACTTTTAATAGTCGCTGG
ACCATAGCAGGCTGGCAGCGGTGCACTTAGCGGAAAGGCTTTGTGTGCTTGCCGGCGAATAGCAATGTCAACATGCGC
GGGGATAAATCCTTTGCATACGACTTAGATGTACAACGGAGTATTGTAAGCAGTAGAGTAGCCTTGTTGTTACGATCTG
CTGAGATTAAGCTTCAGTTGTCTGATTTGTCTAGGAGT
```

Figure 43

***Magnaporthe grisea* rRNA gene (SEQ ID NO: 90)**

CATGTGCCGGAAAGTTGTACGAACTCGGTCGTTTAGAGGAAGTAAAAGTCGTAACAAGGTCTCCGTTGGTGAACCAGC
GGAGGGATCATTACTGAGTTGAAAAACTCCAACCCCTGTGAACATAACCTCTGTCGTTGCTTCGGCGGGCACGCCCGCC
GGAGGTTCAAAACTCTTATTTTTCCAGTATCTCTGAGCCTGAAAGACAAATAATCAAAACTTTCAACAACGGATCTCT
TGGTTCTGGCATCGATGAAGAACGCAGCGAAATGCGATAAGTAATGTGAATTGCAGAATTCAGTGAATCATCGAATCT
TTGAACGCACATTGCGCCCGCCGGTATTCCGGCGGGCATGCCTGTTCGAGCGTCATTTCAACCCTCAAGCCTCGGCTTG
GTGTTGGGGCGCCCGGGCCCTCCGCGGCCCGGGGCCCCCAAGTTCATCGGCGGGCTCGGCGGTACACTGAGCGCAGTA
AAACGCGGTAAAACGCGAACCTCGTTCGGATCGTCCCGGCGTGCTCCAGCCGCTAAACCCCCAATTTTTTAAAGGTTGA
CCTCGGATCAGGTAGGAATACCCGCTGAACTTAAGCATATCAATAAGCGGAGGAAAAGAAACCAACAGGGATTGCCCC
AGTAACGGCGAGTGAAGCGGCAACAGCTCAAATTTGAAATCTGGCCCCCCGGCCCGAGTTGTAATTTGCAGAGGATGC
TTTTGGTGAGGCACCTACCGAGTCCCCTGGAATGGGGCGCCATAGAGGGTGAGAGCCCCGTATGGTAGGACGCCGAAC
CTCTGTAAAGCTCCTTCGACGAGTCGAGTAGTTTGGGAATGCTGCTCTAAATGGGAGGTAAATTTCTTCTAAAGCTAAA
TACCGGCCAGAGACCGATAGCGCACAAGTAGAGTGATCGAAAGATGAAAAGCACTTTGAAAAGAGGGTTAAAAAGTA
CGTGAAATTGTTGAAAGGGAAGCGCTTGTGACCAGACTTGCGCCGGGCGGATCATCCAGCGTTCTCGCTGGTGCACTCC
GCCCGGTTCAGGCCAGCATCGGTTTTCGCCGGGGGACAAAGGCTTCGGGAACGTGGCTCCTTTCGGGGAGTGTTATAGC
CCGTTGCGTAATACCCCGGCGGGGACCGACGACCGCGCTTCGGCAAGGATGCTGGCGTAATGGTCATCAGCGACCCGT
CTTGAAACACGGACCGAGGAGTCAAGCATTAGTGCGAGTGTTTGGGTGTAAAACCCGCACCGTAATGAAAGTGAACG
TAGGTGAGAGCTTCGGCGCATCATCGACCGATCCTGATGTTTTCGGAAGGATTTGAGTAGGAGCATTAACGCTTGGACC
CGAAAGATGGTGAACTATACTTGAATAGGGTGAAGCCAGAGGAAACTCTGGTGGAGGCTCGCAGCGGTTCTGACGTGC
AAATCGATCGTCAAATTTGAGTATAGGGGCGAAAGACTAATCGAACCATCTAGTAGCTGGTTTCAGCCGAAGTTTCCCT
CAGGATAGCAGTGTCGTCTTCAGTTTTATGAGGTAAAGCGAATGATTAGGGACTCGGGGGCGATTTTTAGCCTTCATCC
ATTCTCAAACTTTAAATATGTAAGAAGCCCTTGTTACTTAGTTGAACGTGGGCCTTCGAATGTACCGACACTAGTGGGC
CATTTTTGGTAAGCAGAACTGGCGATGCGGGATGAACCGAACGCGGGGTTAAGGTGCCGGAGTGGACGCTCATCAGAC
ACCACAAAAGGCGTTAGTACATCTTGACAGCAGGACGGTGGCCATGGAAGTCGGAATCCGCTAAGGACTGTGTAACAA
CTCACCTGCCGAATGTACTAGCCCTGAAAATGGATGGCGCTCAAGCGTCCCACCCATACCCCGCCCCCAGGGTAGAAA
CGATGCCCTGGGGAGTAGGCTGACGCGGGGGTAGCGACGAAGGCTAGGGCGTGAGCCCGGCTAGAGCTGCCCCTGGT
GCAGATCTCGGTGAGAGTAGCAAATACTTCAATGAGAACTTGAAGGACCGAAGTGGGGAAAGGTTCCATGTGAACAGC
AGTTGGACGTGGGTTAGCCGATCCTGAGCCATAGGGAAGTTCCGTTTCAAAGGGGCGCTAGCGCCCCGTATGGCGAAA
GGGAAGCAGGTTAATATTCCTGCGCCTGGATGTGGGTTTTTCGCGGCAACGCAACTGAACGCGGAGACGGCGGCGGGG
GCCCCGGGCAGAGTTCTCTTTTCTTCTTAACGATCCACCACCCTGGAAACGGTTTGTCCGGAGATAGGGTTCAGCGGTC
GGAAGAGCCCAGCACTTCTGTTCGCCCTCGACGTCCCTTGAAAATCCGCGGGAGGGAATAATTCTCACGCCAGGTCGTA
CTCATAACCGCAGCAGGTCTCCAAGGTGAACAGCCTCTGGTTGATAGAATAATGTAGATAAGGGAAGTCGGCAAAACA
GATCCGTAACTTCGGGAAAAGGATTGGCTCTAAGGGTTGGGTACGTTGGGCCTTTGGCGGACGCGCCGGGGGCAGGTC
GCCACTAGCCGGGCAACCGGCCGGGGGCTTCCAGCACCTGGTTGCCGACGCCTTTGGCAGGCTTCGGCCGTCCGGCGT
ACGGTTAACAACCAACTTAGAACTGGTACGGACAAGGGGAATCTGACTGTCTAATTAAAACATAGCATTGCGATGGCC
GGAAAGCGGTGTTGACGCAATGTGATTTCTGCCCAGTGCTCTGAATGTCACAGCAAAGTAATTTGACCAAGCGCGGGT
AAACGGCGGGAGTAACTATGACTCTCTTAAGGTAGCCAAATGCCTCGTCATCTAATTAGTGACGCGCATGAATGGATTA
ACGAGATTCCCACTGTCCCTATCTACTATCTAGCGAAACCACAGCCAAGGGAACGGGCTTGGCAGAATCAGCGGGGAA
AGAAGACCCTGTTGAGCTTGACTCTAGTTTGACATTGTGAAAAGACATAGGAGGTGTAGAATAGGTGGGAGCTTCGGC
GCCGGTGAAATACCACTACTCCTATTGTTTTTTTACTTATTCGATTAAGCGGGGCTGGATTTACGTCCAACTTCTGGTTTT
AACGTCCTTCGCGGGCGGACCCGGGTTGAAGACATTGTCAGGTGGGGAGTTTGGCTGGGGCGGCACATCTGTTAAACC
ATAACGCAGGTGTCCTAAGGGGGGCTCATGGAGAACAGAAATCTCCAGTAGAACAAAAGGGTAAAAGTCCCCTTGATT
TTGATTTTCAGTGTGAATACAAACCATGAAAGTGTGGCCTATCGATCCTTTAGTCCCTCGAAATTTGAGGCTAGAGGTG
CCAGAAAAGTTACCACAGGGATAACTGGCTTGTGGCGGCCAAGCGTTCATAGCGACGTCGCTTTTTGATCCTTCGATGT
CGGCTCTTCCTATCATACCGAAGCAGAATTCGGTAAGCGTTGGATTGTTCACCCACTAATAGGGAACGTGAGCTGGGTT
TAGACCGTCGTGAGACAGGTTAGTTTTACCCTACTGATGACCTCGTCGCAATGGTAATTGAGCTTAGTACGAGAGGAAC
CGCTCATTCAGATAATTGGTTTTTGCGGTTGTCCGACAGGGCAGTGCCGCGAAGCTACCATCTGCAGGATAACGGCTGA
ACGCCTCTAAGTCGGAATCCTTGCCAGAACGCGACGATACCTCCCGCACGTTTAGACGGATAAGAATAGGCTTCGGCCT
CGTATCTCAGCAGGCGATAACCCCGCCGGGCTCGAAGCGCCCGGTGGTGATTCGCGTATTGTAATTTTGACACGCGCGG
GGTCAAATCCTTTGCAGACGACTTAGCTGTGCGAAAGGGTCCTGTAAGCAGTAGAGTAGCTTTATCGTTACGATCTGCT
GAGGGTAAGCCCTCCTTCGCCTAGATTTCCCAGACTTTCTACCCCATTC

Figure 44
*Metarhizium anisopliae* rRNA gene (SEQ ID NO: 91)

CCGGAAAGCTCTCCAAACTCGGTCATTTAGAGGAAGTAAAAGTCGTAACAAGGTCTCCGTTGGTGAACCAGCGGAGGG
ATCATTACCGAGTTATCCAACTCCCAACCCCTGTGAATTATACCTTTAATTGTTGCTTCGGCGGGACTTCGCGCCCGCCG
GGGACCCAAACCTTCTGAATTTTTTAATAAGTATCTTCTGAGTGGTTAAAAAAATGAATCAAAACTTTCAACAACGGAT
CTCTTGGTTCTGGCATCGATGAAGAACGCAGCGAAATGCGATAAGTAATGTGAATTGCAGAATTCAGTGAATCATCGA
ATCTTTGAACGCACATTGCGCCCGTCAGTATTCTGGCGGGCATGCCTGTTCGAGCGTCATTACGCCCCTCAAGTCCCCTG
TGGACTTGGTGTTGGGGATCGGCGAGGCTGGTTTTCCAGCACACCGTCCCTTAAAATTAATTGGCGGTCTCGCGTGGCC
CTCCTCTGCGCAGTAGTAAAACTCGCAACAGGAGCCCGGCGCGGTCCACTGCCGTAAAACCCCCAACTTTTTATAGTT
GACCTCGAATCAGGTAGGACTACCCGCTGAACTTAAGCATATCAATAAGCGGAGGAAAAGAAACCAACAGGGATTGCC
CCAGTAACGGCGAGTGAAGCGGCAACAGCTCAAATTTGAAATCTGGTCCCCAGGGCCCGAGTTGTAATTTGCAGAGGA
TGCTTTTGGTGAGGTGCCTTCCGAGTTCCCTGGAACGGGACGCCATAGAGGGTGAGAGCCCCGTCTGGTTGGATACCGA
GCCTCTGTAAAGCTCCTTCGACGAGTCGAGTAGTTTGGGAATGCTGCTCTAAATGGGAGGTATATGTCTTCTAAAGCTA
AATATTGGCCAGAGACCGATAGCGCACAAGTAGAGTGATCGAAAGATGAAAAGCACTTTGAAAAGAGGGTTAAATAG
TACGTGAAATTGTTGAAAGGGAAGCACTTATGACCAGACTTGGCCCCGGTGAATCATCCAGCGGTTCCCCGTGTGCACT
TTGCCGGGGTTCAGGCCAGCATCAGTTCGCTCCGGGGGATAAAGGCTTTGGGAATGTGGCTCCCTCGGGAGTGTTATAG
CCCATTGCGCAATACCCTGTGGCGGGCTGAGGTTCGCGCTTTATGCAAGGATGCTGGCATAATGGTCATCAGTGACCCG
TCTTGAAACACGGACCAAGGAGTCGTCTTCGTATGCGAGTGTTCGGGTGTTAAACCCCTACGCGTAATGAAAGTGAACG
CAGGTGAGAGCCCTCCAGGGCGCATCATCGACCGATCCTGATGTTCTCGGATGGATTTGAGTAAGAGCATACGGGGCC
GGACCCGAAAGAAGGTGAACTATGCCTGTATAGGGTGAAGCCAGAGGAAACTCTGGTGGAGGCTCGCAGCGGTTCTGA
CGTGCAAATCGATCGTCAAATATGGGCATGGGGGCGAAAGACTAATCGAACCTTCTAGTAGCTGGTTTCCGCCGAAGTT
TCCCTCAGGATAGCAGTGTTGATTTCTCAGTTTTATGAGGTAAAGCGAATGATTAGGGACCCGGGGGCGGCTTATAGCC
TTCATCCATTCTCAAACTTTAAATATGTAAGAAGCCCTTGTTGCTTAGGTGAACGTGGGCATTCGAATGTATCAACACTA
GTGGGCCATTTTTGGTAAGCAGAACTGGCGATGCGGGATGAACCGAACGCGAGGTTAAGGTGCCAGAGTAGACGCTCA
TCAACACCACCAAAGGTGTTAGTACATCTTGACAGCAGGACGGTGGCCATGGAAGTCGGAATCCGCTAAGGACTGTGT
AACAACTCACCTGCCGAATGTACTAGCCCTGAAAATGGATGGCGCTCAAGCGTCTCACCCATACCTCGCCCTCGGGGTA
GGAACGATGCCCCGAGGAGTAGGCGGACGTGGGGGTCAGTGACGAAGCCCAGGGCGTGAGCCCGGGTCGAACGGCCC
CTAGTGCAGATCTTGGTGGTAGTAGCAAATACTTCAATGAGAACTTGAAGGACCGAAGTGGGGAAAGGTTCCATGTGA
ACAGCGGTTGGACGTGGGTTAGTCGATCCTAAGCCATAGGGAAGTTCCGTTTCAAAGGTGCACTTGTGCGCCGTCTGGG
CGAAAGGGAAGCCGGTCAATATTCCGGCACCTGGATGTGGGTTTTTCGCGGCAACGCAACTGAACGCGGAGACGACGG
CGGGGGCCCCGAGCAGAGTTCTCTTTTCTTCTTAACAGTCTGTCACCCTGAAATCGGTTTGTCCGGAGCTAGGGTTTAAT
GGCTGGAAGAGCGGCCACTCTGCCGGGTTCGGTGCGCTCCCGACGTCCCTTGAAAATCCGCGGGAGGGAATAATTCTC
ACGCCAGGTCGTACTCATAACCGCAGCAGGTCTCCAAGGTGAACAGCCTCTGGTTGATAGAACAATGTAGATAAGGGA
AGTCGGCAAAATAGATCCGTAACTTCGGGATAAGGATTGGCTCTAAGGGTTGGGTGCGTTGGGCCTCGGGGGGACGCC
TTGGGAGCAGGCAGCCACTAGCCGGGCAACCGTCGGCGGCCGCAGCATCCGAGCGCTGAATCCCTTGGCAGGCTTCGG
CCGTCCGGCGCACGATTAACAACCAACTTAGAACTGGTACGGACAAGGGGAATCTGACTGTCTAATTAAAACATAGCA
TTGCGATGGCCAGAAAGTGGTGTTGACGCAATGTGATTTCTGCCCAGTGCTCTGAATGTCAAAGTGAAGTAATTCAACC
AAGCGCGGGTAAACGGCGGGAGTAACTATGACTCTCTTAAGGTAGCCAAATGCCTCGTCATCTAATTAGTGACGCGCA
TGAATGGATTAACGAGATTCCCACTGTCCCTATCTACTATCTAGCGAAACCACAGCCAAGGGAACGGGCTTGGCAGAA
TCAGCGGGGAAAGAAGACCCTGTTGAGCTTGACTCTAGTTTGACATTGTGAAAAGACATAGGAGGTGTAGAATAGGTG
GGAGCTTCGGCGCCGGTGAAATACCACTACTCCTATTGTTTTTTACTTATTCAATGAAGCGGGGCTGGATTTTCGTCCA
ACTTCTGGTCTTAAGGTCCTTCGCGGGCTGTACCCGGGTTGAAGACATTGTCAGGTGGGGAGTTTGGCTGGGGCGGCAC
ATCTGTTAAACCATAACGCAGGTGTCCTAAGGGGGGGCTCATGGAGAACAGAAATCTCCAGTAGAACAAAAGGGTAAAA
GTCCCCTTGATTTTGATTTTCAGTGTGAATACAAACCATGAAAGTGTGGCCTATCGATCCTTTAGTCCCTCGACATTTGA
GGCTAGAGGTGCCAGAAAAGTTACCACAGGGATAACTGGCTTGTGGCGCCAAGCGTTCATAGCGACGTCGCTTTTTG
ATCCTTCGATGTCGGCTCTTCCTATCATACCGAAGCAGAATTGCCTAAGCGTTGGATTGTTCACCCACTAATAGGGAAC
GTGAGCTGGGTTTAGACCGTCGTGAGACAGGTTAGTTTTACCCTACTGATGACCTCACCGCAATGGTAATTCAGCTTAG
TACGAGAGGAACCGCTGATTCAGATAATTGGTTTTTGCGGCTGTCCGACCGGGCAGTGCCGCGACGCTACCATCTGCTG
GATAATGGCTGAACGCCTCTAAGTCAGAATCCATGCCAGAACGCGGTGATACCCGCCGCACGTACAGATGGACAAGAA
TAGGCTCCGGCTTAGCGTCTTAGCAGGCGATTGTTCCGCTGCGCAGGAAGCGCAGTATTTCGCGTATTGTAATTTCACC
ACGAGCGGGGTCAAATCCTTTGCAGACGACTTAGCTGTGCGAAACGGTCCTGTAAGCAGTAGAGTAGCCTTGTTGTTAC
GATCTGCTGAGGGTTAGCCGTTCTTCGCCTCGATTTCCCCAATATCAGCGCATCCCGTTTCGCGGGGCGGG

Figure 45

*Microsporum gypseum* rRNA gene (SEQ ID NO: 92)

```
TCGGTCATTTAGAGGAAGTAAAAGTCGTAACAAGGTTTCCGTAGGTGAACCTGCGGAAGGATCATTAACGCGCAGGCC
GTAGACGGCCCGTCCCCGGATGCGTCCGGGGGCGGTGTCGCCGGCCACACGCCCATTCTTGTCTATTTACCCAGTTGCC
TCGGCGGGCCGCGCACTCGTGCCGCGCCTCGAGGAGCCGTCCGGGGACAATCAACTCCCTGGATCGCGCCCGCCGGAG
GAGTGATTAAAATCCATGAATACTGTTCCGTCTGAGCGTTAGCAAGTAAAATCAGTTAAAACTTTCAACAACGGATCTC
TTGGTTCCGGCATCGATGAAGAACGCAGCGAAATGCGATAAGTAATGTGAATTGCAGAATTCCGTGAATCATCGAATC
TTTGAACGCACATTGCGCCCTCTGGTATTCCGGGGGGCATGCCTGTTCGAGCGTCATTTCAACCCCTCAAGCCCGGCTT
GTGTGATGGACGACCGTCCCGCCCTCCCTACTCCAGGGGAGGGGGACGCGCCCGAAAAGCAGTGGCCAGGCCGCGATT
CCGGCTCCTGGGCGAATGGGCAACAAACCAACGCCTCTAGGACCGGCCGGTTTTCTGGCCTAGTTTTAGTTAGGGATGA
ACTTCCCTACAATCAGGTTGACCTCGGATCAGGTAGGGATACCCGCTGAACTTAAGCATATCAATAAGCGGAGGAAAA
GAAACCAACAGGGATTGCCCCAGTAACGGCGAGTGAAGCGGCAAAAGCTCAAATTTGAAATCTGGCCTCCTACGGGGG
TCCGAGTTGTAATTTGTAGAGGATGCTTCGGGTGTGGCCGCCGTCTAAGTTCCTTGGAACAGGACGTCAGAGAGGGTGA
GAATCCCGTCTTGGGCGGCCGGTCCGCGCCCGTGTGAAGCTCCTTCGAAGAGTCGAGTTGTTTGGGAATGCAGCTCTAA
GCGGGTGGTAAATTTCATCTAAAGCTAAATACTGGTCGGAGACCGATAGCGCACAAGTAGAGTGATCGAAAGGTTAAA
AGCACCTTGAAAAGGGAGTTAAACAGCACGTGAAATTGTTGAAAGGGAAGCGCTTGCGGCCAGACTCGGGGGCGGGG
TTCAGCGGGTGCTCGTCGCCCGTGCACTCCCCGTCTCCCGGGCCAGCATCAGTTTCGACGGCCGGTCAAAGGCCTCCGG
AATGTGTCGTCTCTCGGGACGTCTTATAGCCGGGGGTGCAATGCGGCCCGTCGGGACTGAGGAACGCGCTTCGGCTCGG
ATGCTGGCGTAATGGCCGTAAGCGGCCCGTCTTGAAACACGGACCAAGGAGTCTAACATCCACGCGAGTGTTCGGGTG
TCAAACCCGTGCGCGCAGTGAAAGCGAACGGAGGTGGGAGCCTTAGGGCGCACCATCGACCGATCCTGAAGTCTTCGG
ATGGTTAGGGTTAGGTTAGGGTTAGGTTAGGTTTTAGGGTTTAGGGTTTAGGGTGTGAAGCCAGAGGGAAACTC
TGGTGGAGGCTCGCAGCGGTTCTGACGTGCAAATCGATCGTCAAATTTGGGCATAGGGGCGAAAGACTAATCGAACCA
TCTAGTAGCTGGTTCCTGCCGAAGTTTCCCTCAGGATAGCAGTGACGATATTCCAGTTTTATGAGGTAAAGCGAATGAT
TAGAGGCCTTGGGGATGAAACATCCTTAACCTATTCTCAAACTTTAAATATGTAAGAAGCCCTTGTTTCTTAAGTGAAC
GTGGGCACTAGAATGGAACGTCACTAGTGGGCCATTTTTGGTAAGCAGAACTGGCGATGCGGGATGAACCGAACGCGA
GGTTAAGGTGCCGGAATGCACGCTCATCAGACACCACAAAAGGTGTTAGTTCATCTAGACAGCCCGACGGTGGCCATG
GAAGTCGGAATCCGCTAAGGAGTGTGTAACAACTCACGGGCCGAATGAACTAGCCCTGAAAATGGATGGCGCTCAAGC
GTGCTACCCATACCTCGCCGCCGGGGTTGAAATGACGCCCCGGCGAGTAGGCAGGCGTGGAGGTCCGTGACGAAGCCC
TGGGGGTGACCCCGGGTCGAACGGCCTCTAGTGCAGATCTTGGTGGTAGTAGCAAATACTCAAATGAGAACTTTGAGG
ACTGAAGTGGGGAAAGGTTCCATGTGAACAGCAGTTGGACATGGGTTAGTCGATCCTAAGGCATAGGGTAGTTCCGAT
TGCATGTGCGCCCTGGTGCGCCGTCAGCCGAAAGGGAAGCCGGTTAAAATTCCGGCACCTGGATGTGGATTCTCCACG
GCAACGTAACTGAACGCGGAGACGTCGGCGGGGGTCCTGGGAAGAGTTATCTTTTCTTCTTGACGGCCTATCACCCTGA
AATCGGTTTGTCCGGAGCTAGGGTTCAATGGCCGGCAGAGCGCCGCACCTTTGCGGCGTCCGGCGTGCCCCCGACGAC
CCTTGAAAATCCGCGGGAAGGAATAGTTTTCACGCCAGGTCGTACTCATAACCGCAGCAGGTCTCCAAGGTGAAAAGC
CTCTAGTTGATAGAACAATGTAGATAAGGGAAGTCGGCAAAATAGATCCGTAACTTCGGGAAAAGGATTGGCTCTAAG
GATCGGGCGCGTTGGGCCTTGGGTGGAGACCCTCGAGGCAGGGCAGCACTAGCCGGGCAACCGGCCGGCGCCGCCCA
GCATCGGGGCGTGGACGCCCTTGGCAGGCCTCTGGCCGTCCGGCGCGCGCTTAACGATCAACTTAGAACTGGTACGGA
CAAGGGGAATCTGACTGTCTAATTAAAACATAGCATTGCGATGGCCAGAAAGTGGTGTTGACGCAATGTGATTTCTGCC
CAGTGCTCTGAATGTCAAAGTGAAGAAATTCAACCAAGCGCGGGTAAACGGCGGGAGTAACTATGACTCTCTTAAGGT
AGCCAAATGCCTCGTCATCTAATTAGTGACGCGCATGAATGGATTAACGAGATTCCCACTGTCCCTATCTACTATCTAG
CGAAACCACAGCCAAGGGAACGGGCTTGGCAGAATCAGCGGGGAAAGAAGACCCTGTTGAGCTTGACTCTAGTTTGAC
ATTGTGAAAAGACATATCGGGTGTAGAATAGGTGGGAGCTTCGGCGCCGGTGAAATACCACTACCTTTATTGTTTTTTT
ACTTATTCAATGAAGCGGAACTGGCCTTTACTGGCCAACTTCTAGCGTTAAGGTCCCTCGCGGGCTGATCCGGGTTGAA
GACATTGTCAGGTGGGGAGTTTGGCTGGGGCGGCACATCTGTTAAACAATAACGCAGGTGTCCTAAGGGGGACTCATG
GAGAACAGAAATCTCCAGTAGAACAAAAGGGTAAAAGTCCCCTTGATTTTGATTTTCAGTGTGAATACAAACCATGAA
AGTGTGGCCTATCGATCCTTTAGTCCCTCGAAATTTGAGGCTAGAGGTGCCAGAAAAGTTACCACAGGGATAACTGGCT
TGTGGCAGCCAAGCGTTCATAGCGACGTTGCTTTTTGATCCTTCGATGTCGGCTCTTCCTATCATACCGAAGCAGAATTC
GGTAAGCGTTGGATTGTTCACCCACTAATAGGGAACGTGAGCTGGGTTTAGACCGTCGTGAGACAGGTTAGTTTTACCC
TACTGATGAAGTTCGCCGCAACGGTAATTCAATTTAGTACGAGAGGAACCGTTGATTCAGATAATTGGTTTTTGCGGCT
GTCTGACAAGGCATTGCCGCGACGCTACCATCTGCCGGATTATGGCTGAACGCCTCTAAGTCAGAATCCGTGCCGGAA
AGCGGCGATACCTGCCCCGCACGTTGTAGTTGGATACAAATAGGCTTCGGCCCTGAACCTCAACAGGCCGGCACCGGC
GCCTCGGCGCTAGCTGGCGGATTGCAATGTCACCACGCGCGGGGATAAATCCTCTGCAGACGACTGAAGTGAGCAAGC
GGGTCGTGTAAGCGGTCAAGTAGCCTTGTTGTTACGAGTCGCTGAGCGTCAGCCCGATCCTTGCCTAGATTTGTTGTAA
CACCCTCCC
```

Figure 46
*Mucor racemosus* rRNA gene (SEQ ID NO: 93)

```
TAGGCTATTTAGAGGAAGTAAAAGTCGTAACAAGGTTTCCGTAGGTGAACCTGCGGAAGGATCATTAAATAATCAATA
ATTTTGGCTTGTCCATCATTATCTATTTACTGTGAAACGTATTATTACTTGACGCCTGAGGGATGTTCCACTGCTATAAG
GATAGGCAGCGGAAATGTTAACCGAGTCATAATCAAGCTTAGGCTTGGTATCCTATTATTATTTACCAAAAGAATTCAG
AATTAATATTGTAACATAGACGTAAAAAATCTATAAAACAACTTTTAACAACGGATCTCTTGGTTCTCGCATCGATGAA
GAACGTAGCAAAGTGCGATAACTAGTGTGAATTGCATATTCAGTGAATCATCGAGTCTTTGAACGCAACTTGCGCTCAT
TGGTATTCCAATGAGCACGCCTGTTTCAGTATCAAAACAAACCCTCTATCCAACTTTTGTTGAATAGGATGACTGAGAG
TCTCTTGATCGTCAGATCTCGAACCTCTTGAAATGTACAAAGGCCTGATCTTGTTTGATGCCTGAACTTTTTTTTAATAT
AAAGAGAAGCTCTTGCGGTAAACTGTGCTGGGGCCTCCCAAATAACACTTTTTTAAATTTGATCTGAAATCAGGTGGGA
TTACCCGCTGAACTTAAGCATATCAATAAGCGGAGGAAAAGAAAATAACAATGATTTCCCTAGTAACGGCGAGTGAAG
AGGAAAGAGCTCAAAGTTGGAAACTGTTTGGCTTAGCTAAACCGTATTGTAAACTGTAGAAACATTTTCCTGGCACACC
AGATTAATAAGTCCTTTGGAACAAGGCATCATGGAGGGTGAGAATCCCGTCTTTGATCTGAGTAGTTGTCTTTTGTGAT
ATGTTTTCAAAGAGTCAGGTTGTTTGGGAATGCAGCCTAAATTGGGTGGTAAATCTCACCTAAAGCTAAATATTTGCGA
GAGACCGATAGCGAACAAGTACCGTGAGGGAAAGATGAAAAGAACTTTGAAAAGAGAGTTAAACAGTATGTGAAATT
GTTAAAAGGGAACCGTTTGGAGCCAGACTGGTTTGCTTGTAATCAACCTAGAATTCGTTTTGGGTGCACTTGCAGGCTA
TACCTGCCAACAACAGTTTGATTTGGAGGAAAAAATTAGTAGGAATGTAGCCTCTCGAGGTGTTATAGCCTACTATCAT
ACTCTGGATTGGACTGAGGAACGCAGCGAATGCCTTTAGGCAAGATTGCTGGGTGCTTTCGCTAATAAATGTTAGAATT
TCTGCTTCGGGTGGTGCTAATGTTTAAAGGAGGAACACATCTAGTATATTTTTTATTCGCTTAGGTTGTTGGCTTAATGA
CTCTAAATGACCCGTCTTGAAACACGGACCAAGGAGTCCACCATAAGTGCAAGTATTTGAGTGACAAACTCATATGCGT
AAGGAAACTGATTGATACGAAGTCTTTTGATGGCAGTATCACCCGGCGTCGACGTTTTAACTGAAATGACCGAGGTAA
AGCACTTATGATGGGACCCGAAAGATGGTGAACTATGCCTGAATAGGGTGAAGCCAGAGGAAACTCTGGTGGAGGCTC
GTAGCGATTCTGACGTGCAAATCGATCGTCAAATTTGGGTATAGGGGCGAAAGACTAATCGAACCATCTAGTAGCTGG
TTCCTGCCGAAGTTTCCCTCAGGATAGCAAAAACTTAAACGCAGTTTTATGAGGTAAAGCGAATGATTAGAGGCCTTGG
GGACGAAATGTCCTTAACCTATTCTCAAACTTTAAATATGTAAGACGACCTGTTTGCTTAATTGAAGCAGGTCATTGAA
TGTGAGTTTTTAGTGGGCCATTTTTGGTAAGCAGAACTGGCGATGCGGGATGAACCGAACGAGAAGTTAAGGTGCCGG
AATACACGCTCATCAGACACCACAAAAGGTGTTAGTTCATCTAGACAGCAGGACGGTGGCCATGGAAGTCGGAATCCG
CTAAGGAGTGTGTAACAACTCACCTGCCGAATGAACTAGCCCTGAAAATGGATGGCGCTTAAGCGTGTTACCCATACTT
CTCCGTTATTGTAAAAGCGAAGCAATAACGAGTAGGCAGGCGTGGAGGTTTTTATAAACTGTTAAGAAGCTCTTGGAGT
GATCCGGAGTGAAACAGCCTCTAGTGCAGATCTTGGTGGTAGTAGCAAATATTCAAATGAGAACTTTGAAGACTGAAG
TGGAGAAAGGTTCCTGGAGAACATTATTTGGTCCAGGGTTAGTCGATCCTAAGAGATAGGGAAATTCCGTTTTTTCAAA
GCAATCAATCTTGATTCGCCTATCGAAAGGGAAACAGTTTAATATTACTGTACTAGGATGAGGATTTTCTGCGGTAACG
CAAATGAACTTGGAGACATCAGTGTGGATCCCAGGAAGAGTTATCTTTTCTTTTTAACAACTTTGTTGTAGACCTTGAA
ATCTGTTTAGCAGGAGAAAAGGTTTACCGGTTGGTAGAGCATAGTACTTTTTGCTATGTCTGGTGCATTCACAACGATC
CTTGAAAATCCAAGGGAAAGAATAATTTTCTCGCCTAGTCGTACTCATAACCGCAGCAGGTCTCCAAGGTGAAAAGCCT
CTAGTTGATAGAACAATGTAGATAAGGGAAGTCGGCAAAATAGATCCGTAACTTCGGGATAAGGATTGGCTCTAAGGG
TTGGGTAGATATGGACTCTTGGTATGGTTGGTTTCTAGGCGATTTTAGGTGATTTCGGTTGCTTGATTTTGCTTGGAGAT
CTTCGTAACCAGGAGAGCCCAGTTTACGCTTAACAACCAACTTAGAACTGGTACGGACAAGGGGAATCTGACTGTCTA
ATTAAAACATAGCATTGCGATGGCCAGAAAGTGGTGTTGACGCAATGTGATTTCTGCCCAGTGCTCTGAATGTCAAAGT
GAAGAAATTCAACCAAGCGCGGGTAAACGGCGGGAGTAACTATGACTCTCTTAAGGTAGCCAAATGCCTCGTCATCTA
ATTAGTGACGCGCATGAATGGATTAACGAGATTCCCACTGTCCCTATCTACTATCTAGCGAAACCACAGCCAAGGGAAC
GGGCTTGGCAGAATCAGCGGGGAAAGAAGACCCTGTTGAGCTTGACTCTAGTTTGACATTGTGAAAAGACATAGAGGG
TGTAGCATAAGTGGGAGCTTCGCGCCAGTGAAATACCACTACCTTTATCGTTTTTTACTTAAATAATTAAGTGGGATT
GAGTCGCAAGATTAACCTTCTAGTATTAAGCATCTTCGGATGTGACCCACGTTATTGACATTGTCAAGTGGGGAGTTTG
GCTGGGGCGGCACATCTGTTAAAAGATAACGCAGGTGTCCTAAGGGGGACTCAACGAGAACAGAAATCTCGTGTAGAA
TAAAAGGGTAAAAGTCCCCTTGATTTTGATTTTCAGTGTGAATACAAACCATGAAAGTGTGGCCTATCGATCCTTTAGA
ATCTCAAGATTTGAGGCTAGAGGTGCCAGAAAAGTTACCACAGGGATAACTGGCTTGTGGCAGCCAAGCGTTCATAGC
GACGTTGCTTTTTGATTCTTCGATGTCGGCTCTTCCTATCATACTGAAGCAGAATTCAGTAAGCGTTGGATTGTTCACCC
ACTAATAGGGAACGTCAGCTGGGTTTAGACCGTCGTGAGACAGGTTAGTTTTACCCTACTGATGGTATTGGTATCGTAA
CAGTAATTGAAGTTAGTACGAGAGGAACCCTTCATTCAGATAATTGGTATTTGCGGCTGGTTGAAAGGCCAATGCCGCG
AAGCTACCATCTGCTGGATAATGCTGAACGCCTCTAAGTCAGAATCCATGCTGAAAACGATACTACTGTGTTTTGATTG
TACCAGATGAGTACTAATAAAGCTTCGGCTTGAAAACCTTACTTGTGAGCTAGGTTTGGTAGCGGAAATGCTGCTAGAT
CTACTTGCTAATGATAATGCTAATACATCAAAATGATAAATCGCATGCAGACGACATGAAATGGACGGGGTATTGTAA
GTACTAGAGTAGCCTTTGTTGCTACGATGTACTGAGATTAAGCCTTTGTCATTGAATTTGTTCCTCTAAGGAACATTTCT
CATCAAAAATTAATAAATTTTTATCTATTTTTTTTTATCTGT
```

Figure 47
*Neurospora crassa* rRNA gene (SEQ ID NO: 94)

```
CGGTTATTTAAAGGAAATAAAAATTGTAATAAAGTTTCTGTTAGTAAATTAGTAGAAAGATTATTATAGAATTACAAAA
CTCCTATAAATTATTGTAAATTTTACTTATATAGTTACTTCGGCGTTAGTAGTTTAAAAAAGCCTTCGAGCCCTCCCGGA
TCCTCGGGTCTCCTACTCGTAAGAAGTTACCCGCCGGAATACTAAAACTAAACTCTTAATATTTTATATCTCTTTAAGTA
AACTTTTAAATAAATTAAAACTTTTAATAATAAATCTCTTAGTTCTAACATTAATAAAAAACGTAATAAAATATAATAA
GTAATATAAATTATAGAATTTAGTAAATTATTAAATCTTTAAACGCACATTGCGCTTACTAATATTCTAGTAAGTATACT
TATTCGAATATTATTTCAACTATTAAGCTCTACTTACGTTAGGGATCCGTAGCTATCCGTAGTCCTTTAAAATTAATAGC
GGGTTTATTAATTATATTGAGTATAGTAATTCTATATTATTATAATTATATAGCGGGTTCTTACTATAAAACCCCCTATTT
TTAAAATTGACCTCGGATTAGGTAGGAATACCCGCTGAATTTAAGTATATTAATAAGTAGAAGAAAAAAAATTAATAG
GGATTACCTTAATAATAGCGAATAAAATAGTAATAGTTCAAATTTGAAATCTAGCTTCGGCCCGAATTATAATTTGTAA
AAGAAGCTTTTAGTAAGGCACTTTCTAAATCCCCTAGAACGGAGCGCTATAGAGGGTGAGAGCCCTATATAATTGGAT
GCCAATCTAATATAAAGCTCCTTTAATAAATCGAATAGTTTAGGAATATTATTTAAAATAGGAGGTAAATTTCTTTTAA
AGCTAAATACCGGCTAGAGATTAATAGTATATAAGTAGAGTAATTAAAAAATGAAAAGTACTTTAAAAAGAGGGTTAA
ATAGTATATGAAATTATTAAAAGGAAAGTGTTTATAATTAGATTTATACTGTTTTAATTATTTAGTATTCTTATTAGTAT
ATTTAGGACGGTTTAAACTAATATTAGTTTTAGTAGGGGGATAAAGGTTTAGGGAATATAACTCCTCTAGGAATATTAT
AGCCCTAGGCGTAATACCTTTACTAGAACTGAAGTTCGTATATTTATAAGAATACTAGTATAATAATTATTAATAACCC
GTTTTAAAATACAGACTAAGGAATTAAAGTTTTACGCAAGTATTTAGGTATAAAACCCGTACGTATAATAAAAGTAAAT
GTAGGTGAGAGCTTCGGTATATTATTAATTAATTCTAATATATTTAGATAAATTTAAATAAGAATATTAAACCTTAAAC
CCGAAAAATAATAAACTATACTTAGATAGGGTAAAGCTAGAAGAAACTCTAATAGAGGCTCGCAACGGTTCTAACGTA
CAAATCGATTGTTAAATCTAAGTATGGGGGCGAAAGACTAATTGAACTATCTAATAGCTAATTACCGCCGAAGTTTCCC
TTAAGATAATAATATTATTCTTCAATTTTATAAGGTAAAGCGAATAATTAGGGACTCGGGGGCGCTTTTTAGCCTTCATC
CATTCTTAAACTTTAAATATATAAGAAGCCCTTATTATTTAATTAAATATAGGTATTCGAATATATTAATACTAATAGGC
TATTTTTAATAAGTAGAACTAGTAATACGGAATAAACCGAACGTAGGGTTAAAGTACTAGAGTAAATACTTATTAAATA
CTATAAAAAGCGTTAGTATATTTTAATAATAGGACGGTGGCTATAGAAATCGGAATTTGCTAAGGACTATATAATAATT
TACTTACCGAATATACTAGCTTTGAAAATAAATAGTACTTAAACGTCCTACTTATACCCCGCCCTTAAAGTAGAAACGA
TATTCTAAAGAGTAGGCGGCTATAGAGGTTAGTAACGAAGCCTAGGGCGTAAGCCCGGGTCGAACGGCCTTTAATATA
AATTTTAATAGTAGTAATAAATATTTTAATAAGAATTTAAAGGACTAAAGTAGGGAAAGGTTCTATATAAATAGCGGTT
GGATATAGGTTAATTAATCTTAAACTATAGGGAAGTTCCGTTTTAAAGGGGTATTTATACTCTATATAGCGAAAGGGAA
GCCGGTTAATATTCCGGTACCTAAATATAGGTTTTACGCGGTAATGTAATTAAATATAGAAACGATAGCGGAGGCCCCA
GGTAAAATTCTCTTTTCTTTTTAATAGTCTATTACCCTAAAAATAATTTATTTAGAGATAGGGTTTAATAGCCGGAAGAG
CCCAATATTTCTATTGGGTCCAGTACGTTTTTAATATCCCTTAAAAATCCGTAGGAGGGAATAATTCTTATATTAAGTTA
TATTTATAATTATAGTAGGTCTTTAAAGTGAATAGCTTCTAATTAATAGAATAATATAGATAAGGGAAGTTAGTAAAAT
AGATTTATAATTTTAGGAAAAGGATTAATTCTAAGGGTTAAGTACGTCGGGCTTTAGGTAAACGCCCTAAGAGTAGATT
GCTATTAGTTAGGTAACCGGCCGGTAGCTTTCAATATCCGGGTATAGAAGCTTTTAATAGACTTCGGTCGTCCGGTGTA
CGTTTAATAATTATTTAAAATTAGTATAGATAGGGGGAATTTAATTATCTAATTAAAATATAGTATTACGATAGTTAG
AAAGTAGTATTAACGTAATATAATTTCTATTTAGTATTTTAAATATTAAAATAAAAAAATTCAACTAAGCGCGGGTAAA
TAGCAGGAATAACTATAATTCTCTTAAAGTAGCCAAATACTTTATTATTTAATTAGTAACGCATATAAATAGATTAATG
AGATTCCTATTATCCCTATTTATTATCTAGCGAAACTATAATTAAAGGAACGGGCTTAGTAGAATTAATGGAGAAAGAA
GACCCTATTAAACTTAATTTTAGTTTAATATTATAAAAAAATATAGGAAGTATAGAATAGGTAGGAGCTTCGGCGCCGG
TAAAATACTACTACTCCTATTGTTTTTTTACTTATTTAATTAAGCGGGGCTAGATTTTTATTCAACTTCTAATTTTAAGGT
CCTTCGTAGGCTAACCCGGATTAAAAATATTATTAAGTAGGGAATTTAGCTAGGGCAGTACATCTATTAAACTATAATG
CAAATATCCTAAGGGGGGCTTATAGAGAATAAAAATCTCTAGTAGAACAAAAGGGTAAAAATCCCCTTAATTTTAATTT
TTAATATAAATATAAATTATAAAAGTATAGCCTATTAATCCTTTAGTCCCTCGAAATTTAAAGTTAGAAGTACTAGAAA
AATTACTATAAGGATAATTAACTTATAATAGCCAAACGTTTATAGCAATATCGCTTTTTAATCCTTCAATATCAGCTCTT
CCTATTATACCGAAGTAGAATTCGGTAAATATTAGATTATTTACCTATTAATAGGGAATGTAAGCTAAATTTAGACTAT
TATAAAATAAATTAGTTTTACCCTACTAATAACTTTATCGCAATAGTAATTAAATTTAGTATAAAAGGAACTACTTATTT
AAATAATTAGTTTTTATAATTATCTAACCGGATAGTACTATAACGCTACTATCTACTAGATAATAACTGAACGCCTCTAA
ATTAGAATTTATATTAGAATACGATAATACTTTTAGTATATTTATAGATATATAAAAATAAGCTCCGGCTTTGTATCTTAG
TAAGCAATTCCTCTATTAGCCTTAAAGTAGCTAGCGGTAATTCGTATATTATAATTTTAATATATATTAGATTAAATCCT
TTATAAATAATTTAAATATACGAAAGGGTTTTATAAATAATAGAATAGCCTTATTATTATAATTTATTAAGAGTAAGCC
CTCCTTCGCTTAAATTTCCCAATAGAAGGATCCGCTTAATAAATAGGCATTT
```

Figure 48

*Paracoccidioides brasiliens* rRNA gene (SEQ ID NO: 95)

```
GTCATTTAGAGGAAGTAAAAGTCGTAACAAGGTTTCCGTAGGTGAACCTGCGGAAGGATCATTAACGCGCCGTGGGGG
GACGGGGCCCGATCGGGTTCCCGGCCCTCTCACCTGGCCACCCTTGTCTATTCTACCTGTTGCTTCGGCGGGCCTGCAGC
GATGCTGCCGGGGGGGCTCGGCCTCCCGGGCTCGTGCCCGCCGGGGACACCGTTGAACTTCTGGTTCGGAGCTTTGACG
TCTGAGACCTATCATAATCAGTAAAAACTTTCAACAACGGATCTCTTGGTTCCGACATCGATGAAGAACGCAGCGAAAT
GCGATAAGTAATGTGAATTGCAGAATTCCGTGAATCATCGAATCTTTGAACGCACATTGCGCCCTCTGGTATTCCGGGG
GGCATGCCTGTCCGAGCGTCATTTCAACCCTCAAGCGCGGCTTGCGTGTTGGGCCCGCGTCCCCCCGTGGACGTGCCCG
AAATGCAGCGGCGGCGTCGCGTTCCGGTGCCCGAGCGTATGGGGCTTCGTCACACGCTCTCAGAGGCCCGGCCGACTC
CGGCCCCACTCATCGACCCCGGCGGGGGGGAAAAAGGTGTCCTCTCTCGATCGACACCCTTCCCCCTTGCCGACCAAGG
TTGACCTCGGATCAGGTAGGGATACCCGCTGAACTTAAGCATATCAATAAGCGGAGGAAAAGAAACCAACAGGGATTG
CCTCAGTAACGGCGAGTGAAGCGGCAAGAGCTCAAATTTGAAATCTGGCTCCTTCGGGGCCCGAGTTGTAATTTGTAGA
GGATGCTTCGGGCGTGGCCGCGGTCTAAGTCCCCTGGAACGGGGCGTCGCAGAGGGTGAGAATCCCGTCTTCGGCCGG
CCGGCCCCGCCCGTGTGAAGCTCCTTCGACGAGTCGAGTTGTTTGGGAATGCAGCTCTAAATGGGTGGTAAATTTCATC
TAAAGCTAAATACTGGTCGGAGACCGATAGCGCACAAGTAGAGTGATCGAAAGATGAAAAGCACTTTGAAAAGAGAG
TTAAACAGCATGTGAAATTGTTGAAAGGGAAGCGCTTGCGACCAGAGTCGGCCGCGGGGGCTCAGCGGGCACTCGTTG
CCCGTGCACTCCCCCGTGGTCGGGCCAGCGTCGGTTTCGACGGCCGGTCAAAGGCCCCCGGAATGTGTCGCCTCTCGGG
GCGTCTTATAGCCGGGGGTGCAATGCGGCCAGTCGGGACCGAGGAACGCGCTCCGGCACGGACGCTGGCTTAATGGTC
GTAAGCGACCCGTCTTGAAACACGGACCAAGGAGTCTAACATCCACGCGAGTGTTCGGGTGTCAAACCCGTCCGCGCA
GTGAAAGCGAACGGAGGTGGGAACCCTCAAGGGTGCACCATCGACCGATCCTGAAGTCTTCGGATGGATTTGAGTAAG
AGCGTGGCTGTTGGGACCCGAAAGATGGTGAACTATGCCTGAATAGGGTGAAGCCAGAGGAAACTCTGGTGGAGGCTC
GCAGCGGTTCTGACGTGCAAATCGATCGTCAAATTTGGGCATAGGGGCGAAAGACTAATCGAACCATCTGGTAGCTGG
TTCCTGCCGAAGTTTCCCTCAGGATAGCAGTAACGTTTTCAGTTTTATGAGGTAAAGCGAATGATTAGAGGCCTTGGGG
TTGAAACAACCTTAACCTATTCTCAAACTTTAAATATGTAAGAAGCCCTTGTTGCTTAGTTGAACGTGGGCACTGGAAT
GGATCGTTACTAGTGGGCCATTTTTGGTAAGCAGAACTGGCGATGCGGGATGAACCGAACGCGAGGTTAAGGTGCCGG
AATGCACGCTCATCAGACACCACAAAAGGTGTTAGTTCATCTAGACAGCCCGACGGTGGCCATGGAAGTCGGAATCCG
CTAAGGAGTGTGTAACAACTCACGGGCCGAATGAACTAGCCCTGAAAATGGATGGCGCTCAAGCGTGCTACCCATACC
TCGCCGTCGGGGCAGAAACGACGCCCCGACGAGTAGGCAGGCGTGGAGGTCCGTGACGAAGCCCTGGGAGTGATCCC
GGGTCGAACGGCCTCTAGTGCAGATCTTGGTGGTAGTAGCAAATACTCAAATGAGAACTTTGAGGACTGAAGTGGGGA
AAGGTTCCATGTGAACAGCAGTTGGACATGGGTTAGTCGATCCTAAGACATAGGGAAGTTCCGTTTCAAAGCGCGCCCT
CGTGCGCCGTCCGTCGAAAGGGAAGCCGGTTAATATTCCGGCACCTGGATGTGGATTCTCCACGGCAACGTAACTGAA
CGCGGAGACGTCGGCGGGGGTCCTGGGAAGAGTTATCTTTTCTTCTTGACGGCCTATCACCCTGAAATCGGTTTGTCCG
GAGCTAGGGTTCAACGGCCGGCAGAGCCCCGCACCTTTGCGGGGTCCGGTGCGCCCCCGACGACCCTTGAAAATCCGC
GGGAAGGAATAGTTTTCACGCCAGGTCGTACTCATAACCGCAGCAGGTCTCCAAGGTGAAAAGCCTCTAGTTGATAGA
ACAATGTAGATAAGGGAAGTCGGCAAAATAGATCCGTAACTTCGGGAAAAGGATTGGCTCTAAGGGTTGGGCACGTTG
GGCCTTGGGCGGAGACCCCCGGAGCAGGAAGGCACTAGCCGGGCAACCGGTGGGGGCCCTCCAGCATCGGGGCGTGG
ACGCCCTTGGCAGGCTTCGGCCGTCCGGCGTGCGATTAACAACCAACTTAGAACTGGTACGGACAAGGGGAATCTGAC
TGTCTAATTAAAACATAGCATTGCGATGGCCAGAAAGTGGTGTTGACGCAATGTGATTTCTGCCCAGTGCTCTGAATGT
CAAAGTGAAGAAATTCAACCAAGCGCGGGTAAACGGCGGGAGTAACTATGACTCTCTTAAGGTAGCCAAATGCCTCGT
CATCTAATTAGTGACGCGCATGAATGGATTAACGAGATTCCCACTGTCCCTATCTACTATCTAGCGAAACCACAGCCAA
GGGAACGGGCTTGGAGAATCAGCGGGGAAAGAAGACCCTGTTGAGCTTGACTCTAGTTTGACATTGTGAAAAGACATA
TCGGGTGTAGAATAGGTGGGAGCTTCGGCGCCGGTGAAATACCACTACCTTTATTGTTTTTTTACTTATTCAATGAAGCG
GAACTGGGCTTTGCTGCCCAACTTCTGGCGTTAAGGTCCCTCGCGGGCCGATCCGGGTTGAAGACATTGTCAGGTGGGG
AGTTTGGCTGGGGCGGCACATCTGTTAAACCATAACGCAGGTGTCCTAAGGGGGACTCATGGAGAACAGAAATCTCCA
GTAGAACAAAAGGGTAAAAGTCCCCTTGATTTTGATTTTCAGTGTGAATACAAACCATGAAAGTGTGGCCTATCGATCC
TTTAGTCCCTCGAAATTTGAGGCTAGAGGTGCCAGAAAAGTTACCACAGGGATAACTGGCTTGTGGCAGCCAAGCGTTC
ATAGCGACGTTGCTTTTTGATCCTTCGATGTCGGCTCTTCCTATCATACCGAAGCAGAATTCGGTAAGCGTTGGATTGTT
CACCCACTAATAGGGAACGTGAGCTGGGTTTAGACCGTCGTGAGACAGGTTAGTTTTACCCTACTGATGTGGTCGCCGC
AACGGTAATTCAATTTAGTACGAGAGGAACCGTTGATTCAGATAATTGGTTTTTGCGGCTGTCTGACCAGGCAGTGCCG
CGACGCTACCATCTGCCGGATTATGGCTGAACGCCTCTAAGTCAGAATCCGTGCCGGAACGCGGCGATGTTGCCCGCA
CGTTGTAGTTGGATACGAATAGGCCTCCGGGCCCAGAACCTCAGCAGGCCGGCGACGGTGCCCGGGAGAGACCCCCG
GGCGCCAGCTGGCGGATTGCAATGTCACCACGCGCGGGGATAGATCCTCTGCAGACGACTGAAATGACCAAGCGGGTC
GTGTAAGCGGTCAAGTAGCCTTGTTGTTACGAGTCGCTGAGCGTCAGCCCGATCCTTGGCTCGATTTGTTGTAGACAAC
CCCCATCGGTACGAACTAGCCCTGGTATATCCGGGGGATCG
```

Figure 49
*Pneumocystis carinii* rRNA gene (SEQ ID NO: 96)

CGAAAGAGAGGAGGTAGCACCGTTCCGTAGGTGAACCTGCGGAAGGATCATTAATGAAATGTTGTCAAGAACTAGTTT
ATCTGGTTCTTGACATTTTCATCATAACACTTGTGAACATTAAAGATTTGCTTTGACAGGATGGGAGTTAGCTTTCGTCC
TGTCAGAGGTTTTCAATTAAAACTTTTTTGGTGTTTCGGTTAAAAATATAATTTTTAAAAACTTTCAGCAATGGATCTCT
TGGTTCCCGCGTCGATGAAGAACGTGGCAAAATGCGATAAGTAGTGTGAATTGCAGAATTCAGTGACTCATCGAATTTT
TGAACGCATATTGCGCTCCTCAGTATTCTGTGGAGCATGCCTGTTTGAGCGTCATTTTTATACTTGAACCTTTTTAAGGT
TTGTGTTGGGCTATGCATTTTAGTATTTTTACAAGATGCTAGTCTAAAATGGAATCCAGAATATTATTTCGTGCAGCGTA
ATAGGGTTAAATTCCAATTCGCTGTTTTTAGAAATGATAGACTGGTTTGTCTATTGTTCCTAGAGAGCAATTTTTGAACC
TTTGACCTCAAATCAGGTAGGATTACCCGCTGAACTTAAGCATATCAATAAGCGGAGGAAAAGAAACTAACAAGGATT
CCCTCAGTAACGGCGAGTGAAGTGGGAAAAGCTCAAAATTAAAATCTGGCGAGGATCCTCGTCCGAGTTGTAATTTAG
AGAAGTGCTTTTGGCTTGATGCTCTATTTAAAGTCCTTTGGAACAAGGCATCATAGAGGGTGATAATCCCGTACGAGTA
GGGTTATTAAGCTATGTAAAAGCACATTCGAAGAGTCGAGTTGTTTGGGATTGCAGCTCAAAATGGGTGGTAAATTTCA
TCTAAAGCTAAATATTAGCGGGAGACCGATAGCGAACAAGTAGAGTGATCGAAAGATGAAAAGAACTTTGAAAAGAG
AGTTAAATAGTACGTGAAATTGCTGAAAGGGAAGCGCTTGCGATCAGACATGCCTTATCAGGATGTTGTTGTCTTGACA
ATAACTATTACTTGGTTTGGCAGGCCAACATCGGTTTCAGCTGCTAGGTAAGTGTCAAGAGAGGGTAGCCTCTTTCGTG
GGGTGGTTAGCTCTTGGCTTCTGTAGTAGCAGGGACCGGAAGGTCTAGCGTCAGCTTGGTTGTTGGCTTAATGGTCTTA
AGCGACCCGTCTTGAAACACGGACCAAGGAGTCTAATATCTATGCGAGTGTTTGAGTGGAAAACTCATACGCGAAATG
AAAGTGAAGCAAAAGGTAGGAACCCTTTAAGGGTGCACTATCGACCGGTTCAAATTTATTTGGATTGAGTAAGAGCAT
AGCTATTGGGACCCGAAAGATGGTGAACTATGCCTGAATAGGGTGAAGCCAGAGGAAACTCTGGTGGAGGCTCGTAGC
GGTTCTGACGTGCAAATCGATCGTCAAATTTGGGCATAGGGGCGAAAGACTAATCGAACCATCTAGTAGCTGGTTCCTG
CCGAAGTTTCCCTCAGGATAGCAGAAACTCAATATCAGTTTTATGAGGTAAAGCGAATGATTAGAGGCATTGGGGTTG
AAACAACCTTAACCTATTCTCAAACTTTAAATATGTAAGAAGTCCTTGTTGCTTAATTGAACATGGACATTAGAATGAG
AGTTTCTAGTGGGCCATTTTTGGTAAGCAGAACTGGCGATGCGGGATGAACCGAACGCGAGGTTAAGGTGCCGGAAGC
ACGCTCATCAGATACCACAAAAGGTGTTAGTTCATCTAGACAGTAGGAGGGTGGCCATGGAAGTCGGAATCCGCTAAG
GAGTGTGTAACAACTCACCTACCGAATGAACTGGCCCTGAAAATGGATGGCGCTCAAGCGTGCTACCTATACCTCGCC
GTCTGGGATAATGATTCCTAGACGAGTAGGCAGGCGTGGGGGTCGTGGCGAAGCCTAGGGCGTGAGCCCGGGTTGAAC
GGCCTCTAGTGCAGATCTTGGTGGTAGTAGCAAATATTCAAATGAGGACTTTGAAGACTGAAGTGGGGAAAGGTTCCA
TGCGAACAGTTATTGGGCATGGGTTAGTCGATCCTAAGAGATAGGGAAACTCCGTTTTAAAGTGCGCGATTTTTCGCGC
CTCTATCGAAAGGGAATCCGGTTAATATTCCGGAACCAGGATATGGATTCTTCACGGCAACGTAAATGAAGTCGGAGA
CGTCAGCGGGGGGCCTGGGAAGAGTTATCTTTTCTTCTTAACAGCCTATCACCCTGGAATCGGTTTATCCGGAGATAGG
GTTCAATGGCTGGTAGAGTTCAGCACTTCTGTTGAATCCAGTGCGCTTTCGATGACCCTTGAAAATCCGACGGAAGGAA
TAGTTTTCATGCCTGGTCGTACTCATAACCGCAACAGGTCTCCAAGGTGAACAGCCTCTAGTTGATAGAATAATGTAGA
TAAGGGAAGTCGGCAAAATAGATCCGTAACTTCGGGATAAGGATTGGCTCTAAGGATTGGGTGCATTGGGCTTTAATC
GGAAGCTATTGGACCAGACGGGAACTACCTTGGGAAACCGAGGCGGATCCTGTTAGGATCGATCAGTGAATGATTTA
GCAGCCCTTTGGGCGTCCGATGCACGCTTAACAATCAACTTAGAACTGGTACGGACAAGGGGAATCTGACTGTCTAATT
AAAACATAGCATTGCGATGGCCAGAAAGTGGTGTTGACGCGATGTGATTTCTGCCCAGTGCTCTGAATGTCAAAGTGA
AGAAATTCAACCAAGCGCGGGTAAACGGCGGGAGTAACTATGACTCACCTTTTGAGGGTCATGAAAGCGGCGCGAAAG
TGTTAGCTAGTGATCCGAAAAATAAATTCGGGTTGCGACACTGTCAAATTGCGGGGAGTCCCTAAAGATTCAACTACTA
AGCAGCTTGTGGAAACACAGTTGTGGCCGAGTTAATAGCCCTGGGTATAGTAACAATGTTGAATATGACTCTTAATTGA
GGAAATGGGTGATCCGCAGCCAAATCCTAAGGACATTTTATTGTCTATGGATGCAGTTCAGCGACTAGACGGCAGTGG
GTATTGTAGAGATATGGGGTTATTTATGGCCTTATCTACAATGCTTAAGGTATAGTCTAATCTCTTTCGAAAGAAAGAG
TAGTGTGCTCTTAAGGTAGCCAAATGCCTCGTCATCTGATTAGTGACGCGCATGAATGGATTAACGAGATTCCCACTGT
CCCTATCTACGATCTAGCGAAACCACAGCCAAGGGAATGGGCTTGGCAAAATCAGCGGGGAAAGAAGACCCTGTTGAG
CTTGACTCTAGTTTGACATTGTGAAAAGACATAGAGGATGTAGAATAGGTGGGAGCTTCGGCGCCTGTGAAATACCAC
CGCCTTTATTGTTTTTTACTTAATCAGTGGAGCGGGACTGAGCTTTTGCTCATCTTTTAGCGTTAAGGTCCTTTTACGGG
CCGACCCGAGTTGATGACATTGTCAGATGGGGAGTTTGGCTGGGGCGGCACATCTGTCAAAAGATAACGCAGGTGTCC
TAAGGGGAGCTCATTGAGAACAGAAATCTCAAGTAGAATAAAAGGGTAAAAGTTCCCTTGATTTTGATTTTCAGTACG
AATACAAACCATGAAAGTGTGGCCTATCGATCCTCTAAATCCTCGAAATTTGAGGCTAGGGGTGCCAGAAAAGTTACC
ACAGGGATAACTGGCTTGTGGCAGCCAAGCGTTCATAGCGACGTTGCTTTTTGATCCTTCGATGTCGGCTCTTCCTATCA
TACCGAAGCAGAATTCGGTAAGCGTTGGATTGTTCACCCACTAATAGGGAACGTGAGCTGGGTTTAGACCGTCGTGAG
ACAGGTTAGTTTTACCCTGCTGATGAAGTTATCGCAATGGTAATTCAGCTTAGTACGAGAGGAACCGTTGATTCAGATA
TTTGGTTTTTGCGGTTGTCTGACCAGGCAGTGCCGCGAAGCTATCATCTGTTGGATTATGGCTGAAAGCCTCTAAGTCAG
AATCCATGCCAGAAAGCGATGATATTTCCTCACGTTTTTTGATACAAATAGGCATCTTGCCAATATCAGTATTTGGACG
GGTGGAGGCGGACGGAAGTGTTCGTCTCTGTCCATTAATATTAATTAATATTCGTGAGGGCGAATCCTTTGTAGACGAC
TTAGTTGAGGAACGGGGTATTGTAAGCAGTAGAGTAGCCTTGTTGTTACGATCTGCTGAGATTAAGCCTTTGTTCCCAA
GATTTGT

Figure 50
*Penicillium verrucosum* rRNA gene (SEQ ID NO: 97)

```
CTTGGTCATTTAGAGGAAGTAAAAGTCGTAACAAGGTTTCCGTAGGTGAACCTGCGGAAGGATCATTACCGAGTGCGG
GCCCTCGCGGCTCAACCTCCCACCCTTGTCTCTATACACCTGTTGCTTTGGCGGGCCCACCGGGGCCACCTGGTCGCCG
GGGGACGTCGTCTCCGGGCCCGCGCCCGCCGAAGCGCTCTGTGAACCCTGATGAAGATGGGCTGTCTGAGTACTATGA
AAATTGTCAAAACTTTCAACAATGGATCTCTTGGTTCCGGCATCGATGAAGAACGCAGCGAAATGCGATAAGTAATGT
GAATTGCAGAATTCCGTGAATCATCGAATCTTTGAACGCACATTGCGCCCCTGGCATTCCGGGGGGCATGCCTGTCCG
AGCGTCATTTCTGCCCTCAAGCACGGCTTGTGTGTTGGGTGCGGTCCCCCCGGGGACCTGCCCGAAAGGCAGCGGCGAC
GTCCGTCTGGTCCTCGAGCGTATGGGGCTCTGTCACTCGCTCGGGACGGACCTGCGGGGGTTGGTCACCACCATATTTT
ACCACGGTTGACCTCGGATCAGGTAGGAGTTACCCGCTGAACTTAAGCATATCAATAAGCGGAGGAAAAGAAACCAAC
CGGGATTGCCTCAGTAACGGCGAGTGAAGCGGCAAGAGCTCAAATTTGAAATCTGGCCCCTTTGGGGTCCGAGTTGTA
ATTTGCAGAGGATGCTTCGGGTGCGGTCCCCATCTAAGTGCCCTGGAACGGGCCGTCATAGAGGGTGAGAATCCCGTCT
GGGATGGGCGGCCGCGCCCGTGTGAAGCTCCTTCGACGAGTCGAGTTGTTTGGGAATGCAGCTCTAAGCGGGTGGTAA
ATTTCATCTAAAGCTAAATACTGGCCGGAGACCGATAGCGCACAAGTAGAGTGATCGAAAGATGAAAAGCACTTTGAA
AAGAGAGTTAAACAGCACGTGAAATTGTTGAAAGGGAAGCGTTGTCCACCAGACTCGCCCGGGGGGGTTCAGCCGGCA
CGTGTGCCGGTGTACTCCTCTCCGGGCGGGCCAGCATCGGTTTGGGCGGCTGGTGAAAGGCCCCGGGAATGTAACACC
CTTCGGGGTGCCTTATAGCCCGGGGTGCCATACAGCCAGCCTGGACCGAGGCCCGCGCTTCGGCGAGGATGCTGGCGT
AATGGTGGTCAACGGCCCGTCTTGAAACACGGACCAAGGAGTCTAACATCTATGCGAGTGTTCGGGTGTCAAACCCGT
CCGCGCAGTGAAAGCGAACGGAGGTGGGAGCCCCTCGGGGGCGCACCATCGACCGATCCTGATGTCTTCGGATGGATTT
GAGTAAGAGCATAGCTGTTGGGACCCGAAAGATGGTGAACTATGCCTGAATAGGGCGAAGCCAGAGGAAACTCTGGT
GGAGGCTCGCAGCGGTTCTGACGTGCAAATCGATCGTCAAATTTGGGTATAGGGGCGAAAGACTAATCGAACCATCTG
GTAGCTGGTTCCTGCCGAAGTTTCCCTCAGGATAGCAGTAACGACATCAGTTTTATGAGGTAAAGCGAATGATTAGAGG
CCTTGGGGGTTGAAACAACCCTTAACCTATTCTCAAACTTTAAATATGTAAGAAGCCCTTGTTGCTTAGTTGAACGTGGGC
GTTAGAATGAAACGTTACTAGTGGGCCCATTTTTGGTAAGCAGAACTGGCGATGCGGGATGAACCGAACGCGAGGTTAA
GGTGCCGGAATGCACGCTCATCAGACACCACAAAAGGTGTTAGTTCATCTAGACAGCCCGACGGTGGCCATGGAAGTC
GGAATCCGCTAAGGAGTGTGTAACAACTCACGGGCGAATGAACTAGCCCTGAAAATGGATGGCGCTCAAGCGTGCTA
CCCATACCTCGCCGTCGGGGTAGAAACGATGCCCCGACGAGTAGGCAGGCGTGGGGGTCCGTGACGAAGCCTTGGGAG
TGATCCCGGGTCGAACGGCCCCTAGTGCAGATCTTGGTGGTAGCAAATACTCAAATGAGAACTTTGAGGACTGAA
GTGGGGAAAGGTTCCATGTGAACAGCAGTTGGACATGGGTGAGTCGATCCTAAGACATAGGGTAGTTCCGTTTGAAAG
TGCGCCCTCGTGCGCCGTCCGTCGAAAGGGAAGCCGGTTAATATTCCGGCACCTGGATGTGGATTCTCCACGGCAACGT
AACTGAACGCGGAGACATCGGCGGGGGTCCTGGGAAGAGTTCTCTTTTCTTCTTGACAGCCTATCACCCTGAAATCGGT
TTGTCCGGAGCTAGGGTTCCACGGCTGGCAGAGCTCGGCACCTTTGCCGGGTCCGGTGCGCCCCCGACGATCCTTGAAA
ATCCGCGGGAAGGAATAGTTTTCACGCCAGGTCGTACTCATAACCGCAGCAGGTCTCCAAGGTGAACAGCCTCTAGTTG
ATAGAACAATGTAGATAAGGGAAGTCGGCAAAATGGATCCGTAACTTCGGGATAAGGATTGGCTCTAAGGGTCGGGCA
CGTTGGGCCTTGGGGGGAAGCCCCTGGAGCAGGTGGGCACTAGCCGGGCAACCGGCCGGCGCCCGCCAGCATCGGGTG
GTGGACGCCCTTGGCAGGCTTCGGCCGTCCGGCGTGCGCTTAACGACCAACTTAGAACTGGTACGGACAAGGGGAATC
TGACTGTCTAATTAAAACATAGCATTGTGATAGCCAGAAAGTGGTATTGACACAATGTGATTTCTGCCCAGTGCTCTGA
ATGTCAAAGTGAAGAAATTCAACCAAGCGCGGGTAAACGGCGGGAGTAACTATGACTCTCTTAAGGTAGCCAAATGCC
TCGTCATCTAATTAGTGACGCGCATGAATGGATTAACGAGATTCCCACTGTCCCTATCTACTATCTAGCGAAACCACAG
CCAAGGGAACGGGCTTGGCAGAATCAGCGGGGAAAGAAGACCCTGTTGAGCTTGACTCTAGTTTGACATTGTGAAAAG
ACATATGGGGTGTAGCATAGGTGGGAGCTTCGGCGCCAGTGAAATACCACTACCTTTATCGTTTTTTTACTTATTCAATG
AAGCGGAACTGGGCTTCACCGCCCAATTTCTAGCGTTAAGGTCCTTCGCGGGCCGATCCGGGTTGAAGACATTGTCAGG
TGGGGAGTTTGGCTGGGGCGGCACATCTGTTAAACCATAACGCAGGTGTCCTAAGGGGGRCTCATGGAGAACAGAAAT
CTCCAGTAGAACAAAAGGGTAAAAGTCCCCTTGATTTTGATTTTCAGTGTGAATACAAACCATGAAAGTGTGGCCTATC
GATCCTTTAGTCCCTCGAMATTTGAGGCTAGAGGTGCCAGAAAAGTTACCACAGGGATAACTGGCTTGTGGCGGCCAA
GCGTTCATAGCGACGTCGCTTTTTGATCCTTCGATGTCGGCTCTTCCTATCATACCGAAGCAGAATTCGGTAAGCGTTGG
ATTGTTCACCCACTAATAGGGAACGTGAGCTGGGTTTAGACCGTCGTGAGACAGGTTAGTTTTACCCTACTGATGACCT
CACCGCAATGGTAATTGAGCTTAGTACGAGAGGAACCGCTCATTCAGATAATTGGTTTTTGCGGCTGTCCGACCGGGCA
GTGCCGCGAAGCTACCATCTGCTGGATAATGCTGAACGCCTCTAAGTCAGAATCCATGCCAGAACGCGGTGATAGCA
CCCGCACGTATAGACGGACAAGAATAGGCTTCGGCTTAGTGTCTCAGCAGGCGATTCCTCCGTGGTCCTCGAAGCGGG
CCGCGGTATTTCGCGTATTGTAATTTCAACACGAGCGGGGTTAAATCCTTTGCAGACGACTTAGCTGTGCGAAACGGTC
C
```

Figure 51
*Pichia stipitis* rRNA gene (SEQ ID NO: 98)

CTTGGTCATTTAGAGGAAGTAAAAGTCGTAACAAGGTTTCCGTAGGTGAACCTGCGGAAGGATCATTACAGTATTCTTT
TTGCCAGCGCTTAACTGCGCGGCGAAAAAACCTTACACACAGTGTTTTCTTTATTAGAAACTATTGCTTTGGTCTGGCTC
AGAAATGAGTTGGGCCAGAGGTTTACCAAACTTCAATTTTATTGAATTGTTATTTTATTAATTTGTCAATTTGTTGATTA
AATTCAAAAATCTTCAAAACTTTCAACAACGGATCTCTTGGTTCTCGCATCGATGAAGAACGCAGCGAAATGCGATAAG
TAATATGAATTGCAGATTTTCGTGAATCATCGAATCTTTGAACGCACATTGCGCCCTTTGGTATTCCAAAGGGCATGCCT
GTTTGAGCGTCATTTCTCTCTCAAACCCTCGGGTTTGGTATTGAGTGATACTCTTAGTCGAACTAGGCGTTTGCTTGAAA
AGTATTGGCACGAGTGGTACTAAATAGTACTGACAGAATATTTCAATGTATTAGGTTTATCCAACTCGTTGAGACTTCT
GGCGGTGAATTTTTGGTATATTGGCTTTGCCTTACAAAACAACAAACAAGTTTGACCTCAAATCAGGTAGGATTACCCG
CTGAACTTAAGCATATCAATAAGCGGAGGAAAAGAAACCAACAGGGATTGCCTTAGTAACGGCGAGTGAAGCGGCAA
AAGCTCAAATTTGAAATCTGGCACCTTCGGTGTCCGAGTTGTAATTTGAAGAAGGTAACTTTGGAGTCAGCTCTTGTCT
ATGTTCCTTGGAACAGGACGTCACAGAGGGTGAGAATCCCGTGCGATGAGATGTCTGATTCTATGTAAAGTGCTTTCGA
AGAGTCGAGTTGTTTGGGAATGCAGCTCTAAGTGGGTGGTAAATTCCATCTAAAGCTAAATATTGGCGAGAGACCGAT
AGCGAACAAGTACAGTGATGGAAAGATGAAAAGAACTTTGAAAAGAGAGTGAAAAAGTACGTGAAATTGTTGAAAGG
GAAGGGTTTGAGATCAGACTTGGTATTTTGTATGTCTTGCTTTCGGGTGGGGCCTCTACAGTTTACTGGGCCAGCATCGG
TTTGGACGGTAGGATAATGACATTGGAATGTGGCACCACTTCGGTGGTGTGTTATAGACTTTGTTGATACTGCCTGTCTA
GACCGAGGACTGCGTCTTTGACTAGGATGCTGGCATAATGATCTTAAACCGCCCGTCTTGAAACACGGACCAAGGAGT
CTAACGTCTATGCAAGTGTTTGGGTGTAAAACCCGTACGCGTAATGAAAGTGAACGTAGGTGAGAGCTCTTTTGAGTGC
ATCATCGACCGATCCTGATGTCTTCGGATGGATTTGAGTAAGAGCATAGCTGTTGGGACCCGAAAGATGGTGAACTATG
CCTGAATAGGGTGAAGCCAGAGGAAACTCTGGTGGAGGCTCGTAGCGGTTCTGACGTGCAAATCGATCGTCGAATTTG
GGTATAGGGGCGAAAGACTAATCGAACCATCTAGTAGCTGGTTCCTGCCGAAGTTTCCCTCAGGATAGCAGAAGCTCG
TATCAGTTTTATGAGGTAAAGCGAATGATTAGAGGTCTTGGGGTTGAAATGACCTTAACCTATTCTCAAACTTTAAATA
TGTAAGAAGTCCTTGTTGCTTAATTGAACGTGGACATATGAATGAAGAGCTTTTAGTGGGCCATTTTTGGTAAGCAGAA
CTGGCGATGCGGGATGAACCGAACGTGAAGTTAAAGTGCCGGAATACACGCTCATCAGACACCACAAAAGGTGTTAGT
TCATCTAGACAGCCGGACGGTGGCCATGGAAGTCGGAATCCGCTAAGGAGTGTGTAACAACTCACCGGCCGAATGAAC
TAGCCCTGAAAAATGGATGGCGCTCAAGCGTGTTACTTATACTTCACCGTCAGGGTTGATATGATGCCCTGACGAGTAGG
CAGGCGTGGAGGTCAGTGACGAAGCCTTTGCTGTAAAGCTGGGTAGAACGGCCTCTAGTGCAGATCTTGGTGGTAGTA
GCAAATATTCAAATGAGAACTTTGAAGACTGAAGTGGGGAAAGGTTCCATGTCAACAGCAGTTGGACATGGGTTAGTC
GATCCTAAGAGATGGGGAAGCTCCGTTTCAAAGATTTGATTTTTCAAGTCACCATCGAAAGGGAATCCGGTTAAAATTC
CGGAACTTGGATATGGATTCTTCACGGTAACGTAACTGAATGTGGAGACGTCGGCGTGAGCCCTGGGAGGAGTTCTCTT
TTCTTCTTAACAGCTTATCACCCTGGAATTGGTTTATCCGGAGATAGGGTCTTATGGCTGGAAGAGTGCAATACTTTTGT
TGCATCCGGTGCGCTTACGACGGTCCTTGAAAATCCACAGGAAGGAATAGTTTTCATGCCAAGTCGTACTCATAACCGC
AGCAGGTCTCCAAGGTTAACAGCCTCTAGTTGATAGAATAATGTAGATAAGGGAAGTCGGCAAAATAGATCCGTAACT
TCGGGATAAGGATTGGCTCTAAGGATCGGGTGTCTTGGGCCTTTACCAGACGCAGCGGAACTGGTGGTGGACTGTTCTT
CCTTGTGTTGAACGGACCGCTACCGGATCTTGCTGTAGACGGTTTAGGTAGGCTTCGGCCGTCCGGGGCACGCTTAACG
ATCAACTTAGAACTGGTACGGACAAGGGGAATCTGACTGTCTAATTAAAACATAGCATTGCGATGGTCAGAAAGTGAT
GTTGACGCAATGTGATTTCTGCCCAGTGCTCTGAATGTCAAAGTGAAGAAATTCAACCAAGCGCGGGTAAACGGCGGG
AGTAACTATGACTCTCTTAAGGTAGCCAAATGCCTCGTCATCTAATTAGTGACGCGCATGAATGGATTAACGAGATTCC
CACTGTCCCTATCTACTATCTAGCGAAACCACAGCCAAGGGAACGGGCTTGGCAGAATCAGCGGGGAAAGAAGACCCT
GTTGAGCTTGACTCTAGTTTGACATTGTGAAAAAGACATGGAGGGGTGTAGAATAAGTGGGAGCTTCGGCGCCGGTGAAA
TACCACTACCTCTATAGTTTTTTTACTTATTCAATTAAGCGGAGCTGGACTTCATCGTCCACGTTCTAGCATTAAGGTCT
CTTTAGAGGCTGATCCGGGTTGAAGACATTGTCAGGTGGGGAGTTTGGCTGGGGCGGCACATCTGTTAAACGATAACG
CAGGTGTCCTAAGGGGGACTCATGGAGAACAGAAATCTCCAGTAGAACAAAAGGGTAAAAGTCCCCTTGATTTTGATT
TTCAGTGTGAATACAAACCATGAAAGTGTGGCCTATCGATCCTTTAGTCCCTCGGAATTTGAGGCTAGAGGTGCCAGAA
AAGTTACCACAGGGATAACTGGCTTGTGGCAGTCAAGCGTTCATAGCGACATTGCTTTTTGATTCTTCGATGTCGGCTCT
TCCTATCATACCGAAGCAGAATTCGGTAAGCGTTGGATTGTTCACCCACTAATAGGGAACGTGAGCTGGGTTTAGACCG
TCGTGAGACAGGTTAGTTTTACCCTACTGATGAATGTTATCGCAATAGTAATTGAACTTAGTACGAGAGGAACCGTTCA
TTCGGATAATTGGTTTTTGCGGCTGTCTGATCAGGCAACGCCGCGAAGCTACCATCCGCTGGATTATGGCTGAACGCCT
CTAAGTCAGAATCCATGCTAGAAAGCGATGATTCTTGCCTCGCACATTTTAGTTGGAATAAGAATAAGGCTCTTTGAGTC
GCTGAACCATAGCAGGCTGGCAATGGTACACTTAACGGAAAGGTTTTGTGTGCTTGCCGGCGAATAGCAATGTCATAAT
GCGCGGGGATAAATCCTTTGCAAACGACTTAAATGTACAACGGAGTATTGTAAGCAGTAGAGTAGCCTTGTTGTTACGA
TCTGCTGAGATTAAGCTTCAGTTGTCCGATTTGTTTGTGTTACACAACACAATCTCCTCTAAGTGATAGTTGGCAGGTGC
TAACTA

Figure 52

*Rhizomucor miehei* rRNA gene (SEQ ID NO: 99)

```
GACTGGCAACGGTCCGAAGCTTTAGCCGAACTATGGCAAACTACTCCATTTAGAGGAAGTAAAAGTCGTAACAAGGTT
TCCGTAAGTGAACCTGCGGAAGGATCATTAAAAAAAAGTTGATATCATGGTGACCCCTTTACGGGGGTGAGCCATGAT
TTCTTCTCCCTTTTTGTGCAATGTTTGAGGGATTGCTCCAAATCTCTCCTTCCCTTTTTTTACGTATTGATTTGACTGAAC
ATTTTTGTTTTAAAATGAAAAAAAGTTTTGAAGCCAATCAATTGGTTCAAGACAAATCAAATTTTGAAACAACTTTAAG
CAATGGATCACTTGGTTCTCGCATCGATGAAGAACGTAGCAAATTGCGAAAAGTAATGCGATCTGCAACCTTTGCGAAT
CATCGAATTCTCGAACGCATCTTGCACCCTTTGGTCATCCAATGGGTACGTCTAGTTCAGTATCTTTTTGAAACCCTAAA
GGTTCAATTTTGTTGTTGACCTTTGGATTTGCGGTAATGATGGGGGGGAAGACAAAGCAAATTTTTTTTTTTCCCCCGT
TAAAAGAAACGGAACAGTTTTTGGGTTTTTGGCCTTTTTGGATTGGGGAACATTTTGGAAGGGCTTACTTTGAAAATAA
AAAATTTGGAATTTTGGGTTACCATTGCTTTGGGAAAACCCAATTTAAAAGCAAAAACTTTTTTTAAACTTTTTTTTTTT
CATTCATGGATCTGAACTTAGACGGGACTACCCGCTGAACTTAAGCATATCAATAAGCGGAGGAAAAGAAAATAACAA
TGATACCCTTAGTAGCGGCGAGCGAAGTGGGTAAAGCTCAAGTTTAAAACCTGTTTGTCATAGACAAACCGGATTGTA
AACTATGGACATGTTATCCAGGCTCTTTGGACCTTCAAGTCCTTTGGAATAAGGCTTCACAGAGGGTGACAATCCCGTT
AGAGGGTCTTGAACAGAGTCTATTGCGATGCATGCTCCAAGAGTCAAGTTGTTTGGGAATGCAACCTAAATTGCAGGGT
AAATCCCTCCTAAAGCTAAATATTGGCGAGAAACCGATAGCAAACAAGTACCGTGAGGGAAAGTTGAAAAGAACTTTG
AAAAGAGAGTCAAAAGTACGTGAAATTGCTTAAAGGGAAGCGTTTGGAGCTAGTTTGGCTAGTCTGTTATCAGCCTGA
GCTTCGGCTTTGGTGTACTATCAGGCTATTTTTGCCGGCCAACTCTCAGGATTGAAAGGAAAGCTTGGTGCTTTGGAGTC
TAAAGAGACCCTCTCCTGAAGCCTCTGGTGGAGCGTGGTCTGCCCTTGGCCCTTTTGAGCCTATAGTTTGGCTTAATGGC
TCTAAACGGCCCGTCTTGAAACACGGGCCAAGGAGTCCACCACTGTTGCGAGTATTTTGGTGGCAAACCCATACGCGA
AATGAAATTGAAAGCTATGAAATCCGCAAGGATGGCAATAGCGTCCAGGCCTTTAGGACCGAGACAAAGCAATAGTGA
TGGGACCCGAAAGATGGTGAACTATGCTTGAGTAGAGTGAAGCCAGAAGAAATTCTGGTGGAAGCTCGTAACGGTTCT
GACGTGCAAATCGATCGTCGAACTTGAGCATAGGGGCGAAAGACTAATCGAACCATCTAGTAGCATGGTTCCTGCCGA
AGTTTCCCTCAGGATAGCAGAAGCTTATAGGCAGTTTTATGTGGTAAAGCGAATGATTAGAGGTCTTGGGACGCAATCC
TTAACCTATTCTCAAACTTTAAATATGTAAGACGTTCTTGCTGCTTGAATTATGAGCTTGAACCGTCGAATGCTGAGCTT
CTAGTGGGCCGTTCTTGGTAAGCAGGACTGGCGATGCGGATGAACCGAACGCAAAGATAAGGCGTCAAAGAACACG
CTCATCAGACACCACAAAAGGTGTTGGTTCATCTAGACAGCAGGACGGTGGCCATGGAAGTCGGCTAAGGAGTGTGTA
ACAACTCACCTGCCGAATGAACCACGCCCTGGAAATAAATGGCGCTGAAGCGTGTCGCCCATACTTTCCCGTCAAAGTT
AAAAGCGAAGCTTTGACGAGTAGGCAGGCGTGGAGTTTTATTGAGCGTTGGAACCCTTTGGCGGTGAGCCGGAGTGGA
CAGCCCTCTAGTGCAGATCTTGGTGGTAGTAGCAAATATTCCAATTGAAATCTTTGAGGACTGAAGTGGAGAAGGTTTC
CTCGAGAACATTAGTTGGTCGAGGGTTAGTCGATCCTAAGAGATAGGGTAGTTCCGTTTTACCAAATGGTCCTTTGGAC
CATCCTATCGAAAGGGAAGCTGGTTAATATTCCAGCACCAAGACATGGATTCTATGCGGCAACGCAGATGAACATAGG
GACATTGGCATGGATCCTGGGAAGAGTTCTCTTTTCTTTTTGACAGCGTTTTCTTAAGCCATGAAATCGGTCTAAACCGG
GGCAATGTTTGCTTAAGAGCTGTTAGAGTAACGCAATTTTTGTGGTAGCCACAGCATTCATGACGATCCTTGAAGACCT
ACGGGAAAGAATGAATTTCATGCTTGGGCGTACCATAACCGCAGCAGGTCCCCAAGGTCTAGAAGCCTCTACTTGATG
GAAGAATGTAGATAAGGGAAGTCGGCAAATTGGATCCGTAACTTCGGGAGAAGGATTGGCTCTAAGGGTTGGGTGCTT
TAAGAACCATGGCCTTAGCGGCCTGAGCAATCGGCTGCTTCCAGGCTTGGAGCTCTTGGGCACGCTTAACAACCAGCT
TAGAACTGGTACGGACCAAGGGAATCTGACTGTCTAATTAAAACATAGCATTGCGATTGCCATAAAGTGGTATTGACG
CAATGTGATTTCTGCCCAGTGCTCTGAATGTCAAGTTGAATAAATTCAACCAAGCGCGGGTAAACCGCGGGTATTACTA
TGAGAGCTTTGTGATATAGTCCAAGTTTCTAGAACTGCTAATTGCACGCGCATGAATGGATTAACGAGATTCCCACT
GTCCCTATCTACTATCCAGCGAAACCACAACCAAGGGAACGGGCTTGGCAAAATCAGCGGGAAAGAAGCGCCAGTTGA
GCTTGACTCTAGTTTGACATTGTGAAAGGACATAGGGGTGTAGAATATGTGGGAGCTTCGGCGCCAGTGAATACCACA
ACCCTTATAGTTTTTTTTACTTAAATAATCAAGTGGGAGAAGGCTTCACGGCCTATCTTCTAGCGTTAAGCAGTCTTCGG
GCTGCGACCCATGTTATTGACATTGTCAAGTGGGGAGTTTGGCTGGGCGGCACATCTGTTAAACGATAACGCAGGTGT
CCTAAGGGGAGCTCAACGAGAACAGAAATCTCGTGTAGAGCAAAAGGGCAAAAGCTCCCTTGATTTTGATTTTCAGCG
TGAATACGAACCATGAAAGTGTGGCCTATCGATCCTTTATGCCATTTCCTTAGGATTTAAGGCGCCAGAAAAGTTACCA
CAGGGATAACTGGCTTGTGGCAGCCAAGCGTTCATAGCGACGTTGCTTTTTGATTCTTCGATGTCGGCTCTTCCTATCAT
ACAGAAGCAGAATTCTGTAAGCGTTGGATTGTTCACCCACTAATAGGGAACGTGAGCTGGGTTTAGACCGTCGTGAGA
CAGGTTAGTTTTACCCTACTGATGAATCAGTAGGCGTCCCGACAGTAATTGAAGTTAGTACGAGGAGACCCTTCATTC
AGATAATTGGTTTTTGCGGTTGGTTGAAAGGCCAATGCCGCGAAGCTACCATCTGCTGGATAATGGCTGAAAGCCTCTA
AGTCAGAATCCATGCTGGTTAAGGGACGCTAAAACCAGACCTTTAAAGCGCGAGAAAGTGCTCAAATAGATCTCTTAT
GGGATCGAATGCCTAATATGAGGTTATCCTCTTGGGTTGAAAGGCTCAAGTCGGATACCTCTCATGATAATGTCTAGCT
TAAAGGTTGTAAATCTCGAGCAGACGACTTGAAATCGACGGGCTATTGTAAGCACTAGAGTAGCCTTTGTTGCTACGAT
GTGCTGAGATTAAGGCCTTGTCTTTAGATTTGT
```

Figure 53
*Rhizopus oryzae* rRNA gene (SEQ ID NO: 100)

```
CTAGGCTATTTAGAGGAAGTAAAAGTCGTAACAAGGTTTCCGTAGGTGAACCTGCGGAAGGATCATTAATTATGTTAA
AGCGCCTTACCTCTTAGGGTTTCCTCTGGGGTAAGTGATTGCTTCTACACTGTGAAAATTTGGCTGAGAGACTCAGACT
GGTCATGGGTAGACCTATCTGGGGTTTGATCGATGCCACTCCTGGTTTCAGGAGCACCCTTCATAATAAACCTAGAAAT
TCAGTATTATAAAGTTTAATAAAAAACAACTTTTAACAATGGATCTCTTGGTTCTCGCATCGATGAAGAACGTAGCAAA
GTGCGATAACTAGTGTGAATTGCATATTCAGTGAATCATCGAGTCTTTGAACGCAGCTTGCACTCTATGGTTTTTCTATA
GAGTACGCCTGCTTCAGTATCATCACAAACCCACACATAACATTTGTTTATGTGGTAATGGGTCGCATCGCTGTTTTATT
ACAGTGAGCACCTAAAATGTGTGTGATTTTCTGTCTGGCTTGCTAGGCAGGAATATTACGCTGGTCTCAGGATCTTTTTC
TTTGGTTCGCCCAGGAAGTAAAGTACAAGAGTATAATCCAGCAACTTTCAAACTATGATCTGAAGTCAGGTGGGATTAC
CCGCTGAACTTAAGCATATCAATAAGCGGAGGAAAAGAAAATAACAATGATTTCCCTAGTAACGGCGAGTGAAGAGG
AAAGAGCTCAAAGTTGGAACCTGTTTGGCCTAGCTAAACCGGATTGTAGACTGTAGAAGTGTTTTCCAGGCAAGCCGA
GTAAATAAGTCCTTTGGAACAGGGCATCATAGAGGGTGAGAATCCCGTCTTTGGCTTGAGCATTTGCCTTTTGTGATAC
GCTTTCAAAGAGTCAGGTTGTTTGGGAATGCAGCCTAAATTGGGTGGTAAATCTCACCTAAAGCTAAATATTGGCGAGA
AACCGATAGCGAACAAGTACCGTGAGGGAAAGATGAAAAGAACTTTGAAAAGAGAGTTAAACAGTATGTGAAATTGT
TAAAAGGGAACCGTTTGGAGCCAGACTGGCTTGTCTGTAATCAATCTAGGCTTCGGCCTGGATGCACTTGCAGGCTATG
CCTGCCAACGACAATTTGACTTGAGGGAAAAAACTAAGGGAAATGTGGCCCACTTGTGGGTGTTATAGTCCCTTAGAA
AATACCTTGGGTTGGATTGAGGAACGCAGCGAATGCTTTTTGGCGAGTTTTCCAGGAAGGTTTTCTGAGGTACTACGGT
ATCAAGGTTGATCTTTTTGGTTATACTTCTATTCGCTTAGGTTGTTGGCTTAATGACTCTAAATGACCCGTCTTGAAACA
CGGACCAAGGAGTCCACCATTAGTGCGAGTATTTGGGTGCCAAACCCATATGCGTAAGGAAACTGATTGATACGAATC
CATTAAGGAGGCAGTATCGTCCGGCGCTGACGTTTTATACTGAATTGACCGAGACAAAGCACTAATGATGGGACCCGA
AAGATGGTGAACTATGCCTGAATAGGGTGAAGCCAGAGGAAACTCTGGTGGAGCCTCGTAGCGATTCTGACGTGCAAA
TCGATCGTCAAATTTGGGTATAGGGGCGAAAGACTAATCGAACCATCTAGTAGCTGGTTCCTGCCGAAGTTTCCCTCAG
GATAGCAGAAACTTATACGCAGTTTTATGTGGTAAAGCGAATGATTGGGGTCACGGGGGGCTAAACGCCCTTCAACCA
CTCTCAAACTTTAAATATGTAAGACGACCTGTTTGCTTAATTGAAGCAGGTCATTGAATGCAGAGTTTCTAGTGGGCCA
TTTTTGGTAAGCAGAACTGGCGATGCGGGATGAACCGAACGCAGAGTTAAGGTGCCGGAATACACGCTCATCAGACAC
CACAAAAGGTGTTAGTTCATCTAGACAGCAGGACGGTGGCCATGGAAGTCGGAATCCGCTAAGGAGTGTGTAACAACT
CACCTGCCGAATGAACTAGCCCTGAAAATGGATGGCGCTTAAGCGTGTTACCCATACTCTGCCGTTATTGTAAAAGCGA
AGCAATAACGAGTAGGCAGGCGTGGAGGTTTTTATAAACTGTTAAGAAGCTCTTGGTGTGAACCGGAGTGAAACAGCC
TCTAGTGACAGATCTTGGTGGTAGTAGCAAATATTCAAATGAGAACTTTGAAGACTGAAGTGGAGAAAGGTTCCTGGAG
AACATCAGTTGGTCCAGGGTTAGTCGATCCTAAGAGATAGGGAAGTTCCGTTTTTTCAAAGCGCCCAATTTTTGGGCCG
CCTATCGAAAGGGAAACCGGTTAATATTCCGGTACTAGGACGAGGATTTTTTGCGGCAACGCGATTGAACTTGGAGAC
ATCAGTATGGGTCCCGGGAAGAGTTATCTTTTCTTTTTGACAGTTAGTATAAACCTTGAAATCTGTTTAGCAGGAGAAA
AGGTTTATCTGCTGGTAGAGCACAGTACTTTTTGCTGTGTCCGGTGCATTCATAACGATCCTTGAAAATCCAAGGGAAA
GAATAATTTTCTCGCCTAGTCGTACTCATAACCGCAGCAGGTCTCCAAGGTGAAAAGCCTCTAGTTGATAGAACAATGT
AGATAAGGGAAGTCGGCAAAATAGATCCGTAACTTCGGAATAAGGATTGGCTCTAAGGGTTGGGTAGAAATGGACCCT
TGGTATTGACCTTGAGGAAGAGAGAATGGGGGCAACTCTGTTCTTCATCTTCTTGGTCTACAACCAAGGGAACCCAGT
CTACGCTTAACAACCAACTTAGAACTGGTACGGACAAGGGGAATCTGACTGTCTAATTAAAACATAGCATTGCGATGG
CCAGAAAGTGGTGTTGACGCAATGTGATTTCTGCCCAGTGCTCTGAAAGTCAAAGTGAAGAAATTCAACCAAGCGCGG
GTAAACGGCGGGAGTAACTATGACTCTCTTAAGGTAGCCAAATGCCTCGTCATCTAATTAGTGACGCGCATGAATGGAT
TAACGAGATTCCCACTGTCCCTATCTACTATCTAGCGAAACCACAGCCAAGGGAACGGGCTTGGCAGAATCAGCGGGG
AAAGAAGACCCTGTTGAGCTTGACTCTAGTTTGACATTGTGAAAAGACATAGAGGGTGTAGCATAAGTGGGAGCTTCG
GCGCCAGTGAAATACCACTACCTCTATTGTTTTTTTACTTAAATAATTAAGTGGGATTGAGTCGCAAGACTCACCTTCTA
GCTTTAAGCATCCATTAGGGTGCGACCCATGTTATTGACATTGTCAAGTGGGGAGTTTGGCTGGGGCGGCACATCTGTT
AAAAGATAACGCAGGTGTCCTAAGGGGGACTCAAGGAGAACAGAAATCTCCTGTAGAATAAAAGGGTAAAAGTCCCC
TTGATTTTGATTTTCAGTGTGAATACAAACCATGAAAGTGTGGCCTATCGATCCTTTAGAATCTCAAGATTTGAGGCTAG
AGGTGCCAGAAAAGTTACCACAGGGATAACTGGCTTGTGGCAGCCAAGCGTTCATAGCGACGTTGCTTTTTGATTCTTC
GATGTCGGCTCTTCCTATCATAATGAAGCAGAATTCATTAAGTGTTGGATTGTTCACCCACTAATAGGGAACGTGAGCT
GGGTTTAGACCGTCGTGAGACAGGTTAGTTTTACCCTACTGATGGTATTGGTATCGCAACAGTAATTGAAGTTAGTACG
AGAGGAACCCTTCATTCAGATAATTGGTATTTGCGGCTGGTTGAAAGGCCAATGCCGCGAAGCTACCATCTGCTGGATA
ATGGCTGAACGCCTCTAAGTCAGAATCCATGCTGGAAGCGATACTACTGTGCTTTGATTGTACTAGTTGTGTACAAATA
AAGCTTCGGCTTGAAAACCTTACTTGCGGGATAGGCTTTGCAGCGGAAATGCTGTGATTCACTACCCTGTGATGATAAT
GCAAATGATCAAAGTGATAAATCGCATGCAGACGACATGAAATGGACGGGGTATTGTAAGTACTAGAGTAGCCTTTGT
TGCTACGATGTACTGAGATTAAGCCCTTGTCATTGAATTTGTTCCTTACG
```

Figure 54
Saccharomyces cerevisiae rRNA gene (SEQ ID NO: 101)

```
GGTCATTTAGAGGAACTAAAAGTCGTAACAAGGTTTCCGTAGGTGAACCTGCGGAAGGATCATTAAAGAAATTTAATA
ATTTTGAAAATGGATTTTTTTGTTTTGGCAAGAGCATGAGAGCTTTTACTGGGCAAGAAGACAAGAGATGGAGAGTCCA
GCCGGGCCTGCGCTTAAGTGCGCGGTCTTGCTAGGCTTGTAAGTTTCTTTCTTGCTATTCCAAACGGTGAGAGATTTCTG
TGCTTTTGTTATAGGACAATTAAAACCGTTTCAATACAACACACTGTGGAGTTTTCATATCTTTGCAACTTTTTCTTTGG
GCATTCGAGCAATCGGGGCCCAGAGGTAACAAACACAAACAATTTTATCTATTCATTAAATTTTTGTCAAAAACAAGAA
TTTTCGTAACTGGAAATTTTAAAATATTAAAAACTTTCAACAACGGATCTCTTGGTTCTCGCATCGATGAAGAACGCAG
CGAAATGCGATACGTAATGTGAATTGCAGAATTCCGTGAATCATCGAATCTTTGAACGCACATTGCGCCCCTTGGTATT
CCAGGGGCATGCCTGTTTGAGCGTCATTTCCTTCTCAAACATTCTGTTTGGTAGTGAGTGATACTCTTTGGAGTTAACT
TGAAATTGCTGGCCTTTTCATTGGATGTTTTTTTTCCAAAGAGAGGTTTCTCTGCGTGCTTGAGGTATAATGCAAGTACG
GTCGTTTTAGGTTTTACCAACTGCGGCTAATCTTTTTTTATACTGAGCGTATTGGAACGTTATCGATAAGAAGAGAGCGT
CTAGGCGAACAATGTTCTTAAAGTTTGACCTCAAATCAGGTAGGAGTACCCGCTGAACTTAAGCATATCAATAAGCGG
AGGAAAAGAAACCAACCGGGATTGCCTTAGTAACGGCGAGTGAAGCGGCAAAAGCTCAAATTTGAAATCTGGTACCTT
CGGTGCCCGAGTTGTAATTTGGAGAGGGCAACTTTGGGGCCGTTCCTTGTCTATGTTCCTTGGAACAGGACGTCATAGA
GGGTGAGAATCCCGTGTGGCGAGGAGTGCGGTTCTTTGTAAAGTGCCTTCGAAGAGTCGAGTTGTTTGGGAATGCAGCT
CTAAGTGGGTGGTAAATTCCATCTAAAGCTAAATATTGGCGAGAGACCGATAGCGAACAAGTACAGTGATGGAAAGAT
GAAAAGAACTTTGAAAAGAGAGTGAAAAAGTACGTGAAATTGTTGAAAGGGAAGGGCATTTGATCAGACATGGTGTTT
TGTGCCCTCTGCTCCTTGTGGGTAGGGGAATCTCGCATTTCACTGGGCCAGCATCAGTTTTGGTGGCAGGATAAATCCA
TAGGAATGTAGCTTGCCTCGGTAAGTATTATAGCCTGTGGGAATACTGCCAGCTGGGACTGAGGACTGCGACGTAAGTC
AAGGATGCTGGCATAATGGTTATATGCCGCCCGTCTTGAAACACGGACCAAGGAGTCTAACGTCTATGCGAGTGTTTGG
GTGTAAAACCCATACGCGTAATGAAAGTGAACGTAGGTTGGGGCCTCGCAAGAGGTGCACAATCGACCGATCCTGATG
TCTTCGGATGGATTTGAGTAAGAGCATAGCTGTTGGGACCCGAAAGATGGTGAACTATGCCTGAATAGGGTGAAGCCA
GAGGAAACTCTGGTGGAGGCTCGTAGCGGTTCTGACGTGCAAATCGATCGTCGAATTTGGGTATAGGGGCGAAAGACT
AATCGAACCATCTAGTAGCTGGTTCCTGCCGAAGTTTCCCTCAGGATAGCAGAAGCTCGTATCAGTTTTATGAGGTAAA
GCGAATGATTAGAGGTTCCGGGGTCGAAATGACCTTGACCTATTCTCAAACTTTAAATATGTAAGAAGTCCTTGTTACT
TAATTGAACGTGGACATTTGAATGAAGAGCTTTTAGTGGGCCATTTTTGGTAAGCAGAACTGGCGATGCGGGATGAACC
GAACGTAGAGTTAAGGTGCCGGAATACACGCTCATCAGACACCACAAAAGGTGTTAGTTCATCTAGACAGCCGGACGG
TGGCCATGGAAGTCGGAATCCGCTAAGGAGTGTGTAACAACTCACCGGCCGAATGAACTAGCCCTGAAAATGGATGGC
GCTCAAGCGTGTTACCTATACTCTACCGTCAGGGTTGATATGATGCCCTGACGAGTAGGCAGGCGTGGAGGTCAGTGAC
GAAGCCTAGACCGTAAGGTCGGGTCGAACGGCCTCTAGTGCAGATCTTGGTGGTAGTAGCAAATATTCAAATGAGAAC
TTTGAAGACTGAAGTGGGGAAAGGTTCCACGTCAACAGCAGTTGGACGTGGGTTAGTCGATCCTAAGAGATGGGGAAG
CTCCGTTTCAAAGGCCTGATTTTATGCAGGCCACCATCGCGAAAGGGAATCCGGTTAAGATTCCGGAACCTGGATATGGAT
TCTTCACGGTAACGTAACTGAATGTGGAGACGTCGGCGCGCGAGCCCTGGGAGGAGTTATCTTTTCTTCTTAACAGCTTAT
CACCCCGGAATTGGTTTATCCGGAGATGGGGTCTTATGGCTGGAAGAGGCCAGCACCTTTGCTGGCTCCGGTGCGCTTG
TGACGGCCCGTGAAAATCCACAGGAAGGAATAGTTTTCATGCCAGGTCGTACTGATAACCGCAGCAGGTCTCCAAGGT
GAACAGCCTCTAGTTGATAGAATAATGTAGATAAGGGAAGTCGGCAAAATAGATCCGTAACTTCGGGATAAGGATTGG
CTCTAAGGGTCGGGTAGTGAGGGCCTTGGTCAGACGCAGCGGGCGTGCTGTGGGAAGTCTGGGGGCTTGCTCTGCT
AGGCGGACTACTTGCGTGCCTTGTTGTAGACGGCCTTGGTAGGTCTCTTGTAGACCGTCGCTTGCTACAATTAACGATC
AACTTAGAACTGGTACGGACAAGGGGAATCTGACTGTCTAATTAAAACATAGCATTGCGATGGTCAGAAAGTGATGTT
GACGCAATGTGATTTCTGCCCAGTGCTCTGAATGTCAAAGTGAAGAAATTCAACCAAGCGCGGGTAAACGGCGGGAGT
AACTATGACTCTCTTAAGGTAGCCAAATGCCTCGTCATCTAATTAGTGACGCGCATGAATGGATTAACGAGATTCCCAC
TGTCCCTATCTACTATCTAGCGAAACCACAGCCAAGGGAACGGGCTTGGCAGAATCAGCGGGGAAAGAAGACCCTGTT
GAGCTTGACTCTAGTTTGACATTGTGAAGAGACATAGAGGGTGTAGAATAAGTGGGAGCTTCGGCGCCAGTGAAATAC
CACTACCTTTATAGTTTCTTTACTTATTCAATGAAGCGGAGCTGGAATTCATTTTCCACGTTCTAGCATTCAAGGTCCCA
TTCGGGGCTGATCCGGGTTGAAGACATTGTCAGGTGGGGAGTTTGGCTGGGGCGGCACATCTGTTAAACGATAACGCA
GATGTCCTAAGGGGGGCTCATGGAGAACAGAAATCTCCAGTAGAACAAAAGGGTAAAAGCCCCCTTGATTTTGATTTT
CAGTGTGAATACAAACCATGAAAGTGTGGCCTATCGATCCTTTAGTCCCTCGGAATTTGAGGCTAGAGGTGCCAGAAA
AGTTACCACAGGGATAACTGGCTTGTGGCAGTCAAGCGTTCATAGCGACATTGCTTTTTGATTCTTCGATGTCGGCTCTT
CCTATCATACCGAAGCAGAATTCGGTAAGCGTTGGATTGTTCACCCACTAATAGGGAACGTGAGCTGGGTTTAGACCGT
CGTGAGACAGGTTAGTTTTACCCTACTGATGAATGTTACCGCAATAGTAATTGAACTTAGTACGAGAGGAACAGTTCAT
TCGGATAATTGGTTTTTGCGGCTGTCTGATCAGGCATTGCCGCGAAGCTACCATCCGCTGGATTATGGCTGAACGCCTCT
AAGTCAGAATCCATGCTAGAACGCGGTGATTTCTTTGCTCCACACAATATAGATGGATACGAATAAGGCGTCCTTGTGG
CGTCGCTGAACCATAGCAGGCTAGCAACGGTGCACTTGGCGGAAAGGCCTTGGGTGCTTGCTGGCGAATTGCAATGTC
ATTTTGCGTGGGGATAAATCATTTGTATACGACTTAGATGTACAACGGGGTATTGTAAGCAGTAGAGTAGCCTTGTTGT
TACGATCTGCTGAGATTAAGCCTTTGTTGTCTGATTTGTTTTTATTTCTTTCTAAG
```

Figure 55
*Schizosaccharomyces japonicus* rRNA gene (SEQ ID NO: 102)

```
ATTTAGAGGAAGTAAAAGTCGTAACAAGGTTTCCGTAGGTGAACCTGCGGAAGGATCATTAGAAAGTAATTATTTGAG
TTTTCAACATTCACCTGCTGAACTCTCAAAAAATCTCTCTATATCTTTCTGTGAACATGTTTTCATATGAGAATGTTTGGT
CAGTCGGTCGAAAGGTTGGTTGGCCAAGCATTTGAACTATAAACTTCATTTTATATTTGATGTCTGATTTATATTTAACT
AAATGTTAAAACTTTCAGCAACGGATCTCTTGGCTCTCGCATCGATGAAGAACGCAGCGAAATGCGATACGTAATGTG
AATTGCAGAATTCCGTGAATCATCGAATCTTTGAACGCACATTGCGCCTTTGGGTTATTCCCAAAGGCATGCCTGTTTGA
GTGTCATTACATTCTTCTTAAATCTAACTTTTTGTTATGGGTTAAGGTGTTGAACTATAATCGCGAAAGCAGATTTGGTT
TTAAATTTAAAGGTAGATTATGGAGATGCTTCAGCAATTCGTTAAGCACGCATATTCATATTTGAACGTAATAGGTTTT
ACCAACTCGTTCAAGTTCATTGATTGTGTTGTGTGAGTTGCTATAGTAAGCATTATCGAACTAATCCTTAATGTCTTTCG
AGACTACATTCATTTGAATGTACTCCTTTGTTTGACCTCAGATCAGGTAGGACTACGCGCTGAACTTAAGCATATCAAT
AAGCGCAGGACAAGAAAATAACCATGATTCCCCTAGTAACGGCGAGTGAAGCGGGAAAAGCTCAAATTTGAAATCTG
GCAAAGTTTTATTCTTTGCCCGAGTTGTAATTTCAAGAAGCTGCTTTGAGTATTGCTACGTCGGTCTAAGTTCCTTGGAA
CAGGACGTCAGAGAGGGTGAGAACCCCGTCTTTGGCCGATGTGCTTTGCCATATAAAGCGCTTTCTAAGAGTCGAGTTG
TTTGGGAATGCAGCTCTAAATGGGTGGTGAATTTCATCTAAAGCTAAATATTGGCGAGAGACCGATAGCGAACAAGTA
GAGTGATCGAAAGATGAAAGAACTTTGAAAAGAGAGTTAAATAGTACGTGAAATTGCTGAAGGGGAAGCATTGGAA
ACCAGTCTTACCTTGGTGAGATCAGCTGTTTACTTGTAGACAGTGCACTCTGAACCTAGGTAGGTCAGCATCAGTTTTCG
GGGACGGAAAAAGAATAAGGGAAAAGTGGCTTTTGGGCTTGCTCAGAAGTGTTATAGCCCTTATTGTAATACGCCCACT
GGGGACTGAGGTCTGCGACTTTGTCAAGGATGCTGACATAATGGTTTTCAATGGCCCGTCTTGAAACACGGACCAAGG
AGTCTAGCATCTATGCGAGTGTTTGGGTGGCTAAACCCATACGCGAAATGAAAGTGAATGCAGGTGGGAACTTTTTGTG
CACCACCGGCCGATCCGGAAGTTTGTCAATGGAAGGATTTGAGCAAGAGCATAGCTGTTGGGACCCGAAAGATGGTGA
ACTATGCCTGAATAGGGCGAAGCCAGAGGAAACTCTGGTGGAGGCTCGTAGCGGTTCTGACGCGCAAATCGATCGTCA
AATTTGGGTATAGGGGCGAAAGACTAATCGAACCATCTAGTAGCTGGTTCCTGCCGAAGTTTCCCTCAGGATAGCAGA
AACTCAGATCAGTTTTATGAGGTAAAGCGAATGATTAGAGGCCTTGGGGAAGTAATTTCCTCAACCTATTCTCAAACTT
TAAATATGTAAGACGCCCTTGTCGCTTAATTGGACGTGGGCTTTCGAATGAGAGTTTCTAGTGGGCCATTTTTGGTAAG
CAGAACTGGCGATGCGGGATGAACCGAACGCGAGGTTAAGGTGCCGGAATGCACGCTCATCAGACACCAGAAAAGGT
GTTAGTTCATCTAGACAGCAGGACGGTGGCCATGGAAGTCGGAATCCGCTAAGGAGTGTGTAACAACTCACCTGCCGA
ATGAACTAGCCCTGAAAATGGATGGCGCTTAAGCGTGCTACCCATACCTCGCCGTCTGGGTTAATTATGAAGCTTAGAC
GAGTAGGCAGGCGTGGAGGTCAGTGACGAAGCCTTGGGCGTAAGCCTGGGTCGAACGGCCTCTAGTGCAGATCTTGGT
GGAAGTAGCAAATATTCAAATGAGAACTTTGAAGACTGAGGTGGGGAAAGGTTCCATGTGAACAGCAGTTGGACATGG
GTTAGTCGATCCTAAGAGATAGGGAAGCTCCGTTTGAAAGTACACGATTCTTCGTGTCACCTATCGAAAGGGAATCCGG
TTAATATTCCGGAACCAGGATGTGGATTCTCCACGGCAACGTAAATGAAGTTGGAGACGTCGGTGGGAGCCCTGGGAA
GAGTTCTCTTTTCTTTTTAACAAACCAATCACCCTGAAATCGGTTTATCCGGAGCTAGGGTATAGTGTTTGGTAGAGCTC
AGCGCCTCTGCTGGGTCCGGTGCGCTCTCAACGGCCCTTGAAAATCCAACGGAAGGAATAGTTTTCACGCCTGGTCGTA
CTCATAACCGCAGCAGGTCTCCAAGGTGAACAGCCTCTAGTTGATAGAACAATGTAGATAAGGGAAGTCGGCAAAATA
GATCCGTAACTTCGGGATAAGGATTGGCTCTAAGGGTTGGGTACGTTGGGCCTTGGTTTTGAACAATTGCTGGACTGGT
TAGGAACTGTCTGACTTCCCCGGAAGACGGATAGATCTTGACTAGACCTTGGCAGTTGGGATGGCCTTGGTAAGGCCTC
TACTTTGTAGAGTGTCCCTCACTGGCGTACGCTTAACAACCAACTTAGAACTGGTACGGACAAGGGGAATCTGACTGTC
TAATTAAAACATAGCATTGCGATGGCCAGAAAGTGGTGTTGACGCAATGTGATTTCTGCCCAGTGCTCTGAATGTCAAA
GTGAAGAAATTCAACCAAGCGCGGGTAAACGGCGGGAGTAACTATGACTCTCTTAAGGTAGCCAAATGCCTCGTCATC
TAATTAGTGACGCGCATGAATGGATTAACGAGATTCCCACTGTCCCTATCTACTATCTAGCGAAACCACAGCCAAGGGA
ACGGGCTTGGCAAAATCAGCGGGGAAAGAAGACCCTGTTGAGCTTGACTCTAGTTTGACATTGTGAAGAGACATAGAG
GGTGTAGCATAAGTGGGAGCTTCGGCGCCAGTGAAATACCACTACCTTTATAGTTTCTTTACTTAATCAATGAAGCGGA
ATTGGAATTCATTTTCCACATTCTAGCGTTAAAGTTCTTTACGAACCGATCCGTGTTGATGACATTGTCAGGTGGGGAGT
TTGGCTGGGGCGGCACATCTGTTAAAAGATAACGCAGGTGTCCTAAGGGGGACTCATCGAGAACAGAAATCTCGAGTA
GAACAAAAGGGTAAAAGTCCCCTTGATTTTGATTTTCAGTGTGAATACAAACCATGAAAGTGTGGCCTATCGATCCTTT
AGTCCCTCGAAATTCGAGGATAGAGGTGCCAGAAAAGTTACCACAGGGATAACTGGCTTGTGGCAGCCAAGCGTTCAT
AGCGACGTTGCTTTTTGATCCTTCGATGTCGGCTCTTCCTATCATACCGAAGCAGAATTCGGTAAGCGTTGGATTGTTCA
CCCACTAATAGGGAACGTGAGCTGGGTTTAGACCGTCGTGAGACAGGTTAGTTTTACCCTACTGATGAATGTCGTCGCA
ATGGTAATTCAACTTAGTACGAGAGGAACCGTTGATTCAGATAATTGGTATTTGCGGCTGCCTGACAAGGCAATGCCGC
GAAGCTATCATCTGCCGGATAACGGCTGAACGCCTCTAAGTCAGAATCCGTGCCAGAAAGCGACGATACCTTATTCCG
CGCATCTTTGGTGCATACAAATAGAGCTTTGCTCCTGTATCGTATAAGGTGGGCGATGGCTAGTAGAACGGAAATGTTT
TATTAGTTTGTCCACGAAATTCCATTGAAAATTTGTGCGGAGTCGAATCCTTTGCATACGACTTAAATGTGGAACGGGG
TATTGTAAGCAGTAGAGTAGCCTTGTTGTTACGATCTGCTGAGATTAAGCCTTTGTTCCCAAGATTTGTTCTATAAGAAC
```

Figure 56
*Schizosaccharomyces pombe* rRNA gene (SEQ ID NO: 103)

```
CATTTAGAGGAAGTAAAAGTCGTAACAAGGTTTCCGTAGGTGAACCTGCGGAAGGATCATTAGAAAAGTTATATGAAA
AGGTTTTAAAAAATTTCCATCTTTTAACTTTTTGGGAATTTTTTTTACCTTTTTCTTCTCTTATCCATTTACCTTTCTGTGA
AAATGTAAAATATTTTCAATTTTGATTTTTTTTTCTTTTTCTTTATATTTTTTTATTAAAAAAAAGTGTTTAGAAAAGAGA
AAAGATGAAAAAAAAAATGAAATTGTAAATATTACGAGTGGATGATTTTTGTTTGGTGTGTTTTTGTTGCATGCCAAGC
ATATCATTACTTTTTTACTATTTTATTTTATTTTATCATTTTTCTATTCTTTCTCTTTTTTTTAATATAAGGAAATTGGAA
AAGAAGCAAAATTAAATTATAAACCTTGAAATTTGTTTTTGAAGTCTGAATTAATTATATCTAATATATAAAATTATTTA
AAACTTTCAGCAACGGATCTCTTGGCTCTCGCATCGATGAAGAACGCAGCGAAATGCGATACGTAATGTGAATTGCAG
AATTCCGTGAATCATCGAATCTTTGAACGCACATTGCGCCTTTGGGTTCTACCAAAGGCATGCCTGTTTGAGTGTCATTA
CAATCTTCTCACAAAAAATGTTTTTTTTTAAATATTTTTGATGAGGTGTTGAACGAAAATTTGTTTTTTTTTTAAAATATA
AATTTAGTTTGAAATCGATTGGTGAAAACAAAAGGAAGATTGAAATTATTTTTCTATGCCTTTTTTCATTTTTTTTCTATT
GAACGTAATAGGTTTTACCACTTTGTTTGATAGAAAAAAAGAAATTAGGAAAGAAAAATAACTAAAAAGTTTTAATCT
CTTTTATATTTGAACCTTAACGAAAAAAAAAGTTATTTTTTTTCACAGTACCTTTTTTATTTGACCTCAAATCAGGTAG
GACTACGCGCTGAACTTAAGCATATCAATAAGCGCAGGAAAAGAAAATAACCATGATTCCCTCAGTAACGGCGAGTGA
AGCGGGAAAAGCTCAAATTTGAAATCTGGCAACATTTCTTTTGTTGTCCGAGTTGTAATTTCAAGAAGCTGCTTTGAGT
GTAGACGATCGGTCTAAGTTCCTTGGAACAGGACGTCAGAGAGGGTGAGAACCCCGTCTTTGGTCGATTGGATATGCC
ATATAAAGCGCTTTCGAAGAGTCGAGTTGTTTGGGAATGCAGCTCTAAATGGGTGGTAAATTTCATCTAAAGCTAAATA
TTGGCGAGAGACCGATAGCGAACAAGTAGAGTGATCGAAAGATGAAAAGAACTTTGAAAAGAGAGTTAAATAGTACG
TGAAATTGCTGAAAGGGAAGCATTGGAAATCAGTCTTACCTGGTGAGATCAGTAGTCTCTTCGCGAGACTATGCACTC
TGAACCTGTGGTAGGTCAGCATCAGTTTTCGGGGGCGGAAAAAGAATAAGGGAAGGTGGCTTTCCGGGTTCTGCCTGG
GGAGTGTTTATAGCCCTTGTTGTAATACGTCCACTGGGGACTGAGGACTGCCGCTTCGTGCCAAGGATGCTGACATAAT
GGTTTTCAATGGCCCGTCTTGAAACACGGACCAAGGAGTCTAGCATCTATGCGAGTGTTTGGGTGATGAAAACCCATCC
GCGAAATGAAAGTGAATGCAGGTGGGAACGCCCTTGTGGCGTGCACCATCGACCGACCCGGAAGTTTGTCAATGGAAG
GGTTTGAGTAAGAGCATAGCTGTTGGGACCCGAAAGATGGTGAACTATGCCTGAATAGGGTGAAGCCAGAGGAAACTC
TGGTGGAGGCTCGTAGAGATTCTGACGTGCAAATCGATCTTCAAATTTGGGTATAGGGGCGAAAGACTAATCGAACCA
TCTAGTAGCTGGTTCCTGCCGAAGTTTCCCTCAGGATAGCAGAAACTCAGATCAGTTTTATGAGGTAAAGCGAATGATT
AGAGGTCTTGGGGAAGGAATTTCCTCAACCTATTCTCAAACTTTAAATATGTAAGACGCCCTTGTCGCTTAATTGGACG
TGGGCCATCGAATGAGAGTTTCTAGTGGGCCATTTTTGGTAAGCAGAACTGGCGATGCGGGATGAACCGAACGTGAGG
TTAAGGTGCCGGAATGTACGCTCATCAGACACCAGAAAAGGTGTTAGTTCATCTAGACAGCAGGACGGTGGCCATGGA
AGTCGGAATCCGCTAAGGAGTGTGTAACAACTCACCTGCCGAATGAACTAGCCCTGAAAATGGATGGCGCTTAAGCGT
ACTACCCATACCTCACCGTCTGGGTTAGCTTTGAGAAGCTCAGACGAGTAGGCAGGCGTGGAGGTTTGTGACGAAGCCT
TGGGCGTGAGCCTGGGTCGAACAGCCTCTAGTGCAGATCTTGGTGGAAGTAGCAAATATTCAAATGAGAACTTTGAAG
ACTGAAGTGGGGAAAGGTTCCATGTGAACAGCAGTTGGACATGGGTTAGTCGATCCTAAGAGATAGGGAAGCTCCGTA
TGAAAGTTGCACGATTTTTCGTGCCTCCTATCGAAAGGGAATCCGGTTAATATTCCGGAACCAGAAGGTGGAATCAACA
CGGCAACGTAAATGAAGTTGGAGACGTCGGCGGGAGCCCTGGGAAGAGTTCTCTTTTCTTTTTAACAAACCATTGAACT
ACCCTGAAATCGGTTTATCCGGAGCTAGGGTATGGTGTTTGGAAGAGTTCAGCGCCTCATGCTGAATCCGGTGCGCTCT
CGACGGCCCTTGAAAATCCAACGGAAGAATGGACCTTCGGGTCCTTGTTTTCACATCTGGTCGTACTCATAACCGCAGC
AGGTCTCCAAGGTGAACAGCCTCTAGTTGATAGAACAATGTAGATAAGGGAAGTCGGCAAAATGGATCCGTAACTTCG
GGATAAGGATTGGCTCTAAGGGTTGGGTACGTTGGGCCTTGGAACCTGAACGGTTGCTGGACTGAGCGTGGACCGATG
TCTTTTCTCGCCTTTCGGGGTGAGAAGGGATGTTGGACCTGCTTGGACCTTGGCGGCCGGGAAGTCCTTGGTCGGGCTTT
TCTCCTTCTCGGGGATTATGCTCTTACTGGCGTACGTTTAACAACCAACTTAGAACTGGTACGGACAAGGGGAATCTGA
CTGTCTAATTAAAACATAGCATTGCGATGGCCAGAAAGTGGTGTTGACGCAATGTGATTTCTGCCCAGTGCTCTGAATG
TCAAAGTGAAGAAATTCAACCAAGCGCGGGTAAACGGCGGGAGTAACTATGACTCTCTTAAGGTAGCCAAATGCCTCG
TCATCTAACTAGTGACGCGCATGAATGGATTAACGAGATTCCCACTGTCCCTATCTACTATCTAGCGAAACCACAGCCT
GGGGAACGGGCCAGGCAAAATCAGCGGGGAAAGAAGACCCTGTTGAGCTTGACTCTAGTTTGACATTGTGAAGAGACA
TAGAGGGTGTAGGATAAGTGGGAGTATGTTTCGCATACGCCGGTGAAATACCACTACCTTTATCGTTTCTTTACTTAA
TCAATGAAGCGGAATTGGGATTTATTTCCCATATTCTAGCGTTAAAGTTTCTTCGCGAACTGATCCGCGTTGATGACATT
GTCAGGTGGGGAGTTTGGCTGGGGCGGCACATCTGTTAAAAGATAACGCAGGTGTCCTAAGGGGGACTCATCGAGAAC
AGAAATCTCGAGTAGAATAAAAGGGTAAAAGTCCCCTTGATTTTGATTTTCAGTGTGAATACAAACCATGAAAGTGTG
GCCTATCGATCCTTTGTTCCCTCGAAATTTGAGGACAGAGGTGCCAGAAAAGTTACCACAGGGATAACTGGCTTGTGGC
AGCCAAGCGTTCATAGCGACGTTGCTTTTTGATTCTTCGATGTCGGCTCTTCCTATCATACCGAAGCAGAATTCGGTAAG
CGTTGGATTGTTCACCCACTAATAGGGAACGTGAGCTGGGTTTAGACCGTCGTGAGACAGGTTAGTTTTACCCTACTGA
TGAAGTGTCGTCGCAATGGTAATTCAACTTAGTACGAGAGGAACCGTTGATTCAGATCATTGGTATTTGCGGCTGCCTG
ACAAGGCAATGCCGCGGAGCTATCATCTGCCGGATAACGGCTGAACGCCTCTAAGCCAGAATCCGTGCCAGAAAGCGA
CGATTTTTTGGTCCGCATGATTTATATGTATAAAAATAGAGGTAGGACTTGTTCCTACTCTCCTGTATCGTAGAAGATGG
GCGATGGTTGATGAAACGGAAGTGTTTTATTGACTTGTCCATGAAATTCCATTGAAATCTTGTGCGGAATCGAATCCAT
TGCATACGACTTTAATGTGGAACGGGGTATTGTAAGCAGTAGAGTAGCCTTGTTGTTACGATCTGCTGAGATTAAGCCT
TTGTTCCCAAGATTTGTTCCATTAAG
```

Figure 57

*Sclerotinia sclerotiorum* rRNA gene (SEQ ID NO: 104)

```
TTAGAGGAAGTAAAAGTCGTAACAAGGTTTCCGTAGGTGAACCTGCGGAAGGATCATTACAGAGTTCATGCCCGAAAG
GGTAGACCTCCCACCCTTGTGTATTATTACTTTGTTGCTTTGGCGAGCTGCTCTTCGGGGCCTTGTATGCTCGCCAGAGA
ATATCAAAACTCTTTTTATTAATGTCGTCTGAGTACTATATAATAGTTAAAACTTTCAACAACGGATCTCTTGGTTCTGG
CATCGATGAAGAACGCAGCGAAATGCGATAAGTAATGTGAATTGCAGAATTCAGTGAATCATCGAATCTTTGAACGCA
CATTGCGCCCCTTGGTATTCCGGGGGGCATGCCTGTTCGAGCGTCATTTCAACCCTCAAGCTCAGCTTGGTATTGAGTCC
ATGTCAGTAATGGCAGGCTCTAAAATCAGTGGCGGCGCCGCTGGGTCCTGAACGTAGTAATATCTCTCGTTACAGGTTC
TCGGTGTGCTTCTGCCAAAACCCAAATTTTCTATGGTTGACCTCGGATCAGGTAGGGATACCCGCTGAACTTAAGCATA
TCAATAAGCGGAGGAAAAGAAACCAACAGGGATTACCTCAGTAACGGCGAGTGAAGCGGTAAAAGCTCAAATTTGAA
ATCTGGCTCTTTCAGAGTCCGAGTTGTAATTTGTAGAAGATGCTTCGGGTGTGGTTCCGGTCTAAGTTCCTTGGAACAGG
ACGTCATAGAGGGTGAGAATCCCGTATGTGACTGGATACCTATGCTCATGTGAAGCTCTTTCGACGAGTCGAGTTGTTT
GGGAATGCAGCTCAAAATGGGTGGTATATTTCATCTAAAGCTAAATATTGGCCAGAGACCGATAGCGCACAAGTAGAG
TGATCGAAAGATGAAAAGCACTTTGGAAAGAGAGTTAAACAGTACGTGAAATTGTTGAAAGGGAAGCGCTTGCAATCA
GACTTGCACTTGGTGTTCATCAGGGTTTCGTGCCCTGTGTACTTCATCAAGTTCAGGCCAGCATCAGTTTGAGTGGTTAG
ATAAAGGCTTGGAGAATGTGGCCCTCTTCGGGGGGTGTTATAGCTCCAGGTGCAATGTAGCCTACTTGGACTGAGGACC
GCGCTTCGGCTAGGATGCTGGCGTAATGGTTGTAAGCGACCCGTCTTGAAACACGGACCAAGGAGTGTACCTAATATG
CGAGTGTTTGGGTGTTAAACCCATACGCGTAATGAAAGTGAACGCTGGTGAGAACCCTTAAGGGTGCATCATCGACCG
ATCTTGATGTCTTCGGATGGATTTGAGTAAGAGCATATTGGGTGCGACCCGAAAGATGATGATCTATACGTGAATAGGG
TGAAGCCAGAGGGAAACTCTGGTGGAGGCTCGCAGCGGTTCTGACGTGCAAATCGATCGTCAAATTTGCGTATAGGGGC
GAAAGACTAATCGAATCATTAAGGAATAGACCAAGCTCTAGGTGATTGAGAAACCTCCTTTGGGGTATTAGTCCTGGA
GACAGGGCGACATTGTCAAATTGTTCGGGGACCACCTGTTAAATTATATGCTACTGCAGCAGTGCTGAAAGGCCTGTGA
GCACTGAGGGTAACGCCCTCAGGGATGGTAATAACGCATATATAGGGTATATCCGCAGCGAAGTTCTAAGGCTTTCGA
GCTATGAATCGCGTTCACAGACTAGACGGCAATGGGCTCCTCGCGGGGCTTAAGATATAGTCGAACCCCTCAGAGATG
AGGATGGAATCAATGCTAGTAGCTGGTTCCTGCCGAAGTTTCCCTCAGGATAGCAGTGTTGTTTTCAGTTTTATGAGGT
AAAGCGAATGATTAGAGGCCTTGGGGTTGAAACAACCTTAACCTATTCTCAAACTTTAAATATGTAAGAAGTCCTTGTT
ACTTAATTGAACGTGGACATTCGAATGTACCAACACTAGTGGGCCATTTTTGGTAAGCAGAACTGGCGATGCGGGATG
AACCGAACGCGAGGTTAAGGTGCCGGAATATACGCTCATCAGACACCACAAAAGGTGTTAGTTCATCTAGACAGCAGG
ACGGTGGCCATGGAAGTCGGAATCCGCTAAGGAATGTGTAACAACTCACCTGCCGAATGAACTAGCCCTGAAAATGGA
TGGCGCTTAAGCGTATTACCCATACCTCGCCGCCAGGGTAGAAACTATGCCCTGGCGAGTAGGCAGGCGTGGAGGTTG
TGACGAAGCCTTGGGAGTGATCCCGGGTAGAACAGCCTCTAGTGCAGATCTTGGTGGTAGTAGCAAATACTCAAATGA
GAACTTTGAGGACTGAAGTGGGGAAAGGTTCCATGTGAACAGCAGTTGGACATGGGTTAGTCGATCCTAAGAGATAGG
GAAACTCCGTTTTAAAGTGCGCACTTGTGCGCCGTCCTCGAAAGGGAAACCGGTTAATATTCCGGTACCTGGATTTGG
ATTCTCCACGGCAACGTAACTGAACGCGGAGACGACGGCGGGGCCCCGGGAAGAGTTCTCTTTTCTTCTTAACAGCCT
ATCACCCTGAAATCGGTTTGTCCGGAGCTAGGGTTTAACGGTTGGTAGAGCTCGACACCTCTGTCGGGTCCGGTGCGCT
CTCGACGTCCCTTGAAAATCCGCGGGAAGGAATAGCTTTCAAGCCAGGTCGTACTCATAACCGCATGCAGGTGCTCCA
AGGTGAACAGCCTCTAGTTGATAGAACAATGTAGATAAGGGAAGTCGGCAAAATAGATCCGTAACTTCGGGAAAAGG
ATTGGCTCTAAGGGTTGGGTACGTTGGGCCATTAGGGGATGCTCTTGGAGCAGAGGAGCACTAGCTTCACGGCCGGCG
CTCTTCAGCATCGAGGGTTTGACGCTTTTGGCAGGCTTCGGTCGTCCGGCGTACAATTAACAACCAACTTAGAACTGGT
ACGGACAAGGGGAATCTGACTGTCTAATTAAAACATAGCATTGCGATGGCCAGAAAGTGGTGTTGACGCAATGTGATT
TCTGCCCAGTGCTCTGAATGTCAAAGTGAAGTAATTCAACCAAGCGCGGGTAAACGGCGGGAGTAACTATGACTCAAC
CCTAAGAGGGTCGTAAGAGGGGATGCGAATAGCATTCCTTTAGTGATGAGATCGCAACACTGTCAAATTGCGGGGAGT
TCCTAAAGCTCAGGCTACCGCCTCAGGTGCTGAAAAGCCCTGAAGGCACCAAGGTTAGCAACCTTGGGTATGGTAATA
ACGCCTGTAGATACTACAATGGATGATCCGCAGCCAAGCTCTAACAATCTTTTCACGATTCACGAGCGGGGTTCAACGA
CTAGACGGCAGTGGGCCTGCAAAACAGGTTTAAGATATAGTCTGCGCCTAGGGAAAAATCCCAAGGAAATAAGTGCTC
TTAAGGTAGCCAAATGCCTCGTCATCTAATTAGTGACGCGCATGAATGGATTAACGAGATTCCCACTGTCCCTATCTAC
TATCTAGCGAAACCACAGCCAAGGGAACGGGCTTGGCAGAATCAGCGGGGAAAGAAGACCCTGTTGAGCTTGACTCTA
GTTTGACATTGTGAAAAGACATAGGGGGTGTAGAATAGGTGGGAGCGCAAGCGCCGGTGAAATACCACTACCCTTATC
GTTTTTTTACTTATTCAATAAAGCGGAACTGGGTGTCAAAGCCCAACTTCTAGCATTAAGGTCCTTCGCGGGCTGATCCG
GGTTGAAGACATTGTCAGGTGGGGAGTTTGGCTGGGGCGGCACATCTGTTAAACCATAACGCAGGTGTCCTAAGGGGG
ACTCATGGAGAACAGAAATCTCCAGTAGAACAAAAGGGTAAAAGTCCCCTTGATTTTGATTTTCAGTGTGAATACAAA
CCATGAAAGTGTGGCCTATCGATCCTTTAGTCCCTCGAAATTTGAGGCTAGAGGTGCCAGAAAAGTTACCACAGGGATA
ACTGGCTTGTGGCAGCCAAGCGTTCATAGCGACGTTGCTTTTTGATCCTTCGATGTCGGCTCTTCCTATCATACCGAAGC
AGAATTCGGTAAGCGTTGGATTGTTCACCCACTAGACCTTATTGGTGGGAAAAAGATCTTATTGATCACTTAGTCGAGT
CACCCACAACTATTGCGGGCGGTGACCGGCGAGACAACCTGGTTCGGGGGAGGCTGTAAAATGCTAATCTCGAGTGCA
GTCTGCTGGGAGTGATCCCTACAAGACGCACGTAACGCGCGGAAAGGTGTCGGTTGCCTCTTTTACAGAGGGAGCTTAT
GGGACGTGCTAAACCTATCCGAAAGGATAACACTGATCTAAGGGCCCGCAGCCTGGAGTTTAGTGTGACCGTCAAGAG
CCTGGGAGGAAATGCCCAAGGTCAGGTTGGTATATTAATGAATAGGGAACGTGAGCTGGGTTTAGACCGTCGTGAGAC
AGGTTAGTTTTACCCTACTGATGACCGTCGCCGCAATGGTAATTCAGCTTAGTACGAGAGGAACCGCTGATTCAGATAA
TTGGTTTTTGCGGCTGTCTGACAAGGCAGTGCCGCGAAGCTACCATCTGCTGGATAATGGCTGAACGCCTCTAAGTCAG
AATCCATGCCAGAAAGCGGTGATTTATACCCACACATCGTAGTCGGATACGAATAGGCCTTTGGCCCTGAATCTTAGCT
GGCTGGTAACGATCCTATTGAAGAAACTCTTTAGGATTAACTGGCGTCTTGCAATTTTACAATGCGTGGGGTTGAATCC
TTTGCATACGACTTAATTGTGCTACACGGTCCTGTAAGTAGTAGAGTAGCCTTGTTGTTACGATCTACTGAGGGTAAGC
CGTCTCGTAGCCTAGATTTGATTTTCAAT
```

Figure 58
*Stagonospora nodorum* rRNA gene (SEQ ID NO: 105)

```
TTTAGAGGAAGTAAAAGTCGTAACAAGGTTTCCGTAGGTGAACCTGCGGAAGGATCATTACACTCAGTAGTTTACTACT
GTAAAAGGGGCTGTTAGTCTGTATAGCGCAAGCTGATGAGCAGCTGGCCTCTTTTATCCACCCTTGTCTTTTGCGTACCC
ACGTTTCCTCGGCAGGCTTGCCTGCCGGTTGGACAAATTTATAACCTTTTTAATTTTCAATCAGCGTCTGAAAAACTTAA
TAATTACAACTTTCAACAACGGATCTCTTGGTTCTGGCATCGATGAAGAACGCAGCGAAATGCGATAAGTAGTGTGAAT
TGCAGAATTCAGTGAATCATCGAATCTTTGAACGCACATTGCGCCCCTTGGTATTCCATGGGGCATGCCTGTTCGAGCG
TCATTTGTACCCTCAAGCTCTGCTTGGTGTTGGGTGTTTGTCCTCTCCCTAGTGTTTGGACTCGCCTTAAAATAATTGGCA
GCCAGTGTTTTGGTATTGAAGCGCAGCACAAGTCGCGATTCGTAACAAACACTTGCGTCCACAAGCCTTTTTAACTTTT
GACCTCGGATCAGGTAGGGATACCCGCTGAACTTAAGCATATCAATAAGCGGAGGAAAAGAAACCAACAGGGATTGC
CCTAGTAACGGCGAGTGAAGCGGCAACAGCTCAAATTTGAAATCTGGCTCTTTCAGAGTCCGAGTTGTAATTTGCAGAG
GGCGCTTTGGCGTTGGCAGCGGTCCAAGTTCTTTGGAACAGGACGTCACAGAGGGTGAGAATCCCGTACGTGGTCGCT
AGCCTTCGCCGTGTAAAGCCCCTTCGACGAGTCGAGTTGTTTGGGAATGCAGCTCTAAATGGGAGGTAAATTTCTTCTA
AAGCTAAATACTGGCCAGAGACCGATAGCGCACAAGTAGAGTGATCGAAAGATGAAAAGCACTTTGGAAAGAGAGTC
AAATAGCACGTGAAATTGTTGAAAGGGAAGCGCTTGCAGCCAGACTTGCCTGTAGTTGCTTATCTGGACTTTTGTCCAG
TGCACTCTTCTGCGGGCAGGCCAGCATCAGTTTGGGCGGTTGGATAAAGGTCTCTGTCATGTACCTCCTTTCGGGGAGG
CCTTATAGGGGAGACGACATGCAACCAGCCTGGACTGAGGTCCGCGCATCTGCTAGGATGCTGGCGTAATGGCTGTAA
GCGGCCCGTCTTGAAACACGGACCAAGGAGTCTAACATCTATGCGAGTGTTTGGGTGTCAAGCCCAGACGCGTAATGA
AAGTGAACGGAGGTGGGAACCTTTTAGGTGCACCATCGACCGATCCTGATGTCTTCGGAAGGATTTGAGTAAGAGCAT
AGCTGTTGGGACCCGAAAGATGGTGAACTATGCTTGAATAGGGTGAAGCCAGAGGAAACTCTGGTGGAGGCTCGCAGC
GGTTCTGACGTGCAAATCGATCGTCAAATTTGGGCATAGGGGCGAAAGACTAATCGAACTATCTAGTAGCTGGTTCCTG
CCGAAGTTTCCCTCAGGATAGCAGTAACGTATTCAGTTTTATGAGGTAAAGCGAATGATTAGAGGCCTGGGGGTTGAA
ACAACCTTCACCTATTCTCAAACTTTAAATATGTAAGAAGTCCTTGTTACTTGATTGAACGTGGACACTTGAATGTACCG
TTACTAGTGGGCCATTTTTGGTAAGCAGAACTGGCGATGCGGGATGAACCGAACGCGGGGTTAAGGTGCCAGAATATA
CGCTCATCAGACACCACAAAAGGTGTTAGTTCATCTAGACAGCAGGACGGTGGCCATGGAAGTCGGAATCCGCTAAGG
AGTGTGTAACAACTCACCTGCCGAATGAACTAGCCCTGAAAATGGATGGCGCTCAAGCGTATTACCCATACCCCGCCG
CCGGGGCAGAATTTATGCCCCGGCGAGTAGGCAGGCGTGGAGGCTCGTGACGAAGCCTTGGGGGTGACCCCGGGTCGA
ACGGCCTCTAGTGCAGATCTTGGTGGTAGTAGCAAATACTCAAATGAGAACTTTGAGGACTGAAGTGGGGAAAGGTTC
CGTGTGAACAGCAGTTGGACACGGGTTAGTCGATCCTAAGAGATAGGGTAGTTCCGTTTTAATGTTGGCGCTTGCGCCA
CGCCCTCGAAAGGGAAGCCGGTTAACATTCCGGCACCTGGATGTAGATTCTCCGCGGCAACGCAACTGAGAGCGGAGA
CCTTGGCGGGAGCCCCAAGAAGAGTTCTCTTTTCTTCTTAACGGTCTGTCACCCTGAAATCGGTTTGTCCGGAGCTAGG
GTTCAATGGCCGGAAGAGCGCTGCACTTTTGTGGCGTTTGGTGCGCTCCCGACGAGCCTTGAAAATCCGCTTGAAGAAA
TAGTTTTTACGCCAGGTCGTACTCATAACCGCAGCAGGTCTCCAAGGTGAAAAGCCTCTAGTTGATAGAACAATGTAGA
TAAGGGAAGTCGGCAAAATAGATCCGTAACTTCGGGAAAAGGATTGGCTCTAAGGGTTGGGTACGTTGGGCCTTGGAG
AGAAGCCTCTGGCGCAGAAGGGCACTAGCCGCAAGGTGGGCGCCTTTCAGCGCTGGGGTGCGGGCATCCTTGGCAGGC
TTCGGCCGTCCGGCGTACGTTTAACAACCAACTTAGAACTGGTACGGACAAGGGGAATCTGACTGTCTAATTAAAACAT
AGCATTGCGATGGCCAGAAAGTGGTGTTGACGCAATGTGATTTCTGCCCAGTGCTCTGAATGTCAAAGCGAAGAGATTC
GACCAAGCGCGGGTAAACGGCGGGAGTAACTATGACTCTCTTAAGGTAGCCAAATGCCTCGTCATCTAATTAGTGACG
CGCATGAATGGATTAACGAGATTCCCACTGTCCCTATCTACTATCTAGCGAAACCACAGCCAAGGGAACGGGCTTGGC
CAAATCAGCGGGGAAAGAAGACCCTGTTGAGCTTGACTCTAGTTTGACATTGTGAAAAGACATAGGGGGTGTAGAATA
GGTGGGAGCTTCGGCGCCGGTGAAATACCACTACCCTTATCGTTTTTTTACTTATTCGATGAAGCGGAGCTGGGCCTCA
CCGCCCAACTTCTAGCGTTAAGGTCCTTCGTGGGCCGATCCGGGTTGAAGACATTGTCAGGTGGGGAGTTTGGCTGGGG
CGGCACATCTGTTAAACCATAACGCAGGTGTCCTAAGGGGGACTCATGGAGAACAGAAATCTCCAGTAGAGCAAAAGG
GCAAAAGTCCCCTTGATTTTGATTTTCAGTGTGAATACAAACCATGAAAGTGTGGCCTATCGATCCTTTAGTCCCTCGAA
ATTTGAGGCTAGAGGTGCCAGAAAAGTTACCACAGGGATAACTGGCTTGTGGCAGCCAAGCGTTCATAGCGACGTTGC
TTTTTGATCCTTCGATGTCGGCTCTTCCTATCATACCGAAGCAGAATTCGTAAGCGTTGGATTGTTCACCCACTAATAG
GGAACGTGAGCTGGGTTTAGACCGTCGTGAGACAGGTTAGTTTTACCCTACTGATGACCTTGCCCCAATGGTAATACCG
CTTAGTACGAGAGGAACCGCGGTTTCAGATAATTGGTTTTTGCGGCTGTCTGACCAGGCATTGCCGCGAAGCTACCATC
TGCTGGATTATGGCTGAACGCCTCTAAGTCAGAATCCATGCCAGAACGGGGTGATTTCCGCCTGCACCAGTCGGATACG
AATAGGCCTTTGGCCCAGAACCTTACCAGATCAGCGTTGGCAGTCTCATTGAAATTGGGGCTGCTAGCTGGTGTATTGC
AATTGTACAGTGCGCAGGATTGAATCCTTTGCAGACGACTTAGTTGTCTAGCCGGGTCGTGTAAGTAGTCGAGTAGCCT
TGTTGTTACGAGCTACTGAGCGTAAGCCCGATGCTAGCTTGGTTGAATATGGGAAT
```

Figure 59
*Umbilicaria esculenta* rRNA gene (SEQ ID NO: 106)

```
CTTGGTCATTTAGAGGAAGTAAAAGTCGTAACAAGGTTTCCGTAGGTGAACCTGCGGAAGGATCATTAAAGAGATAGG
GCCCTCTCTGGGCCCGACCCTCCAACCCTTTGTCTACCTTACCTTCGTTGCTTTGGCGGGCCCGCTGGGGATGACCCACC
GCCGGCGCCAGCCGGTGAGCGCCCGCCGGAGGCCATCAAAACTCCGTCTGTCGGTGCTGTCTGAGTACCCCACAATCG
TTAAAACTTTCAACAACGGATCTCTTGGTTCTGGCATCGATGAAGAACGCAGCGAAATGCGATAAGTAATGTGAATTGC
AGAATTCAGTGAATCATCGAATCTTTGAACGCACATTGCGCCCCTGGTATTCCGGGGGGCATGCCTGTTCGAGCGTCA
TTACAACCCTCAAGCTCTGCTTGGTATTGGGCTTTCACCCCTCCCCGGGGGGGCGTGCCTGAAAGTGAGTGGCGGTGC
AGCCTGACTTCAAGCGTAGTAACTTCAAAACCCGCTTCGGAAGCCTTTCAGGTTGGGCCGGCCAGACAGCCCAACATTA
TTTCTATGGTTGACCTCGGATCAGGTAGGGATACCCGCTGAACTTAAGCATATCAATAAGCGGAGGAAAAGAAACCAA
CAGGGATTGCCTCAGTAACGGCGAGTGAAGCGGCAACAGCTCAAATTTGAAATCTGGCCCCCCGGGGTCCGAGTTGT
AATTTGTAGAGGATGCTTCGGGTGCGGCGCCGGTCTAAGTTCCTTGGAACGGGACGTCATAGAGGGTGAGAATCCCGT
ATGTGACCGGTGACCCAGCCCGTGTGAAGCTCCTTCGACGAGTCGAGTTGTTTGGGAATGCAGCTCTAAATGGGTGGTA
AATTTCATCTAAAGCTAAATACCGGCCAGAGACCGATAGCGCACAAGTAGAGTGATCGAAAGATGAAAAGCACTTTGG
AAAGAGAGTTAAAAAGTACGTGAAATTGTTGAAAGGGAAGCGCTTGCGACCAGACTTGCTCGGGGGTGATCAGCCGTC
CTTCTGGGCGGCGCACTCGCCCACGATCGGGCCAGCATCGGTTCAGGCGGCCGGATAAAGGCCCCGGGAACGTGGCTC
CCTCCGGGGAGTGTTACAGCCCGGGGTGCAATGCGGCCAGCCCGGACCGAGGACCGCGCTTCGGCTAGGATGCTGGC
GTAATGGTCGCAAGCGACCCGTCTTGAAACACGGACCAAGGAGTCTAACATCTATGCGAGTGTTTGGGTGTCAAACCC
ATGCGCGCAATGAAAGTGAACGGAGGTGGGAACCCTCCAGGGTGCACCATCGACCGATCCTGATGTCTTCGGATGGAT
TTGAGTAAGAGCATAGCTGTTGGGACCCGAAAGATGGTGAACTATGCCTGAATAGGGTGAAGCCAGAGGAAACTCTGG
TGGAGGCTCGCAGCGGTTCTGACGTGCAAATCGATCGTCAAATTTGGGTATAGGGGCGAAAGACTAATCGAACCATCT
AGTAGCTGGTTCCTGCCGAAGTTTCCCTCAGGATAGCAGTAACGTTTTCAGTTTTATGAGGTAAAGCGAATGATTAGAG
GCCTTGGGGTTGAAACAACCTTAACCTATTCTCAAACTTTAAATATGTAAGAAGTCCTCGTTGCTCATTTGAACGTGGA
CATTTGAATGCACCGTTACTAGTGGGCCATTTTTGGTAAGCAGAACTGGCGATGCGGGATGAACCGAACGCGAGGTTA
AGGTGCCGGAATGCACGCTCATCAGACACCACAAAAGGTGTTAGTTCATCTAGACAGCCGGACGGTGGCCATGGAAGT
CGGAACCCGCTAAGGAGTGTGTAACAACTCACCGGCCGAATGAACTAGCCCTGAAAATGGATGGCGCTCAAGCGTGCT
ACCCATACCTCGCCGCCAGGGTAGAAACGATGCCCTGGCGAGTAGGCAGGCGTGGGGGTCGGTGACGAAGCCTCGGG
GGTGATCCCGGGTCGAACGGCCCCTAATGCAGATCTTGGTGGTAGTAGCAAATACTCAAATGAGAACTTTGAGGACTG
AAGTGGGGAAAGGTTCCATGTGAACAGCAGTTGGACATGGGTTAGTCGATCCTAAGAGATAGGGAAACTCCGTTTTAA
AGCGCGCACTCGTGCGCCGTCCCTCGAAAGGGAAGCCGGTCAACATTCCGGCACCTGGATGTGGATTCTCCACGGCAA
AGTAACCGAACGCGGACACGTCGGCGGGGCCCCGGGAAGAGTTCTCTTTTCTTCTTAACGGCCCATCACCCTGAAATC
GGTTTGTCCGGAGCTAGGGTTTAACGGCCGGTAGAGCCCCACACCTTTGTGGGGTCCGGTGCGCTCCCGACGACCCTTG
AAAATCCGCGGGAAGGAATAGTTTTCACGCCAGGTCGTACTCATAACCGCAGCAGGTCTCCAAGGTGAAAAGCCTCTA
GTTGATAGAACAATGTAGATAAGGGAAGTCGGCAAAATAGATCCGTAACTTCGGGAAAAGGATTGGCTCTAAGGGTTG
GGTGCGTTGGGCCTTGGGGGGATGCCCCCGGAGCAGGTGGGCACTAGCCGGGCAACCGGCCGGCGCCCTCCAGCATCG
GGCGGCGGACGCCCGTGGCAGGTTTCGGCCGTCCGGCGCACGCTTAACGACCGACTTAGAACTGGTACGGACAAGGGG
AATCTGACTGTCTAATTAAAACATAGCATTGCGATGGCCAGAAAGTGGTGTTGACGCAATGTGATTTCTGCCCAGTGCT
CTGAATGTCAAAGTGAAGAAATTCAAATAAGCGCGGGTAAACGGCGGGAGTAACTATGACTCTCTTAAGGTAGCCAAA
TGCCTCGTCATCTAATTAGTGACGCGCATGAATGGATTAACGAGATTCCCACTGTCCCTATCTACTATCTAGCGAAACC
ACAGCCAAGGGAACGGGCTTGGCGGAATCAGCGGGGAAAGAAGACCCTGTTGAGCTTGACTCTAGTTTGACATTGTGA
AAAGACATAGGGGGTGTAGAATAGGTGGGAGCTTCGGCGCCGGTGAAATACCACTACCCTTATCGTTTTTTACTTATT
CAATGAAGCGGAACTGGGTTTTACCGCCCAACTTCTGGCGTCAAGGTCCCTCGCGGGCCGATCCGGGTTGAAGACATTG
TCAGGTGGGGAGTTTGGCTGGGGCGGCACATCTGTTAAACCATAACGCAGGTGTCCTAAGGGGGACTCATGGAGAACA
GAAATCTCCAGTGGAACAAAAGGGTAAAAGTCCCCTTGATTTTGATTTTCAGTGTGAATACAAACCATGAAAGTGTGGC
CTATCGATCCTTTAGTCCCTCGAAATTTGAGGCTAGAGGTGCCAGAAAAGTTACCACAGGGATAACTGGCTTGTGGCAG
CCAAGCGTTCATAGCGACGTTGCTTTTTGATCCTTCGATGTCGGCTCTTCCTATCATACCGAAGCAGAATTCGGTAAGCG
TTGGATTGTTCACCCACTAATAGGGAACGTGAGCTGGGTTTAGACCGTCGTGAGACAGGTTAGTTTTACCCTACTGATG
ACCGTCACCGCAACGGTAATTCAACTTAGTACGAGAGGAACCGTTGATTCAGATAATTGGTCTTTGCGGCTGTCTGACC
AGGCAGTGCCGCGAAGCTACCCTTCTTT
```

Figure 60
*Uncinocarpus reesii* rRNA gene (SEQ ID NO: 107)

```
TTGGTCATTTAGAGGAAGTAAAAGTCGTAACAAGGTTTCCGTAGGTGAACCTGCGGAAGGATCATTACAGTGGTTTCGG
GCCGTGCCGTTTCCCCGCTCGGGGGGCGCGCGGCCTGCACCTCCCACCCATGTTTACTTGAAACCCTTTGTTGCCTTGGC
AGGACTGCCGCTTGTCGGCTGCCGGGGACCTGCAGCCATGCAGCCCGGGCGAGTGCCTGCCAGAGGACTATTTGAACC
CTAAGTGAAGATTGACAGTCTGAGTATTCTAGCAAGAATAAGTTAAAACTTTCAACAACGGATCTCTTGGTTCCAGCAT
CGATGAAGAACGCAGCGAAATGCGATAAGTAATGTGAATTGCAGAATTCCGTGAATCATCGAATCTTTGAACGCACAT
TGCGCCCCCTGGTATTCCGGGGGGCATGCCTGTCCGAGCGTCATTGCAAATCCTTCAAGCACGGCTTGTGTGTTGGACT
GCGTCCCCGATGGTGTGGACGAGTCTGAAATGCAGTGGCGGCGCCGAGTTCCTGGTGTCTGAGTGTATGGGAAATCTCT
CTTTGCTCAAAGACCCGATCGGTACCGACCGTAGATCTTTCTTTCCGGTTTGACCTCGGATCAGGTAGGAGTACCCGCT
GAACTTAAGCATATCAATAAGCGGAGGAAAAGAAACCAACAGGGATTGCCTCAGTAACGGCGAGTGAAGCGGCAAAA
GCTCAAATTTGAAATCTGGCCCCGTCAGGGGTCCGAGTTGTAATTTGGAGAGGATACTTCGGGTGTGGCCGTGGCTTAA
GTCCCTTGGAACAGGGCGTCATAGAGGGTGAGAATCCCGTCTTGAGTCACCGGTCCACGCCCATGCGAAGTTCCTTCGA
CGAGTCGAGTTGTTTGGGAATGCAGCTCTAAGTGGGTGGTAAATTTCATCTAAAGCTAAATATTGGCTGGAGACCGATA
GCGCACAAGTAGAGTGATCGAAAGGTTAAAAGCACCTTGAAAAGGGAGTTAAATAGCACGTGAAATTGTTGAAAGGG
AAGCGCTTGCAACCAGACTCGAGCGCAGGGTTCAGCGGGCATGCGTGCCCGTGTACTCCCTGTGCTCGGGCCAGCATC
AGTTTCGGCGGTTGGTTAAAGGCCTCTGGAATGTATCGTCCTCCGGGACGTCTTATAGCCAGAGGCGCAATGCGGCCAG
CCGGGACTGAGGAACGCGCTTCGGCACGGATGCTGGCATAATGGTTGTAAGCGGCCCGTCTTGAAACACGGACCAAGG
AGTCTAACATCCACGCGAGTGTTCGGGTGTCAAACCCGTGCGCGCAGTGAAAGCGAACGGAGGTGGGAGCCCATCAGG
GTGCACCATCGACCGATCCTGAAGTCTTCGGATGGATTTGAGTAAGAGCGTGGCTGTTGGGACCCGAAAGATGGTGAA
CTATGCCTGAATAGGGTGAAGCCAGAGGAAACTCTGGTGGAGGCTCGCAGCGGTTCTGACGTGCAAATCGATCGTCAA
ATTTGGGTATAGGGGCGAAAGACTAATCGAACCATCTGGTAGCTGGTTCCTGCCGAAGTTTCCCTCAGGATAGCAGTAA
CGTTTTCAGTTTTATGAGGTAAAGCGAATGATTAGAGGCCTTGGGGTTGAAACAACCTTAACCTATTCTCAAACTTTAA
ATATGTAAGAAGCCCTTGTTACTTAAGTGAACGTGGGCATTAGAATGGATCGTTACTAGTGGGCCATTTTTGGTAAGCA
GAACCTGGCGATGCGGGATGAACCGAACGCGAGGTTAAGGTGCCGGAAATGCACGCTCATCAGACACCACAAAAGGT
GTTAGTTCATCTAGACAGCCCGACGGGTGGCCATGGAAGTCGGAATCCGCTAAGGAGTGTGTAACAACTCCCGGGCCG
AAATGAACTAGCCCCTGAAAATGGATGGCGCTCAAGCGTGCTACCCCCATACCTCGCCGTCCGGGTAGAAACGATGCCC
CGACGAGTAGGCAGGCGTGGAGGTTTGTGACGAAGCCTTGGGAGTGATCCCGGGTCGAACAGCCTCTAGTGCAGATCT
TGGTGGTAGTAGCAAATACTCAAATGAGAACTTTGAGGACTGAAGTGGGGAAAGGTTCCATGTGAACAGCAGTTGGAC
ATGGGTTAGTCGATCCTAAGACATAGGGTAGTTCCGTTTGAAAGCGCGCCCTCGTGCGCCGTTCGTCGAAAGGGAAGCC
GGTCAATATTCCGGCACCTGGATGTGGATTCTCCACGGCAACGTAACTGAACGCGGAGACGTCGGCAGGAGTCCTGGG
AAGAGTTCTCTTTTCTTCTTGACGGCCTATCACCCTGAAATCGGTTTGGTCCGGGGCTTGGGGTTTCATGGCAGGCAGAC
CCCCCGCACCTGTGTGGGGTCCCGGGACACTCCTGACGACCCCTAGAAAAACCGCGGGAAGGGAATAGTTTTCACGCC
AGGTCGTACTCATAAACCGCAGCAGGTCTCCAAGGTGAAAAAGCCTCTAGTTGATAGAACAATGTAGATAAGGGAAGT
CGGCAAAATAGATCCGTAACTTCGGGAAAAGGATTGGCTCTAAGGGTCGGGCGCGTTGGGCCTTGGGGGGAAAGCCTCT
GGAGCAGAAGGGCACTAGCCGGGCAACCGGCGGGCGCCTTTCAGCATCGGGGTGCGGACGCCCTTGGCAGGCTTCGGC
CGTTCCGGCGCGCGATTAACGACCAACTTAGAACTGGTACGGACAAGGGGAATCTGACTGTCTAATTAAAACATAGCAT
TGCGATGGCCAGAAAGTGGTGTTGACGCAATGTGATTTCTGCCCAGTGCTCTGAATGTCAAAGTGAAGAAATTCAACCA
AGCGCGGGTAAACGGCGGGAGTAACTATGACTCTCTTAAGGTAGCCAAATGCCTCGTCATCTAATTAGTGACGCGCAT
GAATGGATTAACGAGATTCCCACTGTCCCTATCTACTATCTAGCGAAACCACAGCCAAGGGAACGGGCTTGGCAGAAT
CAGCGGGGAAAGAAGACCCTGTTGAGCTTGACTCTAGTTTGACATTGTGAAAAGACATATCGGGTGTAGAATAGGTGG
GAGCTTCGGCACAAGTGAAATACCACTACCTTTATTGTTTTTTACTTATTCAATGAAGCGGAACTGGGCTTTACCGCCC
AACTTCTAGCGTTAAGGTCCTTCGCGGGCTGATCCGGGTTGAAGACATTGTCAGGTGGGGAGTTTGGCTGGGCGGCAC
ATCTGTTAAACCATAACGCAGGTGTCCTAAGGGGGACTCATGGAGAACAGAAATCTCCAGTAGAACAAAAGGGTAAAA
GTCCCCTTGATTTTGATTTTCAGTGTGAATACAAACCATGAAAGTGTGGCCTATCGATCCTTTAGTCCCTCGAAATTTGA
GGCTAGAGGTGCCAGAAAAGTTACCACAGGGATAACTGGCTTGTGGCAGCCAAGCGTTCATAGCGACGTTGCTTTTTG
ATCCTTCGATGTCGGCTCTTCCTATCATACCGAAGCAGAATTCGGTAAGCGTTGGATTGTTCACCCACTAATAGGGAAC
GTGAGCTGGGTTTAGACCGTCGTGAGACAGGTTAGTTTTACCCTACTGATGAAGGTCGCCGCAACGGTAATTCAATTTA
GTACGAGAGGAACCGTTGATTCAGATAATTGGTTTTTGCGGCTGTCTGACCAGGCAGTGCCGCGACGCTACCATCTGCC
GGATTATGGCTGAACGCCTCTAAGTCAGAATCCGTGCCGGAACGCGGCGATGTTGCCTCGCACGTCGTAGTTGGATACG
AATAGGCCTTCGGGCCCCGAACCTCAGCAGGTTGGCGGCGGTGTCCGGGGAGAGACCCTCGGGCGCCAGCTAACGGAT
TGCAATGTCACAACGCGCGGGGATAGATCCTCTGCAGACGACTGAAATGACCAAGCGGGTCGTGTAAGCGGTCAAGTA
GCCTAGTTGTTACGAGTCGCTGAGCGTCAGCCCGATCCTTGGCTCGATTTGTTGTAAACACCCTCCATCAAT
```

BROAD RANGE PCR-BASED COMPOSITIONS AND METHODS FOR THE DETECTION AND IDENTIFICATION OF FUNGAL PATHOGENS

CROSS REFERENCE TO RELATED APPLICATIONS

This application claims the benefit of U.S. Provisional Patent Application No. 61/118,230, filed Nov. 26, 2008, and which provisional patent application is incorporated by reference in its entirety herein.

GOVERNMENT SPONSORED RESEARCH OR DEVELOPMENT

This invention was made with government support AI054703 awarded by the National Institutes of Health. The government has certain rights in this invention.

BACKGROUND OF THE DISCLOSURE

Technical Field

The present disclosure is directed, generally, to the detection of fungal pathogens in a patient sample. More specifically, disclosed herein are methods for detecting and/or identifying a fungal pathogen in a patient sample, involving isolating the sample, optionally extracting DNA from the sample, carrying out a PCR reaction on the sample to generate an amplicon that includes a region of the fungal ribosomal RNA (rRNA) gene, such as an internal transcribed spacer 1 (ITS-1) region and/or a 28S rRNA gene region, and detecting the PCR amplicon. The present disclosure also provides primers and primer sets for specifically detecting a broad range of fungal pathogens in the presence of human ribosomal DNA (rDNA). In certain embodiments of the present disclosure, the PCR amplicon is further characterized by sequencing or by using two-dimensional melt-curve analysis. In yet other embodiments, more than one fungal pathogen is detected in a sample using the methods disclosed herein. The present disclosure also provides methods for identifying alternative primers that are useful for detecting fungal pathogens, and for detecting fungal pathogens in the presence of non-fungal DNA.

Description of the Related Art

Fungal infections remain a major cause of morbidity and mortality in immunocompromised patients, such as those undergoing cancer chemotherapy, solid organ transplants, or hematopoietic cell transplants. The rapid detection and accurate identification of fungal pathogens can be critical for initiating treatment in the earliest stages of infection and for guiding antifungal therapy. Cultivation and histological analysis often have poor diagnostic sensitivity, and histopathological findings frequently do not distinguish among fungal species [McLintock and Jones (2004) Br. J. Haematol. 126:289-97; Reichenberger et al. (1999) Bone Marrow Transplant 24:1195-9]. Moreover, some molecular diagnostic tests such as the galactomannan antigen assay detect only pathogens from the Aspergillus genus, and the beta-glucan antigen assay does not detect fungi in the Zygomycete or Basidiomycete taxa [Kedzierska et al. (2007) Eur. J. Clin. Microbiol. Infect. Dis. 26:755-66; McLintock and Jones (2004) Br. J. Haematol. 126:289-97; Ostrosky-Zeichner et al. (2005) Clin. Infect. Dis. 41:654-9; Yeo and Wong (2002) Clin. Microbiol. Rev. 15:465-84]. Such shortcomings may lead to more empiric antifungal therapy because a fungal infection is not completely excluded with negative results from either of these antigen assays. In addition, the spectrum of fungal infections is likely to change with increasing use of antifungal medications for prophylaxis. The next generation of diagnostic tests must be capable of detecting these emerging pathogens. Finally, pathogenic fungi within the same genus may have different antifungal susceptibility profiles, such as Candida albicans and Candida krusei.

PCR assays for the detection of fungal pathogens are an appealing approach due to their potential for rapid, sensitive, and accurate diagnosis of fungal infections. Ribosomal RNA genes are particularly attractive targets because they are present in multiple copies per genome, have conserved regions for designing broad-range primers, and more variable regions for identifying fungi. Most studies have focused on 18S rRNA genes [Einsele et al. (1997) J. Clin. Microbiol. 35:1353-60], internal transcribed spacers (ITS1 and ITS2) [Bergman et al. (2007) Eur. J. Clin. Microbiol. Infect. Dis. 26:813-8; Chen et al. (2001) J Clin Microbiol 38:2302-10; Iwen et al. (2002) Med. Mycol. 40:87-109; Turenne et al. (1999) J. Clin. Microbiol. 37:1846-519 and the 5' end of the 28S rRNA gene (D1-D2 hypervariable region) [(Hinrikson et al. (2005) J. Clin. Microbiol. 43:2092-103; Kurtzman and Robnett (1997) J. Clin. Microbiol. 35:1216-23; Rakeman et al. (2005)J. Clin. Microbiol. 43:3324-33; Sandhu et al. (1995) J. Clin. Microbiol. 33:2913-9; Vollmer et al. (2008) J. Clin. Microbiol. 46:1919-26)] for developing broad-range PCR assays targeting human fungal pathogens.

While certain PCR primers and methods have been developed based on amplification of fungal ITS and D1-D2 regions within the rRNA operon, there are critical limitations of these primers and the approach. First, these PCR primers have not been designed to prevent the interaction with human DNA. The amplification of human DNA in a patient sample substantially diminishes the utility of such PCR primers thereby compromising the sensitivity and/or specificity of methods for the detection of a fungal pathogen in a human sample. Many of these fungal primers have a high degree of sequence similarity (or are exact matches) with human rRNA genes. Second, there can be intraspecies variability for the ITS regions which could lead to inconclusive species identification in the absence of more complete ITS sequence information in public databases [(Chen et al. (2000) J Clin Microbiol 38:2302-10; O'Donnell et al. (1998) Mycologia 90:465-493; Rakeman et al. (2005) J. Clin. Microbiol. 43:3324-33)]. Third, variability in ITS sequence length could result in inconsistent analytical sensitivity of the fungal PCR assay. For instance, an ITS assay may produce a 200 by amplicon from one fungus, and a 600 by amplicon from a second fungus. The detection assay thresholds for these two fungi are not likely to be the same.

What is critically needed in the art are compositions and methods for achieving the rapid detection and identification of a broad-range of fungal pathogens in patient samples without interference from or interaction with human DNA.

SUMMARY OF THE DISCLOSURE

The present disclosure achieves these and other related needs by providing compositions and methods for detecting fungal pathogens in patient samples. In certain aspects, the methods include the steps of (a) isolating a patient sample, (b) carrying out a PCR reaction on the patient sample to generate a PCR amplicon that comprises a region of a fungal ribosomal RNA (rRNA) gene, wherein the PCR reaction uses a primer set including a forward primer and a reverse primer wherein at least one of the forward primer and the reverse primer is complementary to the fungal rRNA gene, and (c) detecting the PCR amplicon.

In certain embodiments of the methods disclosed herein, the region of the fungal rRNA gene includes an internal transcribed spacer 1 (ITS-1) region. In other embodiments, the fungal rRNA gene region includes a 28S rRNA gene. In still further embodiments of the methods disclosed herein, the region of the fungal 28S rRNA gene detected by PCR includes a sequence that is 3' to a D1-D2 highly variable region of the fungal 28S rRNA gene.

The methods for detecting a fungal pathogen may further involve the step of sequencing the PCR amplicon generated by the PCR reaction, such as a quantitative PCR reaction. Typically, the PCR amplicon is between 50 and 1000 base pairs or between 75 and 400 base pairs.

The forward primer used in the presently disclosed methods may be complementary to a fungal 18S rRNA gene and the reverse primer may be complementary to a fungal 28S rRNA gene. For example, the forward primer may comprise the nucleotide sequence 5'-GTAAAAGTCG-TAACAAGGTTTC-3' (SEQ ID NO: 1). In other aspects, the forward primer may be complementary to a fungal 5.8S rRNA gene and the reverse primer may be complementary to a fungal 28S rRNA gene. For example, the forward primer may comprise the nucleotide sequence 5'-GTGAATCATC-GARTCTTTGAAC-3' (SEQ ID NO: 2).

In still further aspects, the forward primer and the reverse primer may both be complementary to a fungal 28S rRNA gene. For example, the forward primer may selected from the group consisting of:

| | |
|---|---|
| 5'-TACCCGCTGAACTTAAGCATA-3', | (SEQ ID NO: 3) |
| 5'-GCATATCAATAAGCGGAGGAAA-3', | (SEQ ID NO: 4) |
| 5'-AGTARCGGCGAGTGAAGCGG-3', | (SEQ ID NO: 5) |
| 5'-AGCTCAAATTTGAAASCTGG-3', | (SEQ ID NO: 6) |
| 5'-CTTCCCTTTCAACAATTTCACRT-3', | (SEQ ID NO: 7) |
| 5'-AGGTAAAGCGAATGATTAG-3', | (SEQ ID NO: 8) |
| 5'-CTTGTTRCTTARTTGAACGTG-3', | (SEQ ID NO: 9) |
| 5'-ACCACAAAAGGTGTTAGTWCATC-3', | (SEQ ID NO: 10) |
| 5'-GAAGTGGGGAAAGGTTCC-3', | (SEQ ID NO: 11) |
| 5'-GACATGGGTTAGTCGATCCTA-3' | (SEQ ID NO: 12) |
| 5'-TCGTACTCATAACCGCAGC-3', | (SEQ ID NO: 13) |
| 5'-GTTGATAGAAYAATGTAGATAAGG-3', | (SEQ ID NO: 14) |
| 5'-CAAGGGGAATCTGACTGTC-3', | (SEQ ID NO: 15) |
| 5'-TTTACTTAWTCAATGAAG CGG-3', | (SEQ ID NO: 16) |
| 5'-CCGGGTTGAWGACATTGTCA-3', | (SEQ ID NO: 17) |
| 5'-GCTGGGGCGGCACATCTGTT-3', | (SEQ ID NO: 18) |
| 5'-GAACAAAAGGGTAAAAGTCCC-3', | (SEQ ID NO: 19) |
| 5'-TTTGATTTTCAGTGTGAATACAAACCA-3', | (SEQ ID NO: 20) |
| 5'-ATGAAAGTGTGGCCTATCG-3' | (SEQ ID NO: 21) |
| 5'-GAGGCTAGAGGTGCCAGAA-3', | (SEQ ID NO: 22) |
| 5'-AGGGATAACTGGCTTGTGGC-3', | (SEQ ID NO: 23) |
| 5'-ACCGAAGCAGAATTCGGTAAG-3', | (SEQ ID NO: 24) |
| 5'-GATAAT TGGTWTTTGCGGCTG-3', | (SEQ ID NO: 25) |
| 5'-GCTGAACGCCTCTAAGTCAGA-3', | (SEQ ID NO: 26) |
| and | |
| 5'-TCGTARCAACAAGGCTACT-3' | (SEQ ID NO: 27) | and the reverse primer may be selected from the group consisting of:

| | |
|---|---|
| 5'-TATGCTTAAGTTCAGCGGGTA-3', | (SEQ ID NO: 30) |
| 5'-TTTCCTCCGCTTATTGATATGC-3', | (SEQ ID NO: 31) |
| 5'-CCGCTTCACTCGCCGYTACT-3', | (SEQ ID NO: 32) |
| 5'-CCAGSTTTCAAATTTGAGCT-3', | (SEQ ID NO: 33) |
| 5'-AYGTGAAATTGTTGAAAGGGAAG-3', | (SEQ ID NO: 34) |
| 5'-CTAATCATTCGCTTTACCTC-3', | (SEQ ID NO: 35) |
| 5'-CACGTTCAAYTAAGYAACAAG-3', | (SEQ ID NO: 36) |
| 5'-GATGWACTAACACCTTTTGTGGT-3', | (SEQ ID NO: 37) |
| 5'-GGAACCTTTCCCCACTTC-3', | (SEQ ID NO: 38) |
| 5'-TAGGATCGACTAACCCATGTC-3', | (SEQ ID NO: 39) |
| 5'-GCTGCGGTTATGAGTACGA-3', | (SEQ ID NO: 40) |
| 5'-CCTTATCTACATTRTTCTATCAAC-3', | (SEQ ID NO: 41) |
| 5'-GACAGTCAGATTCCCCTTG-3', | (SEQ ID NO: 42) |
| 5'-CCGCTTCATTGAWTAAGTAAA-3', | (SEQ ID NO: 43) |
| 5'-TGACAATGTCWTCAACCCGG-3', | (SEQ ID NO: 44) |
| 5'-AACAGATGTGCCGCCCCAGC-3', | (SEQ ID NO: 45) |
| 5'-GGGACTTTTACCCTTTTGTTC-3', | (SEQ ID NO: 46) |
| 5'-TGGTTTGTATTCACACTGAAAATCAAA-3', | (SEQ ID NO: 47) |
| 5'-CGATAGGCCACACTTTCAT-3', | (SEQ ID NO: 48) |
| 5'-TTCTGGCACCTCTAGCCTC-3', | (SEQ ID NO: 49) |
| 5'-GCCACAAGCCAGTTATCCCT-3', | (SEQ ID NO: 50) |
| 5'-CTTACCGAATTCTGCTTCGGT-3', | (SEQ ID NO: 51) |
| 5'-CAGCCGCAAAWACCAATTATC-3', | (SEQ ID NO: 52) |
| 5'-TCTGACTTAGAGGCGTTCAGC-3', | (SEQ ID NO: 53) |
| 5'-AGTAGCCTTGTTGYTACGA-3', | (SEQ ID NO: 54) |
| and | |
| 5'-CCTTATCTACATTATTCTATGGAC-3'. | (SEQ ID NO 108) |

Within certain embodiments disclosed herein, the methods employ primer sets that include a forward and reverse primer pair wherein the primer sets may be selected from the group consisting of (SEQ ID NO: 2 and SEQ ID NO: 31), (SEQ ID NO: 2 and SEQ ID NO: 32), (SEQ ID NO: 11 and SEQ ID NO: 41), (SEQ ID NO: 1 and SEQ ID NO: 29), (SEQ ID NO: 2 and SEQ ID NO: 30), (SEQ ID NO: 12 and SEQ ID NO: 41), (SEQ ID NO: 14 and SEQ ID NO: 42), (SEQ ID NO: 17 and SEQ ID NO: 51), (SEQ ID NO: 20 and SEQ ID NO: 51), (SEQ ID NO: 20 and SEQ ID NO: 52), and (SEQ ID NO: 25 and SEQ ID NO: 54) or may be selected from the group consisting of (SEQ ID NO: 1 and SEQ ID NO: 29), (SEQ ID NO: 2 and SEQ ID NO: 30), (SEQ ID NO: 12 and SEQ ID NO: 41), (SEQ ID NO: 14 and SEQ ID NO: 42), (SEQ ID NO: 17 and SEQ ID NO: 51), (SEQ ID NO: 20 and SEQ ID NO: 51), (SEQ ID NO: 20 and SEQ ID NO: 52), and (SEQ ID NO: 25 and SEQ ID NO: 54) or may be selected from the group consisting of (SEQ ID NO: 2 and SEQ ID NO: 30), (SEQ ID NO: 12 and SEQ ID NO: 41), and (SEQ ID NO: 12, SEQ ID NO: 41, and SEQ ID NO: 108).

Within other embodiments disclosed herein, primer sets are provided for detecting a fungal pathogen in a patient sample. Primer sets include a forward and reverse primer pair/set as exemplified by the primer sets selected from the group consisting of (SEQ ID NO: 11 and SEQ ID NO: 41), (SEQ ID NO: 12 and SEQ ID NO: 41), (SEQ ID NO: 12, SEQ ID NO: 41, and SEQ ID NO: 108), (SEQ ID NO: 14 and SEQ ID NO: 42), (SEQ ID NO: 17 and SEQ ID NO: 51), (SEQ ID NO: 20 and SEQ ID NO: 51), (SEQ ID NO: 20 and SEQ ID NO: 52), and (SEQ ID NO: 25 and SEQ ID NO: 54).

In other aspects disclosed herein, methods for detecting a fungal pathogen in a patient sample are provided, wherein the fungal pathogen is selected from the group consisting of *Absidia corymbifera; Cunninghamella bertholletiae; Fusarium solani; Mucor racemosus; Paecilomyces variotii; Penicillium chrysogenum; Rhizomucor miehei; Rhodotorula glutinis; Scedosporium apiospermum; Antrodia vaillantii; Aspergillus fumigatus; Aspergillus niger; Aspergillus oryzae; Aspergillus terreus; Batrachochytrium dendrobatidis; Botrytis cinerea; Candida albicans; Candida dubliniensis; Candida glabrata; Candida gulliermundei; Candida kefyr; Candida krusei; Candida lipolytica; Candida lusitaniae; Candida parapsilosis; Candida tropicalis; Chaetomium globosum; Coccidioides immitis; Coccidioides posadasii; Cryptococcus neoformans; Fusarium graminearum; Fusarium oxysporum; Histoplasma capsulatum; Hypocrea jecorina; Lodderomyces elongisporus; Magnaporthe grisea; Metarhizium anisopliae; Microsporum gypseum; Mucor racemosus; Neurospora crassa; Paracoccidioides brasiliens; Pneumocystis carinii; Penicillium verrucosum; Pichia stipitis; Rhizomucor miehei; Rhizopus oryzae; Saccharomyces cerevisiae; Schizosaccharomyces japonicus; Schizosaccharomyces pombe; Sclerotinia sclerotiorum; Stagonospora nodorum; Umbilicaria esculenta*; and *Uncinocarpus reesii*. Thus, the methods provided herein may be suitably adapted for detecting a fungal pathogen that causes a fungal infection selected from the group consisting of *aspergillosis, candidiasis, zygomycosis, scedosporiosis, fusariosis, cryptococcosis, histoplasmosis, coccidioidomycosis*, and *blastomycosis*.

Primers disclosed herein were designed to be used in PCR-based methods for detecting fungal DNA in a patient sample. Thus, these primers specifically bind to a fungal DNA but not to DNA in a patient sample. Thus, each primer of the primer set specifically binds only to a fungal DNA in the presence of a non-fungal DNA, such as mammalian DNA, typically human DNA. As demonstrated herein, primers of the present disclosure permit the amplification of fungal DNA in a patient sample where the non-fungal DNA is present in greater than 1,000,000-fold, 5,000,000-fold, or 30,000,000-fold mass excess over the amount of fungal DNA.

Within other embodiments, the present disclosure provides primer sets for detecting a fungal DNA, wherein the primer sets include a forward primer and a reverse primer, wherein at least one of the forward primer and the reverse primer is complementary to a region in the 18S rRNA gene, 5.8S rRNA gene, and/or to a 28S rRNA gene. Typically, the forward primer and/or the reverse primer of the primer set is complementary to a sequence that is 3' to a D1-D2 highly variable region in the fungal 28S ribosomal rRNA gene. In yet other embodiments, the forward primer of the primer set is complementary to a fungal 18S rRNA gene and the reverse primer is complementary to a fungal 28S rRNA gene. An exemplary forward primer suitable for use in such primer sets includes the nucleotide sequence 5'-GTAAAAGTCGTAACAAGGTTTC-3' (SEQ ID NO: 1). In other embodiments, the forward primer of the primer set is complementary to a fungal 5.8S rRNA gene and the reverse primer is complementary to a fungal 28S rRNA gene. An exemplary forward primer suitable for use in such primer sets includes the nucleotide sequence 5'-GTGAAT-CATCGARTCTTTGAAC-3' (SEQ ID NO: 2).

In certain aspects, the forward primer and the reverse primer of the primer set are both complementary to a fungal 28S rRNA gene and include the forward and reverse primers described above, including SEQ ID NOs: 3-27 and SEQ ID NOs: 30-54, respectively.

Exemplary primer sets include a forward and reverse primer pair/set and may be selected from the group consisting of (SEQ ID NO: 2 and SEQ ID NO: 31), (SEQ ID NO: 2 and SEQ ID NO: 32), (SEQ ID NO: 11 and SEQ ID NO: 41), (SEQ ID NO: 1 and SEQ ID NO: 29), (SEQ ID NO: 2 and SEQ ID NO: 30), (SEQ ID NO: 12 and SEQ ID NO: 41), (SEQ ID NO: 14 and SEQ ID NO: 42), (SEQ ID NO: 17 and SEQ ID NO: 51), (SEQ ID NO: 20 and SEQ ID NO: 51), (SEQ ID NO: 20 and SEQ ID NO: 52), and (SEQ ID NO: 25 and SEQ ID NO: 54). Preferably, the forward and reverse primer pair of the primer set is selected from the group consisting of (SEQ ID NO: 1 and SEQ ID NO: 29), (SEQ ID NO: 2 and SEQ ID NO: 30), (SEQ ID NO: 12 and SEQ ID NO: 41), (SEQ ID NO: 12, SEQ ID NO: 41, and SEQ ID NO: 108), (SEQ ID NO: 14 and SEQ ID NO: 42), (SEQ ID NO: 17 and SEQ ID NO: 51), (SEQ ID NO: 20 and SEQ ID NO: 51), (SEQ ID NO: 20 and SEQ ID NO: 52), and (SEQ ID NO: 25 and SEQ ID NO: 54). More preferably, the forward and reverse primer set is selected from the group consisting of (SEQ ID NO: 2 and SEQ ID NO: 30), (SEQ ID NO: 12 and SEQ ID NO: 41), and (SEQ ID NO: 12, SEQ ID NO: 41, and SEQ ID NO: 108).

In certain aspects, the forward primer of the primer set has the sequence set forth in SEQ ID NO: 1 and the reverse primer has the sequence set forth in SEQ ID NO: 30. In other aspects, the forward primer has the sequence set forth in SEQ ID NO: 12 and the reverse primer has the sequence set forth in SEQ ID NO: 41. In some aspects, a second reverse primer with the sequence set forth in SEQ ID NO 108 may be included in a forward and reverse primer set also comprising a forward primer (SEQ ID NO: 12) and a reverse primer (SEQ ID NO: 41), and may be included and/or added at a concentration equivalent to 5-10% (e.g. 9%) of the reverse primer concentration.

Another embodiment of the present disclosure provides methods for determining the identity of a fungal species in a patient sample. Such methods include the steps of: (a) isolating a patient sample; (b) carrying out a first PCR reaction to generate a first PCR amplicon, wherein the first PCR reaction includes a first primer set capable of amplifying a region in a fungal ribosomal RNA (rRNA) gene having an internal transcribed spacer 2 (ITS-2) sequence; (c) carrying out a second PCR reaction to generate a second PCR amplicon, wherein the second PCR reaction has a second primer set capable of amplifying a region in a fungal ribosomal 28-S rRNA gene; and (d) determining the melting temperature of the first PCR amplicon and of the second PCR amplicon, wherein the identity of the fungal species is determined by comparing the melting point of the first PCR amplicon and of the second PCR amplicon to known standards.

In certain aspects of these methods, the first and second PCR reactions are quantitative PCR (qPCR) reactions. In other aspects, the first primer set includes a forward primer sequence as set forth in SEQ ID NO: 2 and a reverse primer sequence as set forth in SEQ ID NO: 30, and the second primer set includes a forward primer sequence as set forth in SEQ ID NO: 12 and a reverse primer sequence as set forth in SEQ ID NO: 41. In some aspects, the second primer set further includes a second reverse primer sequence as set forth in SEQ ID NO: 108. The second reverse primer sequence may be included in or added to the second primer set at a concentration of 5-10% (e.g. 9%) of the reverse primer sequence concentration.

Also disclosed herein are methods for identifying a primer set capable of detecting a fungal pathogen in a sample, wherein the method includes the steps of: (a) obtaining the nucleic acid sequence of at least the 28S region of a fungal rRNA operon, (b) designing a forward primer capable of hybridizing with the nucleic acid sequence at a specific site in said 28S region, (c) designing a reverse primer capable of hybridizing with the nucleic acid sequence at a region in the sequence that is 3' to the region to which the forward primer is capable of hybridizing, and (d) determining whether the forward primer and the reverse primer are capable of generating a PCR amplicon that is useful for identifying fungal DNA in a PCR reaction containing a specific fungal DNA.

Certain embodiments of these methods further include the step of resolving the PCR amplicon on an agarose gel to determine the analytical sensitivity of the forward primer and the reverse primer. The agarose gel may be stained with ethidium bromide and the PCR amplicon may be visualized by ultraviolet light.

Other embodiments of these methods further include the step of determining the cross-reactivity of the forward primer and reverse primer with non-fungal DNA. In certain aspects, the non-fungal DNA is mammalian DNA, such as human DNA.

Yet other embodiments of these methods further include the step of determining the species resolution of the forward primer and the reverse primer, wherein the forward primer and the reverse primer are a primer set. The ability of the primer set to resolve a species may be determined by the following steps: (a) sequencing the PCR amplicon, (b) comparing the sequence of the PCR amplicon with a sequence of a second PCR amplicon generated using the forward and reverse primers in a PCR reaction containing DNA from a different fungal species, and (c) repeating steps (a) and (b) using fungal DNA from at least 30 different fungal species to determine sequences of amplicons for at least 31 different fungal species, and (d) comparing the sequences of each amplicon. The sequences of each amplicon may be compared to each other by generating a multiple sequence alignment of the sequences.

Still further embodiments of these methods include the step of generating a distance matrix for each amplicon from the multiple sequence alignment. The distance matrix may be compared to the distance matrix of each other amplicon, and the comparison used to determine which of the primer sets are capable of resolving a fungal species. In certain aspects, the distance matrix is generated using the Tajima-Nei algorithm.

These and other embodiments, features and advantages of the disclosure will become apparent from the detailed description and the appended claims set forth herein below.

BRIEF DESCRIPTION OF THE FIGURES AND SEQUENCE IDENTIFIERS

The patent or application file contains at least one drawing executed in color. Copies of this patent or patent application publication with color drawing(s) will be provided by the Office upon request and payment of the necessary fee.

FIG. 1 is a matrix of all possible amplicon lengths from unique combinations of 27 broad-range fungal primers. Shaded regions indicate amplicons with lengths between 75 to 400 bp, selected for further analysis.

Figure 2A:
FIG. 2A is a map of fungal rRNA from the 3' end of 18S to the 3' end of 28S rRNA gene based on *Saccharomyces cerevisae*.
Figure 2B:
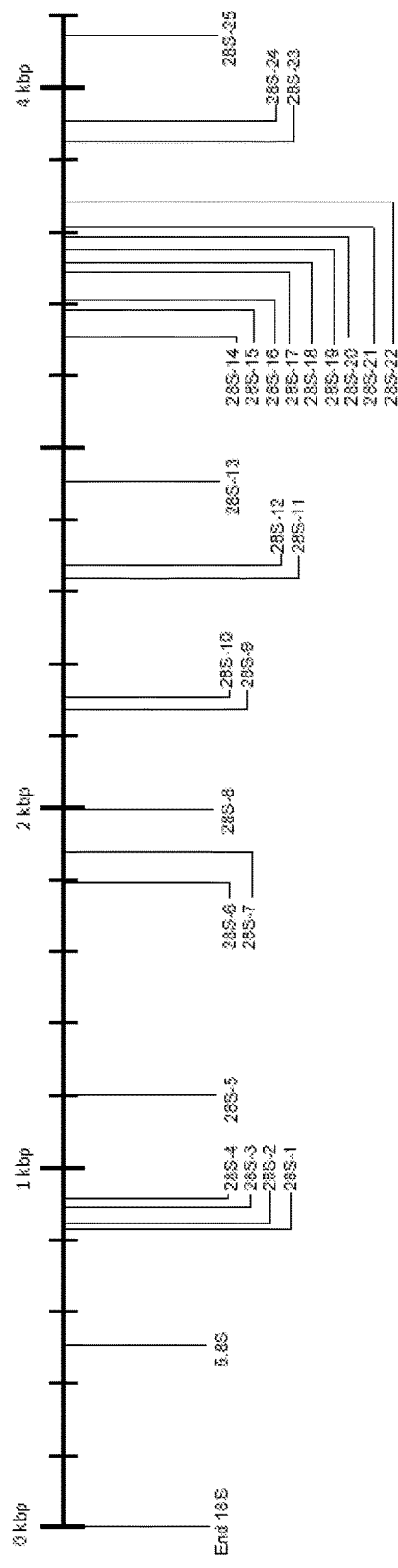

FIG. 2B is a schematic map showing the general location of the 27 broad-range fungal primers along the region spanning from the 3' end of the 18S gene to the 5' end of the 28S gene.

Figure 3:
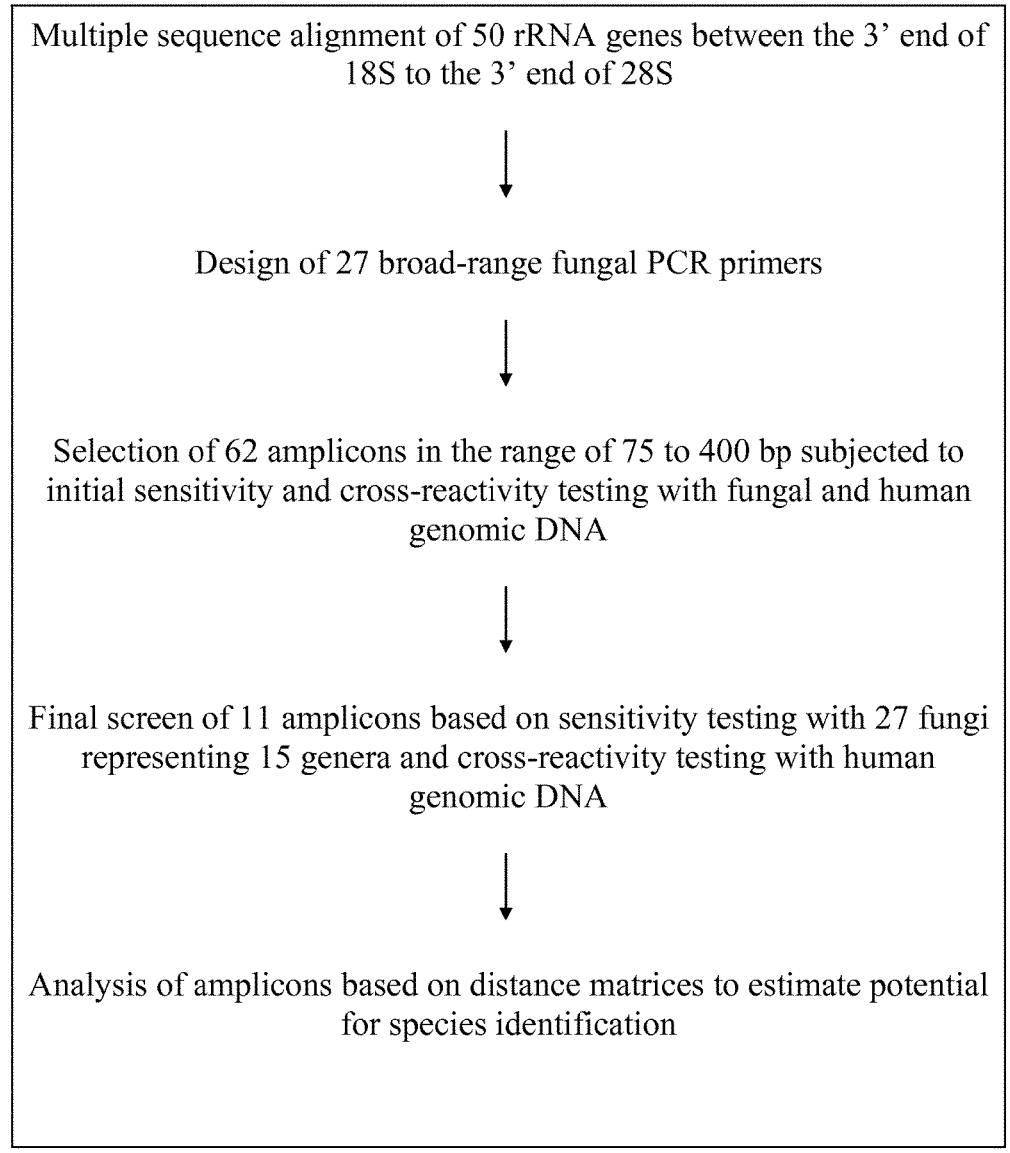

FIG. 3 is a schematic diagram of the approach used for the development of broad-range PCR assays.

FIG. 4A is table showing PCR amplification results for 11 PCR primer pairs on 27 different fungal species or on 1 μg human DNA.

FIG. 4B is an exemplary image of PCR products run on a 1.5% agarose gel, wherein a band having a high intensity is scored as '+++', medium intensity '++', low intensity '+', or no amplification '−'.

Figure 5A:
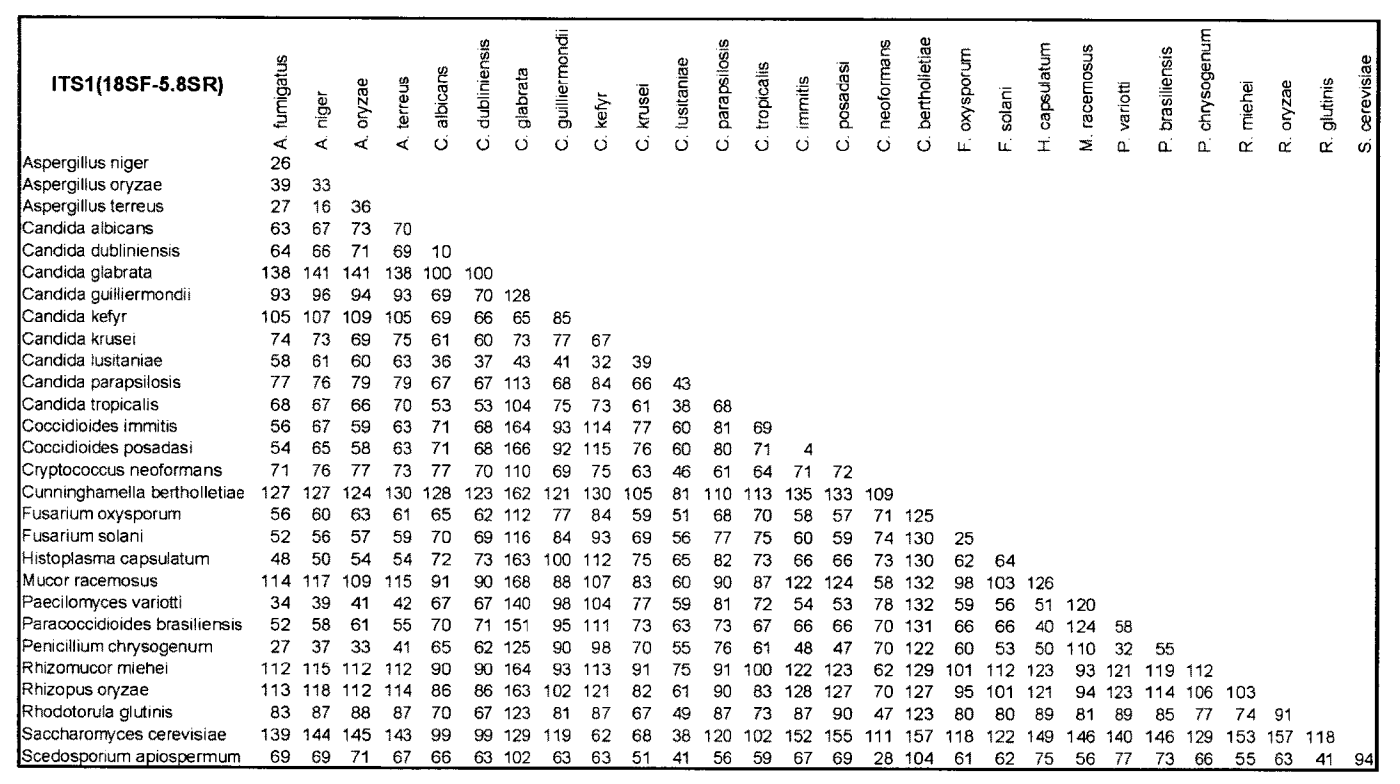

FIG. 5A is a distance matrix of nucleotide differences based on the ITS1(18SF-5.8SR) amplicon of 28 human fungal pathogens.

Figure 5B:
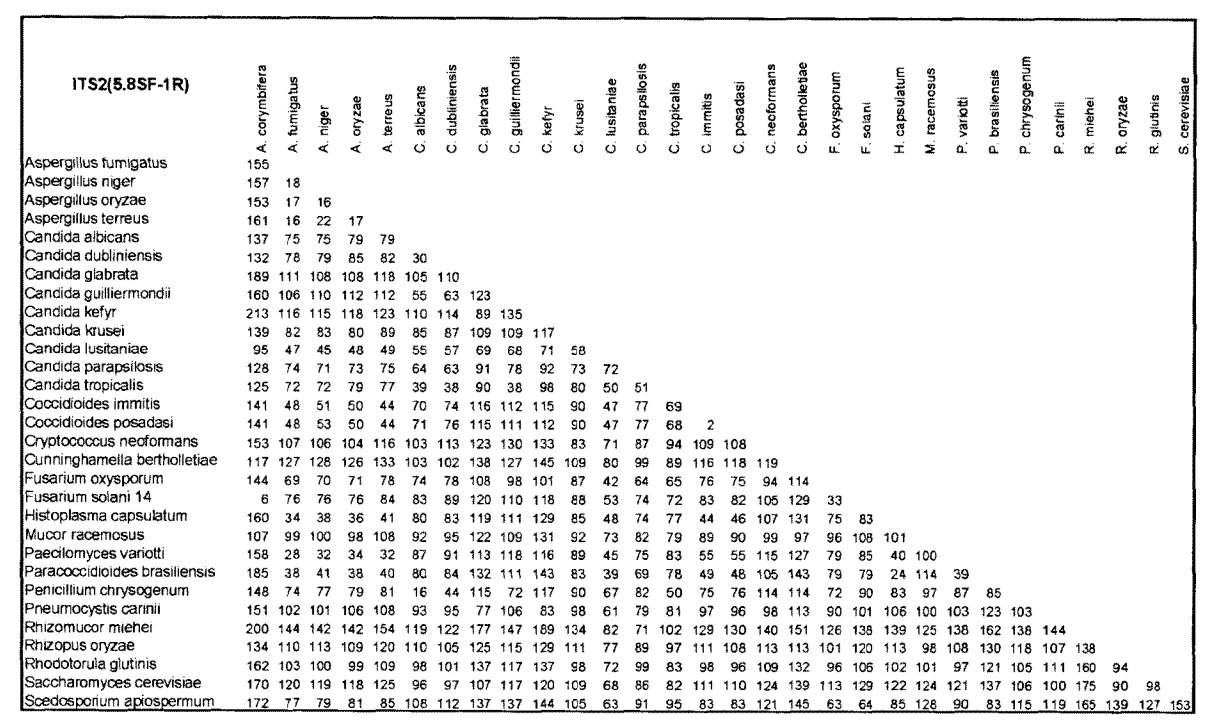

FIG. 5B is a distance matrix of nucleotide differences based on the ITS2(5.8SF-1R) amplicon of 30 human fungal pathogens.

FIG. 5C is a distance matrix of nucleotide differences based on the 28S (10F-12R) amplicon of 30 human fungal pathogens.

Figure 5D:
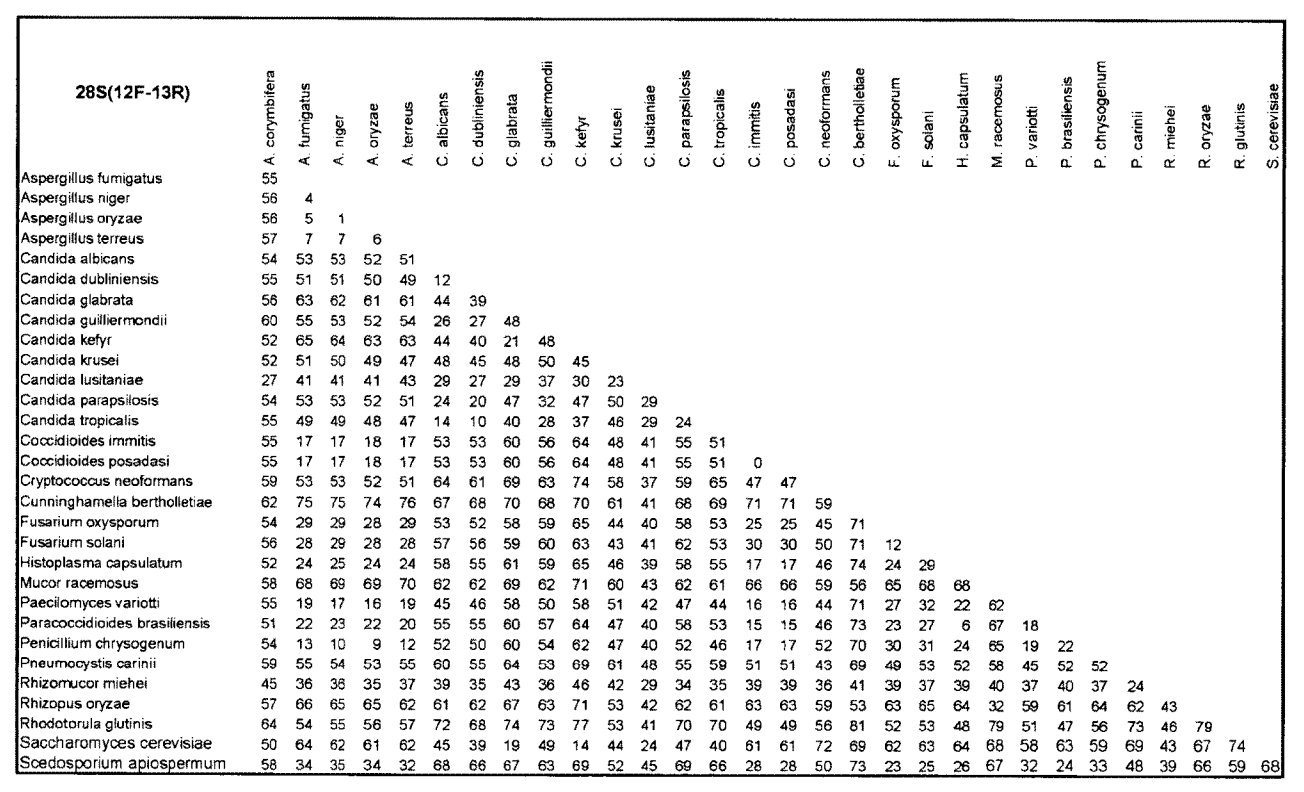

FIG. 5D is a distance matrix of nucleotide differences based on the 28S (12F-13R) amplicon of 30 human fungal pathogens.

FIG. 5E is a distance matrix of nucleotide differences based on the 28S (15F-22R) amplicon of 30 human fungal pathogens.

Figure 5F:
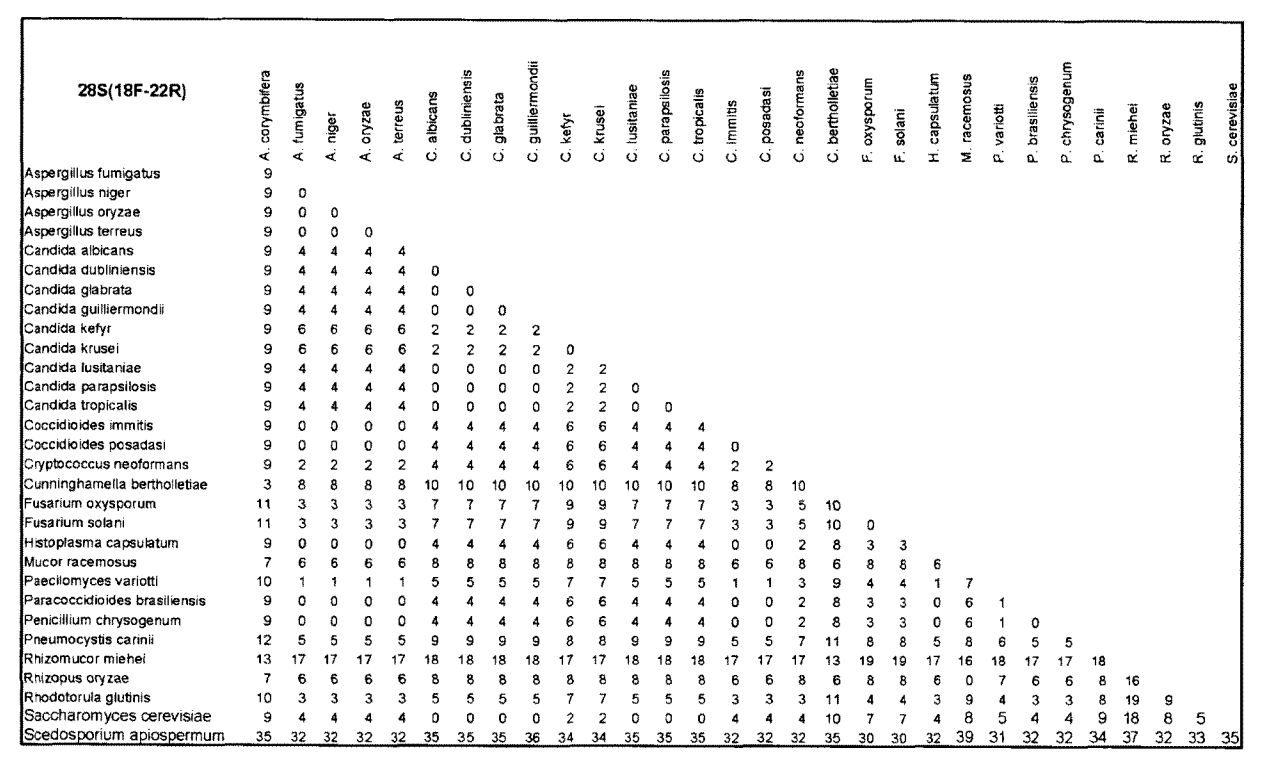

FIG. 5F is a distance matrix of nucleotide differences based on the 28S (18F-22R) amplicon of 30 human fungal pathogens.

Figure 5G:
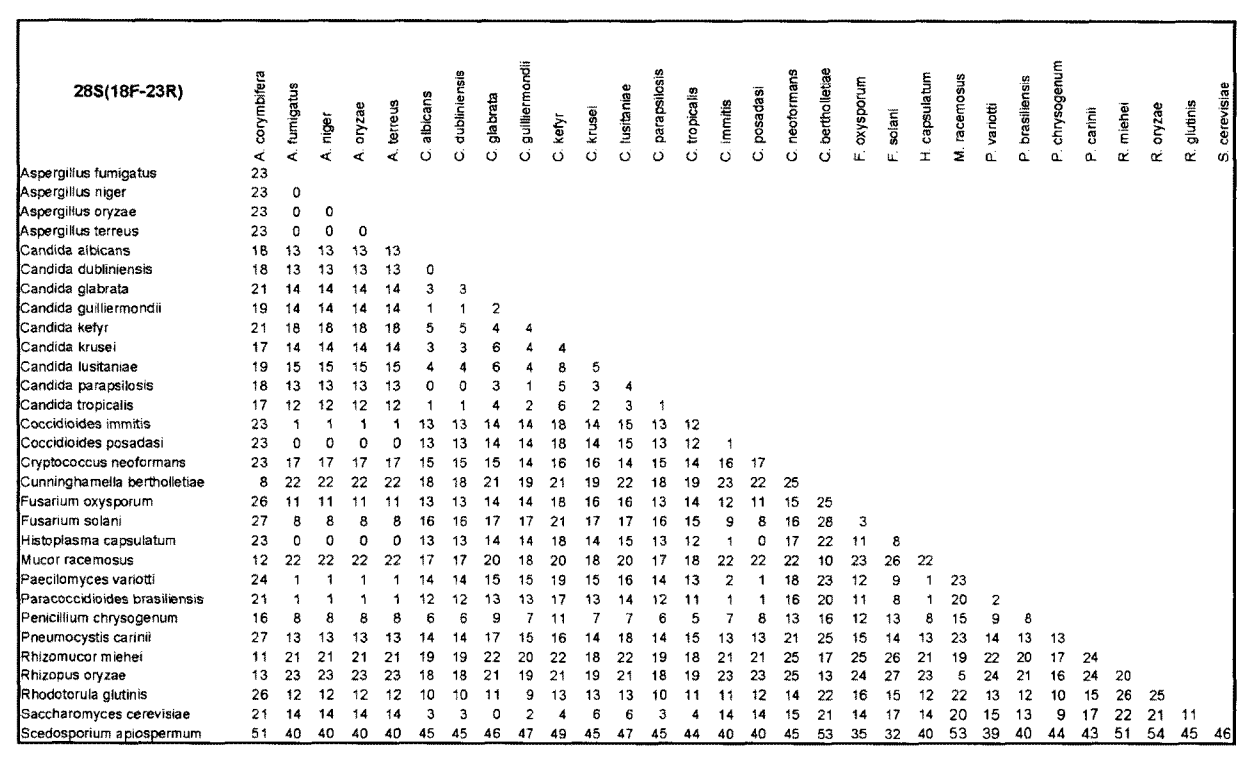

FIG. 5G is a distance matrix of nucleotide differences based on the 28S (18F-23R) amplicon of 30 human fungal pathogens.

FIG. 5H is a distance matrix of nucleotide differences based on the 28S (23F-25R) amplicon of 26 human fungal pathogens.

Figure 6:
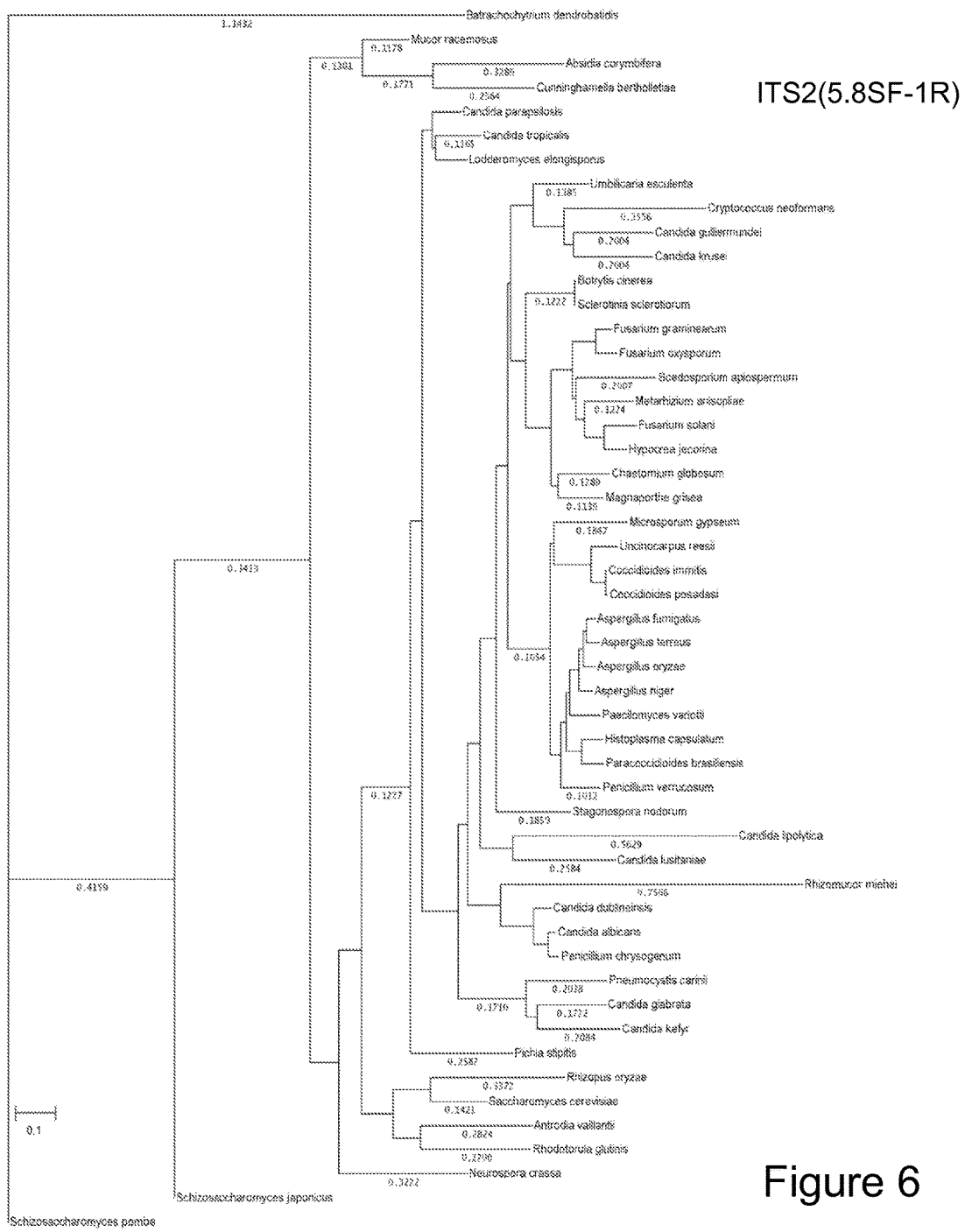

FIG. 6 displays the ability of the 28S(10F-12R) amplicon to distinguish between 51 different fungal species spanning 30 genera as a phylogenetic tree which was constructed based on the neighbor joining tree building method and distances estimated using Tajima-Nei algorithm.

Figure 7:
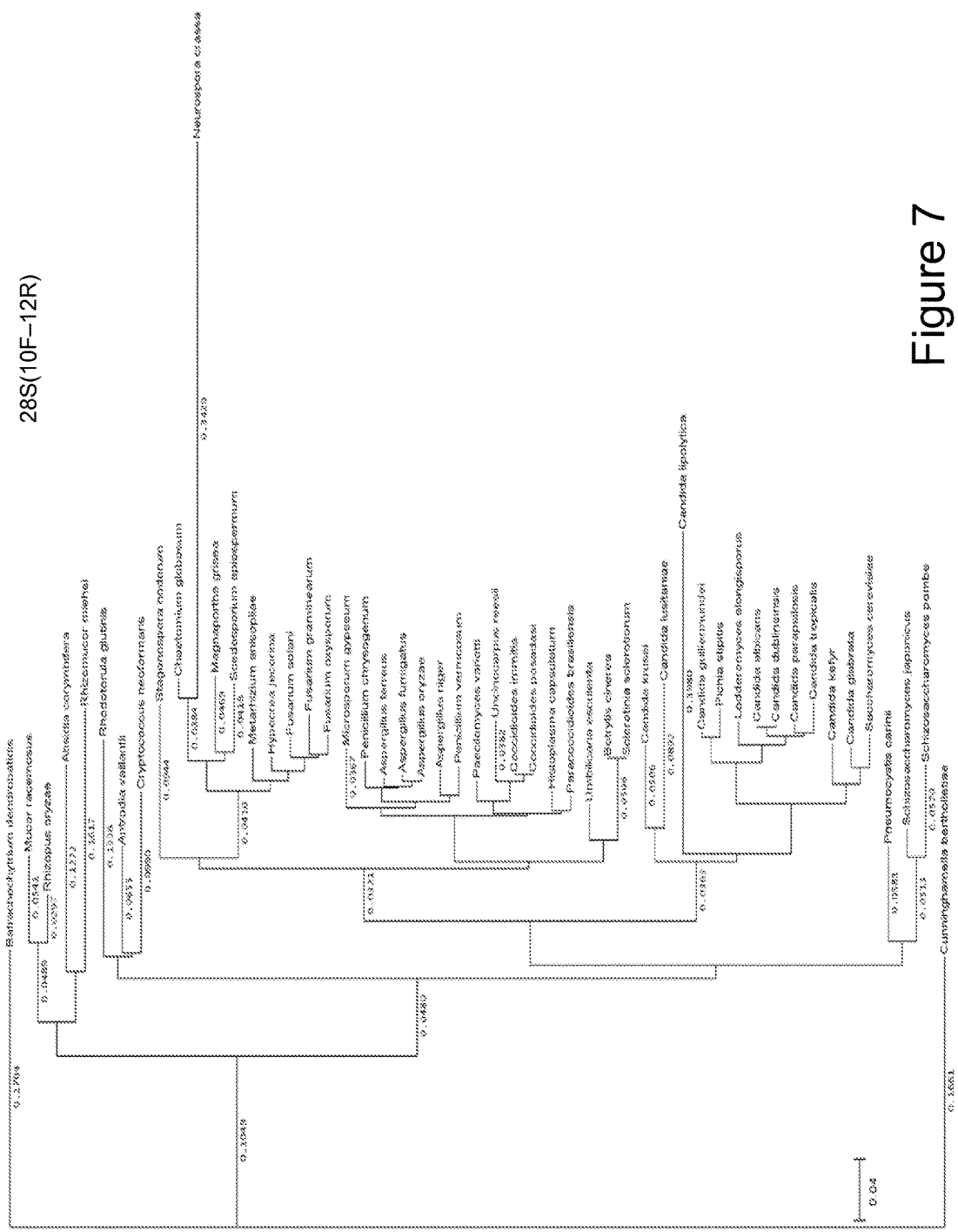

FIG. 7 displays the ability of the ITS2(5.8SF-1R) amplicon to distinguish between 51 different fungal species spanning 30 genera as a phylogenetic tree which was constructed based on the neighbor joining tree building method and distances estimated using Tajima-Nei algorithm.

FIG. 8 is a partial rRNA nucleic acid sequence of *Absidia corymbifera* strain (SEQ ID NO: 55).

FIG. 9 is a partial rRNA nucleic acid sequence of *Cunninghamella bertholletiae* strain ATCC # 42115 (SEQ ID NO: 56).

FIG. 10 is a partial rRNA nucleic acid sequence of *Fusarium solani* strain, ATCC # 56480 (SEQ ID NO: 57).

FIG. 11 is a partial rRNA nucleic acid sequence of *Mucor racemosus* strain, ATCC # 42647, (SEQ ID NO: 58).

FIG. 12 is a partial rRNA nucleic acid sequence of *Paecilomyces variotii* strain, ATCC # 10865, (SEQ ID NO: 59).

FIG. 13 is a partial rRNA nucleic acid sequence of *Penicillium chrysogenum* strain, ATCC # 10108, (SEQ ID NO: 60).

FIG. 14 is a partial rRNA nucleic acid sequence of *Rhizomucor miehei* strain, ATCC # 46345, (SEQ ID NO: 61).

FIG. 15 is a partial rRNA nucleic acid sequence of *Rhodotorula glutinis* strain, ATCC # 16726, (SEQ ID NO: 62).

FIG. 16 is a partial rRNA nucleic acid sequence of *Scedosporium apiospermum* strain, ATCC # 28206, (SEQ ID NO: 63).

FIG. 17 is a partial rRNA nucleic acid sequence of *Antrodia vaillantii* strain (SEQ ID NO: 64).

FIG. 18 is a partial rRNA nucleic acid sequence of *Aspergillus fumigatus* strain (SEQ ID NO: 65).

FIG. 19 is a partial rRNA nucleic acid sequence of *Aspergillus niger* strain (SEQ ID NO: 66).

FIG. 20 is a partial rRNA nucleic acid sequence of *Aspergillus oryzae* strain (SEQ ID NO: 67).

FIG. 21 is a partial rRNA nucleic acid sequence of *Aspergillus terreus* strain (SEQ ID NO: 68).

FIG. 22 is a partial rRNA nucleic acid sequence of *Batrachochytrium dendrobatidis* strain (SEQ ID NO: 69).

FIG. 23 is a partial rRNA nucleic acid sequence of *Botrytis cinerea* strain (SEQ ID NO: 70).

FIG. 24 is a partial rRNA nucleic acid sequence of *Candida albicans* strain (SEQ ID NO: 71).

FIG. 25 is a partial rRNA nucleic acid sequence of *Candida dublineinsis* strain (SEQ ID NO: 72).

FIG. 26 is a partial rRNA nucleic acid sequence of *Candida glabrata* strain (SEQ ID NO: 73).

FIG. 27 is a partial rRNA nucleic acid sequence of *Candida gulliermundei* strain (SEQ ID NO: 74).

FIG. 28 is a partial rRNA nucleic acid sequence of *Candida kefyr* strain (SEQ ID NO: 75).

FIG. 29 is a partial rRNA nucleic acid sequence of *Candida krusei* strain (SEQ ID NO: 76).

FIG. 30 is a partial rRNA nucleic acid sequence of *Candida lipolytica* strain (SEQ ID NO: 77).

FIG. 31 is a partial rRNA nucleic acid sequence of *Candida lusitaniae* strain (SEQ ID NO: 78).

FIG. 32 is a partial rRNA nucleic acid sequence of *Candida parapsilosis* strain (SEQ ID NO: 79).

FIG. 33 is a partial rRNA nucleic acid sequence of *Candida tropicalis* strain (SEQ ID NO: 80).

FIG. 34 is a partial rRNA nucleic acid sequence of *Chaetomium globosum* strain (SEQ ID NO: 81).

FIG. 35 is a partial rRNA nucleic acid sequence of *Coccidioides immitis* strain (SEQ ID NO: 82).

FIG. 36 is a partial rRNA nucleic acid sequence of *Coccidioides posadasii* strain (SEQ ID NO: 83).

FIG. 37 is a partial rRNA nucleic acid sequence of *Cryptococcus neoformans* strain (SEQ ID NO: 84).

FIG. 38 is a partial rRNA nucleic acid sequence of *Fusarium graminearum* strain (SEQ ID NO: 85).

FIG. 39 is a partial rRNA nucleic acid sequence of *Fusarium oxysporum* strain (SEQ ID NO: 86).

FIG. 40 is a partial rRNA nucleic acid sequence of *Histoplasma capsulatum* strain (SEQ ID NO: 87).

FIG. 41 is a partial rRNA nucleic acid sequence of *Hypocrea jecorina* strain (SEQ ID NO: 88).

FIG. 42 is a partial rRNA nucleic acid sequence of *Lodderomyces elongisporus* strain (SEQ ID NO: 89).

FIG. 43 is a partial rRNA nucleic acid sequence of *Magnaporthe grisea* strain (SEQ ID NO: 90).

FIG. 44 is a partial rRNA nucleic acid sequence of *Metarhizium anisopliae* strain (SEQ ID NO: 91).

FIG. 45 is a partial rRNA nucleic acid sequence of *Microsporum gypseum* strain (SEQ ID NO: 92).

FIG. 46 is a partial rRNA nucleic acid sequence of *Mucor racemosus* strain (SEQ ID NO: 93).

FIG. 47 is a partial rRNA nucleic acid sequence of *Neurospora crassa* strain (SEQ ID NO: 94).

FIG. 48 is a partial rRNA nucleic acid sequence of *Paracoccidioides brasiliens* strain (SEQ ID NO: 95).

FIG. 49 is a partial rRNA nucleic acid sequence of *Pneumocystis carinii* strain (SEQ ID NO: 96).

FIG. 50 is a partial rRNA nucleic acid sequence of *Penicillium verrucosum* strain (SEQ ID NO: 97).

FIG. 51 is a partial rRNA nucleic acid sequence of *Pichia stipitis* strain (SEQ ID NO: 98).

FIG. 52 is a partial rRNA nucleic acid sequence of *Rhizomucor miehei* strain (SEQ ID NO: 99).

FIG. 53 is a partial rRNA nucleic acid sequence of *Rhizopus oryzae* strain (SEQ ID NO: 100).

FIG. 54 is a partial rRNA nucleic acid sequence of *Saccharomyces cerevisiae* strain (SEQ ID NO: 101).

FIG. 55 is a partial rRNA nucleic acid sequence of *Schizosaccharomyces japonicus* strain (SEQ ID NO: 102).

FIG. 56 is a partial rRNA nucleic acid sequence of *Schizosaccharomyces pombe* strain (SEQ ID NO: 103).

FIG. 57 is a partial rRNA nucleic acid sequence of *Sclerotinia sclerotiorum* strain (SEQ ID NO: 104).

FIG. 58 is a partial rRNA nucleic acid sequence of *Stagonospora nodorum* strain (SEQ ID NO: 105).

FIG. 59 is a partial rRNA nucleic acid sequence of *Umbilicaria esculenta* strain (SEQ ID NO: 106).

FIG. 60 is a partial rRNA nucleic acid sequence of *Uncinocarpus reesii* strain (SEQ ID NO: 107).

Figure 61:
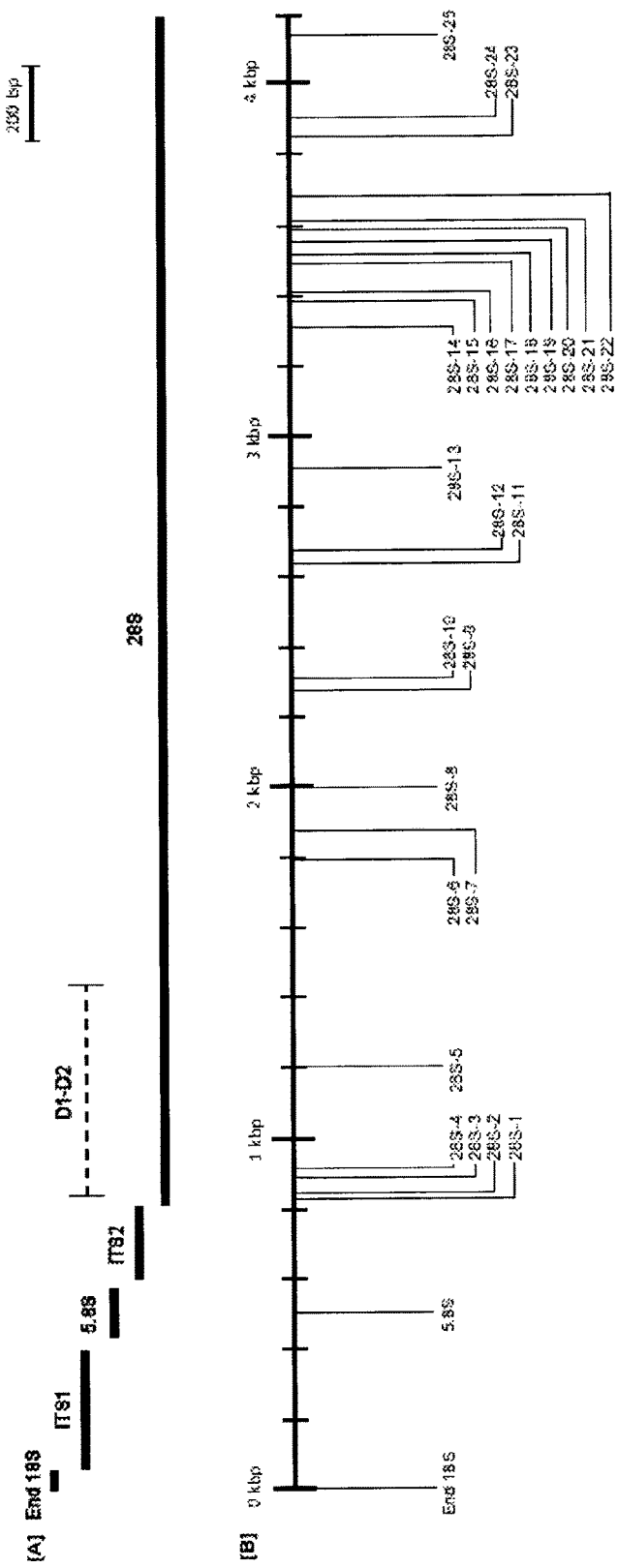

FIG. 61 illustrates a map of a fungal 28S rRNA gene and corresponding positions of twenty-seven broad-range fungal PCR primers for sequencing and PCR assay development.

Figure 62:
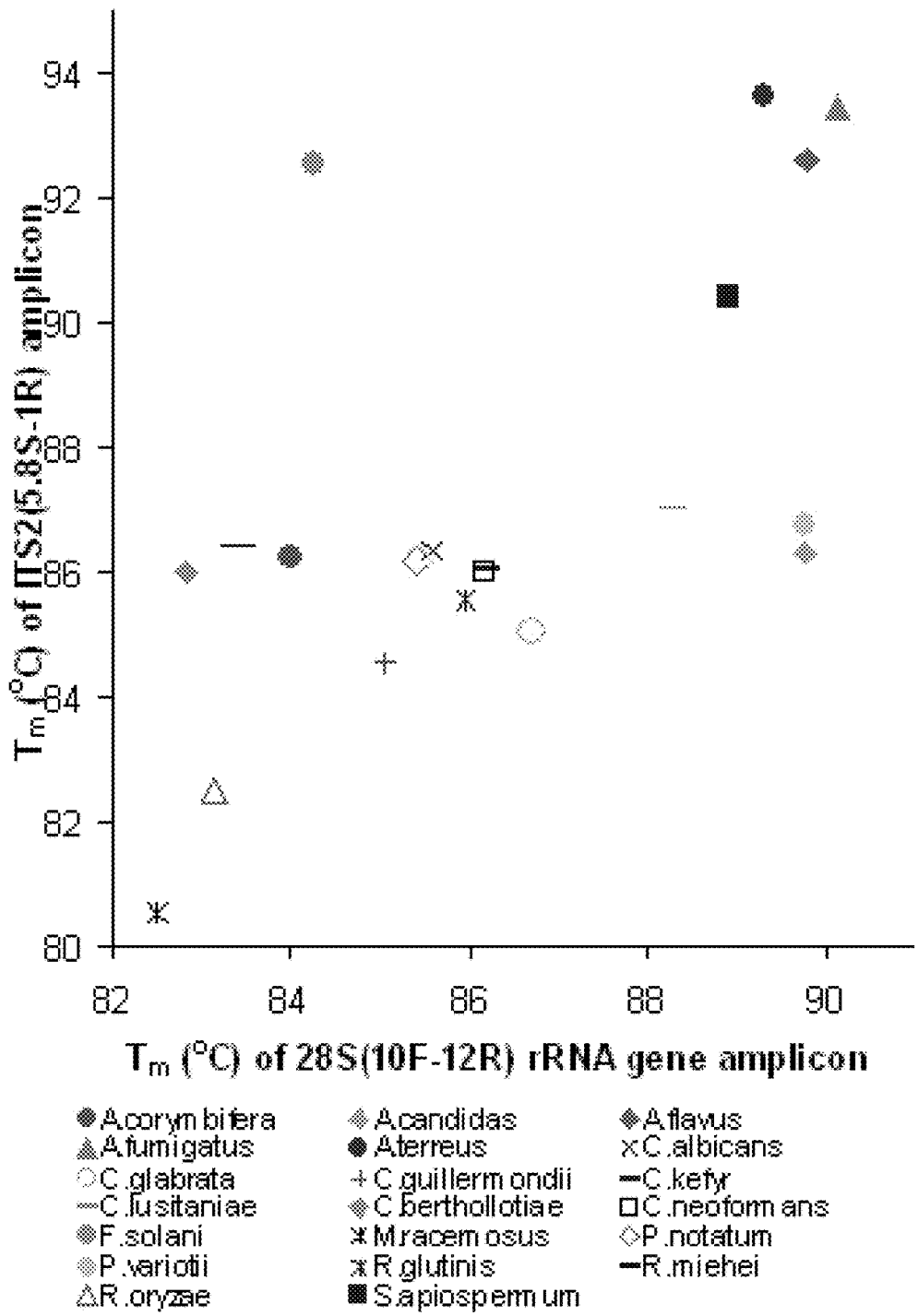

FIG. 62 illustrates a two-dimensional melt curve plot based on the broad-range fungal qPCR assays ITS2(5.8SF-1R) and 28S(10F-12R) allowing rapid identification of species.

Figure 63:
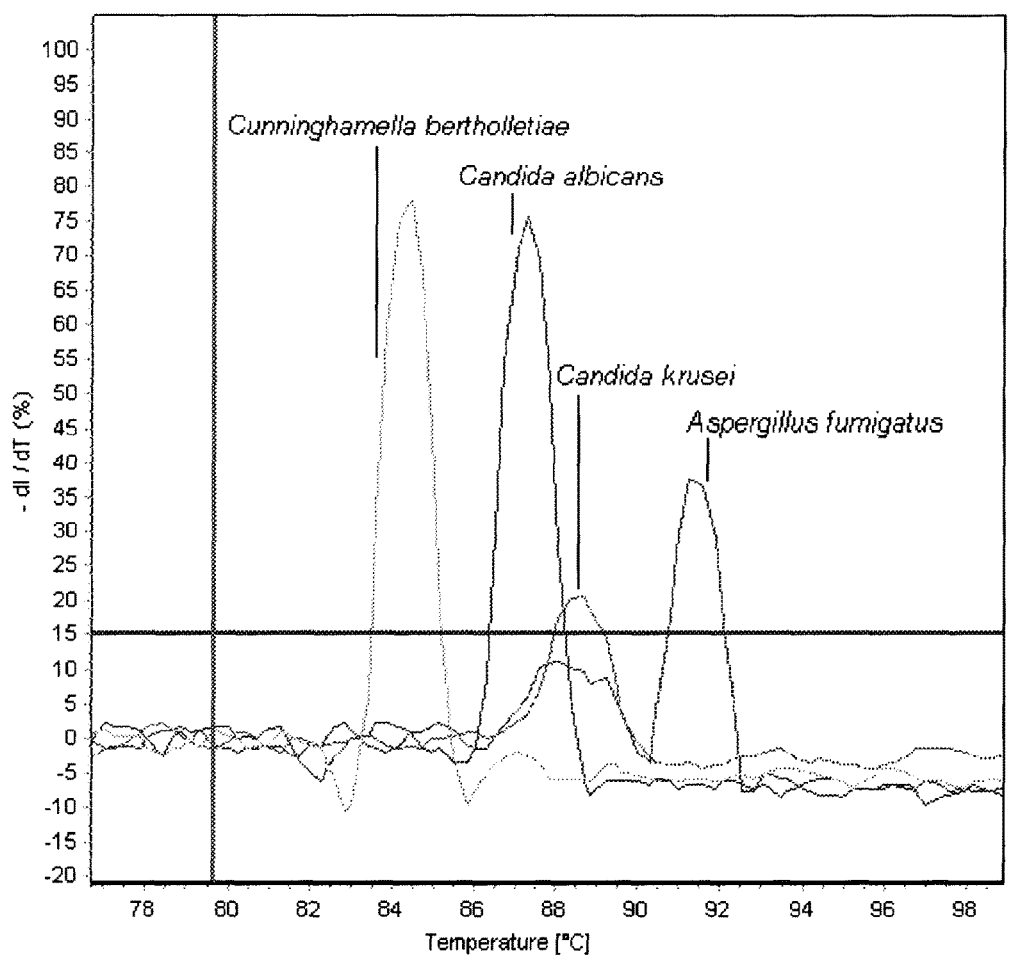

FIG. 63 illustrates melt temperature curves of pathogenic fungi amplified from blood, representing the 10-12 amplicon on the fungal 28S rRNA gene.

DETAILED DESCRIPTION OF THE DISCLOSURE

The present disclosure is based on the unexpected discovery that a specific fungal pathogen in a patient sample may be rapidly identified using broad-range PCR primers that specifically amplify fungal DNA including a portion of the rRNA gene, including a portion of an internal transcribed spacer 1 (ITS-1) region and/or a portion of a 28S rRNA gene. Methods using the primers and primer sets provided herein uniquely identify and differentiate among at least 27 different species of fungal pathogens, even in the presence of human DNA. Thus, the present methods are useful in a clinical setting for the rapid identification of one or more fungal pathogen(s) in a patient sample.

The primers, primer sets, and methods provided herein have both excellent analytical sensitivity and species level resolution which helps to overcome the potential shortcomings of the ITS regions. For PCR assays that use amplicon length or melting temperature of the amplicons to distinguish between species, a single amplicon approach may be insufficient, therefore use of more than one PCR target may be optimal. As described herein, the exemplary combination of ITS2(5.8SF-1R) and 28S(10F-12R) amplicons provides effective analytical sensitivity and potential for fungal species resolution.

To create a database of fungal sequences including the ITS1, 5.8S, ITS2 and 28S rRNA genes, 9 clinically and phylogenetically relevant fungal pathogens were sequenced and sequences from fungal genomic databases or the GenBank® genetic sequence database (herein, "GenBank®") for 41 fungal species were derived, resulting in an alignment of a total of 50 fungal sequences spanning 30 genera. In the nearly 3900 by region from the 3' end of 18S to the 3' end of 28S rRNA genes, 27 broad-range PCR primers were designed. Sixty two amplicons between the sizes of 75 to 400 by were selected for screening, with amplicon sizes minimized to enhance analytical sensitivity. Optimal PCR assays were selected based on their ability to detect phylogenetically diverse fungi and amplify small quantities of fungal DNA in the presence of large quantities of human DNA. The analysis of this region of the rRNA operon showed that there is nearly 2800 by of sequence beyond the D1-D2 region which is useful for the development of broad-range fungal PCR assays. As described herein, the 28S rRNA gene beyond the D1-D2 region was found to be useful for the design of broad-range fungal PCR assays with good species-level resolution and the potential to detect the equivalent of a single fungal genome (30 fg) in a background of 1 μg of human DNA, representing a 30,000,000 fold excess of non-fungal DNA.

The present disclosure will be best understood by reference to the following definitions:

DEFINITIONS

An "individual" or "subject", "mammal", "patient" or "animal", as used herein, refers to vertebrates that support a fungal infection, including, but not limited to, birds (such as water fowl and chickens) and members of the mammalian species, such as canine, feline, lupine, mustela, rodent (racine, and murine, etc.), equine, bovine, ovine, caprine, porcine species, and primates, the latter including humans.

As used herein, the term "isolated" means that the referenced material is removed from its native environment, e.g., a cell or fungus. Thus, an isolated biological material can be free of some or all cellular components, i.e., components of the cells in which the native material occurs naturally (e.g., cytoplasmic or membrane component). A material shall be deemed isolated if it is present in a cell extract or supernatant. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e. contaminants, including native materials from which the material is obtained. For example, a purified fungal DNA is preferably substantially free of cell or culture components, including tissue culture components, contaminants, and the like. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

As used herein, the terms "include" and "comprise" are used synonymously. It should be understood that the terms "a" and "an" as used herein refer to "one or more" of the enumerated components. The use of the alternative (e.g., "or") should be understood to mean either one, both, or any combination thereof of the alternatives.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of" mean±20% of the indicated range, value, or structure, unless otherwise indicated.

In a specific embodiment, the term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

The term "contig" as used herein, refers to one of a set of overlapping clones that represent a continuous region of DNA. However, in certain embodiments, "contig" also refers to a contiguous sequence constructed from many clone sequences or PCR products, and herein, is used synonymously with the term "sequence."

"Endpoint PCR" is understood to mean a semi-quantitative approach to measuring relative amounts of template (DNA) in a sample involving the measurement of the amount of PCR product present at the end of a PCR reaction. In certain embodiments of the present disclosure, end-point PCR is performed by resolving the PCR amplicon on an agarose gel and staining the gel with an "intercalating" dye, such as, for example, ethidium bromide. Ethidium bromide binds between the bases of the DNA helix. When it is inserted into the DNA, it becomes much more fluorescent when exposed to ultraviolet light as compared to ethidium bromide just in solution. This characteristic of ethidium bromide permits semi-quantitative measurements of the amount of DNA in the PCR product by measuring the degree of fluorescence of the PCR product in the gel.

The term "sample" as used in the present disclosure can be any tissue, fluid, or other source of DNA from a patient or mammal.

Techniques to isolate and modify specific nucleic acids and proteins are well known to those of skill in the art. In accordance with the present disclosure there may be employed conventional molecular biology, microbiology, and recombinant DNA techniques within the skill of the art. Such techniques are explained fully in the literature. See, e.g., Sambrook et al., Molecular Cloning: A Laboratory Manual, Second Edition (Cold Spring Harbor, N.Y.: Cold Spring Harbor Laboratory Press, 1989) ("Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); Perbal, "A Practical Guide To Molecular Cloning" (Ausubel, F. M. et al. eds., (1984)). Current Protocols in Molecular Biology (John Wiley & Sons, Inc., 1994). These techniques include site directed mutagenesis employing oligonucleotides with altered nucleotides for generating PCR products with mutations (e.g., the "Quikchange" kit manufactured by Stratagene).

DNA typing (or "genotyping") involves the analysis of alleles of genomic DNA with characteristics of interest, commonly referred to as "markers." Most typing methods in use today are specifically designed to detect and analyze differences in the length and/or sequence of one or more regions of DNA markers known to appear in at least two different forms in a population. Such length and/or sequence variation is referred to as "polymorphism." Any region (i.e., "locus") of DNA in which such a variation occurs is referred to as a "polymorphic locus."

The terms "nucleic acid" and "oligonucleotide," as used herein, refer to polydeoxyribonucleotides (containing 2-deoxy-D-ribose), to polyribonucleotides (containing D-ribose), and to any other type of polynucleotide which is an N glycoside of a purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA. For use in the present disclosure, an oligonucleotide also can comprise non-purine or non-pyrimidine nucleotide analogs. The length of a nucleic acid sequence is referred to as the number of "base pairs (bp)" present in the double-stranded nucleic acid sequence.

The nucleic acid molecules of sequences disclosed herein are written according to The International Union of Pure and Applied Chemistry (IUPAC) DNA codes. Specifically, "A" is Adenine, "C" is Cytosine, "G" is Guanine, "T" is Thymine, "U" is Uracil, "R" is any Purine (A or G), "Y" is any Pyrimidine (C, T, or U), "M" is C or A, "K" is T, U, or G, "W" is T, U, or A, "S" is C or G, "B" is C, T, U, or G (not A), "D" is A, T, U, or G (not C), "H" is A, T, U, or C (not G), "V" is A, C, or G (not T, not U), and "N" is any base (A, C, G, T, or U).

In certain embodiments, the amount of fungal DNA present in a sample is described in terms of the "fold-excess" of human or non-fungal DNA over the amount of fungal DNA present in the same sample. For example, if 1 µg of human genomic DNA is present in a sample that has 0.001 µg of fungal DNA, then the human DNA is understood to be in 1000-fold excess of the fungal DNA.

Oligonucleotides can be prepared by any suitable method, including direct chemical synthesis by a method such as the phosphotriester method of Narang et al. (1979) *Meth. Enzymol.* 68:90-99; the phosphodiester method of Brown et al., (1979) *Meth. Enzymol.* 68:109-151; the diethylphosphoramidite method of Beaucage et al. (1981) *Tetrahedron Lett.* 22:1859-1862; and the solid support method of U.S. Pat. No. 4,458,066, each incorporated herein by reference. A review of synthesis methods of conjugates of oligonucleotides and modified nucleotides is provided in Goodchild (1990) *Bioconjugate Chemistry* 1(3):165-187, incorporated herein by reference.

The term "primer," as used herein, refers to an oligonucleotide capable of acting as a point of initiation of DNA synthesis under conditions in which synthesis of a primer extension product complementary to a nucleic acid strand is induced, i.e., either in the presence of four different nucleoside triphosphates and an agent for extension (e.g., a DNA polymerase or reverse transcriptase) in an appropriate buffer and at a suitable temperature. A primer is preferably a single-stranded DNA. The appropriate length of a primer depends on the intended use of the primer but typically ranges from 6 to 50 nucleotides, preferably from 15-35 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein. As used herein, a "forward primer" is understood to mean a primer that is capable of hybridizing to a region of DNA along the 5' (coding) strand of DNA. A "reverse" primer is understood to mean a primer that is capable of hybridizing to a region of DNA along the 3' (non-coding) strand of DNA.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning of the amplified product. The region of the primer which is sufficiently complementary to the template to hybridize is referred to herein as the hybridizing region.

A "primer set" or "primer pair" refers to a specific combination of a forward primer and one or more reverse primers. Some "primer sets" or "primer pairs" may include, for example, one forward primer and two reverse primers (e.g., a primer set comprising SEQ ID NO: 12, SEQ ID NO: 41, and SEQ ID NO: 108). The "primer set" or "primer pair" may be used in a PCR reaction to generate a specific PCR product or amplicon.

The term "amplicon" as used herein, refers to the DNA sequence generated by a PCR or qPCR reaction. "Amplicon" may further be used synonymously with the term "PCR product."

In certain embodiments, the term "primer" is also intended to encompass the oligonucleotides used in ligation-mediated amplification processes, in which one oligonucleotide is "extended" by ligation to a second oligonucleotide which hybridizes at an adjacent position. Thus, the term "primer extension", as used herein, refers to both the polymerization of individual nucleoside triphosphates using the primer as a point of initiation of DNA synthesis and to the ligation of two oligonucleotides to form an extended product.

The terms "target, "target sequence", "target region", and "target nucleic acid," as used herein, are synonymous and refer to a region or subsequence of a nucleic acid which is to be amplified or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which only fully complementary nucleic acid strands will hybridize are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., (1989) Molecular Cloning—A Laboratory Manual (Cold Spring Harbor Laboratory, Cold Spring Harbor, N.Y.); and Wetmur (1991) *Critical Review in Biochem. and Mol. Biol.* 26(3/4): 227-259; both incorporated herein by reference).

The term "amplification reaction" refers to any chemical reaction, including an enzymatic reaction, which results in increased copies of a template nucleic acid sequence or results in transcription of a template nucleic acid. Amplification reactions include reverse transcription and the polymerase chain reaction (PCR), including Real Time PCR (see U.S. Pat. Nos. 4,683,195 and 4,683,202; PCR Protocols: A Guide to Methods and Applications (Innis et al., eds, 1990)). Exemplary "amplification reactions conditions" or "amplification conditions" typically comprise either two or three step cycles. Two step cycles have a denaturation step followed by a hybridization/elongation step. Three step cycles comprise a denaturation step followed by a hybridization step followed by a separate elongation step.

Polymerase chain reaction (PCR) is a method that allows exponential amplification of short DNA sequences (usually 100 to 600 bases) within a longer double stranded DNA molecule. PCR entails the use of a pair of primers, each about 20 nucleotides in length, that are complementary to a defined sequence on each of the two strands of the DNA. These primers are extended by a DNA polymerase so that a copy is made of the designated sequence. After making this copy, the same primers can be used again, not only to make another copy of the input DNA strand but also of the short copy made in the first round of synthesis. This leads to logarithmic amplification. Since it is necessary to raise the temperature to separate the two strands of the double strand DNA in each round of the amplification process, a major step forward was the discovery of a thermo-stable DNA polymerase (Taq polymerase) that was isolated from *Thermus aquaticus*, a bacterium that grows in hot pools; as a result it is not necessary to add new polymerase in every round of amplification. After several (often about 40) rounds of amplification, the PCR product is analyzed on an agarose gel and is abundant enough to be detected with an ethidium bromide stain.

In other embodiments, real-time PCR, also called quantitative real time PCR, quantitative PCR (Q-PCR/qPCR), or kinetic polymerase chain reaction, is a laboratory technique based on PCR, which is used to amplify and simultaneously quantify a targeted DNA molecule. qPCR enables both detection and quantification (as absolute number of copies or relative amount when normalized to DNA input or additional normalizing genes) of a specific sequence in a DNA sample. For example, in the embodiments disclosed herein, qPCR may be used to quantify the amount of fungal DNA in a patient sample. The procedure follows the general principle of PCR; its key feature is that the amplified DNA is quantified as it accumulates in the reaction in real time after each amplification cycle. Two common methods of quantification are the use of fluorescent dyes that intercalate with double-stranded DNA, and modified DNA oligonucleotide probes that fluoresce upon binding to complementary DNA (such as with molecular beacons) or with completion of each PCR cycle (such as with dual labeled probes rendered more fluorescent with the 5' exonuclease activity of polymerase enzymes).

As used herein, a "polymerase" refers to an enzyme that catalyzes the polymerization of nucleotides. Generally, the enzyme will initiate synthesis at the 3'-end of the primer annealed to a nucleic acid template sequence. "DNA polymerase" catalyzes the polymerization of deoxyribonucleotides. Known DNA polymerases include, for example, *Pyrococcus furiosus* (Pfu) DNA polymerase (Lundberg et al., (1991) *Gene* 108:1), *E. coli* DNA polymerase I (Lecomte and Doubleday (1983) *Nucleic Acids Res.* 11:7505), T7 DNA polymerase (Nordstrom et al. (1981) *J. Biol. Chem.* 256:3112), *Thermus thermophilus* (Tth) DNA polymerase (Myers and Gelfand (1991) *Biochemistry* 30:7661), *Bacillus stearothermophilus* DNA polymerase (Stenesh and McGowan (1977) *Biochim Biophys Acta* 475:32), *Thermococcus litoralis* (Tli) DNA polymerase (also referred to as Vent DNA polymerase, Cariello et al. (1991) *Nucleic Acids Res* 19:4193), *Thermotoga maritima* (Tma) DNA polymerase (Diaz and Sabino (1998) *Braz J. Med. Res* 31:1239), *Thermus aquaticus* (Taq) DNA polymerase (Chien et al., (1976) *J. Bacteriol* 127:1550), *Pyrococcus kodakaraensis* KOD DNA polymerase (Takagi et al. (1997) *Appl. Environ. Microbiol.* 63:4504), JDF-3 DNA polymerase (Patent application WO 0132887), and *Pyrococcus* GB-D (PGB-D) DNA polymerase (Juncosa-Ginesta et al. (1994) *Biotechniques* 16:820). The polymerase activity of any of the above enzymes can be determined by means well known in the art.

As used herein, a primer is "specific," for a target sequence if, when used in an amplification reaction under sufficiently stringent conditions, the primer hybridizes primarily only to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in most cases. Hybridization conditions can be chosen under which the primer can form stable duplexes only with a target sequence. Thus, the use of target-specific primers under suitably stringent amplification conditions enables the specific amplification of those target sequences which contain the target primer binding sites. The use of sequence-specific amplification conditions enables the specific amplification of those target sequences which contain the exactly complementary primer binding sites.

As used herein, "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides.

It is understood in the art that a nucleic acid molecule need not be 100% complementary to a target nucleic acid sequence to be specifically hybridizable. That is, two or more nucleic acid molecules may be less than fully complementary and is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

The term "non-specific amplification," as used herein, refers to the amplification of nucleic acid sequences other than the target sequence which results from primers hybridizing to sequences other than the target sequence and then serving as a substrate for primer extension. The hybridization of a primer to a non-target sequence is referred to as "non-specific hybridization" and is apt to occur especially during the lower temperature, reduced stringency, pre-amplification conditions.

The term "primer dimer," as used herein, refers to a template-independent non-specific amplification product, which is believed to result from primer extensions wherein another primer serves as a template. Although primer dimers frequently appear to be a concatamer of two primers, i.e., a dimer, concatamers of more than two primers also occur. The term "primer dimer" is used herein generically to encompass a template-independent non-specific amplification product.

The term "reaction mixture," as used herein, refers to a solution containing reagents necessary to carry out a given reaction. An "amplification reaction mixture", which refers to a solution containing reagents necessary to carry out an amplification reaction, typically contains oligonucleotide primers and a DNA polymerase or ligase in a suitable buffer. A "PCR reaction mixture" typically contains oligonucleotide primers, a DNA polymerase (most typically a thermostable DNA polymerase), dNTPs, and a divalent metal cation in a suitable buffer. A reaction mixture is referred to as complete if it contains all reagents necessary to enable the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction components which includes the blocked primers of the disclosure.

For the purposes of this disclosure, the term "activated," as used herein, refers to a primer or other oligonucleotide that is capable of participating in a reaction with DNA polymerase or DNA ligase. A primer or other oligonucleotide becomes activated when it hybridizes to a substantially complementary nucleic acid sequence and is chemically modified so that it can interact with a DNA polymerase or a DNA ligase. For example, when the oligonucleotide is a primer, and the primer is hybridized to a template, a 3'-blocking group can be removed from the primer by, for example, a cleaving enzyme such that DNA polymerase can bind to the 3' end of the primer and promote primer extension.

The term "fluorescent generation probe" refers either to a) an oligonucleotide having an attached fluorophore and quencher, and optionally a minor groove binder or to b) a DNA binding reagent such as Sybr® green dye.

The terms "fluorescent label" or "fluorophore" refers to compounds with a fluorescent emission maximum between about 350 and 900 nm. A wide variety of fluorophores can be used, including but not limited to: 5-FAM (also called 5-carboxyfluorescein; also called Spiro(isobenzofuran-1 (3H), 9'-(9H)xanthene)-5-carboxylic acid, 3',6'-dihydroxy-3-oxo-6-carboxyfluorescein); 5-Hexachloro-Fluorescein ([4,7,2',4',5',7'-hexachloro-(3',6'-dipivaloyl-fluoresceinyl)-6-carboxyli-c acid]); 6-Hexachloro-Fluorescein ([4,7,2',4', 5',7'-hexachloro-(3',6'-dipivaloylfluoresceinyl)-5-carboxylic acid]); 5-Tetrachloro-Fluorescein ([4,7,2',7'-tetra-chloro-(3', 6'-dipivaloylfluoresceinyl)-5-carboxylic acid]); 6-Tetra-chloro-Fluorescein ([4,7,2',7'-tetrachloro-(3',6'-dipivaloyl-fluoresceinyl)-6-carboxylic acid]); 5 -TAMRA (5-carboxytetramethylrhodamine; Xanthylium, 9-(2,4-dicarboxyphenyl)-3,6-bis(dimethyl-amino); 6-TAMRA (6-carboxytetramethylrhodamine; Xanthylium, 9-(2,5-dicarboxyphenyl)-3,6-bis(dimethylamino); EDANS (5-((2-aminoethyl)amino)naphthalene-1-sulfonic acid); 1,5-IAEDANS (5-((((2-iodoacetyl)amino)ethyl)amino) naphthalene-1-sulfonic acid); DABCYL (4-((4-(dimethylamino)phenyl)azo)benzoic acid) Cy5 (Indodicarbocyanine-5) Cy3 (Indodicarbocyanine-3); and BODIPY FL (2,6-dibromo-4,4-difluoro-5,7-dimethyl-4-bora-3a,4a-diaza-s-indacene-3-pr-oprionic acid), Quasar-670 (Biosearch Technologies), CalOrange (Biosearch Technologies), Rox, as well as suitable derivatives thereof.

The term "ligation" as used herein refers to the covalent joining of two polynucleotide ends. In various embodiments, ligation involves the covalent joining of a 3' end of a first polynucleotide (the acceptor) to a 5' end of a second polynucleotide (the donor). Ligation results in a phosphodiester bond being formed between the polynucleotide ends. In various embodiments, ligation may be mediated by any enzyme, chemical, or process that results in a covalent joining of the polynucleotide ends. In certain embodiments, ligation is mediated by a ligase enzyme.

As used herein, "ligase" refers to an enzyme that is capable of covalently linking the 3' hydroxyl group of a nucleotide to the 5' phosphate group of a second nucleotide. Examples of ligases include E. coli DNA ligase, T4 DNA ligase, etc.

The ligation reaction can be employed in DNA amplification methods such as the "ligase chain reaction" (LCR), also referred to as the "ligase amplification reaction" (LAR), see Barany (1991) *Proc. Natl. Acad. Sci. U.S.A.* 88:189; and Wu and Wallace (1989) *Genomics* 4:560, incorporated herein by reference. In LCR, four oligonucleotides, two adjacent oligonucleotides which uniquely hybridize to one strand of the target DNA, and a complementary set of adjacent oligonucleotides, that hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA. LCR has also been used in combination with PCR to achieve enhanced detection of single-base changes, see Segev PCT Pub. No. WO/9001069.

As used herein, the term "conserved region" or "conserved sequence" refers to a nucleic acid sequence in a region of a gene that is the same or highly similar across different species. For example, a sequence or region of a gene that is conserved may have the same nucleic acid sequence in several types of fungal species, or, in some cases, may have the same or highly similar sequence across different taxonomic phyla (e.g., a human DNA sequence and a fungal DNA sequence in a highly conserved region of a gene may be the same or highly similar). Conversely, a "highly variable" or "hypervariable" region or sequence of gene is not conserved across species or phyla, and will have many nucleotides differences in the hypervariable region in the gene from each species.

Methods for Identifying Fungal Pathogens

As described above, fungal infections remain a major cause of morbidity and mortality in immunocompromised patients. Cultivation-based methods have poor diagnostic sensitivity for many fungal infections, which has led to the adoption of other diagnostic approaches such as detection of fungal antigens. However, antigen-based assays such as the galactomannan and glucan assays do not detect all fungal species. Thus, there is a need in the art (1), for reliable methods for the detection of fungal pathogen, especially in the context of human DNA (in samples from infected patients, human and fungal DNA are mixed together), and (2), for reliable methods for accurately and rapidly distinguishing among different species of fungi.

Thus, disclosed herein are methods for detecting a fungal pathogen in a patient sample. The methods disclosed herein target the fungal rRNA operon, which is a continuous sequence made of the 18S, ITS1, 5.8S, ITS2, and 28S subunit regions [Iwen et al. (2002) *Med. Mycol.* 40:87-109]. Because certain aspects of the operon are highly conserved among a broad range of fungi, while other regions, such as the D1-D2 hypervariable region are not conserved among species, the DNA sequences of the operon can be targeted by broad range PCR assays for the identification of fungal infection and for the determination of the specific fungal species. The human rRNA operon is also a continuous sequence made of the 18S, ITS1, 5.8S, ITS2, and 28S subunit regions, and has considerable sequence homology with the fungal rRNA operon. Thus, a critical aspect of the present disclosure provides methods and PCR primers which do not cross-react with human DNA. The present disclosure provides PCR primers which amplify regions that are 3' to the D1-D2 hypervariable region specifically because they are discovered to have less cross-reactivity to human DNA. This is especially critical for the identification of fungal DNA in patient samples, which also contain human DNA.

"Broad-range" PCR primers as disclosed herein may be understood to be primers that hybridize with conserved regions of fungal DNA, and thus are useful in PCR assays that detect the presence of a wide range of fungal pathogens.

In certain aspects of the disclosure, the method includes the steps of (a) isolating a patient sample, (b) carrying out a PCR reaction on the patient sample to generate a PCR amplicon that includes a region of a fungal 28S ribosomal RNA (rRNA) gene, wherein the PCR reaction uses a primer set having a forward primer and a reverse primer wherein at least one of the forward primer and the reverse primer is complementary to the fungal 28S rRNA gene, and (c) detecting the PCR amplicon. The patient sample may be, for example, a blood sample, a sputum sample, a lung lavage fluid sample, or a tissue biopsy sample. Any fluid, tissue, or other source of DNA from a patient may constitute a sample in the present disclosure.

The PCR reaction carried out on the patient sample may be performed according to any of the methods known in the art. The purpose of the PCR reaction is to amplify a target sequence within a fungal DNA sequence, thereby generating a PCR amplicon. Preferably, the region amplified by the PCR reaction is in the 28S region of the fungal rRNA gene. More preferably, the region of the fungal 28S rRNA gene detected by PCR includes a sequence that is 3' to a D1-D2 highly variable region of the fungal 28S rRNA gene. The PCR assays of the present disclosure target this region, achieving resolution among different species of fungi without cross-reacting with or being inhibited by the presence of human DNA.

In certain embodiments, PCR reactions are used to detect fungal DNA in a sample. In other embodiments, qPCR reactions are used to detect fungal DNA in a sample. In yet other embodiments, alternative methods other than PCR, such as ligase chain reaction, may be used to detect the presence of fungal DNA in a sample. Alternatively, Nucleic Acid Sequence Based Amplification (NASBA) could be used to amplify fungal rRNA directly from tissues using these primers. Any method suitable for amplifying a region of the target fungal gene (rDNA) or rRNA is contemplated in the present disclosure.

In certain aspects of the present disclosure, the methods for detecting a fungal pathogen disclosed herein further involve the step of sequencing the PCR amplicon derived from sequencing. In some aspects, the PCR amplicon is between 50 and 1000 base pairs, and preferably, between 75 and 400 base pairs. Smaller amplicon sizes are desirable, since they are easier to sequence and useful for qPCR reactions. However, it is also important that the amplicon be large enough to facilitate accurate species identification, e.g., enhance resolution among different fungal species.

Sequencing of the PCR amplicon may be carried out according to any methods known in the art suitable for determining the sequence of a PCR amplicon. The sequences of the PCR amplicons disclosed in the present invention are unique to each type of fungal pathogen, thereby allowing identification of the specific type of fungal DNA in a sample.

In certain embodiments, methods for the detection of fungal DNA involving the step of carrying out a PCR reaction on a patient sample are provided, wherein each primer of the primer set in the PCR reaction specifically binds only to a fungal DNA. Preferably, each primer of the primer set specifically binds only to a fungal DNA in the presence of a non-fungal DNA. In some embodiments, the non-fungal DNA is mammalian DNA. In other embodiments, the mammalian DNA is human DNA. In yet other embodiments, the non-fungal DNA is in greater than 1,000,000-fold, 5,000,000-fold, or 30,000,000-fold mass excess of the fungal DNA.

In some aspects, methods for detecting a fungal pathogen are provided, wherein the fungal pathogen causes a fungal infection selected from the group consisting of aspergillosis, candidiasis, zygomycosis, scedosporiosis, fusariosis, cryptococcosis, histoplasmosis, coccidioidomycosis, and blastomycosis.

Primer Sequences for Identifying Fungal DNA

In certain embodiments of the present disclosure, specific sequences of the forward and reverse primers of the PCR reaction for identifying fungal DNA are disclosed. In certain embodiments, the forward primer of the PCR reaction is complementary to a fungal 18S rRNA gene and the reverse primer is complementary to a fungal 28S rRNA gene. In still other embodiments, the forward primer comprises the nucleotide sequence 5'-GTAAAAGTCGTAACAAGGTTTC-3' (SEQ ID NO: 1). In yet other embodiments, the forward primer is complementary to a fungal 5.8S rRNA gene and the reverse primer is complementary to a fungal 28S rRNA gene. In still other embodiments, the forward primer includes the nucleotide sequence 5'-GTGAATCATCGARTCTTTGAAC-3' (SEQ ID NO: 2). In certain other aspects of the present disclosure, the forward primer and the reverse primer of the PCR reaction for detecting fungal DNA in a patient sample are both complementary to a fungal 28S rRNA gene.

In certain embodiments disclosed herein, a primer set for detecting a fungal DNA by PCR is provided, wherein the primer set includes a forward primer and a reverse primer wherein at least one of the forward primer and the reverse primer is complementary to a fungal 28S ribosomal RNA (rRNA) gene. In certain embodiments, the forward primer or the reverse primer of the primer set is complementary to a sequence that is 3' to a D1-D2 highly variable region in the fungal 28S ribosomal rRNA gene. In yet other embodiments, the forward primer of the primer set is complementary to a fungal 18S rRNA gene and the reverse primer is complementary to a fungal 28S rRNA gene. In other embodiments, the forward primer and the reverse primer of the primer set are both complementary to a fungal 28S rRNA gene.

In other aspects of the present disclosure, the forward primer of the PCR reaction or of the primer set for detecting fungal DNA in a sample may have one of the following sequences:

| Sequence | |
|---|---|
| 5'-GTAAAAGTCGTAACAAGGTTTC-3', | (SEQ ID NO: 1) |
| 5'-GTGAATCATCGARTCTTTGAAC-3', | (SEQ ID NO: 2) |
| 5'-TACCCGCTGAACTTAAGCATA-3', | (SEQ ID NO: 3) |
| 5'-GCATATCAATAAGCGGAGGAAA-3', | (SEQ ID NO: 4) |
| 5'-AGTARCGGCGAGTGAAGCGG-3', | (SEQ ID NO: 5) |
| 5'-AGCTCAAATTTGAAASCTGG-3', | (SEQ ID NO: 6) |
| 5'-CTTCCCTTTCAACAATTTCACRT-3', | (SEQ ID NO: 7) |
| 5'-AGGTAAAGCGAATGATTAG-3', | (SEQ ID NO: 8) |
| 5'-CTTGTTRCTTARTTGAACGTG-3', | (SEQ ID NO: 9) |
| 5'-ACCACAAAAGGTGTTAGTWCATC-3', | (SEQ ID NO: 10) |
| 5'-GAAGTGGGGAAAGGTTCC-3', | (SEQ ID NO: 11) |
| 5'-GACATGGGTTAGTCGATCCTA-3', | (SEQ ID NO: 12) |
| 5'-TCGTACTCATAACCGCAGC-3', | (SEQ ID NO: 13) |
| 5'-GTTGATAGAAYAATGTAGATAAGG-3', | (SEQ ID NO: 14) |
| 5'-CAAGGGGAATCTGACTGTC-3', | (SEQ ID NO: 15) |
| 5'-TTTACTTAWTCAATGAAG CGG-3', | (SEQ ID NO: 16) |
| 5'-CCGGGTTGAWGACATTGTCA-3', | (SEQ ID NO: 17) |
| 5'-GCTGGGCGGCACATCTGTT-3', | (SEQ ID NO: 18) |
| 5'-GAACAAAAGGGTAAAAGTCCC-3', | (SEQ ID NO: 19) |
| 5'-TTTGATTTTCAGTGTGAATACAAACCA-3', | (SEQ ID NO: 20) |
| 5'-ATGAAAGTGTGGCCTATCG-3', | (SEQ ID NO: 21) |
| 5'-GAGGCTAGAGGTGCCAGAA-3', | (SEQ ID NO: 22) |
| 5'-AGGGATAACTGGCTTGTGGC-3', | (SEQ ID NO: 23) |
| 5'-ACCGAAGCAGAATTCGGTAAG-3', | (SEQ ID NO: 24) |
| 5'-GATAAT TGGTWTTTGCGGCTG-3', | (SEQ ID NO: 25) |
| 5'-GCTGAACGCCTCTAAGTCAGA-3', | (SEQ ID NO: 26) |
| and | |
| 5'-TCGTARCAACAAGGCTACT-3'. | (SEQ ID NO: 27) |

In yet other aspects of the present disclosure, the reverse primer of the PCR reaction or of the primer set for detecting fungal DNA may include one of the following sequences:

| Sequence | |
|---|---|
| 5'-GAAACCTTGTTACGACTTTTAC-3', | (SEQ ID NO: 28) |
| 5'-GTTCAAAGAYTCGATGATTCAC-3', | (SEQ ID NO: 29) |
| 5'-TATGCTTAAGTTCAGCGGGTA-3', | (SEQ ID NO: 30) |
| 5'-TTTCCTCCGCTTATTGATATGC-3', | (SEQ ID NO: 31) |
| 5'-CCGCTTCACTCGCCGYTACT-3', | (SEQ ID NO: 32) |
| 5'-CCAGSTTTCAAATTTGAGCT-3', | (SEQ ID NO: 33) |
| 5'-AYGTGAAATTGTTGAAAGGGAAG-3', | (SEQ ID NO: 34) |
| 5'-CTAATCATTCGCTTTACCTC-3', | (SEQ ID NO: 35) |
| 5'-CACGTTCAAYTAAGYAACAAG-3', | (SEQ ID NO: 36) |
| 5'-GATGWACTAACACCTTTTGTGGT-3', | (SEQ ID NO: 37) |
| 5'-GGAACCTTTCCCCACTTC-3', | (SEQ ID NO: 38) |
| 5'-TAGGATCGACTAACCCATGTC-3', | (SEQ ID NO: 39) |
| 5'-GCTGCGGTTATGAGTACGA-3', | (SEQ ID NO: 40) |
| 5'-CCTTATCTACATTRTTCTATCAAC-3', | (SEQ ID NO: 41) |
| 5'-GACAGTCAGATTCCCCTTG-3', | (SEQ ID NO: 42) |
| 5'-CCGCTTCATTGAWTAAGTAAA-3', | (SEQ ID NO: 43) |
| 5'-TGACAATGTCWTCAACCCGG-3', | (SEQ ID NO: 44) |
| 5'-AACAGATGTGCCGCCCCAGC-3', | (SEQ ID NO: 45) |
| 5'-GGGACTTTTACCCTTTTGTTC-3', | (SEQ ID NO: 46) |
| 5'-TGGTTTGTATTCACACTGAAAATCAAA-3', | (SEQ ID NO: 47) |
| 5'-CGATAGGCCACACTTTCAT-3', | (SEQ ID NO: 48) |

```
5'-TTCTGGCACCTCTAGCCTC-3',         (SEQ ID NO: 49)

5'-GCCACAAGCCAGTTATCCCT-3',        (SEQ ID NO: 50)

5'-CTTACCGAATTCTGCTTCGGT-3',       (SEQ ID NO: 51)

5'-CAGCCGCAAAWACCAATTATC-3',       (SEQ ID NO: 52)

5'-TCTGACTTAGAGGCGTTCAGC-3',       (SEQ ID NO: 53)

5'-AGTAGCCTTGTTGYTACGA-3',         (SEQ ID NO: 54)
and

5'-CCTTATCTACATTATTCTATGGAC-3'.    (SEQ ID NO: 108)
```

In certain embodiments disclosed herein, the PCR reaction for detecting fungal DNA includes a forward and reverse primer pair (or primer set) selected from the group consisting of (SEQ ID NO: 2 and SEQ ID NO: 31), (SEQ ID NO: 2 and SEQ ID NO: 32), (SEQ ID NO: 11 and SEQ ID NO: 41), (SEQ ID NO: 1 and SEQ ID NO: 29), (SEQ ID NO: 2 and SEQ ID NO: 30), (SEQ ID NO: 12 and SEQ ID NO: 41), (SEQ ID NO: 14 and SEQ ID NO: 42), (SEQ ID NO: 17 and SEQ ID NO: 51), (SEQ ID NO: 20 and SEQ ID NO: 51), (SEQ ID NO: 20 and SEQ ID NO: 52), and (SEQ ID NO: 25 and SEQ ID NO: 54). More preferably, the primer set includes a forward and reverse primer pair selected from the group consisting of (SEQ ID NO: 1 and SEQ ID NO: 29), (SEQ ID NO: 2 and SEQ ID NO: 30), (SEQ ID NO: 12 and SEQ ID NO: 41), (SEQ ID NO: 14 and SEQ ID NO: 42), (SEQ ID NO: 17 and SEQ ID NO: 51), (SEQ ID NO: 20 and SEQ ID NO: 51), (SEQ ID NO: 20 and SEQ ID NO: 52), and (SEQ ID NO: 25 and SEQ ID NO: 54), and still more preferably, the primer set includes a forward and reverse primer pair selected from the group consisting of (SEQ ID NO: 2 and SEQ ID NO: 30), (SEQ ID NO: 12 and SEQ ID NO: 41), and (SEQ ID NO: 12, SEQ ID NO: 41, and SEQ ID NO: 108).

In certain aspects, the primer set includes a forward and reverse primer pair selected from the group consisting of (SEQ ID NO: 11 and SEQ ID NO: 41), (SEQ ID NO: 12 and SEQ ID NO: 41), (SEQ ID NO: 12, SEQ ID NO: 41, and SEQ ID NO: 108), (SEQ ID NO: 14 and SEQ ID NO: 42), (SEQ ID NO: 17 and SEQ ID NO: 51), (SEQ ID NO: 20 and SEQ ID NO: 51), (SEQ ID NO: 20 and SEQ ID NO: 52), and (SEQ ID NO: 25 and SEQ ID NO: 54).

It is to be understood in the present disclosure that any of the primer sequences disclosed herein may be modified without departing from the intended scope of the disclosure. Specifically, nucleotide substitutions, deletions and/or additions may be introduced into any of the primer sequences disclosed herein without altering the ability of the primers to identify fungal DNA. Moreover, it is to be understood that the lengths of the primers may be shorter or longer than the sequences disclosed herein.

In certain embodiments of the present disclosure, methods and primer sets for detecting fungal DNA are provided which detect DNA from a fungal species such as, but not limited to *Absidia corymbifera*; *Cunninghamella bertholletiae*; *Fusarium solani*; *Mucor racemosus*; *Paecilomyces variotii*; *Penicillium chrysogenum*; *Rhizomucor miehei*; *Rhodotorula glutinis*; *Scedosporium apiospermum*; *Antrodia vaillantii*; *Aspergillus fumigatus*; *Aspergillus niger*; *Aspergillus oryzae*; *Aspergillus terreus*; *Batrachochytrium dendrobatidis*; *Botrytis cinerea*; *Candida albicans*; *Candida dublineinsis*; *Candida glabrata*; *Candida gulliermundei*; *Candida kefyr*; *Candida krusei*; *Candida lipolytica*; *Candida lusitaniae*; *Candida parapsilosis*; *Candida tropicalis*; *Chaetomium globosum*; *Coccidioides immitis*; *Coccidioides posadasii*; *Cryptococcus neoformans*; *Fusarium graminearum*; *Fusarium oxysporum*; *Histoplasma capsulatum*; *Hypocrea jecorina*; *Lodderomyces elongisporus*; *Magnaporthe grisea*; *Metarhizium anisopliae*; *Microsporum gypseum*; *Mucor racemosus*; *Neurospora crassa*; *Paracoccidioides brasiliens*; *Pneumocystis carinii*; *Penicillium verrucosum*; *Pichia stipitis*; *Rhizomucor miehei*; *Rhizopus oryzae*; *Saccharomyces cerevisiae*; *Schizosaccharomyces japonicus*; *Schizosaccharomyces pombe*; *Sclerotinia sclerotiorum*; *Stagonospora nodorum*; *Umbilicaria esculenta*; or *Uncinocarpus reesii*.

In certain embodiments, the methods described herein may be used to detect DNA from other known fungi not specifically disclosed herein and from newly identified fungal species. In other words, the methods provided herein are useful for detecting a broad range of fungal DNA, and are not limited to the specific examples of fungal species disclosed herein.

Methods for Identifying Alternative Primers for Identifying Fungal DNA

Also disclosed herein are methods for identifying a primer set capable of detecting a fungal pathogen in a sample, the method including the steps of: (a) obtaining the DNA sequence of at least the 28S region of a fungal rRNA operon, (b) designing a forward primer capable of hybridizing with the DNA sequence, (c) designing a reverse primer capable of hybridizing with the DNA sequence at a region in the DNA that is 3' to the region to which the forward primer is capable of hybridizing, (d) testing whether the forward and reverse primers are capable of generating a PCR amplicon that is useful for identifying fungal DNA using a PCR reaction containing fungal DNA.

In certain embodiments, the method also includes the steps of testing the forward and reverse primers in a PCR reaction containing fungal DNA and human DNA. In yet other embodiments, the method includes running the PCR amplicon on an agarose gel and determining the product size. In still other embodiments, the method includes sequencing the PCR amplicon.

In yet other embodiments, the analytical sensitivity and cross-reactivity (i.e., degree of species resolution) of a specific primer set may be determined by testing the specific primer set on a panel of individual samples, each sample containing genomic DNA isolated from a single, distinct fungal species. An amplicon is generated by each PCR reaction containing the isolated genomic fungal DNA. Each amplicon is then sequenced and the sequences of each amplicon are compared. In certain embodiments, the sequence of each amplicon is compared using multiple sequence alignment, for example using the Clustal W algorithm. The Clustal W algorithm aligns two or more sequences simultaneously, such that regions of identical and similar residues are aligned. Clustal W does a pairwise comparison of every sequence first and then starts the multiple alignment with the pair of sequences that is most similar. Sequences are added one by one to the alignment based on their similarities to the starting pair. The software for using Clustal W alignment is freely available on the World Wide Web at the European Bioinformatics Institute website (http://www.ebi.ac.uk/Tools/clustalw2/index.html). Any algorithm suitable for comparing multiple sequences may be used, such as, e.g., the Needleman-Wunsch algorithm or the Smith-Waterman algorithm. The number of nucleotide differences among each amplicon is determined and assembled in a distance matrix, such as for example, using Microsoft Excel. The distance matrix is generated using Accelrys Gene® software (Accelrys, Inc., San Diego, Calif.). If species resolution within a genus or between any two species is desired, the comparison of distance matrix data can help select which amplicon (primer pair) would provide the most species resolution.

In other embodiments, phylogenetic trees may be assembled based on the Neighbor-Joining tree building method and distances estimated from the Tajima-Nei or absolute difference algorithms also using the Accelrys Gene® software (Accelrys, Inc.) or other similar tools. The Neighbor-Joining tree building method is described in detail in Saitou and Nei (1987) *Mol. Biol. Evol.* 4:406-25, and the Tajima-Nei algorithm is described in detail in Tajima and Nei (1984) *Mol. Biol. Evol.* 1:269-85, both incorporated herein by reference in their entireties. A phylogenetic tree compares the distance between two species, usually interpreted as evolutionary distance, as determined by the number of varying nucleotide positions in a sequence such as a specific PCR product generated by broad-range fungal PCR. Other examples of algorithms that may be used to construct phylogenetic trees include maximum likelihood, minimum evolution, and parsimony. Other distance-based methods include unweighted pair-group method using arithmetic averages, BIONJ, and the Weighbor algorithm or "weighted NJ". These algorithms and methods are well known in the art and are described in detail in Hollich, V. et al. (2005) Molecular Biology and Evolution; 22(11):2257-2264, which is herein incorporated by reference in its entirety.

In still other embodiments, the distance matrices and phylogenetic trees are used to determine which PCR primer sets generate amplicons that permit the highest degree of species resolution. The primers that give the highest degree of resolution among distinct fungal species are selected for further use.

Two-Dimensional Melt-Curve Analysis for the Identification of Fungal DNA

In certain embodiments, methods are provided for both the detection of fungal DNA in a patient sample, and further, for determining which type of fungal infection is present using two-dimensional melt curve analysis.

In the two-dimensional melt curve analysis, a melting profile of a PCR amplicon can be characterized by measuring fluorescence of a DNA binding dye. Specifically, each double-stranded DNA has its own specific melting temperature (Tm), which is defined as the temperature at which 50% of the DNA becomes single stranded. These melting temperatures are primarily determined by dsDNA length, degree of GC content (Tm is higher in GC-rich fragments), and degree of complementarity between strands (e.g., especially important in heteroduplexes consisting of a probe and a single-stranded target DNA sequence). With the use of DNA-binding dyes such as SYBR® Green I, a melt-curve profile can be generated. A thermal cycler system records the total fluorescence generated by the fluorescent DNA binding dye binding to double-stranded DNA as temperature changes, and plots the fluorescence in real time as a function of temperature. The first derivative of this plot, dF/dT, is the rate of change of fluorescence in the reaction, and a significant change in fluorescence accompanies the melting of the double-stranded PCR products. A plot of −dF/dT vs. temperature will display these changes in fluorescence as distinct peaks. The melting temperature (Tm) of each product is defined as the temperature at which the corresponding peak maximum occurs. Importantly, each unique amplicon will have a unique Tm that distinguishes it from each different amplicon.

The present disclosure provides methods for characterizing the melting profiles of amplicons generated from known fungi, and further, for using this information to infer the identity of a fungus from an unknown sample. Moreover, using information from more than one amplicon, as disclosed in the present invention, further increases species resolution. Specifically, in certain embodiments, a first amplicon is generated in the ITS2 region of the rRNA operon, and a second amplicon is generated in the 28S region. The Tm is determined for each amplicon, and the combination of the two Tm uniquely identifies a fungal species.

In certain embodiments disclosed herein, a method for determining the identity of a fungal species in a patient sample is provided, wherein the method includes the steps of: isolating the patient sample; carrying out a first PCR reaction to generate a first PCR amplicon, wherein the first PCR reaction includes a first primer set capable of amplifying a region in a fungal ribosomal RNA (rRNA) gene having an internal transcribed spacer 2 (ITS-2) sequence; carrying out a second PCR reaction to generate a second PCR amplicon, wherein the second PCR reaction has a second primer set capable of amplifying a region in a fungal ribosomal 28-S rRNA gene; and determining the melting temperature of the first PCR amplicon and of the second PCR amplicon, wherein the identity of the fungal species is determined by comparing the melting point of the first PCR amplicon and of the second PCR amplicon to known standards.

This method has the advantage that the melt curve analysis can be carried out very quickly, without the need for sequencing the PCR amplicon, at the end of each PCR reaction.

In certain aspects disclosed herein, the first and second PCR reactions carried out for determining the identity of a fungal species in a patient sample are each quantitative PCR (qPCR) reactions. In other aspects, the first primer set includes a forward primer sequence as set forth in SEQ ID NO: 2 and a reverse primer sequence as set forth in SEQ ID NO: 30, and the second primer set includes a forward primer sequence as set forth in SEQ ID NO: 12 and a reverse primer sequence as set forth in SEQ ID NO: 41. In some aspects, the second primer set includes a forward primer sequence as set forth in SEQ ID NO: 12, a first reverse primer sequence as set forth in SEQ ID NO: 41, and a second primer sequence as set forth in SEQ ID NO: 108.

In certain embodiments, the two-dimensional melt curve analysis is useful for resolving multiple fungal infections in a single patient sample. For example, if DNA is present from two fungal species, then one primer set, targeted, for example, to the ITS2 region, will generate two distinct amplicons with distinct melting curves. Then, a second primer set, targeted, for example, to the 28S region in a separate PCR reaction, will amplify two distinct amplicons with two distinct melting temperatures. Since each fungal species has a unique combination of melting temperatures for each amplicon, these melting temperatures can be combined to determine which fungal species are present. Certain fungal species are more likely to be present in a co-infection, and this information can also be used to determine the two types of fungal species present in the sample. This method is highly useful in the clinical setting because it can be performed rapidly. According to conventional methods, the individual PCR products would have to be cloned before sequencing in order to resolve multiple fungal species.

In still other embodiments, when two or more fungal infections are present, the two-dimensional melt curve analysis may be used to narrow down the list of possible fungi. Thereafter, a taxon-specific PCR reaction may be performed to confirm the suspected type of fungal infections. These taxon specific PCR reactions amplify regions of fungal DNA that are unique to a specific fungal species.

All U.S. patents, U.S. patent application publications, U.S. patent applications, foreign patents, foreign patent applications, non-patent publications, figures, tables, and websites referred to in this specification are expressly incorporated herein by reference, in their entirety.

EXAMPLES

The above disclosure generally describes the present disclosure, which is further exemplified by the following examples. These specific examples are described solely for purposes of illustration, and are not intended to limit the scope of this disclosure. Although specific targets, terms, and values have been employed herein, such targets, terms, and values will likewise be understood as exemplary and non-limiting to the scope of this disclosure.

Example 1

Materials and Methods used in Examples 2-6

This Example discloses the materials and methods used in Examples 2 through 6 of the present disclosure.

Microorganisms

Table 1 lists 9 clinically or phylogenetically relevant fungal pathogens subjected to sequencing of their ITS, 5.8S, and 28S rRNA genes. Table 2 lists 43 fungi of which the same gene sequences were obtained from publicly available genomic databases or GenBank®. Genomic DNA of the following organisms was used for analytical sensitivity testing to screen broad-range fungal primers: *Aspergillus candidus* (ATCC # 20022), *Aspergillus flavus* (ATCC # MYA-3631), *Aspergillus fumigatus* (ATCC # MYA-1163), *Aspergillus oryzae* (ATCC # 20719), *Aspergillus terreus* (ATCC # 10070), *Aspergillus ustus* (ATCC # 20063), *Candida albicans* (ATCC # 90028), *Candida dubliniensis* (ATCC # MYA-580), *Candida glabrata* (ATCC # 90876), *Candida guilliermondii* (ATCC # 90877), *Candida kefyr* (ATCC # 28838), *Candida krusei* (clinical isolate), *Candida lusitaniae* (ATCC # 42720), *Candida parapsilosis*, *Candida tropicalis* (clinical isolate), *Rhizopus oryzae* (ATCC # 10260), *Saccharomyces cerevisiae* (Novagen, Madison, Wis.), and *Cryptococcus neoformans* (ATCC # 28958D-5). In addition, the genomic DNA of 9 organisms listed in Table 1 was tested.

TABLE 1

Fungal Pathogens in which rRNA Gene Sequence was Obtained De novo

| SEQ ID NO | Fungal Pathogen | ATCC # | GenBank ® Accession # | Length (bp) | Figure |
|---|---|---|---|---|---|
| 55 | Absidia corymbifera | 14058 | FJ345350 | 3733 | 8 |
| 56 | Cunninghamella bertholletiae | 42115 | FJ345351 | 4035 | 9 |
| 57 | Fusarium solani | 56480 | FJ345352 | 3830 | 10 |
| 58 | Mucor racemosus | 42647 | FJ345353 | 3999 | 11 |
| 59 | Paecilomyces variotii | 10865 | FJ345354 | 3972 | 12 |
| 60 | Penicillium chrysogenum | 10108 | FJ345355 | 3916 | 13 |
| 61 | Rhizomucor miehei | 46345 | FJ345356 | 3983 | 14 |
| 62 | Rhodotorula glutinis | 16726 | FJ345357 | 3971 | 15 |
| 63 | Scedosporium apiospermum | 28206 | FJ345358 | 4907 | 16 |

TABLE 2

Fungi in which rRNA Gene Sequence was Derived from Publicly Available Genomes or Larger Sequences Found in GenBank ®

| SEQ ID NO | Microorganism | Source of rRNA gene sequence | Strain | Figure |
|---|---|---|---|---|
| 64 | Antrodia vaillantii | GenBank ® Accession # AM286436 | Isolate 240 | 17 |
| 65 | Aspergillus fumigatus | Broad Institute[1] | Af293 | 18 |
| 66 | Aspergillus niger | GenBank ® Accession # NW_001594105 | CBS 513.88 | 19 |
| 67 | Aspergillus oryzae | GenBank ® Accession # NW_001884680 | RIB40 | 20 |
| 68 | Aspergillus terreus | Broad Institute | NIH 2624 | 21 |
| 69 | Batrachochytrium dendrobatidis | Broad Institute | JEL423 | 22 |
| 70 | Botrytis cinerea | Broad Institute | B05.10 | 23 |
| 71 | Candida albicans | Broad Institute | SC5314 | 24 |
| 72 | Candida dublineinsis | Sanger Institute[2] | CD36 | 25 |
| 73 | Candida glabrata | GenBank ® Accession # AY198398 | CBS 138 | 26 |
| 74 | Candida gulliermundei | Broad Institute | ATCC 6260 | 27 |
| 75 | Candida kefyr | GenBank ® Accession # AF543841 | IFO1777 | 28 |
| 76 | Candida krusei | GenBank ® Accession # EF550222 and # AB369918 | NRRL Y-5396 (28S rRNA gene subunit) and IFM 47973 (ITS1, 5.8S, ITS2 gene subunit) | 29 |

TABLE 2-continued

Fungi in which rRNA Gene Sequence was Derived from Publicly Available Genomes or Larger Sequences Found in GenBank ®

| SEQ ID NO | Microorganism | Source of rRNA gene sequence | Strain | Figure |
|---|---|---|---|---|
| 77 | Candida lipolytica | GenBank ® Accession # AJ616903 and # DQ680839 | E122 (28S rRNA gene subunit) and HN2.4 (ITS1, 5.8S, ITS2 gene subunit) | 30 |
| 78 | Candida lusitaniae | Broad Institute | ATCC 42720 | 31 |
| 79 | Candida parapsilosis | | | 32 |
| 80 | Candida tropicalis | Broad Institute | MYA-3404 | 33 |
| 81 | Chaetomium globosum | Broad Institute | CBS 148.51 | 34 |
| 82 | Coccidioides immitis | Broad Institute | RMSCC 2394 | 35 |
| 83 | Coccidioides posadasii | Broad Institute | RMSCC 1040 | 36 |
| 84 | Cryptococcus neoformans | GenBank ® Accession # AE017342 | JEC21 | 37 |
| 85 | Fusarium graminearum | Broad Institute | PH-1 (NRRL 31084) | 38 |
| 86 | Fusarium oxysporum | Broad Institute | FGSC 4286 (NRRL 34936) | 39 |
| 87 | Histoplasma capsulatum | Broad Institute | NAm1 | 40 |
| 88 | Hypocrea jecorina | GenBank ® Accession # AF510497 | ATCC 13631 | 41 |
| 89 | Lodderomyces elongisporus | Broad Institute | NRLL YB-4239 | 42 |
| 90 | Magnaporthe grisea | GenBank ® Accession # DQ493955 | 70-15 | 43 |
| 91 | Metarhizium anisopliae | GenBank ® Accession # AF218207 | Isolate ME1 | 44 |
| 92 | Microsporum gypseum | Broad Institute | CBS 118893 | 45 |
| 93 | Mucor racemosus | GenBank ® Accession # AJ271061 | ATCC 1216B | 46 |
| 94 | Neurospora crassa | Broad Institute | N150 | 47 |
| 95 | Paracoccidioides brasiliens | Broad Institute | Pb03 | 48 |
| 96 | Pneumocystis carinii | GenBank ® Accession # M86760 | — | 49 |
| 97 | Penicillium verrucosum | GenBank ® Accession # AF510496 | WA30 (ATCC 62396) | 50 |
| 98 | Pichia stipitis | GenBank ® Accession # CP000497 | CBS 6054 | 51 |
| 99 | Rhizomucor miehei | GenBank ® Accession # AF205941 | ATCC 26282 | 52 |
| 100 | Rhizopus oryzae | Broad Institute | 99-880 (FGSC 9543) | 53 |
| 101 | Saccharomyces cerevisiae | GenBank ® Accession # Z73326 | — | 54 |
| 102 | Schizosaccharomyces japonicus | Broad Institute | yFS275 | 55 |
| 103 | Schizosaccharomyces pombe | Broad Institute | 972h- | 56 |
| 104 | Sclerotinia sclerotiorum | Broad Institute | ATCC 18683 | 57 |
| 105 | Stagonospora nodorum | Broad Institute | SN15 | 58 |
| 106 | Umbilicaria esculenta | GenBank ® Accession # EU534208 | Isolate F3 | 59 |
| 107 | Uncinocarpus reesii | Broad Institute | 1704 | 60 |

[1]http://www.broad.mit.edu/annotation/fgi/
[2]http://www.sanger.ac.uk/Projects/Fungi/

Obtaining rRNA Gene Sequences from Fungal Genomic Databases

The fungal rRNA operon is a continuous sequence made of the 18S, ITS1, 5.8S, ITS2, and 28S subunit regions [Iwen et al. (2002) Med. Mycol. 40:87-109]. For most fungi whose genomes are publicly available, the rRNA gene sequences were obtained using the following protocol: the 18S subunit and/or ITS1/5.8S/ITS2 subunit sequence of a specific fungus was first obtained through GenBank®, from the Sanger Institute or from the Broad Institute web sites. The sequences of the fungal species listed in Table 2 are shown in FIGS. 17-61. This section of the sequence was then used to perform a BLASTn search within its genome. Six kilobase pairs (kbp) of sequence was obtained on either side of the match in the genome. This large contig was trimmed to obtain the complete rRNA gene sequence using a combination of sequence analysis tools in Accelrys Gene® software (Accelrys, San Diego, Calif.). Well defined rRNA gene sequence of S. cerevisiae and C. albicans, and other smaller sequence subunits (ITS1/5.85/ITS2 region and D1-D2 region of the 28S) of each fungus, if available through GenBank® were also used to map and confirm the derived complete rRNA gene sequence.

Primers for Sequencing and Broad-Range Fungal Assays

Primers which could be used for either sequencing or broad-range PCR were designed based on the multiple sequence alignment of about 40 fungal rRNA operons. Maximizing nucleotide differences with the human rRNA gene sequence was an important criterion in designing primers. Primers that met this criterion are listed in Tables 3 and 4 (forward and reverse complement orientations, respectively), and the location of these primers is displayed on a map of the rRNA gene operon in FIG. 2B. In addition to these primers, during the initial stages of sequencing, primers from the website of the Vilgalys Lab at Duke University [Vilgalys, Conserved primer sequences for PCR amplification and sequencing from nuclear ribosomal RNA] were used. Most of these primers had significant homology with human rRNA gene sequences and therefore were not considered further for broad-range PCR development. The primers of the Vilgalys lab are mapped for comparison to the distinct primers provided by the present disclosure (FIG. 2C). In addition, FIG. 2C contains several widely used broad-range fungal primers from the literature which target the ITS, 5.8S and D1-D2 region of the 28S. Most of these primers have significant homology with human rRNA gene sequences and thus cross-react with human DNA making them unappealing for diagnostics in human samples.

Sequencing of Ribosomal RNA Operons (i) PCR Amplification

Each 50 µl PCR reaction contained 1.5 U of PfuTurbo® Hotstart Polymerase, 1× PfuTurbo® 10×PCR Buffer (Stratagene, La Jolla, Calif.), 0.8 mM of GeneAmp® dNTP Blend (Applied Biosystems, Foster City, Calif.), 0.4 µM each of forward and reverse primers selected from Table 3 and Table 4, respectively, and 20 ng of extracted fungal genomic DNA. The volume was brought up to 50 µl with DNA-grade water that was filtered through an Amicon Ultra-15 30 kDa centrifugal filter unit (Millipore Corporation, Billerica, Mass.) and UV-irradiated at 240 mJ/cm$^2$ (Spectrolinker™, Westbury, N.Y.).

PCR cycling conditions consisted of a pre-melt time of 2 min at 95° C., followed by 30 cycles of 95° C. for 30 sec (melt), a temperature between 50° C. to 58° C. for 30 sec (annealing), 72° C. for 2 min (extension), and ending with a hold at 72° C. for 10 min. The annealing temperature was selected to be lower than the lowest melting temperature of the two primers chosen for the PCR reaction.

PCR products were visualized on 1.5% agarose gels with ethidium bromide staining. (See a representative example in FIG. 2B). Products with visible bands that came within approximately 200 by of the expected amplicon size according to the primer map (FIG. 2A) were considered positives. Products with one distinct band were sequenced.

ii) Sequencing of Amplicon

PCR products were cleaned with Montage-PCR Filters (Millipore Corporation, Billerica, Mass.), eluted with 30 µl of DNA-grade water, and frozen at −20° C. until use. Sequencing was performed with Big Dye® terminators and an Applied Biosystems capillary sequencer. In addition to the primers used to amplify the original PCR product, 1 to 2 other primers that were expected to be contained in the amplicon were also used to sequence each product.

Broad-Range PCR Amplicon Selection and Screening Criteria

Figure 1:
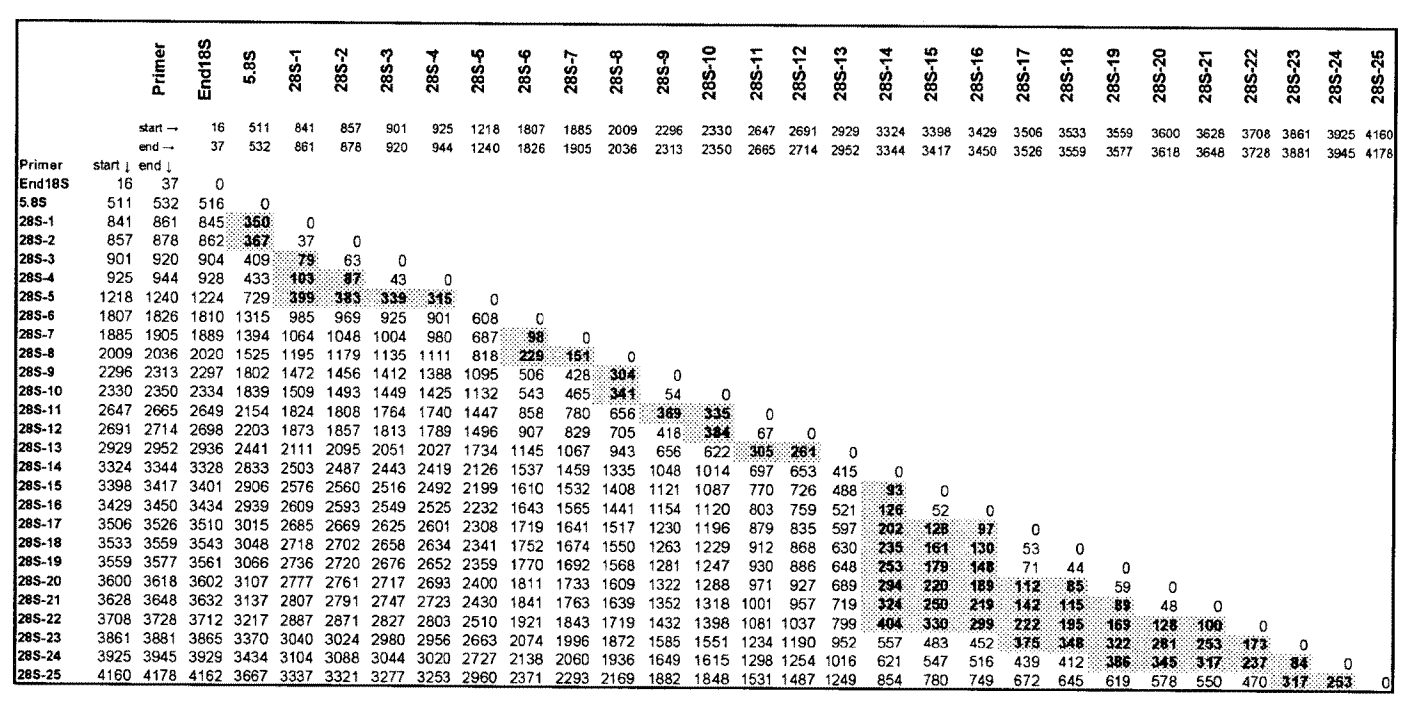

A matrix of all possible amplicon lengths from the 27 broad-range primers was generated in Microsoft Excel (FIG. 1). For the data shown in FIG. 1, the primer start and end positions are based on S. cerevisae from the 3' end of the 18S to the 3' end of the 28S rRNA gene. This 4230 by segment of the S. cerevisae rRNA gene begins with - - -GGTCATT-TAGAGGAACTAAA- - - and ends with - - -GTTTTTT-ATTTCTTTCTAAG- - -. Out of a total of 351 possible amplicons using all possible combinations of these primers, 62 amplicons were chosen for screening based on an amplicon size ranging from 75 to 400 bp. The general screening strategy is shown in FIG. 3. Endpoint PCR was used to assess successful amplification of each fungal target, the impact of human genomic DNA on fungal amplification, and the cross-reactivity of human DNA in the fungal PCR assays. In addition, the ability of each amplicon to identify and differentiate fungal species was analyzed using distance matrices.

(i) Endpoint PCR.

Each 50 µl PCR reaction contained 1× Buffer A, 3 mM of MgCl$_2$, 1 mM of GeneAmp® dNTP Blend (12.5 mM with dUTP), 2.2U of AmpliTaq Gold® DNA Polymerase, 0.05U AmpErase® Uracil N-glycosylase (all from Applied Biosystems, Foster City, Calif.), 0.6 µM each of forward and reverse primer, and 0.002% of Triton-X 100. The primer sequences are shown in FIG. 4A. PCR cycling conditions consisted of a Uracil N-glycosylase activation for 2 min at 50° C., pre-melt for 10 min at 95° C., then 40 cycles of 15 sec at 95° C. (melt), 30 sec at 55° C. (anneal), 40 sec at 72° C. (extend), and finished with a 7 min hold at 72° C.

(ii) Analytical Sensitivity and Cross-Reactivity Testing

The analytical sensitivity for amplicon screening was assessed by testing extracted fungal genomic DNA. Genomic DNA was extracted based on a previously described protocol [Khot et al. (2008) BMC Infect. Dis. 8:73]. An optimized version of the MasterPure™ Yeast DNA Purification Kit (Epicentre® Biotechnologies, Madison, Wis.) was used for fungal DNA extraction. The 100% isopropanol, 70% ethanol and DNA grade water used for extraction were filtered in an Amicon Ultra-15 centrifugal filter unit with a molecular weight cut-off of 30 kDa (Millipore Corporation, Billerica, Mass.). Yeast Cell Lysis™ solution and MPC Protein Precipitation Reagent™ were UV irradiated at 240 mJ/cm$^2$ with pelleted fungal samples approximately 15 cm from the bulbs (Spectrolinker™, Westbury, N.Y.). The silicon carbide sharps were washed 10 times in DNA free water and baked at 180° C. for 48 h. DNA-free microcentrifuge tubes were used with DNA extraction (Eppendorf Biopur tubes, Eppendorf AG, Hamburg, Germany). Sham digest controls consisting of DNA-free water were processed with every extraction run serving as negative controls to monitor for contamination. Two milliliter sterile screw-cap tubes were loaded with silicon carbide sharps of sizes 0.1 mm and 1 mm (BioSpec Products, Inc., Bartlesville, Okla.) at a 1:1 ratio up to a volume equivalent to 250 µl. Yeast Cell Lysis™ solution at a volume of 550 µl and BAL pellet at 100-400 µl, or 200 µl of water as digest control, were added to the tube. The contents of the tube were homogenized in a FastPrep®-24 System (MP Biomedicals, Solon, Ohio) at 5 m/sec for 60 sec. Each tube was incubated at 65° C. for 45 min then kept on ice for 5 min. MPC Protein Precipitation Reagent™ was added at a volume of 325 µl for pellet processing. The tubes were vortexed for 10 sec and centrifuged at 11,000 rcf for 10 min. The resulting supernatant was transferred to a new microcentrifuge tube containing an equal volume of 100% isopropanol pre-cooled to −20° C. The contents of the tube were mixed thoroughly by inversion and incubated at −20° C. for 1 hour. Precipitated DNA was pelleted by centrifugation at 11,000 rcf for 10 min. This supernatant was removed and discarded. The pellet containing DNA was resuspended in 0.5 ml of pre-cooled (−20° C.) 70% ethanol and vortexed. The tube was then centrifuged at 11,000 rcf for 5 min. This supernatant was removed to a level just short of disturbing the pellet. The remaining volume of ethanol was allowed to evaporate by air drying for 5 min within the laminar flow hood. The pellet was resuspended in 100 µl of 0.1% Triton-X prewarmed to 65° C. then incubated at room temperature for one minute with periodic gentle vortexing. The DNA was either used immediately for qPCR, stored at −20° C. overnight or at −80° C. for longer periods. If PCR inhibition was detected in the extracted samples, they were reprocessed from the protein precipitation step onwards.

Cross-reactivity of the primers was assessed in the presence of human genomic DNA (Roche Applied Sciences, Indianapolis, Ind.). A preliminary screen of all 62 amplicons involved amplification of 1000 pg, 10 pg and 30 fg of *C. albicans* genomic DNA, and 30 fg of *C. albicans* genomic DNA in the presence of 100 ng of human genomic DNA. The final screen involved analytical sensitivity testing with 30 fg of genomic DNA from 27 different fungal species spanning 15 genera. Cross-reactivity testing was assessed using 10 fg of *A. fumigatus* genomic DNA in the presence of 1 µg of human genomic DNA.

(iii) Data Analysis

Multiple sequence alignment based on the Clustal W algorithm, distance matrices and phylogenetic trees based on the Neighbor-Joining tree building method [Saitou and Nei (1987) *Mol. Biol. Evol.* 4:406-25] and distances estimated from the Tajima-Nei [Tajima and Nei (1984) *Mol. Biol. Evol.* 1:269-85] or absolute differences algorithms were generated using Accelrys Gene® software. The distance matrices and phylogenetic trees were used to assess the potential of amplicons to resolve species identity.

Example 2

Generation of New Fungal Ribosomal rRNA Gene Sequences

This Example discloses novel sequences of fungal rRNA genes of phylogenetically and clinically relevant fungal species.

Sequence information for several medically important fungi is not available in public databases, limiting one's ability to design broad range fungal PCR assays. To address this limitation, rRNA genes from 9 phylogenetically and clinically relevant fungal species were sequenced. Seven (7) of these fungal species were missing rRNA sequences from the 3' end of 18S rRNA gene to the 3' end of 28S rRNA gene. Table 1, shown in Example 1, above, lists these organisms with their American Type Culture Collection (ATCC) numbers, GenBank® accession numbers for sequences deposited from this study, and their sequence lengths. The full-length sequences of these organisms are shown in FIGS. 8-16. In some cases, the sequences disclosed herein may be up to 90 by short of the true end of the 28S rRNA gene since a conserved primer (28S-25) at the 3' end of the gene was used for both PCR and sequencing. Overlapping reads were generated from all amplicons using multiple sequencing primers. Accelrys Gene® software was used to assemble smaller amplicons into the larger sequence. The sequencing of Zygomycetes like *Rhizomucor miehei*, *Cunninghamella bertholletiae* and *Mucor racemosus* was relatively complicated due to significant divergence of these species from other fungi. Several custom primers had to be used to successfully complete sequencing for these species. In addition, *Scedosporium apiospermum* posed a significant sequencing challenge due to the presence of inserts in the rRNA operon, resulting in multiple bands on agarose gel electrophoresis of PCR products.

Example 3

Selection of Broad Range Fungal rRNA Gene Primers

This Example discloses primer sequences for PCR-based amplification of the fungal rRNA operon of 50 unique fungal species and the method used to design these primer sequences.

A multiple sequence alignment was created using the 52 fungal rRNA gene sequences presented in Tables 1 and 2, which represent 30 genera. The phylogenetic position of these fungi based on the alignment was used to further verify the identity of the fungal sequences. Twenty seven (27) broad-range fungal primers (Tables 3 and 4) were designed by manually reviewing the alignment to select areas of sequence conservation among fungi that had multiple nucleotide differences with the human rRNA operon. Table 3 lists the forward orientation of the primer sequences (SEQ ID NOs: 1-27) and Table 4 lists the reverse complement of the primer sequences (SEQ ID NOs: 28-54), shown in Table 3. Ten (10) primers, including End18S Forward and Reverse (SEQ ID NOs: 1 and 28), 5.8S Forward and Reverse (SEQ ID NOs: 2 and 29), 28S-2 Forward and Reverse (SEQ ID NOs: 4 and 31), 28S-5 Forward and Reverse (SEQ ID NOs: 7 and 34), and 28S-24 Forward and Reverse (SEQ ID NOs: 26 and 53) overlap either completely or partially with those found in the literature, and most lie in the region spanning the 3' end of 18S rRNA gene, the 5.8S rRNA gene, and the 5' end of 28S rRNA gene [(Chen et al. *J Clin Microbiol* 38:2302-10; Hinrikson et al. (2005) *J. Clin. Microbiol.* 43:2092-103; Kurtzman and Robnett (1997) *J. Clin. Microbiol.* 35:1216-23; Sandhu et al. (1995) *J. Clin. Microbiol.* 33:2913-9; Turenne et al. (1999) *J. Clin. Microbiol.* 37:1846-51; Vollmer et al. (2008) *J. Clin. Microbiol.* 46:1919-26)]. Twenty-two (22) primers from the 5' end of the 28S rRNA gene up to its 3' end are newly described in the present disclosure. The positions of these primers are shown on the rRNA gene map (FIG. 2B). The broad-range primers disclosed herein were used for de novo sequencing of fungal rRNA genes. In addition, all primers listed in Table 3 and Table 4 were chosen as candidates for the development of broad-range fungal PCR assays applicable to human tissue samples. In Table 3, the number of base pair mismatches with human fungal rDNA is shown.

TABLE 3

Broad-range Fungal rRNA Gene Forward Primer Sequences

| SEQ ID NO: | Primer Name | Primer sequence (5'-3') | # bp mismatches with human rDNA |
|---|---|---|---|
| SEQ. ID NO: 1 | End 18S | GTAAAAGTCGTAACAAGGTTTC | 7 |
| SEQ. ID NO: 2 | 5.8S | GTGAATCATCGARTCTTTGAAC | 9 |
| SEQ. ID NO: 3 | 28S-1 | TACCCGCTGAACTTAAGCATA | 2 |
| SEQ. ID NO: 4 | 28S-2 | GCATATCAATAAGCGGAGGAAA | 3 |
| SEQ. ID NO: 5 | 28S-3 | AGTARCGGCGAGTGAAGCGG | 2 |
| SEQ. ID NO: 6 | 28S-4 | AGCTCAAATTTGAAASCTGG | 6 |

TABLE 3-continued

Broad-range Fungal rRNA Gene Forward Primer Sequences

| SEQ ID NO: | Primer Name | Primer sequence (5'-3') | # bp mismatches with human rDNA |
|---|---|---|---|
| SEQ. ID NO: 7 | 28S-5 | CTTCCCTTTCAACAATTTCACRT | 6 |
| SEQ. ID NO: 8 | 28S-6 | GAGGTAAAGCGAATGATTAG | 2 |
| SEQ. ID NO: 9 | 28S-7 | CTTGTTRCTTARTTGAACGTG | 8 |
| SEQ. ID NO: 10 | 28S-8 | ACCACAAAAGGTGTTAGTWCATC | 5 |
| SEQ. ID NO: 11 | 28S-9 | GAAGTGGGGAAAGGTTCC | 2 |
| SEQ. ID NO: 12 | 28S-10 | GACATGGGTTAGTCGATCCTA | 4 |
| SEQ. ID NO: 13 | 28S-11 | TCGTACTCATAACCGCAGC | 3 |
| SEQ. ID NO: 14 | 28S-12 | GTTGATAGAAYAATGTAGATAAGG | 5 |
| SEQ. ID NO: 15 | 28S-13 | CAAGGGGAATCTGACTGTC | 3 |
| SEQ. ID NO: 16 | 28S-14 | TTTACTTAWTCAATGAAGCGG | 6 |
| SEQ. ID NO: 17 | 28S-15 | CCGGGTTGAWGACATTGTCA | 7 |
| SEQ. ID NO: 18 | 28S-16 | GCTGGGGCGGCACATCTGTT | 4 |
| SEQ. ID NO: 19 | 28S-17 | GAACAAAAGGGTAAAAGTCCC | 5 |
| SEQ. ID NO: 20 | 28S-18 | TTTGATTTTCAGTGTGAATACAAACCA | 5 |
| SEQ. ID NO: 21 | 28S-19 | ATGAAAGTGTGGCCTATCG | 5 |
| SEQ. ID NO: 22 | 28S-20 | GAGGCTAGAGGTGCCAGAA | 5 |
| SEQ. ID NO: 23 | 28S-21 | AGGGATAACTGGCTTGTGGC | 0 |
| SEQ. ID NO: 24 | 28S-22 | ACCGAAGCAGAATTCGGTAAG | 5 |
| SEQ. ID NO: 25 | 28S-23 | GATAATTGGTWTTTGCGGCTG | 7 |
| SEQ. ID NO: 26 | 28S-24 | GCTGAACGCCTCTAAGTCAGA | 1 |
| SEQ. ID NO: 27 | 28S-25 | TCGTARCAACAAGGCTACT | 7 |

TABLE 4

Broad-range Fungal rRNA Gene Reverse Primers

| SEQ ID NO: | Reverse Primer Name | Primer Sequence (5'-3') |
|---|---|---|
| SEQ ID NO: 28 | End 18S | GAAACCTTGTTACGACTTTTA |
| SEQ ID NO: 29 | 5.8S | GTTCAAAGAYTCGATGATTCAC |
| SEQ ID NO: 30 | 28S-1 | TATGCTTAAGTTCAGCGGGTA |
| SEQ ID NO: 31 | 28S-2 | TTTCCTCCGCTTATTGATATGC |
| SEQ ID NO: 32 | 28S-3 | CCGCTTCACTCGCCGYTACT |
| SEQ ID NO: 33 | 28S-4 | CCAGSTTTCAAATTTGAGCT |
| SEQ ID NO: 34 | 28S-5 | AYGTGAAATTGTTGAAAGGGAAG |
| SEQ ID NO: 35 | 28S-6 | CTAATCATTCGCTTTACCTC |
| SEQ ID NO: 36 | 28S-7 | CACGTTCAAYTAAGYAACAAG |
| SEQ ID NO: 37 | 28S-8 | GATGWACTAACACCTTTTGTGGT |
| SEQ ID NO: 38 | 28S-9 | GGAACCTTTCCCCACTTC |
| SEQ ID NO: 39 | 28S-10 | TAGGATCGACTAACCCATGTC |
| SEQ ID NO: 40 | 28S-11 | GCTGCGGTTATGAGTACGA |
| SEQ ID NO: 41 | 28S-12 | CCTTATCTACATTRTTCTATCAAC |
| SEQ ID NO: 42 | 28S-13 | GACAGTCAGATTCCCCTTG |
| SEQ ID NO: 43 | 28S-14 | CCGCTTCATTGAWTAAGTAAA |
| SEQ ID NO: 44 | 28S-15 | TGACAATGTCWTCAACCCGG |
| SEQ ID NO: 45 | 28S-16 | AACAGATGTGCCGCCCCAGC |
| SEQ ID NO: 46 | 28S-17 | GGGACTTTTACCCTTTTGTTC |
| SEQ ID NO: 47 | 28S-18 | TGGTTTGTATTCACACTGAAAATCAAA |
| SEQ ID NO: 48 | 28S-19 | CGATAGGCCACACTTTCAT |

TABLE 4-continued

Broad-range Fungal rRNA Gene Reverse Primers

| SEQ ID NO: | Reverse Primer Name | Primer Sequence (5'-3') |
|---|---|---|
| SEQ ID NO: 49 | 28S-20 | TTCTGGCACCTCTAGCCTC |
| SEQ ID NO: 50 | 28S-21 | GCCACAAGCCAGTTATCCCT |
| SEQ ID NO: 51 | 28S-22 | CTTACCGAATTCTGCTTCGGT |
| SEQ ID NO: 52 | 28S-23 | CAGCCGCAAAWACCAATTATC |
| SEQ ID NO: 53 | 28S-24 | TCTGACTTAGAGGCGTTCAGC |
| SEQ ID NO: 54 | 28S-25 | AGTAGCCTTGTTGYTACGA |
| SEQ ID NO: 108 | 12R-opt1 | CCTTATCTACATTATTCTATGGAC |

Example 4

Screening of PCR Amplicons Based on Analytical Sensitivity and Cross-reactivity

The following Example describes the development of broad-range PCR primers and methods for characterizing the primers.

Based on the 27 broad-range primers designed in this study, a total of 351 unique amplicons could be generated of various sizes (FIG. 1). To develop broad-range PCR assays with maximum sensitivity, amplicons in the range of 75 to 400 by were selected for screening. A preliminary screen of 62 such amplicons eliminated 51 primer combinations due to amplification of human genomic DNA and/or the inability to amplify 30 fg of C. albicans DNA in the presence of 100 ng of human genomic DNA. The remaining 11 amplicons were subjected to extensive screening using analytical sensitivity testing with 30 fg fungal genomic DNA from 27 fungi spanning 15 genera (FIG. 4A). The top 11 amplicons, and the primers used to generate the amplicons are shown in Table 5, below. None of these top 11 broad-range fungal rRNA gene amplicons generated a product with 1 µg human genomic DNA or were inhibited from amplifying 10 fg of A. fumigatus DNA in the presence of 1 µg of human genomic DNA (FIG. 4A). Five amplicons, ITS2(5.8SF-1R), 28S(9F-12R), 28S(10F-12R), 28S(18F-22R) and 28S(18F-23R) detected the widest range of fungi. The ITS2(5.8SF-1R) amplicon detected all tested fungi, but had some weak detections as evidenced by relatively faint gel bands. The 28S(10F-12R) amplicon strongly detected 26 out of the 27 fungi, but could not detect Rhodotorula glutinis at the 30 fg level. In most cases where amplification was either unsuccessful or weak (FIG. 4A), there was a mismatch between the sequence of the specific organism and the primer. An exemplary image of a 1.5% agarose gel, on which the PCR products were resolved, is shown in FIG. 4B. As indicated in FIG. 4B, a band having high intensity was scored as '+++', medium intensity as '++', low intensity as '+', or no amplification as '−'.

TABLE 5

Primer Pairs Used to Generate Top 11 Amplicons

| Amplicon | Forward Primer | Reverse Primer |
|---|---|---|
| ITS1(End18SF-5.8SR) | GTAAAAGTCGTAACAAGGTTTC (SEQ ID NO: 1) | GTTCAAAGAYTCGATGATTCAC (SEQ ID NO: 29) |
| ITS2(5.8SF-1R) | GTGAATCATCGARTCTTTGAAC (SEQ ID NO: 2) | TATGCTTAAGTTCAGCGGGTA (SEQ ID NO: 30) |
| ITS2(5.8SF-2R) | GTGAATCATCGARTCTTTGAAC (SEQ ID NO: 2) | TTTCCTCCGCTTATTGATATGC (SEQ ID NO: 31) |
| ITS2(5.8SF-3R) | GTGAATCATCGARTCTTTGAAC (SEQ ID NO: 2) | CCGCTTCACTCGCCGYTACT (SEQ ID NO: 32) |
| 28S(9F-12R) | GAAGTGGGGAAAGGTTCC (SEQ ID NO: 11) | CCTTATCTACATTRTTCTATCAAC (SEQ ID NO: 41) |
| 28S(10F-12R) | GACATGGGTTAGTCGATCCTA (SEQ ID NO: 12) | CCTTATCTACATTRTTCTATCAAC (SEQ ID NO: 41) CCTTATCTACATTATTCTATGGAC (SEQ ID NO: 108) |
| 28S(12F-13R) | GTTGATAGAAYAATGTAGATAAGG (SEQ ID NO: 14) | GACAGTCAGATTCCCCTTG (SEQ ID NO: 42) |
| 28S(15F-22R) | CCGGGTTGAWGACATTGTCA (SEQ ID NO: 17) | CTTACCGAATTCTGCTTCGGT (SEQ ID NO: 51) |
| 28S(18F-22R) | TTTGATTTTCAGTGTGAATACAAACCA (SEQ ID NO: 20) | CTTACCGAATTCTGCTTCGGT (SEQ ID NO: 51) |
| 28S(18F-23R) | TTTGATTTTCAGTGTGAATACAAACCA (SEQ ID NO: 20) | CAGCCGCAAAWACCAATTATC (SEQ ID NO: 52) |
| 28S(23F-25R) | AGGGATAACTGGCTTGTGGC (SEQ ID NO: 25) | AGTAGCCTTGTTGYTACGA (SEQ ID NO: 54) |

Example 5

Assessment of the Potential for Species Resolution Among Amplicons

The following Example discloses the generation of distance matrices and phylogenetic trees for characterization of the ability of the top eleven (11) amplicons (primer pairs) of the present disclosure to resolves fungal species identity.

Distances matrices and phylogenetic trees generated from sequence alignments of amplicons for a specific set of PCR primers display the nucleotide differences between fungi and depict the species resolution of amplicons. Such analyses have been used to distinguish species within the *Candida* and *Aspergillus* genus using the D1-D2 region of the 28S rRNA gene and also compare the D1-D2, ITS1 and ITS2 regions for their potential to resolve species of medically important fungi [(Chen, et al. J Clin Microbiol 38:2302-10; Henry, et al. (2000) J. Clin. Microbiol. 38:1510-5; Hinrikson, et al. (2005) Med. Mycol. 43 Suppl. 1:S129-37; Hinrikson, et al. (2005) J. Clin. Microbiol. 43:2092-103; Kurtzman and Robnett (1997) J. Clin. Microbiol. 35:1216-23; Rakeman, et al. (2005). J. Clin. Microbiol. 43:3324-33)]. The parameter in FIG. 4A and Table 6, which represents the sum of all elements of the distance matrix provides a global measure of nucleotide differences between fungal sequences for a specific amplicon.

To evaluate the potential for species identification using the top 11 PCR amplicons, distance matrices were generated from the multiple sequence alignment of 50 fungi for each amplicon. The sequences of the forward and reverse primer were excluded from the analysis. Distance matrices for 3 amplicons ITS2(5.8SF-2R), ITS2(5.8SF-3R) and 28S(9F-12R) were not estimated due to significant sequence overlap with another amplicon that showed greater breadth of analytical sensitivity.

The distance matrices based on the absolute difference algorithm for the remaining top 8 amplicons are shown in FIG. 5A-5H, which show the amplicons ITS1 (end18SF-5.8SR), ITS2(5.8SF-1R), 28S(10F-12R), 28S(12F-13R), 28S(15F-22R), 28S(18F-22R), 28S(18F-23R), and 28S (23F-25R), respectively. The sum of all the elements in the distance matrix resulted in a numerical quantity that reflected the magnitude of species resolution for each amplicon. For distances estimated using the Tajima-Nei algorithm, larger values reflect more nucleotide differences among fungi and therefore greater phylogenetic resolution for species identification. For example, the amplicon ITS2 (5.8SF-1R) overlapping the ITS2 region, for which the distance matrix is shown in FIG. 5B, was expected to have the highest level of sequence variation and had a distance matrix sum of 1055.8 (FIG. 4A and Table 6, below), whereas the amplicon 28S(18F-22R) which covers a highly conserved region of the 28S rRNA gene (distance matrix shown in FIG. 5F) had a distance matrix sum of only 74.5 (FIG. 4A and Table 6, below). A similar and more intuitive trend emerged when the sum of the distance matrix was estimated based on the absolute differences algorithm, which calculates the total number of base differences between fungal sequences in an alignment. In this case the ITS2(5.8SF-1R) amplicon overlapping the ITS2 region also had the highest nucleotide differences with a sum of 113,388, while the 28S(18F-22R) amplicon showed the lowest sum of nucleotide differences at 9,629 (FIG. 4A and Table 6, below). Therefore, based on genetic distances, the ITS2(5.8SF-1R) amplicon had the highest level of species resolution. Among the top 5 amplicons ranked in terms of breadth of fungi detected, 28S(10F-12R) also manifested a high degree of species resolution as evidenced by its distance matrix in FIG. 5C.

TABLE 6

Distance Matrix Sums and Amplicon Lengths of Top 11 Amplicons

| | ITS1(End1 8SF-5.8SR) | ITS2 (5.8SF-1R) | ITS2 (5.8SF-2R) | ITS2 (5.8SF-3R) | 28S (9F-12R) | 28S (10F-12R) | 28S (12F-13R) | 28S (15F-22R) | 28S (18F-22R) | 28S (18F-23R) | 28S (23F-25R) |
|---|---|---|---|---|---|---|---|---|---|---|---|
| Sum of distance matrix based on Tajima-Nei algorithm & Neighbor Joining tree building method | 642.5 | 1055.8 | ND | ND | ND | 310.8 | 470.6 | 67.5 | 74.5 | 117.3 | 358.3. |
| Sum of distance matrix based on absolute nucleotide differences and Neighbor Joining tree building method | 97914 | 113388 | ND | ND | ND | 82452 | 61321 | 17522 | 9629 | 28716 | 66445 |
| Amplicon length ± standard deviation of 50 fungal species representing 30 genera | 297 ± 70 | 254 ± 42 | ND | ND | ND | 339 ± 7 | 200 ± 25 | 299 ± 67 | 157 ± 67 | 318 ± 80 | 263 ± 10 |

Combining information from the amplicon matrix (FIG. 1), primer map (FIG. 2), sensitivity data (FIG. 4A) and distance matrices (FIGS. 5A-5H) provides useful data for selecting broad range fungal PCR assays. Based on the ability to detect the widest range of fungi and simultaneously resolve species identity, the ITS2(5.8SF-1R), and 28S(10F-12R) amplicons emerged as top assays for broad-range fungal PCR.

Conventional endpoint PCR with gel electrophoresis was used to assess amplification. Quantitative PCR can also be used as an indicator of amplification efficiency, but analysis of PCR products by gel electrophoresis provides data on amplicon size, the generation of non-specific amplification products, and product throughput (band intensity). The present invention discloses primers that are primarily specific for the 28S region. However, also contemplated are primers in the 18S rRNA gene that are useful when used in conjunction with primers described in the present disclosure. The method and compositions provided by the present disclosure are useful for targeting regions beyond the D1-D2 region for the identification of novel fungi. Since primers were designed at highly conserved regions, the specificity of the primers is highly unlikely to be affected by the presence of any polymorphic positions at primer site or within the amplicons disclosed in the present description.

An alternative approach for analyzing the species resolution of amplicons uses phylogenetic trees based on the Neighbor-Joining tree building method and Tajima-Nei algorithm for calculation of distances. FIGS. 6 and 7 are phylogenetic trees for amplicons ITS2(5.8SF-1R) and 28S (10F-12R), respectively. Note that the ITS2(5.8SF-1R) amplicon is highly polymorphic and lacks the property of a molecular clock, making it unreliable for inferring evolutionary relationships. The trees demonstrate that closely related fungi are resolved using the proposed amplicon sequences.

Example 6

Identification of Fungal Species Using Two-dimensional Melt Curve Analysis

The following example discloses methods for the identification of DNA from one or more fungal pathogens in a patient sample using two-dimensional melt-curve analysis.

To develop better broad range fungal PCR assays for application to human tissues, an extensive analysis of fungal rRNA gene sequences was performed, focusing on ~3950 by of sequence from the 3' end of the 18S rRNA gene to the 3' end of the 28S gene. See Khot et al. (2009) *Appl Environ Microbiol* 75(6): 1559-1565, incorporated herein by reference. Sequence data was generated de novo for numerous fungal species and collected data from databases and genome projects. The focus was on selecting primers with broadly conserved sequences among fungi while having significant sequence dissimilarity with human rRNA genes. Out of 62 amplicons analyzed, two successfully amplified 30 fg of fungal DNA from 25 of 26 fungi and provided the most phylogenetic information for species identification based on distance matrices. The primers for these top two PCR assays, called ITS2(5.8SF-1R) and 28S(10F-12R), are located illustrated in FIG. 61.

FIG. 61 illustrates a map of a fungal 28S rRNA gene and corresponding positions of twenty-seven broad-range fungal PCR primers for sequencing and PCR assay development. FIG. 61A shows a map of fungal rRNA from the 3' end of 18S to 3' end of 28S rRNA gene based on *Saccharomyces cerevisiae*. FIG. 61B illustrates the positions of 27 newly designed broad-range fungal primers based on differences with human rRNA gene designed for this. See Khot et al. (2009) *Appl Environ Microbiol* 75(6): 1559-1565. The combination of primers 10F and 12R at 50 pmol/PCR each did not amplify *Rhodotorula glutinis* (even at 1000 pg). The inclusion of a second reverse primer (12R-opt1; SEQ ID NO: 57) in the 28S(10F-12R) assay at 9% of total reverse primer concentration resulted in successful amplification of 30 fg of fungal DNA from *Rhodotorula glutinis*. The 28S (10F-12R) assay included primer 10F (SEQ ID NO: 108) at 50 pmol/PCR, primer 12R (SEQ ID NO: 56) at 50 pmol/PCR, and primer 12R-opt1 (SEQ ID NO: 57) at 5 pmol/PCR. 12R-opt1 lacks degeneracies and differs from 12R by three bases.

FIG. 62 illustrates a two-dimensional melt curve plot based on the broad-range fungal qPCR assays ITS2(5.8SF-1R) and 28S(10F-12R) allowing rapid identification of species. Different PCR products can be differentiated from each other based on the characteristic temperature at which they "melt" in going from a double-stranded to single-stranded confirmation. For instance, amplicons which are longer and have higher GC content have higher melting temperatures. The melting profile of an amplicon can be determined by adding a fluorescent double-stranded DNA binding dye to the PCR and measuring fluorescence as the temperature changes. As an amplicon melts, the fluorescence decreases. Assessing the melting temperature of a single broad-range fungal amplicon provides useful information about the possible identity of the fungus, but even more accurate information is gleaned using data from several different broad range fungal PCR assays—an approach called two dimensional (2D) melt curve analysis. See Gigli et al. (2003) *Nucleic Acids Res.* 31(22): e136, incorporated herein by reference.

An approach was developed using the top two broad-range PCR amplicons described above. This strategy allows for the rapid preliminary identification of fungi which may be very clinically useful. The ITS2(5.8SF-1R) and 28S(10F-12R) PCR assays were transformed into a qPCR format using a double stranded DNA binding dye (EvaGreen™, Biotium Inc., Hayward, Calif.). FIG. 62 shows the ability of the two amplicons to identify 25 fungal species based on their melting temperatures. Nucleotide sequencing can be used to resolve the identity of fungi for which the 2D melt temperature analysis provides ambiguous results.

To test the diagnostic ability of the top two broad-range qPCR assays and the feasibility of using a 2D melt curve approach, these assays were applied to 26 BAL samples which were previously tested with our *Aspergillus* 18S rRNA gene qPCR. Of these 26 BAL samples, half were positive with culture for fungus and/or with the *Aspergillus* 18S assay and the other half were not. The 28S(10F-12R) qPCR assay was positive for 13 of 13 and the ITS2(5.8SF-1R) qPCR assay for 10 of 13 of those BALs that were positive with culture and/or with the *Aspergillus* 18S assay. Sequencing of all these amplicons confirmed the identities predicted by the 2D melt curve approach. These preliminary data suggest that broad range fungal PCR with rapid melt curve analysis can be useful for identifying fungal pathogens, though additional testing is necessary to assess the sensitivity and specificity of this approach.

FIG. 63 illustrates melt temperature curves of pathogenic fungi amplified from blood, representing the 10-12 amplicon on the fungal 28S rRNA gene. The ability to distinguish between fungal amplification products in broad-range PCR was demonstrated using one dimensional melt curve analysis as displayed in FIG. 63. Genomic DNA from 4 different fungal species was added to blood. The PCR targeted the same segment of the fungal rRNA operon (28S rRNA 10F-12R), wherein the PCR product was detected using a double stranded DNA binding dye. Amplicon melt analysis was performed after PCR, demonstrating characteristic peaks corresponding to the melting temperature of the different amplicons. The melt temperature at which ds DNA binding dye dissociates from the amplicon with loss of fluorescence depends on amplicon length and base composition. For instance, the *Candida albicans* PCR product has a melting temperature of 87 degrees in this assay. The use of more than one broad range PCR target allows the melt temperature peaks to be plotted on a graph resulting in two dimensional melt curve analysis with even greater ability to resolve fungi. See FIG. 62 for an example of this approach.

All of the compositions and methods disclosed and claimed herein can be made and executed without undue experimentation in light of the present disclosure. While the disclosure has been descried in each of its various embodiments, it is expected that certain modifications thereto may be undertaken and effected by the person skilled in the art without departing from the true spirit and scope of the disclosure, as set forth in the previous description and as further embodied in the following claims. More specifically, it will be apparent that certain agents which are both chemically and physiologically related may be substituted for the agents described herein while the same or similar results would be achieved. All such similar substitutes and modifications apparent to those skilled in the art are deemed to be within the scope of the disclosure as defined by the appended claims.

The present disclosure is not to be limited in scope by the specific embodiments described herein. Indeed, various modifications of the methods and compositions disclosed herein will become apparent to those skilled in the art from the foregoing description and the accompanying figures. Such modifications are intended to fall within the scope of the appended claims. It is further to be understood that all values are approximate, and are provided for description. All patents and patent applications cited herein are hereby incorporated herein by reference in their entireties.

What is claimed is:

1. A method of broad range detection of at least one type of fungal nucleic acid in a patient sample, said method comprising:
   (a) carrying out a combination of PCR reactions on an isolated patient sample, wherein the combination comprises amplification of at least a region of a fungal ITS2 ribosomal RNA (rRNA) gene and a region of a fungal 28S rRNA gene;
      i. wherein the fungal ITS2 rRNA gene is amplified with a first PCR reaction comprising a first primer set comprising a first forward primer and a first reverse primer, wherein said first reverse primer is complementary to a fungal ITS2 rRNA gene in a region of said fungal ITS2 rRNA gene;
      ii. wherein the fungal 28S rRNA gene is amplified with a second PCR reaction comprising a second primer set comprising a second forward primer and a second reverse primer, wherein said reverse primer is complementary to a fungal 28S rRNA gene in a region of said fungal 28S rRNA gene that is 3' to a D1-D2 highly variable region, wherein said second forward primer comprises a sequence selected from the group consisting of:

| | |
|---|---|
| 5'-GTAAAAGTCGTAACAAGGTTTC-3', | (SEQ ID NO: 1) |
| 5'-GTGAATCATCGARTCTTTGAAC-3', | (SEQ ID NO: 2) |
| 5'-GAAGTGGGGAAAGGTTCC-3', | (SEQ ID NO: 11) |
| 5'-GACATGGGTTAGTCGATCCTA-3', | (SEQ ID NO: 12) |
| 5'-GTTGATAGAAYAATGTAGATAAGG-3', | (SEQ ID NO: 14) |
| 5'-CCGGGTTGAWGACATTGTCA-3', | (SEQ ID NO: 17) |
| 5'-TTTGATTTTCAGTGTGAATACAAACCA-3', and | (SEQ ID NO: 20) |
| 5'-GATAATTGGTWTTTGCGGCTG-3', | (SEQ ID NO: 25) | and
wherein said second reverse primer comprises a sequence selected from the group consisting of:

| | |
|---|---|
| 5'-GTTCAAAGAYTCGATGATTCAC-3', | (SEQ ID NO: 29) |
| 5'-TATGCTTAAGTTCAGCGGGTA-3', | (SEQ ID NO: 30) |
| 5'-TTTCCTCCGCTTATTGATATGC-3', | (SEQ ID NO: 31) |
| 5'-CCGCTTCACTCGCCGYTACT-3', | (SEQ ID NO: 32) |
| 5'-CCTTATCTACATTRTTCTATCAAC-3', | (SEQ ID NO: 41) |
| 5'-GACAGTCAGATTCCCCTTG-3', | (SEQ ID NO: 42) |
| 5'-CTTACCGAATTCTGCTTCGGT-3', | (SEQ ID NO: 51) |
| 5'-CAGCCGCAAAWACCAATTATC-3', | (SEQ ID NO: 52) |
| 5'-AGTAGCCTTGTTGYTACGA-3', and | (SEQ ID NO: 54) |
| 5'-CCTTATCTACATTATTCTATGGAC-3'; | (SEQ ID NO: 108) | wherein said second primer set comprises a combination of forward and reverse primers selected from the group consisting of (SEQ ID NO: 2 and SEQ ID NO: 31), (SEQ ID NO: 2 and SEQ ID NO: 32), (SEQ ID NO: 11 and SEQ ID NO: 41), (SEQ ID NO: 1 and SEQ ID NO: 29), (SEQ ID NO: 2 and SEQ ID NO: 30), (SEQ ID NO: 12 and SEQ ID NO: 41), (SEQ ID NO: 12, SEQ ID NO: 41, and SEQ ID NO: 108), (SEQ ID NO: 14 and SEQ ID NO: 42), (SEQ ID NO: 17 and SEQ ID NO: 51), (SEQ ID NO: 20 and SEQ ID NO: 51), (SEQ ID NO: 20 and SEQ ID NO: 52), and (SEQ ID NO: 25 and SEQ ID NO: 54);
      iii. wherein if fungal DNA is present in said patient sample, said second PCR reaction generates a fungal PCR amplicon of between 50 and 1000 base pairs that comprises a region of said fungal ITS2 rRNA gene or a region of said fungal 28S rRNA gene that is 3' to a D1-D2 highly variable region, and
      iv. wherein if human DNA is present in said patient sample, said second PCR reaction does not generate a detectable PCR amplicon that comprises a region of said human DNA; and
   (b) detecting said fungal PCR amplicon;
wherein detection of the fungal PCR amplicon is indicative of the presence of at least one type of fungal nucleic acid; and
wherein the at least one type of fungal nucleic acid is from one or more fungal pathogens selected from the group consisting of Absidia corymbifera; Cunninghamella bertholletiae; Fusarium solani; Mucor racemosus; Paecilomyces variotii; Penicillium chrysogenum; Rhizomucor miehei; Rhodotorula glutinis; Scedosporium apiospermum; Antrodia vaillantii; Aspergillus fumigatus; Aspergillus niger; Aspergillus oryzae; Aspergillus terreus; Batrachochytrium dendrobatidis; Botrytis cinerea; Candida albicans; Candida dublineinsis; Candida glabrata; Candida gulliermundei; Candida kefyr; Candida krusei; Candida hpolytica; Candida lusitaniae; Candida parapsilosis; Candida tropicalis; Chaetomium globosum; Coccidioides immitis; Coccidioides posadasii; Cryptococcus neoformans; Fusarium graminearum; Fusarium oxysporum; Histoplasma capsulatum; Hypocrea jecorina; Lodderomyces elongisporus; Magnaporthe grisea; Metarhizium anisopliae; Microsporum gypseum; Neurospora crassa; Paracoccidioides brasthens; Pneumocystis carinii; Penicillium verrucosum; Pichia aponica; Rhizopus oryzae; Saccharomyces cerevisiae; Schizosaccharomyces aponicas; Schizosaccharomyces pombe; Sclerotinia sclerotiorum; Stagonospora nodorum; Umbilicaria esculenta; and Uncinocarpus reesii.

2. The method of claim 1 further comprising extracting DNA from said patient sample.

3. The method of claim 1 wherein said second forward primer and said second reverse primer are both complementary to a fungal 28S rRNA gene.

4. The method of claim 1 wherein said second primer set is not (SEQ ID NO: 2 and SEQ ID NO: 31), (SEQ ID NO: 2 and SEQ ID NO: 32), (SEQ ID NO: 1 and SEQ ID NO: 29), or (SEQ ID NO: 2 and SEQ ID NO: 30).

5. The method of claim 1 wherein said second primer set is not (SEQ ID NO: 2 and SEQ ID NO: 31), (SEQ ID NO: 2 and SEQ ID NO: 32), or (SEQ ID NO: 11 and SEQ ID NO: 41).

6. The method of claim 5 wherein said second primer set is not (SEQ ID NO: 2 and SEQ ID NO: 31), (SEQ ID NO: 2 and SEQ ID NO: 32), (SEQ ID NO: 11 and SEQ ID NO: 41), (SEQ ID NO: 1 and SEQ ID NO: 29), (SEQ ID NO: 14 and SEQ ID NO: 42), (SEQ ID NO: 17 and SEQ ID NO: 51), (SEQ ID NO: 20 and SEQ ID NO: 51), (SEQ ID NO: 20 and SEQ ID NO: 52), or (SEQ ID NO: 25 and SEQ ID NO: 54).

7. The method of claim 1 wherein said primer set further comprises a second reverse primer, the primer set consisting of SEQ ID NO: 12, SEQ ID NO: 41, and SEQ ID NO: 108.

8. The method of claim 1 wherein said second primer set comprises a combination of forward and reverse primers selected from the group consisting of (SEQ ID NO: 11 and SEQ ID NO: 41), (SEQ ID NO: 12 and SEQ ID NO: 41), (SEQ ID NO: 12,SEQ ID NO: 41, and SEQ ID NO: 108), (SEQ ID NO: 14 and SEQ ID NO: 42), (SEQ ID NO: 17 and SEQ ID NO: 51), (SEQ ID NO: 20 and SEQ ID NO: 51), (SEQ ID NO: 20 and SEQ ID NO: 52), and (SEQ ID NO: 25 and SEQ ID NO: 54).

9. The method of claim 8 wherein said second primer set is not (SEQ ID NO: 11 and SEQ ID NO: 41), (SEQ ID NO: 14 and SEQ ID NO: 42), (SEQ ID NO: 17 and SEQ ID NO: 51), (SEQ ID NO: 20 and SEQ ID NO: 51), (SEQ ID NO: 20 and SEQ ID NO: 52), or (SEQ ID NO: 25 and SEQ ID NO: 54).

10. The method of claim 1 wherein each primer of the second primer set can specifically hybridize to a fungal DNA but not to a non-fungal DNA.

11. The method of claim 10 wherein the non-fungal DNA is mammalian DNA.

12. The method of claim 11 wherein the mammalian DNA is human DNA.

13. The method of claim 1 wherein the second primer set can be used to preferentially amplify fungal DNA over non-fungal DNA when the non-fungal DNA is in greater than 1,000,000-fold mass excess of the fungal DNA and less than 100,000,000-fold mass excess of the fungal DNA.

14. The method of claim 1 wherein the second primer set can be used to preferentially amplify fungal DNA over non-fungal DNA when the non-fungal DNA is in greater than 5,000,000-fold excess of the fungal DNA and less than 100,000,000-fold mass excess of the fungal DNA.

15. The method of claim 1 wherein the second primer set can be used to preferentially amplify fungal DNA over non-fungal DNA when the non-fungal DNA is in greater than 30,000,000-fold excess of the fungal DNA and less than 100,000,000-fold mass excess of the fungal DNA.

16. The method of claim 1, further comprising the step of sequencing said PCR amplicon.

17. The method of claim 1 wherein said PCR amplicon is between 50 and 1000 base pairs.

18. The method of claim 17 wherein said PCR amplicon is between 75 and 400 base pairs.

19. The method of claim 1 wherein said PCR reaction is a quantitative PCR reaction.

20. The method of claim 1 wherein said patient sample is selected from the group consisting of a blood sample, a sputum sample, a lung lavage fluid sample, and a tissue biopsy sample.

21. The method of claim 20 wherein said blood sample is selected from the group consisting of whole blood, plasma, serum, and a white blood cell fraction.

22. The method of claim 1 wherein said fungal pathogen causes a fungal infection selected from the group consisting of *aspergillosis, candidiasis, zygomycosis, scedosporiosis, fusariosis, cryptococcosis, histoplasmosis, coccidioidomycosis,* and *blastomycosis*.

* * * * *

```
                         SEQUENCE LISTING

<160> NUMBER OF SEQ ID NOS: 108

<210> SEQ ID NO 1
    <211> LENGTH: 22
    <212> TYPE: DNA
    <213> ORGANISM: Artificial Sequence
    <220> FEATURE:
    <223> OTHER INFORMATION: Synthetic oligonucleotide

<400> SEQUENCE: 1
gtaaaagtcg taacaaggtt tc                                              22

<210> SEQ ID NO 2
    <211> LENGTH: 22
    <212> TYPE: DNA
    <213> ORGANISM: Artificial Sequence
    <220> FEATURE:
    <223> OTHER INFORMATION: Synthetic oligonucleotide

<400> SEQUENCE: 2
gtgaatcatc gartctttga ac                                              22

<210> SEQ ID NO 3
    <211> LENGTH: 21
    <212> TYPE: DNA
    <213> ORGANISM: Artificial Sequence
    <220> FEATURE:
    <223> OTHER INFORMATION: Synthetic oligonucleotide

<400> SEQUENCE: 3
tacccgctga acttaagcat a                                               21

<210> SEQ ID NO 4
    <211> LENGTH: 22
    <212> TYPE: DNA
    <213> ORGANISM: Artificial Sequence
    <220> FEATURE:
    <223> OTHER INFORMATION: Synthetic oligonucleotide

<400> SEQUENCE: 4
gcatatcaat aagcggagga aa                                              22

<210> SEQ ID NO 5
    <211> LENGTH: 20
    <212> TYPE: DNA
    <213> ORGANISM: Artificial Sequence
    <220> FEATURE:
    <223> OTHER INFORMATION: Synthetic oligonucleotide
```

<400> SEQUENCE: 5
agtarcggcg agtgaagcgg                                          20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
agctcaaatt tgaaasctgg                                          20

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 7
cttccctttc aacaatttca crt                                      23

<210> SEQ ID NO 8
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 8
aggtaaagcg aatgattag                                           19

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
cttgttrctt arttgaacgt g                                        21

<210> SEQ ID NO 10
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 10
accacaaaag gtgttagtwc atc                                      23

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 11
gaagtgggga aaggttcc                                            18

<210> SEQ ID NO 12
<211> LENGTH: 21

```
<212> TYPE: DNA
<213> ORGANISM: Artificial Sequence
<220> FEATURE:
<223> OTHER INFORMATION: Synthetic oligonucleotide

<400> SEQUENCE: 12
gacatgggtt agtcgatcct a                                              21

<210> SEQ ID NO 13
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 13
tcgtactcat aaccgcagc                                                 19

<210> SEQ ID NO 14
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 14
gttgatagaa yaatgtagat aagg                                           24

<210> SEQ ID NO 15
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 15 caagggaat ctgactgtc                                                  19

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 16
tttacttawt caatgaagcg g                                              21

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
ccgggttgaw gacattgtca                                                20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
```
gctggggcgg cacatctgtt                                        20

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 19
gaacaaaagg gtaaaagtcc c                                      21

<210> SEQ ID NO 20
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 20
tttgattttc agtgtgaata caaacca                                27

<210> SEQ ID NO 21
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 21
atgaaagtgt ggcctatcg                                         19

<210> SEQ ID NO 22
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 22
gaggctagag gtgccagaa                                         19

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
agggataact ggcttgtggc                                        20

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 24
accgaagcag aattcggtaa g                                      21

<210> SEQ ID NO 25
<211> LENGTH: 21
<212> TYPE: DNA
<213> ORGANISM: Artificial Sequence

```
<220> FEATURE:
<223> OTHER INFORMATION: Synthetic oligonucleotide

<400> SEQUENCE: 25
gataattggt wtttgcggct g                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 26
gctgaacgcc tctaagtcag a                                              21

<210> SEQ ID NO 27
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 27
tcgtarcaac aaggctact                                                 19

<210> SEQ ID NO 28
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 28
gaaaccttgt tacgactttt ac                                             22

<210> SEQ ID NO 29
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 29
gttcaaagay tcgatgattc ac                                             22

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 30
tatgcttaag ttcagcgggt a                                              21

<210> SEQ ID NO 31
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 31
tttcctccgc ttattgatat gc                                             22
```

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
ccgcttcact cgccgytact                                           20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
ccagstttca aatttgagct                                           20

<210> SEQ ID NO 34
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 34
aygtgaaatt gttgaaaggg aag                                       23

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
ctaatcattc gctttacctc                                           20

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 36
cacgttcaay taagyaacaa g                                         21

<210> SEQ ID NO 37
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 37
gatgwactaa cacctttgt ggt                                        23

<210> SEQ ID NO 38
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 38
ggaacctttc cccacttc                                                   18

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 39
taggatcgac taacccatgt c                                               21

<210> SEQ ID NO 40
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 40
gctgcggtta tgagtacga                                                  19

<210> SEQ ID NO 41
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 41
ccttatctac attrttctat caac                                            24

<210> SEQ ID NO 42
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 42
gacagtcaga ttccccttg                                                  19

<210> SEQ ID NO 43
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 43
ccgcttcatt gawtaagtaa a                                               21

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
tgacaatgtc wtcaacccgg                                                 20

<210> SEQ ID NO 45

<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
aacagatgtg ccgccccagc                                          20

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 46
gggactttta ccctttgtt c                                         21

<210> SEQ ID NO 47
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 47
tggtttgtat tcacactgaa aatcaaa                                  27

<210> SEQ ID NO 48
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 48
cgataggcca cactttcat                                           19

<210> SEQ ID NO 49
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 49
ttctggcacc tctagcctc                                           19

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
gccacaagcc agttatccct                                          20

<210> SEQ ID NO 51
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 51

```
cttaccgaat tctgcttcgg t                                               21

<210> SEQ ID NO 52
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 52
cagccgcaaa waccaattat c                                               21

<210> SEQ ID NO 53
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 53
tctgacttag aggcgttcag c                                               21

<210> SEQ ID NO 54
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 54
agtagccttg ttgytacga                                                  19

<210> SEQ ID NO 55
<211> LENGTH: 3733
<212> TYPE: DNA
<213> ORGANISM: Absidia corymbifera rRNA gene

<400> SEQUENCE: 55
attaactatc cccaaaggtg tttattcttc tcgtgctaaa ccatgatgta cgaaaaagtt      60
agttgttaac ttaaaaacaa ctcttggcaa tggatctctt ggttctcgca tcgatgaaga    120
gcgtagcaaa gtgcgataat tattgcgact tgcattcata gcgaatcatc gagttctcga    180
acgcatcttg cgcctagtag tcaatctact aggcacagtt gtttcagtat ctgcaactac    240
caatcagttc aacttggttc tttgaaccta agcgagctgg aaatgggctt gtgttgatgg    300
cattcagttg ctgtcatggc cttaaataca tttagtccta ggcaattggc tttagtcatt    360
tgccggatgt agactctaga gtgcctgaag agcaacgact tggttagtga gttcataatt    420
ccaagtcaat cagtctcttc ttgaactagg tcttaatctt tacggactag tgagaggatc    480
taacttgggt cttctcttga acaaactcac atctagatct gaaatcaact gagatcaccc    540
gctgaactta agcatatcaa taagcggagg aaagaaaat aaccatggat tcccctagta     600
acggcgagtg aagagggaaa agctcaaagt tggaacctgg ctgccctagg cagtccggat    660
tgtaaactaa agagcgtgat tccaggcaag ccggttgacc aagtcctttg gaatgaggcg    720
ccactgaggg tgagagcccc gtaagtcgac tgagcatttg tcttttgtgt ttcgcgttca    780
aagagtcagg ttgtttggga atgcagccta agctggtgg taaatcccac ctaaagctaa     840
atacaggcga gagaccgata gcgaacaagt accgtgaggg aaagatgaaa agaactttga    900
aaagagagtt aaacagtatg tgaaattgcc aagagggaag catttggagt tagattgact    960
```

```
aggagttaat cagcttggtc tttggactgg gtgtacttga cttcttacag tctgccaata      1020
gcagttagtc ctagtggaaa aaaccagagg gaaggtagtc cttcgggatg tttatagacc      1080
tttggaaaat acactgggat tgactgagga atgcagtaga tgccactaag gcttcgtcta      1140
gtgggtgcta ggcaaaggta cttggtattt tcagcttgct gatgtgctag gttactcgag      1200
tctagtcgcc tactagaact gtaatctact ttggttattg gcttaatgac tctaaatggc      1260
ccgtcttgaa acacggacca aggagtccac cacaggtgcg agtattaggg tggcaaaccc      1320
ataatgcgca atgaaagtga cactttaagc taccaaggtt ccttcggggg cctgcagtag      1380
cctcaggcat ggacgtttta tactgaaatg acctagagaa agcacttgtg atgggacccg      1440
aaagatggtg aactatgctt gagtaggatg aagccagagg aaactctggt ggaggtccga      1500
agcggttctg acgtgcaaat cgatcgtcaa acttgagcat aggggcgaaa gactaatcga      1560
accatctagt agctggttcc tgccgaagtt tccctcagga tagcagaaac tcaaaggcag      1620
ttttacgtgg taaagcgaat gattagaggc cttgggacg aaatgtcctt aacctattct       1680
caaactttaa atatgtaaga tgtccttctt tcttagttga agttggacca tcgaatgtcg      1740
agtttctagt gggccatttt tggtaagcag aactggcgat gcgggatgaa ccgaacgcaa      1800
agttaaagcg ccggaatact cgctcatcag acaccacaaa aggtgttagt tcatctagac      1860
agcaggacgg tggccatgga agtcggaatc cgctaaggag tgtgtaacaa ctcacctgcc      1920
gaatgaacta gccctgaaaa tggatggcgc ttaagcgagt tgcttatact ttgcccatag      1980
ggtaaaagcg atgctctatg gagtaggcag gcgtggaggt ctagttgcga agctctgacc      2040
gtaaggttga gtggaacggc ctctagtgca gatcttggtg gtagtagcaa atattcaagt      2100
gagaaccttg aagactgaag tggagaaggg ttcctcgaga acattagttg gtcgagggtt      2160
agtcgatcct aagagatagg gaagttccgt tttatcaaag tgctcaattt acttgggccg      2220
cctatcgaaa gggaaactgg ttaaaattcc agtactggga cacaggtctt tgcggcaac       2280 gcaaatgaac ttggcgacgc tggcatggat cccgagaaga gttctctttt cttttttaaca    2340 gtttatcttt gaccatgaaa tcagtttatc tggagaaatg gttaaagtgc tggaagagtc     2400
ctacactttt agtaggattc ggtgcatcca ttacagtcct tgaaaagcca ggggaaactt     2460
atagactttg tgcctagtcg tacccataac cgcagcaggt ctcctaggtg ttaagcctct    2520
agttgatgga acaatgtaga taagggaagt cggcaaaata gatccgtaac ttcgggataa    2580
ggattggctc taagggctgg gtagatttga gcctaggtct tcggtgagtt gggacttggt    2640
gctgggcttc gggctctg gtgctaggat ctagcttgcc acttggccta ggaagttcgg       2700
tctacaatta acagccaact tagaactggt acggacaagg ggaatctgac tgtctaatta    2760
aaacatagca ttgcgatggt cagaaagtga ttttgacgca atgtgatttc tgcccagtgc    2820
tctgaatgtc aaagtgaaga aattcaacca agcgcgggta aacggcggga gtaactatga    2880
ctctcttaag gtagccaaat gcctcgtcat ctaattagtg acgcgcatga atggattaac    2940
gagattccca ctgtccctat ctactatcta gcgaaaccac agccaaggga acgggcttgg   3000
cagaatcagc ggggaaagaa gaccctgttg agcttgactc tagtttgcat tgtgaaaaga   3060
catagagggt gtagcatatg agggagactt cggtcgccag tgaaatacct caacctctat    3120
tgttttttta cttaaatatt caagtgggac tgggtagcaa tacctatgtt ctagtattaa   3180
gcctacattg ttaggtgacc cacgatattg acattgtcaa gtgggagtt tggctggggc     3240 ggcacatctg ttaaacaata acgcaggtgt cctaaggggg actcagtgag aacagaaatc   3300
tcacgtagag caaaagggca aaagtcccct tgattttgat tttcagtgtg aatacaaacc   3360
```

-continued

| | |
|---|---|
| atgaaagtgt ggcctatcga tcctttagtt sctyrgratt tragsctaga ggtgccagaa | 3420 |
| aagttaccac agggataact ggcttgtggc agccaagcgt tcatagcgac gttgcttttt | 3480 |
| gattcttcga tgtcggctct tcctatcata ctgaagcaga attcagtaag cgttggattg | 3540 |
| ttcacccact aatagggaac gtgagctggg tttagaccgt cgtgagacag gttagtttta | 3600 |
| ccctactgat ggaattggtg tctcaacagt aattgaagtt agtacgagag gaacccttca | 3660 |
| ttcagataat tggtatttgc gcctggttga aaggccaatg gcgcgaagct accatctgct | 3720 |
| ggataatggc tga | 3733 |

<210> SEQ ID NO 56
<211> LENGTH: 4035
<212> TYPE: DNA
<213> ORGANISM: Cunninghamella bertholletiae rRNA gene

<400> SEQUENCE: 56

| | |
|---|---|
| cgattgaatg gtcatagtga gcatgtggga tctttgaagg ctggttggca acaaccggct | 60 |
| tttgaggaga actatggcaa actagattat ttagaggaag taaaagtcgt aacaaggttt | 120 |
| ccgtaggtga acctgcggaa ggatcattac atattgggtc aaaagaatag tttgaaaaag | 180 |
| gctatttttt tttgacttaa aaaacttatc cacagtgtgg gaaatgtctt ctaacgcttg | 240 |
| tgcctggttc agtctagtgc tgccacttga gtttatcctt agatcaaggg atctttgggt | 300 |
| agttgttcat tattttctct ctcttttag gggggggag attaatgatg ggcacctctt | 360 |
| gtaaagggga taagattact tttattatac taaattttac tgaactgata gaccataaat | 420 |
| ctatggttgt tttttattat aattaaaaaa aaaaacaac tttcagcaat ggatctctcg | 480 |
| gctttcgtat cgatgaagaa cgcagcaaat cgcgatatgt aatgtgatct gcctatagtg | 540 |
| aatcatcaaa tctttgaacg catcttgcac cttatggtat tccataaggt acgtctgttt | 600 |
| cagtaccact aataaatctc tctctatcct tgatgataga aaaaagaga taaattatta | 660 |
| ctggtcctgg tgattctttt tttttttttt attaaaaaga accactctcg gcctaaatat | 720 |
| aaggctcgac ttttttttac cagatcttgc atctagtaaa aacctagtcg gctttaatag | 780 |
| atttttattt tctattaagt ttatagccat tcttatattt tttaaaatct tggcctgaaa | 840 |
| tcagatggga ctacccgctg aacttaagca tatcaataag cggaggaaaa gaaaataaca | 900 |
| atgattcccc tagtarcggc gagtgaagag ggaaaagctc aaagttggaa cctggtaggc | 960 |
| atagcttacc cggattgtaa actaaagttt tcgagtcgtt tagtcagcca ggtaaataag | 1020 |
| tcctctggaa aggggcgaca tagagggtga aatccccgtc tttggcctga gttttgatta | 1080 |
| ggcgtttggc ttggaaacga agagtcaggt tgtttgggaa tgcagcctaa aatgggaggt | 1140 |
| aaatctctcc taaagctaaa tattgacgaa agaccgatag cgaacaagta ccgtgaggga | 1200 |
| aagatgaaaa gcactttgaa aagagggtca aaaagtacgt gaaattgctg aaagggaacc | 1260 |
| gtatgaaatc agatctactg gtaggtaatc aatctttcct ttgggaagga tgcacttgcc | 1320 |
| tactatgtat gccagcgaca ttttggttgg gaggaaaaaa ataaaggaaa tgtagcttag | 1380 |
| gtttcggctt aggtgttata gtcctttata aaatactctc ggctggaatg aggaacgcag | 1440 |
| caaaccgtaa ggcgaagatt tcaggcgctt agagggaata attagagaat ttctgcttcg | 1500 |
| ggtggtgctt tgattattac ctttaacacg cttggagttc ttttaatttg cttaggttgt | 1560 |
| tggcttaatg atttatatg acccgtcttg aaacacggac caaggagtcc accataggcg | 1620 |
| cgagtctttg ggtgtaaaaa cccatgggcg gaaggaaatt gactaagata ccaaggcgca | 1680 |

```
agctggcagt atcccccggc gtagacgttt ttatactgaa atgactgagg gcaagcgctt    1740
atgatgggac ccgaaagatg gtgaactata cttgaatagg gtaaagccag aggaaactct    1800
ggtggaagct cgcagcgatt ctgacgtgca aatcgatcgt caaatttgag tataggggcg    1860
aaagactaat cgaaccatct agtagctggt tcctgccgaa gtttccctca ggatagcaga    1920
agctcgtagg cagttttatg aggtaaagcg aatgattaga ggcctagggg cttattgcc    1980
ctttacctat tctcaaactt taaatatgta agacgtttgg cttgcttaat tgaagtcaaa    2040
catatgaatg cagagctttt agtgggccat ttttggtaag cagaactggc gatgcgggat    2100
gaaccgaacg taaagttaag gtgcccaaat tcacgctcat cagacaccag aaaaggtgtt    2160
agttcatcta gacagcagga cggtggccat ggaagtcgga atccgctaag gagtgtgtaa    2220
caactcacct gccgaatgaa ctagccctga aatggatgg cgcttaagcg tgatacctat    2280
actttaccgt caaagtaaaa gcgaagcttt gacgagtagg caggcgtgga ggttttgtat    2340
agaagccttg ggcgtgagct cgggtgaaac ggcctctagt gcagatcttg gtggtagtag    2400
caaatattct aatgagaatt tgaagactg aagtggagaa aggttcctag agaacagtag    2460
ttggtctagg gttagtcgct cctaaggcac agggaagttc tgtcaaatgc agatccattt    2520
tatgggtcca ggtgccgaaa gggaaactgg ttaatattcc agtactagga taggggttc    2580
taatatggta acataacgga tcttggggac attggtatga agcccagaaa gagttaactt    2640
ttctttctta cggtctctta agttgatatt ccttggaaac ggtttagccg gagcaaaggt    2700
gtatcggccg gtaaagcatg attttttatg atcatgtctg gagccttcat aacgatcctt    2760
gaaaacccaa gggacatata tggccttcct acctaggcgt actcataacc gcagcaggtc    2820
tccaaggtta acagcctcta gttgatagaa taatgtaggt aagggaagtc ggcaaattag    2880
atccgtaact tcgggataag gattggctct aagggttagg taggaaacgt attagatgga    2940
tgaagaggtg agtctggaga aggctggttg gggcaacctg actggctttt tttgggcaat    3000
cctcttgtac cgtctaatgg cggcctacaa taataaccac ttagaactgg tacgacaaa    3060
gggaatctga ctgtctaatt aaaacatagc attgtgatag tcagaaagtg attttgacac    3120
aatgtgattt ctgcccagtg ctctgaatgt caaagtgaag aaattcaacc aagcgcgggt    3180
aaacggcggg agtaactatg actctcttaa ggtagccaaa tgcctcgtca tctaattagt    3240
gacgcgcatg aatggattaa cgagattccc actgtcccta tctactatct agcgaaacca    3300
cagccaaggg aacgggcttg gcagaatcag cggggaaaga agaccctgtt gagcttgact    3360
ctagtttgac attgtgaaaa gacatagagg gtgtagaata agtgggagct ccggcgccag    3420
tgaaatacca ctacctctat tgtttttta cttagataat tataagggat taggtggcaa    3480
cacctacttt ctagacagaa tccacttcgt gtggagaccc tcgttattga cattgtcaag    3540
tggggagttt ggctggggcg gcacatctgt taaacaataa cgcaggtgtc ctaaggggg    3600
ctcagcgaga cgagaaattt cgcgtagagt aaaaggcaa aagtccccctt gattttgatt    3660
ttcagtgtga atacaaacca tgaaagtgtg gcctatcgat cctttagttg ctaaagattt    3720
tagcctagag gtgccagaaa agttaccaca gggataactg gcttgtggca gccaagcgtt    3780
catagcgacg ttgctttttg attcttcgat gtcggctctt cctatcatac tgaagcagaa    3840
ttcagtaagc gttggattgt tcacccacta atagggaacg tgagctgggt ttagaccgtc    3900
gtgagacagg ttagttttac cctactgatg ttaatgggta tcgtaacagt aattgaagtt    3960
agtacgagag gaacccttca ttcagataat tggtatttgc ggctggttgt ccagccaatg    4020
ccgcgaagct accgt                                                     4035
```

<210> SEQ ID NO 57
<211> LENGTH: 3830
<212> TYPE: DNA
<213> ORGANISM: Fusarium solani rRNA gene
<220> FEATURE:
<221> NAME/KEY: misc_feature
<222> LOCATION: (2099)..(2099)
<223> OTHER INFORMATION: n is a, c, g, or t

<400> SEQUENCE: 57

```
taagaggaag taaaagtcgt aacaaggttt cgttggtgaa ccagcggagg gatcattacc      60
gagttataca actcatcaac cctgtgaaca tacctataac gttgcctcgg cgggaacaga     120
cggccccgta acacgggccg ccccgccag aggaccccct aactctgttt ctataatgtt      180
tcttctgagt aaacaagcaa ataaattaaa actttcaaca acggatctct tggctctggc     240
atcgatgaag aacgcagcga atgcgataa gtaatgtgaa ttgcagaatt cagtgaatca      300
tcgaatcttt gaacgcacat tgcgcccgcc agtattctgg cggcatgcc tgttcgagcg      360
tcattacaac cctcaggccc ccgggcctgg cgttggggat cggcggaagc ccctgcggg      420
cacaacgccg tcccccaaat acagtggcgg tcccgccgca gcttccattg cgtagtagct     480
aacacctcgc aactggagag cggcgcggcc acgccgtaaa acacccaact tctgaatgtt     540
gacctcgaat caggtaggaa tacccgctga acttaagcat atcaataagc ggaggaaaag     600
aaaccaacag ggattgcccc agtaacggcg agtgaagcgg caacagctca aatttgaaat     660
ctggctctcg ggcccgagtt gtaatttgta gaggatgctt ttggtgaggt gccttccgag     720
ttccctggaa cgggacgcca tagagggtga gagccccgtc tggttggaca ccgatcctct     780
gtaaagcttc ttcgacgagt cgagtagttt gggaatgctg ctctaaatgg gaggtatatg     840
tcttctaaag ctaaataccg gccagagacc gatagcgcac aagtagagtg atcgaaagat     900
gaaaagaact ttgaaaagag agttaaaaag tacgtgaaat tgttgaaagg gaagcgcttg     960
tgaccagact tgggcttggt tgatcatccg gggttctccc cggtgcactc ttccggctca    1020
ggccagcatc agttcgccct gggggataaa ggcttcggga atgtggctct ctccggggag    1080
tgttatagcc cgctgcgtaa taccctgtgg cggactgagg ttcgcgcatt cgcaaggatg    1140
ctggcgtaat ggtcatcagt gacccgtctt gaaacacgga ccaaggagtc gtcttcgtat    1200
gcgagtgttc gggtgtcaaa cccctacgcg aaatgaaagt gaacgcaggt gagagcttcg    1260
gcgcatcatc gaccgatcct gatgttatcg gatggatttg agtaagagca tacggggccg    1320
gacccgaaag aaggtgaact atgcctgtgt agggtgaagc cagaggaaac tctggtggag    1380
gctcgcagcg ttctgacgt gcaaatcgat cgtcaaacat gggcatgggg cgaaagact    1440
aatcgaacct tctagtagct ggtttccgcc gaagtttccc tcaggatagc agtgttgaac    1500
tcagttttat gaggtaaagc gaatgattag ggactcgggg cgctattta gccttcatcc    1560
attctcaaac tttaaatatg taagaagcc ttgttgctta attgaacgtg ggcattcgaa    1620
tgaatcaaca ctagtgggcc attttttggta agcagaactg gcgatgcggg atgaaccgaa    1680
cgcgaggtta aggtgccaga gtagacgctc atcagacacc acaaaaggtg ttagtacatc    1740
ttgacagcag gacggtggcc atggaagtcg gaatccgcta aggactgtgt aacaactcac    1800
ctgccgaatg tactagccct gaaaatggat ggcgctcaag cgtctcaccc atacctcgcc    1860
ctcagggtag aaacgatgcc ctgaggagta ggcggacgtg gaggtcagtg acgaagccta    1920
gggcgtgagc ccgggttgaa cggcctctag tgcagatctt ggtggtagta gcaaatactt    1980
```

```
caatgagaac ttgaaggacc gaagtgggga aaggttccat gtgaacagcg gttggacatg    2040
ggttagtcga tcctaagcca tagggaagtt ccgtttcaaa ggcgcactat gcgccgtcnt    2100
ggcgaaaggg gagccggtca atattccggc acctggatgt gggttttgcg cggcaacgca    2160
actgaacgcg gagacgacgg cggggccccc gggcagagtt ctcttttctt cttaacagtc    2220
tctcaccctg aaatcggttt gtccggagct agggtttaat ggctggaaga gcccagcacc    2280
tctgctgggt ccggtgcgct ctcgacgtcc cttgaaaatc gcggaagaa ataattctc     2340 acgccaggtc gtactcataa ccgcagcagg tctccaaggt gaacagcctc tggttgatag    2400
aacaatgtag ataagggaag tcggcaaaat agatccgtaa cttcgggata aggattggct    2460
ctaagggttg ggcacgcagg gccttgggcg gacgccatgg gggcaggctg cttctagccg    2520
ggcaaccggc cggcggcggc cagcacccgt gcgctgatgc ccttggcagg cttcggccgt    2580
ccggcgtgcg gttaacaacc aacttagaac tggtacggac aaggggaatc tgactgtcta    2640
attaaaacat agcattgcga tggccagaaa gtggtgttga cgcaatgtga tttctgccca    2700
gtgctctgaa tgtcaaagtg aagtaattca accaagcgcg ggtaaacggc gggagtaact    2760
atgactctct taaggtagcc aaatgcctcg tcatctaatt agtgacgcgc atgaatggat    2820
taacgagatt cccactgtcc ctatctacta tctagcgaaa ccacagccaa gggaacgggc    2880
ttggcagaat cagcggggaa agaagaccct gttgagcttg actctagttt gacattgtga    2940
aaagacatag gaggtgtaga ataggtggga gcttcggcgc ggtgaaatac cactactcct    3000 attgttttt tacttattca atgaagcggg gctggatttt cgtccaactt ctggttttaa    3060
ggtccttcgc gggccgaccc gggttgaaga cattgtcagg tggggagttt ggctggggcg    3120
gcacatctgt taaaccataa cgcaggtgtc ctaaggggt ctcatggaga acagaaatct    3180
ccagtagagc aaaagggcaa aagtcccctt gattttgatt ttcagtgtga atacaaacca    3240
tgaaagtgtg gcctatcgat cctttagtcc ctcgacattt gaggctagag gtgccagaaa    3300
agttaccaca gggataactg gcttgtggcg gccaagcgtt catagcgacg tcgctttttg    3360
atccttcgat gtcggctctt cctatcatac cgaagcagaa ttcggtaagc gttggattgt    3420
tcacccacta atagggaacg tgagctgggt ttagaccgtc gtgagacagg ttagttttac    3480
cctactgatg acctcgccgc aatggtaatt cagcttagta cgagaggaac cgctgattca    3540
gataattggt ttttgcggct gtccgaccgg gcagtgccgc gaagctacca tctgctggat    3600
aatggctgaa cgcctctaag tcagaatcca tgccagaacg cggtgatacc gcccgcacgt    3660
acagatggac aagaataggc ttcggcttag cgtcttagca ggcgattctt ccgcggcgca    3720
cgaagcgcgt cgtggtattt cgcgtattgt aatttcaaca cgagcggggt caaatccttt    3780
gcagacgact tagctgtgcg aaacggtcct gtaagcagta gagtagcctg              3830

<210> SEQ ID NO 58
<211> LENGTH: 3999
<212> TYPE: DNA
<213> ORGANISM: Mucor racemosus rRNA gene

<400> SEQUENCE: 58
taggtgaacc tgcggaagga tcattaaata atcaataatc ttggcttgtc cattattatc      60
tatttactgt gaactgtatt attatttgac atttgaggga tgttccaatg ttataaggat     120
agacattgga aatgttaacc gagtcataat caggtttagg cctggtatcc tattattatt     180
taccaaatga attcagaatt aatattgtaa catagaccta aaaatctat aaaacaactt      240 ttaacaacgg atctcttggt tctcgcatcg atgaagaacg tagcaaagtg cgataactag     300
```

```
tgtgaattgc atattcagtg aatcatcgag tctttgaacg caacttgcgc tcattggtat    360
tccaatgagc acgcctgttt cagtatcaaa acaaaccctc tatccaactt ttgttgtata    420
ggattattgg gggcctctcg atctgtatag atcttgaaat ccctgaaatt tactaaggcc    480
tgaacttgtt taaatgcctg aacttttttt taatataaag gaaagctctt gtaattgact    540
ttgatggggc ctcccaaata aatctttttt aaatttgatc tgaaatcagg cgggattacc    600
cgctgaactt aagcatatca ataagcggag gaaaagaaaa taacaatgat ttccctagta    660
acggcgagtg aagaggaaag agctcaaagt tggaacctgt ttggcttagc taaaccggat    720
tgtaaactgt agaaacattt tccagataca ctagacaaaa agtcctttg gaacagggca     780 tcatagaggg tgagaatccc gtctttggtc aagtagttg tctattgtga tatgttttca     840
aagagtcagg ttgtttggga atgcagccta aattgggtgg taaatctcac ctaaagctaa    900
atatttgcga gagaccgata gcgaacaagt accgtgaggg aaagatgaaa agaactttga    960
aaagagagtt aaacagtatg tgaaattgtt aaaagggaac cgtttggagc cagattggct   1020
tgattgtaat caacctagaa ttcgttttgg gtgcacttgc agtctatgcc tgccaacgac   1080
agtttgattt ggaggaaaaa attaatagga atgtggcctt tcgaggtgtt atagcctatt   1140
atcatactct ggattggact gaggaacgca gcgaatgcct ttaggcaaga ttgctgggcg   1200
ctttccctaa taaatgttag aatttctgct tcgggtggtg ctaatgttta aaggaggaac   1260
ccgcttagta tattttttat tcgcttaggt ttgttggctt aatgactcta aatgacccgt   1320
cttgaaacac ggaccaagga gtccaccata agtgcaagta tttgggtgcc aaacccatat   1380
gcgtaaggaa actgattgat acgaaatcgc gagatggcag tatcacccgg cgctgacgtt   1440
ttatactgaa ttgaccgagg taaagcactt atgatgggac ccgaaagatg gtgaactatg   1500
cctgaatagg gtgaagccag aggaaactct ggtggaggct cgtagcgatt ctgacgtgca   1560
aatcgatcgt caaatttggg tatagggcg aaagactaat cgaaccatct agtagctggt    1620
tcctgccgaa gtttccctca ggatagcaaa aacttaaaag cagttttatg aggtaaagcg   1680
aatgattaga ggccttgggg acgaaatgtc cttaacctat tctcaacttt aaatatgtaa   1740
gacgacctgt ttgcttaatt gaagcaggtc attgaatgtg agttttagt gggccatttt    1800 tggtaagcag aactggcgat gcgggatgaa ccgaacggaa agttaaggtg ccggaataca   1860
cgctcatcag acaccacaaa aggtgttagt tcatctagac agcaggacgg tggccatgga   1920
agtcggaatc cgctaaggag tgtgtaacaa ctcacctgcc gaatgaacta gccctgaaaa   1980
tggatggcgc ttaagcgtgt tacccatact ttcccgttat tgtaaaagcg aagcaataac   2040
gagtaggcag gcgtggaggt ttttataaac tgttaagaag ctcttggtgt gaaccggagt   2100
gaaacagcct ctagtgcaga tcttggtggt agtagccaaa tattcaaatg gaactttga    2160 agactgaagt ggagaaggtt cctggagaac attatttggt cccggggtag tcgatcctag   2220
aggtagggaa gttccgttat ttcaaagtga tcaattttga tccgcctatc gaaagggaaa   2280
cagtttaata ttactgtact aggacgagga ttttctgcgg caacgcaaat gaacttggag   2340
acatcagtgt gggtcccggg aagagttatc ttttctttt aacaactttg ttgtagacct    2400
tgaaatctgt ttagcaggag aaaaggttta ccggttggta gagcatagta cttttgcta    2460 tgtccggtgc attcacaacg atccttgaaa atccaaggga aagaataatt ttctcgccta   2520
gtcgtactca taaccgcagc aggtctccaa ggtgaaaagc ctctagttga tagaacaatg   2580
tagataaggg aagtcggcaa aatagatccg taacttcggg ataaggattg gctctaaggg   2640
```

```
ttgggtagat atggactttt ggtatggttg atttctaggc gatttcaaat gatttcggtt      2700
gtttgatttt gctcggagat cttcgttaac caagagagcc cagtttacgt ttaacaacca      2760
acttagaact ggtacggaca aggggaatct gactgtctaa ttaaaacata gcattgcgat      2820
ggccagaaag tggtgttgac gcaatgtgat ttctgcccag tgctctgaat gtcaaagtga      2880
agaaattcaa ccaagcgcgg gtaaacggcg ggagtaacta tgactctctt aaggtagcca      2940
aatgcctcgt catctaatta gtgacgcgca tgaatggatt aacgagattc ccactgtccc      3000
tatctactat ctagcgaaac cacagccaag ggaacgggct tggcagaatc agcggggaaa      3060
gaagaccctg ttgagcttga ctctagtttg acattgtgaa aagacataga gggtgtagca      3120
taagtgggag cttcggcgcc agtgaaatac cactaccttt atcgtttttt tacttaaata      3180
attaagtggg attgagtcgc aagactcacc ttctagtatt aagcatcttc ggatgtgacc      3240
cacgttattg acattgtcaa gtggggagtt tggctggggc ggcacatctg ttaaaagata      3300
acgcaggtgt cctaaggggg actcaacgag aacagaaatc tcgtgtagaa taaaagggta      3360
aaagtcccct tgattttgat tttcagtgtg aatacaaacc atgaaagtgt ggcctatcga      3420
tcctttagaa tctcaagatt tgaggctaga ggtgccagaa aagttaccac agggataact      3480
ggcttgtggc agccaagcgt tcatagcgac gttgcttttt gattcttcga tgtcggctct      3540
tcctatcata ctgaagcaga attcagtaag cgttggattg ttcacccact aatagggaac      3600
gtgagctggg tttagaccgt cgtgagacag gttagttttta ccctactgat ggtattggta      3660
tcgtaacagt aattgaagtt agtacgagag gaacccttca ttcagataat tggtatttgc      3720
ggctggttga aaggccaatg ccgcgaagct accatctgct ggataatggc tgaacgcctc      3780
taagtcagaa tccatgctga aaacgatact actgtgtttt gattgtacca gatgagtact      3840
aataaagctt cggcttgaaa acctttactt gtgagctagg cttggtaacg gaaatgttgc      3900
taggtctact tgctaatgat aatgctaata catcaaaatg ataaatcgca tgcagacgac      3960
atgaaatgga cggggtattg taagtactag agtagcctg                             3999
```

<210> SEQ ID NO 59
<211> LENGTH: 3972
<212> TYPE: DNA
<213> ORGANISM: Paecilomyces variotii rRNA gene

<400> SEQUENCE: 59

```
cgattgaatg gccttcggac tggctcaggg gggttggcaa cgaccgccca                  60
gagccggaaa gttggtcaaa cttggtcatt tagaggaagt aaaagtcgta acaaggtttc      120
cgtaggtgaa cctgcggaag gatcattacc gagtgagggt ccctcggggc ccaacctccc      180
atccgtgttg tcctgacacc tgttgcttcg gcgggcccgc cgtggttcac gccccggccg      240 ccgggggggtt cacgccccccg ggcccgcgcc cgccgaagac ccctggaacg ctgcctggaa      300
ggttgccgtc tgagtataca atcaatcaat taaaactttc aacaacggat ctcttggttc      360
cggcatcgat gaagaacgca gcgaaatgcg ataagtaatg tgaattgcag aattccgtga      420
atcatcgaat ctttgaacgc acattgcgcc ccctggcatt ccgggggggca tgcctgtccg      480 agcgtcattg ctaaccctcc agcccggctg gtgtgttggg ccgccgtccc cctccccgg       540 gggacgggcc cgaaaggcag cggcggcgtc gcgtccggtc ctcgagcgta tggggctctg      600
tcacacgctt cagtagaacc ggccggcttg ctggccatca cctatatttt tctcttaggt      660
tgacctcgga tcaggtaggg atacccgctg aacttaagca tatcaataag cggaggaaaa      720
gaaaccaaca gggattgccc cagtaacggc gagtgaagcg gcaagagctc aaatttgaaa      780
```

```
tctggcccct ccggggtccg agttgtaatt tgcagaggat gcttcgggcg cggtccccgt      840
ctaagtaccc tggaacgggt cgtcatagag ggtgagaatc ccgtctggga cgggtggccg      900
tgtccgtgtg aagctccttc gacgagtcga gttgtttggg aatgcagctc taaatgggtg      960
gtaaatttca tctaaagcta atattggcc ggagaccgat agcgcacaag tagagtgatc      1020
gaaagatgaa aagcactttg aaagagagt taaacagcac gtgaaattgt tgaaagggaa      1080
gcgcttgcga ccagactcgc ccgcgggggt tcagccggta ctcgtaccgg tgtactcccc      1140
cgggggcggg ccagcgtcgg tttgggcggt cggtcaaagg cctccggaat gtgtcgcccc      1200
ccggggcgtc ttatagccgg aggtgcaatg cggccagcct ggaccgagga acgcgcttcg      1260
gctcggacgc tggcgtaatg gtcgtaagcg gcccgtcttg aaacacggac caaggagtct      1320
aacatctacg cgagtgttcg ggtgtcaaac ccgtccgcgc agtgaaagcg aacggaggtg      1380 ggaaccccc ccggggtgca ccatcgaccg atcctgatgt cttcggatgg atttgagtaa      1440
gagcgtagct gttgggaccc gaaagatggt gaactatgcc tgaataggggc gaagccagag      1500 gaaactctgg tggaggctcg cagcggttct gacgtgcaaa tcgatcgtcg aatttgggta      1560
taggggcgaa agactaatcg aaccatctgg tagctggttc ctgccgaagt ttccctcagg      1620
atagcagtaa cgttttcagt tttatgaggt aaagcgaatg attagaggcc ttggggttga      1680 aacaaccta acctattctc aaactttaaa tatgtaagaa gcccttgttg cttagttgaa      1740
cgtgggcatt tgaatgtatc gttactagtg ggccattttt ggtaagcaga actggcgatg      1800
cgggatgaac cgaacgcgag gttaaggtgc cggaatgcac gctcatcaga caccacaaaa      1860
ggtgttagtt catctagaca gcccgacggt ggccatggaa gtcggaatcc gctaaggagt      1920
gtgtaacaac tcacgggccg aatgaactag ccctgaaaat ggatggcgct caagcgtgct      1980
acccatacct cgccgtcggg gtagaaacga tgccccgacg agtaggcagg cgtggaggtc      2040
cgtgacgaag ccttgggagt gatcccgggt cgaacggcct ctagtgcaga tcttggtggt      2100
agtagcaaat actcaaatga gaactttgag gactgaagtg gggaaaggtt ccatgtgaac      2160
agcagttgga catgggttag tcgatcctaa gacatagga aattccgttt gaaagcgcgc      2220
cctcgtgcgc cgttcgtcga aagggaagcc ggttaatatt ccggcacctg gatgtggatt      2280
ctccacggca acgtaactga acgcggagac gtcggcgggg gtcctgggaa gagttctctt      2340
ttcttcttga cggcctatca ccctgaaatc ggtttgtccg gagctagggt tccatggccg      2400
gcagagcccc gcacctttgc ggggtccggt gcactcccga cgaccccttga aaatccgcgg      2460 gaaggaatag ttttcacgcc aggtcgtact cataaccgca gcaggtctcc aaggtgaaaa      2520
gcctctagtt gatagaacaa tgtagataag ggaagtcggc aaaatagatc cgtaacttcg      2580
ggataaggat tggctctaag gatcgggtac gttgggcctt ggggggaagc ccccggagca      2640
ggagggcact agccgggcaa ccggccggcg ccctccagca tcgggcggtg gacgcccttg      2700
gcaggcctcg gccgtccggc gtacgcttaa cgatcaactt gaactggta cggacaaggg      2760 gaatctgact gtctaattaa aacatagcat tgcgatggcc agaaagtggt gttgacgcaa      2820
tgtgatttct gcccagtgct ctgaatgtca aagtgaagaa attcaaccaa gcgcgggtaa      2880
acggcgggag taactatgac tctcttaagg tagccaaatg cctcgtcatc taattagtga      2940
cgcgcatgaa tggattaacg agattcccac tgtccctatc tactatctag cgaaaccaca      3000
gccaagggaa cgggcttggc agaatcagcg gggaagaag accctgttga gcttgactct      3060
agtttgacat tgtgaaaaga catatggggt gtagaatagg tgggagctcc ggcgccagtg      3120
```

```
aaataccact acctttatcg ttttttttact tattcaatga agcggaactg ggcttcaccg    3180
cccaacttct ggcgttaagg tccttcgcgg gccgatccgg gttgaagaca ttgtcaggtg    3240
gggagtttgg ctggggcggc acatctgtta aaccataacg caggtgtcct aagggggact    3300
catggagaac agaaatctcc agtagaacaa aagggtaaaa gtccccttga ttttgatttt    3360
cagtgtgaat acaaaccatg aaagtgtggc ctatcgatcc tttagtccct cgaaatttga    3420
ggctagaggt gccagaaaag ttaccacagg gataactggc ttgtggcagc caagcgttca    3480
tagcgacgtt gcttttttgat ccttcgatgt cggctcttcc tatcataccg aagcagaatt    3540
cggtaagcgt tggattgttc acccactaat agggaacgtg agctgggttt agaccgtcgt    3600
gagacaggtt agttttaccc tactgatgaa ggtcgccgca acggtaattc aatttagtac    3660
gagaggaacc gttgattcag ataattggtt tttgcggctg tctgaccagg cagtgccgcg    3720
acgctaccat ctgccggatt atggctgaac gcctctaagt cagaatccgt gccggaacgc    3780
ggcgatttcg ccccgcacgt cgtagttgga tacgaatagg ccttcgggcc atgcacctca    3840
gcaggctggc gacggccccc ggggagaaac ccccgggggc tggctggcgg attgcaatgt    3900
cacctcgcgc ggggatagat cctctgcaga cgactgaagt gaccaagcgg gtcgtgtaag    3960
cggtcaagta ct                                                       3972

<210> SEQ ID NO 60
<211> LENGTH: 3916
<212> TYPE: DNA
<213> ORGANISM: Penicillium chrysogenum rRNA gene

<400> SEQUENCE: 60 gacccccccag agccgaraac ttggtcaaac tcggtcattt agaggaagta aaagtcgtaa      60
caaggtttcc gtaggtgaac ctgcggaagg atcattaccg agtgagggcc ctctgggtcc     120
aacctcccac ccgtgtttat tttaccttgt tgcttcggcg ggcccgcctt aactggccgc     180
cgggggggctt acgcccccgg gcccgcgccc gccaagacaa ccctcgaact ctgtctgaag     240
attgtagtct gagtgaaaat ataaattatt taaaactttc aacaacggat ctcttggttc     300
cggcatcgat gaagaacgca gcgaaatgcg atacgtaatg tgaattgcaa attcagtgaa     360
tcatcgagtc tttgaacgca cattgcgccc cctggtattc cggggggcat gcctgtccga     420
gcgtcattgc tgcccctcaag cacggcttgt gtgttgggcc ccgtcctccg atcaatacga     480
cttgggtttg cttgaaagac ggtagtggta aggcgggatc gctttgacaa tggcttaggt     540
ctaaccaaaa acattgcttg cggcggtaac gtccaccacg tatatcttca aacttttgacc     600
tcaaatcagg taggactacc cgctgaactt aagcatatca ataagcggag gaaaagaaac     660
caacagggat tgcctcagta gcggcgagtg aagcggcaaa agctcaaatt tgaaatctgg     720
cgtctttggc gtccgagttg taatttgaag aaggtatctt tgggcccggc tcttgtctat     780
gttccctgga acgggacgtc atagagggtg agaatcccgt atgggatggg gtgtccgcgc     840
ccgtgtgaag ctccttcgac gagtcgagtt gtttgggaat gcagctctaa atgggtggta     900
aatttcatct aaagctaaat attggccgga gaccgatagc gcacaagtag agtgatcgaa     960
agatgaaaag cactttgaaa agagagttaa aaagcacgtg aaattgttga agggaagcg    1020
cttgcgacca gactcgctcg cggggttcag ccggcattcg tgccggtgta cttccccgcg    1080
ggcgggccag cgtcggtttg ggcggtcggt caaaggccct cggaaggtaa cgcccctagg    1140
ggcgtcttat agccgagggt gcaatgcgac ctgcctagac cgaggaacgc gcttcggctc    1200
ggacgctggc ataatggtcg taaacgaccc gtcttgaaac acggaccaag gagtctaaca    1260
```

```
tctacgcgag tgttcgggtg tcaacccgtg cgcgaagtga aagcgaacgg aggtgggaac   1320
cctcacgggt gcaccatcga ccgatcctga agtcttcgga tggatttgag taagagcgta   1380
gctgttggga cccgaaagat ggtgaactat gcctgaatag ggcgaagcca gaggaaactc   1440
tggtggaggc tcgtagcggt tctgacgtgc aaatcgatcg tcgaatttgg gtataggggc   1500
gaaagactaa tcgaaccatc tggtagctgg ttcctgccga agtttccctc aggatagcag   1560
taacgcgaat tcagttttat gaggtaaagc gaatgattag aggccttggg gttgaaacaa   1620
ccttaaccta ttctcaaact ttaaatatgt aagaagccct tgttgcttaa ttgaacgtgg   1680
gcattagaat gatgcgttac tagtgggcca tttttggtaa gcagaactgg cgatgcggga   1740
tgaaccgaac gcgaggttaa ggtgccggaa tacacgctca tcagacacca caaaaggtgt   1800
tagttcatct agacagcccg acggtggcca tggaagtcgg aatccgctaa ggagtgtgta   1860
acaactcacg ggccgaatga actagccctg aaaatggatg gcgcttaagc gtgttaccca   1920
tacctcgccg tcagggtaga aacgatgccc tgacgagtag gcaggcgtgg gggtccgtga   1980
cgaagccttg ggagtgatcc cgggtcgaac ggcccctagt gcagatcttg gtggtagtag   2040
caaatactca aatgagaact ttgaggactg aagtggggaa aggttccatg tgaacagcag   2100
ttggacatgg gttagtcgat cctaaggcat agggaagttc cgtttgaaag gcgccctcgt   2160
gcgccgtgtg ccgaaaggga agccggttaa cattccggca cctagatgtg gattctccac   2220
ggcaacgtaa ctgaacgcgg agacgtcggc ggggtcctg ggaagagttc tcttttcttc   2280
ttgacagcct atcaccctga aatcggtttg tccggagcta gggttctatg ctggcagag   2340 cgccgcactt ttgcggcgtc cggtgcgccc ccgacgaccc ttgaaaatcc gcgggaagga   2400
atagttttca cgctaggtcg tactcataac cgcagcaggt ctccaaggtg aacagcctct   2460
agttgataga acaatgtaga taagggagtc ggcaaaatgg atccgtaact tcgggataag   2520
gattggctct aagggtcggg ctcgctgggc cttgggggga acctcctgga gcagtagggc   2580
actagccggg caaccggccg gcgccccgca gcaccgggtt ggggacgccc ttggcaggct   2640
tcggccgtcc ggcgggcgat taacgaccaa cttagaactg gtacggacaa ggggaatctg   2700
actgtctaat taaaacatag cattgcgatg gccagaaagt ggtgttgacg caatgtgatt   2760
tctgcccagt gctctgaatg tcaaagtgaa gaaattcaac caagcgcggg taaacggcgg   2820
gagtaactat gactctctta aggtagccaa atgcctcgtc atctaattag tgacgcgcat   2880
gaatggatta acgagattcc cactgtccct atctactatc tagcgaaacc acagccaggg   2940
gaacgggcct ggcagaatca gcggggaaag aagaccctgt tgagcttgac tctagtttga   3000
cattgtgaaa agacatatgg ggtgtagaat aggtgggagc tccggcgcca gtgaaatacc   3060 actacctttat tcgttttttt acttattcaa tgaagcggaa ctgggcttca ccgcccatct   3120
tctagcgtta aggtccttcg cgggccgatc cgggttgaag acattgtcag gtggggagtt   3180 tggctgggc ggcacatctg ttaaacaaca acgcaggtgt cctaaggggg actcatggag   3240
aacagaaatc tccagtagaa caaaagggta aaagtcccct tgattttgat tttcagtgtg   3300
aatacaaacc atgaaagtgt ggcctatcga tcctttagtc cctcgaaatt tgaggctaga   3360
ggtgccagaa aagttaccac agggataact ggcttgtggc agccaagcgt tcatagcgac   3420
gttgcttttt gattcttcga tgtcggctct tcctatcata ccgaagcaga attcggtaag   3480
cgttggattt tcacccact aatagggaac gtgagctggg tttagaccgt cgtgagacag   3540
gttagtttta ccctactgat gaaggttgtc gcaacagtaa ttgaacttag tacgagagga   3600
```

```
accgttcatt cagataattg gttttttgcgg ctgtctgacc aggcagtgcc gcgacgctac    3660
catctgccgg attatggctg aacgcctcta agtcagaatc cgtgccggaa cgcggcgatt    3720
tcgccccgca cgtcgtagtt ggatacgaat aggccttcgg gccatgcacc tcagcaggct    3780
ggcgacggct cccggggaga aaccctcggg agctggctag cggattgtaa tgtcacctcg    3840
cgcggggata gatcctctgc agacgactga agtgaccaag cgggtcgtgt aagcggtcaa    3900
gtagccttgt tgctac                                                    3916
```

<210> SEQ ID NO 61  
<211> LENGTH: 3983  
<212> TYPE: DNA  
<213> ORGANISM: Rhizomucor miehei rRNA gene

<400> SEQUENCE: 61

```
ggtccgaagc tttagccgaa ctatggcaaa cttctccatt tagaggaagt aaaagtcgta      60
acaaggtttc cgtaggtgaa cctgcggaag acattaaaaa agttgatatc atggtgaccc     120
ctttacgggg gtgagccatg atttcttctc ccttttttgtg caatgtttga gggattgctc    180
cagatctctc tttcctttttt tttacgtatt gatttgactg aacatttttg tttttaaaatg   240 aaaaaaagtt ttgaagccaa tcaattggtt caagacaaat caaattttga aacaacttta     300
agcaatggat cacttggttc tcgcatcgat gaagagcgta gcaaattgcg aaaagtaatg     360
cgatctgcag cctttgcgaa tcatcgaatt ctcgaacgca tcttgcaccc tttggttcat     420
ccattgggta cgtctagttc agtatctttt tgaaacccta agattcaat tttgttgttg      480 aatctttgga tttgcggtgc tgatgggggg aggacaaag caaatctttt gtgttccccc      540
gttcaagcta ctcgaacagt ttttgagttt ttggcctttt tagattggtg aacattcttg     600
aagggcttac tttgatatct aaaattttcg aattttgggt tatcattgct ttgagaaaac     660
cccatctaaa agcaaaaact ctatataaac tttttttttt tttcattcat ggatctgaac     720
ttagacggga ctaccgctg aacttaagca tatcaataag cggaggaaaa gaaaataaca      780 atgatacct tagtagcggc gagcgaagtg ggtaaagctc aagtttaaaa cctgtttgtc      840
atagacaaac cggattgtaa actatggaca tgttatccag gctctttgga ccttcaagtc     900 cttttggaata aggcttcaca gagggtgaca atcccgtaga gggtcttgaa cagagtctat    960
tgcgatgcat gctccaagag tcaggttgtt tgggaatgca gcctaaagtg ggaggtaaat   1020
ccctcctaaa gctaaatatt ggcgagaaac cgatagcaaa caagtaccgt gagggaaagt   1080
tgaaaaggac tttgaaaaga gagtcaaaag tacgtgaaat tgcttaaagg gaagcgtttg   1140
gagctagttt ggctagtctg ttatcagcct gagcttcggc tttggtgtac tatcaggcta   1200
tttttgccgg ccaactctca ggattgaaag gaaagcttgg tgcttggag tctaaagaga    1260 ccctcgcgga agcctctggt ggagcgtggt ctgcccttgg cccttttgag cctatagttg    1320
gcttaatggc tctaaacggc ccgtcttgaa acacggacca aggagtccac cactgttgcg   1380
agtgtttggg tggcaaaccc atacgcgaaa tgaaagtgaa agctatgaaa tccgcaagga   1440
tggcaatagc gtccggcctt taggaccgag acaaagcaat agtgatggga cccgaaagat   1500
ggtgaactat gcttgagtag agtgaagcca gaagaaattc tggtggaagc tcgtaacggt   1560
tctgacgtgc aaatcgatcg tcgaacttga gcataggggc gaaagactaa tcgaaccatc   1620
tagtagctgg ttcctgccga agtttccctc aggatagcag aagcttatag gcagttttat   1680
gtggtaaagc gaatgattag aggtcttggg gacgcaatgt ccttaaccta ttctcaaact   1740
ttaaatatgt aagacgttct tgctgcttga attatgagct tgaaccgtcg aatgctgagc   1800
```

-continued

```
ttctagtggg ccgttcttgg taagcaggac tggcgatgcg ggatgaaccg aacgcaaaga    1860
taaggcgtca aagaacacgc tcatcagaca ccacaaaagg tgttggttca tctagacagc    1920
aggacggtgg ccatggaagt cggaatccgc taaggagtgt gtaacaactc acctgccgaa    1980
tgaaccagcc ctgaaaatta atgacgctga agcgtgtcgc ctatactttg ccgtcaaagt    2040
ttaagcgaag ctttgacgag taggcaggcg tggaggttat gagcatcgaa gcctttggcg    2100
tgagcctagg tggagcagcc tctagtgcag atcttggtgg tagtagcaaa tattcaaatg    2160
agatctttga agactgaagt ggagaagggt cctcgagaa cattggttgg tcgagggtta     2220
gtcgatccta agagataggg tagttccgtt ttaccaaatg gtcctttgga ccatcctatc    2280
gaaagggaag ctggttaata ttccagcacc aagacatgga ttctatgcgg caacgcagat    2340
gaacataggg acattggcat ggatcctggg aagagttctc tttctttttt gacagcgttt    2400
tcttaagcca tgaaatcggt ctaaccggtg caatgtttgc ttaagagctg ttagagtacc    2460 gcaattttg tggtatccag agcattcatg acgatccttg aaaacctatg ggaaagaatg    2520
aatttcatgc ttggtcgtac ccataaccgc atcaggtctc caaggtgaaa agcctctagt    2580
tgatggaaga atgtagataa gggaagtcgg caaattggat ccgtaacttc gggagaagga    2640
ttggctctaa gggttgggtg ctttaagaac caggccttag cggcctgagc aatcgggctg    2700
cttccaggct tggagctctt gggcacgctt aacaaccagc ttagaactgg tacgaccaa     2760 gggaatctga ctgtctaatt aaaacatagc attgcgattg ccataaagtg gtattgacgc    2820
aatgtgattt ctgcccagtg ctctgaatgt caaagtgaag aaattcaacc aagcgcgggt    2880
aaacggcggg agtaactatg agagctttgt gatatagtcc agtttcagaa ctgctaatta    2940
gtgacgcgca tgaatggatt aacgagattc ccactgtccc tatctactat ccagcgaaac    3000
cacagccaag ggaacgggct tggcaaaatc agcggggaaa gaagaccctg ttgagcttga    3060
ctctagtttg acattgtgaa aagacatagg ggggtgtaga atatgtggga gcttcggcgc    3120
cagtgaaata ccacaaccct tatagttttt ttacttaaat aatcaagtgg gagaaggctt    3180
cacggcctat cttctagcgt taagcagtct tcgggctgcg acccatgtta ttgacattgt    3240
caagtgggga gtttggctgg ggcggcacat ctgttaaacg ataacgcagg tgtcctaagg    3300
ggagctcaac gagaacagaa atctcgtgta gagcaaaagg gcaaaagctc ccttgatttt    3360
gattttcagc gtgaatacga accatgaaag tgtggcctat cgatcctta tgccatttcc      3420 ttaggattta aggctagagg tgccggaaaa gttaccacag ggataactgg cttgtggcag    3480
ccaagcgttc atagcgacgt tgcttttga ttcttcgatg tcggctcttc ctatcataca     3540
gaagcagaat tctgtaagcg ttggattgtt cacccactaa tagggaacgt gagctgggtt    3600
tagaccgtcg tgagacaggt tagttttacc ctactgatga atcagtaggc gtcccgacag    3660
taattgaagt tagtacgaga ggaacccttc attcagataa ttggttttg cggttggttg     3720 aaaggccaat gccgcgaagc taccatctgc tggataatgg ctgaaagcct ctaagtcaga    3780
atccatgctg gttaagggac gctaaaacca gacctttaaa gcgcgagaaa gtgctcaaat    3840
agatctctta tgggatcgaa tgcctaatat gaggttatcc tcttgggttg aaaggctcaa    3900
gtcggatacc tctcatgata atgtctagct taaaggttgt aaatctcgag cagacgactt    3960
gaaatcgacg ggctattgta agc                                            3983
```

<210> SEQ ID NO 62
<211> LENGTH: 3971
<212> TYPE: DNA

<213> ORGANISM: Rhodotorula glutinis rRNA gene

<400> SEQUENCE: 62

```
cgattgaatg gcttagtgag gcctccggat tggctattgg gagctcgcga gagcacctga      60
ctgctgagaa gttgtacgaa cttggtcatt tagaggaagt aaaagtcgta acaaggtttc     120
cgtaggtgaa cctgcggaag gatcattagt gaatctaggg tgtccaattt aacttggagc     180
ccgaactctc actttctaac cctgtgcatc tgttattggt tagtagctct tcggagtgaa     240
ctccattcac ttacaaacac aaagtctatg aatgtataca aaattataac aaaacaaaac     300
tttcaacaac ggatctcttg gctctcgcat cgatgaagaa cgcagcgaaa tgcgatacgt     360
aatgtgaatt gcagaattca gtgaatcatc gaatctttga acgcaccttg cgctccttgg     420
tattccgagg agcatgcctg tttgagtgtc atgaaatctt caacccacct ctttcttagt     480
gaatctggtg gtgcttggtt tctgagcgct gctctgcttc ggcttagctc gttcgtaatg     540
cattagcatc cgcaaccgaa cttcggattg acttggcgta atagactatt cgctgaggat     600
tctagtctcg tactagagcc gggttgggtt aaaggaagct tctaatccta aagtctattt     660
tttgattaga tctcaaatca ggtaggacta cccgctgaac ttaagcatat caataagcgg     720
aggaaaagaa actaacaagg attccccctag tagcggcgag cgaagcggga agagctcaaa     780
tttataatct ggcaccttcg gtgtccgagt tgtaatctct agaagtgttt ccgcgttgg      840
accgcacaca agtctgttgg aatacagcgg cacagtggtg atacccccgt acacggtgcg     900
gacgcccagc gctttgtgat acactttcaa tgagtcgagt tgtttgggaa tgcagctcaa     960
attgggtggt aaattccatc taaagctaaa tattggcgag agaccgatag cgaacaagta    1020
ccgtgaggga aagatgaaaa gcactttgga aagagagtta acagtacgtg aaattgttgg    1080
aagggaaacg cttgaagtca gacttgcttg ccggagcttg cttcggtttg caggccagca    1140
tcagttttcc ggggtggata atggtggttt gaaggtagca gcctcggctg tgttatagct    1200
ttccactgga tacatcctgg gggactgagg aacgcagcgt gcttttttgcg aaggtttcga    1260
ccttttcacg cttaggatgc tggtgtaatg actttaaacg acccgtcttg aaacacggac    1320
caaggagtct aacatgctcg cgagtatttg ggtgtcaaac ccggatgcgc aatgaaagtg    1380
aatgtaggtg ggaaccgcaa ggtgcaccat cgaccgatct ggatcttttg agatggattt    1440
gagtaagagc gcgtatgttg ggacccgaaa gatggtgaac tatgcctgaa tagggcgaag    1500
ccagaggaaa ctctggtgga ggctcgtagc ggttctgacg tgcaaatcga tcgtcgaatt    1560
tgggtatagg ggcgaaagac taatcgaacc atcagtagc tggttcctgc cgaagtttcc     1620
ctcaggatag cagaaactca catcagttct atgaggtaaa gcgaatgatt agaggccttg    1680
gggttgaaac aaccttaacc tattctcaaa ctttaaatat gtaggaagtc cttgctactt    1740
aattgagcga ggacatgcga atgagagttt ctagtgggcc atttttggta agcagaactg    1800
gcgatgcggg atgaaccgaa cgcgaggtta aggtgccgga atacacgctc atcagacacc    1860
acaaaaggtg ttagttcatc tagacagccg cacggtggcc atggaagtcg gaatccgcta    1920
aggagtgtgt aacaactcaa cggccgaatg aactagccct gaaaatggat ggcgctcaag    1980
cgtgttaccc atacctcgcc gtcagcgcta ttgatacgtt gacgagtagg caggcgtgga    2040
ggtccgtata gaagctttcg gagtgatccg gagtagaacg gcctctagtg cagatcttgg    2100
tggtagtagc aaatattcaa gtgagaacct tgaagactga agtggggaag ggttccatgg    2160
taacagcagt tggacatggg tgagtcggtc ctaagagata gggaaactcc gttttaaagt    2220
gtgcgcttgt tcgcacggcc tatcgaaagg gaatacggtt aaaattccgt aaccgcgatg    2280
```

```
cagattctga acggcaacgt aaatgaactt ggagacgtcg gtgaaggccc tgggaagagt    2340
tatcttttct cctttacagc ttataaccct ggaatcggat tatccggaga tagggtctaa    2400
tggctggtag agcagcgcta ttttgtgctg tccggtgcgt cttcaacggc ccgtgaaaat    2460
ccgagggaat gaaaaagtct tgcacgcgat cgtacccata tccgcatcag gtccccaagg    2520
tgatcagcct ctagtccata gaataatgta gataagggaa gtcggcaaaa tagatccgta    2580
acttcgggaa aaggattggc tcatagggta gggtacgtcg gggccttggg caaagacaag    2640
ggaccgcggt gggactactg cggcgcaagc tgcggcggac tgctgtggga cccgagtcgg    2700
cgcccctggc cagtcttcgg acgtctggcg tacgattaac taccaactat gaactggtac    2760
ggacaagggg aatctgactg tctaattaaa acatagcatt gcgatggcca gaaagtggtg    2820
ttgacgcaat gtgattctg cccagtgctc tgaatgtcaa agtgaagaaa ttcaaccaag    2880
cgcgggtaaa cggcgggagt aactatgact ctcttaaggt agccaaatgc ctcgtcatct    2940
aattagtgac gcgcatgaat ggattaacga gattcccact gtccctatct actatctagc    3000
gaaaccacag ccaagggaac gggcttggca aaataagcgg ggaaagaaga ccctgttgag    3060
cttgactcta gtttgacatt gtgaagagac atagagggtg tagaataagt gggagcttcg    3120
gcgccggtga ataccactca cctttatcgt ttctttactt attcaatgaa gcggagctgg    3180
gattaacgtc ccacgttttg gcattaaggt ccttcgcggg ctgatccggg ttgaagacat    3240
tgtcaggtgg ggagtttggc tggggcggca catctgttaa acaataacgc aggtgtccta    3300
agggggactc aatgagaaca gaaatctcat gtagaacaaa agggtaaaag tccccttgat    3360
tttgattttc agtgtgaata caaaccatga aagtgtggcc tatcgatcct ttagtccctc    3420
ggaatttgag gctagaggtg ccagaaaagt taccacaggg ataactggct tgtggcagcc    3480
aagcgttcat agcgacgttg ctttttgatc cttcgatgtc ggctcttcct atcataccga    3540
agcagaattc ggtaagcgtt ggattgttca cccactaata gggaacgtga gctgggttta    3600
gaccgtcgtg agacaggtta gttttaccct acttttgaag ggttatcgta atagtaattc    3660
aacttagtac gagaggaacc gttgattcgc gtaattggta tttgcggctg tccgatcggg    3720
caatgccgcg aagctaccac gcgttggatt atggctgaac gcctctaagc cagaatccgt    3780
gctagaaacg atgatgttag tcccgcaaat cttagtcgag taaagataga gcttcggctc    3840
gtaaaccata gttggctggt catgttcagt agggcggaaa ggccttgctg ttctaccggc    3900
gaatagcatt cgaaatattt gcggggtaa atccttgcag acgacttgaa tagaacggag    3960
tgctgtacgc c                                                         3971

<210> SEQ ID NO 63
<211> LENGTH: 4907
<212> TYPE: DNA
<213> ORGANISM: Scedosporium apiospermum rRNA gene

<400> SEQUENCE: 63
ctactacccg attgaatggc ttagtgagac cctcggattg gcgttaagaa gccggcaacg     60
gcatcttttg gccgagaagt tggtcaaact tggtcattta gaggaagtaa aagtcgtaac    120
aaggtttccg taggtgaacc tgcggaagga tcattagtga attgctcttt gagcgttaaa    180
ctatatccat ctacacctgt gaactgttga ttgacttcgg tcaattactt ttacaaacat    240
tgtgtaatga acgtcatgtt attataacaa aaataacttt caacaacgga tctcttggct    300
ctcgcatcga tgaagaacgc agcgaaatgc gataagtaat gtgaattgca gaattcagtg    360
```

```
aatcatcgaa tctttgaacg cacattgcgc ccggcagtaa tctgccgggc atgcctgtcc    420
gagcgtcatt tcaaccctcg aacctctgtt tcccagcgaa gctcagggtc ggcgttgggg    480
cgctacggcg agtcttcgcg accccgtagg ccctgaaata cagtggcggt cccgccgcgg    540
ttgccttctg cgtagtaaaa gtcttctttt gcaagcttcg cattgggtcc cggcggaggc    600
ctgccgtcaa accacattat aacttaagat ggtttgacct cggatcaggt agggttaccc    660
gctgaactta agcatatcaa taagcggagg aaaagaaacc aacagggatt gcctcagtaa    720
cggcgagtga agcggcaaca gctcaaattt gaaatctggc agcctccggg cggtccgagt    780
tgtaatttga agaggatgct tttggcgagg cgccttccga gtgccctgga acgggacgcc    840
acagagggtg agagccccgt atggttggac gccgagcctc tgtaaagctc cttcgacgag    900
tcgagtagtt tgggaatgct gctcaaaatg ggaggtaaac cccttctaaa gctaaatact    960
ggccagagac cgatagcgca caagtagagt gatcgaaaga tgaaaagcac tttgaaaaga   1020
gagttaaata gcacgtgaaa ttgttgaaag ggaagcgctt gcaccagac ttgtgcccgt   1080
cgaatcagcc gccgctcgtc ggcggcgcac ttcggcgggc tcaggccagc atcagttcgc   1140
tgcaggggga gaaaggcggt gggaatgtgg ctcttcggag tgttatagcc cgccgcgcaa   1200
taccctcgg cggactgagg accgcgcatc tgcaaggatg ctggcgtaat ggtcgtcagc   1260
gacccgtctt gaaacacgga ccaaggagtc gtcctaatat gcgagtgttc gggtgtaaaa   1320
cccctgcgcg taatgaaagt gaacggaggt gagagcttcg gcgcatcatc gaccgatcct   1380
gatgttctcg gatggatttg agtaagagca tattgggccg gacccgaaag aaggtgaact   1440
atgcctgtat agggtaaagc cagaggaaac tctggtggag gctcgcagcg gttctgacgt   1500
gcaaatcgat cgtcaaatat gggcatgggg gcgaaagact aatcgaacct tctagtagct   1560
ggtttccgcc gaagtttccc tcaggatagc agtgttgaat ttctcagttt tatgaggtaa   1620
agcgaatgat tagggactcg ggggcgctat taagccttca tccattctca aactttaaat   1680
atgtaagaag cccttgttac ttaactgaac gtgggcattc gaatgtatca acactagtgg   1740
gccattttg gtaagcagaa ctggcgatgc gggatgaacc gatcgcgggg ataaggtgcc   1800
ggagtggacg ctcatcagac accacaaaag gtgttatcac atcttgacag caggacggtg   1860
gccatggaag tcggaatccg ctaaggactg tgtaacaact cacctgccga atgtgatagc   1920
cctgaaaatg gatggcgctc aagcgtccca cccataccc gccctcaggg tagacactat   1980
gccctgagga gtaggcggac gtggaggtca gtgacgaagc ctagggcgtg agcccgggtc   2040
gaacggcctc tagtgcagat cttggtggta gtagcaaata cttcaatgag atcttgaagg   2100
accgaagtgg ggaaaggttc catatgaaca gcggttggat atgggtaagc cgatcctaag   2160
ccatagggaa gttccgtttc aaagggcac taatcgcccc gtatggcgaa agggaagccg   2220
gtcaatattc cggcgcctgg atgtgggttt tacgcggcaa cgcaaacgaa agcggagacg   2280
agggcggggg ccctgggtag agttctcttt tcttcttaac ggcctagtga ccctggaatc   2340
ggtttgtccg gagatagggt tcaacggccg gaagagccca gcacttctgc tgggtccggt   2400
gcgctcccga cctcccttga aaatccgctg gagggaataa ttctcacgcc agttcgtact   2460
cataaccgca gcaggtctcc aaggtgaaca gcctctggtt gatagaacaa cgtagataag   2520
ggaagtcggc aaaatagatc cgtaacttcg ggaaaaggat tggctctaag ggttgggcac   2580
gttgggcttc tggcggacgc cccgggagca gacggccact agccgggcaa ccggccgggg   2640
gctgtcagca tctgggcgcg gaagccttta gcaggcttc gggccgtccg gcgtgcagtt   2700
aacaaccaac ttagaactgg tgcggacagg gggaatctga ctgtctaatt aaaacatagc   2760
```

```
attgcgatgg ccagaaagtg gtgttgacgc aatgtgattt ctgcccagtg ctctgaatgt    2820
caaagtgaag aaattcaacc aagcgcgggt aaacggcggg agtaactatg actcaacgtg    2880
cagctccgga acggaaacgc acagcgttgc ctgtagtgga agaaacaaca gcaacttaag    2940
agggtcaagc agcgtaaaag gcgactgcta gtggacccgg gcctgctggg gaggcccgcg    3000
gattccgcga cactgtcaaa ttgcggggag ttcctaaagc ctcttgctac cgcggcccgc    3060
cgaaaggtag ggtgcagcac cagggtaatg acctcgggga tggtaaaaac gcagaggatg    3120
ctaacaatgg atgatccgca gccaagtcct acgtcccagg gggcccccga cacttcgttt    3180
tgctcggagg gggccaggca ccgggatagg gatgcagttc aacgactaga cggcagtggg    3240
tccgaggggg gcgagcaagc gtcccacccg tgctgggtgg gagccccccg ctgaacgggc    3300
ttaaggtata gtctgctggt ctcccgaaag ggatgcaccc actgaagaaa tgctcttaag    3360
gtagccaaat gcctcgtcat ctaattagtg acgcgcatga atggatcaac gagattccca    3420
ctgtccctat ctaccatcta gcgaaaccac agccaaggga acgggcttgg cagaatcagc    3480
ggggaaagaa gaccctgttg agcttgactc tagtttgaca ttgtgaaaag acataggagg    3540
tgtagaatag gtgggagctt cggcgccggt gaaataccac tactcctatt gttttttttac   3600 ttattcagtg aagcggggct ggacttacgt ccaacttctg gtgttaaggt ccttcgcggg    3660
ccgacccggt tgaagacat tgtcaggtgg ggagtttggc tggggcggca catctgctaa    3720
accataacgc agatgtccta aggggggctc atggagaaca gaaatctcca gtagaacaaa    3780
agggtaaaag tccccttgat tttgattttc agtgtgaata caaaccatga aagtgtggcc    3840
tatcgatcct ttagtccctc gggtttgag gctagaggtg ccagaaaagt taccacaggg    3900
attaacgaaa aaaacgttac ggctatcgta atgaaaatag tcccaggcgg cgccatgaca    3960
agcgccgcct agtccggcag gccccgtaca gcgctgggc ctgcgactgt tctgtaactc     4020
agtcggcttc gggggaggtt caggcctccc ccgcggcttg gcaaaacac ctggatgcgg     4080 ggaagtctcg ttaggtcagc ggtagcaagc ccgtggtggt aacgccccg ggttaagcca     4140 gtgtcaaggc ggctaataac ccactgaata gagataatcc gcagctcgac ccggccacac    4200
tcaccggcaa acggtgcaag ggctgggcag ttcaacgctc gctaaggtgt tggtgagagg    4260
gtcccagtgg acctcttgct taaggtacgg gctactccca cccgagaggg tgtcgtgtct    4320
accggctgcg cacgccgaga agcacgaagc agggcggtaa aacgaagccc tgtgggtaga    4380
aaggaactgg cttgtggcgg ccaagcgttc atagcgacgt cgcttttga tccttcgatg     4440 tcggctcttc ctatcatacc gaagcagaat tcggtaagcg ttggattgtt cacccactaa    4500
tagggaacgt gagctgggtt tagaccgtcg tgagacaggt tagttttacc ctactgatga    4560
actcgccgca atggtaattc agctcagtac gagaggaacc gctgattcag ataattggtt    4620
tttgcggctg tccgaccggg cagtgccgcg acgctaccat ctgctggata atggctgaac    4680
gcctctaagt cagaatccat gccagaaagc ggcgatatac ccgcacgtct agacggacaa    4740
gaataggctc cggcttagtg tcttagcggg cggatggtcc gccaggctcg aagtgcctgg    4800
cggtgattcg cgaattgtaa tttcgatgcg cgcggggatg aatccttgca gacgacttag    4860
ttgtgcgaaa gggtcctgta agcagtagag tagcctgttt ggttacg                  4907
```

<210> SEQ ID NO 64
<211> LENGTH: 4034
<212> TYPE: DNA
<213> ORGANISM: Antrodia vaillantii rRNA gene

```
<400> SEQUENCE: 64
cttggtcatt tagaggaagt aaaagtcgta acatccgtag gtgaacctgc ggaaggatca        60
ttaatgaatt tcaatggagt tgtagctggc tctaacaagg gcatgtgcac actctattcg       120
ttatattata cacctgtgca ccttttgtag ttcggttgtt acggggagag tcgaaaggct       180
ttctcagacc cccgttctat gttttttatta taaacctttg aatgtctttg aatgtctgca     240
ttaataatgc attttataca actttcagca acggatctct tggctctcgc atcgatgaag      300
aacgcagcga aatgcgataa gtaatgtgaa ttgcagaatt cagtgaatca tcgaatcttt      360
gaacgcacct tgcgctcctt ggtattccga ggagcatgcc tgtttgagtg tcatggaatt      420
atcaaacctt tctttaaatt tattttaaag gttggcttgg acttggaggt tgctggccgc      480
gccattttgt agtcagtcag ctcctcttga atgcattagc ttgagtcttt aatgagtcgg      540
cttatcggtg tgataaactt atgccgttag tcaacttgta aacaaatcga gcttctaatc      600
gtctttggac aaacattata atatgacctc tgacttcaaa tcaggtagga ttacccgctg      660
aacttaagca tatcaataag cggaggaaaa gaaactaaca aggattcccc tagtaactgc      720
gagtgaagcg ggaaaagctc aaatttaaaa tctggcagtt taatagctgt ccgagttgta      780
gtctggagaa gtgcttttccg tgctagaccg tgtacaagtc ccttggaaca gggcgtcata    840
gagggtgaga atcccgtctt tgacacggac tactagtgct ttgtgatgcg ctctcaaaga      900
gtcgagttgt ttgggaatgc agctcaaaat gggtggtaaa ttccatctaa agctaaatac      960
aggcgagaga ccgatagcga acaagtaccg tgagggaaag atgaaaagca ctttggaaag    1020
agagttaaac agtacgtgaa attgctgaaa gggaaacgct tgaagtcagt cgcgttgtcc    1080
ggaaatcagc cttgcattta tttgcttggt gtattttctg gttgacgggc cagcatcgat    1140
tttaatcgtt ggataaaggc gagggaaatg tggcaccttc gggtgtgtta tagtcccttg    1200
tcacatacaa cggtcgggat cgaggaactc agcacgcctt tattggtcgg ggttcgccca    1260
cgtttcgtgc ttaggatgtt ggcataatgg ctttaaacga cccgtcttga aacacggacc    1320
aaggagtcta acatacctgc gagtgtttgg gtggtaaacc cgagcgcgta attaaagtaa    1380
tagttgagat ccccgttaca agggagcatc gacgcccgga cttgaccttc tgtgatagct    1440
ctgcggtaga gcatgtatgt tgggacccga agatggtgaa actatgcctg aatagggtga    1500
agccagagga aactctggtg gaggctcgta gcgattctga cgtgcaaatc gatcgtcaaa    1560
tttgggtata ggggcgaaag actaatcgaa ccatctagta gctggttcct gccgaagttt    1620
ccctcaggat agcagaaact cgtatcagat ttatgtggta aagcgaatga ttagaggcct    1680
tggggttgaa acaaccttaa cctattctca aactttaaat atgtaagaac gagccgtcac    1740
ttaattggac cgctcggcga ttgaggtttc tagtgggcca tttttggtaa gcagaactgg    1800
cgatgcggga tgaaccgaac gtgaggttaa ggtgccggaa tacacgctca tcagacacca    1860
caaaaggtgt tagttcatct agacagcagg acggtggcca tggaagtcgg aatccgctaa    1920
ggagtgtgta acaactcacc tgccgaatga actagccctg aaaatggatg cgctcaagc     1980
gtgttaccca tacctcaccg tcagtgttta agtgaaacat tgacgagtag caggcgtgg     2040
aggtcagtga agaagcctag gcagtaatgc tgggtgaaac ggcctctagt gcagatcttg    2100
gtggtagtag caaatattca agtgagaacc ttgaagactg aagtggagaa aggttccatg    2160
gtaacagcag ttggacatgg gttagtcgat cctaagagat agggaagctc cgtttcaaag    2220
tgtacgattt ttcgtaccgc ctatcgaaag ggaatccggt taagattccg gaaccaggat    2280
gtggattttt aacggcaacg taaatgaact tggagacgct ggcgagggcc ccgggaagag    2340
```

```
ttatctttc  tccttaacag  tctaacaccc  tgaaatcggt  ttgtccggag  ctagggttta    2400
atgactggta gagctcgaca cttctgtcgg gtccggtgcg ttcttgacag cccttgaaaa    2460
tccaagggaa tgaataattt tcacacctgg tcgtactcat aaccgcagca ggtctcctag    2520
gtgaacagcc tctagttgat agaacaatgt agataaggga agtcggcaaa atagatccgt    2580
aacttcggga aaaggattgg ctctaagggt tgggtacatc gggccttagt tggaagctac    2640
gggaccaggt aggactgtt tcggggcaac ctgggacgga cttggccagg gacctgtcag    2700
tggatggctt tggctgctct cgggcgtccg gtgtacgctt aacaaccaac ttagaactgg    2760
tacggacaag gggaatctga ctgtctaatt aaaacatagc attgcgatgg ccagaaagtg    2820
gtgttgacgc aatgtgattt ctgcccagtg ctctgaatgt caaagtgaag aaattcaacc    2880
aagcgcgggt aaacggcggg agtaactatg actctcttaa ggtagccaaa tgcctcgtca    2940
tctaattagt gacgcgcatg aatggattaa cgagattccc actgtccta  tctactatct    3000 agcgaaacca cagccaaggg aacgggcttg cagaatcag  cggggaaaga agaccctgtt    3060
gagcttgact ctagtttgac attgtgaaaa gacatagagg gtgtagaata agtgggagct    3120
tcggcgccgg tgaaatacca ctacctttat cgtctttta  cttattcaat gaggcggagc    3180
tgggattaac agtcccacct tttggcttca aggtccttta agggctgatc cgggttgaag    3240
acattgtcag gtggggagtt tggctggggc ggcacatctg ttaaaagata acgcaggtgt    3300
cctaaggggg actcatcgag aacagaaatc tcgagtagaa caaaagggta aaagtccct   3360 tgatttgat tttcagtgtg aatacaaacc atgaaagtgt ggcctatcga tcctttagtc    3420
cctcggaatt tgaggctaga ggtgccagaa aagttaccac agggataact ggcttgtggc    3480
agccaagcgt tcatagcgac gttgcttttt gatccttcga tgtcggctct tcctatcata    3540
ccgaagcaga attcggtaag cgttggattg ttcacccact aataggaac gtgagctggg    3600 tttagaccgt cgtgagacag gttagtttta ccctactgat ggagtgttat cgtaatagta    3660
attgaactta gtacgagagg aaccgttcat tcagatattt ggtatttgcg cctgtccgat    3720
cgggcaatgg cgcgaagcta tcatctgctg gattatggct gaacgcctct aagccagaat    3780
ccgtgctaga aacgatgatg ttggtcccgc acatataagt tgcgttgaaa tagagctttg    3840
ctcgtgaacc aaatcaggtg ggctgggtcg ttcaagcgga aatgcttgtt cgatttgtct    3900
acgaattgta atcatcatat gcgcggggt gaatcctttg cagacgactt gaatgggaac    3960
ggggtactgt aagcagtaga gtagccttgt tgctacgatc tgctgaggtt aagcccttgt    4020
tctatagatt tgtt                                                      4034
```

<210> SEQ ID NO 65
<211> LENGTH: 3971
<212> TYPE: DNA
<213> ORGANISM: Aspergillus fumigatus rRNA gene
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (783)..(783)

```
<223> OTHER INFORMATION: n is a, c, g, or t
<220> FEATURE:
<221> NAME/KEY: misc_feature
<222> LOCATION: (1330)..(1330)
<223> OTHER INFORMATION: n is a, c, g, or t
<220> FEATURE:
<221> NAME/KEY: misc_feature
<222> LOCATION: (3488)..(3488)
<223> OTHER INFORMATION: n is a, c, g, or t
<220> FEATURE:
<221> NAME/KEY: misc_feature
<222> LOCATION: (3577)..(3577)
<223> OTHER INFORMATION: n is a, c, g, or t

<400> SEQUENCE: 65
```

| | | | | | |
|---|---|---|---|---|---|
| ggtcatttag | aggaagtaaa | agtcgtaaca | aggtttccgt | aggtgaacct | gcggaaggat | 60
| cattaccgag | tgagggccct | ctgggtccaa | cctcccaccc | gtgtctatcg | taccttgttg | 120
| cttcggcggg | cccgccgttt | cgacggccgc | cggggaggcc | ttgcgccccc | gggcccgcgc | 180
| ccgccgaaga | ccccaacatg | aacgctgttc | tgaaagtatg | cagtctgagt | tgattatcgt | 240
| aatcagttaa | aactttcaac | aacgatctct | tggttccgg | catcgatgaa | gaacgcagcg | 300
| aaatgcgata | agtaatgtga | attgcagaat | tcagtgaatc | atcgagtctt | tgaacgcaca | 360
| ttgcgccccc | tggtattccg | gggggcatgc | ctgtccgagc | gtcattgctg | ccctcaagca | 420
| cggcttgtgt | gttgggcccc | cgtccccctc | tcccggggga | cgggcccgaa | aggcagcggc | 480
| ggcaccgcgt | ccggtcctcg | agcgtatggg | gctttgtcac | ctgctctgta | ngcccggccg | 540
| gcgccagccg | acacccaact | ttattttctt | aangttgacc | tcggatcang | tagggatacc | 600
| cgctgaactt | aagcatatca | ataagcggag | gaaaagaaac | caacagggat | tgcctcagta | 660
| acggcgagtg | aagcggcaag | agctcaaatt | tgaaagctgg | ccccttcggg | gtccgcgttg | 720
| taatttgcag | aggatgcttc | gggtgcagcc | cccgtctaag | tgccctggaa | cgggccgtca | 780
| tanagggtga | gaatcccgtc | tgggacgggg | tgtctgcgtc | cgtgtgaagc | tccttcgacg | 840
| agtcgagttg | tttgggaatg | cagctctaaa | tgggtggtaa | atttcatcta | aagctaaata | 900
| ctggccggag | accgatagcg | cacaagtaga | gtgatcgaaa | gatgaaaagc | actttgaaaa | 960
| gagagttaaa | cagcacgtga | aattgttgaa | agggaagcgt | ttgcgaccag | actcgcccgc | 1020
| ggggttcagc | cggcattcgt | gccggtgtac | ttccccgtgg | gcgggccagc | gtcggtttgg | 1080
| gcggccggtc | aaaggccctc | ggaatgtatc | acctctcggg | gtgtcttata | gccgagggtg | 1140
| caatgcggcc | tgcctggacc | gaggaacgcg | cttcggctcg | gacgctggcg | taatggtcgt | 1200
| aaatgacccg | tcttgaaaca | cggaccaagg | agtctaacat | ctacgcgagt | gttcgggtgt | 1260
| caaacccgta | cgcgcagtga | aagcgaacgg | aggtgggagc | cccctcgcgg | ggcgcaccat | 1320
| cgaccgatcn | tgatgtcttc | ggatggattt | gagtacgagc | gtagctgtgg | ggacccgaaa | 1380
| gatggtgaac | tatgcctgaa | tagggcgaag | ccagaggaaa | ctctggtgga | ggctcgcagc | 1440
| ggttctgacg | tgcaaatcga | tcgtcaaatt | tgggtatagg | ggcgaaagac | taatcgaacc | 1500
| atctagtagc | tggttcctgc | cgaagtttcc | ctcaggatag | cagtaacgcg | gatcagtttt | 1560
| atgaggtaaa | gcgaatgatt | agaggccttg | gggttgaaac | aaccttaacc | tattctcaaa | 1620
| ctttaaatat | gtaagaagcg | cttgttgctt | agttgaacgt | gcgcattaga | atgaagcgtt | 1680
| actagtgggc | cattttggt | aagcagaact | ggcgatgcgg | gatgaaccga | acgcgaggtt | 1740
| aaggtgccgg | aatgcacgct | catcagacac | cacaaaaggt | gttagttcat | ctagacagcc | 1800
| cgacggtggc | catggaagtc | ggaatccgct | aaggagtgtg | taacaactca | cgggccgaat | 1860
| gaactagccc | tgaaaatgga | tggcgctcaa | gcgtgctacc | catacctcgc | cgtcggggta | 1920

```
gaaacgacgc cccgacgagt aggcaggcgt gggggtccgt gacgaagcct tgggagtgat    1980
cccgggtcga acggcccta gtgcagatct tggtggtagt agcaaatact caaatgagaa    2040
ctttgaggac tgaagtgggg aaaggttcca tgtgaacagc agttggacat gggttagtcg    2100
atcctaaggc atagggaagt tccgtttgaa aggcgccctc gtgcgccgtg tgccgaaagg    2160
gaagccggtt aacattccgg cacctggatg tggattctcc acggcaacgt aactgaacgc    2220
ggagacgtcg gcgggggtcc tgggaagagt tctcttttct tcttgacagc cttccaccct    2280
gaaatcggtt tgtccggagc tagggttcca tggctggcag agccccgcac ctttgcgggg    2340
tccggtgcgc ccccgacgac ccttgaaaat ccgcggaag gaatagtttt cacgccaggt    2400
cgtactcata accgcagcag gtctccaagg tgaacagcct ctagttgata aacaatgta    2460 gataagggaa gtcggcaaaa tggatccgta acttcgggat aaggattggc tctaagggtc    2520
gggcccgctg ggccttgggg gaaacccctc ggagcagggg ggcactagcc gggcaaccgg    2580
ccggcgcccc ccagcactgg ggcggggacg ccctggcag gcttcggccg tccggcgggc    2640
gcttaacgac caacttagaa ctggtacgga caaggggaat ctgactgtct aattaaaaca    2700
tagcattgcg atggccagaa agtggtgttg acgcaatgtg atttctgccc agtgctctga    2760
atgtcaaagt gaagaaattc aaccaagcgc gggtaaacgg cgggagtaac tatgactctc    2820
ttaaggtagc caaatgcctc gtcatctaat tagtgacgcg catgaatgga ttaacgagat    2880
tcccactgtc cctatctact atctagcgaa accacagcca agggaacggg cttggcagaa    2940
tcagcgggga aagaagaccc tgttgagctt gactctagtt tgacattgtg aaaagacata    3000
tggggtgtag aataggtggg agcttcggcg ccagtgaaat accactacct ttatcgtttt    3060
tttacttatt caatgaagcg gaactgggct tcaccgccca tcttctggcg ttaaggtcct    3120
tcgcgggccg atccggggtt gaagacattgt caggtgggga gtttggctgg ggcggcacat    3180
ctgttaaacc acaacgcagg tgtcctaagg gggactcatg gagaacagaa atctccagta    3240
gaacaaaagg gtaaaagtcc ccttgatttt gattttcagt gtgaatacaa accatgaaag    3300
tgtggcctat cgatccttta gtccctcgaa atttgaggct agaggtgcca gaaaagttac    3360
cacagggata actggcttgt ggcagccaag cgttcatagc gacgttgctt tttgatcctt    3420
cgatgtcggc tcttcctatc ataccgaagc agaattcggt aagcgttgga ttgttcaccc    3480
actaatangg aacgtgagct gggtttagac cgtcgtgaga caggttagtt ttaccctact    3540
gatgaaggtc gccgcaacgg taattcaatt tagtacnaga ggaaccgttg attcagataa    3600 ttggttttg cggctgtctg accaggcagt gccgcgacgc taccatctgc cggataatgg    3660
ctgaacgcct ctaagtcaga atccgtgccg gaacgcggcg atgtagcccc gcacgtcgta    3720
gttggatacg aataggcctc cgggccatgt acctcagcag gctggcgacg gccccgggg    3780 agaaaccccc gagggctggc tggcggattg caatgtcacc tcgcgcgggg atgaatcctc    3840
tgcagacgac tgaagtgacc aagcgggtcg tgtaagcggt caagtagcct tgttgctacg    3900
agtcgctgag cgtcagcccg atccttggct agatttgttg gcaaacacct cccatcaacg    3960
ggcccggcag c                                                        3971
```

<210> SEQ ID NO 66
<211> LENGTH: 3974
<212> TYPE: DNA
<213> ORGANISM: Aspergillus niger rRNA gene

<400> SEQUENCE: 66

-continued

```
ggtcatttag aggaagtaaa agtcgtaaca aggtttccgt aggtgaacct gcggaaggat    60
cattaccgag tgcgggtcct ttgggcccaa cctcccatcc gtgtctattg taccctgttg   120
cttcggcggg cccgccgctt gtcggccgcc ggggggcgc ctctgccccc cgggcccgtg    180
cccgccggaa accccaacac gaacactgtc tgaaagcgtg cagtctgagt tgattgaatg   240
caatcagtta aaactttcaa caatggatct cttggttccg gcatcgatga agaacgcagc   300
gaaatgcgat aactaatgtg aattgcagaa ttcagtgaat catcgagtct ttgaacgcac   360
attgcgcccc ctggtattcc gggggcatg cctgtccgag cgtcattgct gccctcaagc    420
ccggcttgtg tgtttgggtcg ccgtcccct ctccggggg acgggcccga aaggcagcgg    480
cggcaccgcg tccgatcctc gagcgtatgg ggctttgtca catgctctgt aggattggcc   540
ggcgcctgcc gacgttttcc aaccattctt tccaggttga cctcggatca ggtaggata    600
cccgctgaac ttaagcatat caataagcgg aggaaaagaa accaaccggg attgcctcag   660
taacggcgag tgaagcggca agagctcaaa tttgaaagct ggctccttcg gagtccgcat   720
tgtaatttgc agaggatgct ttgggtgcgg cccccgtcta agtgccctgg aacgggccgt   780
cagagagggt gagaatcccg tcttgggcgg ggtgtccgtg cccgtgtaaa gctccttcga   840
cgagtcgagt tgtttgggaa tgcagctcta aatggggtgg aaatttcatc taaagctaaa   900
tactggccgg agaccgatag cgcacaagta gagtgatcga agatgaaaaa gcactttgaa   960
aagagagtta aacagcacgt gaaattgttg aaagggaagc gcttgcgacc agactcgccc  1020
gcggggttca gccggcattc gtgccggtgt acttccccgt gggcgggcca gcgtcggttt  1080
gggcggccgg tcaaaggccc ctggaatgta gtgccctccg gggcaccta tagccagggg   1140
tgcaatgcgg ccagcctgga ccgaggaacg cgcttcggca cggacgctgg cataatggtc  1200
gtaaacgacc cgtcttgaaa cacggaccaa ggagtctaac atctacgcga gtgttcgggt  1260
gtcaaacccg tgcgcgcagt gaaagcgaac ggaggtggga gcccccttgc ggggcgcacc  1320
atcgaccgat cctgatgtct tcggatggat ttgagtaaga gcgtagctgt ggggacccga  1380
aagatggtga actatgcctg aatagggcga agccagagga aactctggtg gaggctcgca  1440
gcggttctga cgtgcaaatc gatcgtcaaa tttgggtata ggggcgaaag actaatcgaa  1500
ccatctagta gctggttcct gccgaagttt ccctcaggat agcagtaacg caaaatcagt  1560
tttatgaggt aaagcgaatg attagaggca ttggggttga acaaccttaa acctattctc  1620
aaactttaaa tatgtaagaa gcccttgttg cttagttgaa cgtgggcatt agaatggagc  1680
gttactagtg ggccattttt ggtaagcaga actggcgatg cgggatgaac cgaacgcgag  1740
gttaaggtgc cggaatgcac gctcatcaga caccacaaaa ggtgttagtt catctagaca  1800
gcccgacggt ggccatggaa gtcggaatcc gctaaggagt gtgtaacaac tcacgggccg  1860
aatgaactag ccctgaaaat ggatggcgct caagcgtgct acccatacct cgccgtcggg  1920
gtagaaacga tgccccgacg agtaggcagg cgtgggggtc cgtgacgaag ccttgggagt  1980
gatcccgggt cgaacggccc ctagtgcaga tcttggtggt agtagcaaat actcaaatga  2040
gaactttgag gactgaagtg gggaaaggtt ccatgtgaac agcagttgga catgggttag  2100
tcgatcctaa ggcatagggga agttccgttt gaaaggcgcc ctcgtgcgcc gtgtgccgaa  2160
agggaagccg gttaacattc cggcacctgg atgtggattc tccacggcaa cgtaactgaa  2220
cgcggagaca tcggcggggg tcctgggaag agttctcttt tcttcttgac ggcctatcac  2280
cctgaaatcg gtttgtccgg agctagggtt ccacggccgg cagagccctg cacctttgca  2340
gggtccggtg cgccccgac gatccttgaa aatccgcggg aaggaatagt tttcacgcca  2400
```

-continued

```
ggtcgtactc ataaccgcag caggtctcca aggtgaacag cctctagttg atagaacaat    2460
gtagataagg gaagtcggca aaatggatcc gtaacttcgg gataaggatt ggctctaagg    2520
gtcgggctcg ctgggccttg ggggaaaccc ctcggagcag gggggcacta gccgggcaac    2580
cggccggcgc cccccagcac cgggtggggg acgcccttgg caggcttcgg ccgtccggcg    2640
ggcgcttaac gaccaactta gaactggtac ggacaagggg aatctgactg tctaattaaa    2700
acatagcatt gcgatggcca gaaagtggtg ttgacgcaat gtgatttctg cccagtgctc    2760
tgaatgtcaa agtgaagaaa ttcaaccaag cgcgggtaaa cggcgggagt aactatgact    2820
ctcttaaggt agccaaatgc ctcgtcatct aattagtgac gcgcatgaat ggattaacga    2880
gattcccact gtccctatct actatctagc gaaaccacag ccaagggaac gggcttggca    2940
gaatcagcgg ggaaagaaga ccctgttgag cttgactcta gtttgacatt gtgaaaagac    3000
atatggggtg tagaataggt gggagcttcg gcgccagtga ataccactat cctttatcgt    3060 tttttttactt attcaatgaa gcggaactgg gcttcaccgc ccatcttctg gcgttaaggt    3120
ccttcgcggg ccgatccggg ttgaagacat tgtcaggtgg ggagtttggc tggggcggca    3180
catctgttaa accacaacgc aggtgtccta aggggactc atggagaaca gaaatctcca    3240
gtagaacaaa agggtaaaag tccccttgat tttgattttc agtgtgaata caaaccatga    3300
aagtgtggcc tatcgatcct ttagtccctc gaaatttgag gctagaggtg ccagaaaagt    3360
taccacaggg ataactggct tgtggcagcc aagcgttcat agcgacgttg cttttttgatc    3420 cttcgatgtc ggctcttcct atcataccga agcagaattc ggtaagcgtt ggattgttca    3480
cccactaata gggaacgtga gctgggttta gaccgtcgtg agacaggtta gttttaccct    3540
actgatgaag gtcgccgcaa cggtaattca atttagtacg agaggaaccg ttgattcaga    3600
taattggttt ttgcggctgt ctgaccaggc agtgccgcga cgctaccatc tgccggataa    3660
tggctgaacg cctctaagtc agaatccgtg ccggaacgcg gcgatgttgc cccgcacgtc    3720
gtagttggat acgaataggc ctccgggcca tgcacctcag caggctggcg acggctccta    3780
gggagaagcc cctgggagct ggctggcgaa ttgcaatgtc acctcgcgcg ggatgaatc    3840 ctctgcagac gactgaagtg accaagcggg tcgtgtacgc ggtcaagtag ccttgttgct    3900
acgagtcgct gagcgtcagc ccgtccttgg ctagatttgt gttatacacc tcccccactg    3960
acaggtccgg cagc                                                       3974

<210> SEQ ID NO 67
<211> LENGTH: 3951
<212> TYPE: DNA
<213> ORGANISM: Aspergillus oryzae rRNA gene

<400> SEQUENCE: 67
gtcaaacccg gtcatttaga ggaagtaaaa gtcgtaacaa ggtttccgta ggtgaacctg     60
cggaaggatc attaccgagt gtagggttcc tagcgagccc aacctcccac ccgtgtttac    120
tgtaccttag ttgcttcggc gggcccgcca ttcatggccg ccggggggctc tcagccccgg    180 gcccgcgccc gccggagaca ccacgaactc tgtctgatct agtgaagtct gagttgattg    240
tatcgcaatc agttaaaact ttcaacaatg gatctcttgg ttccggcatc gatgaagaac    300
gcagcgaaat gcgataacta gtgtgaattg cagaattccg tgaatcatcg agtctttgaa    360
cgcacattgc gccccctggt attccggggg gcatgcctgt ccgagcgtca ttgctgccca    420
tcaagcacgg cttgtgtgtt gggtcgtcgt cccctctccg gggggacgg gccccaaagg    480
```

-continued

| | |
|---|---|
| cagcggcggc accgcgtccg atcctcgagc gtatggggct tgtcacccg ctctgtaggc | 540 |
| ccggccggcg cttgccgaac gcaaatcaat cttttttccag gttgacctcg gatcaggtag | 600 |
| ggatacccgc tgaacttaag catatcaata agcggaggaa aagaaaccaa ccgggattgc | 660 |
| ctcagtaacg gcgagtgaag cggcaagagc tcaaatttga agctggctc cttcggggtc | 720 |
| cgcattgtaa tttgcagagg atgcttcggg tgcggcccct gtctaagtgc cctggaacgg | 780 |
| gccgtcagag agggtgagaa tcccgtctgg gatggggtgt ccgcgcccgt gtgaagctcc | 840 |
| ttcgacgagt cgagttgttt gggaatgcag ctctaaatgg gtggtaaatt tcatctaaag | 900 |
| ctaaatactg gccggagacc gatagcgcac aagtagagtg atcgaaagat gaaaagcact | 960 |
| ttgaaaagag agttaaaaag cacgtgaaat tgttgaaagg gaagcgcttg cgaccagact | 1020 |
| cgcctccagg gttcagccgg cattcgtgcc ggtgtacttc cctgggggcg ggccagcgtc | 1080 |
| ggtttgggcg gccggtcaaa ggctcccgga atgtagtgcc ctccgggca ccttatagcc | 1140 |
| gggagtgcaa tgcggccagc ctggaccgag gaacgcgctt cggcacggac gctggcataa | 1200 |
| tggtcgtaaa cgacccgtct tgaaacacgg accaaggagt ctaacatcta cgcgagtgtt | 1260 |
| cgggtgtcaa acccgtacgc gcagtgaaag cgaacggagg tgggagcccc ctcgtggggc | 1320 |
| gcaccatcga ccgatcctga tgtcttcgga tggatttgag taagagcgta aatgtgggga | 1380 |
| cccgaaagat ggtgaactat gcctgaatag ggcgaagcca gaggaaactc tggtggaggc | 1440 |
| tcgcagcggt tctgacgtgc aaatcgatcg tcaaatttgg gtatagggc gaaagactaa | 1500 |
| tcgaaccatc tagtagctgg ttcctgccga agtttccctc aggatagcag taacgcgaat | 1560 |
| tcagttttat gaggtaaagc gaatgattag aggcattggg gttgaaacaa ccttaaccta | 1620 |
| ttctcaaact ttaaatatgt aagaagccct tgttgcttag ttgaacgtgg gcattagaat | 1680 |
| ggagcgttat tagtgggcca ttttttggtaa gcagaactgg cgatgcggga tgaaccgaac | 1740 |
| gcgaggttaa ggtgccggaa tgcacgctca tcagacacca caaaaggtgt tagttcatct | 1800 |
| agacagcccg acgtggcca tggaagtcgg aatccgctaa ggagtgtgta acaactcacg | 1860 |
| ggccgaatga actagccctg aaaatggatg gcgctcaagc gtgttaccca tacctcgccg | 1920 |
| ccggggtaga aacgatgccc cggcgagtag gcaggcgtgg aggtccgtga cgaagccttg | 1980 |
| ggagtgatcc cgggtcgaac ggcctctagt gcagatcttg gtggtagtag caaatactca | 2040 |
| aatgagaact ttgaggactg aagtggggaa aggttccatg tgaacagcag ttggacatgg | 2100 |
| gttagtcgat cctaaggcat agggaagttc cgtttgaaag gcgccctcgt gcgccgtgtg | 2160 |
| ccgaaaggga agccggttaa cattccggca cctggatgtg gattctccac ggcaacgtaa | 2220 |
| ctgaacgcgg agacgtcggc gggggtcctg ggaagagttc tcttttcttc ttgacagcct | 2280 |
| accaccctga aatcggtttg tccggagcta gggttcaatg gctggcagag ccccgcacct | 2340 |
| ttgcggggtc cggtgcgccc ccgacgaccc ttgaaaatcc gcgggaagga atagttttca | 2400 |
| cgccaggtcg tactcataac cgcagcaggt ctccaaggtg aacagcctct agttgataga | 2460 |
| acaatgtaga taagggaagt cggcaaaatg gatccgtaac ttcgggataa ggattggctc | 2520 |
| taagggtcgg gctcgctggg ccttgggggg aaccctcgg agcagggggg cactagccgg | 2580 |
| gcaaccggcc ggcgcccccc agcaccgggt ggggacgcc cttggcaggc ttcggccgtc | 2640 |
| cggcgggcgc ttaacgacca acttagaact ggtacggaca aggggaatct gactgtctaa | 2700 |
| ttaaaacata gcattgcgat ggccagaaag tggtgttgac gcaatgtgat ttctgcccag | 2760 |
| tgctctgaat gtcaaagtga agaaattcaa ccaagcgcgg gtaaacgcg ggagtaacta | 2820 |
| tgactctctt aaggtagcca aatgcctcgt catctaatta gtgacgcgca tgaatggatt | 2880 |

```
aacgagattc ccactgtccc tatctactat ctagcgaaac cacagccaag ggaacgggct    2940
tggcagaatc agcggggaaa gaagaccctg ttgagcttga ctctagtttg acattgtgaa    3000
aagacatatg gggtgtagaa taggtgggag ctccggcgcc agtgaaatac cactacccttt   3060 atcgtttttt tacttattca atgaagcgga actgggcttc accgcccatc ttctggcgtt    3120
aaggtccttc gcgggccgat ccggttgaa gacattgtca ggtggggagt ttggctgggg     3180
cggcacatct gttaaaccac aacgcaggtg tcctaagggg gactcatgga gaacagaaat    3240
ctccagtaga acaaaagggt aaaagtcccc ttgattttga ttttcagtgt gaatacaaac    3300
catgaaagtg tggcctatcg atcctttagt ccctcgaaat ttgaggctag aggtgccaga    3360
aaagttacca cagggataac tggcttgtgg cagccaagcg ttcatagcga cgttgctttt    3420
tgatccttcg atgtcggctc ttcctatcat accgaagcag aattcggtaa gcgttggatt    3480
gttcacccac taatagggaa cgtgagctgg gtttagaccg tcgtgagaca ggttagtttt    3540
accctactga tgaaggtcgc cgcaacggta attcaattta gtacgagagg aaccgttgat    3600
tcagataatt ggttttttgcg gctgtctgac caggcagtgc cgcgacgcta ccatctgccg   3660
gataatggct gaacgcctct aagtcagaat ccgtgccgga acgcggcgat gttgccccgc    3720
acgtcgtagt tggatacgaa taggcctccg ggccacgaac ctcagcaggc tggcgacggc    3780
tccccgggag aagccccggg gagctggctg gcggattgca atgtcacctc gcgcggggat    3840
gaatcctctg catacgactg aagtgaccaa gcgggtcgtg taagcggtca agtagccttg    3900
ttgctacgag tcgctgagcg tcagcccgac cttggctaga tttgtgtacc a             3951
```

<210> SEQ ID NO 68
<211> LENGTH: 3981
<212> TYPE: DNA
<213> ORGANISM: Aspergillus terreus rRNA gene

<400> SEQUENCE: 68

```
cggaaagttg gtcaaacccg gtcatttaga ggaagtaaaa gtcgtaacaa ggtttccgta    60
ggtgaacctg cggaaggatc attaccgagt gcgggtcttt atggcccaac ctcccacccg    120
tgactattgt accttgttgc ttcggcgggc ccgccagcgt tgctgccgc cggggggcga    180 ctcgcccccg ggcccgtgcc cgccggagac cccaacatga accctgttct gaaagcttgc   240
agtctgagtg tgattctttg caatcagtta aaactttcaa caatggatct cttggttccg    300
gcatcgatga agaacgcagc gaaatgcgat aactaatgtg aattgcagaa ttcagtgaat   360
catcgagtct ttgaacgcac attgcgcccc ctggtattcc ggggggcatg cctgtccgag   420
cgtcattgct gccctcaagc ccggcttgtg tgttgggccc tcgtccccg gctcccgggg    480 gacgggcccg aaaggcagcg gcgggcaccg cgtccggtcc tcgagcgtat ggggcttcgt    540
cttccgctcc gtaggcccgg ccggcgcccg ccgacgcatt tatttgcaac ttgttttttt    600
ccaggttgac ctcggatcag gtagggatac ccgctgaact taagcatatc aataagcgga   660
ggaaaagaaa ccaaccggga ttgcctcagt aacggcgagt gaagcggcaa gagctcaaat    720
ttgaaagctg gctccttcgg ggtccgcatt gtaatttgca gaggatgctt cgggtgcagc    780
ccccgtctaa gtgccctgga acgggccgtc atagagggtg agaatcccgt atggggcggg    840
gtgtctgcgt ccgtgtgaag ctccttcgac gagtcgagtt gtttgggaat gcagctctaa    900
atgggtggta aatttcatct aaagctaaat actggccgga gaccgatagc gcacaagtag    960
agtgatcgaa agatgaaaag cactttgaaa agagagttaa acagcacgtg aaattgttga    1020
```

```
aagggaagcg cttgcaacca gactcgctcg cggggttcag ccgggcttcg gcccggtgta      1080
cttccccgcg ggcgggccag cgtcggtttg ggcggccggt caaaggcctc cggaatgtag      1140
cgcccttcgg ggcgccttat agccggggt gcaatgcggc cagcctggac cgaggaacgc       1200
gcttcggcac ggacgctggc ataatggttg taaacgaccc gtcttgaaac acggaccaag      1260
gagtctaaca tctacgcgag tgttcgggtg tcaaacccgt acgcgcagtg aaagcgaacg      1320
gaggtgggag cccctcgcg gggcgcacca tcgaccgatc ctgatgtctt cggatggatt       1380
tgagtacgag cgtagctgtg gggacccgaa agatggtgaa ctatgcctga atagggcgaa      1440
gccagaggaa actctggtgg aggctcgcag cggttctgac gtgcaaatcg atcgtcaaat      1500
ttgggtatag gggcgaaaga ctaatcgaac catctggtag ctggttcctg ccgaagtttc      1560
cctcaggata gcagtaacgc ggatcagttt tatgaggtaa agcgaatgat tagaggcatt      1620
ggggttgaaa caaccttaac ctattctcaa actttaaata tgtaagaagc gcttgttgct      1680
tagttgaacg tgcgcattag aatggagcgt tactagtggg ccattttggg taagcagaac      1740
tggcgatgcg ggatgaaccg aacgcgaggt taaggtgccg gaatgcacgc tcatcagaca      1800
ccacaaaagg tgttagttca tctagacagc ccgacggtgg ccatggaagt cggaatccgc      1860
taaggagtgt gtaacaactc acgggccgaa tgaactagcc ctgaaaatgg atggcgctca      1920
agcgtgctac ccatacctcg ccgtcggggt agaaacgatg ccccgacgag taggcaggcg      1980
tggaggtccg tgacgaagcc ttgggcgtga gcccgggtcg aacggcctct agtgcagatc      2040
ttggtggtag tagcaaatac tcaaatgaga actttgagga ctgaagtggg gaaaggttcc      2100
atgtgaacag cagttggaca tgggttagtc gatcctaagg catagggaag ttccgtttga      2160
aaggcgccct cgtgcgccgt gtgccgaaag ggaagccggt taacattccg gcacctggat      2220
gtggattctc cacggcaacg taactgaacg cggagacgtc ggcgggagtc ctgggaagag      2280
ttctcttttc ttcttgacag cctatcaccc tgaaatcggt ttgtccggag ctagggttcc      2340
atggctggca gagccccgca cctttgcggg gtccggtgcg ctcccgacga cccttgaaaa      2400
tccgcgggaa ggaatagttt tcacgccagg tcgtactcat aaccgcagca ggtctccaag      2460
gtgaacagcc tctagttgat agaacaatgt agataaggga agtcggcaaa atggatccgt      2520
aacttcggga taaggattgg ctctaagggt cgggctcgct gggccttggg gggaaccccc      2580
cggagcaggg aggcactagc cgggcaaccg gccggcgctt cccagcaccg gggcggggac      2640
gcccttggca ggcttcggcc gtccggcggg cgcttaacga ccaacttaga actggtacgg      2700 acaagggaa tctgactgtc taattaaaac atagcattgc gatggccaga aagtggtgtt      2760
gacgcaatgt gatttctgcc cagtgctctg aatgtcaaag tgaagaaatt caaccaagcg      2820
cgggtaaacg gcgggagtaa ctatgactct cttaaggtag ccaaatgcct cgtcatctaa      2880
ttagtgacgc gcatgaatgg attaacgaga ttcccactgt ccctatctac tatctagcga      2940
aaccacagcc aagggaacgg gcttggcaga atcagcgggg aaagaagacc ctgttgagct      3000
tgactctagt ttgacattgt gaaaagacat atggggtgta aataggtgg gagctccggc       3060 gccagtgaaa taccactacc tttatcgttt ttttacttat tcaatgaagc ggaactgggc      3120
ttcaccgccc atcttctggc gttaaggtcc ttcgcgggcc gatccgggtt gaagacattg      3180
tcaggtgggg agtttggctg gggcggcaca tctgttaaac cacaacgcag gtgtcctaag      3240
ggggactcat ggagaacaga atctccagt agaacaaaag gtgtaaagtc cccttgattt       3300
tgattttcag tgtgaataca aaccatgaaa gtgtggccta cgatcccttt agtccctcga      3360
aatttgaggc tagaggtgcc agaaaagtta ccacagggat aactggcttg tggcagccaa      3420
```

```
gcgttcatag cgacgttgct ttttgatcct tcgatgtcgg ctcttcctat cataccgaag    3480
cagaattcgg taagcgttgg attgttcacc cactaatagg gaacgtgagc tgggtttaga    3540
ccgtcgtgag acaggttagt tttaccctac tgatgaaggt cgccgcaacg gtaattcaat    3600
ttagtacgag aggaaccgtt gattcagata attggttttt gcggctgtct gaccaggcag    3660
tgccgcgacg ctaccatctg ccggataatg gctgaacgcc tctaagtcag aatccgtgcc    3720
ggaacgcggc gatgtagccc cgcacgtcgt agttggatac gaataggcct tcgggccctg    3780
aacctcagca ggctggcgac ggcgcccggg gagaagccct cgggtgctgg ctggcggatt    3840
gcaatgtcac ctcgcgcggg gatgaatcct ctgcagacga ctgaagtgac caagcgggtc    3900
gtgtaagcgg tcaagtagcc ttgttgctac gagtcgctga gcgtcagccc gcccttggct    3960
agatttgtgt ttacaccctc c                                              3981

<210> SEQ ID NO 69
<211> LENGTH: 3844
<212> TYPE: DNA
<213> ORGANISM: Batrachochytrium dendrobatidis rRNA gene

<400> SEQUENCE: 69
tttaaaagaa gctggtcaaa cttggtcatt tagaggaagt aaaagtcgta ccaaggtaac      60
cgtaggtgac cctgcggttg gatcattaat atttgtttgg gggggggtt gttttattga     120 tgtgtaaatg ttgatggaat gacccattgt tttttcaaaa acacccttg atataataca     180 gtgtgccata tgtcacgagt cgaacaaaat ttatttattt tttcgacaaa ttaattggaa     240
attgaataat ttaattgaaa aaattgaaa ataatatta aaacaacttt tgacaacgg       300 atctcttggc tctcgcaacg atgaagaacg cagcgaaatg cgatacgtaa tgtgaattgc     360
aaacctttgt gaatcattaa atctttgaac gcacattgca ctcgtaaaag agtatacatg     420
tttgagaatt ataaaaatac attgtccgaa ttgactggac agatatgaac catgtcaaaa     480
atatttgaca ggttttaaaa gtagtagtaa aaaagagtga tacaaaaagt agtaatacaa     540
cgtcacacca acaaaaatat aatctcaaat catgcaagat tacccgctga acttaagcat     600
atcaataagc ggtggaaaag aaactaacaa ggattcccct agtaacggcg agtgaagcgg     660
gaatagctca aatttgaaat ctcacaatag tgcgaattgt agtttagaga accccatttt     720
ttttactaga caatcaaaaa gtttttttgga ataaacatc atagagggtg acaatcccgt     780
ttttgattgc caagtaataa tgtattggga tatccaagag tcggtttgtt tgggaatgca     840
gaccaaaatg ggtggtaaat accatctaaa gctaaatatt ggcagagac cgatagcgaa     900 caagtaccgt gagggaaaga tgaaagaac tttgaaaaga gagttaaaca gtacgtgaaa     960
ttgtcaaaag ggaaacgctt gaaaccagta tttaaacatg aatttcaatt caccatgtgg    1020
tgagtctata tttgatgatt agagtcaaca agggtttgac aagtgataaa aacggctaga    1080
gtagacctat taggacaaag tctagtcaaa tgtcacgggt tggacttttt ttagtgtaat    1140
gtataacatg tcttgttttg actgtggtgg tgttgaaatg catgcagatc aatgacactc    1200
caacaaatca attcatactt acccaccaca aaaacgttga ggaaatggtt ttaaacgacc    1260
cgtcttgaaa cacggaccaa ggagtccaac atatatgcaa gtatttgagt gaataaaccc    1320
aaatgcaaaa taaaagtgaa aaggtgggaa tatatagcac cattggccaa ttaataataa    1380
ttgagcaaga gcatacatgt tgggacccga aagatggtga actatgcctg aatagggtga    1440
agccagagga aactctggtg gaggctcgta gcggttctga cgtgcaaatc gatcgtcgaa    1500
```

```
tttgggtata ggggcgaaag actaatcgaa ccatctagta gctggttccc tccgaagttt    1560
ccctcaggat agcagaagct cagtatcagt tttatgaggt aaagcgaatg attagaggcc    1620
tcggggaagt aaattccttg acctattctc aaactttaaa tatgtaagac gttgtggtta    1680
cttgaatgaa ccgcgacagc gaatgagagt ttctagtggg ccattttttgg taagcagaac   1740 tggcgatgcg ggatgaaccg aacgtcgagt taaggtgcca gaatgcacgc tcatttagac    1800
accacaaaag gtgttggttc atctagacag caggacggtg gccatggaag ttggaacccg    1860
ccaaggagtg tgtaacaact cacctgccga atgaactagc cctgaaaatg gatggcgctc    1920
aagcgtgcta cccatactcg accgtcggac caaatacaat ggtttgacga gtaggagggc    1980
gtggaggttt gtgtggaagc tttggatgtg aatccgagtg aaacggcctc tagtgcagat    2040
cttggtggta gtagcaaata ttcaaaagag aactttgaag actgaagtgg agaaaggttc    2100
cgtgtgaaca gcagttggac acgggtcagt cgatcctaaa gagtaaggga aacctggtaa    2160
tgcacagtgt gcggactctg aaagggcatc cggttaatat tccggaactg ggaggtggaa    2220
taagcggcaa cgcaagacaa cttggtgacg ttggtaggaa ccctagaaag agatgtcttt    2280 tcttttttaac caaacaacaa ccttggaaac ggatgaaccg gagaagaggt ttgggatggg    2340
caaagcactg cttcagcagt gtctggagcg tttctaacga cccgtgaaaa accaagggac    2400
taattttcac acctagtcgt actcataacc gcagcaggtc tccaaggtga acagcctcta    2460
gttgatagaa caatgtagat aagggaagtc ggcaaaatag atccgtaact ttgggaaaag    2520
gattggctcc aggggttgcg atgtaatcga tatcaactaa tctggaactg gtacggacat    2580
ggggaatctg actgtctaat taaaacatag cattgcgatg gccagaaagt ggtgttgacg    2640
caatgtgatt tctgcccagt gctctgaatg tcaaagtgaa gaaattcaac caagcgcggg    2700 taaacgcgg gagtaactat gactctctta aggtagccaa atgcctcgtc atctaattag     2760
tgacgcgcat gaatggatta acgagattcc cactgtccct atctactatc tagcgaaacc    2820
acagccaagg gaacgggctt ggcagaatca gcggggaaag aagaccctgt tgagcttgac    2880
tctagtttga cattgtgaaa aaacatgggg ggcgtagaat aagtgggagc tttggcaccg    2940
gtgaaatacc actaccccca atgtttttt  acttattcaa tgaagcagga ttggccgtca    3000
tggccatatt gtagtgtttg aacctgggtt gaagacattg tcaggtgggg agtttggctg    3060
gggcggcaca tctgttaaaa gataacgcag gtgtcccaag ggaaactcat cgagaacaga    3120
aatctcgagt agaacaaaag ggtaaacgtt tccttgattt tgattttcag tgtgaataca    3180
aaccatgaaa gtgtggccta tcgatccttt aaattctggg tatttcaggt tagaggtgtc    3240
agaaaagtta ccacagggat aactggcttg tggcagccaa gcgttcatag cgacgttgct    3300
ttttgatcct tcgatgtcgg ctcttcctat cattgagaag caaaattctc aaagcgtcgg    3360
attgttcacc cgccaacagg gaacgtgagc tgggtttaga ccgtcgtgag acaggttagt    3420
tttaccctac tgatgagggg ttgtcacaat agtaattcaa cgtagtacga gaggaactgt    3480
tgattcacat aattggtttt tgcggttagc tgatcagcta gtgccgcgac gctaccatgt    3540
gtaggattac ggctgaacgc ctctaagtcg gaatccatgc taaaagtgat gatgtgtctc    3600
tggattgttg atgaaaatag atgcaaatcg tgtattgttt tggtgttgag atgaaaggga    3660
tgaaatccgt tttatttgcg cctaataaca agtttggaat tcagagtgga aataaagaga    3720
agacgacttt taatcacccg ggtattgtaa gcagtagagt agccttgttg ttacgatctg    3780
gtgagattaa gccttgggtt ttttgatttt tttttgggggt ggagttacct gagggtgttg    3840
tatt                                                                 3844
```

<210> SEQ ID NO 70
<211> LENGTH: 3901
<212> TYPE: DNA
<213> ORGANISM: Botrytis cinerea rRNA gene

<400> SEQUENCE: 70

| | | | | | |
|---|---|---|---|---|---|
| cttggtcatt | tagaggaagt | aaaagtcgta | acaaggtttc | cgtaggtgaa | cctgcggaag | 60 |
| gatcattaca | gagttcatgc | ccgaaagggt | agacctccca | cccttgtgta | ttattacttt | 120 |
| gttgctttgg | cgagctgcct | tcgggccttg | tatgctcgcc | agagaatacc | aaaactcttt | 180 |
| ttattaatgt | cgtctgagta | ctatataata | gttaaaactt | tcaacaacgg | atctcttggt | 240 |
| tctggcatcg | atgaagaacg | cagcgaaatg | cgataagtaa | tgtgaattgc | agaattcagt | 300 |
| gaatcatcga | atctttgaac | gcacattgcg | cccccttggta | ttccgggggg | catgcctgtt | 360 |
| cgagcgtcat | ttcaaccctc | aagcttagct | tggtattgag | tctatgtcag | taatggcagg | 420 |
| ctctaaaatc | agtggcggcg | ccgctgggtc | ctgaacgtag | taatatctct | cgttacaggt | 480 |
| tctcggtgtg | cttctgccaa | acccaaatt | tttctatggt | tgacctcgga | tcaggtaggg | 540 |
| atacccgctg | aacttaagca | tatcaataag | cggaggaaaa | gaaaccaaca | gggattacct | 600 |
| cagtaacggc | gagtgaagcg | gtaaaagctc | aaatttgaaa | tctggctctt | ttagagtccg | 660 |
| aattgtaatt | tgtagaagat | gcttcgggtg | tggttccggt | ctaagttcct | tggaacagga | 720 |
| cgtcatagag | ggtgagaatc | ccgtatgtga | ctggatacct | atgctcatgt | gaagctcttt | 780 |
| cgacgagtcg | agttgtttgg | gaatgcagct | caaaatggga | ggtatatttc | ttctaaagct | 840 |
| aaatattggc | cagagaccga | tagcgcacaa | gtagagtgat | cgaaagatga | aaagcacttt | 900 |
| ggaaagagag | ttaaacagta | cgtgaaattg | ttgaaaggga | agcgcttgca | atcagacttg | 960 |
| cacttggtgt | tcatcagggt | ctcgtaccct | gtgtacttca | tcaagttcag | gccagcatca | 1020 |
| gtttgagtgg | ttagataaag | gcttagaaa | tgtggccctc | ttcggggggt | gttatagctc | 1080 |
| taggtgcaat | gtagcctact | tggactgagg | accgcgcttc | ggctaggatg | ctggcgtaat | 1140 |
| ggttgtaagc | gacccgtctt | gaaacacgga | ccaaggagtg | tacctaatat | gcgagtgttt | 1200 |
| gggtgttaaa | cccatacgcg | taatgaaagt | gaacgctggt | gagaacccctt | aagggtgcat | 1260 |
| catcgaccga | tcttgatgtc | ttcggatgga | tttgagtaag | agcatattgg | gtgcgacccg | 1320 |
| aaagatggtg | atctatacgt | gaatagggtg | aagccagagg | aaactctggt | ggaggctcgc | 1380 |
| agcggttctg | acgtgcaaat | cgatcgtcaa | atttgcgtat | aggggcgaaa | gactaatcga | 1440 |
| accatctagt | agctggttcc | tgccgaagtt | tccctcagga | tagcagtgtt | gttttcagtt | 1500 |
| ttatgaggta | aagcgaatga | ttagaggcct | tggggttgaa | acaaccttaa | cctattctca | 1560 |
| aactttaaat | atgtaagaag | tccttgttac | ttaattgaac | gtggacattc | gaatgtacca | 1620 |
| acactagtgg | gccattttg | gtaagcagaa | ctggcgatgc | gggatgaacc | gaacgcgagg | 1680 |
| ttaaggtgcc | ggaatatacg | ctcatcagac | accacaaaag | gtgttagttc | atctagacag | 1740 |
| caggacggtg | gccatggaag | tcggaatccg | ctaaggaatg | tgtaacaact | cacctgccga | 1800 |
| atgaactagc | cctgaaaatg | gatggcgctt | aagcgtatta | cccatacctc | gccgccaggg | 1860 |
| tagaaactat | gccctggcga | gtaggcaggc | gtggaggttg | tgacgaagcc | ttgggagtga | 1920 |
| tcccgggtag | aacagcctct | agtgcagatc | ttggtggtag | tagcaaatac | tcaaatgaga | 1980 |
| actttgagga | ctgaagtggg | gaaaggttcc | atgtgaacag | cagttggaca | tgggttagtc | 2040 |
| gatcctaaga | gatagggaaa | ctccgtttta | aagtgcgcac | ttgtgcgccg | tccctcgaaa | 2100 |

| | |
|---|---:|
| gggaaaccgg ttaatattcc ggtacctgga tttggattct ccacggcaac gtaactgaac | 2160 |
| gcggagacga cggcggggc cccgggaaga gttctctttt cttcttaaca gcctatcacc | 2220 |
| ctgaaatcgg tttgtccgga gctagggttt aacggttggt agagctcgac acctctgtcg | 2280 |
| ggtccggtgc gctctcgacg tcccttgaaa atccgcggga aggaatagct ttcaagccag | 2340 |
| gtcgtactca taaccgcagc aggtctccaa ggtgaacagc ctctagttga tagaacaatg | 2400 |
| tagataaggg aagtcggcaa aatagatccg taacttcggg aaaaggattg gctctaaggg | 2460 |
| ttgggtacgt tgggccatta ggggatgctc ttggagcaga ggagcactag cctcacggcc | 2520 |
| ggcgcacctc agcatcgagg gtttgacgct tttggcagac ttcggtcgtc cggcgtacaa | 2580 |
| ttaacaacca acttagaact ggtacggaca aggggaatct gactgtctaa ttaaaacata | 2640 |
| gcattgcgat ggccagaaag tggtgttgac gcaatgtgat ttctgcccag tgctctgaat | 2700 |
| gtcaaagtga agtaattcaa ccaagcgcgg gtaaacggcg ggagtaacta tgactctctt | 2760 |
| aaggtagcca aatgcctcgt catctaatta gtgacgcgca tgaatggatt aacgagattc | 2820 |
| ccactgtccc tatctactat ctagcgaaac cacagccaag gaacgggct tggcagaatc | 2880 |
| agcggggaaa aagaccctg ttgagcttga ctctagtttg acattgtgaa aagacatagg | 2940 |
| gggtgtagaa taggtgggag cgcaagcgcc ggtgaaatac cactacccctt atcgtttttt | 3000 |
| tacttattca ataaagcgga actgggtgtc aaagcccaac ttctagcatt aaggtccttc | 3060 |
| gcgggctgat ccgggttgaa gacattgtca ggtggggagt ttggctgggg cggcacatct | 3120 |
| gttaaaccat aacgcaggtg tcctaagggg gactcatgga gaacagaaat ctccagtaga | 3180 |
| acaaagggt aaaagtcccc ttgatttga ttttcagtgt gaatacaaac catgaaagtg | 3240 |
| tggcctatcg atcctttagt ccctcgaaat ttgaggctag aggtgccaga aaagttacca | 3300 |
| cagggataac tggcttgtgg cagccaagcg ttcatagcga cgttgctttt tgatccttcg | 3360 |
| atgtcggctc ttcctatcat accgaagcag aattcggtaa gcgttggatt gttcacccac | 3420 |
| taatagggaa cgtgagctgg gtttagaccg tcgtgagaca ggttagtttt accctactga | 3480 |
| tgaccgtcgc cgcaatggta attcagctta gtacgagagg aaccgctgat tcagataatt | 3540 |
| ggttttttgcg gctgtctgac aaggcagtgc cgcgaagcta ccatctgctg gataatggct | 3600 |
| gaacgcctct aagtcagaat ccatgccaga aagcggtgat ttatacccac acatcgtagt | 3660 |
| cggatacgaa taggccttttg gccctgaatc ttagctggct ggtaacggtc ctattgaaga | 3720 |
| aactctttag gactaactgg cgtcttgcaa ttttacaatg cgtggggttg aatcctttgc | 3780 |
| atacgactta attgtgctat acggtcctgt aagtagtaga gtagccttgt tgttacgatc | 3840 |
| tactgagggt aagccgtcca tagcctagat ttgatttata atctcccatt tttagcttgt | 3900 |
| c | 3901 |

```
<210> SEQ ID NO 71
<211> LENGTH: 3875
<212> TYPE: DNA
<213> ORGANISM: Candida albicans rRNA gene

<400> SEQUENCE: 71
```

| | |
|---|---:|
| ttggtcattt agaggaagta aaagtcgtaa caaggtttcc gtaggtgaac ctgcggaagg | 60 |
| atcattactg atttgcttaa ttgcaccaca tgtgtttttc tttgaaacaa acttgctttg | 120 |
| gcggtgggcc cagcctgccg ccagaggtct aaacttacaa ccaatttttt atcaacttgt | 180 |
| cacaccagat tattactaat agtcaaaact ttcaacaacg gatctcttgg ttctcgcatc | 240 |
| gatgaagaac gcagcgaaat gcgatacgta atatgaattg cagatattcg tgaatcatcg | 300 |

```
aatctttgaa cgcacattgc gccctctggt attccggagg gcatgcctgt ttgagcgtcg      360
tttctccctc aaaccgctgg gtttggtgtt gagcaatacg acttgggttt gcttgaaaga      420
cggtagtggt aaggcgggat cgctttgaca atggcttagg tctaaccaaa aacattgctt      480
gcggcggtaa cgtccaccac gtatatcttc aaactttgac ctcaaatcag gtaggactac      540
ccgctgaact taagcatatc aataagcgga ggaaaagaaa ccaacaggga ttgcctcagt      600
agcggcgagt gaagcggcaa aagctcaaat ttgaaatctg gcgtctttgg cgtccgagtt      660
gtaatttgaa gaaggtatct ttgggcccgg ctcttgtcta tgttccttgg aacaggacgt      720
cacagagggt gagaatcccg tgcgatgaga tgacccgggt ctgtgtaaag ttccttcgac      780
gagtcgagtt gtttgggaat gcagctctaa gtgggtggta aattccatct aaagctaaat      840
attggcgaga gaccgatagc gaacaagtac agtgatggaa agatgaaaag aactttgaaa      900
agagagtgaa aaagtacgtg aaattgttga agggaaggg cttgagatca gacttggtat      960
tttgcatgct gctctctcgg gggcggccgc tgcggtttac cgggccagca tcggtttgga     1020
gcggcaggat aatggcggag gaatgtggca cggcttctgc tgtgtgttat agcctctgac     1080
gatactgcca gcctagaccg aggactgcgg tttttaccta ggatgttggc ataatgatct     1140
taagtcgccc gtcttgaaac acggaccaag gagtctaacg tctatgcgag tgtttgggtg     1200
taaaacccgt acgcgtaatg aaagtgaacg aaggtggggg cccattaggg tgcaccatcg     1260
accgatcctg atgtgttcgg atggatttga gtaagagcat agctgttggg acccgaaaga     1320
tggtgaacta tgcctgaata gggtgaagcc agaggaaact ctggtggagg ctcgtagcgg     1380
ttctgacgtg caaatcgatc gtcgaatttg ggtatagggg cgaaagacta atcgaaccat     1440
ctagtagctg gttcctgccg aagtttccct caggatagca gaagctcgta tcagttttat     1500
gaggtaaagc gaatgattag aagtcttggg gttgaaatga ccttaactta ttctcaaact     1560
ttaaatatgt aagaagtcct tgttgcttaa ttgaacgtgg acaattgaat gaagagcttt     1620
tagtgggcca ttttttggtaa gcagaactgg cgatgcggga tgaaccgaac gtgaagttaa     1680
agtgccggaa tgcacgctca tcagacacca caaaaggtgt tagttcatct agacagccgg     1740
acggtggcca tggaagtcgg aatccgctaa ggagtgtgta acaactcacc ggccgaatga     1800
actagccctg aaaatggatg cgctcaagc gtgctactta tacttcaccg tgattgctgt     1860
tttgacgctt tcacgagtag gcaggcgtgg aggtcagtga cgaagccttt gctgtaaagc     1920
tgggtcgaac ggcctctagt gcagatcttg gtggtagtag caaatattca aatgagaact     1980
ttgaagacta aagtgggggaa aggttccatg tcaacagcag ttggacatgg gttagtcgat     2040
cctaagagat ggggaagctc cgtttcaacg tgcttgatt ttcaggccaa ccatcgaaag     2100
ggaatccggt taaaattccg gaacttggat atggattctt cacggcaacg taactgaatg     2160
tggagacgtc ggcgtgagcc ctgggaggag ttatcttttc ttcttaacag cttatcaccc     2220
tggaattggt ttatccggag atggggtctt atggctggaa gagcgcggta attttgccgc     2280
gtccggtgcg cttacgacgg tccttgaaaa tccacaggaa ggaatagttt tcatgccaag     2340
tcgtactcat aaccgcagca ggtctccaag gttaacagcc tctagttgat agaataatgt     2400
agataaggga agtcggcaaa atagatccgt aacttcggga taaggattgg ctctaaggat     2460
cgggtgtctt gggccttgtg tagacgcggc ggtgactgtt ggcgggctgt tttacgacgg     2520
actgctggtg gatgctgctg tagacacgct tggtaggtct ttatggccgt ccggggcacg     2580
tttaacgatc aacttagaac tggtacggac aaggggaatc tgactgtcta attaaaacat     2640
```

```
agcattgtga tggtcagaaa gtgatgttga cacaatgtga tttctgccca gtgctctgaa    2700
tgtcaaagtg aagaaattca accaagcgcg ggtaaacggc gggagtaact atgactctct    2760
taaggtagcc aaatgcctcg tcatctaatt agtgacgcgc atgaatggat taacgagatt    2820
cccactgtcc ctatctacta tctagcgaaa ccacagccaa gggaacgggc ttggcagaat    2880
cagcggggaa agaagaccct gttgagcttg actctagttt gacattgtga aaagacatgg    2940
agggtgtaga ataagtggga gcttcggcgc cggtgaaata ccactacctc tatagttttt    3000
ttacttattc aatgaagcgg agctggaggt caaactccac gttctagcat aagccctct     3060 gggcgatccg ggttgaagac attgtcaggt ggggagtttg gctggggcgg cacatctgtt    3120
aaacgataac gcaggtgtcc taaggggggac tcatggagaa cagaaatctc cagtagaaca    3180
aaagggtaaa agtccccttg attttgattt tcagtgtgaa tacaaaccat gaaagtgtgg    3240
cctatcgatc ctttagtccc tcggaatttg aggctagagg tgccagaaaa gttaccacag    3300
ggataactgg cttgtggcag tcaagcgttc atagcgacat tgcttttga ttcttcgatg      3360 tcggctcttc ctatcatacc gaagcagaat tcggtaagcg ttggattgtt cacccactaa    3420
tagggaacgt gagctgggtt tagaccgtcg tgagacaggt tagttttacc ctactgatga    3480
atgttatcgc aatagtaatt gaacttagta cgagaggaac cgttcattca gataattggt    3540
ttttgcggct gtctgatcag gcaacgccgc gaagctacca tctgctggat tatggctgaa    3600
cgcctctaag tcagaatcca tgctagaacg cgatgatttt tgccctgcac attttagatg    3660
gatacgaata agactttta gtcgctggac catagcaggc tggcaacggt gcgcttagcg      3720
gaaaggcttt gtgcgcttgc cggcggatag caatgtcaac atgcgcgggg ataaatcctt    3780
tgcatacgac ttagatgtac aacggagtat tgtaagcagt agagtagcct tgttgttacg    3840
atctgctgag attaagctct tgttgtctga tttgt                                3875

<210> SEQ ID NO 72
<211> LENGTH: 4515
<212> TYPE: DNA
<213> ORGANISM: Candida dublineinsis rRNA gene

<400> SEQUENCE: 72
cttggtcatt tagaggaagt aaaagtcgta acaaggtttc cgtaggtgaa cctgcggaag      60
gatcattact gatttgctta attgcaccac atgtgttttg ttctggacaa acttgctttg     120
gcggtgggcc cctgcctgcc gccagaggac ataaacttac aaccaaattt tttataaact     180
tgtcacgaga ttatttttaa tagtcaaaac tttcaacaac ggatctcttg gttctcgcat     240
cgatgaagaa cgcagcgaaa tgcgatacgt aatatgaatt gcagatattc gtgaatcatc     300
gaatctttga acgcacattg cgccctctgg tattccggag gcatgcctg tttgagcgtc      360 gtttctccct caaaccccta gggtttggtg ttgagcaata cgacttgggt ttgcttgaaa     420
gatgatagtg gtataaggcg gagatgcttg acaatggctt aggtgtaacc aaaaacattg     480
ctaaggcggt ctctggcgtc gcccatttta ttcttcaaac tttgacctca atcaggtag      540 gactacccgc tgaacttaag catatcaata agcggaggaa agaaaccaa cagggattgc      600 ctcagtagcg gcgagtgaag cggcaaaagc tcaaatttga aatctggcgt cttttggcgtc    660 cgagttgtaa tttgaagaag gtatctttgg gcccggctct tgtctatgtt ccttggaaca    720
ggacgtcaca gagggtgaga atcccgtgcg atgagatggc ccgggtctat gtaaagttcc    780
ttcgacgagt cgagttgttt gggaatgcag ctctaagtgg gtggtaaatt ccatctaaag    840
ctaaatattg gcgagagacc gatagcgaac aagtacagtg atggaaagat gaaaagaact    900
```

```
ttgaaaagag agtgaaaaag tacgtgaaat tgttgaaagg gaagggcttg agatcagact    960
tggtattttg caagttactc tttcggggt ggcctctgcg gtttaccggg ccagcatcgg   1020
tttggagcgg taggataatg gcggggaat gtggcacgac tttggttgtg tgttatagcc   1080
tctgacgata ctgccagcct agaccgagga ctgcggtttt tacctaggat gttggcataa   1140
tgatcttaag tcgcccgtct tgaaacacgg accaaggagt ctaacgtcta tgcgagtgtt   1200
tgggtgtaaa acccgtacgc gtaatgaaag tgaacgaaga tggggccctg tatgggtgca   1260
ccatcgaccg atcctgatgt gttcggatgg atttgagtaa gagcatagct gttgggaccc   1320
gaaagatggt gaactatgcc tgaataggt gaagccagag gaaactctgg tggaggctcg   1380
tagcggttct gacgtgcaaa tcgatcgtcg aatttgggta taggggcgaa agactaatcg   1440
aaccatctag tagctggttc ctgccgaagt ttccctcagg atagcagaag ctcgtatcag   1500
ttttatgagg taaagcgaat gattagaagt cttggggttg aaatgacctt aacttattct   1560
caaactttaa atatgtaaga agtccttgtt gcttaattga acgtggacaa ttgaatgaag   1620
agcttttagt gggccatttt tggtaagcag aactggcgat gcgggatgaa ccgaacgtga   1680
agttaaagtg ccggaatgca cgctcatcag acaccacaaa aggtgttagt tcatctagac   1740
agccggacgg tggccatgga agtcggaatc cgctaaggag tgtgtaacaa ctcaccggcc   1800
gaatgaacta gccctgaaaa tggatggcgc tcaagcgtgc tacttatact tcaccgtgat   1860
tgcttttttg acgctttcac gagtaggcag gcgtggaggt cagtgacgaa gcctttgctg   1920
taaagctggg tcgaacggcc tctagtgcag atcttggtgg tagtagcaaa tattcaaatg   1980
agaactttga agactgaagt ggggaaaggt tccatgtcaa cagcagttgg acatgggtta   2040
gtcgatccta agagatgggg aagctccgtt tcaacgcgct tgattttca ggccaaccat   2100
cgaaagggaa tccggttaaa attccggaac ttggatatgg attcttcacg gcaacgtaac   2160
tgaatgtgga gacgtcggcg tgagccctgg gaggagttat ctttcttct taacagctta   2220
tcaccctgga attggtttat ccggagatgg ggtcttatgg ctggaagagc gcggtaattt   2280
tgccgcgtcc ggtgcgctta cgacggtcct tgaaaatcca caggaaggaa tagttttcat   2340
gccaagtcgt actcataacc gcagcaggtc tccaaggtta acagcctcta gttgatagaa   2400
taatgtagat aagggaagtc ggcaaaatag atccgtaact tcgggataag gattggctct   2460
aaggatcggg tgttttgggc cttgtgtaga cgcggtggtg actggtggcg ggctgtttca   2520
cgacggactg ctgttggacg ctgctgtaga cacgcttggt aggctcttgt agccgtccgg   2580
ggcacgctta acgatcaact tagaactggt acggacaagg ggaatctgac tgtctaatta   2640
aaacatagca ttgtgatggt cagaaagtga tgttgacaca atgtgatttc tgcccagtgc   2700
tctgaatgtc aaagtgaaga aattcaacca agcgcgggta aacggcggga gtaactatga   2760
ctctcaacct ataagggagg caaaagtagg gacgctatgg tttccagaaa tgggccgagg   2820
tgttttgac ctgctagtcg atctggttaa ttaggtattt tgtatattac ttatcagagt   2880
attctcctgg tattatacat tttactttat gacgacaact attacccgcg ggacaaccat   2940
ttcttgattt atttactgca agtgattcta gaatatggtg attccagtta taacaccaac   3000
tgttatgaca caagtgtgat acagtcataa gctgtggta accagcggcg ataacctg   3060
gtacggggaa ggcctcgaag cagtatat tttgggattg aaaatcgggt tgcaaaactt   3120
ttgttttgg aaacacggtt ggtgaggaaa aaaaaatatt ttttcccgc acttgaagaa   3180
atatatgttg tatggggtta atcccgtggc gagccgtcag agcgcgagtt ctggcagtgg   3240
```

```
ccgtcgtaga gcacggaaag gtatgggctg gctctctgag tcggcttaag gtacgtgccg      3300
tcccacacga tgaaaagtgt gcggtgcaga atagttccca cagaacgaag ctgcgccgga      3360
gaaagcgatt tcttggagca atgcttaagg tagccaaatg cctcgtcatc taattagtga      3420
cgcgcatgaa tggattaacg agattcccac tgtccctatc tactatctag cgaaaccaca      3480
gccaagggaa cgggcttggc agaatcagcg gggaagaag  accctgttga gcttgactct      3540
agtttgacat tgtgaaaaga catggagggt gtagaataag tgggagcttc ggcgccggtg      3600
aaataccact acctctatag ttttttttact tattcaatga agcggagctg gaggtcaaac      3660
tccacgttct agcattaagt ccttttgggc gatccgggtt gaagacattg tcaggtgggg      3720
agtttggctg gggcggcaca tctgttaaac gataacgcag gtgtcctaag ggggactcat      3780
ggagaacaga atctccagt  agaacaaaag ggtaaaagtc cccttgattt tgattttcag      3840
tgtgaataca aaccatgaaa gtgtggccta tcgatccttt agtccctcgg aatttgaggc      3900
tagaggtgcc agaaaagtta ccacagggat aactggcttg tggcagtcaa gcgttcatag      3960
cgacattgct ttttgattct tcgatgtcgg ctcttcctat cataccgaag cagaattcgg      4020
taagcgttgg attgttcacc cactaatagg gaacgtgagc tgggtttaga ccgtcgtgag      4080
acaggttagt tttaccctac tgatgaatgt tatcgcaata gtaattgaac ttagtacgag      4140
aggaaccgtt cattcagata attggttttt gcggctgtct gatcaggcaa cgccgcgaag      4200
ctaccatctg ctggattatg gctgaacgcc tctaagtcag aatccatgct agaacgcgat      4260 gattttgcc  ctgcacattt tagatggata cgaataagac ttttgtcgct ggaccatagc      4320
aggctggcaa cggtgcgctt agcggaaagg ctttgtgtgc ttgccggcgg atagcaatgt      4380
caacatgcgc ggggataaat cctttgcata cgacttagat gtacaacgga gtattgtaag      4440
cagtagagta gccttgttgt tacgatctgc tgagattaag cttttgttgt ctgatttgtc      4500
taatcctggt tgccc                                                      4515

<210> SEQ ID NO 73
<211> LENGTH: 4230
<212> TYPE: DNA
<213> ORGANISM: Candida glabrata rRNA gene

<400> SEQUENCE: 73
ggtcatttag aggaactaaa agtcgtaaca aggtttccgt aggtgaacct gcggaaggat       60
cattaaagaa atttaattga tttgtctgag ctcggagaga gacatctctg gggaggacca      120
gtgtagacac tcaggaggct cctaaaatat tttctctgct gtgaatgcta tttctcctgc      180
ctgcgcttaa gtgcgcggtt ggtgggtgtt ctgcagtggg gggagggagc cgacaaagac      240
ctgggagtgt gcgtggatct ctctattcca aaggaggtgt tttatcacac gactcgacac      300
tttctaatta ctacacacag tggagtttac tttactacta ttcttttgtt cgttggggga      360
acgctctctt tcggggggga gttctcccag tggatgcaaa cacaaacaaa tatttttta     420 aactaattca gtcaacacaa gatttctttt agtagaaaac aacttcaaaa ctttcaacaa      480
tggatctctt ggttctcgca tcgatgaaga acgcagcgaa atgcgatacg taatgtgaat      540
tgcagaattc cgtgaatcat cgaatctttg aacgcacatt gcgccctctg gtattccggg      600
gggcatgcct gttttgagcgt catttccttc tcaaacacat tgtgtttggt agtgagtgat      660
actcgttttt gagttaactt gaaattgtag gccatatcag tatgtgggac acgagcgcaa      720
gcttctctat taatctgctg ctcgtttgcg cgagcggcgg gggttaatac tgtattaggt      780
tttaccaact cggtgttgat ctagggaggg ataagtgagt gttttgtgcg tgctgggcag      840
```

```
acagacgtct ttaagtttga cctcaaatca ggtagggtta cccgctgaac ttaagcatat    900
caataagcgg aggaaaagaa accaactggg attgccttag taacggcgag tgaagcggca    960
aaagctcaaa tttgaaatct ggtacctttg gtgcccgagt tgtaatttgg agagtaccac   1020
tttgggactg tactttgcct atgttccttg aacaggacg tcatggaggg tgagaatccc   1080
gtgtggcgag ggtgtcagtt ctttgtaaag ggtgctcgaa gagtcgagtt gtttgggaat   1140
gcagctctaa gtgggtggta aattccatct aaagctaaat acaggcgaga gaccgatagc   1200
gaacaagtac agtgatggaa agatgaaaag aactttgaaa agagagtgaa aaagtacgtg   1260
aaattgttga aagggaaggg catttgatca gacatggtgt tttgcgcccc ttgcctctcg   1320
tgggcttggg actctcgcag ctcactgggc cagcatcggt tttggcggcc ggaaaaaacc   1380
tagggaatgt ggctctgcgc ctcggtgtag agtgttatag ccctgggaa tacgccagt   1440
cgggaccgag gactgcgata cttgttatct aggatgctgg cataatggtt atatgccgcc   1500
cgtcttgaaa cacggaccaa ggagtctaac gtctatgcga gtgtttgggt gttaaacccg   1560
tacgcgtaat gaaagtgaac gtaggttggg gccctccacc tgggggtgc acaatcgacc   1620
gatcctgatg tcttcggatg gatttgagta agagcatagc tgttgggacc cgaaagatgg   1680
tgaactatgc ctgaataggg tgaagccaga ggaaactctg gtggaggctc gtagcggttc   1740
tgacgtgcaa atcgatcgtc gaatttgggt ataggggcga aagactaatc gaaccatcta   1800
gtagctggtt cctgccgaag tttccctcag gatagcagaa gctcgtatca gttttatgag   1860
gtaaagcgaa tgattagagg taccgggggtt gaaatgacct tgacctattc tcaaacttta   1920
aatatgtaag aagtccttgt tgcttaattg aacgtggaca tttgaatgaa gagcttttag   1980
tgggccattt ttggtaagca gaactggcga tgcgggatga accgaacgtg gagttaaggt   2040
gccggaatac acgctcatca gacaccacaa aaggtgttag ttcatctaga cagccggacg   2100
gtggccatgg aagtcggaat ccgctaagga gtgtgtaaca actcaccggc cgaatgaact   2160
agccctgaaa atggatggcg ctcaagcgtg ttacctatac tccgccgtca gggttgaaat   2220
gaggccctga cgagtaggca ggcgtggggg tcagtgacga agcctaggcc gtaaggtcgg   2280
gtcgaacggc ccctagtgca gatcttggtg gtagtagcaa atattcaaat gagaactttg   2340
aagactgaag tggggaaagg ttccacgtca acagcagttg gacgtgggtt agtcgatcct   2400
aagagatggg gaagctccgt ttcaaaggcc tgatttatgc aggccaccat cgaaagggaa   2460
tccggttaag attccggaac ctggatgtgg attcttcacg gcaacgtaac tgaatgtgga   2520
gacgtcggcg cgagccctgg gaggagttat cttttcttct taacagctta tcaccctgga   2580
attggtttat ccggagatgg ggtcttatgg ctggaagagg cgagctcata tgctcgctcc   2640
ggtgcgcttg cgacggccct tgaaaatcca caggaaggaa tagttttcac gccaggtcgt   2700
actgataacc gcagcaggtc tccaaggtga acagcctcta gttgatagaa taatgtagat   2760
aagggaagtc ggcaaaatag atccgtaact tcgggataag gattggctct aagggtcggg   2820
tagtgagggc cttggtcaga cgcggcgggg ctgcgtgcgg actgcctggt ggggcttgct   2880
ctgccgggcg gactgcatgc ggctcctgtc gtagacggtc ttggtaggtc tcttgtaggc   2940
cgtcgcttgc tgcgattaac gatcaactta gaactggtac ggacaagggg aatctgactg   3000
tctaattaaa acatagcatt gcgatggtca gaaagtgatg ttgacgcaat gtgatttctg   3060
cccagtgctc tgaatgtcaa agtgaagaaa ttcaaccaag cgcgggtaaa cggcgggagt   3120
aactatgact ctcttaaggt agccaaatgc ctcgtcatct aattagtgac gcgcatgaat   3180
```

```
ggattaacga gattcccact gtccctatct actatctagc gaaaccacag ccaagggaac    3240
gggcttggca gaatcagcgg ggaaagaaga ccctgttgag cttgactcta gtttgacatt    3300
gtgaagagac atagagggtg tagcataagt gggagctccg gcgccagtga ataccacta    3360 cctttatagt ttctttactt attcaattaa gcggagctgg aattcatttt ccacgttcta    3420
gctttcaaag tgccattcgg tgctgatccg ggttgaagac attgtcaggt ggggagtttg    3480
gctggggcgg cacatctgtt aaacgataac gcagatgtcc taaggggac tcatggagaa     3540 cagaaatctc cagtagaaca aaagggtaaa agtccccttg attttgattt tcagtgtgaa    3600
tacaaaccat gaaagtgtgg cctatcgatc ctttagtccc tcggaatttg aggctagagg    3660
tgccagaaaa gttaccacag ggataactgg cttgtggcag tcaagcgttc atagcgacat    3720 tgcttttga ttcttcgatg tcggctcttc ctatcatacc gaagcagaat tcggtaagcg      3780
ttggattgtt cacccactaa tagggaacgt gagctgggtt tagaccgtcg tgagacaggt    3840
tagttttacc ctactgatga atgttaccgc aatagtaatt gaacttagta cgagaggaac    3900
agttcattcg gataattggt ttttcgggct gtctgatcag gcaatgccgc gaagctacca    3960
tccgctggat tatggctgaa cgcctctaag tcagaatcca tgctagaacg cggtgattct    4020
ttgccctgca aacgtagat ggatacgaat aaggcgtcct tttgggcgtc gctgaaccat      4080
agcaggctgg cgacggtgcg cttggcggaa aggccttgcg tgcttgccgg cggatagcaa    4140
tgtcattttg cgcggggata aatcatttgt atacgactta gatgtacaac ggggtattgt    4200
aagcagtaga gtagccttgt tgttacgatc                                       4230

<210> SEQ ID NO 74
<211> LENGTH: 4006
<212> TYPE: DNA
<213> ORGANISM: Candida gulliermundei rRNA gene

<400> SEQUENCE: 74
ttggtcattt agaggaagta aaagtcgtaa caaggtttcc gtaggtgaac ctgcggaagg      60
atcattacag tattctttg ccagcgctta actgcgcggc gaaaaacctt acacacagtg      120 tcttttgat acagaactct ctgctttggg tttggcctag ataggttg ggccagaggt         180 ttaacataaa cacaatttaa ttattttac agttagtcaa attttgaatt aatcttcaaa      240
actttcaaca acggatctct tggttctcgc atcgatgaag aacgcagcga atgcgataa      300 gtaatatgaa ttgcagattt cgtgaatca tcgaatcttt gaacgcacat tgcgccctct       360
gggtattcca gagggcatgc ctgttttgag cgtcatttct ctctcaaacc cccgggtttg    420
gtattgagtg atactcttag tcgggactag gcgtttgctt gaaaagtaat tggcatgggt    480
agtactggat agtgctgtcg acctctcaat gtattaggtt tatccaactc gttgaatggt    540
gtggcgggat atttctggta ttgttggccc ggccttacaa caaccaaaca gcttgacct      600 caaatcaggt aggaataccc gctgaactta agcatatcaa taagcggagg aaaagaaacc    660
aacagggatt gccttagtag cggcgagtga agcggcaaaa gctcaaattt gaaatctggc    720
gccttcggtg tccgagttgt aatttgaaga ttgtaacctt gggggttggc tcttgtctat    780
gtttcttgga acaggacgtc acagagggtg agaatcccgt gcgatgagat gcccaattct    840
atgtaacggt gctttcgaag agtcgagttg gtttggggaa tgcagctcct aagtgggtgg    900
taaattccat ctaaagctaa atattggcga gagaccgata gcgaacaagt acagtgatgg    960
aaagatgaaa agaactttga aaagagagtg aaaaagtacg tgaaattgtt gaagggaag    1020 ggtttgagat cagactcgat attttgtgag ccttgccttc gtggcggggt gacccgcagc    1080
```

```
ttatcgggcc agcatcggtt tgggcggtag gataatggcg taggaatggt gactttactt      1140
cggtgaagtg ttaatagcct gcgttgatgc tgcctgccta gaccgaggac tgcgatttta      1200
tcaaggatgc tggcataatg atcccaaacc gcccgtcttg aaacacggac ccaaggagtc      1260
taacgtctat gcgagtgttt gggtgttaaa cccgtacgcg taatgaaagt gaacgtaggt      1320
gagggctctt ttgagtgcat catcgaccga tcctgatgtc ttcggatgga tttgagtaag      1380
agcatagctg ttgggacccg aaagatggtg aactatacct gaatagggtg aagccagagg      1440
aaactctggt ggaggctcgt agcggttctg acgtgcaaat cgatcgtcga atttgggtat      1500
aggggcgaaa gactaatcga accatctagt agctggttcc tgccgaagtt ccctcagga       1560 tagcagaagc tcgtatcagt tttatgaggt aaagcgaatg attagaggta ttggggttga      1620
aatgacctta acctattctc aaactttaaa tatgtaagaa gtccttgttg cttaattgaa      1680
acgtggacat ttgaatgaag agcttttagt gggccatttt tggtaagcag aactggcgat      1740
gcgggatgaa ccgaacgtga agttaaagtg ccggaataca cgctcatcag acaccacaaa      1800
aggtgttagt tcatctagac agccggacgg tggccatgga agtcggaatc cgctaaggag      1860
tgtgtaacaa ctcaccggcc gaatgaacta gccctgaaaa gtggatggcg ctcaagcgtg      1920
ttacttatac ttcgccgtcg agggttgata tgatgccctg acgagtaggc aggcgtggag      1980
gtcagtgacg aagcctttgc tgtaaagctg ggtcgaacgg cctctagtgc agatcttggt      2040
ggtagtagca atattcaaa tgagaacttt gaagactgaa gtggggaaag gttccatgtc       2100
aacagcagtt ggacatgggt tagtcgatcc taagagatgg ggaagctccg tttcaaagtg      2160
cttgattttt caagccgcca tcgaaaggga atccggttaa tattccggaa cttggatatg      2220
gattcttcac ggtaacgtaa ctgaatgtgg agacgtcggc gtgagccctg ggaggagttc      2280
tcttttcttc ttaacagctt atcaccctgg aattggttta tccggagata gggtcttatg      2340
gctggaagag cgcaatactt tgttgcgtc cggtgcgctt acgacggtcc ttgaaaatcc        2400
acaggaagga atagttttca tgccaagtcg tactcataac acgcagcagg tctccaaggt      2460
taacagcctc tagttgatag aataatgtag ataagggaag tcggcaaaat agatccgtaa      2520
cttcgggata aggattggct ctaaggatcg ggtgtcttgg gcctttacca gacgcagcgg      2580 aaccggcgt ggactgtcta ggagcaatct tggacggacc gctgttggat cttgttgtag        2640
acggttttgg taggcttta gccgtccggg gcacgcttaa cgatcaactt agaactggta       2700
cggacaaagg ggaatctgac tgtctaatta aaacatagca ttgcgatggt cagaaaggtg      2760
aatgttgacg caatgtgatt tctgcccag ttgctctgaa atgtcaaagt ggaagaaatt       2820
caaccaagcg cgggtaaacg ggcgggagta actatgactc tcttaaggta gccaaatgcc      2880
tcgtcatcta attagtgacg cgcatgaatg gattaacgag attcccactg tccctatcta      2940
ctatctagcg aaaccacagc caagggaacg ggcttggcag aatcagcggg gaaagaagac      3000
cctgttgagc ttgactctag tttgacattg tgaaagaca tagagggtgt agaataagtg       3060
ggagctttcg gcgccggtga ataccacta cctctatagt tttttacttt attcaattaa       3120
gcggagctgg acttcatcgt ccacgttcta gcattaaggt ctcattagag gctgatcccg      3180
ggttgaagac attgtcaggt gggggagttt ggctggggcg gcacatctgt taaacgataa      3240
cgcaggtgtc ctaaggggga ctcatggaga acagaaatct ccagtagaac aaaaggggta      3300
aaagtcccct tgattttgat tttcagtgtg aatacaaacc atgaaagtgt ggcctatcgg      3360
atcctttagt ccctcggaat ttgaggctag aggtgccagg aaaagttacc acagggataa      3420
```

| | |
|---|---|
| ctggcttgtg gcagtcaagc gttcatagcg acattgcttt ttgattcttc gatgtcggct | 3480 |
| cttcctatca taccgaagca gaattcggta agcgttggaa ttgttcaccc cactaatagg | 3540 |
| gaacgtgagc tgggtttaga ccgtcgtgag acaggttagt tttaccctac tgatgaatgt | 3600 |
| tatcgcaata gtaattgaac ttagtacgag aggaaccgtt cattcggata attggttttt | 3660 |
| gcggctgtct gatcaggcaa cgccgcgaag ctaccatccg ctggattatg gctgaacgcc | 3720 |
| tctaagtcag aatccatgct agaaagcgat gattcttgcc tcgcacattt tagttggata | 3780 |
| agaataaggc tctttgagtc gctgaaccat agcaggccta ggtaacggta cacttaacgg | 3840 |
| aaaggttttg tgtgcttgcc ggcggatagc aatgtcataa tgagcgggga taaatccttt | 3900 |
| gcatacgact tacatgtaca acggagtatt gtaagcagta gagtagcctt gttgttacag | 3960 |
| atctgctgag attaagcttc agttgtccga tttgtttagt gtctac | 4006 |

<210> SEQ ID NO 75
<211> LENGTH: 4073
<212> TYPE: DNA
<213> ORGANISM: Candida kefyr rRNA gene

<400> SEQUENCE: 75

| | |
|---|---|
| tccgtaggtg aacctgcgga aggatcatta aagattatga atgaatagat tactgggggga | 60 |
| atcgtctgaa caaggcctgc gcttaattgc gcggccagtt cttgattctc tgctatcagt | 120 |
| tttctatttc tcatcctaaa cacaatggag ttttttctct atgaactact ccctggagaa | 180 |
| gctcgtctct ccagtggaca taaacacaaa caatattttg tattatgaaa aactattata | 240 |
| ctataaaatt aatattcaaa actttcaaca acgatctctc tggttctcgc atcgatgaag | 300 |
| aacgcagcga attgcgatat gtattgtgaa ttgcagattt tcgtgaatca tcaaatcttt | 360 |
| gaacgcacat tgcgccctct ggtattccag ggggcatgcc tgtttgagcg tcatttctct | 420 |
| ctcaaacctt tgggtttggt agtgagtgat actcgtctcg ggttaacttg aaagtggcta | 480 |
| gccgttgcca tctgcgtgag cagggctgcg tgtcaagtct atggactcga ctcttgcaca | 540 |
| tctacgtctt aggtttgcgc caattcgtgg taagcttggg tcatagagac tcataggtgt | 600 |
| tataaagact cgctggtgtt tgtctccttg aggcatacgg cttttaaccaa aactctcaaa | 660 |
| gtttgacctc aaatcaggta ggagtacccg ctgaacttaa gcatatcaat aagcggagga | 720 |
| aaagaaacca accgggattg ccttagtaac ggcgagtgaa gcggcaaaag ctcaaatttg | 780 |
| aaatctggcg tcttcgacgt ccgagttgta atttgaagaa ggcgactttg tagctggtcc | 840 |
| ttgtctatgt tccttggaac aggacgtcat agagggtgag aatcccgtgt ggcgaggatc | 900 |
| ccagttattt gtaaagtgct ttcgacgagt cgagttgttt gggaatgcag ctctaagtgg | 960 |
| gtggtaaatt ccatctaaag ctaaatattg gcgagagacc gatagcgaac aagtacagtg | 1020 |
| atggaaagat gaaaagaact ttgaaaagag agtgaaaaag tacgtgaaat tgttgaaagg | 1080 |
| gaagggcatt tgatcagaca tggcgtttgc ttcggctttc gctgggccag catcagtttt | 1140 |
| agcggttgga taaatcctcg ggaatgtggc tctgcttcgg tagagtgtta tagcccgtgg | 1200 |
| gaatacagcc agctgggact gaggattgcg acttttgtca aggatgctgg cgtaatggtt | 1260 |
| aaatgccgcc cgtcttgaaa cacgaccaa ggagtctaac gtctatgcga gtgtttgggt | 1320 |
| gtaaaacccg tacgcgtaat gaaagtgaac gtaggtgagg cccgcaagg gtgcatcatc | 1380 |
| gaccgatcct gatgtcttcg gatggatttg agtaagagca tagctgttgg gacccgaaag | 1440 |
| atggtgaact atgcctgaat agggtgaagc cagaggaaac tctggtggag gctcgtagcg | 1500 |
| gttctgacgt gcaaatcgat cgtcgaattt gggtataggg gcgaaagact aatcgaacca | 1560 |

```
tctagtagct ggttcctgcc gaagtttccc tcaggatagc agaagctcgt atcagtttta   1620
tgaggtaaag cgaatgatta gaggtaccgg ggttgaaatg accttgacct attctcaaac   1680
tttaaatatg taagaagtcc ttgttgctta attgaacgtg gacatttgaa tgaagagctt   1740
ttagtgggcc atttttggta agcagaactg gcgatgcggg atgaaccgaa cgtggagtta   1800
aggtgccgga atacacgctc atcagacacc acaaaaggtg ttagttcatc tagacagccg   1860
gacggtggcc atggaagtcg gaatccgcta aggagtgtgt aacaactcac cggccgaatg   1920
aactagccct gaaaatggat ggcgctcaag cgtgttacct atactccacc gtcagggtta   1980
atatgatgcc ctgacgagta ggcaggcgtg gaggtcagtg acgaagccta ggctgtaaag   2040
ctgggtagaa cggcctctag tgcagatctt ggtggtagta gcaaatattc aaatgagaac   2100
tttgaagact gaagtgggga aaggttccac gtcaacagca gttggacgtg ggttagtcga   2160
tcctaagaaa tggggaagct ccgtttcaaa ggcctaattt tctaggccac catcgaaagg   2220
gaatccggtt aatattccgg aacctggata tggattcttc acgtaacgt aactgaatgt   2280 ggagacgtcg gcgcgagccc tgggaggagt tatcttttct tcttaacagc ttatcacccc   2340
ggaattggtt tatccggaga gggggtctta tggctggaag agcccagccc ttgtgctggg   2400
tccggtgcgc ccgcgacggc ccttgaaaat ccacaggaag gaatagtttt catgccaggt   2460
cgtactgata accgcagcag gtctccaagg tgaacagcct ctagttgata gaataatgta   2520
gataagggaa gtcggcaaaa tagatccgta acttcgggat aaggattggc tctaagaagt   2580
cggcaaaata gatccgtaat ttcgggataa ggattggctc taaggatcgg gtagtgaggg   2640
ccttggtcag acgcggcggg catgcttgtg gactgtctta ctgggcttgc tcggtgggac   2700
ggactgcttg cgggccttgt cgtagacggc cttggtaggt ctcttgtaga ccgtcgcttg   2760
ctacaattaa cgatcaactt agaactggta cggacaaggg gaatctgact gtctaattaa   2820
aacatagcat tgcgatggtc agaaagtgat gttgacgcaa tgtgatttct gcccagtgct   2880
ctgaatgtca aagtgaagaa attcaaccaa gcgcgggtaa acggcgggag taactatgac   2940
tctcttaagg tagccaaatg cctcgtcatc taattagtga cgcgcatgaa cggattaacg   3000
agattcccac tgtccctatc tactatctag cgaaaccaca gccaagggaa cgggcttggc   3060
agaatcagcg gggaaagaag accctgttga gcttgactct agtttgacat tgtgaagaga   3120
catagagggt gtagcataag tgggagcttc ggcgccagtg aaataccact acctttatag   3180
tttctttact tattcaatta agcggagctg gaattcattt tccacgttct agcattcaaa   3240
gtcctatacg ggctgatccc gggttgaaga cattgtcagg tggggagttt ggctggggcg   3300
gcacatctgt taaacgataa cgcagatgtc ctaggggga ctcatggaga acagaaatct   3360
ccagtagaac aaaagggtaa aagtcccctt gattttgatt ttcagtgtga atacaaacca   3420
tgaaagtgtg gcctatcgat cctttaggtc ctcggaattt gaggctagag gtgccagaaa   3480
agttaccaca gggataactg gcttgtggca gtcaagcgtt catagcgaca ttgcttttg   3540 attcttcgat gtcggctctt cctatcatac cgaagcagaa ttcggtaagc gttggattgt   3600
tcacccacta taggaaacg tgagctgggt ttagaccgtc gtgagacagg ttagtttac   3660 cctactgatg aatgttatcg caatagtaat tgaacctagt acgagaggaa cagttcattc   3720
ggataattgg ttttgcggc tgtctgacca ggcattgccg cgaagctacc atccgctgga   3780
ttatggctga acgcctctaa gtcagaatcc atgctagaac gcgatgattt ctttgccttg   3840
cacaatatag aaggatacga ataaggcgtc tttatggcgt cgctgaacca tagcaggctg   3900
```

```
gcaacggtgc tcttagcgga aaggctttgg gtgcttgccg gcgaattgca atgtcatttt     3960
gcgcaaggat aaatcatttg tatacgactt aaatgtacaa cagggtattg taagcagtag     4020
agtagccttg ttgttacgat ctgctgagat taagccttcg ttgtctgatt tgt            4073
```

<210> SEQ ID NO 76
<211> LENGTH: 3768
<212> TYPE: DNA
<213> ORGANISM: Candida krusei rRNA gene
<220> FEATURE:
<221> NAME/KEY: misc_feature
<222> LOCATION: (2690)..(2690)
<223> OTHER INFORMATION: n is a, c, g, or t
<220> FEATURE:
<221> NAME/KEY: misc_feature
<222> LOCATION: (2718)..(2718)
<223> OTHER INFORMATION: n is a, c, g, or t
<220> FEATURE:
<221> NAME/KEY: misc_feature
<222> LOCATION: (3765)..(3765)
<223> OTHER INFORMATION: n is a, c, g, or t

<400> SEQUENCE: 76

```
ggaagtaaaa gtcgtaacaa ggtttccgta ggtgaacctg cggaaggatc attactgtga       60
tttagtacta cactgcgtga gcggaacgaa acaacaacaa cctaaaatgt ggaatatagc      120
atatagtcga caagagaaat ctacgaaaaa caaacaaaac tttcaacaac ggatctcttg      180
gttctcgcat cgatgaagag cgcagcgaaa tgcgatacct agtgtgaatt gcagccatcg      240
tgaatcatcg agttcttgaa cgcacattgc gcccctcggc attccggggg gcatgcctgt      300
ttgagcgtcg tttccatctt gcgcgtgcgc agagttgggg gagcggagcg gacgacgtgt      360
aaagagcgtc ggagctgcga ctcgcctgaa agggagcgaa gctggccgag cgaactagac      420
tttttttcag gacgcttgg cggccgagag cgagtgttgc gagacaacaa aaagctcgac      480
ctcaaatcag gtaggaatac ccgctgaact taagcatatc aataagcgga ggaaaagaaa      540
ccaacaggga ttgcctcagt agcggcgagt gaagcggcaa gagctcagat ttgaaatcgt      600
gctttgcggc acgagttgta gattgcaggt tggagtctgt gtggaaggcg gtgtccaagt      660
cccttggaac agggcgccca ggagggtgag agccccgtgg gatgccggcg gaagcagtga      720 ggccccttctg acgagtcgag ttgtttggga atgcagctcc aagcgggtgg taaattccat      780
ctaaggctaa atactggcga gagaccgata gcgaacaagt actgtgaagg aaagatgaaa      840
agcactttga aaagagagtg aaacagcacg tgaaattgtt gaaagggaag ggtattgcgc      900
ccgacatggg gattgcgcac cgctgcctct cgtgggcggc gctctgggct ttccctgggc      960
cagcatcggt tcttgctgca ggagaagggg ttctggaacg tggctcttcg gagtgttata     1020
gccagggcca gatgctgcgt gcggggaccg aggactgcgg ccgtgtaggt cacgatgct      1080 ggcagaacgg cgcaacaccg cccgtcttga aacatggacc aaggagtcta acgtctatgc     1140
gagtgtttgg gtgtgaaacc cgtacgcgta atgaaagtga acgtaggtcg accccctgc      1200 cctcggggag gggagcacga tcgaccgatc ccgatgttta tcgaaggat ttgagtagga      1260 gcatagctgt tgggacccga aagatggtga actatgcctg aataggtgga agccagagga     1320
aactctggtg gaggctcgta gcggttctga cgtgcaaatc gatcgtcgaa tttgggtata     1380
ggggcgaaag actaatcgaa ccatctagta gctggttcct gccgaagttt ccctcaggat     1440
agcagaagct cgtatcagtt ttatgaggta aagcgaatga ttagacgtct cggggtcgaa     1500
atgaccttag cgtattctca aactttaaat atgtaagaag tccctgttgc tttattgaac     1560
gcggacgttt gaatgcagag cttttagtgg gccattttg gtaagcagaa ctggcgatgc     1620
```

```
gggatgaacc gaacgcgaag ttaaggtgcc ggaatgcacg ctcatcgac accacaaaag      1680
gtgttagttc atccagacag ccggacggtg gccatgaag tcggaatccg ctaaggagtg      1740
tgtaacaact caccggccga atgaactagc cctgaaaatg gatggcgctc aagcgtgtta      1800
cctatacttc gccgccatgg cgcaaggcct tggcgagtag gcaggcgtgg gggtttgtga      1860
cgaagccttg ggcgtgagcc tgggtcgaac ggcccctagt gcagatcttg gtggtagtag      1920
caaatattca aatgggaact ttgaagactg aagtggggaa aggttccgcg tcaacagcag      1980
ttggacgcgg gtcagtcgat cctaagagat ggggaagctc cgtttcaacg agcgcaattc      2040
gcttgcgcca ccatcgaaag ggaatccggt taagattccg gaacttggat gtggattctt      2100
cacggcaacg taacagaatg cggagacgcc ggcgggagcc ctgggaggag ttttcttttc      2160
ttcttaacag cctaacaccc tggaattggt ttatccggag agggggtctt atggctggaa      2220
gagcgtcgcc cttgctgcga cgtccggtgc gcttgcgacg gtccttgaaa atccgcagga      2280
aggaatagtt ttcacgccaa gtcgtactca taaccgcagc aggtctccaa ggttaacagc      2340
ctctagttga tagaataatg tagataaggg aagtcggcaa aatagatccg taacttcggg      2400
ataaggattg gctctaaggg ttgggcggag tgctggggct gccggcgcgt gccgggtgct      2460
gcggagacgc atctgtgttt ctgcggctgc ctggcggcgg gcttgcggcc tgttttcag      2520
tcccgcggtt aacaaccgac ttagaactgg tacggacaag gggaatctga ctgtctaatt      2580
aaaacatagc attgcgatgg tcagaaagtg atgttgacgc aatgtgattt ctgcccagtg      2640
ctctgaatgt caaagtgaag aaattcaacc aagcgcgggt aaacggcggn agtaactatg      2700
actctcttaa ggtagccnaa tgcctcgtca tctaattagt gacgcgcatg aatggattaa      2760
cgagattccc actgtcccta tctactatct agcgaaacca cagccaaggg aacgggcttg      2820
gcagaatcag cggggaaaga agaccctgtt gagcttgact ctagtttgac attgtgaaaa      2880
gacatagagg gtgtagcata agtgggagct ccggcgccag tgaaatacca ctacctttat      2940
cgtttttta cttattcaat gaagcggagc tggtcttgac gaccacgttc tggagcgaag      3000
gcgccttgtg cgctgatccg ggttgaagac attgtcaggt ggggagtttg gctggggcgg      3060
cacatctgtt aaacgataac gcagatgtcc taaggggac tcatggagaa cagaaatctc      3120
cagtagaaca aaagggtaaa agtcccctttg atttttgattt tcagtgtgaa tacaaaccat      3180
gaaagtgtgg cctatcgatc cttttagtccc tcggaatttg aggctagagg tgccagaaaa      3240
gttaccacag ggataactgg cttgtggcag tcaagcgctc atagcgacat gcttttttga      3300
ttcttcgatg tcggctcttc ctatcatacc gaagcagaat tcggtaagcg ttggattgtt      3360
cacccactaa tagggaacgt gagctgggtt tagaccgtcg tgagacaggt tagttttacc      3420
ctactgatga atgttgtcgc aatagtaatt gaacttagta cgagaggaac cgttcattca      3480
gataattggt ttttgcggct gtctgagcag acactgccgc gacgctacca tctgctggat      3540
aatggctgaa cgcctctaag tcagaatcca tgctagaacg cgacgattac ctgccctcgc      3600
acatttgaga aggatacgaa taaggccctg tggccgcaga accgtagcag gccggcagcg      3660
gtgcgcatgg cggaaaggcc gtgtgtgctt gccggcggat ggcaatgtca ggatgcgcga      3720
ggataaatcc tatgcatacg acttagatgt acaacggggt attgnaag                  3768
```

<210> SEQ ID NO 77
<211> LENGTH: 3558
<212> TYPE: DNA
<213> ORGANISM: Candida lipolytica rRNA gene

```
<400> SEQUENCE: 77 acgaatctttt ggaagtaaaa aagcgtaaca aggtttccgt aggtgaacct gcggaaggat     60
cattattgat tttatctatt tctgtggatt tctattctat tacagcgtca ttttatctca    120
attataacta tcaacaacgg atctcttggc tctcacatcg atgaagaacg cagcgaaccg    180 cgatatttttt tgtgacttgc agatgtgaat catcaatctt tgaacgcaca ttgcgcggta    240
tggcattccg taccgcacgg atggaggagc gtgttccctc tgggatcgca ttgctttctt    300
gaaatggatt ttttttaaact ctcaattatt acgtcattca cctcctcatc cgagatagct    360
tagccacgga tttcacctcc ttcatccgag attacccgct gaacttaagc atatcaataa    420
gcggaggaaa agaaaccaac agggattgcc tcagtaacgg cgagtgaagc ggcaaaagct    480
caaatttgaa accctcggga ttgtaatttg aagatttggc attggagaaa gctaacccaa    540
gttgcttgga atagtacgtc atagagggtg acaaccccgt ctggctaacc gttctccatg    600
tattgcctta tcaaagagtc gagttgtttg ggaatgcagc tcaaagtggg tggtaaactc    660
catctaaagc taaatactgg tgagagaccg atagcgaaca agtactgtga aggaaaggtg    720
aaaagaactt tgaaaagaga gtgaaatagt atgtgaaatt gttgataggg aaggaaatga    780
gtggagagtg gccgaggttt cagccgcccc tcgtgggcgg tgtactgccg acgccgagtc    840
atcgatagcg agacgagggt tacaaatggg agcgcctttc gggcgttctc ccctaacct    900 ccacactgcc accgacgaca taatccaccc atttcacccg tcttgaaaca cggaccaagg    960
agtctaatgg atatgtgagt gttagggtgg caaaccccag cgcgcaatga aagtgaatgg   1020
attcgttcag aatcgaccga acttgattat tatgacagtt ttgagtaaac acatccattg   1080
ggacccgaaa gatggtgaac tatgcctgga tagggtgaag tcagaggaaa ctctgatgga   1140
ggctcgtagc ggttctgacg tgcaaatcga tcgtaggatc tgggtatagg ggcgaaagac   1200
taatcgaacc atctagtagc tggttcctgc cgaagtttcc ctcaggatag cagaagctca   1260 tatcagttttt atgaggtaaa gcgaatgatt agaagtattg ggggcgaaat gccctcggct   1320
tattctcaaa ctttaaatat gtaagaagcc ttggttactt aatcgaaccg tggctacgaa   1380
tgaagagctt ctagtgggcc atttttggta agcagaactg gcgatgcggg atgaaccgaa   1440
cgtggagtta aggtgccgga atacacgctc atcagacacc acaaaaggtg ttagttttatc   1500 tagacagccg gacggtggcc atggaagtcg gaatccgcta aggagtgtgt cacaactcac   1560
cggccgaatg aactagccct gaaaatggat ggcgcttaag cgtgttacct atactctacc   1620
gagaggaggt ttcctctcga gtaggcaggc gtgggggttg ttgagaagcg ttggccgaga   1680
agctgcgtcg aacggcccct agtgcagatc ttggtggtag tagcaaatat tcaaatgaga   1740
actttgaaga ctgaagtggg gaaaggttcc gtgtgaacag cagttggaca cgggtaagtc   1800
gatcctaagg ggtggcataa ctgtcgcgta cggcccgata agggccttct ccaaaaggga   1860
agccggttga aattccggca cttggatgtg gattctccac ggcaacgtaa ctgaatgtgg   1920
ggacggtggc acaagtcttg gaaggagtta tcttttcttt ttaacggagt caacaccctg   1980
gaattagttt gtctagagat agggtatcgt tccggaagag ggggcagct ttgtcccctc    2040 cgatgcactt gtgacgcccc ttgaaaaccc gcaggaagga atagttttca cgccaagtcg   2100
tactgataac cgcagcaggt ctccaaggtg aacagcctct agttgataga ataatgtaga   2160
taagggaagt cggcaaaata gatccgtaac ttcgggataa ggattggctc tgggggttgg   2220 tggatgaag cgtgggagac cccaagggac tggcagctgg gcaactggca gccggacccg   2280
cggcagacac tgcgtcgctc cgtccacatc atcaaccgcc ccagaactgg tacggacaag   2340
```

```
gggaatctga ctgtctaatt aaaacatagc tttgcgatgg ttgtaaaaca atgttgacgc    2400
aaagtgattt ctgcccagtg ctctgaatgt caaagtgaag aaattcaacc aagcgcgcgg    2460
gtaaacggcg ggagtaacta tgctctctta aggtagccaa atgcctcgtc atctaattag    2520
tgacgcgcat gaatggatta acgagattcc cactgtccct atctactatg tagcgaaacc    2580
acagccaagg gaacgggctt ggcagaatca gcggggaaag aagaccctgt tgagcttgac    2640
tctagtttga cattgtgaag agacataggg ggtgtagaat aagtgggagc ttcggcgccg    2700
gtgaaatacc actacccta tcgtttcttt acttatttag taagtggaag tggtttaaca    2760
accattttct agcattcctt tccaggctga agacattgtc aggtggggag tttggctggg    2820
gcggcacatc tgttaaaaga taacgcagat gtcctaaggg ggactcaatg agaacagaaa    2880
tctcatgtag aacaaaaggg taaaagtccc cttgattttg attttcagtg tgaatacaaa    2940
ccatgaaagt gtggcctatc gatcctttag ttgttcggag tttgaaccta gaggtgccag    3000
aaaagttacc acagggataa ctggcttgtg gcagtcaagc gttcatagcg acattgcttt    3060
ttgatccttc gatgtcggct cttcctatca taccgaagca gaattcggta agcgttggat    3120
tgttcaccca ctaataggga acgtgagctg ggtttagacc gtcgtgagac aggttagttt    3180
taccctactg atggacttgt tgcaatagta attgaactta gtacgagagg aacagttcat    3240
tcggataatt ggtgtttgct gctgtctgac caggcaatgc agcgaagcac cacccgctgg    3300
gttatggccg aacgcctcca agtcagaacc catgccagaa gggaagaatc aggggggaagg    3360 agggatatga agaagtaccg cagtaccgga gggggagggg gggtggataa ggaaaccgcc    3420 cgccccccc cgactggaaa gacccaccct tgtgaaatcc attgtagacg actttagtat    3480
gcgacgaggt attgtaagta gtagagtagc cttgttgtta cgatctattg agattaagcc    3540
tttgttgttt agattcga                                                  3558

<210> SEQ ID NO 78
<211> LENGTH: 4031
<212> TYPE: DNA
<213> ORGANISM: Candida lusitaniae rRNA gene

<400> SEQUENCE: 78
ttttgaggaa gtaaaagtcg taacaaggtt tccgtaggtg aacctgcgga aggatcatta     60
aaaaatacat tacacattgt ttttgcgaac aaaaaaaata aatttttta ttcgaatttc    120 ttaatatcaa aactttcaac aacggatctc ttggttctcg catcgatgaa gaacgcagcg    180
aattgcgata cgtagtatga cttgcagacg tgaatcatcg aatctttgaa cgcacattgc    240
gcctcgaggc attcctcgag gcatgcctgt ttgagcgtcg catcccctct aaccccggt    300 taggcgttgc tccgaaatat caagccgcgc tgtcaaacac gtttacagca cgacatttcg    360
ccctcaaatc aggtaggact acccgctgag acttaagcat atcaataagc ggaggaaaag    420
aaaccaacag ggattgcccc agtaacggcg agtgaagcgg caaaagctca aatttgaaat    480
cctgcgggaa ttgtaatttg aaggtttcgt ggtctgagtc ggccgcgccc aagtccattg    540
gaacatggcg cctgggaggg tgagagcccc gtatggcgca cgccgactct ttgtacaccg    600
cggctccgac gagtcgagtt gtttgggaat gcagctctaa gtgagtggt aaattccatc    660 taaagctaaa tattggcgag agaccgatag cgaacaagta cagtgatgga agatgaaaa    720 gcactttgaa aagagagtga aacagcacgt gaaattgttg aagggaagg cttgcaagc    780 agacacggtt ttaccgggcc agcgtcgaaa agggggagg aacaagaact cgagaatgtg    840
```

```
gcgcgcacct tcgggcgcgc gtgttatagc tcgtgttgac gcctccatcc cttttcgagg    900
cctgcgattc taggacgctg gcgtaatggt tgcaagccgc ccgtcttgaa acacggacca    960
aggagtctaa cgtctatgcg agtgtttggg tgcaaaaccc cagcgcggaa tgaaagtaag   1020
aggttggagc cgcaaggcgc acaatcgacc gaccctgaag tgctcggacg ggtttgagta   1080
ggagcatagc tgttgggacc cgaaagatgg tgaactatgc ctggataggg tgaagccaga   1140
ggaaactctg gtgaggctc gcagcggttc tgacgtgcaa atcgatcgtc gaatctgggt    1200
ataggggcga aagactaatc gaaccatcta gtagctgctc ttatgctctt cctgccgaag   1260
ttcctgacgc ctccatccct tttcgaggcc tgcgattcta ggacgctggc gtaatggttg   1320
caagccgccc gtcttgaaac acggaccaag gagtctaacg tctatgcgag tgtttgggtg   1380
caaaacccca gcgcggaatg aaagtaagag gttggagccg caaggcgcac aatcgaccga   1440
ccctgaagtg ctcggacggg tttgagtagg agcatagctg ttgggacccg aaagatggtg   1500
aactatgcct ggataggtg aagccagagg aaactctggt ggaggctcgc agcggttctg    1560
acgtgcaaat cgatcgtcga atctgggtat aggggcgaaa gactaatcga accatctagt   1620
agctggttcc tgccgaagtt ccctcagga tagcagaagc tcgttacaaa cagttttatg    1680
aggtaaagcg aatgattaga ggtctcgggg cggaaatagc cttagcctat tctcaaactt   1740
taaatatgta agaagtcctt gttgcttaat tgaacgtgga catacgaatg tagagcttt   1800
agtgggccat ttttggtaag cagaactggc gatgcgggat gaaccgaacg cgaagttaaa   1860
gtgccggaat gcacgctcat cagacaccac aaaaggtgtt agttcatcta gacagccgga   1920
cggtggccat ggaagtcgga attccgctaa ggagtgtgta acaactcacc ggccgaatga   1980
actagccctg aaaatggatg gcgctcaagc gtgctactta tacttcgccg gcatttttt    2040
tggaaatgcc gagtaggcag gcgtggaggt ggtgacgaag ccttggctgt gaagctgggt   2100
cgaaccgcct ctagtgcaga tcttggtggt agtagcaaat attcaaatgg gaactttgaa   2160
gactgaagtg gggaaaggtt ccatgtcaac agcagatgga catgggtgag tcgatcctaa   2220
gagctaaggt agttctgact gaacagcttc tttgcgaagt gtgctcgaaa gggaatccgg   2280
ttaagattcc ggaacttgga tgcggaacta cacggcaacg taactgaatg cggagacgcc   2340
ggcgtgggcc ctgggaggag ttttcttttt cttctaacag cctgtgaccc tggaattgga   2400
ttatccggag aggggttttt gtggctggaa gagcgcggca tcttcgccgc gtccggtgcg   2460
cctacgacgg tccttgaaaa tccgcaggaa gcaattgttt tcgcgccaag tcgtactgat   2520
aaccgcagca ggtctccaag gttaacagcc tctagttgat agaacaatgt agataaggga   2580
agtcggcaaa atagatccgt aacttcggga taaggattgg ctctaagggt tgggagtgta   2640
agggacgggg gtgacgtgga tgagtgtagt gtggacggtg ctggcttcaa ggccggcgct   2700
gtctgcgccg tgcttgtcct ccaacccccc gttccccgct tcaataacaa ccaacttaga   2760
actggtacgg acaaggggaa tctgactgtc taattaaaac atagcattgc gatggtcaga   2820
aagtgatgtt gacgcaatgt gatttctgcc cagtgctctg aatgtcaaag tgaagaaatt   2880
caaccaagcg cgggtaaacg gcgggagtaa ctatgactct cttaaggtag ccaaatgcct   2940
cgtcatctaa ttagtgacgc gcatgaatgg attaacgaga ttcccactgt ccctatctac   3000
tatctagcga aaccacagcc aagggaacgg gcttggcaga atcagcgggg aaagaagacc   3060
ctgttgagct tgactctagt ttgacattgt gaaagacat ggagggtgta gaataagtgg    3120
gagcttcggc gccgagtgaa ataccactac ctccatcgtt ttttacttac tgaatgaag    3180
gggagctggt tgtcatgacc acgttctgga tttaagcagc aatgcaatcc cggttcaaga   3240
```

```
cattgtcagg tggggagttt ggctggggcg gcacatctgt taaacgataa cgcagatgtc    3300 ctaaggggg  ctcatggaga acagaaatct ccagtagaac aaaagggtaa agcccccctt   3360
gattttgatt ttcagtgtga atacaaacca tgaaagtgtg gcctatcgat cctttagtcc   3420
ctcggaattt gaggctagag gtgccagaaa agttaccaca gggataactg gcttgtggca   3480
gtcaagcgtt catagcgaca ttgcttttg  attcttcgat gtcggctctt cctatcatac   3540
cgaagcagaa ttcggtaagc gttggattgt cacccacta  atagggaacg tgagctgggt   3600
ttagaccgtc gtgagacagg ttagttttac cctactgatg gaccgttgtt gcaatagtaa   3660
ttgaacttag tacgagagga accgttcatt cagataattg gtatttggcc ctgtctgatc   3720
aggcaccggg ccgaagctac catctgctgg attatggctg aacgcctcta agtcagaatc   3780
catgctagaa gcgacgactc tgcctcgcgc gttgcagttg gatacaaata cgatgtggac   3840
catacaaggc ggcgtttggc ggcggtgcgg aaaggcgctg tcgctggctg cggatagcaa   3900
tgtctcgatg cgcggggata aatcctttgc atacgactta gatgtacaac ggagtattgt   3960
aagcggtaga gtagccttgt tgttacgatc cgctgagatt aagctcttgt tggctggttt   4020
gtctacctag a                                                        4031

<210> SEQ ID NO 79
<211> LENGTH: 3882
<212> TYPE: DNA
<213> ORGANISM: Candida parapsilosis rRNA gene

<400> SEQUENCE: 79
ttggtcattt agaggaagta aaagtcgtaa caaggtttcc gtaggtgaac ctgcggaagg     60
atcattacag aatgaaaagt gcttaactgc atttttcctt acacatgtgt ttttcttttt    120
ttgaaaactt tgctttggta ggccttctat atggggcctg ccagagatta aactcaacca    180 aatttattt  aatgtcaacc gattatttaa tagtcaaaac tttcaacaac ggatctcttg    240
gttctcgcat cgatgaagaa cgcagcgaaa tgcgataagt aatatgaatt gcagatattc    300
gtgaatcatc gaatctttga acgcacattg cgcccttgg  tattccaaag gcatgcctg    360 tttgagcgtc atttctccct caaaccctcg ggtttggtgt tgagcgatac gctgggtttg    420
cttgaaagaa aggcggagta taaactaatg gataggtttt ttccactcat tggtacaaac    480
tccaaaactt cttccaaatt cgacctcaaa tcaggtagga ctacccgctg aacttaagca    540
tatcaataag cggaggaaaa gaaaccaaca gggattgcct tagtagcggc gagtgaagcg    600
gcaaaagctc aaatttgaaa tctggcactt tcagtgtccg agttgtaatt tgaagaaggt    660
atctttgggt ctggctcttg tctatgtttc ttggaacaga acgtcacaga gggtgagaat    720
cccgtgcgat gagatgtccc agacctatgt aaagttcctt cgaagagtcg agttgtttgg    780
gaatgcagct ctaagtgggt ggtaaattcc atctaaagct aaatattggc gagagaccga    840
tagcgaacaa gtacagtgat ggaaagatga aagaacttt  gaaagagag  tgaaaaagta    900 cgtgaaattg ttgaaaggga agggcttgag atcagacttg gtattttgta tgttactctc    960 tcggggtgg  cctctacagt ttaccgggcc agcatcagtt tgagcggtag gataagtgca   1020
aagaaatgtg gcactgcttc ggtagtgtgt tatagtcttt gtcgatactg ccagcttaga   1080
ctgaggactg cggcttcggc ctaggatgtt ggcataatga tcttaagtcg cccgtcttga   1140
aacacggacc aaggagtcta acgtctatgc gagtgttgg  gtgtaaaacc cgtacgcgta   1200
atgaaagtga acgtaggtag gacctccttt aggagtgcac tatcgaccga tcctgatgtc   1260
```

```
ttcggatgga tttgagtaag agcatagctg ttgggacccg aaagatggtg aactatgcct    1320
gaatagggtg aagccagagg aaactctggt ggaggctcgt agcggttctg acgtgcaaat    1380
cgatcgtcga atttgggtat aggggcgaaa gactaatcga accatctagt agctggttcc    1440
tgccgaagtt tccctcagga tagcagaagc tcgtatcagt tttatgaggt aaagcgaatg    1500
attagaagtc ttggggttga aatgacctta acttattctc aaactttaaa tatgtaagaa    1560
gtccttgttg cttaattgaa cgtggacata tgaatgaaga gcttttagtg gccattttt     1620 ggtaagcaga actggcgatg cgggatgaac cgaacgtgaa gttaaagtgc ggaatacac     1680 gctcatcaga caccacaaaa ggtgttagtt catctagaca gccggacggt ggccatggaa    1740
gtcggaatcc gctaaggagt gtgtaacaac tcaccggccg aatgaactag ccctgaaaat    1800
ggatggcgct caagcgtgtt acttatactt cgccgtgaga ggttgatatg atgccctcac    1860
gagtaggcag gcgtggaggt cagtgaagaa gcctttgctg tgaagctggg tcgaacggcc    1920
tctagtgcag atcttggtgg tagtagcaaa tattcaaatg agaactttga agactgaagt    1980
ggggaaaggt tccatgtcaa cagcagttgg acatgggtta gtcgatccta agagatgggg    2040
aagctccgtt tcaatgcgct tgattttca agccaaccat cgaaagggaa tccggttaaa     2100
attccggaac ttggatatgg attcttcacg gcaacgtaac tgaatgtgga gacgtcggcg    2160
tgagccctgg gaggagttat ctttcttct taacagctta tcaccctgga attggtttat     2220
ccggagatgg ggtcttatgg ctggaagagc gcggtaattt tgccgcgtcc ggtgcgctca    2280
cgacggtcct tgaaaatcca caggaaggaa tagttttcat gccaagtcgt actcataacc    2340
gcagcaggtc tccaaggtta acagcctcta gttgatagaa taatgtagat aagggaagtc    2400
ggcaaaatag atccgtaact tcgggataag gattggctct aaggatcggg tggtttgggc    2460
cttgcgtaga agtggtggtg actggcggcg ggctgctttc gggcggactg ctgttggacg    2520
tcgctataga cacacttggt aggcatttat gtcgtccgga tcacgcttaa cgatcaactt    2580
agaactggta cggacaaggg gaatctgact gtctaattaa aacatagcat tgtgatggtc    2640
agaaagtgat gttgacacaa tgtgatttct gcccagtgct ctgaatgtca agtgaagaa     2700 attcaaccaa cgcgggtaa acggcggag taactatgac tctcttaagg tagccaaatg      2760
cctcgtcatc taattagtga cgcgcatgaa tggattaacg agattcccac tgtccctatc    2820
tactatctag cgaaaccaca gccaagggaa cgggcttggc agaatcagcg gggaaagaag    2880
accctgttga gcttgactct agtttgacat tgtgaaaaga catggagggt gtagaataag    2940
tgggagcttc ggcgccggtg aaataccact acctctatag ttttttttact tattcaatga   3000 agcggagctg gaggtaaaac tccacgttct agcattaagg ccttttggct gatccgggtt    3060
gaagacattg tcaggtgggg agtttggctg gggcggcaca tctgttaaac gataacgcag    3120
gtgtcctaag ggggactcat ggagaacaga aatctccagt agaacaaaag ggtaaaagtc    3180
cccttgattt tgattttcag tgtgaataca aaccatgaaa gtgtggccta tcgatccttt    3240
agtccctcgg aatttgaggc tagaggtgcc agaaaagtta ccacagggat aactggcttg    3300
tggcagtcaa gcgttcatag cgacattgct ttttgattct tcgatgtcgg ctcttcctat    3360
cataccgaag cagaattcgg taagcgttgg attgttcacc cactaatagg gaacgtgagc    3420
tgggttagaa ccgtcgtgag acaggttagt tttaccctac tgatgaatgt tatcgcaata    3480
gtaattgaac ttagtacgag aggaaccgtt cattcagata attggttttt gcggctgtct    3540
gatcaggcaa cgccgcgaag ctaccatctg ctggattatg gctgaacgcc tctaagtcag    3600
aatccatgct agaaagcgat gattttttgcc ctgcacattt tagatggata agaataagac   3660
```

-continued

```
tttttagtcg ctagaccata gcaggctggc aacggtgcgc ttagcggaaa ggctttgtgt    3720
gcttgccggc gaatagcaat gtcgacatgc gcggggataa atcctttgta tacgacttag    3780
atgtacaacg gagtattgta agcagtagag tagccttgtt gttacgatct gctgagatta    3840
agcttcagtt gtctgatttg tctacgagtt tgcgggcgag ag                       3882
```

<210> SEQ ID NO 80
<211> LENGTH: 3889
<212> TYPE: DNA
<213> ORGANISM: Candida tropicalis rRNA gene

<400> SEQUENCE: 80

```
cttggtcatt tagaggaagt aaaagtcgta acaaggtttc cgtaggtgaa cctgcggaag      60
gatcattact gatttgctta attgcaccac atgtgttttt tattgaacaa atttctttgg     120
tggcgggagc aatcctaccg ccagaggtta taactaaacc aaacttttta tttacagtca     180
aacttgattt attattacaa tagtcaaaac tttcaacaac ggatctcttg gttctcgcat     240
cgatgaagaa cgcagcgaaa tgcgatacgt aatatgaatt gcagatattc gtgaatcatc     300
gaatctttga acgcacattg cgcccttttg gattccaaag gcatgcctg tttgagcgtc      360 atttctccct caaaccccg ggtttggtgt tgagcaatac gctaggtttg tttgaaagaa      420
tttaacgtgg aaacttattt taagcgactt aggtttatcc aaaacgctta ttttgctagt     480
ggccaccaca atttatttca taactttgac ctcaaatcag gtaggactac ccgctgaact     540
taagcatatc aataagcgga ggaaaagaaa ccaacaggga ttgccttagt agcggcgagt     600
gaagcggcaa aagctcaaat ttgaaatctg gctctttcag agtccgagtt gtaatttgaa     660
gaaggtatct ttgggtctgg ctcttgtcta tgtttcttgg aacagaacgt cacagagggt     720
gagaatcccg tgcgatgaga tgatccaggc ctatgtaaag ttccttcgaa gagtcgagtt     780
gtttgggaat gcagctctaa gtgggtggta aattccatct aaagctaaat attggcgaga     840
gaccgatagc gaacaagtac agtgatggaa agatgaaaag aactttgaaa agagagtgaa     900
aaagtacgtg aaattgttga agggaaggg cttgagatca gacttggtat tttgtatgtt     960
acttcttcgg gggtggcctc tacagtttat cgggccagca tcagtttggg cggtaggaga    1020
attgcgttgg aatgtggcac ggcttcggtt gtgtgttata gccttcgtcg atactgccag    1080
cctagactga ggactgcggt ttatacctag gatgttggca taatgatctt aagtcgcccg    1140
tcttgaaaca cggaccaagg agtctaacgt ctatgcgagt gtttgggtgt aaacccgta     1200 cgcgtaatga aagtgaacgt aggtggggc ccgtatgggt gcaccatcga ccgatcctga    1260
tgtcttcgga tggatttgag taagagcata gctgttggga cccgaaagat ggtgaactat    1320
gcctgaatag ggtgaagcca gaggaaactc tggtggaggc tcgtagcggt tctgacgtgc    1380
aaatcgatcg tcgaatttgg gtatagggc gaaagactaa tcgaaccatc tagtagctgg    1440
ttcctgccga gtttccctc aggatagcag aagctcgtat cagttttatg aggtaaagcg    1500
aatgattaga agtattgggg ttgaaatgac cttaacttat tctcaaactt taaatatgta    1560
agaagtcctt gttgcttaat tgaacgtgga caattgaatg aagagctttt agtgggccat    1620
ttttggtaag cagaactggc gatgcgggat gaaccgaacg tgaagttaaa gtgccggaat    1680
gcacgctcat cagacaccac aaaaggtgtt agttcatcta gacagccgga cggtggccat    1740
ggaagtcgga atccgctaag gagtgtgtaa caactcaccg gccgaatgaa ctagccctga    1800
aaatggatgg cgctcaagcg tgctactat acttcaccgt gattgctaat ttatgatgct    1860
```

```
ttcacgagta ggcaggcgtg gaggtcagtg aagaagcctt tgctgtaaag ctgggtcgaa      1920
cggcctctag tgcagatctt ggtggtagta gcaaatattc aaatgagaac tttgaagact      1980
gaagtgggga aaggttccat gtcaacagca gttggacatg ggttagtcga tcctaagaga      2040
tggggaagct ccgtttcaaa gcgcttgatt tttcaagcct accatcgaaa gggaatccgg      2100
ttaaaattcc ggaacttgga tatggattct tcacggtaac gtaactgaat gtggagacgt      2160
cggcatgagc cctaggagga gttatctttt cttcttaaca gcttatcacc ctggaattgg      2220
tttatccgga gatggggtct tatggctgga agagcgcggt aattttgccg cgtctggtgc      2280
gctcatgacg gtccttgaaa atccacagga aggaatagtt ttcatgccaa gtcgtactca      2340
taaccgcagc aggtctccta ggttaacagc ctctagttga tagaataatg tagataaggg      2400
aagtcggcaa aatagatccg taactttcgg gataaggatt ggctctaagg atcgggtgtc      2460
ttgggccttg tgtagacgcg gtggtgactg atggcgggct gtcttcggac ggactgctgc      2520
cggacgctgc tgtagacacg cttggtaggt tcttgtaacc gtccggggca cgcttaacga      2580
tcaacttaga actggtacgg acaagggaaa tctgactgtc taattaaaac atagcattgt      2640
gatggtcaga aagtgatgtt gacacaatgt gatttctgcc cagtgctctg aatgtcaaag      2700
tgaagaaatt caaccaagcg cgggtaaacg gcgggagtaa ctatgactct cttaaggtag      2760
ccaaatgcct cgtcatctaa ttagtgacgc gcatgaatgg attaacgaga ttcccactgt      2820
ccctatctac tatctagcga aaccacagcc aaggaacgg gcttggcaga atcagcgggg       2880
aaagaagacc ctgttgagct tgactctagt ttgacattgt gaaagacat ggagggtgta       2940 gaataagtgg gagcttcggc gccggtgaaa taccactacc tctatagttt ttttacttat     3000
tcaatgaagc ggagctggag gtcaaactcc acgttctagc attaagcctt tttaggtgat     3060
ccgggttgaa gacattgtca ggtggggagt ttggctgggg gcgggcacat attgttaac      3120 gataacgcag gtgtcctaag ggggactcat ggagaacagg aaatctccca gtagaacaaa     3180
aagggtaaaa gtccccttga ttttgatttt cagtgtgaat acaaaccatg aaagtgtggc     3240
ctatcgatcc tttagtccct cggaatttga ggctagaggt gccagaaaag ttaccacagg     3300
gataactggc ttgtggcagt caagcgttca tagcgacatt gcttttttgat tcttcgatgt    3360 cggctcttcc tatcataccg aagcagaatt cggtaagcgt tggattgttc acccactaat    3420
agggaacgtg agctgggttt agaccgtcgt gagacaggtt agttttaccc tactgatgaa    3480
tgttgtcgca atagtaattg aacttagtac gagaggaacc gttcattcag ataattggtt   3540
tttgcggctg tctgatcagg caacgccgcg aagctaccat ctgctggatt atggctgaac   3600
gcctctaagt cagaatccat gctagaacgc gacgattttt gccctacaca ttttagatgg   3660
atacgaataa gactttatgt cgctggacca tagcaggctg gcaacggtac acttagcgga   3720
aaggctttgt gtgcttgccg gcggatagca atgtcaacat gcgtggggat aaatcctttg   3780
catacgactt agatgtacaa cggagtattg taagcagtag agtagccttg ttgttacgat   3840
ctgctgagat taagctcttg ttgtctgatt tgtctaggtg tagtactgt               3889
```

<210> SEQ ID NO 81
<211> LENGTH: 3945
<212> TYPE: DNA
<213> ORGANISM: Chaetomium globosum rRNA gene

<400> SEQUENCE: 81

```
ccaaacttcg gtcatttaga ggaaagtaaa agtcgtaaca aggtctccgt tggtgaacca       60
gcggagggat cattacagag ttgcaaaact ccctaaacca ttgtgaacgt tacctatacc      120
```

```
gttgcttcgg cgggcggccc cggggtttac cccccgggcg ccctgggcc ccaccgcggg    180 cgcccgccgg aggtcaccaa actcttgata atttatggcc tctctgagtc ttctgtactg    240
aataagtcaa aactttcaac aacggatctc ttggttctgg catcgatgaa gaacgcagcg    300
aaatgcgata agtaatgtga attgcagaat tcagtgaatc atcgaatctt tgaacgcaca    360
ttgcgcccgc cagcattctg gcgggcatgc ctgttcgagc gtcatttcaa ccatcaagcc    420
cccgggcttg tgttggggac ctgcggctgc cgcaggccct gaaaagcagt ggcgggctcg    480
ctgtcgcacc gagcgtagta gcatacatct cgctctggtc gcgccgcggg ttccggccgt    540
taaaccacct tttaacccaa ggttgacctc ggatcaggta ggaagacccg ctgaacttaa    600
gcatatcaat aagcggagga aaagaaacca acagggattg ccctagtaac ggcgagtgaa    660
gcggcaacag ctcaaatttg aaatctggct tcggcccgag ttgtaatttg cagaggaagc    720
tttaggcgcg gcaccttctg agtcccctgg aacggggcgc catagagggt gagagccccg    780
tatagttgga tgcctagcct gtgtaaagct ccttcgacga gtcgagtagt ttgggaatgc    840
tgctcaaaat gggaggtaaa tttcttctaa agctaaatac cggccagaga ccgatagcgc    900
acaagtagag tgatcgaaag atgaaaagca ctttgaaaag agggttaaat agcacgtgaa    960
attgttgaaa gggaagcgct tgtgaccaga cttgcgccgg gcggatcatc cggtgttctc   1020
accggtgcac tccgcccggc tcaggccagc atcggttctc gcggggggat aaaggtcctg   1080
ggaacgtagc tcctccggga gtgttatagc ccggggcgta atgccctcgc ggggaccgag   1140
gttcgcgcat ctgcaaggat gctggcgtaa tggtcatcag cgacccgtct tgaaacacgg   1200
accaaggagt caaggttttg cgcgagtgtt tgggtgtaaa acccgcacgc gtaatgaaag   1260
tgaacgtagg tgagagcttc ggcgcatcat cgaccgatcc tgatgttttc ggatggattt   1320
gagtaggagc gttaagcctt ggacccgaaa gatggtgaac tatgcttgga tagggtgaag   1380
ccagaggaaa ctctggtgga ggctcgcagc ggttctgacg tgcaaatcga tcgtcaaatc   1440
tgagcatggg ggcgaaagac taatcgaacc atctagtagc tggttaccgc cgaagtttcc   1500
ctcaggatag cagtgttgtc ttcagtttta tgaggtaaag cgaatgatta gggactcggg   1560
ggcgcttttt agccttcatc cattctcaaa ctttaaatat gtaagaagcc cttgttactt   1620
aattgaacgt gggcattcga atgtaccaac actagtgggc cattttggt aagcagaact   1680 ggcgatgcgg gatgaaccga acgcggggtt aaggtgccgg agtggacgct catcagacac   1740 cacaaaggc gttagtacat cttgacagca ggacggtggc catggaagtc ggaatccgct   1800
aaggactgtg taacaactca cctgccgaat gtactagccc tgaaaatgga tggcgctcaa   1860
gcgtcccacc cataccccgc cctcagggta gaaacgatgc cctgaggagt aggcggccgt   1920
ggaggtcagt gacgaagcct agggcgtgag cccgggtcga acggcctcta gtgcagatct   1980
tggtggtagt agcaaatact tcaatgagaa cttgaaggac cgaagtgggg aaaggttcca   2040
tgtgaacagc ggttggacat gggttagtcg atcctaagcc atagggaagt tccgtttcaa   2100 agggcactc gtgccccgtg tggcgaaagg gaagccggtt aacattccgg cacctggatg   2160
tgggttttgc gcggtaacgc aactgaacac ggagacgacg gcggggcccc gggcagagt   2220 tctcttttct tcttaacggt ccatcaccct gaaaacagtt tgtctggaga tagggtttaa   2280
cggccggaag agcccgacac ttctgtcggg tccggtgcgc tctcgacgtc ccttgaaaat   2340
ccgtgggagg gaataattct cacgccaggt cgtactcata accgcagcag gtctccaagg   2400
tgaacagcct ctggttgata gaacaatgta gataagggaa gtcggcaaaa tagatccgta   2460
```

| | |
|---|---|
| acttcgggaa aaggattggc tctaagggtt gggcacgttg ggctttgggc ggacgccctg | 2520 |
| ggagcaggtc gcctctagcc gggcaaccgg cgggggcett ccagcatccg ggtgcagatg | 2580 |
| cccttagcag gcttcggccg tccggcgtgc ggttaacaac caacttagaa ctggtacgga | 2640 |
| caggggaat ctgactgtct aattaaaaca tagcattgcg atggccagaa agtggtgttg | 2700 |
| acgcaatgtg atttctgccc agtgctctga atgtcaaagt gaagaaattc aaccaagcgc | 2760 |
| gggtaaacgg gcggggagta actattgact ctttcttaag gttagccaaa tgcctcgtca | 2820 |
| ttctaattaa gtgacgcgca tgaaatggat ttaacgagat tcccaactgt cccttatcta | 2880 |
| ctatctaggc gaaaccacca gccaaggaa cgggcttggc cagaatccag cggggaaaga | 2940 |
| agacccctgt tgagcttgac tctagttttg acattgtgaa aagacatagg gaggtgtaga | 3000 |
| ataggtgggg agcttcggcg cccgtgaaa taccactact cctattgttt tttttactta | 3060 |
| ttcaatgaag cggggctgga ttttcgtccc aacttctggt tttaaggtcc ttcgcgggcc | 3120 |
| gacccgggtt gaagacattg tcaggtgggg agtttggctg gggcggcaca tctgttaaac | 3180 |
| cataacgcag gtgtcctaag gggggctcat ggagaacaga aatctccagt agaacaaaag | 3240 |
| ggtaaaagtc cccttgattt tgattttcag tgtgaataca aaccatgaaa gtgtggccta | 3300 |
| tcgatccttt agtccctcga aatttgaggc tagaggtgcc agaaaagtta ccacagggat | 3360 |
| aactggcttg tggcggccaa gcgttcatag cgacgtcgct ttttgatcct tcgatgtcgg | 3420 |
| ctcttcctat cataccgaag cagaattcgg taagcgttgg attgttcacc cactaatagg | 3480 |
| gaacgtgagc tgggtttaga ccgtcgtgag acaggttagt tttaccctac tgatgaactc | 3540 |
| atcgcaatgg taattcagct tagtacgaga ggaaccgctg attcagataa ttggttttg | 3600 |
| cggttgtccg accgggcagt gccgacgaag ctaccatctg ctggataatg gctgaacgcc | 3660 |
| tctaagtcag aatccatgcc agaacgcgat gatactaccc gcacgttgta gacgtataag | 3720 |
| aataggctcc ggcctcgtat cttagcaggc gattcctccg ccggcctcga gtggtcggc | 3780 |
| ggtaattcgc gtattgtaat tcggcacgc gcgggatcaa atcctttgca gacgacttag | 3840 |
| ctgtgcgaaa ggggtcctgt aagcagtaga gtagccttgt tgttacgatc tgctgagggt | 3900 |
| aagcccttct tcgcctagat ttcccagcga gagcccgcca gcgaa | 3945 |

<210> SEQ ID NO 82
<211> LENGTH: 4021
<212> TYPE: DNA
<213> ORGANISM: Coccidioides immitis rRNA gene

<400> SEQUENCE: 82

```
gtcatttaga ggaagtaaaa gtcgtaacaa ggtttccgta ggtgaacctg cggaaggatc     60
attaaagtgg cgtccggctg cgcacctccc ccgcgggggt cgcgcggtcc gtacctccca    120
cccgtgttta ctgaactatt gttgccttgg caggcctgcc gggcctctgg ctgccgggga    180
tcgcccgcct tgcgcggcgt cccgggcgcg cgcctgccag tggatcaatt gaactcttat    240
gtgaagattg tcagtctgag catcatagca aaaaatcaaa caaaactttc aacaacggat    300
ctcttggttc cggcatcgat gaagaacgca gcgaaatgcg ataagtaatg tgaattgcag    360
aattccgtga atcatcgaat ctttgaacgc acattgcgcc ctctggtatt ccggggggca    420
tgcctgttcg agcgtcattg caaacccttc aagcacggct tgtgtgttgg gccaacgtcc    480
ccgcttgtgt ggacgggcct gaaatgcagt ggcggcaccg agttcctggt gtctgagtgt    540
atgggaaatc acttcatcgc tcaaagaccc gatcggggcc gatctttttt ttttttttaat    600 atccggtttg acctcggatc aggtaggagt acccgctgaa cttaagcata tcaataagcg    660
```

-continued

```
gaggaaaaga aaccaacagg gattgcctca gtaacggcga gtgaagcggc aaaagctcaa    720
atttgaaatc tggctccatg cggagcccga gttgtaattt ggagaggaca cttcgggtgc    780
ggccacggca taagttcctt ggaacaggac gtcatagagg gtgagaatcc cgtctttggc    840
tgctggaccg cgcccatgcg aagttccttc gacgagtcga gttgtttggg aatgcagctc    900
taagtgggtg gtaaatttca tctaaagcta aatattggcc ggagaccgat agcgcacaag    960
tagagtgatc gaaaggttaa aagcaccttg aaaagggagt aaatagcac gtgaaattgt    1020 tgaaagggaa gcgcttgcaa ccagactcgg tcgtgggggc tcagcgggca tgagtgcccg    1080
tgtactcccc catgctccgg gccagcatca gttctggcgg ttggttaaag gcctctggaa    1140
tgtatcgtcc tccgggacgt cttatagcca ggggcgcaat gcggccagcc gggactgagg    1200
aacgcgcttc ggcacggatg ctggcataat ggttgtaagc ggcccgtctt gaaacacgga    1260
ccaaggagtc taacatccac gcgagtgttc gggtgtcaaa cccgtgcgcg cagtgaaagc    1320
gaacggaggt gggagctccg caagggtgca cctatcgacc gatcctgaag tcttcggatg    1380
gatttgagta agagcgtggc tgtgtgggac ccgaaagatg gtgaactatg cctgaatagg    1440
gtgaagccag aggaaactct ggtggaggct cgcagcggtt ctgacgtgca aatcgatcgt    1500
caaatttggg tataggggcg aaagactaat cgaaccatct ggtagctggt tcctgccgaa    1560
gtttccctca ggatagcagt aacgttttca gttttatgag gtaaagcgaa tgattagagg    1620
ccttggggtt gaaacaacct taacctattc tcaaacttta aatatgtaag aagcccttgt    1680
tacttaagtg aatcgtgggc attagaatgg atcgttacta gtgggccatt tttggtaagc    1740
agaactggcg atgcgggatg aaccgaacgc gaggttaagg tgccggaatg cacgctcatc    1800
agacaccaca aaaggtgtta gttcatctag acagcccgac ggtggccatg gaagtcggaa    1860
tccgctaagg agtgtgtaac aactcacggg ccgaatgaac tagccctgaa aatggatggc    1920
gctcaagcgt gctacccata cctcgccgtc ggggtagaaa cgaagcccg acgagtaggc    1980 aggcgtggag gtttgtgacg aagccttggg agtgatcccg ggtcgaacag cctctagtgc    2040
agatcttggt ggtagtagca aatactcaaa tgagaacttt gaggactgaa gtggggaaag    2100
gttccatgtg aacagcagtt ggacatgggt tagtcgatcc taagacatag ggtagttccg    2160
tttgaaagcg cgccctagtg cgccgtttgt cgaaagggaa gccggttaat attccggcac    2220
ctggatgtgg attctccacg gcaacgtaac tgaacgcgga gacgtcggca ggagtcctgg    2280
gaagagttct ctttcttct tgacggccta tcaccctgaa atcggtttgt ccggagctag    2340
ggtttcatgg ccggcagagc cccgcacctt tgcggggtcc ggtgcgctcc tgacgaccct    2400
tgaaaatccg cgggaaggaa tagttttcac gccaggtcgt actcataacc gcagcaggtc    2460
tccaaggtga aaagcctcta gttgatagaa caatgtagat aagggaagtc ggcaaaatag    2520
atccgtaact tcgggaaaag gattggctct aagggtcggg cgcgttgggc cttggggaa    2580 agcctccgga gcaggagggc actagccggg caaccgcgg gcgccttcca gcatcggggt    2640
gcggacgccc ttggcaggct tcggccgtcc ggcgcgcgat taacgaccaa cttagaactg    2700
gtacggacaa ggggaatctg actgtctaat taaaacatag cattgcgatg ccagaaagt    2760 ggtgttgacg caatgtgatt tctgcccagt gctctgaatg tcaaagtgaa gaaattcaac    2820
caagcgcggg taaacggcgg gagtaactat gactctctta aggtagccaa atgcctcgtc    2880
atctaattag tgacgcgcat gaatggatta acgagattcc cactgtccct atctactatc    2940
tagcgaaacc acagccaagg gaacgggctt ggcaaaatca gcggggaaag aagaccctgt    3000
```

```
tgagcttgac tctagtttga cattgtgaaa agacatatcg ggtgtagaat aggtgggagc   3060
ttcggcgccg gtgaaatacc actaccttta ttgttttttt acttattcaa tgaagcggaa   3120
ctgggcttta ccgcccaact tctagcgtta aggtccttcg cgggctgatc cgggttgaag   3180
acattgtcag gtggggagtt tggctggggc ggcacatctg ttaaaccata acgcaggtgt   3240
cctaaggggg actcatggag aacagaaatc tccagtagaa caaaagggta aaagtcccct   3300
tgattttgat tttcagtgtg aatacaaacc atgaaagtgt ggcctatcga tcctttagtc   3360
cctcgaaatt tgaggctaga ggtgccagaa aagttaccac agggataact ggcttgtggc   3420
agccaagcgt tcatagcgac gttgcttttt gatccttcga tgtcggctct tcctatcata   3480
ccgaagcaga attcggtaag cgttggattg ttcacccact aatagggaac gtgagctggg   3540
tttagaccgt cgtgagacag ggttagtttt accctactga tgaagggtcg ccgcaacggt   3600
aattcaattt agtacgagag ggaaccgttg attcagataa ttggtttttg cggctgtctg   3660
accaggcagt gccgcgaagc taccatctgc cggattatgg ctgaacgcct ctaagtcaga   3720
atccgtaccg gaacgcggcg atgttgcccc gcacgttgta gttggatacg aataggccta   3780
cgggccctga acctcagcag gtcggcgacg gctcccggga agagactctc gggcgccagc   3840
tgacggattg caatgtcacc acgcgcgggg atagatcctc tgcagacgac tgaaatgacc   3900
aagcgggtcg tgtaagcggt caagtagcct agttgttacg agtcgctgag cgtcagcccg   3960
atccttggct cgatttgttg taaacaccct ccatcaacat gtttgtcttc ggcaacgccg   4020
g                                                                  4021
```

<210> SEQ ID NO 83
<211> LENGTH: 3981
<212> TYPE: DNA
<213> ORGANISM: Coccidioides posadasii rRNA gene

<400> SEQUENCE: 83

```
atttagagga agtaaaagtc gtaacaaggt ttccgtaggt gaacctgcgg aaggatcatt     60
aaagtggcgt ccggctgcgc acctcccccg cgggggttcg cgcggtccgt acctcccacc    120
cgtgtttact gaaccattgt tgccttggca ggcctgccgg gcctccggct gccggggatc    180
gcccgtcttg cgcggcgtcc cgggcgcgcg cctgccagcg gatcaattga actcttatgt    240
gaagattgtc agtctgagca tcatagcaaa aatcaaacaa aactttcaac aacggatctc    300
ttggttccgg catcgatgaa gaacgcagcg aaatgcgata agtaatgtga attgcagaat    360
tccgtgaatc atcgaatctt tgaacgcaca ttgcgccctc tggtattccg gggggcatgc    420
ctgttcgagc gtcattgcaa acccttcaag cacggcttgt gtgttgggcc aacgtccccg    480
cttgtgtgga cgggcctgaa atgcagtggc ggcaccgagt tcctggtgtc tgagtgtatg    540
ggaaatcact tcatcgctca aagacccgat cggggccgat ctcttttttt tattatatcc    600
ggtttgacct cggatcaggt aggagtaccc gctgaactta agcatatcaa taagcggagg    660
aaaagaaacc aacagggatt gcctcagtaa cggcgagtga agcggcaaaa gctcaaattt    720
gaaatctggc tccatgcgga gcccgagttg taatttggag aggacacttc gggtgcggcc    780
acggcataag ttccttggaa caggacgtca tagagggtga gaatcccgtc tttggctgct    840
ggaccgcgcc catgcgaagt tccttcgacg agtcgagttg tttgggaatg cagctctaag    900
tgggtggtaa atttcatcta aagctaaata ttggccggag accgatagcg cacaagtaga    960
gtgatcgaaa ggttaaaagc accttgaaaa gggagttaaa tagcacgtga aattgttgaa   1020
agggaagcgc ttgcaaccag actcggtcgt gggggctcag cgggcatgcg tgcccgtgta   1080
```

```
ctcccccatg ctccgggcca gcatcagttc tggcggttgg ttaaaggcct ctggaatgta    1140
tcgtcctccg ggacgtctta tagccagggg cgcaatgcgg ccagccggga ctgaggaacg    1200
cgcttcggca cggatgctgg cataatggtt gtaagcggcc cgtcttgaaa cacggaccaa    1260
ggagtctaac atccacgcga gtgttcgggt gtcaaacccg tgcgcgcagt gaaagcgaac    1320
ggaggtggga gcccgcaagg gtgcaccatc gaccgatcct gaagtcttcg gatggatttg    1380
agtaagagcg tggctgttgg gacccgaaag atggtgaact atgcctgaat agggtgaagc    1440
cagaggaaac tctggtggag gctcgcagcg gttctgacgt gcaaatcgat cgtcaaattt    1500
gggtataggg gcgaaagact aatcgaacca tctggtagct ggttcctgcc gaagtttccc    1560
tcaggatagc agtaacgttt tcagttttat gaggtaaagc gaatgattag aggccttggg    1620
gttgaaacaa ccttaaccta ttctcaaact ttaaatatgt aagaagccct tgttacttaa    1680
gtgaacgtgg gcattagaat ggatcgttac tagtgggcca tttttggtaa gcagaactgg    1740
cgatgcggga tgaaccgaac gcgaggttaa ggtgccggaa tgcacgctca tcagacacca    1800 caaaggtgt tagttcatct agacagcccg acggtggcca tggaagtcgg aatccgctaa     1860
ggagtgtgta acaactcacg ggccgaatga actagccctg aaaatggatg gcgctcaagc    1920
gtgctaccca tacctcgccg tcggggtaga aacgaagccc cgacgagtag gcaggcgtgg    1980
aggtttgtga cgaagccttg ggagtgatcc cgggtcgaac agcctctagt gcagatcttg    2040
gtggtagtag caaatactca aatgagaact ttgaggactg aagtggggaa aggttccatg    2100
tgaacagcag ttggacatgg gttagtcgat cctaagacat agggtagttc cgtttgaaag    2160
cgcgccctag tgcgccgttt gtcgaaaggg aagccggtta atattccggc acctggatgt    2220
ggattctcca cggcaacgta actgaacgcg gagacgtcgg caggagtcct gggaagagtt    2280
ctcttttctt cttgacggcc tatcaccctg aaatcggttt gtccggagct agggtttcat    2340
ggccggcaga gccccgcacc tttgcggggt ccggtgcgct cctgacgacc cttgaaaatc    2400
cgcgggaagg aatagttttc acgccaggtc gtactcataa ccgcagcagg tctccaaggt    2460
gaaaagcctc tagttgatag aacaatgtag ataaggaag tcggcaaaat agatccgtaa     2520
cttcgggaaa aggattggct ctaagggtcg ggcgcgttgg gccttggggg aaagcctccg    2580
gagcaggagg gcactagccg ggcaaccggc gggcgccttc cagcatcggg gtgcggacgc    2640
ccttggcagg cttcggccgt ccggcgcgcg attaacgacc aacttagaac tggtacggac    2700
aaggggaatc tgactgtcta attaaaacat agcattgcga tggccagaaa gtggtgttga    2760
cgcaatgtga tttctgccca gtgctctgaa tgtcaaagtg aagaaattca accaagcgcg    2820
ggtaaacggc gggagtaact atgactctct taaggtagcc aaatgcctcg tcatctaatt    2880
agtgacgcgc atgaatggat taacgagatt cccactgtcc ctatctacta tctagcgaaa    2940
ccacagccaa gggaacgggc ttggcaaaat cagcgggaa agaagaccct gttgagcttg     3000
actctagttt gacattgtga aaagacatat cgggtgtaga ataggtggga gcttcggcgc    3060
cggtgaaata ccactacctt tattgttttt ttacttattc aatgaagcgg aactgggctt    3120
taccgcccaa cttctagcgt taaggtcctt cgcgggctga tccggttgaa gacattgtc    3180 aggtggggag tttggctggg gcggcacatc tgttaaacca taacgcaggt gtcctaaggg    3240
ggactcatgg agaacagaaa tctccagtag aacaaagggg taaaagtccc cttgattttg    3300
attttcagtg tgaatacaaa ccatgaaagt gtggcctatc gatcctttag tccctcgaaa    3360
tttgaggcta gaggtgccag aaaagttacc acagggataa ctggcttgtg gcagccaagc    3420
```

| | |
|---|---|
| gttcatagcg acgttgctttt tgatccttc gatgtcggct cttcctatca taccgaagca | 3480 |
| gaattcggta agcgttggat tgttcaccca ctaataggga acgtgagctg ggtttagacc | 3540 |
| gtcgtgagac aggttagttt taccctactg atgaaggtcg ccgcaacggt aattcaattt | 3600 |
| agtacgagag gaaccgttga ttcagataat tggttttttgc ggctgtctga ccaggcagtg | 3660 |
| ccgcgaagct accatctgcc ggattatggc tgaacgcctc taagtcagaa tccgtaccgg | 3720 |
| aacgcggcga tgttgccccg cacgttgtag ttggatacga ataggcctac gggccctgaa | 3780 |
| cctcagcagg tcggcgacgg ctcccgggaa gagactctcg ggcgccagct gacggattgc | 3840 |
| aatgtcacca cgcgcgggga tagatcctct gcagacgact gaaatgacca agcgggtcgt | 3900 |
| gtaagcggtc gagtagccta gttgttacga gtcgctgagc gtcagcccga tccttggctc | 3960 |
| gatttgttgt aaacaccctc c | 3981 |

<210> SEQ ID NO 84
<211> LENGTH: 3927
<212> TYPE: DNA
<213> ORGANISM: Cryptococcus neoformans rRNA gene

<400> SEQUENCE: 84

| | |
|---|---|
| agaggaagta aaagtcgtaa caaggttttcc gtaggtgaac ctgcggaagg atcagtagag | 60 |
| aatattggac tttggtccat ttatctaccc atctacacct gtgaactgtt tatgtgcttc | 120 |
| ggcacgtttt acacaaactt ctaaatgtaa tgaatgtaat catattataa caataataaa | 180 |
| actttcaaca acggatctct tggcttccac atcgatgaag aacgcagcga aatgcgataa | 240 |
| gtaatgtgaa ttgcagaatt cagtgaatca tcgagtcttt gaacgcaact tgcgcccttt | 300 |
| ggtattccga agggcatgcc tgtttgagag tcatgaaaat ctcaatccct cgggttttat | 360 |
| tacctgttgg acttggatttt gggtgtttgc cgcgacctgc aaaggacgtc ggctcgcctt | 420 |
| aaatgtgtta gtgggaaggt gattacctgt cagcccggcg taataagttt cgctgggcct | 480 |
| atggggtagt cttcggcttg ctgataacaa ccatctcttt ttgtttgacc tcaaatcagg | 540 |
| tagggctacc cgctgaactt aagcatatca ataagcggag gaaaagaaac taacaaggat | 600 |
| tcccttagta acggcgagtg aaccgggaag agctcaaatt tgaaatctgg cgtcctccgg | 660 |
| gcgtccgagt tgtaatctac agaaacgttt tccgtgctgg accgtgtcta agtcccttgg | 720 |
| aatagggtat caaagagggt gacaatcccg tacttgacac gatcaccagt gctctgtgat | 780 |
| acgttttcta cgagtcgcgt tacttgggag tgtagcgcaa aatgggtggt aaactccatc | 840 |
| taaagctaaa tattggtgga agaccgatag cgaacaagta ccgtgaggga agatgaaaa | 900 |
| gcactttgga aagagagtta aacagtacgt gaaattgttg aaagggaaac gattgaagtc | 960 |
| agtcgtgtct attgggttca gccagttctg ctggtgtatt cccttagac gggtcaacat | 1020 |
| cagttctgat cggtggataa gggctggagg aatgtggcac tcttcggggt gtgttatagc | 1080 |
| ctcctgtcgc atacactggt tgggactgag gaatgcagct cgcctttatg gccgggttc | 1140 |
| gcccacgttc gagcttagga tgttgacaaa atggctttaa cgacccgtc ttgaaacacg | 1200 |
| gaccaaggag tctaacatat ctgcgagtgt tgagtgtca aactcgagcg cgaaatgaaa | 1260 |
| gtgaatgtag gagggatccg caaggagcac cttcgaccga tccggatctt ctgtgatgga | 1320 |
| tttgagtaag agcatatatg ctgggacccg aaagatggtg aactatgcct gaataggcg | 1380 |
| aagccagggg aaactctggt ggaggctcgt agcgattctg acgtgcaaat cgatcgtcga | 1440 |
| atttgggtat aggggcgaaa gactaatcga accatctagt agctggttcc tgccgaagtt | 1500 |
| tccctcagga tagcagaaac tcgcatcagt tttatgaggt aaagcgaatg attagaggcc | 1560 |

```
ttggggacga aacgtcctta acctattctc aaactttaaa tgtgtaagaa gcacttgtca   1620
cttaattgga cgagcgcatg cgaatgagag tttctagtgg gccattttg gtaagcagaa    1680
ctggcgatgc gggatgaacc gatcgtgagg ttaaggtgcc ggaatacacg ctcatcagac   1740
accacaaaag gtgttagttc atctagacag caggacggtg gccatggaag tcggaatccg   1800
ctaaggagtg tgtaacaact cacctgccga atgaactagc cctgaaaatg gatggcgctc   1860
aagcgtgtta cccatacctc accgtcagcg ttgtagtgac gcgctgacga gtaggcaggc   1920
gtggaggtca gtgtagaagc ctaggcagtg atgtcgggtg gaacggcctc tagtgcagat   1980
cttggtggta gtagcaaata ttcaagtgag aaccttgaag actgaagtgg agaaaggttc   2040
catggtaaca gcagttggac atgggtcagt cgatcctaag agatagggaa actccgtttt   2100
aaagcgcacg attttccgtg ccgcctatcg aaagggaatc cggttaagat tccgaaccca   2160
ggatgtggat cattgacggt aacgtaaatg aagttggaga cgtcggcaag ggccctggga   2220
agagttctct tttctcctta accgcctacg acctcgaaat cggattatcc ggagctgagg   2280
ttatatggtg ggtaaagcac aacacctctg ttgtgtccgg tgcgtccttg acgatccttg   2340
aaaatccgac ggaacgtata agtctcacgc ctggtcgtac tcataaccgc agcaggtctc   2400
caaggtgaac agcctctagt tgatggaaca atgtagataa gggaagtcgg caaaatagat   2460
ccgtaacttc gggataagga ttggctctaa ggggttgggtg cgtcgggccg ttgacggaag   2520
gaagctggac ctggcgggac tgcatggggc aacctgtgtg gacctgctgg gatcggcgac   2580
tggaagtctt tggcagccct cgggcgtccg gcgtacgctt aacaaccaac ttagaactgg   2640
tacggacaag gggaatctga ctgtctaatt aaaacatagc attgcgatgg ccagaaaatg   2700
gtgttgacgc aatgtgattt ctgcccagtg ctctgaatgt caaagtgaag aaattcaacc   2760
aagcgcgggt aaacggcggg agtaactatg actctcttaa ggtagccaaa tgcctcgtca   2820
tctaattagt gacgcgcatg aatggattaa cgagattccc actgtccta tctactatct    2880
agcgaaacca cagccaaggg aacgggcttg gcagaatcag cggggaaaga agaccctgtt   2940
gagcttgact ctagtttgac attgtgaaaa gacatggagg gtgtagaata agtgggagct   3000
tcggcgccgg tgaaatacca ctacctccat cgttttttta cttattcaat gaagcggagc   3060
tgggatgaaa gtcccacctt ctagcgttaa ggtcgtttac cggccgatcc gggttgaaga   3120
cattgtcagg tggggagttt ggctgggcg gcacatctgt taaaaataa cgcaggtgtc    3180
ctaaggggga ctcatggaga acagaaatct ccagtggaac aaaagggtaa aagtcccctt   3240
gatttttgatt tcagtgtga atacaaacca tgaaagtgtg gcctatcgat cctttagtcc    3300
ctcggagttt gaggctagag gtgccagaaa agttaccaca gggataactg gcttgtggca   3360
gccaagcgtt catagcgacg ttgctttttg atccttcgat gtcggctctt cctatcatac   3420
cgaagcagaa ttcggtaagc gttggattgt tcacccacta atagggaacg tgagctgggt   3480
ttagaccgtc gtgagacagg ttagttttac cctactgatg gagtgtcgtc gtaatagtaa   3540
ttgagggtag tacgagagga actgctcatt cgtataattg gtatttgcgt ctgtccgatc   3600
gggcaatgac gcgaagctat catacgccag attatggctg aacgcctcta agtcagaatc   3660
tgtactagaa acgacgattt tggtcccgca catgttagtt gtgtttaaat aggcttcggc   3720
tgtgaaccat atctgagggt tgggctgctt aggcggaaag gcttaggtag tctccttcgt   3780
attgaaatgg aatatgggcg ggggtaaatc ctttgcagac gacttgaatg gaacggggt    3840
gctgtaagtg gtagagtagc cttgttgcta cgatccactg aggctaagcc cttgttctat   3900
```
agatttgtct ctaacatgtt gggtctc  3927

<210> SEQ ID NO 85
<211> LENGTH: 3911
<212> TYPE: DNA
<213> ORGANISM: Fusarium graminearum rRNA gene

<400> SEQUENCE: 85

| | |
|---|---|
| cggaaagctc tccaaactcg gtcatttaga ggaagtaaaa gtcgtaacaa ggtctccgtt | 60 |
| ggtgaaccag cggagggatc attaccgagt ttacaactcc caaaccctg tgaacatacc | 120 |
| ttatgttgcc tcggcggatc agcccgcgcc ccgtaaaaag ggacggcccg ccgcaggaac | 180 |
| cctaaactct gtttttagtg gaacttctga gtataaaaaa caaataaatc aaaactttca | 240 |
| acaacggatc tcttggttct ggcatcgatg aagaacgcag caaaatgcga taagtaatgt | 300 |
| gaattgcaga attcagtgaa tcatcgaatc tttgaacgca cattgcgccc gccagtattc | 360 |
| tggcgggcat gcctgttcga gcgtcatttc aaccctcaag cccagcttgg tgttgggagc | 420 |
| tgcagtcctg ctgcactccc caaatacatt ggcggtcacg tcgagcttcc atagcgtagt | 480 |
| aatttacaca tcgttactgg taatcgtcgc ggccacgccg ttaaacccca acttctgaat | 540 |
| gttgacctcg gatcaggtag gaataccgc tgaacttaag catatcaata agcggaggaa | 600 |
| aagaaaccaa cagggattgc cctagtaacg gcgagtgaag cggcaacagc tcaaatttga | 660 |
| aatctggctt tcgggcccga gttgtaattt gtagaggatg attttgatgc ggtgccttcc | 720 |
| gagttccctg gaacgggacg ccatagaggg tgagagcccc gtctggttgg atgccaaatc | 780 |
| tctgtaaatc tccttcgacg agtcgagtag tttgggaatg ctgctctaaa tgggaggtat | 840 |
| atgtcttcta aagctaaata ccggccagag accgatagcg cacaagtaga gtgatcgaaa | 900 |
| gatgaaaagc actttgaaaa gagagttaaa aagtacgtga aattgttgaa agggaagcgt | 960 |
| ttatgaccag acttgggctt ggttaatcat ctggggttct ctccagtgca cttttccagt | 1020 |
| ccaggccagc atcagttttc gccggggat aaaggcttcg ggaatgtggc tcccctcggg | 1080 |
| gagtgttata gcccgttgtg taatacctg gtggggactg aggttcgcgc ttctgcaagg | 1140 |
| atgctggcgt aatggtcatc aacgacccgt cttgaaacac ggaccaagga gtcgtcttcg | 1200 |
| tatgcgagtg ttcgggtgtc aaaccctac gcgtaatgaa agtgaacgca ggtgagagct | 1260 |
| tcggcgcatc atcgaccgat cctgatgttc tcggatggat ttgagtaaga gcatacgggg | 1320 |
| ccggacccga aagaaggtga actatgcctg tgtagggtga agccagagga aactctggtg | 1380 |
| gaggctcgca gcggttctga cgtgcaaatc gatcgtcaaa catgggcatg ggggcgaaag | 1440 |
| actaatcgaa ccttctagta gctggtttcc gccgaagttt ccctcaggat agcagtgttg | 1500 |
| aactcagttt tatgaggtaa agcgaatgat tagggactcg ggggcgctat ttagccttca | 1560 |
| tccattctca aactttaaat atgtaagaag ctcttgttgc ttaattgaac gtgagcattc | 1620 |
| gaatgtatca acactagtgg gccatttttg gtaagcagaa ctggcgatgc gggatgaacc | 1680 |
| gaacgcgagg ttaaggtgcc agagtagacg ctcatcagac accacaaaag gtgttagtac | 1740 |
| atcttgacag caggacggtg gccatggaag tcggaatccg ctaaggactg tgtaacaact | 1800 |
| cacctgccga atgtactagc cctgaaaatg gatggcgctc aagcgtctca cccataccct | 1860 |
| gccctcaggg tagaaacgaa gccctgagga gtaggcggac gtggaggtca gtgacgaagc | 1920 |
| ctagggcgtg agcccgggtt gaacggcctc tagtgcagat cttggtggta gtagcaaata | 1980 |
| cttcaatgag aacttgaagg accgaagtgg ggaaaggttc catgtgaaca gcggttggac | 2040 |
| atgggttagt cgatcctaag ctatagggaa gttccgtttc aaaggcgcac tttgcgccgt | 2100 |

```
ctagcgaaag gggagccggt caatattccg gcacctggat gtgggttttg cgcggcaacg    2160
caactgaacg tggagacgac ggcgggggcc ccaagcagag ttctcttttc ttcttaacag    2220
tctctcaccc tgaaatcggt ttgtccggag ctagggttta atggctggaa gagcccggca    2280
cctctgccgg gtttggtgcg ctctcgacgt cccttgaaaa tccacgggaa gaaataattc    2340
tcacgccagg tcgtactcat aaccgcagca ggtctccaag gtgaacagcc tctggttgat    2400
agaacaatgt agataaggga agtcggcaaa atagatccgt aacttcggga aaaggattgg    2460
ctctaagggt tgggcacgtt gggccttggg cggacgtcct gggagcaggc agccactagt    2520
cgggcaaccg accggaggcg gccagcatcc gggtgctgat gcccttggca ggcttcggcc    2580
gtccggcgtg cggttaacaa ccaacttaga actggtacgg acaaggggaa tctgactgtc    2640
taattaaaac atagcattgc gatggccaga agtggtgtt gacgcaatgt gatttctgcc     2700
cagtgctctg aatgtcaaag tgaagtaatt caaccaagcg cgggtaaacg gcgggagtaa    2760
ctatgactct cttaaggtag ccaaatgcct cgtcatctaa ttagtgacgc gcatgaatgg    2820
attaacgaga ttcccactgt ccctatctac tatctagcga aaccacagcc aagggaacgg    2880
gcttggcaga atcagcgggg aaagaagacc ctgttgagct tgactctagt ttgacattgt    2940
gaaaagacat aggaggtgta gaataggtgg gagcttcggc gccggtgaaa taccactact    3000
cctattgttt ttttacttat tcaatgaagc ggggctggat ttacgtccaa cttctggttt    3060
taaggtcctt cgcgggccga cccgggttga agacattgtc aggtggggag tttggctggg    3120
gcggcacatc tgttaaacca taacgcaggt gtcctaaggg gggctcatgg agaacagaaa    3180
tctccagtag aacaaaaggg taaaagtccc cttgattttg attttcagtg tgaatacaaa    3240
ccatgaaagt gtggcctatc gatcctttag tccctcgaca tttgaggcta gaggtgccag    3300
aaaagttacc acagggataa ctggcttgtg gcggccaagc gttcatagcg acgtcgcttt    3360
ttgatccttc gatgtcggct cttcctatca taccgaagca gaattcggta agcgttggat    3420
tgttcaccca ctaatagggga acgtgagctg ggtttagacc gtcgtgagac aggttagttt    3480
taccctactg atgacctcac cgcaatggta attcagctta gtacgagagg aaccgctgat    3540
tcagataatt ggttttttgcg gctgtccgac cgggcagtgc cgcgaagcta ccatctgctg    3600
gataatggct gaacgcctct aagtcagaat ccatgccaga acgcggtgat accacccgca    3660
cgtatagatg gacaagaata ggcctcggct tagcgtctta gcaggcgatt cctccacggc    3720
gctcgaagcg cgtcgtggta tttcgcgtat tgtaatttca acacgagcgg ggtcaaatcc    3780
tttgcagaca acttagctgt gcgaaacggt cctgtaagca gtagagtagc cttgttgtta    3840
cgatctgctg agggtaagcc gtccttcgcc tcgatttccc caacgatgac tctcgcaggg    3900
cgagggcgtg g                                                        3911
```

<210> SEQ ID NO 86
<211> LENGTH: 3911
<212> TYPE: DNA
<213> ORGANISM: Fusarium oxysporum rRNA gene

<400> SEQUENCE: 86

```
gccggaaagc tctccaaact cggtcattta gaggaagtaa aagtcgtaac aaggtctccg      60
ttggtgaacc agcggaggga tcattaccga gtttacaact cccaaacccc tgtgaacata     120
ccacttgttg cctcggcgga tcagcccgct cccggtaaaa cgggacggcc cgccagagga     180
cccctaaact ctgtttctat atgtaacttc tgagtaaaac cataaataaa tcaaaacttt     240
```

```
caacaacgga tctcttggtt ctggcatcga tgaagaacgc agcaaaatgc gataagtaat    300
gtgaattgca gaattcagtg aatcatcgaa tctttgaacg cacattgcgc ctgccagtat    360
tctggcgggc atgcctgttc gagcgtcatt tcaaccctca agcacagctt ggtgttggga    420
ctcgcgttaa ttcgcgttcc ccaaattgat tggcggtcac gtcgagcttc catagcgtag    480
tagtaaaacc ctcgttactg gtaatcgtcg cggccacgcc gttaaacccc aacttctgaa    540
tgttgacctc ggatcaggta ggaatacccg ctgaacttaa gcatatcaat aagcggagga    600
aaagaaacca acagggattg ccctagtaac ggcgagtgaa gcggcaacag ctcaaatttg    660
aaatctggct ctcgggcccg agttgtaatt tgtagaggat acttttgatg cggtgccttc    720
cgagttccct ggaacgggac gccatagagg gtgagagccc cgtctggttg gatgccaaat    780
ctctgtaaag ttccttcaac gagtcgagta gtttgggaat gctgctctaa atggaggta    840 tatgtcttct aaagctaaat accggccaga gaccgatagc gcacaagtag agtgatcgaa    900
agatgaaaag cactttgaaa agagagttaa aaagtacgtg aaattgttga agggaagcg    960 tttatgacca gacttgggct tggttaatca tctgggttc tccccagtgc acttttccag   1020
tccaggccag catcagtttt ccccggggga taaaggcggc gggaatgtgg ctctcttcgg   1080
ggagtgttat agcccaccgt gtaatacct gggggggact gaggttcgcg catctgcaag   1140
gatgctggcg taatggtcat caacgacccg tcttgaaaca cggaccaagg agtcgtcttc   1200
gtatgcgagt gttcgggtgt caaacccta cgcgtaatga aagtgaacgc aggtgagagc   1260
ttcggcgcat catcgaccga tcctgatgtt ctcggatgga tttgagtaag agcatacggg   1320 gccgacccg aaagaaggtg aactatgcct gtataggtg aagccagagg aaactctggt   1380
ggaggctcgc agcggttctg acgtgcaaat cgatcgtcaa atatgggcat gggggcgaaa   1440
gactaatcga accttctagt agctggtttc cgccgaagtt ccctcagga tagcagtgtt   1500 gaactcagtt ttatgaggta agcgaatga ttagggactc gggggcgcta tttagccttc   1560
atccattctc aaactttaaa tatgtaagaa gctcttgttg cttaattgaa cgtgagcatt   1620
cgaatgtatc aacactagtg ggccattttt ggtaagcaga actggcgatg cgggatgaac   1680
cgaacgcgag gttaaggtgc cagagtagac gctcatcaga caccacaaaa ggtgttagta   1740
catcttgaca gcaggacggt ggccatggaa gtcggaatcc gctaaggact gtgtaacaac   1800
tcacctgccg aatgtactag ccctgaaaat ggatggcgct caagcgtctc acccatacct   1860
cgccctcagg gtagaaacga tgccctgagg agtaggcgga cgtggaggtc agtgacgaag   1920
cctagggcgt gagcccgggt tgaacggcct ctagtgcaga tcttggtggt agtagcaaat   1980
acttcaatga gaacttgaag gaccgaagtg gggaaaggtt ccatgtgaac agcggttgga   2040
catgggttag tcgatcctaa gccataggga agttccgttt caaggtgca ctttgcaccg   2100 tctggcgaaa gggaagccgg tcaatattcc ggcacctgga tgtgggtttt gcgcggcaac   2160
gcaactgaac gtggagacga cggcggggc cccgggcaga gttctctttt cttcttaaca   2220
gtctctcacc ctgaaatcgg tttgtccgga gctagggttt aatggctgga agagcccagc   2280
acctctgctg ggtccggtgc gctctcgacg tcccttgaaa atccacggga ggaaataatt   2340
ctcacgccag tcgtactca taaccgcagc aggtctccaa ggtgaacagc ctctggttga   2400
tagaacaatg tagataaggg aagtcggcaa aatagatccg taacttcggg ataaggattg   2460
gctctaaggg ttgggcacgt tgggccttgg gcggacgcct tgggagcagg ctgccactag   2520
tcgggcaacc gaccggcggc ggccagcatc cgagtgttga tgcccttggc aggcttcggc   2580
cgtccggcgt gcggttaaca accaacttag aactggtacg gacaagggga atctgactgt   2640
```

```
ctaattaaaa catagcattg cgatggccag aaagtggtgt tgacgcaatg tgatttctgc   2700
ccagtgctct gaatgtcaaa gtgaagtaat tcaaccaagc gcgggtaaac ggcgggagta   2760
actatgactc tcttaaggta gccaaatgcc tcgtcatcta attagtgacg cgcatgaatg   2820
gattaacgag attcccactg tccctatcta ctatctagcg aaaccacagc caagggaacg   2880
ggcttggcag aatcagcggg gaaagaagac cctgttgagc ttgactctag tttgacattg   2940
tgaaaagaca taggaggtgt agaataggtg ggagcttcgg cgccggtgaa ataccactac   3000
tcctattgtt tttttactta ttcaatgaag cggcgctgga tttacgtcca acttctggtt   3060
ttaaggtcct tcgcgggccg agccgggttg aagacattgt caggtgggga gtttggctgg   3120
ggcggcacat ctgttaaacc ataacgcagg tgtcctaagg ggggctcatg gagaacagaa   3180
atctccagta gaacaaaagg gtaaaagtcc ccttgatttt gattttcagt gtgaatacaa   3240
accatgaaag tgtggcctat cgatccttta gtccctcgac atttgaggct agaggtgcca   3300
gaaaagttac cacagggata actggcttgt ggcggccaag cgttcatagc gacgtcgctt   3360
tttgatcctt cgatgtcggc tcttcctatc ataccgaagc agaattcggt aagcgttgga   3420
ttgttcaccc actaataggg aacgtgagct gggtttagac cgtcgtgaga caggttagtt   3480
ttaccctact gatgacctca ccgcaatggt aattgagctt agtacgagag gaaccgctca   3540
ttcagataat tggtttttgc ggctgtccga ccgggcagtg ccgcgaagct accatctgct   3600
ggataatggc tgaacgcctc taagtcagaa tccatgccag aacgcggtga taccacccgc   3660
acgtatagat ggacaagaat aggcttcggc ttagcgtctt agcaggcgat tcttccacgg   3720
cgctcgaagc gcgtcgtggt atttcgcgta ttgtaatttc aacacgagcg ggtcaaatc    3780
ctttgcagac gacttagctg tgcgaaacgg tcctgtaagc agtagagtag ccttgttgtt   3840
acgatctgct gagggtaagc cgtccttcgc ctcgatttcc ccaatgggtt ctccggattt   3900
ctggagactt g                                                        3911
```

<210> SEQ ID NO 87
<211> LENGTH: 3983
<212> TYPE: DNA
<213> ORGANISM: Histoplasma capsulatum rRNA gene

<400> SEQUENCE: 87

```
ggtcatttag aggaagtaaa agtcgtaaca aggtttccgt aggtgaacct gcggaaggat     60
cattaccacg ccgtgggggg ctgggagcct ctgaccggga cccctccgcc ctcctacccg    120
gccacccttg tctaccggac ctgttgcctc ggcggtcctg cagcgatgct gccgggggag    180
cttctcctcc ccgggcccgt gtccgccggg gacaccgcaa gaaccgtcgg tgaatgattg    240
gcgtctgagc atgagagcga taataatcca gtcaaaactt tcaacaacgg atctcttggt    300
tccgacatcg atgaagaacg cagcgaaatg cgataagtaa tgtgaattgc agaattccgt    360
gaatcatcga atctttgaac gcacattgcg ccccctggta ttccgggggg catgcctgtc    420
cgagcgtcat tgcaaccctc aagcgcggct tgtgtgttgg gccatcgtcc ccctgaccgg    480
tgggacgtgc ccgaaatgca gtggcggtgt cgagttccgg tgcccgagtg tatggggctt    540
tgccacccgc tctggaggcc cggccggctc cggcccacca tctcaacctc ctttttcaca    600
ccaggttgac ctcggatcag gtagggatac ccgctgaact taagcatatc aataagcgga    660
ggaaaagaaa ccaacaggga ttgcctcagt aacggcgagt gaagcggcaa gagctcaaat    720
ttgaaatccg gcccctctgg gggcctgagt tgtaatttgc agaggatgct tcgggcgcga    780
```

```
ccgcggtcca agtcccctgg aacggggcgt cgtagagggt gagaatcccg tctccggccg    840
gccggtctcg cccgtgtgaa gctccttcga cgagtcgagt tgtttgggaa tgcagctcta    900
aatgggtggt aaatttcatc taaagctaaa tactggtcgg agaccgatag cgcacaagta    960
gagtgatcga agatgaaaa gcactttgaa aagagagtta aacagcatgt gaaattgttg    1020
aaagggaagc gcttgcgatc agagtcggcc gcggggttc agcgggcatt cgttgcccgt    1080
gcaatccccc gcggccgggc cagcgtcggt ttcgacggcc ggtcaaaggc ccccggaatg    1140
tgtcgcctct cggggcgtct tatagccggg ggtgcaatgc ggccagtcgg gaccgaggaa    1200
cgcgctccgg cacggacgct ggcttaatgg tcgtcagcga cccgtcttga aacacggacc    1260
aaggagtcta acatccacgc gagtgttcgg gtgtcaaacc cgtccgcgca gtgaaagcga    1320
atggaggtgg gaaccctga gggtgcacca tcgaccgatc ctgaagtttt cggatggatt    1380
tgagtaggag cgtggctgtt gggacccgaa agatggtgaa ctatgcctga atagggtgaa    1440
gccagaggaa actctggtgg aggctcgcag cggttctgac gtgcaaatcg atcgtcaaat    1500
ttgggtatag gggcgaaaga ctaatcgaac catctggtag ctggttcctg ccgaagtttc    1560
cctcaggata gcagtaacgt tttcagtttt atgaggtaaa gcgaatgatt agaggccttg    1620
gggttgaaac aaccttaacc tattctcaaa ctttaaatat gtaagaagcc cttgttactt    1680
cgttgaacgt gggcactgga atggatcgtt actagtgggc cattttggt aagcagaact    1740
ggcgatgcgg gatgaaccga acgcgaggtt aaggtgccgg aatgcacgct catcagacac    1800
cacaaaaggt gttagttcat ctagacagcc cgacggtggc catggaagtc ggaatccgct    1860
aaggagtgtg taacaactca cgggccgaat gaactagccc tgaaaatgga tggcgctcaa    1920
gcgtgctacc catacctcgc cgtcggggta ggatcgatgc cccgacgagt aggcaggcgt    1980
ggaggtccgt gacgaagccc ggggagtgat cccgggtcga acggcctcta gtgcagatct    2040
tggtggtagt agcaaatact caaatgagaa ctttgaggac tgaagtgggg aaaggttcca    2100
tgtgaacagc agttggacat gggttagtcg atcctaagac atagggaaat tccgtttgaa    2160
agcgcgccct cgtgcgccgt ccgtcgaaag ggaagccggt taacattccg gcacctggat    2220
gtggattctc cacggcaacg taactgaacg cggagacgtc ggcggggtc ctgggaagag    2280
ttctcttttc ttcttgacgg cctgtcaccc tgaaatcggt ttgtccggag ctagggttca    2340
atggccggca gagcccgca ccttttgcggg gtccggtgcg cccccgacga cccttgaaaa    2400
tccgcgggag ggaatagttt tcacgccagg tcgtactcat aaccgcagca ggtctccaag    2460
gtgaaaagcc tctagttgat agaacaatgt agataaggga agtcggcaaa atagatccgt    2520
aacttcggga aaaggattgg ctctaagggt tgggcacgtt gggccttggg cggagacctc    2580
tggagcaggg gggcactagc cgggcaaccg gtgggggccc tccagcatcg gggcgtggac    2640
gccctcggca ggcttcggcc gtccggcgtg cgattaacaa ccgacttaga actggtacgg    2700
acaaggggaa tctgactgtc taattaaaac atagcattgc gatggccaga agtggtgtt    2760
gacgcaatgt gatttctgcc cagtgctctg aatgtcaaag tgaagaaatt caaccaagcg    2820
cgggtaaacg gcgggagtaa ctatgactct cttaaggtag ccaaatgcct cgtcatctaa    2880
ttagtgacgc gcatgaatgg attaacgaga ttcccactgt ccctatctac tatctagcga    2940
aaccacagcc aagggaacgg gcttggcgga atcagcgggg aaagaagacc ctgttgagct    3000
tgactctagt ttgacattgt gaaaagacat atcgggtgta gaataggtgg gagcttcggc    3060
gccggtgaaa taccactacc tttatcgttt ttttacttat tcaatgaagc ggaactgggc    3120
ttcaccgccc aacttctggc gttaaggtcc ctcgcggacc gatccgggtt gaagacattg    3180
```

-continued

```
tcaggtgggg agtttggctg gggcggcaca tctgttaaac cataacgcag gtgtcctaag    3240
ggggactcat ggagaacaga aatctccagt agaacaaaag ggtaaaagtc cccttgattt    3300
tgattttcag tgtgaataca aaccatgaaa gtgtggccta tcgatccttt agtccctcga    3360
aatttgaggc tagaggtgcc agaaaagtta ccacagggga aactggcttg tggcagccaa    3420
gcgttcatag cgacgttgct ttttgatcct tcgatgtcgg ctcttcctat cataccgaag    3480
cagaattcgg taagcgttgg attgttcacc cactaatagg gaacgtgagc tgggtttaga    3540
ccgtcgtgag acaggttagt tttaccctac tgatgaaggt cgccgcaacg gtaattcaat    3600
ttagtacgag aggaaccgtt gattcagata attggttttt gcggctgtct gaccaggcag    3660
tgccgcgacg ctaccatctg ccggattatg gctgaacgcc tctaagtcag aatccgtgcc    3720
ggaacgcggc gatgtcgccc cgcacgtcgt agttggatac gaataggcct ccgggtccag    3780
aacctcagca ggccggcgat ggtgttccgg ggagagaccc ccggggaccc gccggcggat    3840
tgcaatgtca ccacgcgcgg ggatagatcc tctgcagacg actgaaatga ccaagcgggt    3900
cgtgtaagcg gtcaagtagc cttgttgcta cgagtcgctg agcgtcagcc cgatccttgg    3960
ctcgatttgt tgtaacaacc ccc                                            3983
```

<210> SEQ ID NO 88
<211> LENGTH: 3884
<212> TYPE: DNA
<213> ORGANISM: Hypocrea jecorina rRNA gene

<400> SEQUENCE: 88

```
tcggtcattt agaggaagta aaagtcgtaa caaggtctcc gttggtgaac cagcggaggg      60
atcattaccg agtttacaac tcccaaaccc caatgtgaac gttaccaatc tgttgcctcg     120
gcgggattct ctgccccggg cgcgtcgcag ccccggatcc catggcgccc gccggaggac     180
caactcaaac tctttttcct ctccgtcgcg gcttccgtcg cggctctgtt ttacctttgc     240
tctgagcctt tctcggcgac cctagcgggc gtctcgaaaa tgaatcaaaa ctttcaacaa     300
cggatctctt ggttctggca tcgatgaaga acgcagcgaa atgcgataag taatgtgaat     360
tgcagaattc agtgaatcat cgaatctttg aacgcacatt gcgcccgcca gtattctggc     420
gggcatgcct gtccgagcgt catttcaacc ctcgaacccc tccggggggt cggcgttggg     480
gatcggcccc tcaccgggcc gccccgaaa tacagtggcg gtctcgccgc agcctctcct     540
gcgcagtagt ttgcacactc gcaccgggag cgcggcgcgg ccacagccgt aaaacacccc     600
aaactctgaa atgttgacct cggatcaggt aggaataccc gctgaactta agcatatcaa     660
taagcggagg aaaagaaacc aacagggatt gccccagtaa cggcgagtga agcggcaaca     720
gctcaaattt gaaatctggc cctttcgggt ccgagttgta atttgtagag gatgcttttg     780
gcaaggcgcc gcccgagttc cctggaacgg gacgccacag agggtgagag ccccgtctgg     840
ctggccgccg agcctctgta aagctccttc gacgagtcga gtagtttggg aatgctgctc     900
aaaatgggag gtatatgtct tctaaagcta aatattggcc agagaccgat agcgcacaag     960
tagagtgatc gaaagatgaa aagcaccttg aaaagagggt taaatagtac gtgaaattgt    1020
tgaaagggaa gcgcttgtga ccagacttgg gcgcggcgga tcatccgggg ttctccccgg    1080
tgcacttcgc cgtgtccagg ccagcatcag ttcgtcgcgg gggaaaaagg cttcgggaac    1140
gtggctcccc tgggagtgtt atagcccgtt gcataatacc ctgcggtgga ctgaggaccg    1200
cgcatctgca aggatgctgg cgtaatggtc accagcgacc cgtcttgaaa cacggaccaa    1260
```

```
ggagtcgtct tcgtatgcga gtgttcgggt gtcaaacccc tacgcgtaat gaaagtgaac    1320
gcaggtgaga gcttcggcgc atcatcgacc gatcctgatg ttctcggatg gatttgagta    1380
agagcatacg gggccggacc cgaaagaagg tgaactatgc ctgtataggg tgaagccaga    1440
ggaaactctg gtggaggctc gcagcggttc tgacgtgcaa atcgatcgtc aaatatgggc    1500
atgggggcga aagactaatc gaaccttcta gtagctggtt tccgccgaag tttccctcag    1560
gatagcagtg ttgaactcag ttttatgagg taaagcgaat gattagggac ccggggcgc     1620 tatattgcct tcatccattc tcaaacttta aatatgtaag aagcccttgt tgcttaattg    1680
aacgtgggca ttcgaatgta tcaacactag tgggccatttt ttggtaagca gaactggcga   1740
tgcgggatga accgaacgcg aggttaaggt gccagagtag acgctcatca gacaccacaa    1800
aaggcgttag tacatcttga cagcaggacg gtggccatgg aagtcggaat ccgctaagga    1860
ctgtgtaaca actcacctgc cgaatgtact agccctgaaa atggatggcg ctcaagcgtc    1920
tcacccatac ctcgccctcg gggtagaaac gatgcccga  ggagtaggcg gacgtggagg    1980
tcgtgacgaa gcctagggcg tgagcccggg tcgaacggcc tctagtgcag atcttggtgg    2040
tagtagcaaa tacttcaatg agaacttgaa ggaccgaagt ggggaaaggt tccatgtgaa    2100
cagcggttgg acgtgggtta gtcgatccta agccataggg aagttccgtt tcaaaggcgc    2160
acttcgcgcc gtttggcgaa aggggagccg gtcaatattc cggcacctgg atgtgggttt    2220
tgcgcggcaa cgcaactgaa cgcggagacg acggcggggg ccccgggcag agttctcttt    2280
tcttcttaac agtctatcac cctgaaatcg gtttgtccgg agctagggtt taatggctgg    2340
aagagcccag cacctctgct gggtccggtg cgccctcgac gtcccttgaa atccgcggg     2400 aaggaataat tctcacgcca ggtcgtactc ataaccgcag caggtctcca aggtgaacag    2460
cctctggttg atagaacaat gtagataagg gaagtcggca aaatagatcc gtaacttcgg    2520
gataaggatt ggctctaagg gttgggcacg ttgggctttg gacggacgcc tcgggagcag    2580
gcggccacta gccgggcaac cggccggcgg ctgccagcat ctgggtgctg atgtcccttg    2640
caggcttcgg ccgtccggcg tgcggttaac aaccaactta gaactggtac ggacaagggg    2700
aatctgactg tctaattaaa acatagcatt gcgatggcca gaaagtggtg ttgacgcaat    2760
gtgatttctg cccagtgctc tgaatgtcaa agtgaagtaa ttcaaccaag cgcgggtaaa    2820
cggcgggagt aactatgact ctcttaaggt agccaaatgc ctcgtcatct aattagtgac    2880
gcgcatgaat ggattaacga gattcccact gtccctatct actatctagc gaaaccacag    2940
ccaagggaac gggcttggca gaatcagcgg ggaaagaaga ccctgttgag cttgactcta    3000
gtttgacatt gtgaaaagac ataggaggtg tagaataggt gggagcttcg gcgccggtga    3060
aataccacta ctcctattgt tttttttactt attcaatgaa gcggggctgg atttacgtcc    3120
aacttctggt attaaggtcc ttcgcgggcc gacccgggtt gaagacattg tcaggtgggg    3180
agtttggctg gggcggcaca tctgttaaac cataacgcag gtgtcctaag gggggctcat    3240
ggagaacaga aatctccagt agaacaaaag ggtaaaagtc cccttgattt tgattttcag    3300
tgtgaataca aaccatgaaa gtgtggccta tcgatccttt agtccctcga catttgaggc    3360
tagaggtgcc agaaaagtta ccacagggat aactggcttg tggcggccaa gcgttcatag    3420
cgacgtcgct ttttgatcct tcgatgtcgg ctcttcctat cataccgaag cagaattcgg    3480
taagcgttgg attgttcacc cactaatagg gaacgtgagc tgggtttaga ccgtcgtgag    3540
acaggttagt tttaccctac tgatgacctc accgcaatgg taattgagct tagtacgaga    3600
ggaaccgctc attcagataa ttggtttttg cggctgtccg accgggcagt gccgcgaagc    3660
```

-continued

```
taccatctgc tggataatgg ctgaacgcct ctaagtcaga atccatgcca gaacgcggtg    3720
atagcacccg cacgtataga cggacaagaa taggcttcgg cttagtgtct cagcaggcga    3780
ttcctccgcg gtcctcgaag cgggccgcgg tatttcgcgt attgtaattt caacacgagc    3840
ggggttaaat cctttgcaga cgacttagct gtgcgaaacg gtcc                     3884

<210> SEQ ID NO 89
<211> LENGTH: 3897
<212> TYPE: DNA
<213> ORGANISM: Lodderomyces elongisporus rRNA gene

<400> SEQUENCE: 89
tttagaggaa gtaaaagtcg taacaaggtt ccgtaggtg aacctgcgga aggatcatta      60
cagaattttg agaattgtgc ttaactgcac ttttcttatc tacacacgtg ttttttgtttt    120 attcttaaaa cttgctttgg cagtggctgc ttaattgctc tgctgccaga ggataaactc    180
aacctaaatt ttttatttta aactagtcaa ctgattatat ttattaatag tcaaaacttt    240
caacaacgga tctcttggtt ctcgcatcga tgaagaacgc agcgaaatgc gataagtaat    300
atgaattgca gatattcgtg aatcatcgaa tctttgaacg cacattgcgc cctctggtat    360
tccggagggc atgcctgttt gagcgtcatt tctccctcaa accccgggt ttggtgatga     420 gcaatacgcc aggtttgctt gaaagttagg aggagtattt ataacaatgt attaggtcta    480
accactccat tgtgcttaat aaaaagctcc aatctatatt tcaaacttcg acctcaaatc    540
aggtaggatt acccgctgaa cttaagcata tcaataagcg gaggaaaaga aaccaacagg    600
gattgcctta gtagcggcga gtgaagcggc aatagctcaa atttgaaatc tggcactttc    660
agtgtccgag ttgtaatttg aagaaggtat ctttgggtct agctcttgtc tatgtttctt    720
ggaacagaac gtcacagagg gtgagaatcc cgtgcgatga gatgtctaga tctatgtaaa    780
gttccttcga agagtcgagt tgtttgggaa tgcagctcta agtgggtggt aaattccatc    840
taaagctaaa taatggcgag agaccgatag cgaacaagta cagtgatgga agatgaaaa     900 gaactttgaa agagagtga aaaagtacgt gaaattgttg aaagggaagg gcttgagatc     960
agacttggta ttttgtatgt tactctctcg ggggtggcct ctacagttta ccgggccagc   1020
atcagtttga gcggtaggag aattgcgtag gaatgtggct cggcctcggt cgagtgttat   1080
agccttcgtc gatactgcca gcttagactg aggactgcgg cttcggccta ggatgttggc   1140
ataatgatct taagtcgccc gtcttgaaac acggaccaag gagtctaacg tctatgcgag   1200
tgtttgggtg taaaacccgt acgcgtaatg aaagtgaacg taggtaggac cttcttttga   1260
agcgcactat cgaccgatcc tgatgtcttc ggatggattt gagtaagagc atagctgttg   1320
ggacccgaaa gatggtgaac tatgcctgaa tagggtgaag ccagaggaaa ctctggtgga   1380
ggctcgtagc ggttctgacg tgcaaatcga tcgtcgaatt tgggtatagg ggcgaaagac   1440
taatcgaacc atctagtagc tggttcctgc gaagtttcc ctcaggatag cagaagctcg    1500
tatcagtttt atgaggtaaa gcgaatgatt agaagtcttg gggttgaaat gaccttaact   1560
tattctcaaa ctttaaatat gtaagaagtc cttgttgctt aattgaacgt ggacatatga   1620
atgaagagct tttagtgggc catttttggt aagcagaact ggcgatgcgg gatgaaccga   1680
acgcgaagtt aaagtgccgg aatacacgct catcagacac cacaaaaggt gttagttcat   1740
ctagacagcc ggacggtggc catggaagtc ggaatccgct aaggagtgtg taacaactca   1800
ccggccgaat gaactagccc tgaaaatgga tggcgctcaa gcgtgttact tatacttcgc   1860
```

```
cgtgagaggt tgatatgatg ccctcacgag taggcaggcg tggaggtcag tgaagaagcc    1920
tttgctgtaa agctgggtcg aacggcctct agtgcagatc ttggtggtag tagcaaatat    1980
tcaaatgaga actttgaaga ctgaagtggg gaaaggttcc atgtcaacag cagttggaca    2040
tgggttagtc gatcctaaga gatagggaag ctccgtttca atgcgcctga ttattcaggc    2100
cactatcgaa agggaatccg gttaaaattc cggaacttgg atatggattc ttcacggtaa    2160
cgtaactgaa tgtggagacg tcggcgtgag ccctgggagg agttatcttt tcttcttaac    2220
agcttatcac cctggaattg gtttatccgg agatgggtc ttatggctgg aagagcgtgg     2280
taattttgcc acgtccggtg cgcttacgac ggtccttgaa aatccacagg aaggaatagt    2340
tttcatgcca agtcgtactc ataaccgcag caggtctcca aggttaacag cctctagttg    2400
atagaataat gtagataagg gaagtcggca aaatagatcc gtaacttcgg gataaggatt    2460
ggctctaagg atcgggtgtt tgggcctcg cgaagacgtg gtggcgactg acggcggact     2520
gctttcgggc ggactgctgt tggatgctgc catagacacg cttggtaggg atttatcccg    2580
tccggagcac gcttaacgat caacttagaa ctggtacgga caaggggaat ctgactgtct    2640
aattaaaaca tagcattgtg atggtcagaa agtgatgttg acacaatgtg atttctgccc    2700
agtgctctga atgtcaaagt gaagaaattc aaccaagcgc gggtaaacgg cgggagtaac    2760
tatgactctc ttaaggtagc caaatgcctc gtcatctaat tagtgacgcg catgaatgga    2820
ttaacgagat tcccactgtc cctatctact atctagcgaa accacagcca agggaacggg    2880
cttggcagaa tcagcgggga agaagaccc tgttgagctt gactctagtt tgacattgtg     2940
aaaagacatg gagggtgtag aataagtggg agcttcggcg ccgtgaaat accactacct     3000 ctatagtttt tttacttatt caatgaagcg gagctggagg taaaactcca cgttctagca    3060
ttaaggcctt ttggctgatc cgggttgaag acattgtcag gtgggagtt tggctggggc     3120 ggcacatctg ttaaacgata acgcaggtgt cctaaggggg gctcatggag aacagaaatc    3180
tccagtagaa caaagggta aaagcccccct tgattttgat tttcagtgtg aatacaaacc    3240
atgaaagtgt ggcctatcga tcctttagtc cctcggaatt tgaggctaga ggtgccagaa    3300
aagttatcac agggataact ggcttgtggc agtcaagcgt tcatagcgac attgcttttt    3360
gattcttcga tgtcggctct tcctatcata ccgaagcaga attcggtaag cgttggattg    3420
ttcacccact aatagggaac gtgagctggg tttagaccgt cgtgagacag gttagttta    3480 ccctactgat gaatgttatc gcaatagtaa ttgaacttag tacgagagga accgttcatt    3540
cagataattg gttttttgcgg ctgtctgatc aggcaacgcc gcgaagctac catctgctgg   3600
attatggctg aacgcctcta agtcagaatc catgctagaa agcgatgatt tttgccctgc    3660
acattttaga tggatacgaa taagactttt aatagtcgct ggaccatagc aggctggcag    3720
cggtgcactt agcggaaagg ctttgtgtgc ttgccggcga atagcaatgt caacatgcgc    3780
ggggataaat cctttgcata cgacttagat gtacaacgga gtattgtaag cagtagagta    3840
gccttgttgt tacgatctgc tgagattaag cttcagttgt ctgatttgtc taggagt      3897
```

<210> SEQ ID NO 90
<211> LENGTH: 3894
<212> TYPE: DNA
<213> ORGANISM: Magnaporthe grisea rRNA gene

<400> SEQUENCE: 90

```
catgtgccgg aaagttgtac gaactcggtc gtttagagga agtaaaagtc gtaacaaggt     60
ctccgttggt gaaccagcgg agggatcatt actgagttga aaaactccaa cccctgtgaa    120
```

```
cataacctct gtcgttgctt cggcgggcac gcccgccgga ggttcaaaac tcttattttt      180
tccagtatct ctgagcctga aagacaaata atcaaaactt tcaacaacgg atctcttggt      240
tctggcatcg atgaagaacg cagcgaaatg cgataagtaa tgtgaattgc agaattcagt      300
gaatcatcga atctttgaac gcacattgcg cccgccggta ttccggcggg catgcctgtt      360
cgagcgtcat ttcaaccctc aagcctcggc ttggtgttgg ggcgcccggg ccctccgcgg      420
cccgggcccc ccaagttcat cggcgggctc ggcggtacac tgagcgcagt aaaacgcggt      480
aaaacgcgaa cctcgttcgg atcgtcccgg cgtgctccag ccgctaaacc cccaattttt      540
taaaggttga cctcggatca ggtaggaata cccgctgaac ttaagcatat caataagcgg      600
aggaaaagaa accaacaggg attgccccag taacggcgag tgaagcggca acagctcaaa      660
tttgaaatct ggccccccgg cccgagttgt aatttgcaga ggatgctttt ggtgaggcac      720
ctaccgagtc ccctggaatg gggcgccata gagggtgaga gccccgtatg gtaggacgcc      780
gaacctctgt aaagtccctt cgacgagtcg agtagtttgg gaatgctgct ctaaatggga      840
ggtaaatttc ttctaaagct aaataccggc cagagaccga tagcgcacaa gtagagtgat      900
cgaaagatga aaagcacttt gaaaagaggg ttaaaaagta cgtgaaattg ttgaaaggga      960
agcgcttgtg accagacttg cgccgggcgg atcatccagc gttctcgctg gtgcactccg     1020
cccggttcag gccagcatcg gttttcgccg ggggacaaag gcttcgggaa cgtggctcct     1080
ttcggggagt gttatagccc gttgcgtaat accccggcgg ggaccgacga ccgcgcttcg     1140
gcaaggatgc tggcgtaatg gtcatcagcg acccgtcttg aaacacggac cgaggagtca     1200
agcattagtg cgagtgtttg ggtgtaaaac ccgcacgcgt aatgaaagtg aacgtaggtg     1260
agagcttcgg cgcatcatcg accgatcctg atgttttcgg aaggatttga gtaggagcat     1320
taacgcttgg acccgaaaga tggtgaacta tacttgaata gggtgaagcc agaggaaact     1380
ctggtggagg ctcgcagcgg ttctgacgtg caaatcgatc gtcaaatttg agtatagggg     1440
cgaaagacta atcgaaccat ctagtagctg gtttcagccg aagtttccct caggatagca     1500
gtgtcgtctt cagttttatg aggtaaagcg aatgattagg gactcgggggg cgattttttag     1560 ccttcatcca ttctcaaact ttaaatatgt aagaagccct tgttacttag ttgaacgtgg     1620
gccttcgaat gtaccgacac tagtgggcca tttttggtaa gcagaactgg cgatgcggga     1680
tgaaccgaac gcggggttaa ggtgccgag tggacgctca tcagacacca caaaggcgt     1740 tagtacatct tgacagcagg acggtggcca tggaagtcgg aatccgctaa ggactgtgta     1800
acaactcacc tgccgaatgt actagccctg aaaatggatg cgctcaagc gtcccaccca     1860 taccccgccc ccagggtaga aacgatgccc tggggagtag gctgacgcgg gggtagcgac     1920
gaaggctagg gcgtgagccc ggctagagct gccctggtg cagatctcgg tgagagtagc     1980
aaatacttca atgagaactt gaaggaccga agtggggaaa ggttccatgt gaacagcagt     2040
tggacgtggg ttagccgatc ctgagccata gggaagttcc gtttcaaagg ggcgctagcg     2100
ccccgtatgg cgaaagggaa gcaggttaat attcctgcgc ctggatgtgg gttttcgcg     2160 gcaacgcaac tgaacgcgga gacggcggcg ggggcccccgg gcagagttct cttttcttct     2220
taacgatcca ccaccctgga aacggttgt ccggagatag ggttcagcgg tcggaagagc     2280
ccagcacttc tgttcgccct cgacgtccct tgaaaatccg cgggagggaa taattctcac     2340
gccaggtcgt actcataacc gcagcaggtc tccaaggtga acagcctctg ttgatagaa     2400 taatgtagat aagggaagtc ggcaaaacag atccgtaact tcgggaaaag gattggctct     2460
```

```
aagggttggg tacgttgggc ctttggcgga cgcgccgggg gcaggtcgcc actagccggg    2520
caaccggccg ggggcttcca gcacctggtt gccgacgcct ttggcaggct tcggccgtcc    2580
ggcgtacggt taacaaccaa cttagaactg gtacggacaa ggggaatctg actgtctaat    2640
taaaacatag cattgcgatg gccggaaagc ggtgttgacg caatgtgatt tctgcccagt    2700
gctctgaatg tcacagcaaa gtaatttgac caagcgcggg taaacggcgg gagtaactat    2760
gactctctta aggtagccaa atgcctcgtc atctaattag tgacgcgcat gaatggatta    2820
acgagattcc cactgtccct atctactatc tagcgaaacc acagccaagg gaacgggctt    2880
ggcagaatca gcggggaaag aagaccctgt tgagcttgac tctagtttga cattgtgaaa    2940
agacatagga ggtgtagaat aggtgggagc ttcggcgccg gtgaaatacc actactccta    3000 ttgtttttt acttattcga ttaagcgggg ctggatttac gtccaacttc tggttttaac    3060
gtccttcgcg ggcggacccg ggttgaagac attgtcaggt ggggagtttg gctggggcgg    3120
cacatctgtt aaaccataac gcaggtgtcc taaggggggc tcatggagaa cagaaatctc    3180
cagtagaaca aaagggtaaa agtccccttg attttgattt tcagtgtgaa tacaaaccat    3240
gaaagtgtgg cctatcgatc ctttagtccc tcgaaatttg aggctagagg tgccagaaaa    3300
gttaccacag ggataactgg cttgtggcgg ccaagcgttc atagcgacgt cgcttttga    3360 tccttcgatg tcggctcttc ctatcatacc gaagcagaat tcggtaagcg ttggattgtt    3420
cacccactaa tagggaacgt gagctgggtt tagaccgtcg tgagacaggt tagttttacc    3480
ctactgatga cctcgtcgca atggtaattg agcttagtac gagaggaacc gctcattcag    3540
ataattggtt tttgcggttg tccgacaggg cagtgccgcg aagctaccat ctgcaggata    3600
acggctgaac gcctctaagt cggaatcctt gccagaacgc gacgatacct cccgcacgtt    3660
tagacggata agaataggct tcggcctcgt atctcagcag gcgataaccc cgccgggctc    3720
gaagcgcccg gtggtgattc gcgtattgta atttttgacac gcgcggggtc aaatcctttg    3780
cagacgactt agctgtgcga aagggtcctg taagcagtag agtagcttta tcgttacgat    3840
ctgctgaggg taagccctcc ttcgcctaga tttcccagac tttctacccc attc          3894
```

<210> SEQ ID NO 91
<211> LENGTH: 3923
<212> TYPE: DNA
<213> ORGANISM: Metarhizium anisopliae rRNA gene

<400> SEQUENCE: 91

```
ccggaaagct ctccaaactc ggtcatttag aggaagtaaa agtcgtaaca aggtctccgt     60
tggtgaacca gcggagggat cattaccgag ttatccaact cccaacccct gtgaattata    120
cctttaattg ttgcttcggc gggacttcgc gcccgccggg gacccaaacc ttctgaattt    180
tttaataagt atcttctgag tggttaaaaa aatgaatcaa aactttcaac aacggatctc    240
ttggttctgg catcgatgaa gaacgcagcg aaatgcgata agtaatgtga attgcagaat    300
tcagtgaatc atcgaatctt tgaacgcaca ttgcgcccgt cagtattctg gcgggcatgc    360
ctgttcgagc gtcattacgc ccctcaagtc ccctgtggac ttggtgttgg ggatcggcga    420
ggctggtttt ccagcacacc gtcccttaaa attaattggc ggtctcgcgt ggccctcctc    480
tgcgcagtag taaaactcgc aacaggagcc cggcgcggtc cactgccgta aaccccccca    540 acttttttata gttgacctcg aatcaggtag gactacccgc tgaacttaag catatcaata    600
agcggaggaa aagaaaccaa cagggattgc cccagtaacg gcgagtgaag cggcaacagc    660
tcaaatttga aatctggtcc ccagggcccg agttgtaatt tgcagaggat gcttttggtg    720
```

```
aggtgccttc cgagttccct ggaacgggac gccatagagg gtgagagccc cgtctggttg    780
gataccgagc ctctgtaaag ctccttcgac gagtcgagta gtttgggaat gctgctctaa    840
atgggaggta tatgtcttct aaagctaaat attggccaga gaccgatagc gcacaagtag    900
agtgatcgaa agatgaaaag cactttgaaa agagggttaa atagtacgtg aaattgttga    960
aagggaagca cttatgacca gacttggccc cggtgaatca tccagcggtt ccccgtgtgc   1020
actttgccgg ggttcaggcc agcatcagtt cgctccgggg gataaaggct ttgggaatgt   1080
ggctccctcg ggagtgttat agcccattgc gcaataccct gtggcgggct gaggttcgcg   1140
ctttatgcaa ggatgctggc ataatggtca tcagtgaccc gtcttgaaac acggaccaag   1200
gagtcgtctt cgtatgcgag tgttcgggtg ttaaaccccct acgcgtaatg aaagtgaacg   1260
caggtgagag ccctccaggg cgcatcatcg accgatcctg atgttctcgg atggatttga   1320
gtaagagcat acggggccgg acccgaaaga aggtgaacta tgcctgtata gggtgaagcc   1380
agaggaaact ctggtggagg ctcgcagcgg ttctgacgtg caaatcgatc gtcaaatatg   1440
ggcatggggg cgaaagacta atcgaacctt ctagtagctg gtttcgccgg aagtttccct   1500
caggatagca gtgttgattt ctcagtttta tgaggtaaag cgaatgatta gggacccggg   1560
ggcggcttat agccttcatc cattctcaaa ctttaaatat gtaagaagcc cttgttgctt   1620
aggtgaacgt gggcattcga atgtatcaac actagtgggc cattttggt aagcagaact   1680 ggcgatgcgg gatgaaccga acgcgaggtt aaggtgccag agtagacgct catcaacacc   1740
accaaaggtg ttagtacatc ttgacagcag gacggtggcc atggaagtcg gaatccgcta   1800
aggactgtgt aacaactcac ctgccgaatg tactagccct gaaaatggat ggcgctcaag   1860
cgtctcaccc atacctcgcc ctcggggtag gaacgatgcc ccgaggagta ggcggacgtg   1920
ggggtcagtg acgaagccca gggcgtgagc ccgggtcgaa cggcccctag tgcagatctt   1980
ggtggtagta gcaaatactt caatgagaac ttgaaggacc gaagtgggga aaggttccat   2040
gtgaacagcg gttggacgtg ggttagtcga tcctaagcca tagggaagtt ccgtttcaaa   2100
ggtgcacttg tgcgccgtct gggcgaaagg gaagccggtc aatattccgg cacctggatg   2160
tgggtttttc gcggcaacgc aactgaacgc ggagacgacg cgggggccc cgagcagagt   2220 tctcttttct tcttaacagt ctgtcaccct gaaatcggtt tgtccggagc tagggtttaa   2280
tggctggaag agcggcacct ctgccgggtt cggtgcgctc ccgacgtccc ttgaaaatcc   2340
gcgggaggga ataattctca cgccaggtcg tactcataac cgcagcaggt ctccaaggtg   2400
aacagcctct ggttgataga acaatgtaga taagggaagt cggcaaaata gatccgtaac   2460
ttcgggataa ggattggctc taagggttgg gtgcgttggg cctcgggggg acgccttggg   2520
agcaggcagc cactagccgg gcaaccgtcg gcggccgcag catccgagcg ctgaatccct   2580
tggcaggctt cggccgtccg gcgcacgatt aacaaccaac ttagaactgg tacggacaag   2640
gggaatctga ctgtctaatt aaaacatagc attgcgatgg ccagaaagtg gtgttgacgc   2700
aatgtgattt ctgcccagtg ctctgaatgt caaagtgaag taattcaacc aagcgcgggt   2760
aaacggcggg agtaactatg actctcttaa ggtagccaaa tgcctcgtca tctaattagt   2820
gacgcgcatg aatggattaa cgagattccc actgtcccta tctactatct agcgaaacca   2880
cagccaaggg aacgggcttg gcagaatcag cggggaaaga agaccctgtt gagcttgact   2940
ctagtttgac attgtgaaaa gacataggag gtgtagaata ggtgggagct tcggcgccgg   3000
tgaaatacca ctactcctat tgtttttttta cttattcaat gaagcggggc tggattttcg   3060
```

| | |
|---|---|
| tccaacttct ggtcttaagg tccttcgcgg gctgtacccg ggttgaagac attgtcaggt | 3120 |
| ggggagtttg gctggggcgg cacatctgtt aaaccataac gcaggtgtcc taaggggggc | 3180 |
| tcatggagaa cagaaatctc cagtagaaca aaagggtaaa agtccccttg atttttgattt | 3240 |
| tcagtgtgaa tacaaaccat gaaagtgtgg cctatcgatc ctttagtccc tcgacatttg | 3300 |
| aggctagagg tgccagaaaa gttaccacag ggataactgg cttgtggcgg ccaagcgttc | 3360 |
| atagcgacgt cgcttttga tccttcgatg tcggctcttc ctatcatacc gaagcagaat | 3420 |
| tgcctaagcg ttggattgtt cacccactaa tagggaacgt gagctgggtt tagaccgtcg | 3480 |
| tgagacaggt tagttttacc ctactgatga cctcaccgca atggtaattc agcttagtac | 3540 |
| gagaggaacc gctgattcag ataattggtt tttgcggctg tccgaccggg cagtgccgcg | 3600 |
| acgctaccat ctgctggata atggctgaac gcctctaagt cagaatccat gccagaacgc | 3660 |
| ggtgataccc gccgcacgta cagatggaca agaataggct ccggcttagc gtcttagcag | 3720 |
| gcgattgttc cgctgcgcag gaagcgcagt atttcgcgta ttgtaatttc accacgagcg | 3780 |
| gggtcaaatc ctttgcagac gacttagctg tgcgaaacgg tcctgtaagc agtagagtag | 3840 |
| ccttgttgtt acgatctgct gagggttagc cgttcttcgc ctcgatttcc ccaatatcag | 3900 |
| cgcatcccgt ttcgcggggc ggg | 3923 |

<210> SEQ ID NO 92
<211> LENGTH: 4007
<212> TYPE: DNA
<213> ORGANISM: Microsporum gypseum rRNA gene

<400> SEQUENCE: 92

| | |
|---|---|
| tcggtcattt agaggaagta aaagtcgtaa caaggtttcc gtaggtgaac ctgcggaagg | 60 |
| atcattaacg cgcaggccgt agacggcccg tccccggatg cgtccggggg cggtgtcgcc | 120 |
| ggccacacgc ccattcttgt ctatttaccc agttgcctcg gcgggccgcg cactcgtgcc | 180 |
| gcgcctcgag gagccgtccg gggacaatca actccctgga tcgcgcccgc cggaggagtg | 240 |
| attaaaatcc atgaatactg ttccgtctga gcgttagcaa gtaaaatcag ttaaaacttt | 300 |
| caacaacgga tctcttggtt ccggcatcga tgaagaacgc agcgaaatgc gataagtaat | 360 |
| gtgaattgca gaattccgtg aatcatcgaa tctttgaacg cacattgcgc cctctggtat | 420 |
| tccgggggc atgcctgttc gagcgtcatt tcaacccctc aagcccggct tgtgtgatgg | 480 |
| acgaccgtcc cgccctccct actccagggg aggggacgc gcccgaaaag cagtggccag | 540 |
| gccgcgattc cggctcctgg gcgaatgggc aacaaaccaa cgcctctagg accggccggt | 600 |
| tttctggcct agttttagtt agggatgaac ttccctacaa tcaggttgac ctcggatcag | 660 |
| gtagggatac ccgctgaact taagcatatc aataagcgga ggaaaagaaa ccaacaggga | 720 |
| ttgccccagt aacggcgagt gaagcggcaa aagctcaaat ttgaaatctg gcctcctacg | 780 |
| ggggtccgag ttgtaattg tagaggatgc ttcgggtgtg ccgccgtct aagttccttg | 840 |
| gaacaggacg tcagagaggg tgagaatccc gtcttgggcg gccggtccgc gcccgtgtga | 900 |
| agctccttcg aagagtcgag ttgtttggga atgcagctct aagcgggtgg taaatttcat | 960 |
| ctaaagctaa atactggtcg gagaccgata gcgcacaagt agagtgatcg aaaggttaaa | 1020 |
| agcaccttga aagggagtt aaacagcacg tgaaattgtt gaagggaag cgcttgcggc | 1080 |
| cagactcggg ggcggggttc agcgggtgct cgtcgcccgt gcactcccg tctcccgggc | 1140 |
| cagcatcagt ttcgacggcc ggtcaaaggc ctccggaatg tgtcgtctct cgggacgtct | 1200 |
| tatagccggg ggtgcaatgc ggcccgtcgg gactgaggaa cgcgcttcgg ctcggatgct | 1260 |

-continued

```
ggcgtaatgg ccgtaagcgg cccgtcttga acacggacc aaggagtcta acatccacgc  1320
gagtgttcgg gtgtcaaacc cgtgcgcgca gtgaaagcga acggaggtgg gagccttagg  1380
gcgcaccatc gaccgatcct gaagtcttcg gatggttagg gttaggttag ggttaggtta  1440
ggttttaggg tttagggtta gggtttaggg tgtgaagcca gaggaaactc tggtggaggc  1500
tcgcagcggt tctgacgtgc aaatcgatcg tcaaatttgg gcatagggc gaaagactaa  1560 tcgaaccatc tagtagctgg ttcctgccga agtttccctc aggatagcag tgacgatatt  1620
ccagttttat gaggtaaagc gaatgattag aggccttggg gatgaaacat ccttaaccta  1680
ttctcaaact ttaaatatgt aagaagccct tgtttcttaa gtgaacgtgg gcactagaat  1740
ggaacgtcac tagtgggcca ttttttggtaa gcagaactgg cgatgcggga tgaaccgaac  1800
gcgaggttaa ggtgccggaa tgcacgctca tcagacacca caaaaggtgt tagttcatct  1860
agacagcccg acgtggcca tggaagtcgg aatccgctaa ggagtgtgta caactcacg  1920 ggccgaatga actagccctg aaaatggatg gcgctcaagc gtgctaccca tacctcgccg  1980
ccggggttga aatgacgccc cggcgagtag gcaggcgtgg aggtccgtga cgaagccctg  2040
ggggtgaccc cgggtcgaac ggcctctagt gcagatcttg gtggtagtag caaatactca  2100
aatgagaact ttgaggactg aagtggggaa aggttccatg tgaacagcag ttggacatgg  2160
gttagtcgat cctaaggcat agggtagttc cgattgcatg tgcgccctgg tgcgccgtca  2220
gccgaaaggg aagccggtta aaattccggc acctggatgt ggattctcca cggcaacgta  2280
actgaacgcg gagacgtcgg cggggtcct gggaagagtt atcttttctt cttgacggcc  2340
tatcaccctg aaatcggttt gtccggagct agggttcaat ggccggcaga gcgccgcacc  2400 tttgcgcgt ccggcgtgcc cccgacgacc cttgaaaatc cgcgggaagg aatagttttc  2460
acgccaggtc gtactcataa ccgcagcagg tctccaaggt gaaaagcctc tagttgatag  2520
aacaatgtag ataagggaag tcggcaaaat agatccgtaa cttcgggaaa aggattggct  2580
ctaaggatcg ggcgcgttgg gccttgggtg gagaccctcg aggcagggca gcactagccg  2640
ggcaaccggc cggcgccgcc cagcatcggg gcgtggacgc ccttggcagg cctctgccg  2700 tccggcgcgc gcttaacgat caacttagaa ctggtacgga caaggggaat ctgactgtct  2760
aattaaaaca tagcattgcg atggccagaa agtggtgttg acgcaatgtg atttctgccc  2820
agtgctctga atgtcaaagt gaagaaattc aaccaagcgc gggtaaacgg cgggagtaac  2880
tatgactctc ttaaggtagc caaatgcctc gtcatctaat tagtgacgcg catgaatgga  2940
ttaacgagat tcccactgtc cctatctact atctagcgaa accacagcca agggaacggg  3000
cttggcagaa tcagcgggga agaagaccc tgttgagctt gactctagtt tgacattgtg  3060
aaaagacata tcgggtgtag aataggtggg agcttcggcg ccgtgaaat accactacct  3120 ttattgtttt tttacttatt caatgaagcg gaactggcct ttactggcca acttctagcg  3180
ttaaggtccc tcgcgggctg atccggggttg aagacattgt caggtgggga gtttggctgg  3240
ggcggcacat ctgttaaaca ataacgcagg tgtcctaagg gggactcatg gagaacagaa  3300
atctccagta gaacaaaagg gtaaaagtcc ccttgatttt gattttcagt gtgaatacaa  3360
accatgaaag tgtggcctat cgatcctta gtccctcgaa atttgaggct agaggtgcca  3420
gaaaagttac cacagggata actggcttgt ggcagccaag cgttcatagc gacgttgctt  3480
tttgatcctt cgatgtcggc tcttcctatc ataccgaagc agaattcggt aagcgttgga  3540
ttgttcaccc actaataggg aacgtgagct gggtttagac cgtcgtgaga caggttagtt  3600
```

-continued

```
ttaccctact gatgaagttc gccgcaacgg taattcaatt tagtacgaga ggaaccgttg    3660
attcagataa ttggtttttg cggctgtctg acaaggcatt gccgcgacgc taccatctgc    3720
cggattatgg ctgaacgcct ctaagtcaga atccgtgccg gaaagcggcg atacctgccc    3780
cgcacgttgt agttggatac aaataggctt cggccctgaa cctcaacagg ccggcaccgg    3840
cgcctcggcg ctagctggcg gattgcaatg tcaccacgcg cggggataaa tcctctgcag    3900
acgactgaag tgagcaagcg ggtcgtgtaa gcggtcaagt agccttgttg ttacgagtcg    3960
ctgagcgtca gcccgatcct tgcctagatt tgttgtaaca ccctccc                  4007
```

<210> SEQ ID NO 93
<211> LENGTH: 4140
<212> TYPE: DNA
<213> ORGANISM: Mucor racemosus rRNA gene

<400> SEQUENCE: 93

```
taggctattt agaggaagta aaagtcgtaa caaggtttcc gtaggtgaac ctgcggaagg      60
atcattaaat aatcaataat tttggcttgt ccatcattat ctatttactg tgaaacgtat     120
tattacttga cgcctgaggg atgttccact gctataagga taggcagcgg aaatgttaac     180
cgagtcataa tcaagcttag gcttggtatc ctattattat ttaccaaaag aattcagaat     240
taatattgta acatagacgt aaaaaatcta taaaacaact tttaacaacg gatctcttgg     300
ttctcgcatc gatgaagaac gtagcaaagt gcgataacta gtgtgaattg catattcagt     360
gaatcatcga gtctttgaac gcaacttgcg ctcattggta ttccaatgag cacgcctgtt     420
tcagtatcaa acaaacccct ctatccaact tttgttgaat aggatgactg agagtctctt     480
gatcgtcaga tctcgaacct cttgaaatgt acaaaggcct gatcttgttt gatgcctgaa     540
cttttttta atataaagag aagctcttgc ggtaaactgt gctggggcct cccaaataac     600
actttttaa atttgatctg aaatcaggtg ggattacccg ctgaacttaa gcatatcaat     660
aagcggagga aaagaaaata acaatgattt ccctagtaac ggcgagtgaa gaggaaagag     720
ctcaaagttg gaaactgttt ggcttagcta accgtattg taaactgtag aaacattttc      780
ctggcacacc agattaataa gtcctttgga acaaggcatc atggagggtg agaatcccgt     840
ctttgatctg agtagttgtc ttttgtgata tgttttcaaa gagtcaggtt gtttgggaat     900
gcagcctaaa ttgggtggta aatctcacct aaagctaaat atttgcgaga gaccgatagc     960
gaacaagtac cgtgagggaa agatgaaaag aactttgaaa agagagttaa acagtatgtg    1020
aaattgttaa aagggaaccg tttggagcca gactggtttg cttgtaatca acctagaatt    1080
cgttttgggt gcacttgcag gctatacctg ccaacaacag tttgatttgg aggaaaaaat    1140
tagtaggaat gtagcctctc gaggtgttat agcctactat catactctgg attggactga    1200
ggaacgcagc gaatgccttt aggcaagatt gctgggtgct ttcgctaata aatgttagaa    1260
tttctgcttc gggtggtgct aatgtttaaa ggaggaacac atctagtata ttttttattc    1320
gcttaggttg ttggcttaat gactctaaat gacccgtctt gaaacacgga ccaaggagtc    1380
caccataagt gcaagtattt gagtgacaaa ctcatatgcg taaggaaact gattgatacg    1440
aagtctttg atggcagtat cacccggcgt cgacgtttta actgaaatga ccaggtaaa    1500
gcacttatga tgggacccga aagatggtga actatgcctg aatagggtga agccagagga    1560
aactctggtg gaggctcgta gcgattctga cgtgcaaatc gatcgtcaaa tttgggtata    1620
ggggcgaaag actaatcgaa ccatctagta gctggttcct gccgaagttt ccctcaggat    1680
agcaaaaact taaacgcagt tttatgaggt aaagcgaatg attagaggcc ttggggacga    1740
```

```
aatgtcctta acctattctc aaactttaaa tatgtaagac gacctgtttg cttaattgaa    1800
gcaggtcatt gaatgtgagt ttttagtggg ccattttggg taagcagaac tggcgatgcg    1860
ggatgaaccg aacgagaagt taaggtgccg gaatacacgc tcatcagaca ccacaaaagg    1920
tgttagttca tctagacagc aggacggtgg ccatggaagt cggaatccgc taaggagtgt    1980
gtaacaactc acctgccgaa tgaactagcc ctgaaaatgg atggcgctta agcgtgttac    2040
ccatacttct ccgttattgt aaaagcgaag caataacgag taggcaggcg tggaggtttt    2100
tataaactgt taagaagctc ttggagtgat ccggagtgaa acagcctcta gtgcagatct    2160
tggtggtagt agcaaatatt caaatgagaa ctttgaagac tgaagtggag aaaggttcct    2220
ggagaacatt atttggtcca gggttagtcg atcctaagag atagggaaat tccgtttttt    2280
caaagcaatc aatcttgatt cgcctatcga aagggaaaca gtttaatatt actgtactag    2340
gatgaggatt ttctgcggta acgcaaatga acttggagac atcagtgtgg atcccaggaa    2400
gagttatctt ttcttttttaa caactttgtt gtagaccttg aaatctgttt agcaggagaa    2460
aaggtttacc ggttggtaga gcatagtact ttttgctatg tctggtgcat tcacaacgat    2520
ccttgaaaat ccaagggaaa gaataatttt ctcgcctagt cgtactcata accgcagcag    2580
gtctccaagg tgaaaagcct ctagttgata gaacaatgta gataagggaa gtcggcaaaa    2640
tagatccgta acttcgggat aaggattggc tctaagggtt gggtagatat ggactcttgg    2700
tatggttggt ttctaggcga ttttaagtga tttcggttgc ttgattttgc ttggagatct    2760
tcgtaaccag gagagcccag tttacgctta acaaccaact tagaactggt acggacaagg    2820
ggaatctgac tgtctaatta aaacatagca ttgcgatggc cagaaagtgg tgttgacgca    2880
atgtgatttc tgcccagtgc tctgaatgtc aaagtgaaga aattcaacca agcgcgggta    2940
aacggcggga gtaactatga ctctcttaag gtagccaaat gcctcgtcat ctaattagtg    3000
acgcgcatga atggattaac gagattccca ctgtccctat ctactatcta gcgaaaccac    3060
agccaaggga acgggcttgg cagaatcagc ggggaaagaa gaccctgttg agcttgactc    3120
tagtttgaca ttgtgaaaag acatagaggg tgtagcataa gtgggagctt cggcgccagt    3180
gaaataccac tacctttatc gttttttttac ttaaataatt aagtgggatt gagtcgcaag    3240
attaaccttc tagtattaag catcttcgga tgtgacccac gttattgaca ttgtcaagtg    3300
gggagtttgg ctggggcggc acatctgtta aaagataacg caggtgtcct aagggggact    3360
caacgagaac agaaatctcg tgtagaataa aagggtaaaa gtccccttga ttttgatttt    3420
cagtgtgaat acaaaccatg aaagtgtggc ctatcgatcc tttagaatct caagatttga    3480
ggctagaggt gccagaaaag ttaccacagg gataactggc ttgtggcagc caagcgttca    3540
tagcgacgtt gcttttttgat tcttcgatgt cggctcttcc tatcatactg aagcagaatt    3600
cagtaagcgt tggattgttc acccactaat agggaacgtc agctgggttt agaccgtcgt    3660
gagacaggtt agttttaccc tactgatggt attggtatcg taacagtaat tgaagttagt    3720
acgagaggaa cccttcattc agataattgg tatttgcggc tggttgaaag gccaatgccg    3780
cgaagctacc atctgctgga taatgctgaa cgcctctaag tcagaatcca tgctgaaaac    3840
gatactactg tgttttgatt gtaccagatg agtactaata aagcttcggc ttgaaaacct    3900
tacttgtgag ctaggtttgg tagcggaaat gctgctagat ctacttgcta atgataatgc    3960
taatacatca aaatgataaa tcgcatgcag acgacatgaa atggacgggg tattgtaagt    4020
actagagtag cctttgttgc tacgatgtac tgagattaag cctttgtcat tgaatttgtt    4080
```
cctctaagga acatttctca tcaaaaatta ataaattttt atctattttt ttttatctgt    4140

<210> SEQ ID NO 94
<211> LENGTH: 3936
<212> TYPE: DNA
<213> ORGANISM: Neurospora crassa rRNA gene

<400> SEQUENCE: 94 cggttatta aaggaaataa aaattgtaat aaagtttctg ttagtaaatt agtagaaaga      60
ttattataga attacaaaac tcctataaat tattgtaaat tttacttata tagttacttc     120
ggcgttagta gtttaaaaaa gccttcgagc cctcccggat cctcgggtct cctactcgta    180
agaagttacc cgccggaata ctaaaactaa actcttaata ttttatatct ctttaagtaa    240
acttttaaat aaattaaaac ttttaataat aaatctctta gttctaacat taataaaaaa    300
cgtaataaaa tataataagt aatataaatt atagaattta gtaaattatt aaatctttaa    360
acgcacattg cgcttactaa tattctagta agtatactta ttcgaatatt atttcaacta    420
ttaagctcta cttacgttag ggatccgtag ctatccgtag tcctttaaaa ttaatagcgg    480
gtttattaat tatattgagt atagtaattc tatattatta taattatata gcgggttctt    540
actataaaac cccctatttt taaaattgac ctcggattag gtaggaatac ccgctgaatt    600
taagtatatt aataagtaga agaaaaaaaa ttaataggga ttaccttaat aatagcgaat    660
aaaatagtaa tagttcaaat ttgaaatcta gcttcggccc gaattataat ttgtaaaaga    720
agcttttagt aaggcacttt ctaaatcccc tagaacggag cgctatagag ggtgagagcc    780
ctatataatt ggatgccaat ctaatataaa gctcctttaa taaatcgaat agtttaggaa    840
tattatttaa aataggaggt aaatttcttt taaagctaaa taccggctag agattaatag    900
tatataagta gagtaattaa aaaatgaaaa gtacttttaaa aagagggtta aatagtatat    960
gaaattatta aaaggaaagt gtttataatt agatttatac tgttttaatt atttagtatt   1020
cttattagta tatttaggac ggtttaaact aatattagtt ttagtagggg gataaaggtt   1080
tagggaatat aactcctcta ggaatattat agccctaggc gtaataccctt tactagaact   1140
gaagttcgta tatttataag aatactagta taataattat taataacccg ttttaaaata   1200
cagactaagg aattaaagtt ttacgcaagt atttaggtat aaaacccgta cgtataataa   1260
aagtaaatgt aggtgagagc ttcggtatat tattaattaa ttctaatata tttagataaa   1320
tttaaataag aatattaaac cttaaacccg aaaaataata aactatactt agatagggta   1380
aagctagaag aaactctaat agaggctcgc aacggttcta acgtacaaat cgattgttaa   1440
atctaagtat gggggcgaaa gactaattga actatctaat agctaattac cgccgaagtt   1500
tcccttaaga taataatatt attcttcaat tttataaggt aaagcgaata attagggact   1560
cggggcgct tttagccttt catccattct taaactttaa atatataaga agcccttatt   1620
atttaattaa atataggtat tcgaatatat taatactaat aggctatttt taataagtag   1680
aactagtaat acgaataaaa ccgaacgtag ggttaaagta ctagagtaaa tacttattaa   1740
atactataaa aagcgttagt atatttaat aataggacgg tggctataga aatcggaatt   1800
tgctaaggac tatataataa tttacttacc gaatatacta gctttgaaaa taaatagtac   1860
ttaaacgtcc tacttatacc ccgcccttaa agtagaaacg atattctaaa gagtaggcgg   1920
ctatagaggt tagtaacgaa gcctagggcg taagcccggg tcgaacggcc tttaatataa   1980
attttaatag tagtaataaa tatttaata agaatttaaa ggactaaagt agggaaaggt   2040
tctatataaa tagcggttgg atataggtta attaatctta aactataggg aagttccgtt   2100

```
ttaaagggt atttatactc tatatagcga aagggaagcc ggttaatatt ccggtaccta   2160
aatataggtt ttacgcggta atgtaattaa atatagaaac gatagcggag gccccaggta   2220
aaattctctt ttcttttaa tagtctatta ccctaaaaat aatttattta gagatagggt    2280
ttaatagccg gaagagccca atatttctat tgggtccagt acgttttaa tatcccttaa    2340 aaatccgtag gagggaataa ttcttatatt aagttatatt tataattata gtaggtcttt   2400
aaagtgaata gcttctaatt aatagaataa tatagataag ggaagttagt aaaatagatt   2460
tataatttta ggaaaaggat taattctaag ggttaagtac gtcgggcttt aggtaaacgc   2520
cctaagagta gattgctatt agttaggtaa ccggccggta gctttcaata tccgggtata   2580 gaagcttta atagacttcg gtcgtccggt gtacgtttaa taattaattt aaaattagta    2640 tagataggg gaatttaatt atctaattaa aatatagtat tacgatagtt agaaagtagt    2700
attaacgtaa tataattcct atttagtatt ttaaatatta aaataaaaaa attcaactaa   2760
gcgcgggtaa atagcaggaa taactataat tctcttaaag tagccaaata ctttattat    2820 taattagtaa cgcatataaa tagattaatg agattcctat tatccctatt tattatctag   2880
cgaaactata attaaggaa cgggcttagt agaattaatg gagaaagaag accctattaa   2940 acttaattt agtttaatat tataaaaaaa tataggaagt atagaatagg taggagcttc    3000
ggcgccggta aaatactact actcctattg tttttttact tatttaatta agcggggcta    3060 gattttatt caacttctaa ttttaaggtc cttcgtaggc taacccggat taaaaatatt    3120
attaagtagg gaatttagct agggcagtac atctattaaa ctataatgca aatatcctaa    3180
gggggcctta tagagaataa aaatctctag tagaacaaaa gggtaaaaat cccttaatt    3240 ttaattttta ataaaatat aaattataaa agtatagcct attaatcctt tagtccctcg    3300
aaatttaaag ttagaagtac tagaaaaatt actataagga taattaactt ataatagcca    3360 aacgttata gcaatatcgc ttttaatcc ttcaatatca gctcttccta ttataccgaa    3420
gtagaattcg gtaaatatta gattatttac ctattaatag ggaatgtaag ctaaatttag    3480
actattataa aataaattag ttttacccta ctaataactt tatcgcaata gtaattaaat    3540
ttagtataaa aggaactact tatttaaata attagttttt ataattatct aaccggatag    3600
tactataacg ctactatcta ctagataata actgaacgcc tctaaattag aatttatatt    3660
agaatacgat aatacttta gtatattata gatatataaa aataagctcc ggctttgtat    3720
cttagtaagc aattcctcta ttagccttaa agtagctagc ggtaattcgt atattataat    3780
tttaatatat attagattaa atcctttata aataatttaa atatacgaaa gggttttata    3840
aataatagaa tagccttatt attataattt attaagagta agccctcctt cgcttaaatt    3900
tcccaataga aggatccgct taataaatag gcattt                              3936
```

```
<210> SEQ ID NO 95
<211> LENGTH: 4043
<212> TYPE: DNA
<213> ORGANISM: Paracoccidioides brasiliens rRNA gene

<400> SEQUENCE: 95
gtcatttaga ggaagtaaaa gtcgtaacaa ggtttccgta ggtgaacctg cggaaggatc     60
attaacgcgc cgtgggggga cggggcccga tcgggttccc ggccctctca cctggccacc    120
cttgtctatt ctacctgttg cttcggcggg cctgcagcga tgctgccggg ggggctcggc    180
ctcccgggct cgtgcccgcc ggggacaccg ttgaacttct ggttcggagc tttgacgtct    240
```

```
gagacctatc ataatcagta aaaactttca acaacggatc tcttggttcc gacatcgatg    300
aagaacgcag cgaaatgcga taagtaatgt gaattgcaga attccgtgaa tcatcgaatc    360
tttgaacgca cattgcgccc tctggtattc cggggggcat gcctgtccga gcgtcatttc    420
aaccctcaag cgcggcttgc gtgttgggcc cgcgtccccc cgtggacgtg cccgaaatgc    480
agcggcggcg tcgcgttccg gtgcccgagc gtatggggct tcgtcacacg ctctcagagg    540
cccggccgac tccggcccca ctcatcgacc cggcggggg ggaaaaaggt gtcctctctc    600
gatcgacacc cttccccctt gccgaccaag gttgacctcg gatcaggtag ggatacccgc    660
tgaacttaag catatcaata agcggaggaa aagaaaccaa cagggattgc ctcagtaacg    720
gcgagtgaag cggcaagagc tcaaatttga aatctggctc cttcggggcc cgagttgtaa    780
tttgtagagg atgcttcggg cgtggccgcg gtctaagtcc cctggaacgg ggcgtcgcag    840
agggtgagaa tcccgtcttc ggccggccgg ccccgcccgt gtgaagctcc ttcgacgagt    900
cgagttgttt gggaatgcag ctctaaatgg gtggtaaatt tcatctaaag ctaaatactg    960
gtcggagacc gatagcgcac aagtagagtg atcgaaagat gaaaagcact ttgaaaagag   1020
agttaaacag catgtgaaat tgttgaaagg gaagcgcttg cgaccagagt cggccgcggg   1080
ggctcagcgg gcactcgttg cccgtgcact ccccgtggt cgggccagcg tcggtttcga   1140
cggccggtca aaggccccg gaatgtgtcg cctctcgggg cgtcttatag ccggggtgc    1200 aatgcggcca gtcgggaccg aggaacgcgc tccggcacgg acgctggctt aatggtcgta   1260
agcgacccgt cttgaaacac ggaccaagga gtctaacatc cacgcgagtg ttcgggtgtc   1320
aaacccgtcc gcgcagtgaa agcgaacgga ggtgggaacc ctcaagggtg caccatcgac   1380
cgatcctgaa gtcttcggat ggatttgagt aagagcgtgg ctgttgggac ccgaaagatg   1440
gtgaactatg cctgaatagg gtgaagccag aggaaactct ggtggaggct cgcagcggtt   1500
ctgacgtgca aatcgatcgt caaatttggg catagggcg aaagactaat cgaaccatct   1560
ggtagctggt tcctgccgaa gtttccctca ggatagcagt aacgttttca gttttatgag   1620
gtaaagcgaa tgattagagg ccttggggtt gaaacaacct taacctattc tcaaacttta   1680
aatatgtaag aagcccttgt tgcttagttg aacgtgggca ctggaatgga tcgttactag   1740
tgggccattt ttggtaagca gaactggcga tgcgggatga accgaacgcg aggttaaggt   1800
gccggaatgc acgctcatca gacaccacaa aaggtgttag ttcatctaga cagcccgacg   1860
gtggccatgg aagtcggaat ccgctaagga gtgtgtaaca actcacgggc cgaatgaact   1920
agccctgaaa atggatggcg ctcaagcgtg ctacccatac ctcgccgtcg ggcagaaaac   1980
gacgccccga cgagtaggca ggcgtggagg tccgtgacga agccctggga gtgatcccgg   2040
gtcgaacggc ctctagtgca gatcttggtg gtagtagcaa atactcaaat gagaactttg   2100
aggactgaag tggggaaagg ttccatgtga acagcagttg gacatgggtt agtcgatcct   2160
aagacatagg gaagttccgt ttcaaagcgc gccctcgtgc gccgtccgtc gaaagggaag   2220
ccggttaata ttccggcacc tggatgtgga ttctccacgg caacgtaact gaacgcggag   2280
acgtcggcgg gggtcctggg aagagttatc ttttcttctt gacggcctat caccctgaaa   2340
tcggtttgtc cggagctagg gttcaacggc cggcagagcc ccgcaccttt gcgggtccg    2400 gtgcgccccc gacgacccctt gaaaatccgc gggaaggaat agttttcacg ccaggtcgta   2460
ctcataaccg cagcaggtct ccaaggtgaa aagcctctag ttgatagaac aatgtagata   2520
agggaagtcg gcaaaataga tccgtaactt cgggaaaagg attggctcta agggttgggc   2580
acgttgggcc ttgggcggag acccccggag caggaaggca ctagccgggc aaccggtggg   2640
```

```
ggccctccag catcggggcg tggacgccct tggcaggctt cggccgtccg gcgtgcgatt    2700
aacaaccaac ttagaactgg tacgacaag  gggaatctga ctgtctaatt aaaacatagc    2760
attgcgatgg ccagaaagtg gtgttgacgc aatgtgattt ctgcccagtg ctctgaatgt    2820
caaagtgaag aaattcaacc aagcgcgggt aaacggcggg agtaactatg actctcttaa    2880
ggtagccaaa tgcctcgtca tctaattagt gacgcgcatg aatggattaa cgagattccc    2940
actgtcccta tctactatct agcgaaacca cagccaaggg aacgggcttg agaatcagc     3000 ggggaaagaa gaccctgttg agcttgactc tagtttgaca ttgtgaaaag acatatcggg    3060
tgtagaatag gtgggagctt cggcgccggt gaaataccac tacctttatt gtttttttac    3120
ttattcaatg aagcggaact gggctttgct gcccaacttc tggcgttaag gtccctcgcg    3180
ggccgatccg ggttgaagac attgtcaggt ggggagtttg gctggggcgg cacatctgtt    3240
aaaccataac gcaggtgtcc taaggggac  tcatggagaa cagaaatctc cagtagaaca     3300
aaagggtaaa agtccccttg attttgattt tcagtgtgaa tacaaaccat gaaagtgtgg    3360
cctatcgatc ctttagtccc tcgaaatttg aggctagagg tgccagaaaa gttaccacag    3420
ggataactgg cttgtggcag ccaagcgttc atagcgacgt tgcttttga  tccttcgatg    3480 tcggctcttc ctatcatacc gaagcagaat tcggtaagcg ttggattgtt cacccactaa    3540
tagggaacgt gagctgggtt tagaccgtcg tgagacaggt tagttttacc ctactgatgt    3600
ggtcgccgca acggtaattc aatttagtac gagaggaacc gttgattcag ataattggtt    3660
tttgcggctg tctgaccagg cagtgccgcg acgctaccat ctgccggatt atggctgaac    3720
gcctctaagt cagaatccgt gccggaacgc ggcgatgttg ccccgcacgt tgtagttgga    3780
tacgaatagg cctccgggcc cagaacctca gcaggccggc gacggtgccc ggggagagac    3840
ccccgggcgc cagctggcgg attgcaatgt caccacgcgc ggggatagat cctctgcaga    3900
cgactgaaat gaccaagcgg gtcgtgtaag cggtcaagta gccttgttgt tacgagtcgc    3960
tgagcgtcag cccgatcctt ggctcgattt gttgtagaca accccatcg  gtacgaacta    4020 gccctggtat atccggggga tcg                                            4043
```

<210> SEQ ID NO 96
<211> LENGTH: 4256
<212> TYPE: DNA
<213> ORGANISM: Pneumocystis carinii rRNA gene

<400> SEQUENCE: 96

```
cgaaagagag gaggtagcac cgttccgtag gtgaacctgc ggaaggatca ttaatgaaat      60
gttgtcaaga actagtttat ctggttcttg acattttcat cataacactt gtgaacatta     120
aagatttgct ttgacaggat gggagttagc tttcgtcctg tcagaggttt tcaattaaaa     180
cttttttggt gtttcggtta aaaatataat ttttaaaaac tttcagcaat ggatctcttg     240
gttcccgcgt cgatgaagaa cgtggcaaaa tgcgataagt agtgtgaatt gcagaattca     300
gtgactcatc gaattttga  acgcatattg cgctcctcag tattctgtgg agcatgcctg     360
tttgagcgtc attttttatac ttgaaccttt ttaaggtttg tgttgggcta tgcattttag    420 tattttttaca agatgctagt ctaaaatgga atccagaata ttatttcgtg cagcgtaata    480
gggttaaatt ccaattcgct gttttttagaa atgatagact ggtttgtcta ttgttcctag   540
agagcaattt ttgaaccttt gacctcaaat caggtaggat tacccgctga acttaagcat    600
atcaataagc ggaggaaaag aaactaacaa ggattccctc agtaacggcg agtgaagtgg    660
```

```
gaaaagctca aaattaaaat ctggcgagga tcctcgtccg agttgtaatt tagagaagtg    720
cttttggctt gatgctctat ttaaagtcct ttggaacaag gcatcataga gggtgataat    780
cccgtacgag tagggttatt aagctatgta aaagcacatt cgaagagtcg agttgtttgg    840
gattgcagct caaaatgggt ggtaaatttc atctaaagct aaatattagc gggagaccga    900
tagcgaacaa gtagagtgat cgaaagatga aaagaacttt gaaaagagag ttaaatagta    960
cgtgaaattg ctgaaaggga agcgcttgcg atcagacatg ccttatcagg atgttgttgt    1020
cttgacaata actattactt ggtttggcag gccaacatcg gtttcagctg ctaggtaagt    1080
gtcaagagag ggtagcctct ttcgtggggt ggttagctct tggcttctgt agtagcaggg    1140
accggaaggt ctagcgtcag cttggttgtt ggcttaatgg tcttaagcga cccgtcttga    1200
aacacggacc aaggagtcta atatctatgc gagtgtttga gtggaaaact catacgcgaa    1260
atgaaagtga agcaaaaggt aggaacccct taagggtgca ctatcgaccg gttcaaattt    1320
atttggattg agtaagagca tagctattgg gacccgaaag atggtgaact atgcctgaat    1380
agggtgaagc cagaggaaac tctggtggag gctcgtagcg gttctgacgt gcaaatcgat    1440
cgtcaaattt gggcataggg gcgaaagact aatcgaacca tctagtagct ggttcctgcc    1500
gaagtttccc tcaggatagc agaaactcaa tatcagtttt atgaggtaaa gcaatgatt    1560 agaggcattg gggttgaaac aaccttaacc tattctcaaa ctttaaatat gtaagaagtc    1620
cttgttgctt aattgaacat ggacattaga atgagagttt ctagtgggcc attttggta    1680 agcagaactg gcgatgcggg atgaaccgaa cgcgaggtta aggtgccgga agcacgctca    1740
tcagatacca caaaggtgt tagttcatct agacagtagg acggtggcca tggaagtcgg    1800
aatccgctaa ggagtgtgta acaactcacc taccgaatga actggccctg aaaatggatg    1860
gcgctcaagc gtgctaccta tacctcgccg tctgggataa tgattcctag acgagtaggc    1920
aggcgtgggg gtcgtggcga agcctagggc gtgagcccgg gttaacggc ctctagtgca    1980 gatcttggtg gtagtagcaa atattcaaat gaggactttg aagactgaag tggggaaagg    2040
ttccatgcga acagttattg ggcatgggtt agtcgatcct aagagatagg gaaactccgt    2100
tttaaagtgc gcgatttttc gcgcctctat cgaaagggaa tccggttaat attccggaac    2160
caggatatgg attcttcacg gcaacgtaaa tgaagtcgga gacgtcagcg gggggcctgg    2220
gaagagttat cttttcttct taacagccta tcaccctgga atcggtttat ccggagatag    2280
ggttcaatgg ctggtagagt tcagcacttc tgttgaatcc agtgcgcttt cgatgaccct    2340
tgaaaatccg acgaaggaa tagttttcat gcctggtcgt actcataacc gcaacaggtc    2400
tccaaggtga acagcctcta gttgatagaa taatgtagat aagggaagtc ggcaaaatag    2460
atccgtaact tcgggataag gattggctct aaggattggg tgcattggc tttaatcgga    2520 agctattgga ccagacggga actaccttgg gaaaccgagg cggatcctgt taggatcgat    2580
cagtgaatga ttttagcagc cctttgggcg tccgatgcac gcttaacaat caacttagaa    2640
ctggtacgga caagggaat ctgactgtct aattaaaaca tagcattgcg atggccagaa    2700
agtggtgttg acgcgatgtg atttctgccc agtgctctga atgtcaaagt gaagaaattc    2760
aaccaagcgc gggtaaacgg cgggagtaac tatgactcac cttttgaggg tcatgaaagc    2820
ggcgcgaaag tgttagctag tgatccgaaa aataaattcg ggttgcgaca ctgtcaaatt    2880
gcggggagtc cctaaagatt caactactaa gcagcttgtg gaaacacagt tgtggccgag    2940
ttaatagccc tgggtatagt aacaatgttg aatatgactc ttaattgagg aaatgggtga    3000
tccgcagcca aatcctaagg acattttatt gtctatggat gcagttcagc gactagacgg    3060
```

```
cagtgggtat tgtagagata tggggttatt tatggcctta tctacaatgc ttaaggtata    3120
gtctaatctc tttcgaaaga aagagtagtg tgctcttaag gtagccaaat gcctcgtcat    3180
ctgattagtg acgcgcatga atggattaac gagattccca ctgtccctat ctacgatcta    3240
gcgaaaccac agccaaggga atgggcttgg caaaatcagc ggggaaagaa gaccctgttg    3300
agcttgactc tagtttgaca ttgtgaaaag acatagagga tgtagaatag gtgggagctt    3360
cggcgcctgt gaaataccac cgcctttatt gttttttac ttaatcagtg gagcgggact    3420
gagcttttgc tcatctttta gcgttaaggt ccttttacgg gccgacccga gttgatgaca    3480
ttgtcagatg gggagtttgg ctggggcggc acatctgtca aaagataacg caggtgtcct    3540
aaggggagct cattgagaac agaaatctca agtagaataa aagggtaaaa gttcccttga    3600
ttttgatttt cagtacgaat acaaaccatg aaagtgtggc ctatcgatcc tctaaatcct    3660
cgaaatttga ggctaggggt gccagaaaag ttaccacagg gataactggc ttgtggcagc    3720
caagcgttca tagcgacgtt gcttttgat ccttcgatgt cggctcttcc tatcataccg    3780
aagcagaatt cggtaagcgt tggattgttc acccactaat agggaacgtg agctgggttt    3840
agaccgtcgt gagacaggtt agttttaccc tgctgatgaa gttatcgcaa tggtaattca    3900
gcttagtacg agaggaaccg ttgattcaga tatttggttt ttgcggttgt ctgaccaggc    3960
agtgccgcga agctatcatc tgttggatta tggctgaaag cctctaagtc agaatccatg    4020
ccagaaagcg atgatatttc ctcacgtttt ttgatacaaa taggcatctt gccaatatca    4080
gtatttggac gggtggaggc ggacggaagt gttcgtctct gtccattaat attaattaat    4140
attcgtgagg gcgaatcctt tgtagacgac ttagttgagg aacggggtat tgtaagcagt    4200
agagtagcct tgttgttacg atctgctgag attaagcctt tgttcccaag atttgt       4256

<210> SEQ ID NO 97
<211> LENGTH: 3844
<212> TYPE: DNA
<213> ORGANISM: Penicillium verrucosum rRNA gene

<400> SEQUENCE: 97
cttggtcatt tagaggaagt aaaagtcgta acaaggtttc cgtaggtgaa cctgcggaag      60
gatcattacc gagtgcgggc cctcgcggct caacctccca cccttgtctc tatacacctg     120
ttgctttggc gggccaccg gggccacctg gtcgccgggg gacgtcgtct ccgggcccgc     180
gcccgccgaa gcgctctgtg aaccctgatg aagatgggct gtctgagtac tatgaaaatt     240
gtcaaaactt tcaacaatgg atctcttggt tccggcatcg atgaagaacg cagcgaaatg     300
cgataagtaa tgtgaattgc agaattccgt gaatcatcga atctttgaac gcacattgcg     360
ccccctggca ttccggggg catgcctgtc cgagcgtcat ttctgccctc aagcacggct     420
tgtgtgttgg gtgcggtccc cccggggacc tgcccgaaag gcagcggcga cgtccgtctg     480
gtcctcgagc gtatgggct ctgtcactcg ctcgggacgg acctgcgggg gttggtcacc     540
accatatttt accacggttg acctcggatc aggtaggagt tacccgctga acttaagcat     600
atcaataagc ggaggaaaag aaaccaaccg ggattgcctc agtaacggcg agtgaagcgg     660
caagagctca aatttgaaat ctggccccctt tgggtccga gttgtaattt gcagaggatg    720
cttcgggtgc ggtccccatc taagtgccct ggaacgggcc gtcatagagg gtgagaatcc     780
cgtctgggat gggcggccgc gcccgtgtga agctccttcg acgagtcgag ttgtttggga     840
atgcagctct aagcgggtgg taaatttcat ctaaagctaa atactggccg gagaccgata     900
```

```
gcgcacaagt agagtgatcg aaagatgaaa agcactttga aaagagagtt aaacagcacg    960
tgaaattgtt gaaagggaag cgttgtccac cagactcgcc cggggggtt cagccggcac    1020
gtgtgccggt gtactcctct ccgggcgggc cagcatcggt ttgggcggct ggtgaaaggc    1080
cccgggaatg taacacccctt cggggtgcct tatagcccgg ggtgccatac agccagcctg   1140
gaccgaggcc cgcgcttcgg cgaggatgct ggcgtaatgg tggtcaacgg cccgtcttga    1200
aacacggacc aaggagtcta acatctatgc gagtgttcgg gtgtcaaacc cgtccgcgca    1260
gtgaaagcga acggaggtgg gagcccctcg gggcgcacca tcgaccgatc ctgatgtctt    1320
cggatggatt tgagtaagag catagctgtt gggacccgaa agatggtgaa ctatgcctga    1380
atagggcgaa gccagaggaa actctggtgg aggctcgcag cggttctgac gtgcaaatcg    1440
atcgtcaaat ttgggtatag gggcgaaaga ctaatcgaac catctggtag ctggttcctg    1500
ccgaagtttc cctcaggata gcagtaacga catcagtttt atgaggtaaa gcgaatgatt    1560
agaggccttg gggttgaaac aaccttaacc tattctcaaa cttaaatat gtaagaagcc     1620
cttgttgctt agttgaacgt gggcgttaga atgaaacgtt actagtgggc catttttggt    1680
aagcagaact ggcgatgcgg gatgaaccga acgcgaggtt aaggtgccgg aatgcacgct    1740
catcagacac cacaaaaggt gttagttcat ctagacagcc cgacggtggc catggaagtc    1800
ggaatccgct aaggagtgtg taacaactca cgggccgaat gaactagccc tgaaaatgga    1860
tggcgctcaa gcgtgctacc catacctcgc cgtcggggta gaaacgatgc cccgacgagt    1920
aggcaggcgt gggggtccgt gacgaagcct tgggagtgat cccgggtcga acggcccccta   1980
gtgcagatct tggtggtagt agcaaatact caaatgagaa ctttgaggac tgaagtgggg    2040
aaaggttcca tgtgaacagc agttggacat gggtgagtcg atcctaagac atagggtagt    2100
tccgtttgaa agtgcgccct cgtgcgccgt ccgtcgaaag gaagccggt taatattccg     2160
gcacctggat gtggattctc cacggcaacg taactgaacg cggagacatc ggcgggggtc    2220
ctgggaagag ttctcttttc ttcttgacag cctatcaccc tgaaatcggt ttgtccggag    2280
ctagggttcc acggctggca gagctcggca cctttgccgg gtccggtgcg ccccccgacga   2340
tccttgaaaa tccgcgggaa ggaatagttt tcacgccagg tcgtactcat aaccgcagca    2400
ggtctccaag gtgaacagcc tctagttgat agaacaatgt agataaggga agtcggcaaa    2460
atggatccgt aacttcggga taaggattgg ctctaagggt cggcacgtt gggccttggg     2520
gggaagcccc tggagcaggt gggcactagc cgggcaaccg gccggcgccc gccagcatcg    2580
ggtggtggac gcccttggca ggcttcggcc gtccggcgtg cgcttaacga ccaacttaga    2640
actggtacgg acaaggggaa tctgactgtc taattaaaac atagcattgt gatagccaga    2700
aagtggtatt gacacaatgt gatttctgcc cagtgctctg aatgtcaaag tgaagaaatt    2760
caaccaagcg cgggtaaacg gcgggagtaa ctatgactct cttaaggtag ccaaatgcct    2820
cgtcatctaa ttagtgacgc gcatgaatgg attaacgaga ttcccactgt ccctatctac    2880
tatctagcga aaccacagcc aagggaacgg gcttggcaga atcagcgggg aaagaagacc    2940
ctgttgagct tgactctagt ttgacattgt gaaaagacat atgggtgta gcataggtgg      3000
gagcttcggc gccagtgaaa taccactacc tttatcgttt ttttacttat tcaatgaagc    3060
ggaactgggc ttcaccgccc aatttctagc gttaaggtcc ttcgcgggcc gatccgggtt    3120
gaagacattg tcaggtgggg agtttggctg ggcggcaca tctgttaaac cataacgcag     3180
gtgtcctaag ggggrctcat ggagaacaga aatctccagt agaacaaaag ggtaaaagtc    3240
cccttgattt tgattttcag tgtgaataca aaccatgaaa gtgtggccta tcgatccttt    3300
```

```
agtccctcga matttgaggc tagaggtgcc agaaaagtta ccacagggat aactggcttg      3360
tggcggccaa gcgttcatag cgacgtcgct ttttgatcct tcgatgtcgg ctcttcctat      3420
cataccgaag cagaattcgg taagcgttgg attgttcacc cactaatagg gaacgtgagc     3480
tgggtttaga ccgtcgtgag acaggttagt tttaccctac tgatgacctc accgcaatgg     3540
taattgagct tagtacgaga ggaaccgctc attcagataa ttggttttg cggctgtccg      3600 accgggcagt gccgcgaagc taccatctgc tggataatgg ctgaacgcct ctaagtcaga     3660
atccatgcca gaacgcggtg atagcacccg cacgtataga cggacaagaa taggcttcgg    3720
cttagtgtct cagcaggcga ttcctccgtg gtcctcgaag cgggccgcgg tatttcgcgt    3780
attgtaattt caacacgagc ggggttaaat cctttgcaga cgacttagct gtgcgaaacg    3840
gtcc                                                                  3844
```

<210> SEQ ID NO 98
<211> LENGTH: 4026
<212> TYPE: DNA
<213> ORGANISM: Pichia stipitis rRNA gene

<400> SEQUENCE: 98

```
cttggtcatt tagaggaagt aaaagtcgta acaaggtttc cgtaggtgaa cctgcggaag       60
gatcattaca gtattctttt tgccagcgct taactgcgcg gcgaaaaaac cttacacaca      120
gtgttttctt tattagaaac tattgctttg gtctggctca gaaatgagtt gggccagagg      180
tttaccaaac ttcaattttta ttgaattgtt attttattaa tttgtcaatt tgttgattaa    240
attcaaaaat cttcaaaact ttcaacaacg gatctcttgg ttctcgcatc gatgaagaac     300
gcagcgaaat gcgataagta atatgaattg cagattttcg tgaatcatcg aatctttgaa    360
cgcacattgc gcccttggt attccaaagg gcatgcctgt ttgagcgtca tttctctctc     420
aaaccctcgg gtttggtatt gagtgatact cttagtcgaa ctaggcgttt gcttgaaaag   480
tattggcacg agtggtacta aatagtactg acagaatatt tcaatgtatt aggttttatcc  540 aactcgttga gacttctggc ggtgaatttt tggtatattg gctttgcctt acaaaacaac    600
aaacaagttt gacctcaaat caggtaggat tacccgctga acttaagcat atcaataagc    660
ggaggaaaag aaaccaacag ggattgcctt agtaacggcg agtgaagcgg caaaagctca    720
aatttgaaat ctggcacctt cggtgtccga gttgtaattt gaagaaggta actttggagt    780
cagctcttgt ctatgttcct tggaacagga cgtcacagag ggtgagaatc ccgtgcgatg    840
agatgtctga ttctatgtaa agtgcttccg aagagtcgag ttgtttggga atgcagctct    900
aagtgggtgg taaattccat ctaaagctaa atattggcga gagaccgata gcgaacaagt    960
acagtgatga aagatgaaa agaactttga aagagagtg aaaagtacg tgaaattgtt       1020 gaaagggaag ggtttgagat cagacttggt attttgtatg tcttgctttc gggtggggcc    1080
tctacagttt actgggccag catcggtttg gacggtagga taatgacatt ggaatgtggc    1140
accacttcgg tggtgtgtta tagactttgt tgatactgcc tgtctagacc gaggactgcg    1200
tctttgacta ggatgctggc ataatgatct taaccgcccc gtcttgaaac acggaccaag    1260
gagtctaacg tctatgcaag tgtttgggtg taaaacccgt acgcgtaatg aaagtgaacg    1320
taggtgagag ctcttttgag tgcatcatcg accgatcctg atgtcttcgg atggatttga    1380
gtaagagcat agctgttggg acccgaaaga tggtgaacta tgcctgaata gggtgaagcc    1440
agaggaaact ctggtggagg ctcgtagcgg ttctgacgtg caaatcgatc gtcgaatttg    1500
```

```
ggtataggggg cgaaagacta atcgaaccat ctagtagctg gttcctgccg aagtttccct   1560
caggatagca gaagctcgta tcagttttat gaggtaaagc gaatgattag aggtcttggg   1620
gttgaaatga ccttaaccta ttctcaaact ttaaatatgt aagaagtcct tgttgcttaa   1680
ttgaacgtgg acatatgaat gaagagcttt tagtgggcca tttttggtaa gcagaactgg   1740
cgatgcggga tgaaccgaac gtgaagttaa agtgccggaa tacacgctca tcagacacca   1800
caaaaggtgt tagttcatct agacagccgg acggtggcca tggaagtcgg aatccgctaa   1860
ggagtgtgta acaactcacc ggccgaatga actagccctg aaaatggatg gcgctcaagc   1920
gtgttactta tacttcaccg tcaggggtga tatgatgccc tgacgagtag gcaggcgtgg   1980
aggtcagtga cgaagccttt gctgtaaagc tgggtagaac ggcctctagt gcagatcttg   2040
gtggtagtag caaatattca aatgagaact ttgaagactg aagtggggaa aggttccatg   2100
tcaacagcag ttggacatgg gttagtcgat cctaagagat ggggaagctc cgtttcaaag   2160
atttgatttt tcaagtcacc atcgaaaggg aatccggtta aaattccgga acttggatat   2220
ggattcttca cggtaacgta actgaatgtg agacgtcgg cgtgagccct gggaggagtt   2280
ctctttcctt cttaacagct tatcaccctg gaattggttt atccggagat agggtcttat   2340
ggctggaaga gtgcaatact tttgttgcat ccggtgcgct tacgacggtc cttgaaaatc   2400
cacaggaagg aatagttttc atgccaagtc gtactcataa ccgcagcagg tctccaaggt   2460
taacagcctc tagttgatag aataatgtag ataagggaag tcggcaaaat agatccgtaa   2520
cttcgggata aggattggct ctaaggatcg ggtgtcttgg gcctttacca gacgcagcgg   2580
aactggtggt ggactgttct tccttgtgtt aacggaccg ctaccggatc ttgctgtaga   2640
cggtttaggt aggcttcggc cgtccggggc acgcttaacg atcaacttag aactggtacg   2700
gacaagggga atctgactgt ctaattaaaa catagcattg cgatggtcag aaagtgatgt   2760
tgacgcaatg tgatttctgc ccagtgctct gaatgtcaaa gtgaagaaat tcaaccaagc   2820
gcgggtaaac ggcgggagta actatgactc tcttaaggta gccaaatgcc tcgtcatcta   2880
attagtgacg cgcatgaatg gattaacgag attcccactg tccctatcta ctatctagcg   2940
aaaccacagc caagggaacg ggcttggcag aatcagcggg gaagaagac cctgttgagc   3000 ttgactctag tttgacattg tgaaaagaca tggagggtgt agaataagtg ggagcttcgg   3060
cgccggtgaa ataccactac ctctatagtt ttttttactta ttcaattaag cggagctgga   3120
cttcatcgtc cacgttctag cattaaggtc tctttagagg ctgatccggg ttgaagacat   3180
tgtcaggtgg ggagtttggc tggggcggca catctgttaa acgataacgc aggtgtccta   3240
agggggactc atggagaaca gaaatctcca gtagaacaaa agggtaaaag tccccttgat   3300
tttgattttc agtgtgaata caaaccatga aagtgtggcc tatcgatcct ttagtccctc   3360
ggaatttgag gctagaggtg ccagaaaagt taccacaggg ataactggct tgtggcagtc   3420
aagcgttcat agcgacattg ctttttgatt cttcgatgtc ggctcttcct atcataccga   3480
agcagaattc ggtaagcgtt ggattgttca cccactaata gggaacgtga gctgggttta   3540
gaccgtcgtg agacaggtta gttttacccct actgatgaat gttatcgcaa tagtaattga   3600
acttagtacg agaggaaccg ttcattcgga taattggttt ttgcggctgt ctgatcaggc   3660
aacgccgcga agctaccatc cgctggatta tggctgaacg cctctaagtc agaatccatg   3720
ctagaaagcg atgattcttg cctcgcacat tttagttgga taagaataag gctctttgag   3780
tcgctgaacc atagcaggct ggcaatggta cacttaacgg aaaggttttg tgtgcttgcc   3840
ggcgaatagc aatgtcataa tgcgcgggga taaatccttt gcaaacgact taaatgtaca   3900
```

```
acggagtatt gtaagcagta gagtagcctt gttgttacga tctgctgaga ttaagcttca    3960
gttgtccgat ttgtttgtgt tacacaacac aatctcctct aagtgatagt tggcaggtgc    4020
taacta                                                                4026
```

<210> SEQ ID NO 99
<211> LENGTH: 4051
<212> TYPE: DNA
<213> ORGANISM: Rhizomucor miehei rRNA gene

<400> SEQUENCE: 99

```
gactggcaac ggtccgaagc tttagccgaa ctatggcaaa ctactccatt tagaggaagt      60
aaaagtcgta acaaggtttc cgtaagtgaa cctgcggaag gatcattaaa aaaaagttga     120
tatcatggtg acccctttac gggggtgagc catgatttct tctccctttt tgtgcaatgt     180
ttgagggatt gctccaaatc tctccttccc ttttttacg  tattgatttg actgaacatt     240
tttgttttaa aatgaaaaaa agttttgaag ccaatcaatt ggttcaagac aaatcaaatt     300
ttgaaacaac tttaagcaat ggatcacttg gttctcgcat cgatgaagaa cgtagcaaat     360
tgcgaaaagt aatgcgatct gcaacctttg cgaatcatcg aattctcgaa cgcatcttgc     420
accctttggt catccaatgg gtacgtctag ttcagtatct ttttgaaacc ctaaaggttc     480
aattttgttg ttgacctttg gatttgcggt aatgatgggg gggaagacaa agcaaatttt     540
ttttttttcc cccgttaaaa gaaacggaac agttttttggg ttttttggcct ttttggattg    600 gggaacattt tggaagggct tactttgaaa ataaaaaatt tggaattttg ggttaccatt     660
gctttgggaa aacccaattt aaaagcaaaa actttttttta aactttttttt tttttcattc    720 atggatctga acttagacgg gactacccgc tgaacttaag catatcaata agcgaggaa      780 aagaaaataa caatgatacc cttagtagcg gcgagcgaag tgggtaaagc tcaagtttaa     840
aacctgtttg tcatagacaa accggattgt aaactatgga catgttatcc aggctctttg     900
gaccttcaag tcctttggaa taaggcttca cagagggtga caatcccgtt agagggtctt     960
gaacagagtc tattgcgatg catgctccaa gagtcaagtt gtttgggaat gcaacctaaa    1020
ttgcagggta aatccctcct aaagctaaat attggcgaga accgatagc  aaacaagtac    1080 cgtgagggaa agttgaaaag aactttgaaa agagagtcaa aagtacgtga aattgcttaa    1140
agggaagcgt ttggagctag tttggctagt ctgttatcag cctgagcttc ggctttggtg    1200
tactatcagg ctattttgc  cggccaactc tcaggattga aggaaagct  tggtgctttg    1260 gagtctaaag agaccctctc ctgaagcctc tggtggagcg tggtctgccc ttggcccttt    1320
tgagcctata gtttggctta atggctctaa acggcccgtc ttgaaacacg gccaaggag     1380 tccaccactg ttgcgagtat tttggtggca aacccatacg cgaaatgaaa ttgaaagcta    1440
tgaaatccgc aaggatggca atagcgtcca ggcctttagg accgagacaa agcaatagtg    1500
atgggacccg aaagatggtg aactatgctt gagtagagtg aagccagaag aaattctggt    1560
ggaagctcgt aacggttctg acgtgcaaat cgatcgtcga acttgagcat aggggcgaaa    1620
gactaatcga accatctagt agcatggttc ctgccgaagt ttccctcagg atagcagaag    1680
cttataggca gttttatgtg gtaaagcgaa tgattagagg tctgggacg  caatccttaa    1740 cctattctca aactttaaat atgtaagacg ttcttgctgc ttgaattatg agcttgaacc    1800
gtcgaatgct gagcttctag tgggccgttc ttggtaagca ggactggcga tgcgggatga    1860
accgaacgca aagataaggc gtcaaagaac acgctcatca gacaccacaa aaggtgttgg    1920
```

```
ttcatctaga cagcaggacg gtggccatgg aagtcggcta aggagtgtgt aacaactcac    1980
ctgccgaatg aaccacgccc tggaaataaa tggcgctgaa gcgtgtcgcc catactttcc    2040
cgtcaaagtt aaaagcgaag cttttgacgag taggcaggcg tggagtttta ttgagcgttg   2100 gaacccttg gcggtgagcc ggagtggaca gccctctagt gcagatcttg gtggtagtag    2160
caaatattcc aattgaaatc tttgaggact gaagtggaga aggtttcctc gagaacatta   2220
gttggtcgag ggttagtcga tcctaagaga tagggtagtt ccgttttacc aaatggtcct   2280
ttggaccatc ctatcgaaag ggaagctggt taatattcca gcaccaagac atggattcta   2340
tgcggcaacg cagatgaaca tagggacatt ggcatggatc ctgggaagag ttctctttc    2400 tttttgacag cgttttctta agccatgaaa tcggtctaaa ccggggcaat gtttgcttaa   2460
gagctgttag agtaacgcaa ttttgtggt agccacagca ttcatgacga tccttgaaga    2520
cctacgggaa agaatgaatt tcatgcttgg gcgtaccata accgcagcag gtccccaagg   2580
tctagaagcc tctacttgat ggaagaatgt agataaggga agtcggcaaa ttggatccgt   2640
aacttcggga gaaggattgg ctctaagggt tgggtgcttt aagaaccatg gccttagcgg   2700
cctgagcaat cgggctgctt ccaggcttgg agctcttggg cacgcttaac aaccagctta   2760
gaactggtac ggaccaaggg aatctgactg tctaattaaa acatagcatt gcgattgcca   2820
taaagtggta ttgacgcaat gtgatttctg cccagtgctc tgaatgtcaa gttgaataaa   2880
ttcaaccaag cgcgggtaaa ccgcgggtat tactatgaga gctttgtgat atagtccaag   2940
tttctagaac tgctaattag tgacgcgcat gaatggatta acgagattcc cactgtccct   3000
atctactatc cagcgaaacc acaaccaagg gaacgggctt ggcaaaatca gcgggaaaga   3060
agcgccagtt gagcttgact ctagtttgac attgtgaaag gacataggggg tgtagaatat   3120 gtgggagctt cggcgccagt gaataccaca acccttatag tttttttac ttaaataatc    3180 aagtgggaga aggcttcacg gcctatcttc tagcgttaag cagtcttcgg gctgcgaccc   3240
atgttattga cattgtcaag tggggagttt ggctggggcg gcacatctgt taaacgataa   3300
cgcaggtgtc ctaaggggag ctcaacgaga acagaaatct cgtgtagagc aaaagggcaa   3360
aagctccctt gattttgatt ttcagcgtga atacgaacca tgaaagtgtg gcctatcgat   3420
cctttatgcc atttccttag gatttaaggc gccagaaaag ttaccacagg gataactggc   3480
ttgtggcagc caagcgttca tagcgacgtt gcttttgat tcttcgatgt cggctcttcc    3540
tatcatacag aagcagaatt ctgtaagcgt tggattgttc acccactaat agggaacgtg   3600
agctgggttt agaccgtcgt gagacaggtt agttttaccc tactgatgaa tcagtaggcg   3660
tcccgacagt aattgaagtt agtacgagag gaacccttca ttcagataat tggttttgc    3720 ggttggttga aaggccaatg ccgcgaagct accatctgct ggataatggc tgaaagcctc   3780
taagtcagaa tccatgctgg ttaagggacg ctaaaaccag acctttaaag cgcgagaaag   3840
tgctcaaata gatctcttat gggatcgaat gcctaatatg aggttatcct cttgggttga   3900
aaggctcaag tcggatacct ctcatgataa tgtctagctt aaaggttgta aatctcgagc   3960
agacgacttg aaatcgacgg gctattgtaa gcactagagt agcctttgtt gctacgatgt   4020
gctgagatta aggccttgtc tttagatttg t                                  4051
```

<210> SEQ ID NO 100
<211> LENGTH: 4061
<212> TYPE: DNA
<213> ORGANISM: Rhizopus oryzae rRNA gene

<400> SEQUENCE: 100

```
ctaggctatt tagaggaagt aaaagtcgta acaaggtttc cgtaggtgaa cctgcggaag      60
gatcattaat tatgttaaag cgccttacct cttagggttt cctctggggt aagtgattgc     120
ttctacactg tgaaaatttg gctgagagac tcagactggt catgggtaga cctatctggg     180
gtttgatcga tgccactcct ggtttcagga gcacccttca taataaacct agaaattcag     240
tattataaag tttaataaaa aacaactttt aacaatggat ctcttggttc tcgcatcgat     300
gaagaacgta gcaaagtgcg ataactagtg tgaattgcat attcagtgaa tcatcgagtc     360
tttgaacgca gcttgcactc tatggttttt ctatagagta cgcctgcttc agtatcatca     420
caaacccaca cataacattt gtttatgtgg taatgggtcg catcgctgtt ttattacagt     480
gagcacctaa aatgtgtgtg attttctgtc tggcttgcta ggcaggaata ttacgctggt     540
ctcaggatct ttttctttgg ttcgcccagg aagtaaagta caagagtata atccagcaac     600
tttcaaacta tgatctgaag tcaggtggga ttacccgctg aacttaagca tatcaataag     660
cggaggaaaa gaaaataaca atgatttccc tagtaacggc gagtgaagag aaagagctc     720 aaagttggaa cctgtttggc ctagctaaac cggattgtag actgtagaag tgttttccag     780
gcaagccgag taaataagtc ctttggaaca gggcatcata gagggtgaga atcccgtctt     840
tggcttgagc atttgccttt tgtgatacgc tttcaaagag tcaggttgtt tgggaatgca     900
gcctaaattg ggtggtaaat ctcacctaaa gctaaatatt ggcgagaaac cgatagcgaa     960
caagtaccgt gagggaaaga tgaaaagaac tttgaaaaga gagttaaaca gtatgtgaaa    1020
ttgttaaaag gaaccgtttt ggagccgact tggcttgtct gtaatcaatc taggcttcgg    1080
cctggatgca cttgcaggct atgcctgcca acgacaattt gacttgaggg aaaaaactaa    1140
gggaaatgtg gcccacttgt gggtgttata gtcccttaga aaatacctt ggttggattg    1200 aggaacgcag cgaatgcttt ttggcgagtt ttccaggaag gttttctgag gtactacggt    1260
atcaaggttg atctttttgg ttatacttct attcgcttag gttgttggct taatgactct    1320
aaatgacccg tcttgaaaca cggaccaagg agtccaccat tagtgcgagt atttgggtgc    1380
caaacccata tgcgtaagga aactgattga tacgaatcca ttaaggaggc agtatcgtcc    1440
ggcgctgacg ttttatactg aattgaccga gacaaagcac taatgatggg acccgaaaga    1500
tggtgaacta tgcctgaata gggtgaagcc agaggaaact ctggtggagg ctcgtagcga    1560
ttctgacgtg caaatcgatc gtcaaatttg gtatagggg cgaaagacta atcgaaccat    1620
ctagtagctg gttcctgccg aagtttccct caggatagca gaaacttata cgcagtttta    1680
tgtggtaaag cgaatgattg gggtcacggg ggctaaacg cccttcaacc actctcaaac    1740
tttaaatatg taagacgacc tgtttgctta attgaagcag gtcattgaat gcagagtttc    1800
tagtgggcca ttttttggtaa gcagaactgg cgatgcggga tgaaccgaac gcagagttaa    1860
ggtgccggaa tacacgctca tcagacacca caaaaggtgt tagttcatct agacagcagg    1920
acggtggcca tggaagtcgg aatccgctaa ggagtgtgta acaactcacc tgccgaatga    1980
actagccctg aaaatggatg cgcttaagc gtgttaccca tactctgccg ttattgtaaa    2040
agcgaagcaa taacgagtag gcaggcgtgg aggtttttat aaactgttaa gaagctcttg    2100
gtgtgaaccg gagtgaaaca gcctctagtg cagatcttgg tggtagtagc aaatattcaa    2160
atgagaactt tgaagactga agtggagaaa ggttcctgga gaacatcagt tggtccaggg    2220
ttagtcgatc ctaagagata gggaagttcc gttttttcaa agcgcccaat ttttgggccg    2280
cctatcgaaa gggaaaccgg ttaatattcc ggtactagga cgaggatttt ttgcggcaac    2340
```

| | | | | |
|---|---|---|---|---|
| gcgattgaac | ttggagacat | cagtatgggt | cccgggaaga | gttatctttt | cttttttgaca | 2400 |
| gttagtataa | accttgaaat | ctgtttagca | ggagaaaagg | tttatctgct | ggtagagcac | 2460 |
| agtactttt | gctgtgtccg | gtgcattcat | aacgatcctt | gaaaatccaa | gggaaagaat | 2520 |
| aattttctcg | cctagtcgta | ctcataaccg | cagcaggtct | ccaaggtgaa | aagcctctag | 2580 |
| ttgatagaac | aatgtagata | agggaagtcg | gcaaaataga | tccgtaactt | cggaataagg | 2640 |
| attggctcta | agggttgggt | agaaatggac | ccttggtatt | gaccttgagg | aagagagaat | 2700 |
| gggggcaact | ctgttctttc | atcttcttgg | tctacaacca | agggaaccca | gtctacgctt | 2760 |
| aacaaccaac | ttagaactgg | tacggacaag | gggaatctga | ctgtctaatt | aaaacatagc | 2820 |
| attgcgatgg | ccagaaagtg | gtgttgacgc | aatgtgattt | ctgcccagtg | ctctgaatgt | 2880 |
| caaagtgaag | aaattcaacc | aagcgcgggt | aaacggcggg | agtaactatg | actctcttaa | 2940 |
| ggtagccaaa | tgcctcgtca | tctaattagt | gacgcgcatg | aatggattaa | cgagattccc | 3000 |
| actgtcccta | tctactatct | agcgaaacca | cagccaaggg | aacgggcttg | gcagaatcag | 3060 |
| cggggaaaga | agaccctgtt | gagcttgact | ctagtttgac | attgtgaaaa | gacatagagg | 3120 |
| gtgtagcata | agtgggagct | tcggcgccag | tgaaatacca | ctacctctat | tgttttttta | 3180 |
| cttaaataat | taagtgggat | tgagtcgcaa | gactcacctt | ctagctttaa | gcatccatta | 3240 |
| gggtgcgacc | catgttattg | acattgtcaa | gtggggagtt | tggctggggc | ggcacatctg | 3300 |
| ttaaaagata | acgcaggtgt | cctaagggg | actcaaggag | aacagaaatc | tcctgtagaa | 3360 |
| taaagggta | aaagtcccct | tgattttgat | tttcagtgtg | aatacaaacc | atgaaagtgt | 3420 |
| ggcctatcga | tcctttagaa | tctcaagatt | tgaggctaga | ggtgccagaa | aagttaccac | 3480 |
| agggataact | ggcttgtggc | agccaagcgt | tcatagcgac | gttgcttttt | gattcttcga | 3540 |
| tgtcggctct | tcctatcata | atgaagcaga | attcattaag | tgttggattg | ttcacccact | 3600 |
| aatagggaac | gtgagctggg | tttagaccgt | cgtgagacag | gttagttttta | ccctactgat | 3660 |
| ggtattggta | tcgcaacagt | aattgaagtt | agtacgagag | gaacccttca | ttcagataat | 3720 |
| tggtatttgc | ggctggttga | aaggccaatg | ccgcgaagct | accatctgct | ggataatggc | 3780 |
| tgaacgcctc | taagtcagaa | tccatgctgg | aagcgatact | actgtgcttt | gattgtacta | 3840 |
| gttgtgtaca | aataaagctt | cggcttgaaa | accttacttg | cgggataggc | tttgcagcgg | 3900 |
| aaatgctgtg | attcactacc | ctgtgatgat | aatgcaaatg | atcaaagtga | taatcgcat | 3960 |
| gcagacgaca | tgaaatggac | ggggtattgt | aagtactaga | gtagcctttg | ttgctacgat | 4020 |
| gtactgagat | taagcccttg | tcattgaatt | tgttccttac | g | | 4061 |

<210> SEQ ID NO 101
<211> LENGTH: 4230
<212> TYPE: DNA
<213> ORGANISM: Saccharomyces cerevisiae rRNA gene

<400> SEQUENCE: 101

| | | | | | | |
|---|---|---|---|---|---|---|
| ggtcatttag | aggaactaaa | agtcgtaaca | aggtttccgt | aggtgaacct | gcggaaggat | 60 |
| cattaaagaa | atttaataat | tttgaaaatg | gatttttttg | ttttggcaag | agcatgagag | 120 |
| cttttactgg | gcaagaagac | aagagatgga | gagtccagcc | gggcctgcgc | ttaagtgcgc | 180 |
| ggtcttgcta | ggcttgtaag | tttctttctt | gctattccaa | acggtgagag | atttctgtgc | 240 |
| ttttgttata | ggacaattaa | aaccgtttca | atacaacaca | ctgtggagtt | ttcatatctt | 300 |
| tgcaactttt | tctttgggca | ttcgagcaat | cggggcccag | aggtaacaaa | cacaaacaat | 360 |
| tttatctatt | cattaaattt | ttgtcaaaaa | caagaatttt | cgtaactgga | aattttaaaa | 420 |

```
tattaaaaac tttcaacaac ggatctcttg gttctcgcat cgatgaagaa cgcagcgaaa    480
tgcgatacgt aatgtgaatt gcagaattcc gtgaatcatc gaatctttga acgcacattg    540
cgccccttgg tattccaggg ggcatgcctg tttgagcgtc atttccttct caaacattct    600
gtttggtagt gagtgatact ctttggagtt aacttgaaat tgctggcctt ttcattggat    660
gttttttttc caaagagagg tttctctgcg tgcttgaggt ataatgcaag tacggtcgtt    720
ttaggtttta ccaactgcgg ctaatctttt tttatactga gcgtattgga acgttatcga    780
taagaagaga gcgtctaggc gaacaatgtt cttaaagttt gacctcaaat caggtaggag    840
tacccgctga acttaagcat atcaataagc ggaggaaaag aaaccaaccg ggattgcctt    900
agtaacggcg agtgaagcgg caaaagctca aatttgaaat ctggtacctt cggtgcccga    960
gttgtaattt ggagagggca actttggggc cgttccttgt ctatgttcct tggaacagga   1020
cgtcatagag ggtgagaatc ccgtgtggcg aggagtgcgg ttctttgtaa agtgccttcg   1080
aagagtcgat tgtttggga atgcagctct aagtgggtgg taaattccat ctaaagctaa   1140
atattggcga gagaccgata gcgaacaagt acagtgatgg aaagatgaaa agaactttga   1200
aaagagagtg aaaaagtacg tgaaattgtt gaagggaag gcatttgat cagacatggt    1260 gttttgtgcc ctctgctcct tgtgggtagg ggaatctcgc atttcactgg gccagcatca   1320
gttttggtgg caggataaat ccataggaat gtagcttgcc tcggtaagta ttatagcctg   1380
tgggaatact gccagctggg actgaggact gcgacgtaag tcaaggatgc tggcataatg   1440
gttatatgcc gcccgtcttg aaacacggac caaggagtct aacgtctatg cgagtgtttg   1500
ggtgtaaaac ccatacgcgt aatgaaagtg aacgtaggtt ggggcctcgc aagaggtgca   1560
caatcgaccg atcctgatgt cttcggatgg atttgagtaa gagcatagct gttgggaccc   1620
gaaagatggt gaactatgcc tgaataggt gaagccagag gaaactctgg tggaggctcg   1680
tagcggttct gacgtgcaaa tcgatcgtcg aatttgggta taggggcgaa agactaatcg   1740
aaccatctag tagctggttc ctgccgaagt ttccctcagg atagcagaag ctcgtatcag   1800
ttttatgagg taaagcgaat gattagaggt tccggggtcg aaatgacctt gacctattct   1860
caaactttaa atatgtaaga agtccttgtt acttaattga acgtggacat ttgaatgaag   1920
agcttttagt gggccatttt tggtaagcag aactggcgat gcgggatgaa ccgaacgtag   1980
agttaaggtg ccggaataca cgctcatcag acaccacaaa aggtgttagt tcatctagac   2040
agccggacgg tggccatgga agtcggaatc cgctaaggag tgtgtaacaa ctcaccggcc   2100
gaatgaacta gccctgaaaa tggatggcgc tcaagcgtgt tacctatact ctaccgtcag   2160
ggttgatatg atgccctgac gagtaggcag gcgtggaggt cagtgacgaa gcctagaccg   2220
taaggtcggt cgaacggcc tctagtgcag atcttggtgg tagtagcaaa tattcaaatg    2280
agaactttga agactgaagt ggggaaaggt tccacgtcaa cagcagttgg acgtgggtta   2340
gtcgatccta agagatgggg aagctccgtt tcaaaggcct gattttatgc aggccaccat   2400
cgaaagggaa tccggttaag attccggaac ctggatatgg attcttcacg gtaacgtaac   2460
tgaatgtgga gacgtcggcg cgagccctgg gaggagttat cttttcttct taacagctta   2520
tcaccccgga attggtttat ccggagatgg ggtcttatgg ctggaagagg ccagcacctt   2580
tgctggctcc ggtgcgcttg tgacggcccg tgaaaatcca caggaaggaa tagttttcat   2640
gccaggtcgt actgataacc gcagcaggtc tccaaggtga acagcctcta gttgatagaa   2700
taatgtagat aagggaagtc ggcaaaatag atccgtaact tcgggataag gattggctct   2760
```

```
aagggtcggg tagtgagggc cttggtcaga cgcagcgggc gtgcttgtgg actgcttggt      2820
ggggcttgct ctgctaggcg gactacttgc gtgccttgtt gtagacggcc ttggtaggtc      2880
tcttgtagac cgtcgcttgc tacaattaac gatcaactta gaactggtac ggacaagggg      2940
aatctgactg tctaattaaa acatagcatt gcgatggtca gaaagtgatg ttgacgcaat      3000
gtgatttctg cccagtgctc tgaatgtcaa agtgaagaaa ttcaaccaag cgcgggtaaa      3060
cggcgggagt aactatgact ctcttaaggt agccaaatgc ctcgtcatct aattagtgac      3120
gcgcatgaat ggattaacga gattcccact gtccctatct actatctagc gaaaccacag      3180
ccaagggaac gggcttggca gaatcagcgg ggaaagaaga ccctgttgag cttgactcta      3240
gtttgacatt gtgaagagac atagagggtg tagaataagt gggagcttcg gcgccagtga      3300
aataccacta cctttatagt ttctttactt attcaatgaa gcggagctgg aattcatttt      3360
ccacgttcta gcattcaagg tcccattcgg ggctgatccg ggttgaagac attgtcaggt      3420
ggggagtttg gctggggcgg cacatctgtt aaacgataac gcagatgtcc taagggggc      3480 tcatggagaa cagaaatctc cagtagaaca aaagggtaaa agccccttg attttgattt      3540 tcagtgtgaa tacaaaccat gaaagtgtgg cctatcgatc ctttagtccc tcggaatttg      3600
aggctagagg tgccagaaaa gttaccacag ggataactgg cttgtggcag tcaagcgttc      3660
atagcgacat tgctttttga ttcttcgatg tcggctcttc ctatcatacc gaagcagaat      3720
tcggtaagcg ttggattgtt cacccactaa tagggaacgt gagctgggtt tagaccgtcg      3780
tgagacaggt tagttttacc ctactgatga atgttaccgc aatagtaatt gaacttagta      3840
cgagaggaac agttcattcg gataattggt ttttgcggct gtctgatcag gcattgccgc      3900
gaagctacca tccgctggat tatggctgaa cgcctctaag tcagaatcca tgctagaacg      3960
cggtgatttc tttgctccac acaatataga tggatacgaa taaggcgtcc ttgtggcgtc      4020
gctgaaccat agcaggctag caacggtgca cttggcggaa aggccttggg tgcttgctgg      4080
cgaattgcaa tgtcattttg cgtggggata aatcatttgt atacgactta gatgtacaac      4140
ggggtattgt aagcagtaga gtagccttgt tgttacgatc tgctgagatt aagcctttgt      4200
tgtctgattt gtttttttatt tctttctaag                                      4230

<210> SEQ ID NO 102
<211> LENGTH: 4096
<212> TYPE: DNA
<213> ORGANISM: Schizosaccharomyces japonicus rRNA gene

<400> SEQUENCE: 102
atttagagga agtaaaagtc gtaacaaggt ttccgtaggt gaacctgcgg aaggatcatt        60
agaaagtaat tatttgagtt ttcaacattc acctgctgaa ctctcaaaaa atctctctat       120
atctttctgt gaacatgttt tcatatgaga atgtttggtc agtcggtcga aaggttggtt       180
ggccaagcat ttgaactata aacttcattt tatatttgat gtctgattta tatttaacta       240
aatgttaaaa ctttcagcaa cggatctctt ggctctcgca tcgatgaaga acgcagcgaa       300
atgcgatacg taatgtgaat tgcagaattc cgtgaatcat cgaatctttg aacgcacatt       360
gcgcctttgg gttattccca aaggcatgcc tgtttgagtg tcattacatt cttcttaaat       420
ctaacttttt gttatgggtt aaggtgttga actataatcg cgaaagcaga tttggttttta      480 aatttaaagg tagattatgg agatgcttca gcaattcgtt aagcacgcat attcatattt       540
gaacgtaata ggttttacca actcgttcaa gttcattgat tgtgttgtgt gagttgctat       600
agtaagcatt atcgaactaa tccttaatgt ctttcgagac tacattcatt tgaatgtact       660
```

```
cctttgtttg acctcagatc aggtaggact acgcgctgaa cttaagcata tcaataagcg    720
caggacaaga aaataaccat gattcccta gtaacggcga gtgaagcggg aaaagctcaa     780
atttgaaatc tggcaaagtt ttattctttg cccgagttgt aatttcaaga agctgctttg    840
agtattgcta cgtcggtcta agttcctgg aacaggacgt cagagagggt gagaaccccg     900
tctttggccg atgtgctttg ccatataaag cgctttctaa gagtcgagtt gtttgggaat    960
gcagctctaa atgggtggtg aatttcatct aaagctaaat attggcgaga gaccgatagc   1020
gaacaagtag agtgatcgaa agatgaaaag aactttgaaa agagagttaa atagtacgtg   1080
aaattgctga aggggaagca ttggaaacca gtcttacctt ggtgagatca gctgtttact   1140
tgtagacagt gcactctgaa cctaggtagg tcagcatcag ttttcgggga cggaaaaaga   1200
ataagggaaa gtggcttttg ggcttgctca gaagtgttat agcccttatt gtaatacgcc   1260
cactggggac tgaggtctgc gactttgtca aggatgctga cataatggtt ttcaatggcc   1320
cgtcttgaaa cacggaccaa ggagtctagc atctatgcga gtgtttgggt ggctaaaccc   1380
atacgcgaaa tgaaagtgaa tgcaggtggg aacttttgt gcaccaccgg ccgatccgga    1440
agtttgtcaa tggaaggatt tgagcaagag catagctgtt gggacccgaa agatggtgaa   1500
ctatgcctga atagggcgaa gccagaggaa actctggtgg aggctcgtag cggttctgac   1560
gcgcaaatcg atcgtcaaat ttgggtatag gggcgaaaga ctaatcgaac catctagtag   1620
ctggttcctg ccgaagtttc cctcaggata gcagaaactc agatcagttt tatgaggtaa   1680
agcgaatgat tagaggcctt ggggaagtaa tttcctcaac ctattctcaa actttaaata   1740
tgtaagacgc ccttgtcgct taattggacg tgggctttcg aatgagagtt tctagtgggc   1800 cattttggt aagcagaact ggcgatgcg gatgaaccga acgcgaggtt aaggtgccgg      1860
aatgcacgct catcagacac cagaaaaggt gttagttcat ctagacagca ggacggtggc   1920
catggaagtc ggaatccgct aaggagtgtg taacaactca cctgccgaat gaactagccc   1980
tgaaaatgga tggcgcttaa gcgtgctacc catacctcgc cgtctgggtt aattatgaag   2040
cttagacgag taggcaggcg tggaggtcag tgacgaagcc ttgggcgtaa gcctgggtcg   2100
aacggcctct agtgcagatc ttggtggaag tagcaaatat tcaaatgaga actttgaaga   2160
ctgaagtggg gaaaggttcc atgtgaacag cagttggaca tgggttagtc gatcctaaga   2220
gatagggaag ctccgtttga aagtacacga ttcttcgtgt cacctatcga aagggaatcc   2280
ggttaatatt ccggaaccag gatgtggatt ctccacggca acgtaaatga agttggagac   2340
gtcggtggga gccctgggaa gagttctctt ttcttttaa caaaccaatc accctgaaat    2400
cggtttatcc ggagctaggg tatagtgttt ggtagagctc agcgcctctg ctgggtccgg   2460
tgcgctctca acgcccttg aaaatccaac ggaaggaata gttttcacgc ctggtcgtac    2520
tcataaccgc agcaggtctc caaggtgaac agcctctagt tgatagaaca atgtagataa   2580
gggaagtcgg caaaatagat ccgtaacttc gggataagga ttggctctaa gggttgggta   2640
cgttgggcct tggttttgaa caattgctgg actggttagg aactgtctga cttccccgga   2700
agacggatag atcttgacta gaccttggca gttgggatgg ccttggtaag gcctctactt   2760
tgtagagtgt ccctcactgg cgtacgctta acaaccaact agaactggt acggacaagg    2820 ggaatctgac tgtctaatta aaacatagca ttgcgatggc cagaaagtgg tgttgacgca   2880
atgtgatttc tgcccagtgc tctgaatgtc aaagtgaaga aattcaacca agcgcgggta   2940
aacggcggga gtaactatga ctctcttaag gtagccaaat gcctcgtcat ctaattagtg   3000
```

```
acgcgcatga atggattaac gagattccca ctgtccctat ctactatcta gcgaaaccac    3060
agccaaggga acgggcttgg caaaatcagc ggggaaagaa gaccctgttg agcttgactc    3120
tagtttgaca ttgtgaagag acatagaggg tgtagcataa gtgggagctt cggcgccagt    3180
gaaataccac tacctttata gtttctttac ttaatcaatg aagcgaatt ggaattcatt     3240 ttccacattc tagcgttaaa gttctttacg aaccgatccg tgttgatgac attgtcaggt    3300
ggggagtttg gctggggcgg cacatctgtt aaaagataac gcaggtgtcc taaggggac     3360 tcatcgagaa cagaaatctc gagtagaaca aaagggtaaa agtccccttg attttgattt    3420
tcagtgtgaa tacaaaccat gaaagtgtgg cctatcgatc ctttagtccc tcgaaattcg    3480
aggatagagg tgccagaaaa gttaccacag ggataactgg cttgtggcag ccaagcgttc    3540
atagcgacgt tgcttttga tccttcgatg tcggctcttc ctatcatacc gaagcagaat     3600
tcggtaagcg ttggattgtt cacccactaa tagggaacgt gagctgggtt tagaccgtcg    3660
tgagacaggt tagttttacc ctactgatga atgtcgtcgc aatggtaatt caacttagta    3720
cgagaggaac cgttgattca gataattggt atttgcggct gcctgacaag gcaatgccgc    3780
gaagctatca tctgccggat aacggctgaa cgcctctaag tcagaatccg tgccagaaag    3840
cgacgatacc ttattccgcg catctttggt gcatacaaat agagctttgc tcctgtatcg    3900
tataaggtgg gcgatggcta gtagaacgga aatgttttat tagtttgtcc acgaaattcc    3960
attgaaaatt tgtgcggagt cgaatccttt gcatacgact taaatgtgga acggggtatt    4020
gtaagcagta gagtagcctt gttgttacga tctgctgaga ttaagccttt gttcccaaga    4080
tttgttctat aagaac                                                    4096

<210> SEQ ID NO 103
<211> LENGTH: 4446
<212> TYPE: DNA
<213> ORGANISM: Schizosaccharomyces pombe rRNA gene

<400> SEQUENCE: 103
catttagagg aagtaaaagt cgtaacaagg tttccgtagg tgaacctgcg gaaggatcat     60
tagaaaagtt atatgaaaag gttttaaaaa atttccatct tttaactttt tgggaatttt    120
ttttaccttt tcttctctct atccatttac cttttctgtga aaatgtaaaa tattttcaat    180 tttgatttt ttttcttttt ctttatattt ttttattaaa aaaaagtgtt tagaaaagag     240
aaaagatgaa aaaaaaatg aaattgtaaa tattacgagt ggatgatttt tgtttggtgt     300 gttttgttg catgccaagc atatcattac ttttttacta ttttatttta ttttatcatt    360
tttctattct ttctcttttt tttaatatata aggaaattgg aaaagaagca aaattaaatt    420
ataaaccttg aaatttgttt ttgaagtctg aattaattat atctaatata taaaattatt    480
taaaactttc agcaacggat ctcttggctc tcgcatcgat gaagaacgca gcgaaatgcg    540
atacgtaatg tgaattgcag aattccgtga atcatcgaat ctttgaacgc acattgcgcc    600
tttgggttct accaaaggca tgcctgtttg agtgtcatta caatcttctc acaaaaaatg    660 tttttttta atatttttg atgaggtgtt gaacgaaaat tgtttttttt tttaaaatat    720
aaatttagtt tgaaatcgat tggtgaaaac aaaaggaaga ttgaaattat ttttctatgc    780
cttttttcat tttttttcta ttgaacgtaa taggttttac cactttgttt gatagaaaaa    840
aagaaattag gaaagaaaaa taactaaaaa gttttaatct cttttatatt tgaaccttaa    900
cgaaaaaaaa agttatttt ttttcacagt acctttttta tttgacctca aatcaggtag     960
gactacgcgc tgaacttaag catatcaata agcgcaggaa aagaaaataa ccatgattcc    1020
```

```
ctcagtaacg gcgagtgaag cgggaaaagc tcaaatttga aatctggcaa catttctttt    1080
gttgtccgag ttgtaatttc aagaagctgc tttgagtgta gacgatcggt ctaagttcct    1140
tggaacagga cgtcagagag ggtgagaacc ccgtctttgg tcgattggat atgccatata    1200
aagcgctttc gaagagtcga gttgtttggg aatgcagctc taaatgggtg gtaaatttca    1260
tctaaagcta aatattggcg agagaccgat agcgaacaag tagagtgatc gaaagatgaa    1320
aagaactttg aaaagagagt taaatagtac gtgaaattgc tgaaagggaa gcattggaaa    1380
tcagtcttac ctgggtgaga tcagtagtct cttcgcgaga ctatgcactc tgaacctgtg    1440
gtaggtcagc atcagttttc gggggcggaa aaagaataag ggaaggtggc tttccgggtt    1500
ctgcctgggg agtgtttata gcccttgttg taatacgtcc actggggact gaggactgcg    1560
gcttcgtgcc aaggatgctg acataatggt tttcaatggc ccgtcttgaa cacggacca    1620
aggagtctag catctatgcg agtgtttggg tgatgaaaac ccatccgcga aatgaaagtg    1680
aatgcaggtg ggaacgccct tgtggcgtgc accatcgacc gacccggaag tttgtcaatg    1740
gaagggtttg agtaagagca tagctgttgg gacccgaaag atggtgaact atgcctgaat    1800
agggtgaagc cagaggaaac tctggtggag gctcgtagag attctgacgt gcaaatcgat    1860
cttcaaattt gggtataggg gcgaaagact aatcgaacca tctagtagct ggttcctgcc    1920
gaagtttccc tcaggatagc agaaactcag atcagtttta tgaggtaaag cgaatgatta    1980
gaggtcttgg ggaaggaatt tcctcaacct attctcaaac tttaaatatg taagacgccc    2040
ttgtcgctta attggacgtg ggccatcgaa tgagagtttc tagtgggcca ttttttggtaa   2100
gcagaactgg cgatgcggga tgaaccgaac gtgaggttaa ggtgccggaa tgtacgctca    2160
tcagacacca gaaaaggtgt tagttcatct agacagcagg acggtggcca tggaagtcgg    2220
aatccgctaa ggagtgtgta acaactcacc tgccgaatga actagccctg aaaatggatg    2280
gcgcttaagc gtactaccca tacctcaccg tctgggttag ctttgagaag ctcagacgag    2340
taggcaggcg tggaggtttg tgacgaagcc ttgggcgtga gcctgggtcg aacagcctct    2400
agtgcagatc ttggtggaag tagcaaatat tcaaatgaga actttgaaga ctgaagtggg    2460
gaaaggttcc atgtgaacag cagttggaca tgggttagtc gatcctaaga gatagggaag    2520
ctccgtatga aagttgcacg atttttcgtg cctcctatcg aaagggaatc cggttaatat    2580
tccggaacca gaaggtggaa tcaacacggc aacgtaaatg aagttggaga cgtcggcggg    2640
agccctggga agagttctct tttcttttta acaaaccatt gaactaccct gaaatcggtt    2700
tatccggagc tagggtatgg tgtttggaag agttcagcgc tcatgctgaa tccggtgcg    2760
ctctcgacgg cccttgaaaa tccaacggaa gaatggacct tcgggtcctt gttttcacat    2820
ctggtcgtac tcataaccgc agcaggtctc caaggtgaac agcctctagt tgatagaaca    2880
atgtagataa gggaagtcgg caaaatggat ccgtaacttc gggataagga ttggctctaa    2940
gggttgggta cgttgggcct tggaacctga acgttgctg gactgagcgt ggaccgatgt    3000
ctttctcgc ctttcggggt gagaagggat gttggacctg cttggacctt ggcggccggg    3060
aagtccttgg tcgggctttt ctccttctcg gggattatgc tcttactggc gtacgtttaa    3120
caaccaactt agaactggta cggacaaggg gaatctgact gtctaattaa acatagcat    3180
tgcgatggcc agaaagtggt gttgacgcaa tgtgatttct gcccagtgct ctgaatgtca    3240
aagtgaagaa attcaaccaa gcgcgggtaa acggcgggag taactatgac tctcttaagg    3300
tagccaaatg cctcgtcatc taactagtga cgcgcatgaa tggattaacg agattcccac    3360
```

| | |
|---|---|
| tgtccctatc tactatctag cgaaaccaca gcctgggaa cgggccaggc aaaatcagcg | 3420 |
| gggaaagaag accctgttga gcttgactct agtttgacat tgtgaagaga catagagggt | 3480 |
| gtaggataag tgggagtatg tttcggcata cgccggtgaa ataccactac ctttatcgtt | 3540 |
| tctttactta atcaatgaag cggaattggg atttatttcc catattctag cgttaaagtt | 3600 |
| tcttcgcgaa ctgatccgcg ttgatgacat tgtcaggtgg ggagtttggc tggggcggca | 3660 |
| catctgttaa aagataacgc aggtgtccta aggggactc atcgagaaca gaaatctcga | 3720 |
| gtagaataaa agggtaaaag tccccttgat tttgattttc agtgtgaata caaaccatga | 3780 |
| aagtgtggcc tatcgatcct tgttccctc gaaatttgag gacagaggtg ccagaaaagt | 3840 |
| taccacaggg ataactggct tgtggcagcc aagcgttcat agcgacgttg cttttttgatt | 3900 |
| cttcgatgtc ggctcttcct atcataccga agcagaattc ggtaagcgtt ggattgttca | 3960 |
| cccactaata gggaacgtga gctgggttta daccgtcgtg agacaggtta gttttaccct | 4020 |
| actgatgaag tgtcgtcgca atggtaattc aacttagtac gagaggaacc gttgattcag | 4080 |
| atcattggta tttgcggctg cctgacaagg caatgccgcg gagctatcat ctgccggata | 4140 |
| acggctgaac gcctctaagc cagaatccgt gccagaaagc gacgattttt tggtccgcat | 4200 |
| gatttatatg tataaaaata gaggtaggac ttgttcctac tctcctgtat cgtagaagat | 4260 |
| gggcgatggt tgatgaaacg gaagtgtttt attgacttgt ccatgaaatt ccattgaaat | 4320 |
| cttgtgcgga atcgaatcca ttgcatacga ctttaatgtg gaacgggta ttgtaagcag | 4380 |
| tagagtagcc ttgttgttac gatctgctga gattaagcct ttgttcccaa gatttgttcc | 4440 |
| attaag | 4446 |

<210> SEQ ID NO 104
<211> LENGTH: 4821
<212> TYPE: DNA
<213> ORGANISM: Sclerotinia sclerotiorum rRNA gene

<400> SEQUENCE: 104

| | |
|---|---|
| ttagaggaag taaaagtcgt aacaaggttt ccgtaggtga acctgcggaa ggatcattac | 60 |
| agagttcatg cccgaaaggg tagacctccc acccttgtgt attattactt tgttgctttg | 120 |
| gcgagctgct cttcggggcc ttgtatgctc gccagagaat atcaaaactc tttttattaa | 180 |
| tgtcgtctga gtactatata atagttaaaa cttttcaacaa cggatctctt ggttctggca | 240 |
| tcgatgaaga acgcagcgaa atgcgataag taatgtgaat tgcagaattc agtgaatcat | 300 |
| cgaatctttg aacgcacatt gcgcccttg gtattccggg gggcatgcct gttcgagcgt | 360 |
| catttcaacc ctcaagctca gcttggtatt gagtccatgt cagtaatggc aggctctaaa | 420 |
| atcagtggcg gcgccgctgg gtcctgaacg tagtaatatc tctcgttaca ggttctcggt | 480 |
| gtgcttctgc caaaacccaa attttctatg gttgacctcg gatcaggtag ggatacccgc | 540 |
| tgaacttaag catatcaata agcggaggaa aagaaaccaa cagggattac ctcagtaacg | 600 |
| gcgagtgaag cggtaaaagc tcaaatttga aatctggctc tttcagagtc cgagttgtaa | 660 |
| tttgtagaag atgcttcggg tgtggttccg gtctaagttc cttggaacag gacgtcatag | 720 |
| agggtgagaa tcccgtatgt gactggatac ctatgctcat gtgaagctct ttcgacgagt | 780 |
| cgagttgttt gggaatgcag ctcaaaatgg gtggtatatt tcatctaaag ctaaatattg | 840 |
| gccagagacc gatagcgcac aagtagagtg atcgaaagat gaaaagcact ttggaaagag | 900 |
| agttaaacag tacgtgaaat tgttgaaagg gaagcgcttg caatcagact tgcacttggt | 960 |
| gttcatcagg gtttcgtgcc ctgtgtactt catcaagttc aggccagcat cagtttgagt | 1020 |

```
ggttagataa aggcttggag aatgtggccc tcttcggggg gtgttatagc tccaggtgca   1080
atgtagccta cttggactga ggaccgcgct tcggctagga tgctggcgta atggttgtaa   1140
gcgacccgtc ttgaaacacg gaccaaggag tgtacctaat atgcgagtgt ttgggtgtta   1200
aacccatacg cgtaatgaaa gtgaacgctg gtgagaaccc ttaagggtgc atcatcgacc   1260
gatcttgatg tcttcggatg gatttgagta agagcatatt gggtgcgacc cgaaagatga   1320
tgatctatac gtgaataggg tgaagccaga ggaaactctg gtggaggctc gcagcggttc   1380
tgacgtgcaa atcgatcgtc aaatttgcgt ataggggcga agactaatc gaatcattaa    1440 ggaatagacc aagctctagg tgattgagaa acctcctttg gggtattagt cctggagaca   1500
gggcgacatt gtcaaattgt tcggggacca cctgttaaat tatatgctac tgcagcagtg   1560
ctgaaaggcc tgtgagcact gagggtaacg ccctcaggga tggtaataac gcatatatag   1620
ggtatatccg cagcgaagtt ctaaggcttt cgagctatga atcgcgttca cagactagac   1680
ggcaatgggc tcctcgcggg gcttaagata tagtcgaacc cctcagagat gaggatggaa   1740
tcaatgctag tagctggttc ctgccgaagt ttccctcagg atagcagtgt tgttttcagt   1800
tttatgaggt aaagcgaatg attagaggcc ttggggttga aacaaccta acctattctc    1860 aaactttaaa tatgtaagaa gtccttgtta cttaattgaa cgtggacatt cgaatgtacc   1920
aacactagtg ggccattttt ggtaagcaga actggcgatg cgggatgaac cgaacgcgag   1980
gttaaggtgc cggaatatac gctcatcaga caccacaaaa ggtgttagtt catctagaca   2040
gcaggacggt ggccatggaa gtcggaatcc gctaaggaat gtgtaacaac tcacctgccg   2100
aatgaactag ccctgaaaat ggatggcgct taagcgtatt acccatacct cgccgccagg   2160
gtagaaacta tgccctggcg agtaggcagg cgtggaggtt gtgacgaagc cttgggagtg   2220
atcccgggta gaacagcctc tagtgcagat cttggtggta gtagcaaata ctcaaatgag   2280
aactttgagg actgaagtgg ggaaaggttc catgtgaaca gcagttggac atgggttagt   2340
cgatcctaag agatagggaa actccgtttt aaagtgcgca cttgtgcgcc gtccctcgaa   2400
agggaaaccg gttaatattc cggtacctgg atttggattc tccacggcaa cgtaactgaa   2460
cgcggagacg acggcggggg ccccgggaag agttctcttt tcttcttaac agcctatcac   2520
cctgaaatcg gtttgtccgg agctagggtt taacggttgg tagagctcga cacctctgtc   2580
gggtccggtg cgctctcgac gtcccttgaa aatccgcggg aaggaatagc tttcaagcca   2640
ggtcgtactc ataaccgcat gcaggtgctc caaggtgaac agcctctagt tgatagaaca   2700
atgtagataa gggaagtcgg caaaatagat ccgtaacttc gggaaaagga ttggctctaa   2760
gggttgggta cgttgggcca ttaggggatg ctcttggagc agaggagcac tagcttcacg   2820
gccggcgctc ttcagcatcg agggtttgac gcttttggca ggcttcggtc gtccggcgta   2880
caattaacaa ccaacttaga actggtacgg acaaggggaa tctgactgtc taattaaaac   2940
atagcattgc gatggccaga aagtggtgtt gacgcaatgt gatttctgcc cagtgctctg   3000
aatgtcaaag tgaagtaatt caaccaagcg cgggtaaacg gcgggagtaa ctatgactca   3060
accctaagag ggtcgtaaga ggggatgcga atagcattcc tttagtgatg agatcgcaac   3120
actgtcaaat tgcggggagt tcctaaagct caggctaccg cctcaggtgc tgaaaagccc   3180
tgaaggcacc aaggttagca accttgggta tggtaataac gcctgtagat actacaatgg   3240
atgatccgca gccaagctct aacaatcttt tcacgattca cgagcggggt tcaacgacta   3300
gacggcagtg ggcctgcaaa acaggtttaa gatatagtct gcgcctaggg aaaaatccca   3360
```

```
aggaaataag tgctcttaag gtagccaaat gcctcgtcat ctaattagtg acgcgcatga      3420
atggattaac gagattccca ctgtccctat ctactatcta gcgaaaccac agccaaggga      3480
acgggcttgg cagaatcagc ggggaaagaa gaccctgttg agcttgactc tagtttgaca      3540
ttgtgaaaag acataggggg tgtagaatag gtgggagcgc aagcgccggt gaaataccac      3600
tacccttatc gttttttttac ttattcaata aagcggaact gggtgtcaaa gcccaacttc      3660
tagcattaag gtccttcgcg ggctgatccg ggttgaagac attgtcaggt ggggagtttg      3720
gctggggcgg cacatctgtt aaaccataac gcaggtgtcc taaggggggac tcatggagaa      3780 cagaaatctc cagtagaaca aaagggtaaa agtccccttg attttgattt tcagtgtgaa      3840
tacaaaccat gaaagtgtgg cctatcgatc ctttagtccc tcgaaatttg aggctagagg      3900
tgccagaaaa gttaccacag ggataactgg cttgtggcag ccaagcgttc atagcgacgt      3960 tgcttttttga tccttcgatg tcggctcttc ctatcatacc gaagcagaat tcggtaagcg      4020
ttggattgtt cacccactag accttattgg tgggaaaaag atcttattga tcacttagtc      4080
gagtcaccca caactattgc gggcggtgac cggcgagaca acctggttcg ggggaggctg      4140
taaaatgcta atctcgagtg cagtctgctg ggagtgatcc ctacaagacg cacgtaacgc      4200
gcggaaaggt gtcggttgcc tcttttacag agggagctta tgggacgtgc taaacctatc      4260
cgaaaggata acactgatct aagggcccgc agcctggagt ttagtgtgac cgtcaagagc      4320
ctgggaggaa atgcccaagg tcaggttggt atattaatga atagggaacg tgagctgggt      4380
ttagaccgtc gtgagacagg ttagttttac cctactgatg accgtcgccg caatggtaat      4440
tcagcttagt acgagaggaa ccgctgattc agataattgg ttttttgcggc tgtctgacaa      4500 ggcagtgccg cgaagctacc atctgctgga taatggctga acgcctctaa gtcagaatcc      4560
atgccagaaa gcggtgattt atcccacac atcgtagtcg gatacgaata ggcctttggc      4620
cctgaatctt agctggctgg taacgatcct attgaagaaa ctctttagga ttaactggcg      4680
tcttgcaatt ttacaatgcg tggggttgaa tcctttgcat acgacttaat tgtgctacac      4740
ggtcctgtaa gtagtagagt agccttgttg ttacgatcta ctgagggtaa gccgtctcgt      4800
agcctagatt tgattttcaa t                                                4821

<210> SEQ ID NO 105
<211> LENGTH: 3911
<212> TYPE: DNA
<213> ORGANISM: Stagonospora nodorum rRNA gene

<400> SEQUENCE: 105
tttagaggaa gtaaaagtcg taacaaggtt tccgtaggtg aacctgcgga aggatcatta       60
cactcagtag tttactactg taaaagggggc tgttagtctg tatagcgcaa gctgatgagc      120
agctggcctc ttttatccac ccttgtcttt tgcgtaccca cgtttcctcg gcaggcttgc      180
ctgccggttg gacaaattta taaccttttt aattttcaat cagcgtctga aaaacttaat      240
aattacaact ttcaacaacg gatctcttgg ttctggcatc gatgaagaac gcagcgaaat      300
gcgataagta gtgtgaattg cagaattcag tgaatcatcg aatctttgaa cgcacattgc      360
gccccttggt attccatggg gcatgcctgt tcgagcgtca tttgtaccct caagctctgc      420
ttggtgttgg gtgtttgtcc tctccctagt gtttggactc gccttaaaat aattggcagc      480
cagtgttttg gtattgaagc gcagcacaag tcgcgattcg taacaaacac ttgcgtccac      540 aagcctttttt aactttgac ctcggatcag gtagggatac ccgctgaact taagcatatc      600
aataagcgga ggaaaagaaa ccaacaggga ttgccctagt aacggcgagt gaagcggcaa      660
```

```
cagctcaaat ttgaaatctg gctctttcag agtccgagtt gtaatttgca gagggcgctt      720
tggcgttggc agcggtccaa gttctttgga acaggacgtc acagagggtg agaatcccgt      780
acgtggtcgc tagccttcgc cgtgtaaagc cccttcgacg agtcgagttg tttgggaatg      840
cagctctaaa tgggaggtaa atttcttcta aagctaaata ctggccagag accgatagcg      900
cacaagtaga gtgatcgaaa gatgaaaagc actttggaaa gagagtcaaa tagcacgtga      960
aattgttgaa agggaagcgc ttgcagccag acttgcctgt agttgcttat ctggactttt     1020
gtccagtgca ctcttctgcg ggcaggccag catcagtttg ggcggttgga taaaggtctc     1080
tgtcatgtac ctccttccgg ggaggcctta taggggagac gacatgcaac cagcctggac     1140
tgaggtccgc gcatctgcta ggatgctggc gtaatggctg taagcggccc gtcttgaaac     1200
acggaccaag gagtctaaca tctatgcgag tgtttgggtg tcaagcccag acgcgtaatg     1260
aaagtgaacg gaggtgggaa ccttttaggt gcaccatcga ccgatcctga tgtcttcgga     1320
aggatttgag taagagcata gctgttggga cccgaaagat ggtgaactat gcttgaatag     1380
ggtgaagcca gaggaaactc tggtggaggc tcgcagcggt tctgacgtgc aaatcgatcg     1440
tcaaatttgg gcatagggc gaaagactaa tcgaactatc tagtagctgg ttcctgccga     1500
agtttccctc aggatagcag taacgtattc agttttatga ggtaaagcga atgattagag     1560
gcctgggggt tgaaacaacc ttcacctatt ctcaaacttt aaatatgtaa gaagtccttg     1620
ttacttgatt gaacgtggac acttgaatgt accgttacta gtgggccatt tttggtaagc     1680
agaactggcg atgcgggatg aaccgaacgc ggggttaagg tgccagaata tacgctcatc     1740
agacaccaca aaaggtgtta gttcatctag acagcaggac ggtggccatg gaagtcggaa     1800
tccgctaagg agtgtgtaac aactcacctg ccgaatgaac tagccctgaa aatggatggc     1860
gctcaagcgt attacccata ccccgccgcc ggggcagaat ttatgccccg gcgagtaggc     1920
aggcgtggag gctcgtgacg aagccttggg ggtgaccccg ggtcgaacgg cctctagtgc     1980
agatcttggt ggtagtagca aatactcaaa tgagaacttt gaggactgaa gtggggaaag     2040
gttccgtgtg aacagcagtt ggacacgggt tagtcgatcc taagagatag ggtagttccg     2100 tttttaatgtt ggcgcttgcg ccacgccctc gaaagggaag ccggttaaca ttccggcacc     2160
tggatgtaga ttctccgcgg caacgcaact gagagcggag accttggcgg gagcccaag     2220 aagagttctc ttttcttctt aacggtcgtg caccctgaaa tcggtttgtc cggagctagg     2280
gttcaatggc cggaagagcg ctgcactttt gtggcgtttg gtgcgctccc gacgagcctt     2340
gaaaatccgc ttgaagaaat agtttttacg ccaggtcgta ctcataaccg cagcaggtct     2400
ccaaggtgaa aagcctctag ttgatagaac aatgtagata agggaagtcg gcaaaataga     2460
tccgtaactt cgggaaaagg attggctcta agggttgggt acgttgggcc ttggagagaa     2520
gcctctggcg cagaagggca ctagccgcaa ggtgggcgcc tttcagcgct ggggtgcggg     2580
catccttggc aggcttcggc cgtccggcgt acgtttaaca accaacttag aactggtacg     2640
gacaagggga atctgactgt ctaattaaaa catagcattg cgatggccag aaagtggtgt     2700
tgacgcaatg tgatttctgc ccagtgctct gaatgtcaaa gcgaagagat tcgaccaagc     2760
gcgggtaaac ggcgggagta actatgactc tcttaaggta gccaaatgcc tcgtcatcta     2820
attagtgacg cgcatgaatg gattaacgag attcccactg tccctatcta ctatctagcg     2880
aaaccacagc caagggaacg ggcttggcca aatcagcggg gaaagaagac cctgttgagc     2940
ttgactctag tttgacattg tgaaaagaca taggggggtgt agaataggtg ggagcttcgg     3000
```

| | |
|---|---|
| cgccggtgaa ataccactac ccttatcgtt tttttactta ttcgatgaag cggagctggg | 3060 |
| cctcaccgcc caacttctag cgttaaggtc cttcgtgggc cgatccgggt tgaagacatt | 3120 |
| gtcaggtggg gagtttggct ggggcggcac atctgttaaa ccataacgca ggtgtcctaa | 3180 |
| gggggactca tggagaacag aaatctccag tagagcaaaa gggcaaaagt ccccttgatt | 3240 |
| ttgattttca gtgtgaatac aaaccatgaa agtgtggcct atcgatcctt tagtccctcg | 3300 |
| aaatttgagg ctagaggtgc cagaaaagtt accacaggga taactggctt gtggcagcca | 3360 |
| agcgttcata gcgacgttgc tttttgatcc ttcgatgtcg gctcttccta tcataccgaa | 3420 |
| gcagaattcg gtaagcgttg gattgttcac ccactaatag ggaacgtgag ctgggtttag | 3480 |
| accgtcgtga gacaggttag ttttacccta ctgatgacct tgccccaatg gtaataccgc | 3540 |
| ttagtacgag aggaaccgcg gtttcagata attggttttt gcggctgtct gaccaggcat | 3600 |
| tgccgcgaag ctaccatctg ctggattatg gctgaacgcc tctaagtcag aatccatgcc | 3660 |
| agaacgggt gatttccgcc tgcaccagtc ggatacgaat aggcctttgg cccagaacct | 3720 |
| taccagatca gcgttggcag tctcattgaa attgggctg ctagctggtg tattgcaatt | 3780 |
| gtacagtgcg caggattgaa tcctttgcag acgacttagt tgtctagccg ggtcgtgtaa | 3840 |
| gtagtcgagt agccttgttg ttacgagcta ctgagcgtaa gcccgatgct agcttggttg | 3900 |
| aatatgggaa t | 3911 |

<210> SEQ ID NO 106
<211> LENGTH: 3636
<212> TYPE: DNA
<213> ORGANISM: Umbilicaria esculenta rRNA gene

<400> SEQUENCE: 106

| | |
|---|---|
| cttggtcatt tagaggaagt aaaagtcgta acaaggtttc cgtaggtgaa cctgcggaag | 60 |
| gatcattaaa gagatagggc cctctctggg cccgaccctc aaccctttg tctaccttac | 120 |
| cttcgttgct ttggcgggcc cgctggggat gacccaccgc cggcgccagc cggtgagcgc | 180 |
| ccgccggagg ccatcaaaac tccgtctgtc ggtgctgtct gagtacccca caatcgttaa | 240 |
| aactttcaac aacggatctc ttggttctgg catcgatgaa gaacgcagcg aaatgcgata | 300 |
| agtaatgtga attgcagaat tcagtgaatc atcgaatctt tgaacgcaca ttgcgccccc | 360 |
| tggtattccg gggggcatgc ctgttcgagc gtcattacaa ccctcaagct ctgcttggta | 420 |
| ttgggctttc accccctccc cggggggggcg tgcctgaaag tgagtggcgg tgcagcctga | 480 |
| cttcaagcgt agtaacttca aaacccgctt cggaagcctt tcaggttggg ccggccagac | 540 |
| agcccaacat tatttctatg gttgacctcg gatcaggtag ggataccgc tgaacttaag | 600 |
| catatcaata agcggaggaa agaaaccaa cagggattgc ctcagtaacg gcgagtgaag | 660 |
| cggcaacagc tcaaatttga aatctggccc ccccgggtc cgagttgtaa tttgtagagg | 720 |
| atgcttcggg tgcggcgccg gtctaagttc cttggaacgg gacgtcatag agggtgagaa | 780 |
| tcccgtatgt gaccggtgac ccagcccgtg tgaagctcct tcgacgagtc gagttgtttg | 840 |
| ggaatgcagc tctaaatggg tggtaaattt catctaaagc taaataccgg ccagagaccg | 900 |
| atagcgcaca gtagagtga tcgaaagatg aaaagcactt tggaaagaga gttaaaaagt | 960 |
| acgtgaaatt gttgaaaggg aagcgcttgc gaccagactt gctcgggggt gatcagccgt | 1020 |
| ccttctgggc ggcgcactcg cccacgatcg ggccagcatc ggttcaggcg gccggataaa | 1080 |
| ggccccggga acgtggctcc ctccggggga gtgttacagc ccggggtgca atgcggccag | 1140 |
| cccggaccga ggaccgcgct tcggctagga tgctggcgta atggtcgcaa gcgacccgtc | 1200 |

```
ttgaaacacg gaccaaggag tctaacatct atgcgagtgt ttgggtgtca aacccatgcg    1260
cgcaatgaaa gtgaacggag gtgggaaccc tccagggtgc accatcgacc gatcctgatg    1320
tcttcggatg gatttgagta agagcatagc tgttgggacc cgaaagatgg tgaactatgc    1380
ctgaataggg tgaagccaga ggaaactctg gtggaggctc gcagcggttc tgacgtgcaa    1440
atcgatcgtc aaatttgggt ataggggcga aagactaatc gaaccatcta gtagctggtt    1500
cctgccgaag tttccctcag gatagcagta acgttttcag ttttatgagg taaagcgaat    1560
gattagaggc cttggggttg aaacaacctt aacctattct caaactttaa atatgtaaga    1620
agtcctcgtt gctcatttga acgtggacat ttgaatgcac cgttactagt gggccatttt    1680
tggtaagcag aactggcgat gcgggatgaa ccgaacgcga ggttaaggtg ccggaatgca    1740
cgctcatcag acaccacaaa aggtgttagt tcatctagac agccggacgg tggccatgga    1800
agtcggaacc cgctaaggag tgtgtaacaa ctcaccggcc gaatgaacta gccctgaaaa    1860
tggatggcgc tcaagcgtgc tacccatacc tcgccgccag ggtagaaacg atgccctggc    1920
gagtaggcag gcgtgggggt cggtgacgaa gcctcggggg tgatcccggg tcgaacggcc    1980
cctaatgcag atcttggtgg tagtagcaaa tactcaaatg agaactttga ggactgaagt    2040
ggggaaaggt tccatgtgaa cagcagttgg acatgggtta gtcgatccta agagatcgg    2100 aaactccgtt ttaaagcgcg cactcgtgcg ccgtccctcg aaagggaagc cggtcaacat    2160
tccggcacct ggatgtggat tctccacggc aaagtaaccg aacgcggaga cgtcggcggg    2220 ggcccccggga agagttctct tttcttctta acggcccatc accctgaaat cggtttgtcc    2280
ggagctaggg tttaacggcc ggtagagccc cacacctttg tggggtccgg tgcgctcccg    2340
acgacccttg aaaatccgcg ggaaggaata gttttcacgc caggtcgtac tcataaccgc    2400
agcaggtctc caaggtgaaa agcctctagt tgatagaaca atgtagataa gggaagtcgg    2460
caaaatagat ccgtaacttc gggaaaagga ttggctctaa gggttgggtg cgttgggcct    2520 tgggggatg ccccggagc aggtgggcac tagccgggca accggccggc gccctccagc    2580
atcgggcggc ggacgcccgt ggcaggtttc ggccgtccgg cgcacgctta acgaccgact    2640
tagaactggt acgacaagg ggaatctgac tgtctaatta aaacatagca ttgcgatggc    2700
cagaaagtgg tgttgacgca atgtgatttc tgcccagtgc tctgaatgtc aaagtgaaga    2760
aattcaaata agcgcgggta acggcgggga gtaactatga ctctcttaag gtagccaaat    2820
gcctcgtcat ctaattagtg acgcgcatga atggattaac gagattccca ctgtccctat    2880
ctactatcta gcgaaaccac agccaaggga acgggcttgg cggaatcagc ggggaaagaa    2940
gaccctgttg agcttgactc tagtttgaca ttgtgaaaag acataggggg tgtagaatag    3000
gtgggagctt cggcgccgt gaaataccac tacccttatc gttttttac ttattcaatg    3060 aagcggaact gggttttacc gcccaacttc tggcgtcaag gtccctcgcg ggccgatccg    3120
ggttgaagac attgtcaggt ggggagtttg gctgggggcgg cacatctgtt aaaccataac    3180
gcaggtgtcc taagggggac tcatggagaa cagaaatctc cagtggaaca aaagggtaaa    3240
agtccccttg attttgattt tcagtgtgaa tacaaaccat gaaagtgtgg cctatcgatc    3300
ctttagtccc tcgaaatttg aggctagagg tgccagaaaa gttaccacag gataactgg    3360 cttgtggcag ccaagcgttc atagcgacgt tgcttttga tccttcgatg tcggctcttc    3420
ctatcatacc gaagcagaat tcggtaagcg ttggattgtt cacccactaa tagggaacgt    3480
gagctgggtt tagaccgtcg tgagacaggt tagttttacc ctactgatga ccgtcaccgc    3540
```

```
aacggtaatt caacttagta cgagaggaac cgttgattca gataattggt ctttgcggct    3600
gtctgaccag gcagtgccgc gaagctaccc ttcttt                              3636

<210> SEQ ID NO 107
<211> LENGTH: 3996
<212> TYPE: DNA
<213> ORGANISM: Uncinocarpus reesii rRNA gene

<400> SEQUENCE: 107
ttggtcattt agaggaagta aaagtcgtaa caaggtttcc gtaggtgaac ctgcggaagg      60
atcattacag tggtttcggg ccgtgccgtt tccccgctcg gggggcgcgc ggcctgcacc     120
tcccacccat gtttacttga aacccttcgt tgccttggca ggactgccgc ttgtcggctg     180
ccggggacct gcagccatgc agcccgggcg agtgcctgcc agaggactat ttgaaccta     240 agtgaagatt gacagtctga gtattctagc aagaataagt taaaacttct aacaacggat     300
ctcttggttc cagcatcgat gaagaacgca gcgaaatgcg ataagtaatg tgaattgcag     360
aattccgtga atcatcgaat ctttgaacgc acattgcgcc cctggtatt ccgggggca     420 tgcctgtccg agcgtcattg caaatccttc aagcacggct tgtgtgttgg actgcgtccc     480
cgatggtgtg gacgagtctg aaatgcagtg gcggcgccga gttcctggtg tctgagtgta     540
tgggaaatct ctctttgctc aaagacccga tcggtaccga ccgtagatct ttctttccgg     600
tttgacctcg gatcaggtag gagtacccgc tgaacttaag catatcaata agcggaggaa     660
aagaaaccaa cagggattgc ctcagtaacg gcgagtgaag cggcaaaagc tcaaatttga     720
aatctggccc cgtcagggcgt ccgagttgta atttggagag gatacttcgg gtgtggccgt     780
ggcttaagtc ccttggaaca gggcgtcata gagggtgaga atcccgtctt gagtcaccgg     840
tccacgccca tgcgaagttc cttcgacgag tcgagttgtt tgggaatgca gctctaagtg     900
ggtggtaaat ttcatctaaa gctaaatatt ggctggagac cgatagcgca caagtagagt     960
gatcgaaagg ttaaaagcac cttgaaaagg gagttaaata gcacgtgaaa ttgttgaaag    1020
ggaagcgctt gcaaccagac tcgagcgcag ggttcagcgg gcatgcgtgc ccgtgtactc    1080
cctgtgctcg ggccagcatc agtttcggcg gttggttaaa ggcctctgga atgtatcgtc    1140
ctccgggacg tcttatagcc agaggcgcaa tgcggccagc cgggactgag gaacgcgctt    1200
cggcacggat gctggcataa tggttgtaag cggcccgtct tgaaacacgg accaaggagt    1260
ctaacatcca cgcgagtgtt cgggtgtcaa acccgtgcgc gcagtgaaag cgaacggagg    1320
tgggagccca tcagggtgca ccatcgaccg atcctgaagt cttcggatgg atttgagtaa    1380
gagcgtggct gttgggaccc gaaagatggt gaactatgcc tgaatagggt gaagccagag    1440
gaaactctgg tggaggctcg cagcggttct gacgtgcaaa tcgatcgtca aatttgggta    1500
taggggcgaa agactaatcg aaccatctgg tagctggttc ctgccgaagt ttccctcagg    1560
atagcagtaa cgttttcagt tttatgaggt aaagcgaatg attagaggcc ttggggttga    1620
aacaaccttt acctattctc aaactttaaa tatgtaagaa gcccttgtta cttaagtgaa    1680
cgtgggcatt agaatggatc gttactagtg ggccattttt ggtaagcaga acctggcgat    1740
gcgggatgaa ccgaacgcga ggttaaggtg ccggaaatgc acgctcatca gacaccacaa    1800
aaggtgttag ttcatctaga cagcccgacg ggtggccatg gaagtcggaa tccgctaagg    1860
agtgtgtaac aactcccggg ccgaaatgaa ctagccctg aaaatggatg gcgctcaagc     1920
gtgctacccc atcctcgcc gtccgggtag aaacgatgcc ccgacgagta ggcaggcgtg    1980
gaggtttgtg acgaagcctt gggagtgatc ccgggtcgaa cagcctctag tgcagatctt    2040
```

```
ggtggtagta gcaaatactc aaatgagaac tttgaggact gaagtgggga aaggttccat    2100
gtgaacagca gttggacatg ggttagtcga tcctaagaca tagggtagtt ccgtttgaaa    2160
gcgcgccctc gtgcgccgtt cgtcgaaagg gaagccggtc aatattccgg cacctggatg    2220
tggattctcc acggcaacgt aactgaacgc ggagacgtcg gcaggagtcc tgggaagagt    2280
tctcttttct tcttgacggc ctatcaccct gaaatcggtt tggtccgggg cttggggttt    2340
catggcaggc agaccccccg cacctgtgtg gggtcccggg acactcctga cgaccectag    2400
aaaaaccgcg ggaagggaat agttttcacg ccaggtcgta ctcataaacc gcagcaggtc    2460
tccaaggtga aaaagcctct agttgataga acaatgtaga taagggaagt cggcaaaata    2520
gatccgtaac ttcgggaaaa ggattggctc taagggtcgg gcgcgttggg ccttggggga    2580
aagcctctgg agcagaaggg cactagccgg gcaaccggcg ggcgcctttc agcatcgggg    2640
tgcggacgcc cttggcaggc ttcggccgtc cggcgcgcga ttaacgacca acttagaact    2700
ggtacggaca aggggaatct gactgtctaa ttaaaacata gcattgcgat ggccagaaag    2760
tggtgttgac gcaatgtgat ttctgcccag tgctctgaat gtcaaagtga agaaattcaa    2820
ccaagcgcgg gtaaacggcg ggagtaacta tgactctctt aaggtagcca aatgcctcgt    2880
catctaatta gtgacgcgca tgaatggatt aacgagattc ccactgtccc tatctactat    2940
ctagcgaaac cacagccaag gaacgggct tggcagaatc agcggggaaa gaagaccctg    3000
ttgagcttga ctctagtttg acattgtgaa aagacatatc gggtgtagaa taggtgggag    3060
cttcggcaca agtgaaatac cactaccttt attgttttt tacttattca atgaagcgga    3120
actgggcttt accgcccaac ttctagcgtt aaggtccttc gcgggctgat ccgggttgaa    3180
gacattgtca ggtggggagt ttggctgggg cggcacatct gttaaaccat aacgcaggtg    3240
tcctaagggg gactcatgga gaacagaaat ctccagtaga acaaagggt aaaagtcccc    3300
ttgattttga ttttcagtgt gaatacaaac catgaaagtg tggcctatcg atcctttagt    3360
ccctcgaaat ttgaggctag aggtgccaga aaagttacca cagggataac tggcttgtgg    3420
cagccaagcg ttcatagcga cgttgctttt tgatccttcg atgtcggctc ttcctatcat    3480
accgaagcag aattcggtaa gcgttggatt gttcacccac taatagggaa cgtgagctgg    3540
gtttagaccg tcgtgagaca ggttagtttt accctactga tgaaggtcgc cgcaacggta    3600
attcaattta gtacgagagg aaccgttgat tcagataatt ggttttgcg gctgtctgac    3660
caggcagtgc cgcgacgcta ccatctgccg gattatggct gaacgcctct aagtcagaat    3720
ccgtgccgga acgcggcgat gttgcctcgc acgtcgtagt tggatacgaa taggccttcg    3780
ggccccgaac ctcagcaggt tggcggcggt gtccggggag agaccctcgg gcgccagcta    3840
acggattgca atgtcacaac gcgcgggat agatcctctg cagacgactg aaatgaccaa    3900
gcgggtcgtg taagcggtca agtagcctag ttgttacgag tcgctgagcg tcagcccgat    3960
ccttggctcg atttgttgta aacaccctcc atcaat                             3996
```

<210> SEQ ID NO 108
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 108

```
ccttatctac attattctat ggac                                            24
```